US012673932B2

(12) United States Patent
Lee et al.

(10) Patent No.: US 12,673,932 B2
(45) Date of Patent: Jul. 7, 2026

(54) HETEROCYCLIC COMPOUND AND ORGANIC LIGHT EMITTING DEVICE COMPRISING SAME

(71) Applicant: LT MATERIALS CO., LTD., Yongin-si (KR)

(72) Inventors: Young-Jin Lee, Yongin-si (KR); Seong-Jong Park, Yongin-si (KR); Won-Jang Jeong, Yongin-si (KR); Dong-Jun Kim, Yongin-si (KR)

(73) Assignee: LT MATERIALS CO., LTD., Yongin-si (KR)

( * ) Notice: Subject to any disclaimer, the term of this patent is extended or adjusted under 35 U.S.C. 154(b) by 821 days.

(21) Appl. No.: 17/600,149

(22) PCT Filed: Aug. 31, 2020

(86) PCT No.: PCT/KR2020/011620
§ 371 (c)(1),
(2) Date: Sep. 30, 2021

(87) PCT Pub. No.: WO2021/045460
PCT Pub. Date: Mar. 11, 2021

(65) Prior Publication Data

US 2022/0223795 A1 Jul. 14, 2022

(30) Foreign Application Priority Data

Sep. 6, 2019 (KR) ........................ 10-2019-0110890

(51) Int. Cl.
*C07D 213/22* (2006.01)
*C07D 401/14* (2006.01)
(Continued)

(52) U.S. Cl.
CPC ............ *C07D 401/14* (2013.01); *C09K 11/06* (2013.01); *H10K 50/18* (2023.02); *H10K 85/654* (2023.02);
(Continued)

(58) Field of Classification Search
CPC .. H10K 85/654; C07D 401/14; C07D 405/14; C07D 213/22; C07D 409/14; C09K 2211/1018; C07F 9/58
See application file for complete search history.

(56) References Cited

U.S. PATENT DOCUMENTS

2010/0288362 A1* 11/2010 Hatwar ................ H10K 50/131 257/E51.026
2010/0308322 A1 12/2010 Yokoyama et al.
(Continued)

FOREIGN PATENT DOCUMENTS

CN 102532002 A * 7/2012
CN 102532003 A * 7/2012
(Continued)

OTHER PUBLICATIONS

CN-102532002-A—translation (Year: 2012).*
(Continued)

*Primary Examiner* — Rachel Simbana
(74) *Attorney, Agent, or Firm* — NKL Law; Jae Youn Kim

(57) ABSTRACT

The present specification relates to a heterocyclic compound represented by Chemical Formula 1, and an organic light emitting device including the same.

8 Claims, 2 Drawing Sheets

(51) Int. Cl.

| | |
|---|---|
| ***C07D 405/14*** | (2006.01) |
| ***C07D 409/14*** | (2006.01) |
| ***C07D 471/04*** | (2006.01) |
| ***C07D 491/048*** | (2006.01) |
| ***C07D 495/04*** | (2006.01) |
| ***C07F 9/58*** | (2006.01) |
| ***C09K 11/06*** | (2006.01) |
| ***H10K 50/11*** | (2023.01) |
| ***H10K 50/13*** | (2023.01) |
| ***H10K 50/15*** | (2023.01) |
| ***H10K 50/16*** | (2023.01) |
| ***H10K 50/17*** | (2023.01) |
| ***H10K 50/18*** | (2023.01) |
| ***H10K 50/19*** | (2023.01) |
| ***H10K 85/60*** | (2023.01) |

(52) U.S. Cl.

CPC .. *H10K 85/6572* (2023.02); *C09K 2211/1018* (2013.01); *H10K 50/16* (2023.02); *H10K 50/17* (2023.02); *H10K 50/19* (2023.02)

(56) References Cited

U.S. PATENT DOCUMENTS

| | | | | |
|---|---|---|---|---|
| 2010/0327265 | A1 | 12/2010 | Kimura et al. | |
| 2016/0372524 | A1* | 12/2016 | Yun | C09K 11/06 |
| 2017/0092870 | A1* | 3/2017 | Kim | H10K 85/654 |
| 2017/0092871 | A1* | 3/2017 | Kim | H10K 50/13 |
| 2018/0090686 | A1* | 3/2018 | Yoon | H10K 85/622 |
| 2019/0312211 | A1 | 10/2019 | Lee et al. | |
| 2019/0341558 | A1 | 11/2019 | Yang et al. | |
| 2020/0131133 | A1 | 4/2020 | La | |
| 2025/0169275 | A1* | 5/2025 | Tokuda | H10K 85/622 |

FOREIGN PATENT DOCUMENTS

| | | | | | |
|---|---|---|---|---|---|
| CN | 109411631 | A | | 3/2019 | |
| CN | 109476608 | A | | 3/2019 | |
| CN | 109721595 | A | | 5/2019 | |
| JP | 2003-123983 | A | | 4/2003 | |
| JP | 2011-98948 | A | | 5/2011 | |
| JP | 2017-137284 | A | | 8/2017 | |
| JP | 2020123477 | A | * | 8/2020 | |
| KR | 2014094408 | A | * | 7/2014 | C07D 401/14 |
| KR | 10-2015-0026055 | A | | 3/2015 | |
| KR | 10-1609397 | B1 | | 4/2016 | |
| KR | 10-2016-0068683 | A | | 6/2016 | |
| KR | 10-2017-0037787 | A | | 4/2017 | |
| TW | 201838992 | A | | 11/2018 | |
| TW | 291930582 | A | | 8/2019 | |
| WO | WO-2009102016 | A1 | * | 8/2009 | C07D 471/04 |
| WO | WO-2016089165 | A2 | * | 6/2016 | |

OTHER PUBLICATIONS

JP-2020123477-A—translation (Year: 2020).*
KR-2014094408-A—translation (Year: 2014).*
CN-102532003-A—translation (Year: 2012).*
WO-2009102016-A1—translation (Year: 2009).*
WO-2016089165-A2—translation (Year: 2016).*
Constable et al., "Cinnamil—An Oligopyridine Precursor", Tetrahedron Letters, 1994, vol. 35, No. 36, pp. 6657-6660.
International Search Report for PCT/KR2020/011620 mailed on Dec. 11, 2020.

* cited by examiner

【FIG. 1】
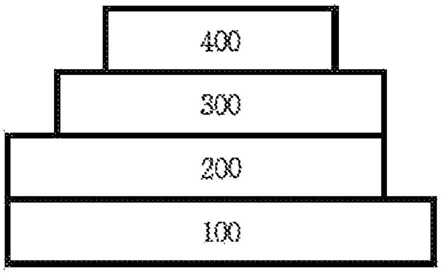
【FIG. 2】
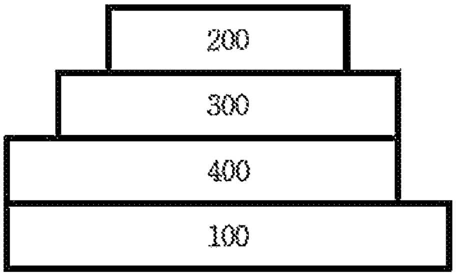
【FIG. 3】
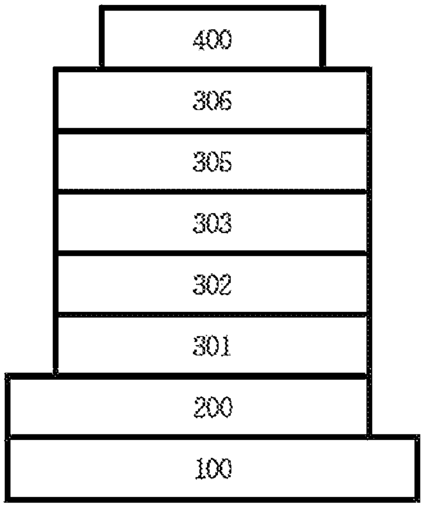

【FIG. 4】
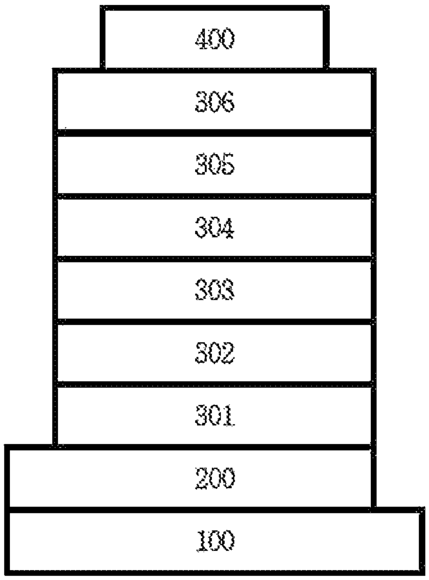
【FIG. 5】
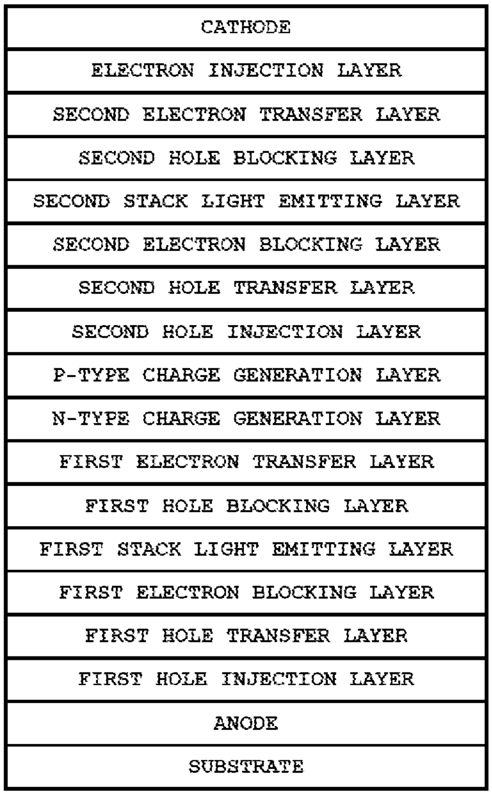

HETEROCYCLIC COMPOUND AND ORGANIC LIGHT EMITTING DEVICE COMPRISING SAME

TECHNICAL FIELD

The present specification relates to a heterocyclic compound, and an organic light emitting device including the same.

This application claims priority to and the benefits of Korean Patent Application No. 10-2019-0110890, filed with the Korean Intellectual Property Office on Sep. 6, 2019, the entire contents of which are incorporated herein by reference.

BACKGROUND ART

An electroluminescent device is one type of self-emissive display devices, and has an advantage of having a wide viewing angle, and a high response speed as well as having an excellent contrast.

An organic light emitting device has a structure disposing an organic thin film between two electrodes. When a voltage is applied to an organic light emitting device having such a structure, electrons and holes injected from the two electrodes bind and pair in the organic thin film, and light emits as these annihilate. The organic thin film may be formed in a single layer or a multilayer as necessary.

A material of the organic thin film may have a light emitting function as necessary. For example, as a material of the organic thin film, compounds capable of forming a light emitting layer themselves alone may be used, or compounds capable of performing a role of a host or a dopant of a host-dopant-based light emitting layer may also be used. In addition thereto, compounds capable of performing roles of hole injection, hole transfer, electron blocking, hole blocking, electron transfer, electron injection and the like may also be used as a material of the organic thin film.

Development of an organic thin film material has been continuously required for enhancing performance, lifetime or efficiency of an organic light emitting device.

DISCLOSURE

Technical Problem

The present specification is directed to providing a heterocyclic compound, and an organic light emitting device including the same.

Technical Solution

One embodiment of the present specification provides a heterocyclic compound represented by the following Chemical Formula 1.

[Chemical Formula 1]

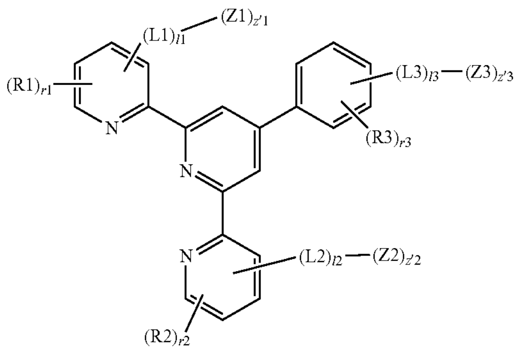

In Chemical Formula 1,

R1 to R3 are the same as or different from each other, and each independently hydrogen; deuterium; a halogen group; a cyano group; —P(═O)R(104)(R105); a substituted or unsubstituted C1 to C60 alkyl group; a substituted or unsubstituted C2 to C60 alkenyl group; a substituted or unsubstituted C1 to C60 alkoxy group; a substituted or unsubstituted C3 to C60 cycloalkyl group; a substituted or unsubstituted C6 to C60 aryl group; or a substituted or unsubstituted C2 to C60 heterocyclic group, or two or more groups adjacent to each other bond to each other to form a substituted or unsubstituted aliphatic or aromatic hydrocarbon ring, or a substituted or unsubstituted heteroring, L1 to L3 are the same as or different from each other, and each independently a direct bond; a substituted or unsubstituted C6 to C60 arylene group; or a substituted or unsubstituted C2 to C60 divalent heterocyclic group, Z1 to Z3 are the same as or different from each other, and each independently hydrogen; deuterium; a halogen group; a cyano group; —P(═O)R(104')(R105'); a substituted or unsubstituted C1 to C60 alkyl group; a substituted or unsubstituted C2 to C60 alkenyl group; a substituted or unsubstituted C1 to C60 alkoxy group; a substituted or unsubstituted C3 to C60 cycloalkyl group; a substituted or unsubstituted C6 to C60 aryl group; or a substituted or unsubstituted C2 to C60 heterocyclic group, at least one of Z1 and Z2 is a halogen group; a cyano group; —P(═O)R(104')(R105'); a substituted or unsubstituted C1 to C60 alkyl group; a substituted or unsubstituted C2 to C60 alkenyl group; a substituted or unsubstituted C1 to C60 alkoxy group; a substituted or unsubstituted C3 to C60 cycloalkyl group; a substituted or unsubstituted C6 to C60 aryl group; or a substituted or unsubstituted C2 to C60 heterocyclic group, R104, R105, R104' and R105' are each independently hydrogen; deuterium; a halogen group; an alkyl group; an alkenyl group; an alkoxy group; a cycloalkyl group; an aryl group; or a heterocyclic group, r1 and r2 are each an integer of 1 to 3, r3 is an integer of 1 to 4, l1 to l3 and z'1 to z'3 are each independently an integer of 1 to 5, and when r1 to r3, l1 to l3 and z'1 to z'3 are each 2 or greater, substituents in the parentheses are the same as or different from each other.

Another embodiment of the present application provides an organic light emitting device including a first electrode; a second electrode provided opposite to the first electrode;

and an organic material layer provided between the first electrode and the second electrode, wherein the organic material layer includes one or more types of the heterocyclic compound represented by Chemical Formula 1.

Advantageous Effects

A compound described in the present specification can be used as a material of an organic material layer of an organic light emitting device. In the organic light emitting device, the compound is capable of performing a role of a hole injection material, a hole transfer material, a light emitting material, an electron transfer material, an electron injection material or the like. Particularly, the compound can be used as an electron transfer layer material, a hole blocking layer material or a charge generation layer material of an organic light emitting device.

By Chemical Formula 1 having a structure in which terpyridine is disubstituted or trisubstituted, molecular stability increases by increasing electron delocalization compared to monosubstituted compounds, which enhances device performance by affecting device stability.

Specifically, when using the compound represented by Chemical Formula 1 in an organic material layer, a driving voltage of the device can be lowered, light efficiency can be enhanced, and lifetime properties of the device can be enhanced.

DESCRIPTION OF DRAWINGS

FIG. 1 to FIG. 5 are diagrams each illustrating a lamination structure of an organic light emitting device according to one embodiment of the present specification.

100: Substrate
200: Anode
300: Organic Material Layer
301: Hole Injection Layer
302: Hole Transfer Layer
303: Light Emitting Layer
304: Hole Blocking Layer
305: Electron Transfer Layer
306: Electron Injection Layer
400: Cathode

MODE FOR DISCLOSURE

Hereinafter, the present specification will be described in more detail.

In the present specification, a certain part "including" certain constituents means capable of further including other constituents, and does not exclude other constituents unless particularly stated on the contrary.

The term "substitution" means a hydrogen atom bonding to a carbon atom of a compound being changed to another substituent, and the position of substitution is not limited as long as it is a position at which the hydrogen atom is substituted, that is, a position at which a substituent can substitute, and when two or more substituents substitute, the two or more substituents may be the same as or different from each other.

In the present specification,

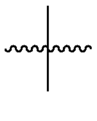

means a substituted position.

In the present specification, "substituted or unsubstituted" means being substituted with one or more substituents selected from the group consisting of a C1 to C60 linear or branched alkyl group; a C2 to C60 linear or branched alkenyl group; a C2 to C60 linear or branched alkynyl group; a C1 to C60 alkoxy group; a C3 to C60 monocyclic or polycyclic cycloalkyl group; a C2 to C60 monocyclic or polycyclic heterocycloalkyl group; a C6 to C60 monocyclic or polycyclic aryl group; a C2 to C60 monocyclic or polycyclic heterocyclic group; a silyl group; a phosphine oxide group; and an amine group, or being unsubstituted, or being substituted with a substituent linking two or more substituents selected from among the substituents illustrated above.

In the present specification, a "case of a substituent being not indicated in a chemical formula or compound structure" means that a hydrogen atom bonds to a carbon atom. However, since deuterium ($^2H$) is an isotope of hydrogen, some hydrogen atoms may be deuterium.

In one embodiment of the present application, a "case of a substituent being not indicated in a chemical formula or compound structure" may mean that positions that may come as a substituent may all be hydrogen or deuterium. In other words, since deuterium is an isotope of hydrogen, some hydrogen atoms may be deuterium that is an isotope, and herein, a content of the deuterium may be from 0% to 100%.

In one embodiment of the present application, in a "case of a substituent being not indicated in a chemical formula or compound structure", hydrogen and deuterium may be mixed in compounds when deuterium is not explicitly excluded such as a deuterium content being 0%, a hydrogen content being 100% or substituents being all hydrogen.

In one embodiment of the present application, deuterium is one of isotopes of hydrogen, is an element having deuteron formed with one proton and one neutron as a nucleus, and may be expressed as hydrogen-2, and the elemental symbol may also be written as D or 2H.

In one embodiment of the present application, an isotope means an atom with the same atomic number (Z) but with a different mass number (A), and may also be interpreted as an element with the same number of protons but with a different number of neutrons.

In one embodiment of the present application, a meaning of a content T % of a specific substituent may be defined as $T2/T1 \times 100 = T$ % when the total number of substituents that a basic compound may have is defined as T1, and the number of specific substituents among these is defined as T2.

In other words, in one example, having a deuterium content of 20% in a phenyl group represented by

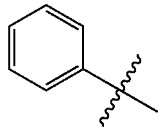 [SMILES: *c1ccccc1]

means that the total number of substituents that the phenyl group may have is 5 (T1 in the formula), and the number of deuterium among these is 1 (T2 in the formula). In other words, having a deuterium content of 20% in a phenyl group may be represented by the following structural formulae.

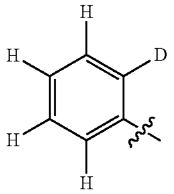

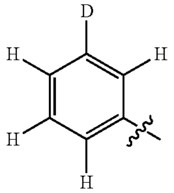

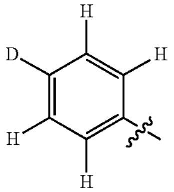

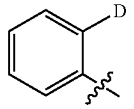

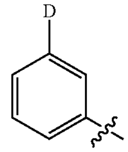

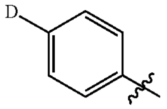

In addition, in one embodiment of the present application, "a phenyl group having a deuterium content of 0%" may mean a phenyl group that does not include a deuterium atom, that is, a phenyl group that has 5 hydrogen atoms.

In the present specification, the halogen may be fluorine, chlorine, bromine or iodine.

In the present specification, the alkyl group includes linear or branched having 1 to 60 carbon atoms, and may be further substituted with other substituents. The number of carbon atoms of the alkyl group may be from 1 to 60, specifically from 1 to 40 and more specifically from 1 to 20. Specific examples thereof may include a methyl group, an ethyl group, a propyl group, an n-propyl group, an isopropyl group, a butyl group, an n-butyl group, an isobutyl group, a tert-butyl group, a sec-butyl group, a 1-methyl-butyl group, a 1-ethyl-butyl group, a pentyl group, an n-pentyl group, an isopentyl group, a neopentyl group, a tert-pentyl group, a hexyl group, an n-hexyl group, a 1-methylpentyl group, a 2-methylpentyl group, a 4-methyl-2-pentyl group, a 3,3-dimethylbutyl group, a 2-ethylbutyl group, a heptyl group, an n-heptyl group, a 1-methylhexyl group, a cyclopentylmethyl group, a cyclohexylmethyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethyl-propyl group, a 1,1-dimethyl-propyl group, an isohexyl group, a 2-methylpentyl group, a 4-methylhexyl group, a 5-methylhexyl group and the like, but are not limited thereto.

In the present specification, the alkenyl group includes linear or branched having 2 to 60 carbon atoms, and may be further substituted with other substituents. The number of carbon atoms of the alkenyl group may be from 2 to 60, specifically from 2 to 40 and more specifically from 2 to 20. Specific examples thereof may include a vinyl group, a 1-propenyl group, an isopropenyl group, a 1-butenyl group, a 2-butenyl group, a 3-butenyl group, a 1-pentenyl group, a 2-pentenyl group, a 3-pentenyl group, a 3-methyl-1-butenyl group, a 1,3-butadienyl group, an allyl group, a 1-phenylvinyl-1-yl group, a 2-phenylvinyl-1-yl group, a 2,2-diphenylvinyl-1-yl group, a 2-phenyl-2-(naphthyl-1-yl)vinyl-1-yl group, a 2,2-bis(diphenyl-1-yl)vinyl-1-yl group, a stilbenyl group, a styrenyl group and the like, but are not limited thereto.

In the present specification, the alkynyl group includes linear or branched having 2 to 60 carbon atoms, and may be further substituted with other substituents. The number of carbon atoms of the alkynyl group may be from 2 to 60, specifically from 2 to 40 and more specifically from 2 to 20.

In the present specification, the alkoxy group may be linear, branched or cyclic. The number of carbon atoms of the alkoxy group is not particularly limited, but is from 1 to 60 and preferably from 1 to 30. Specific examples thereof may include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy and the like, but are not limited thereto.

In the present specification, the cycloalkyl group includes monocyclic or polycyclic having 3 to 60 carbon atoms, and may be further substituted with other substituents. Herein, the polycyclic means a group in which the cycloalkyl group is directly linked to or fused with other cyclic groups. Herein, the other cyclic groups may be a cycloalkyl group, but may also be different types of cyclic groups such as a heterocycloalkyl group, an aryl group and a heteroaryl group. The number of carbon groups of the cycloalkyl group may be from 3 to 60, specifically from 3 to 40 and more specifically from 5 to 20. Specific examples thereof may include a cyclopropyl group, a cyclobutyl group, a cyclopentyl group, a 3-methylcyclopentyl group, a 2,3-dimethylcyclopentyl group, a cyclohexyl group, a 3-methylcyclohexyl group, a 4-methylcyclohexyl group, a 2,3-dimethylcyclohexyl group, a 3,4,5-trimethylcyclohexyl group, a 4-tert-butylcyclohexyl group, a cycloheptyl group, a cyclooctyl group and the like, but are not limited thereto.

In the present specification, the heterocycloalkyl group includes O, S, Se, N or Si as a heteroatom, includes monocyclic or polycyclic having 2 to 60 carbon atoms, and may be further substituted with other substituents. Herein, the polycyclic means a group in which the heterocycloalkyl group is directly linked to or fused with other cyclic groups. Herein, the other cyclic groups may be a heterocycloalkyl group, but may also be different types of cyclic groups such as a cycloalkyl group, an aryl group and a heterocyclic group. The number of carbon atoms of the heterocycloalkyl group may be from 2 to 60, specifically from 2 to 40 and more specifically from 3 to 20.

In the present specification, the aryl group includes monocyclic or polycyclic having 6 to 60 carbon atoms, and may be further substituted with other substituents. Herein, the polycyclic means a group in which the aryl group is directly linked to or fused with other cyclic groups. Herein, the other cyclic groups may be an aryl group, but may also be different types of cyclic groups such as a cycloalkyl group, a heterocycloalkyl group and a heteroaryl group. The aryl group includes a spiro group. The number of carbon atoms of the aryl group may be from 6 to 60, specifically from 6 to 40 and more specifically from 6 to 25. Specific examples of the aryl group may include a phenyl group, a biphenyl group, a triphenyl group, a naphthyl group, an anthryl group, a chrysenyl group, a phenanthrenyl group, a perylenyl group, a fluoranthenyl group, a triphenylenyl group, a phenalenyl group, a pyrenyl group, a tetracenyl group, a pentacenyl group, a fluorenyl group, an indenyl group, an acenaphthylenyl group, a benzofluorenyl group, a spirobifluorenyl group, a 2,3-dihydro-1H-indenyl group, a fused ring thereof, and the like, but are not limited thereto.

In the present specification, the silyl group is a substituent including Si, having the Si atom directly linked as a radical, and is represented by —Si(R101)(R102)(R103). R101 to R103 are the same as or different from each other, and may be each independently a substituent formed with at least one of hydrogen; deuterium; a halogen group; an alkyl group; an alkenyl group; an alkoxy group; a cycloalkyl group; an aryl group; and a heterocyclic group. Specific examples of the silyl group may include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the fluorenyl group may be substituted, and adjacent substituents may bond to each other to form a ring.

When the fluorenyl group is substituted,

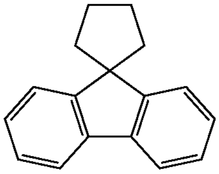
,

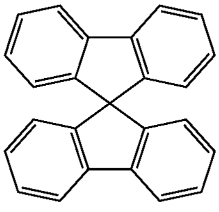
,

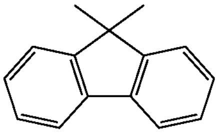
,

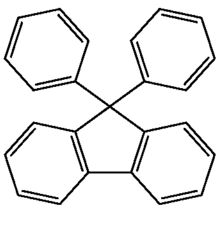
,

-continued

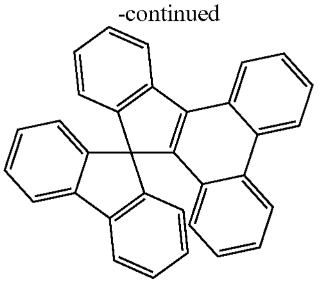
,

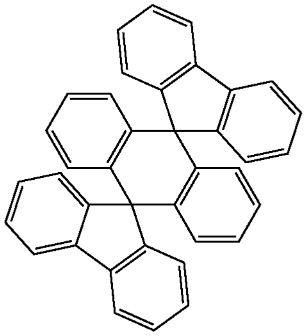

and the like may be included, however, the structure is not limited thereto.

In the present specification, the heterocyclic group includes O, S, SO, $SO_2$, Se, N or Si as a heteroatom, includes monocyclic or polycyclic having 2 to 60 carbon atoms, and may be further substituted with other substituents. Herein, the polycyclic means a group in which the heterocyclic group is directly linked to or fused with other cyclic groups. Herein, the other cyclic groups may be a heterocyclic group, but may also be different types of cyclic groups such as a cycloalkyl group, a heterocycloalkyl group and an aryl group. The number of carbon atoms of the heterocyclic group may be from 2 to 60, specifically from 2 to 40 and more specifically from 3 to 25. Specific examples of the heterocyclic group may include a pyridyl group, a pyrrolyl group, a pyrimidyl group, a pyridazinyl group, a furanyl group, a thiophene group, an imidazolyl group, a pyrazolyl group, an oxazolyl group, an isoxazolyl group, a thiazolyl group, an isothiazolyl group, a triazolyl group, a furazanyl group, an oxadiazolyl group, a thiadiazolyl group, a dithiazolyl group, a tetrazolyl group, a pyranyl group, a thiopyranyl group, a diazinyl group, an oxazinyl group, a thiazinyl group, a dioxynyl group, a triazinyl group, a tetrazinyl group, a quinolyl group, an isoquinolyl group, a quinazolinyl group, an isoquinazolinyl group, a qninozolinyl group, a naphthyridyl group, an acridinyl group, a phenanthridinyl group, an imidazopyridinyl group, a diazanaphthalenyl group, a triazaindene group, an indolyl group, an indolizinyl group, a benzothiazolyl group, a benzoxazolyl group, a benzimidazolyl group, a benzothiophene group, a benzofuran group, a dibenzothiophene group, a dibenzofuran group, a carbazolyl group, a benzocarbazolyl group, a dibenzocarbazolyl group, a phenazinyl group, a dibenzosilole group, spirobi(dibenzosilole), a dihydrophenazinyl group, a phenoxazinyl group, a phenanthridyl group, an imidazopyridinyl group, a thienyl group, an indolo[2,3-a]carbazolyl group, an indolo[2,3-b]carbazolyl group, an indolinyl group, a 10,11-dihydro-dibenzo[b,f]azepine group, a 9,10-dihydroacridinyl group, a phenanthrazinyl group, a phenothiathiazinyl group, a phthalazinyl group, a naphthylidinyl group, a phenanthrolinyl group, a benzo[c][1,2,5]thiadiazolyl group, a 5,10-dihydrobenzo[b,e][1,4]azasilinyl group, a pyrazolo[1,5-c]quinazolinyl group, a pyrido[1,2-b]indazolyl group, a pyrido[1,2-a]imidazo[1,2-e]indolinyl group, a 5,11-dihydroindeno[1,2-b]carbazolyl group, spiro[fluorene-9,9'-xanthene], dibenzothiophene sulfoxide

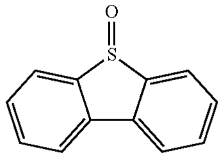

, (Dibenzothiophene sulfoxide)

dibenzosulfolane

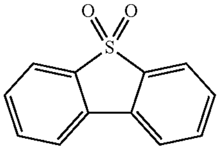

, (Dibenzosulfolane)

a benzo[4,5]thieno[3,2-d]pyrimidyl group, a benzofuro[2,3-c]quinolinyl group, a benzofuro[3,2-c]quinolinyl group, a benzothieno[2,3-c]quinolinyl group, a benzothieno[3,2-c]quinolinyl group, a pyrazolo[5,1-a]isoquinolinyl group and the like, but are not limited thereto.

In the present specification, the phosphine oxide group is represented by —P(═O)(R104)(R105), and R104 and R105 are the same as or different from each other and may be each independently a substituent formed with at least one of hydrogen; deuterium; a halogen group; an alkyl group; an alkenyl group; an alkoxy group; a cycloalkyl group; an aryl group; and a heterocyclic group. Specifically, the phosphine oxide group may be substituted with an aryl group, and as the aryl group, the examples described above may be applied. Examples of the phosphine oxide group may include a diphenylphosphine oxide group, a dinaphthylphosphine oxide group and the like, but are not limited thereto.

In the present specification, the amine group is represented by —N(R106)(R107), and R106 and R107 are the same as or different from each other and may be each independently a substituent formed with at least one of hydrogen; deuterium; a halogen group; an alkyl group; an alkenyl group; an alkoxy group; a cycloalkyl group; an aryl group; and a heterocyclic group. The amine group may be selected from the group consisting of a monoalkylamine group; a monoarylamine group; a monoheteroarylamine group; —$NH_2$; a dialkylamine group; a diarylamine group; a diheteroarylamine group; an alkylarylamine group; an alkylheteroarylamine group; and an arylheteroarylamine group, and although not particularly limited thereto, the number of carbon atoms is preferably from 1 to 30. Specific examples of the amine group may include a methylamine group, a dimethylamine group, an ethylamine group, a diethylamine group, a phenylamine group, a naphthylamine group, a biphenylamine group, a dibiphenylamine group, an anthracenylamine group, a 9-methyl-anthracenylamine group, a diphenylamine group, a phenylnaphthylamine group, a ditolylamine group, a phenyltolylamine group, a triphenylamine group, a biphenylnaphthylamine group, a phenylbiphenylamine group, a biphenylfluorenylamine group, a phenyltriphenylenylamine group, a biphenyltriphenylenylamine group and the like, but are not limited thereto.

In the present specification, an "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

As the aliphatic hydrocarbon ring, the aliphatic heteroring the aromatic hydrocarbon ring or the aromatic heteroring that the adjacent groups may form, the structures illustrated as the cycloalkyl group, the heterocycloalkyl group, the aryl group and the heterocyclic group described above may be applied except for those that are not a monovalent group.

One embodiment of the present specification provides a heterocyclic compound represented by Chemical Formula 1.

In one embodiment of the present specification, L1 to L3 are the same as or different from each other, and each independently a direct bond; a substituted or unsubstituted C6 to C60 arylene group; or a substituted or unsubstituted C2 to C60 divalent heterocyclic group.

In one embodiment of the present specification, L1 to L3 are the same as or different from each other, and each independently a direct bond; a substituted or unsubstituted C6 to C40 arylene group; or a substituted or unsubstituted C2 to C40 divalent heterocyclic group.

In one embodiment of the present specification, L1 to L3 are the same as or different from each other, and each independently a direct bond; a substituted or unsubstituted C6 to C20 arylene group; or a substituted or unsubstituted C2 to C20 divalent heterocyclic group.

In one embodiment of the present specification, L1 to L3 are the same as or different from each other, and each independently a direct bond; or a substituted or unsubstituted C6 to C20 arylene group.

In one embodiment of the present specification, L1 to L3 are the same as or different from each other, and each independently a direct bond; a substituted or unsubstituted phenylene group; or a substituted or unsubstituted biphenylene group.

In one embodiment of the present specification, L1 to L3 are the same as or different from each other, and each independently a direct bond; a phenylene group; or a biphenylene group.

In one embodiment of the present specification, L1 is a direct bond; a phenylene group; or a biphenylene group.

In one embodiment of the present specification, L2 and L3 are the same as or different from each other, and each independently a direct bond; or a phenylene group.

In one embodiment of the present specification, Z1 to Z3 are the same as or different from each other and each independently hydrogen; deuterium; a halogen group; a cyano group; —P(═O)R(104')(R105'); a substituted or unsubstituted C1 to C60 alkyl group; a substituted or unsubstituted C2 to C60 alkenyl group; a substituted or unsubstituted C1 to C60 alkoxy group; a substituted or unsubstituted C3 to C60 cycloalkyl group; a substituted or unsubstituted C6 to C60 aryl group; or a substituted or unsubstituted C2 to C60 heterocyclic group, and at least one of Z1 and Z2 is a halogen group; a cyano group; —P(═O)R(104')(R105'); a substituted or unsubstituted C1 to C60 alkyl group; a substituted or unsubstituted C2 to C60 alkenyl group; a substituted or unsubstituted C1 to C60 alkoxy group; a substituted or unsubstituted C3 to C60 cycloalkyl group; a substituted or unsubstituted C6 to C60 aryl group; or a substituted or unsubstituted C2 to C60 heterocyclic group.

In one embodiment of the present specification, Z1 to Z3 are the same as or different from each other and each independently hydrogen; deuterium; a halogen group; a cyano group; —P(═O)R(104')(R105'); a substituted or unsubstituted C1 to C40 alkyl group; a substituted or unsubstituted C2 to C40 alkenyl group; a substituted or unsubstituted C1 to C40 alkoxy group; a substituted or unsubstituted C3 to C40 cycloalkyl group; a substituted or unsubstituted C6 to C40 aryl group; or a substituted or unsubstituted C2 to C40 heterocyclic group, and at least one of Z1 and Z2 is a halogen group; a cyano group; —P(═O)R(104')(R105'); a substituted or unsubstituted C1 to C40 alkyl group; a substituted or unsubstituted C2 to C40 alkenyl group; a substituted or unsubstituted C1 to C40 alkoxy group; a substituted or unsubstituted C3 to C40 cycloalkyl group; a substituted or unsubstituted C6 to C40 aryl group; or a substituted or unsubstituted C2 to C40 heterocyclic group.

In one embodiment of the present specification, Z1 to Z3 are the same as or different from each other and each independently hydrogen; deuterium; a halogen group; a cyano group; —P(═O)R(104')(R105'); a substituted or unsubstituted C1 to C20 alkyl group; a substituted or unsubstituted C2 to C20 alkenyl group; a substituted or unsubstituted C1 to C20 alkoxy group; a substituted or unsubstituted C3 to C20 cycloalkyl group; a substituted or unsubstituted C6 to C20 aryl group; or a substituted or unsubstituted C2 to C20 heterocyclic group, and at least one of Z1 and Z2 is a halogen group; a cyano group; —P(═O)R(104')(R105'); a substituted or unsubstituted C1 to C20 alkyl group; a substituted or unsubstituted C2 to C20 alkenyl group; a substituted or unsubstituted C1 to C20 alkoxy group; a substituted or unsubstituted C3 to C20 cycloalkyl group; a substituted or unsubstituted C6 to C20 aryl group; or a substituted or unsubstituted C2 to C20 heterocyclic group.

In one embodiment of the present specification, Z1 to Z3 are the same as or different from each other and each independently hydrogen; deuterium; a halogen group; a cyano group; —P(═O)R(104')(R105'); a substituted or unsubstituted C1 to C60 alkyl group; a substituted or unsubstituted C6 to C60 aryl group; or a substituted or unsubstituted C2 to C60 heterocyclic group, and at least one of Z1 and Z2 is a halogen group; a cyano group; —P(═O)R(104')(R105'); a substituted or unsubstituted C1 to C60 alkyl group; a substituted or unsubstituted C6 to C60 aryl group; or a substituted or unsubstituted C2 to C60 heterocyclic group.

In one embodiment of the present specification, Z1 to Z3 are the same as or different from each other and each independently hydrogen; deuterium; a halogen group; a cyano group; —P(═O)R(104')(R105'); a substituted or unsubstituted C1 to C40 alkyl group; a substituted or unsubstituted C6 to C40 aryl group; or a substituted or unsubstituted C2 to C40 heterocyclic group, and at least one of Z1 and Z2 is a halogen group; a cyano group; —P(═O)R(104')(R105'); a substituted or unsubstituted C1 to C40 alkyl group; a substituted or unsubstituted C6 to C40 aryl group; or a substituted or unsubstituted C2 to C40 heterocyclic group.

In one embodiment of the present specification, Z1 to Z3 are the same as or different from each other and each independently hydrogen; deuterium; a halogen group; a cyano group; —P(═O)R(104')(R105'); a substituted or unsubstituted C1 to C20 alkyl group; a substituted or unsubstituted C6 to C20 aryl group; or a substituted or unsubstituted C2 to C20 heterocyclic group, and at least one of Z1 and Z2 is a halogen group; a cyano group; —P(═O)R(104')(R105'); a substituted or unsubstituted C1 to C20 alkyl group; a substituted or unsubstituted C6 to C20 aryl group; or a substituted or unsubstituted C2 to C20 heterocyclic group.

In one embodiment of the present specification, Z1 is —P(═O)R(104')(R105'); a substituted or unsubstituted C6 to C60 aryl group; or a substituted or unsubstituted C2 to C60 heterocyclic group, and Z2 and Z3 are the same as or different from each other and each independently hydrogen; deuterium; a halogen group; a cyano group; a substituted or unsubstituted C1 to C60 alkyl group; a substituted or unsubstituted C6 to C60 aryl group; or a substituted or unsubstituted C2 to C60 heterocyclic group.

In one embodiment of the present specification, Z1 is —P(═O)R(104')(R105'); a substituted or unsubstituted C6 to C40 aryl group; or a substituted or unsubstituted C2 to C40 heterocyclic group, and Z2 and Z3 are the same as or different from each other and each independently hydrogen; deuterium; a halogen group; a cyano group; a substituted or unsubstituted C1 to C40 alkyl group; a substituted or unsubstituted C6 to C40 aryl group; or a substituted or unsubstituted C2 to C40 heterocyclic group.

In one embodiment of the present specification, Z1 is —P(═O)R(104')(R105'); a substituted or unsubstituted C6 to C20 aryl group; or a substituted or unsubstituted C2 to C20 heterocyclic group, and Z2 and Z3 are the same as or different from each other and each independently hydrogen; deuterium; a halogen group; a cyano group; a substituted or unsubstituted C1 to C20 alkyl group; a substituted or unsubstituted C6 to C20 aryl group; or a substituted or unsubstituted C2 to C20 heterocyclic group.

In one embodiment of the present specification, R1 to R3 are the same as or different from each other, and each independently hydrogen; deuterium; a substituted or unsubstituted C1 to C60 alkyl group; a substituted or unsubstituted C6 to C60 aryl group; or a substituted or unsubstituted C2 to C60 heterocyclic group, or two or more groups adjacent to each other bond to each other to form a substituted or unsubstituted C3 to C60 aliphatic hydrocarbon ring, a substituted or unsubstituted C6 to C60 aromatic hydrocarbon ring, or a substituted or unsubstituted C2 to C60 heteroring.

In one embodiment of the present specification, R1 to R3 are the same as or different from each other, and each independently hydrogen; deuterium; a substituted or unsubstituted C1 to C40 alkyl group; a substituted or unsubstituted C6 to C40 aryl group; or a substituted or unsubstituted C2 to C40 heterocyclic group, or two or more groups adjacent to each other bond to each other to form a substituted or unsubstituted C3 to C40 aliphatic hydrocarbon ring, a substituted or unsubstituted C6 to C40 aromatic hydrocarbon ring, or a substituted or unsubstituted C2 to C40 heteroring.

In one embodiment of the present specification, R1 to R3 are the same as or different from each other, and each independently hydrogen; deuterium; a substituted or unsubstituted C1 to C20 alkyl group; a substituted or unsubstituted C6 to C20 aryl group; or a substituted or unsubstituted C2 to C20 heterocyclic group, or two or more groups adjacent to each other bond to each other to form a substituted or unsubstituted C3 to C20 aliphatic hydrocarbon ring, a substituted or unsubstituted C6 to C20 aromatic hydrocarbon ring, or a substituted or unsubstituted C2 to C20 heteroring.

In one embodiment of the present specification, R1 to R3 are the same as or different from each other, and each independently hydrogen; deuterium; a substituted or unsubstituted C1 to C20 alkyl group; a substituted or unsubstituted C6 to C20 aryl group; or a substituted or unsubstituted C2 to C20 heterocyclic group, or two or more groups adjacent to each other bond to each other to form a substituted or unsubstituted C6 to C20 aromatic hydrocarbon ring.

In one embodiment of the present specification, R1 to R3 are the same as or different from each other, and each independently hydrogen; deuterium; a substituted or unsubstituted C1 to C20 alkyl group; a substituted or unsubstituted C6 to C20 aryl group; or a substituted or unsubstituted C2 to C20 heterocyclic group, or two or more groups adjacent to each other bond to each other to form a substituted or unsubstituted benzene ring.

In one embodiment of the present specification, R1 is hydrogen; or deuterium.

In one embodiment of the present specification, R1 is hydrogen.

In one embodiment of the present specification, R2 and R3 are the same as or different from each other, and each independently hydrogen; deuterium; a substituted or unsubstituted C1 to C20 alkyl group; or a substituted or unsubstituted C6 to C20 aryl group, or two or more groups adjacent to each other bond to each other to form a substituted or unsubstituted C6 to C20 aromatic hydrocarbon ring.

In one embodiment of the present specification, r2 is 1, and R2 is hydrogen; deuterium; or a substituted or unsubstituted C6 to C60 aryl group.

In one embodiment of the present specification, r2 is 1, and R2 is hydrogen; deuterium; or a substituted or unsubstituted C6 to C40 aryl group.

In one embodiment of the present specification, r2 is 1, and R2 is hydrogen; deuterium; or a substituted or unsubstituted C6 to C20 aryl group.

In one embodiment of the present specification, r2 is 1, and R2 is hydrogen; deuterium; or a substituted or unsubstituted phenyl group.

In one embodiment of the present specification, r2 is 1, and R2 is hydrogen; deuterium; or a phenyl group.

In another embodiment, r2 is 2, and a plurality of R2s bond to each other to form a substituted or unsubstituted C3 to C20 aliphatic hydrocarbon ring, a substituted or unsubstituted C6 to C20 aromatic hydrocarbon ring, or a substituted or unsubstituted C2 to C20 heteroring.

In another embodiment, r2 is 2, and a plurality of R2s bond to each other to form a substituted or unsubstituted C3 to C20 aliphatic hydrocarbon ring, or a substituted or unsubstituted C6 to C20 aromatic hydrocarbon ring.

In another embodiment, r2 is 2, and a plurality of R2s bond to each other to form a substituted or unsubstituted C6 to C20 aromatic hydrocarbon ring.

In another embodiment, r2 is 2, and a plurality of R2s bond to each other to form a C6 to C20 aromatic hydrocarbon ring.

In another embodiment, r2 is 2, and a plurality of R2s bond to each other to form a benzene ring.

In one embodiment of the present specification, r3 is 1, and R3 is hydrogen; deuterium; or a substituted or unsubstituted C6 to C60 aryl group.

In one embodiment of the present specification, r3 is 1, and R3 is hydrogen; deuterium; or a substituted or unsubstituted C6 to C40 aryl group.

In one embodiment of the present specification, r3 is 1, and R3 is hydrogen; deuterium; or a substituted or unsubstituted C6 to C20 aryl group.

In one embodiment of the present specification, r3 is 1, and R3 is hydrogen; deuterium; or a substituted or unsubstituted phenyl group.

In one embodiment of the present specification, r3 is 1, and R3 is hydrogen; deuterium; or a phenyl group.

In another embodiment, r3 is 2, and a plurality of R3s bond to each other to form a substituted or unsubstituted C3 to C20 aliphatic hydrocarbon ring, a substituted or unsubstituted C6 to C20 aromatic hydrocarbon ring, or a substituted or unsubstituted C2 to C20 heteroring.

In another embodiment, r3 is 2, and a plurality of R3s bond to each other to form a substituted or unsubstituted C3 to C20 aliphatic hydrocarbon ring, or a substituted or unsubstituted C6 to C20 aromatic hydrocarbon ring.

In another embodiment, r3 is 2, and a plurality of R3s bond to each other to form a substituted or unsubstituted C6 to C20 aromatic hydrocarbon ring.

In another embodiment, r3 is 2, and a plurality of R3s bond to each other to form a C6 to C20 aromatic hydrocarbon ring.

In another embodiment, r3 is 2, and a plurality of R3s bond to each other to form a benzene ring.

In one embodiment of the present specification, Chemical Formula 1 may be represented by any one of the following Chemical Formulae 1-1 to 1-4.

[Chemical Formula 1-1]

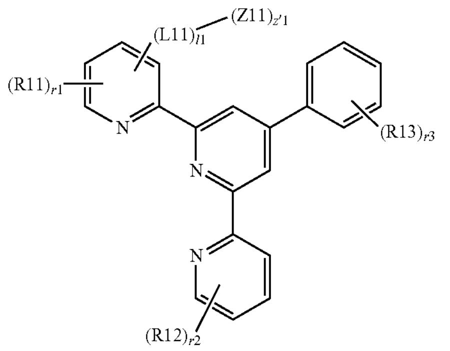

[Chemical Formula 1-2]

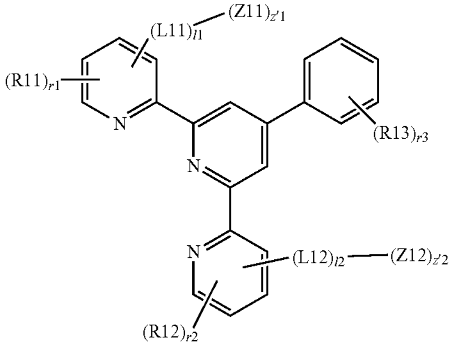

-continued

[Chemical Formula 1-3]

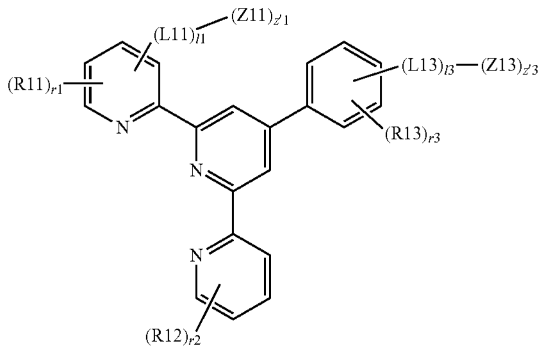

[Chemical Formula 1-4]

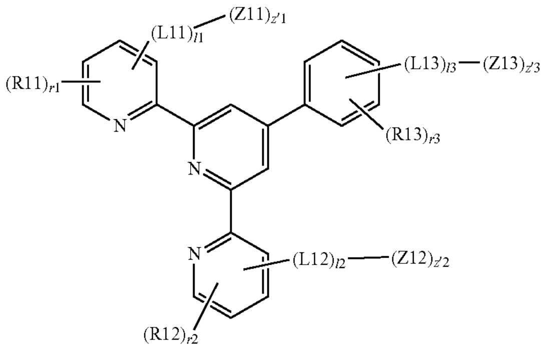

In Chemical Formulae 1-1 to 1-4, r1 to r3, l1 to l3 and z'1 to z'3 have the same definitions as in Chemical Formula 1, R11 to R13 are the same as or different from each other, and each independently hydrogen; deuterium; a halogen group; a cyano group; —P(═O)R(104)(R105); a substituted or unsubstituted C1 to C60 alkyl group; a substituted or unsubstituted C6 to C60 aryl group; or a substituted or unsubstituted C2 to C60 heterocyclic group, or two or more groups adjacent to each other bond to each other to form a substituted or unsubstituted C6 to C60 aromatic hydrocarbon ring, L11 to L13 are the same as or different from each other, and each independently a direct bond; or a substituted or unsubstituted C6 to C60 arylene group, Z11 to Z13 are the same as or different from each other, and each independently a halogen group; a cyano group; —P(═O)R(104')(R105'); a substituted or unsubstituted C1 to C60 alkyl group; a substituted or unsubstituted C2 to C60 alkenyl group; a substituted or unsubstituted C1 to C60 alkoxy group; a substituted or unsubstituted C3 to C60 cycloalkyl group; a substituted or unsubstituted C6 to C60 aryl group; or a substituted or unsubstituted C2 to C60 heterocyclic group, and R104, R105, R104' and R105' are each independently hydrogen; deuterium; a halogen group; an alkyl group; an alkenyl group; an alkoxy group; a cycloalkyl group; an aryl group; or a heterocyclic group.

In one embodiment of the present specification, L11 to L13 are the same as or different from each other, and each independently a direct bond; or a substituted or unsubstituted C6 to C40 arylene group.

In one embodiment of the present specification, L11 to L13 are the same as or different from each other, and each independently a direct bond; or a substituted or unsubstituted C6 to C20 arylene group.

In one embodiment of the present specification, L11 to L13 are the same as or different from each other, and each independently a direct bond; a substituted or unsubstituted phenylene group; or a substituted or unsubstituted biphenylene group.

In one embodiment of the present specification, L11 to L13 are the same as or different from each other, and each independently a direct bond; a phenylene group; or a biphenylene group.

In one embodiment of the present specification, L11 is a direct bond; a phenylene group; or a biphenylene group.

In one embodiment of the present specification, L12 and L13 are the same as or different from each other, and each independently a direct bond; or a phenylene group.

In one embodiment of the present specification, Z11 to Z13 are the same as or different from each other, and each independently a halogen group; a cyano group; —P(═O)R(104')(R105'); a substituted or unsubstituted C1 to C60 alkyl group; a substituted or unsubstituted C6 to C60 aryl group; or a substituted or unsubstituted C2 to C60 heterocyclic group.

In one embodiment of the present specification, Z11 to Z13 are the same as or different from each other, and each independently a halogen group; a cyano group; —P(═O)R(104')(R105'); a substituted or unsubstituted C1 to C40 alkyl group; a substituted or unsubstituted C6 to C40 aryl group; or a substituted or unsubstituted C2 to C40 heterocyclic group.

In one embodiment of the present specification, Z11 to Z13 are the same as or different from each other, and each independently a halogen group; a cyano group; P(═O)R(104')(R105'); a substituted or unsubstituted methyl group; a substituted or unsubstituted phenyl group; a substituted or unsubstituted biphenyl group; a substituted or unsubstituted terphenyl group; a substituted or unsubstituted naphthyl group; a substituted or unsubstituted anthracenyl group; a substituted or unsubstituted phenanthrenyl group; a substituted or unsubstituted pyrenyl group; a substituted or unsubstituted triphenylenyl group; a substituted or unsubstituted fluorenyl group; a substituted or unsubstituted fluoranthenyl group; a substituted or unsubstituted pyrimidine group; a substituted or unsubstituted triazine group; a substituted or unsubstituted quinazolinyl group; a substituted or unsubstituted carbazole group; a substituted or unsubstituted phenanthrolinyl group; a substituted or unsubstituted phenanthridinyl group; a substituted or unsubstituted benzophenanthridinyl group; a substituted or unsubstituted dibenzofuran group; a substituted or unsubstituted dibenzothiophene group; substituted or unsubstituted dibenzosulfolane; substituted or unsubstituted spiro[fluorene-9,9'-xanthene]; a substituted or unsubstituted benzo[4,5]thieno[3,2-d]pyrimidyl group; a substituted or unsubstituted benzofuro[2,3-c]quinolinyl group; a substituted or unsubstituted benzofuro[3,2-c]quinolinyl group; a substituted or unsubstituted benzothieno[2,3-c]quinolinyl group; a substituted or unsubstituted benzothieno[3,2-c]quinolinyl group; or a substituted or unsubstituted pyrazolo[5,1-a]isoquinolinyl group.

In one embodiment of the present specification, Z11 is —P(═O)R(104')(R105'); a phenyl group unsubstituted or substituted with an aryl group or a heterocyclic group; a biphenyl group; a terphenyl group; a naphthyl group; an anthracenyl group; a phenanthrenyl group unsubstituted or substituted with an aryl group; a pyrenyl group; a triphenylenyl group; a fluorenyl group unsubstituted or substituted with an alkyl group or an aryl group; a fluoranthenyl group; a pyrimidine group unsubstituted or substituted with an aryl group; a triazine group unsubstituted or substituted with an aryl group; a quinazolinyl group unsubstituted or substituted with an aryl group; a carbazole group unsubstituted or substituted with an aryl group; a phenanthrolinyl group unsubstituted or substituted with an aryl group; a phenanthridinyl group unsubstituted or substituted with an aryl group; a benzophenanthridinyl group; a dibenzofuran group; a dibenzothiophene group; dibenzosulfolane; spiro [fluorene-9,9'-xanthene]; a benzo[4,5]thieno[3,2-d]pyrimidyl group unsubstituted or substituted with an aryl group; a benzofuro[2,3-c]quinolinyl group; a benzofuro[3,2-c]quinolinyl group; a benzothieno[2,3-c]quinolinyl group; a benzothieno[3,2-c]quinolinyl group; or a pyrazolo[5,1-a]isoquinolinyl group unsubstituted or substituted with an aryl group, and R104' and R105' are each independently an aryl group.

In one embodiment of the present specification, Z12 and Z13 are the same as or different from each other, and each independently a halogen group; a cyano group; a substituted or unsubstituted methyl group; a substituted or unsubstituted pyrimidine group; a substituted or unsubstituted triazine group; or a substituted or unsubstituted carbazole group.

In one embodiment of the present specification, Z12 and Z13 are the same as or different from each other, and each independently a halogen group; a cyano group; a methyl group; a pyrimidine group unsubstituted or substituted with an aryl group; a triazine group unsubstituted or substituted with an aryl group; or a carbazole group unsubstituted or substituted with an aryl group.

In one embodiment of the present specification, R11 to R13 are the same as or different from each other, and each independently hydrogen; deuterium; a substituted or unsubstituted C1 to C60 alkyl group; a substituted or unsubstituted C6 to C60 aryl group; or a substituted or unsubstituted C2 to C60 heterocyclic group, or two or more groups adjacent to each other bond to each other to form a substituted or unsubstituted C6 to C60 aromatic hydrocarbon ring.

In one embodiment of the present specification, R11 to R13 are the same as or different from each other, and each independently hydrogen; deuterium; a substituted or unsubstituted C1 to C40 alkyl group; a substituted or unsubstituted C6 to C40 aryl group; or a substituted or unsubstituted C2 to C40 heterocyclic group, or two or more groups adjacent to each other bond to each other to form a substituted or unsubstituted C6 to C40 aromatic hydrocarbon ring.

In one embodiment of the present specification, R11 to R13 are the same as or different from each other, and each independently hydrogen; deuterium; a substituted or unsubstituted C1 to C20 alkyl group; a substituted or unsubstituted C6 to C20 aryl group; or a substituted or unsubstituted C2 to C20 heterocyclic group, or two or more groups adjacent to each other bond to each other to form a substituted or unsubstituted C6 to C20 aromatic hydrocarbon ring.

In one embodiment of the present specification, R11 is hydrogen; or deuterium.

In one embodiment of the present specification, R11 is hydrogen.

In one embodiment of the present specification, R12 and R13 are the same as or different from each other, and each independently hydrogen; deuterium; a substituted or unsubstituted C1 to C20 alkyl group; or a substituted or unsubstituted C6 to C20 aryl group, or two or more groups adjacent to each other bond to each other to form a substituted or unsubstituted C6 to C20 aromatic hydrocarbon ring.

In one embodiment of the present specification, r2 is 1, and R12 is hydrogen; deuterium; or a substituted or unsubstituted C6 to C60 aryl group.

In one embodiment of the present specification, r2 is 1, and R12 is hydrogen; deuterium; or a substituted or unsubstituted C6 to C40 aryl group.

In one embodiment of the present specification, r2 is 1, and R12 is hydrogen; deuterium; or a substituted or unsubstituted C6 to C20 aryl group.

In one embodiment of the present specification, r2 is 1, and R12 is hydrogen; deuterium; or a substituted or unsubstituted phenyl group.

In one embodiment of the present specification, r2 is 1, and R12 is hydrogen; deuterium; or a phenyl group.

In another embodiment, r2 is 2, and a plurality of R12s bond to each other to form a substituted or unsubstituted C3 to C20 aliphatic hydrocarbon ring, a substituted or unsubstituted C6 to C20 aromatic hydrocarbon ring, or a substituted or unsubstituted C2 to C20 heteroring.

In another embodiment, r2 is 2, and a plurality of R12s bond to each other to form a substituted or unsubstituted C3 to C20 aliphatic hydrocarbon ring, or a substituted or unsubstituted C6 to C20 aromatic hydrocarbon ring.

In another embodiment, r2 is 2, and a plurality of R12s bond to each other to form a substituted or unsubstituted C6 to C20 aromatic hydrocarbon ring.

In another embodiment, r2 is 2, and a plurality of R12s bond to each other to form a C6 to C20 aromatic hydrocarbon ring.

In another embodiment, r2 is 2, and a plurality of R12s bond to each other to form a benzene ring.

In one embodiment of the present specification, r3 is 1, and R13 is hydrogen; deuterium; or a substituted or unsubstituted C6 to C60 aryl group.

In one embodiment of the present specification, r3 is 1, and R13 is hydrogen; deuterium; or a substituted or unsubstituted C6 to C40 aryl group.

In one embodiment of the present specification, r3 is 1, and R13 is hydrogen; deuterium; or a substituted or unsubstituted C6 to C20 aryl group.

In one embodiment of the present specification, r3 is 1, and R13 is hydrogen; deuterium; or a substituted or unsubstituted phenyl group.

In one embodiment of the present specification, r3 is 1, and R13 is hydrogen; deuterium; or a phenyl group.

In another embodiment, r3 is 2, and a plurality of R13s bond to each other to form a substituted or unsubstituted C3 to C20 aliphatic hydrocarbon ring, a substituted or unsubstituted C6 to C20 aromatic hydrocarbon ring, or a substituted or unsubstituted C2 to C20 heteroring.

In another embodiment, r3 is 2, and a plurality of R13s bond to each other to form a substituted or unsubstituted C3 to C20 aliphatic hydrocarbon ring, or a substituted or unsubstituted C6 to C20 aromatic hydrocarbon ring.

In another embodiment, r3 is 2, and a plurality of R13s bond to each other to form a substituted or unsubstituted C6 to C20 aromatic hydrocarbon ring.

In another embodiment, r3 is 2, and a plurality of R13s bond to each other to form a C6 to C20 aromatic hydrocarbon ring.

In another embodiment, r3 is 2, and a plurality of R13s bond to each other to form a benzene ring.

In one embodiment of the present specification, Chemical Formula 1 may be represented by any one of the following compounds, but is not limited thereto.

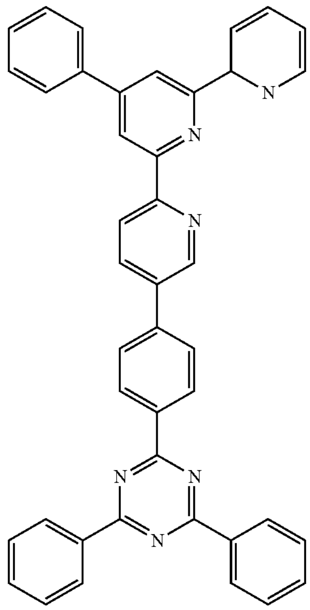
1
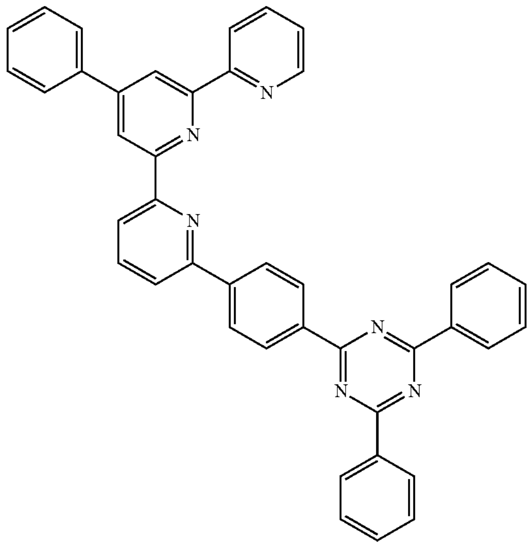
2
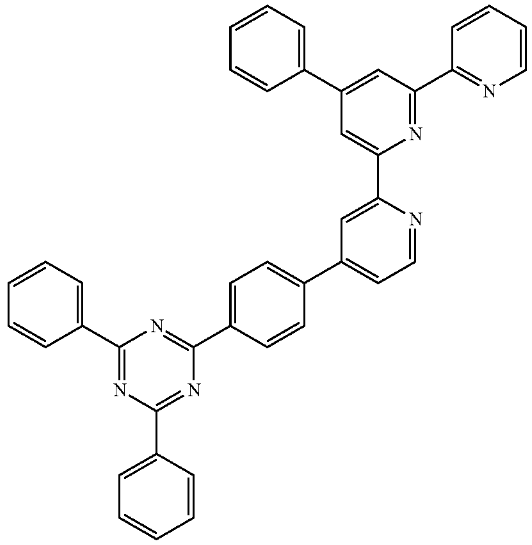
3
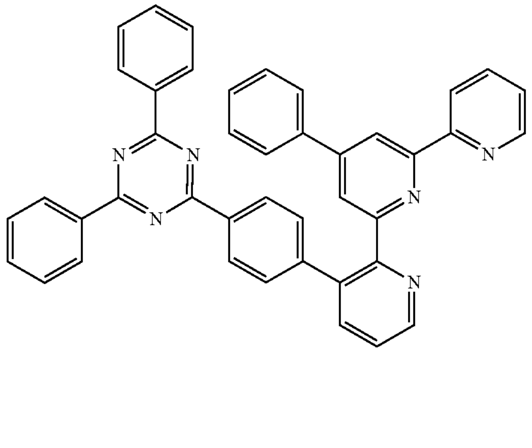
4

-continued
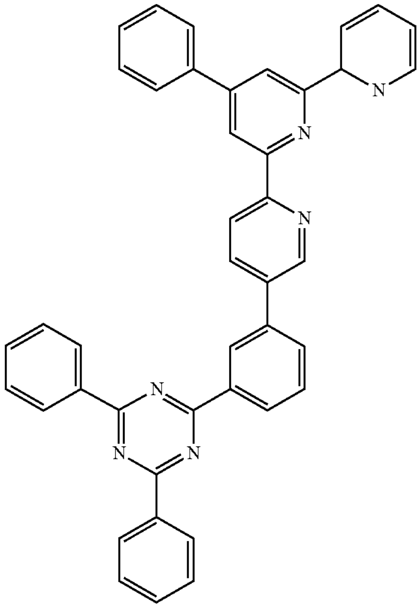
5
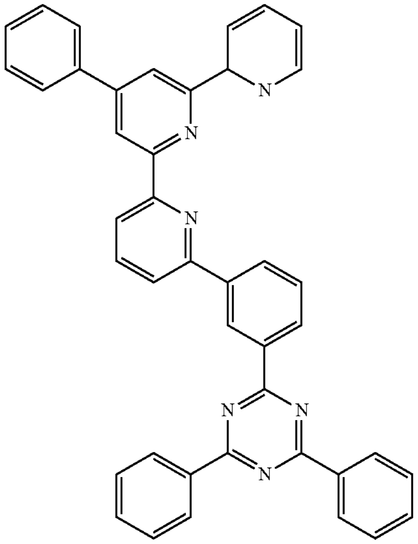
6
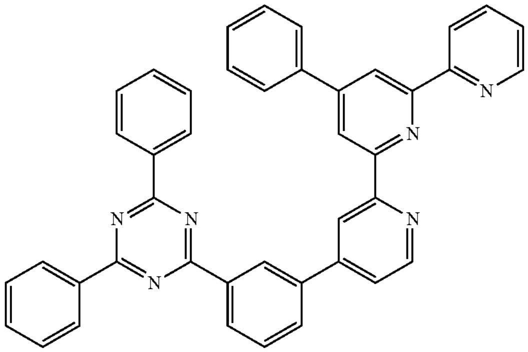
7
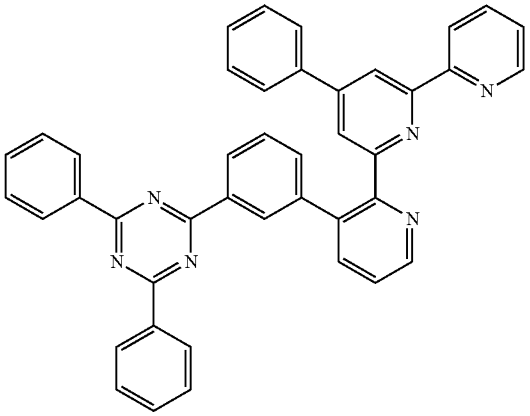
8
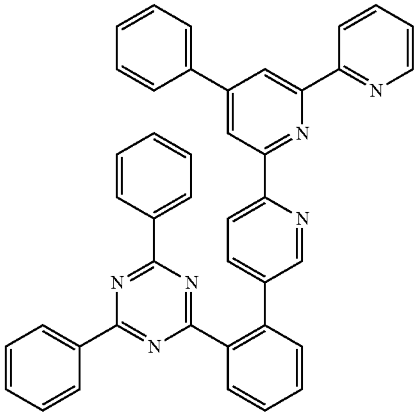
9
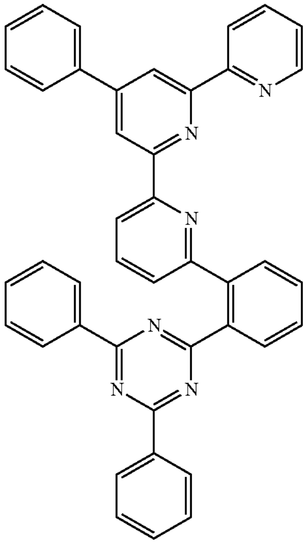
10

-continued
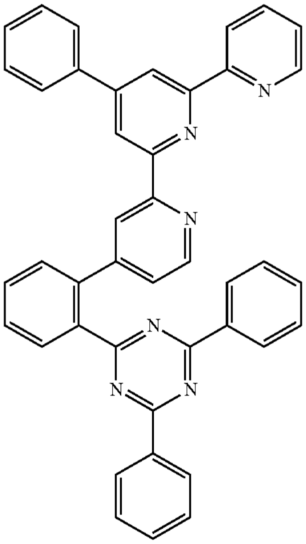
11
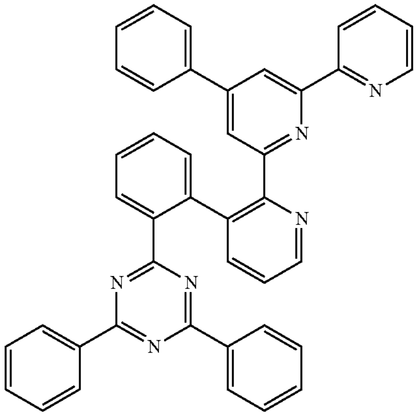
12
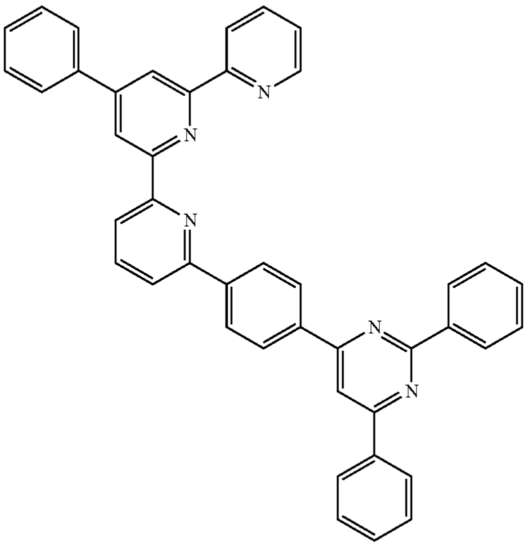
13
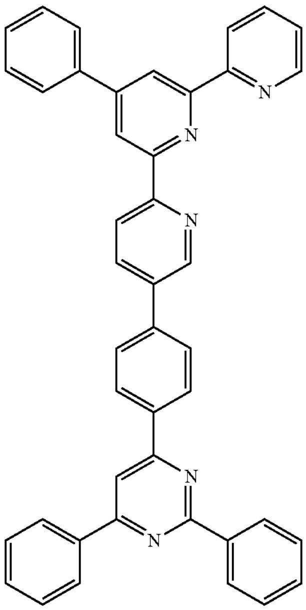
14

-continued
15
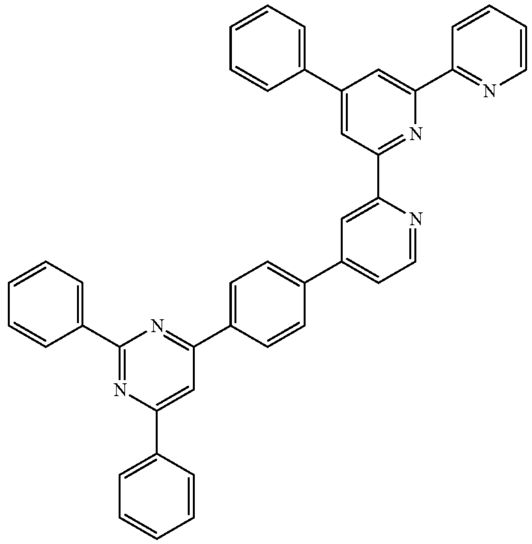
16
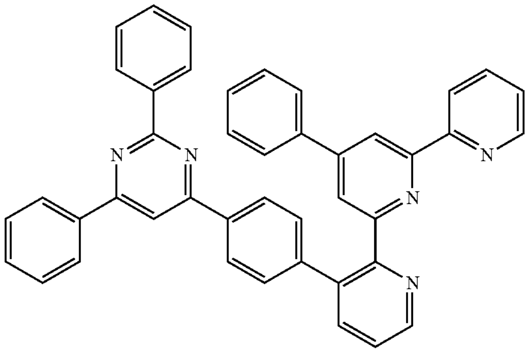
17
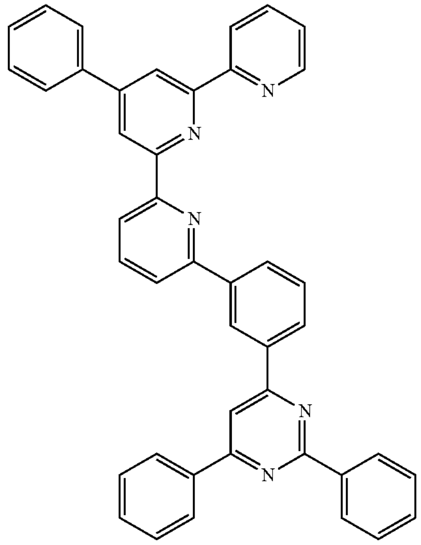
18
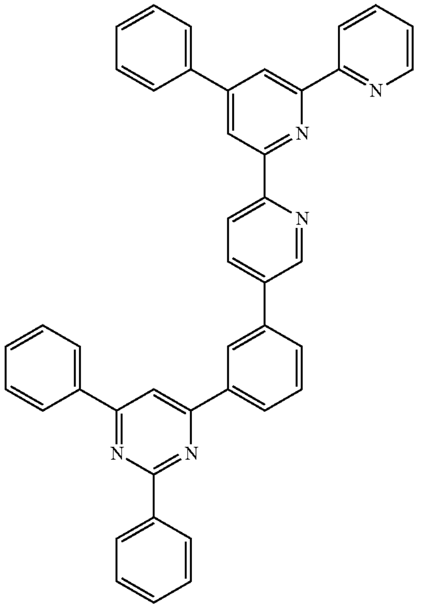
19
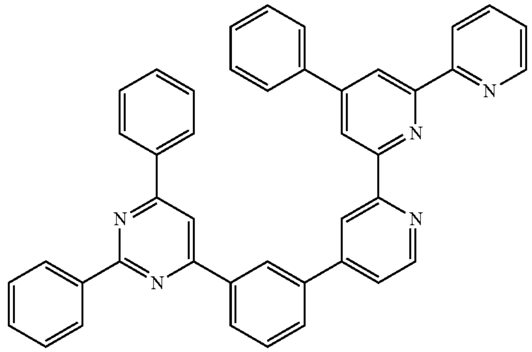
20
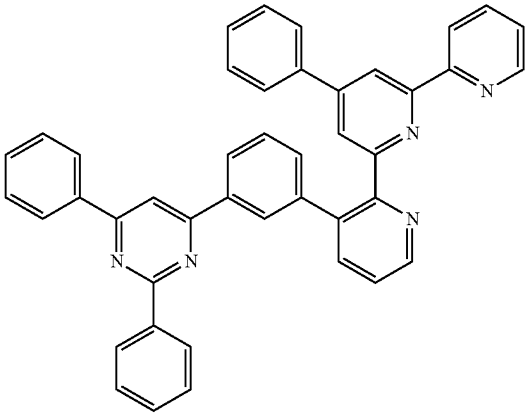

-continued
21
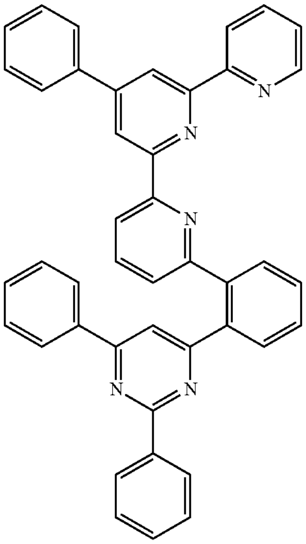
22
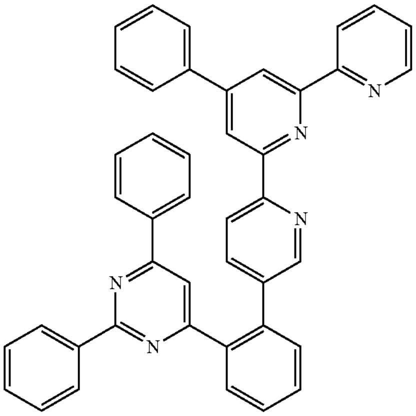
23
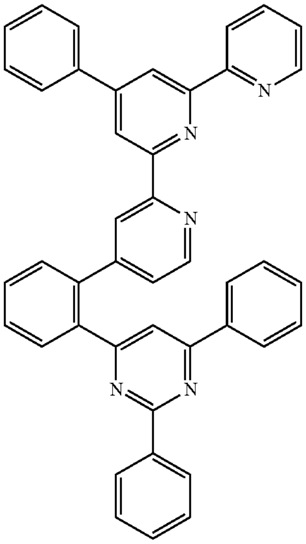
24
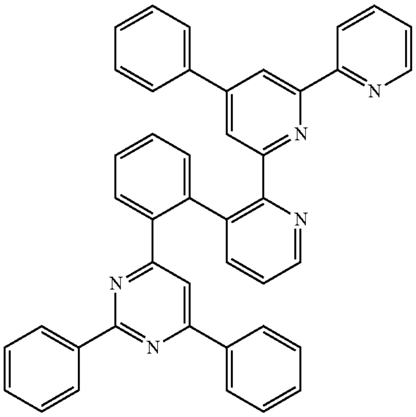

-continued
25
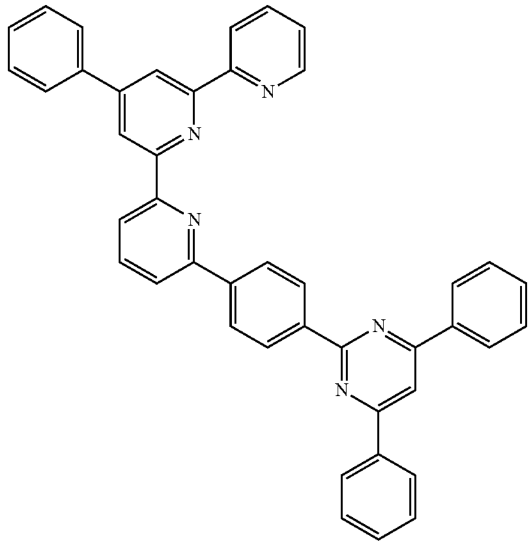
26
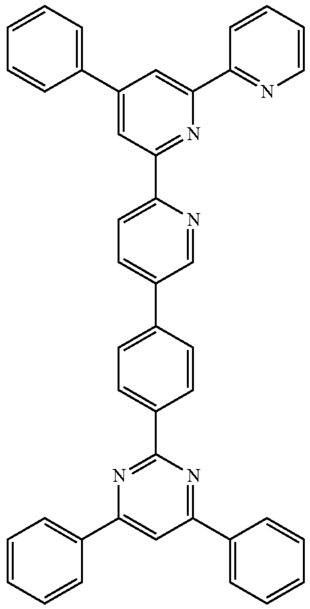
27
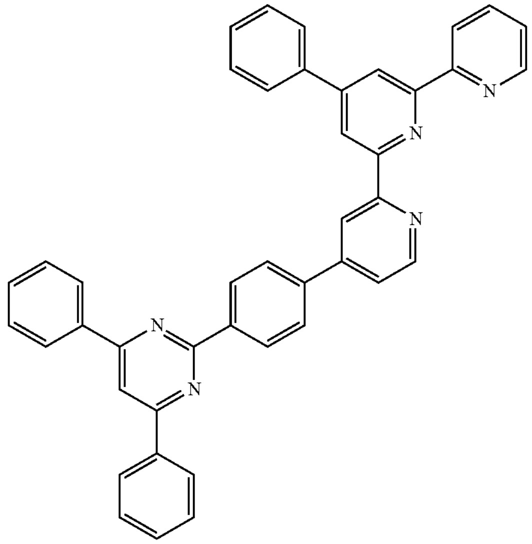
28
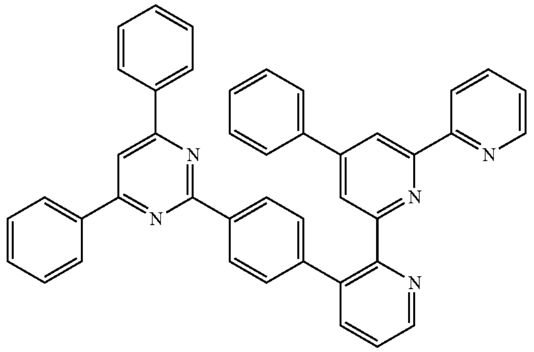

-continued
29
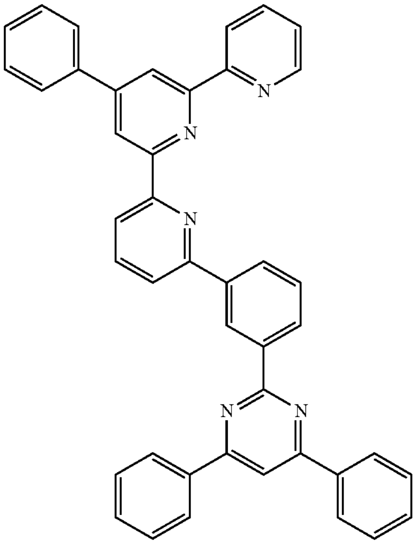
30
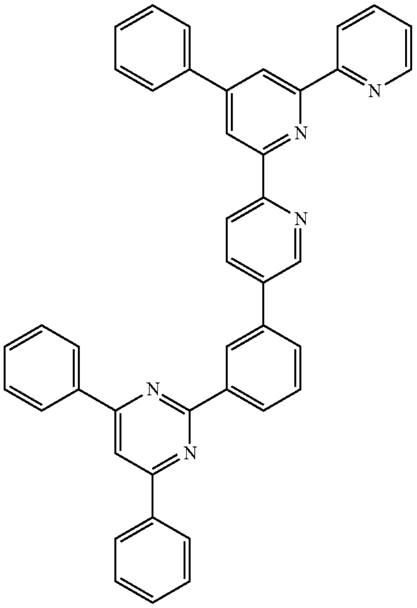
31
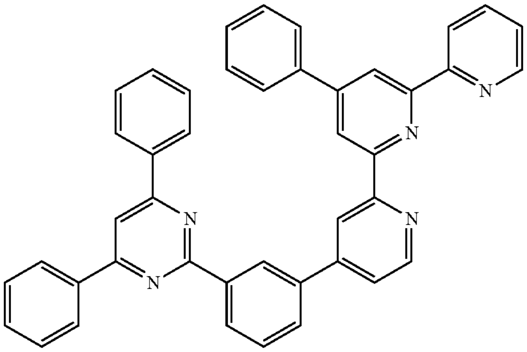
32
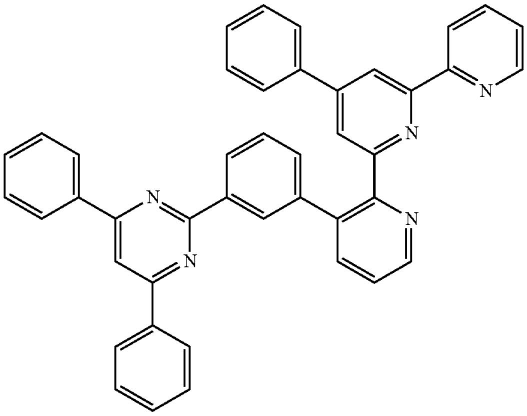
33
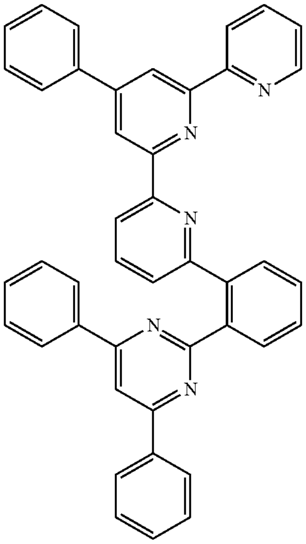
34
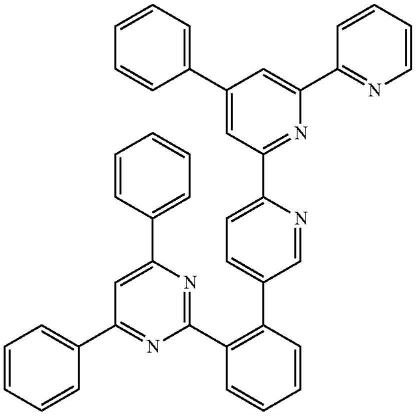

-continued
35
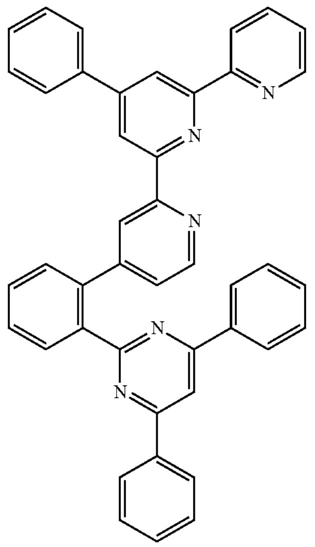
36
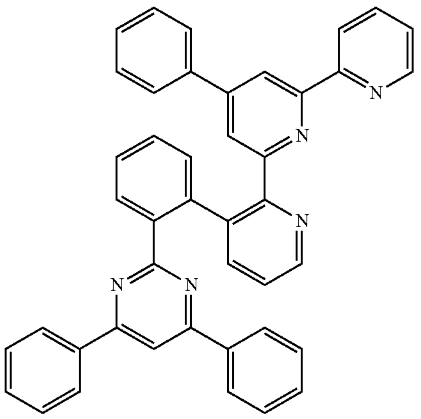
37
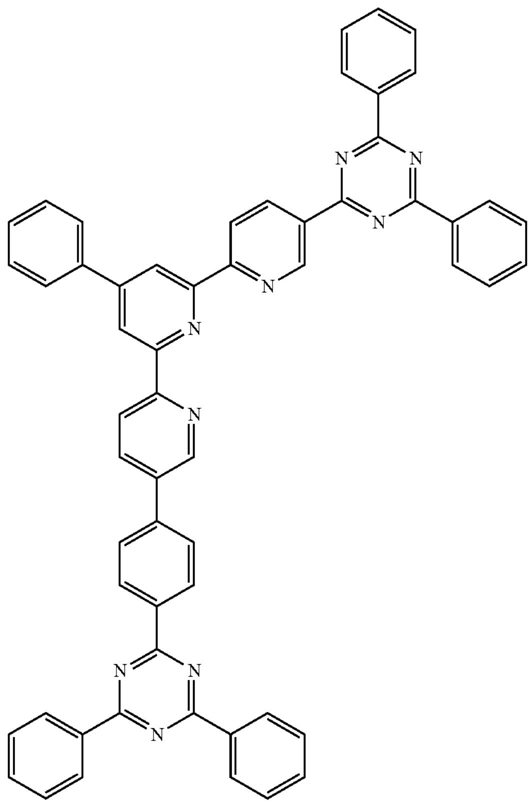
38
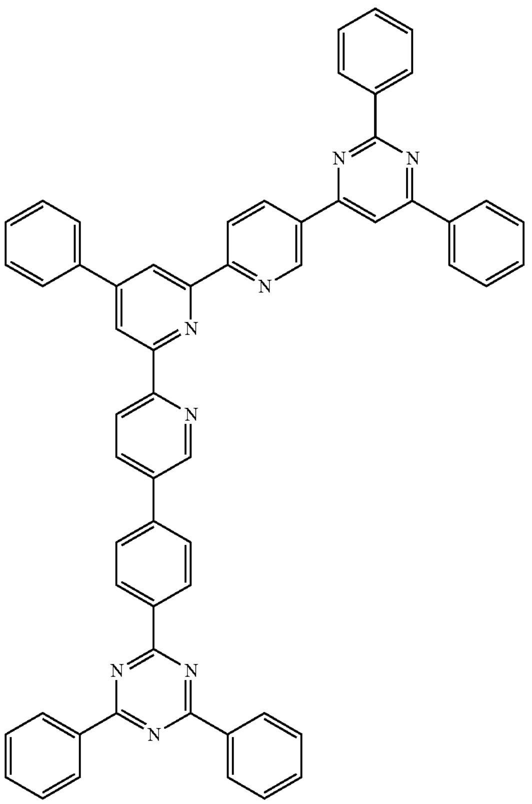

-continued
39
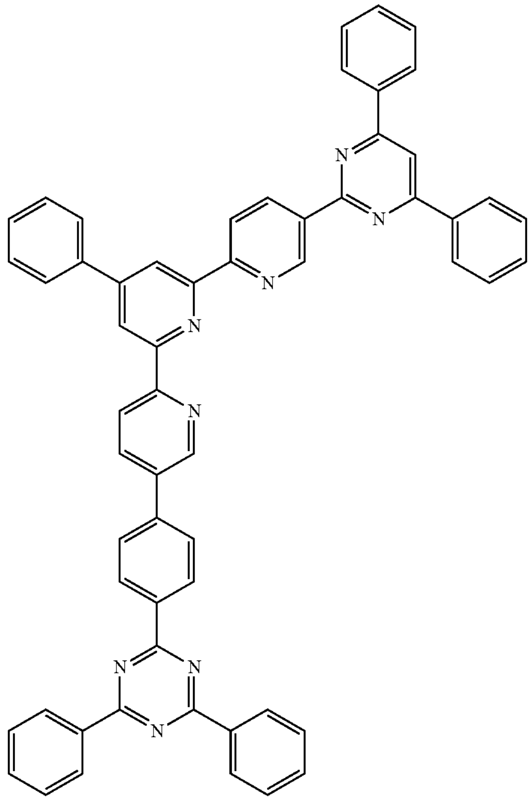
40
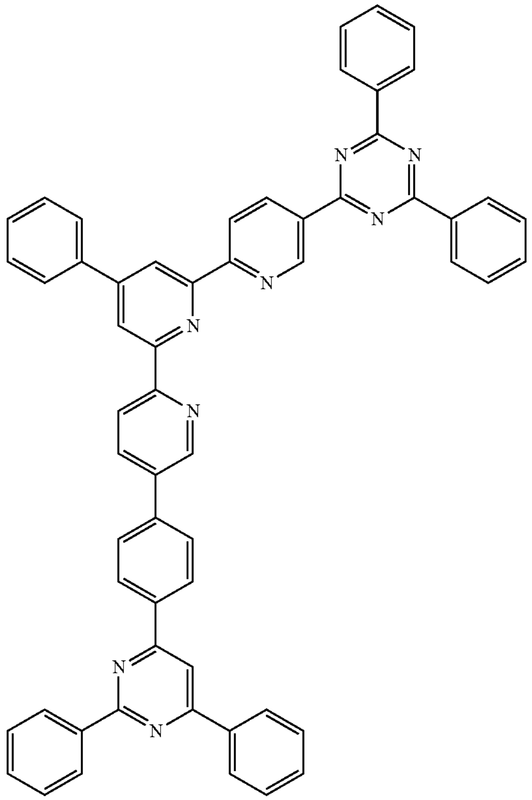
41
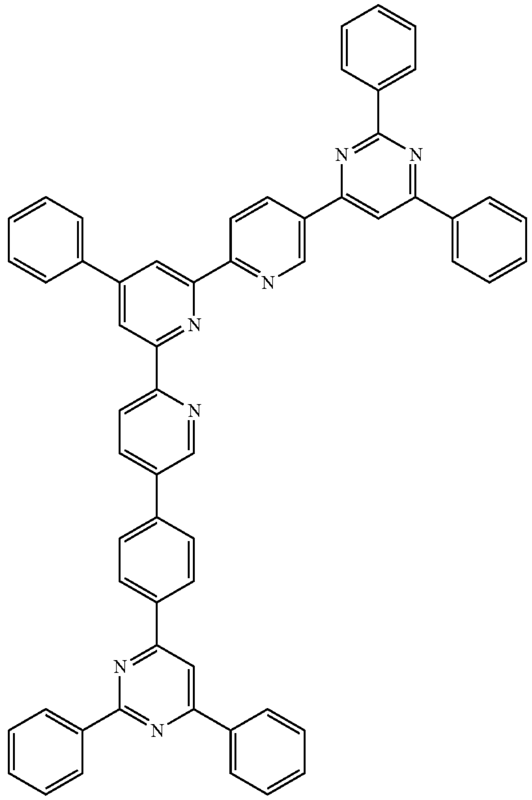
42
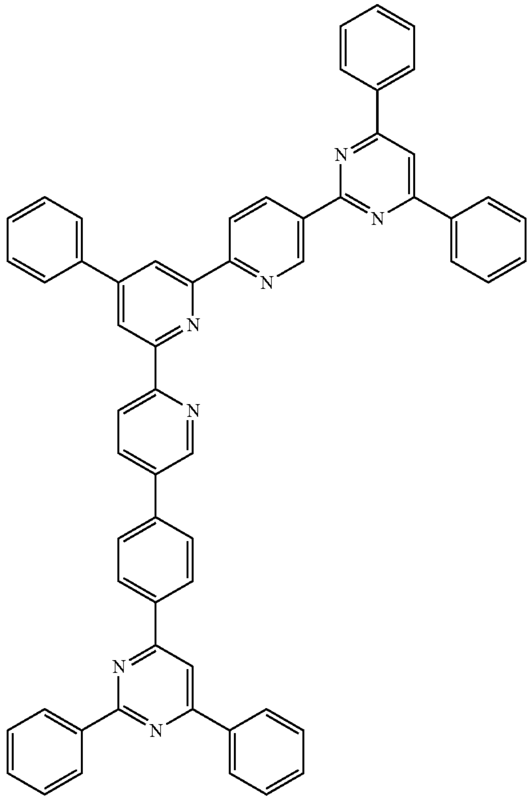

-continued
43
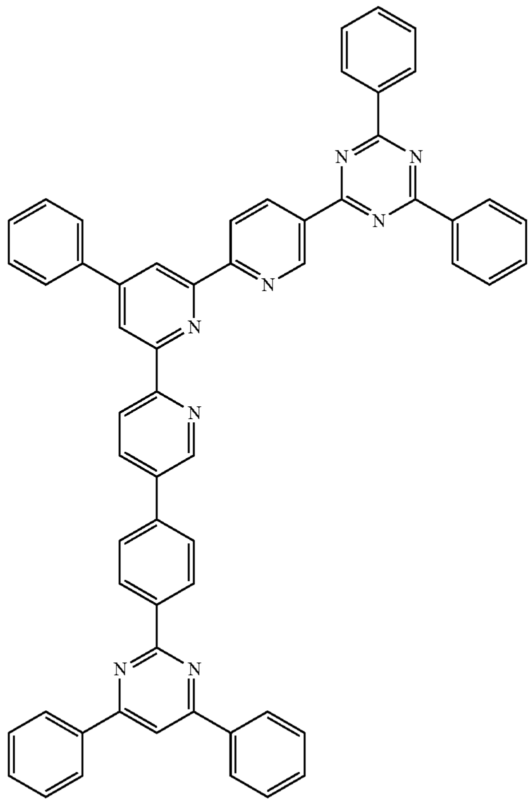
44
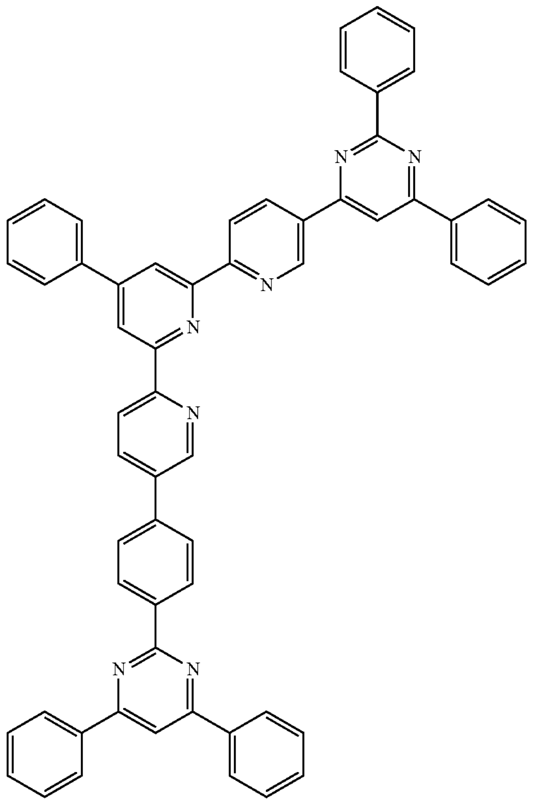
45
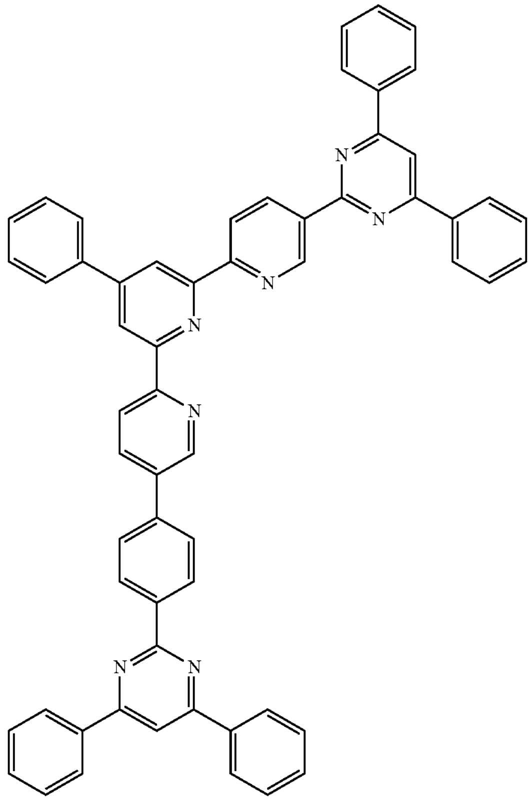
46
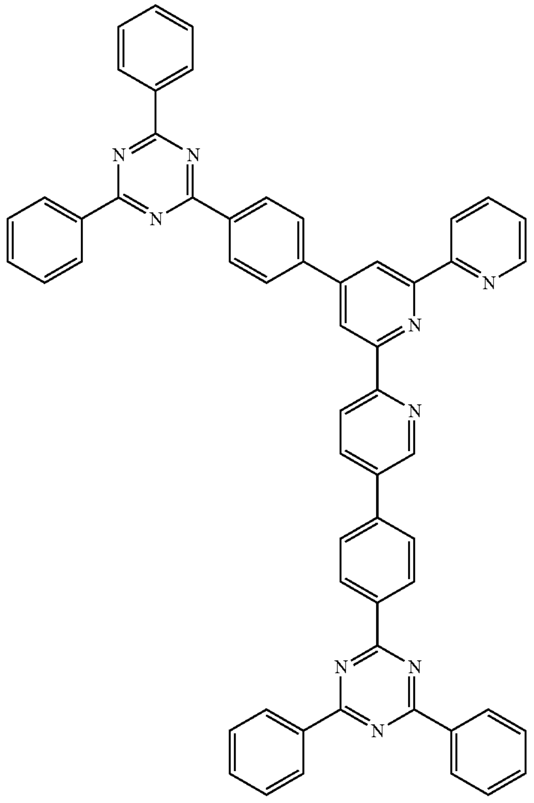

-continued
47
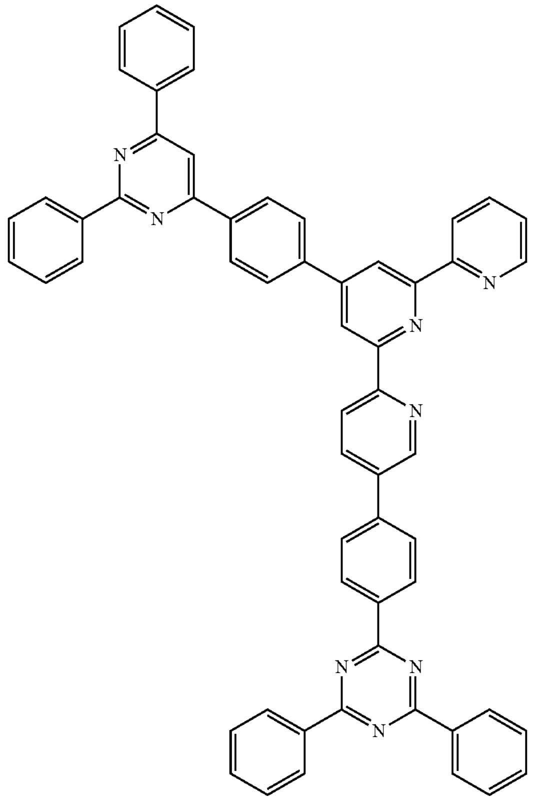
48
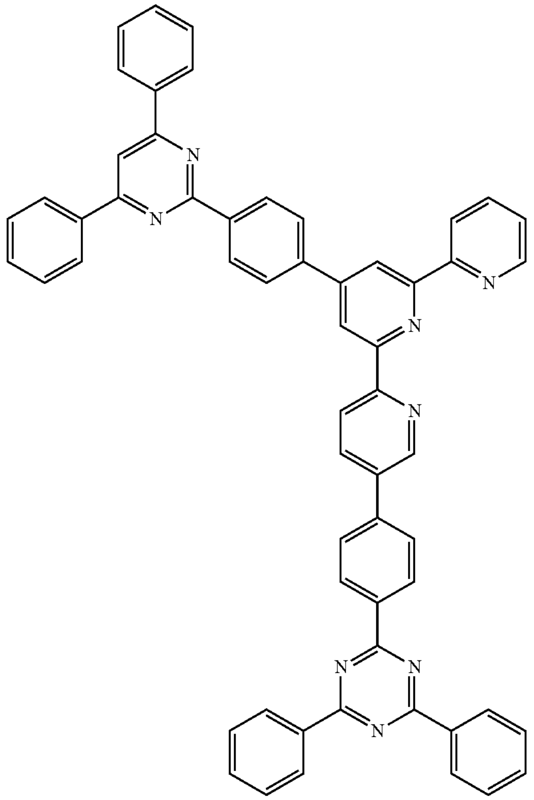
49
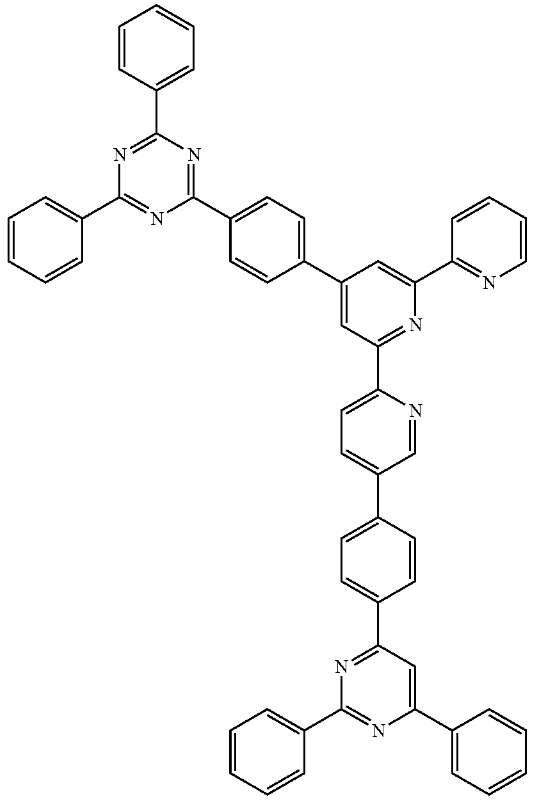
50
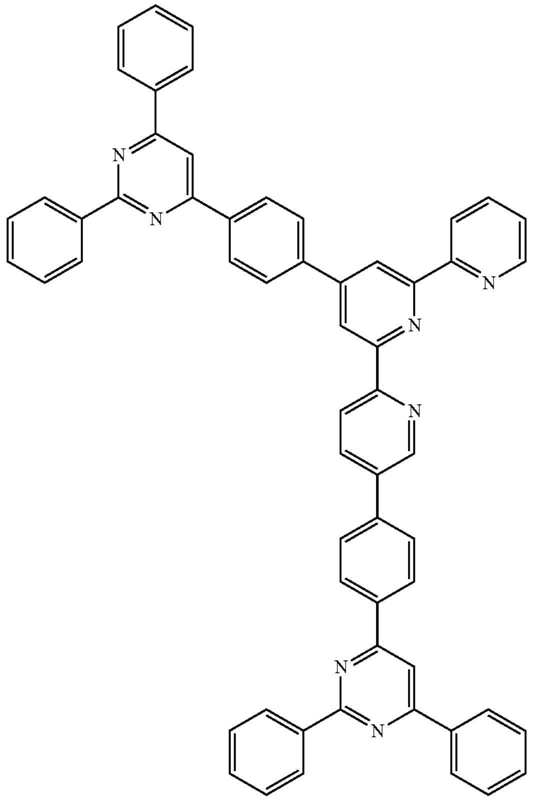

-continued
51
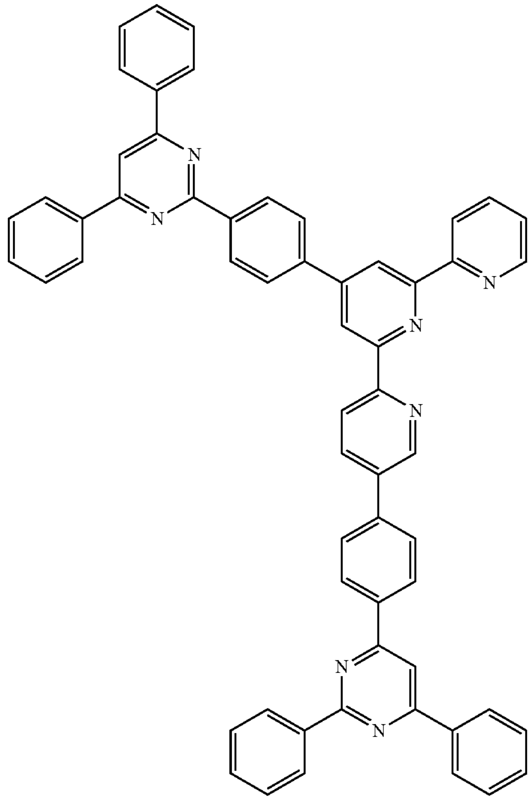
52
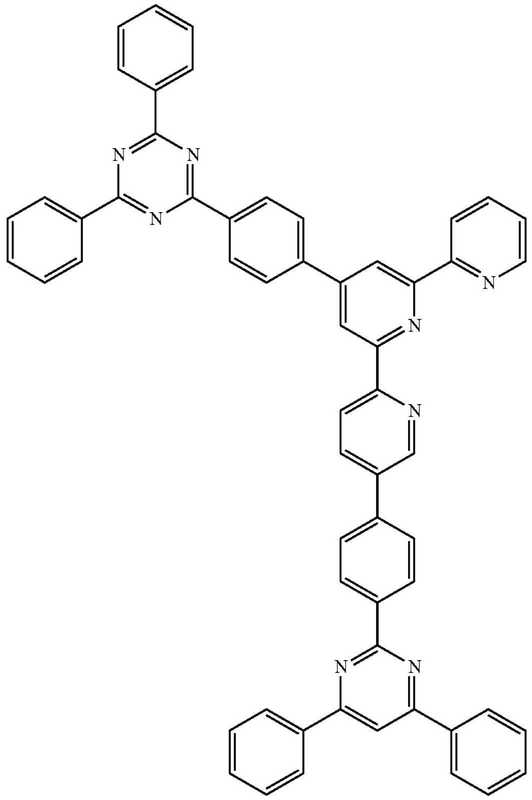
53
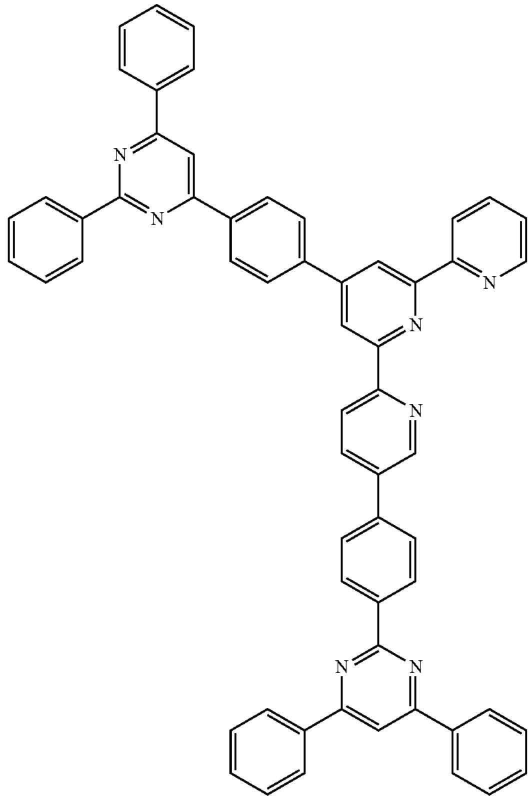
54
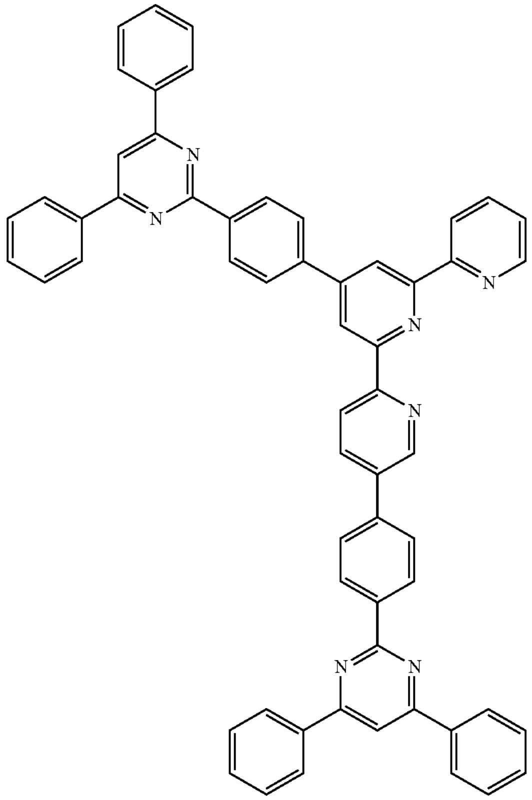

-continued
55
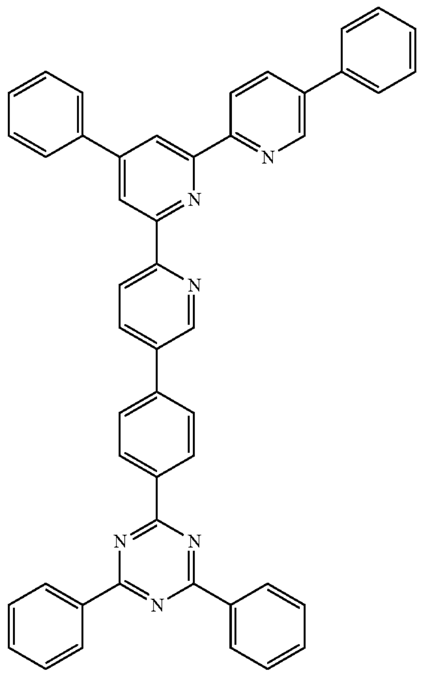
56
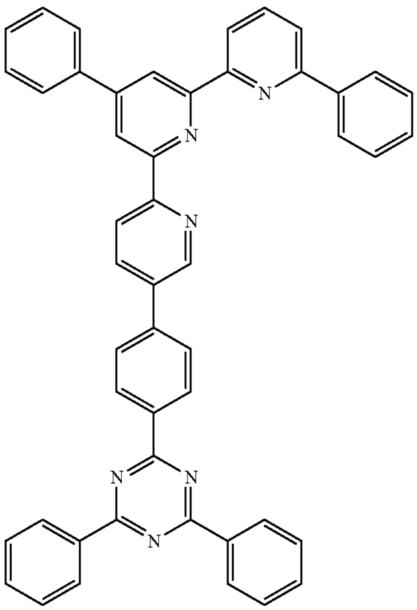
57
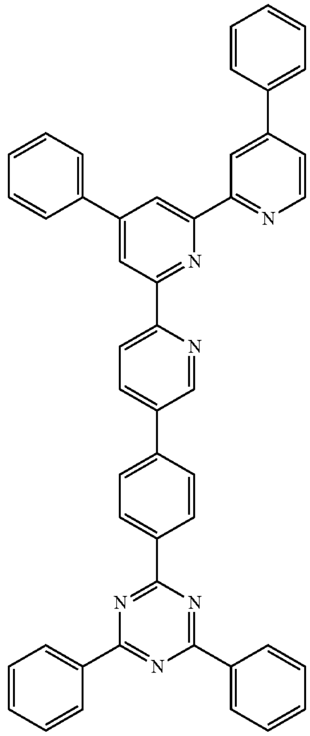
58
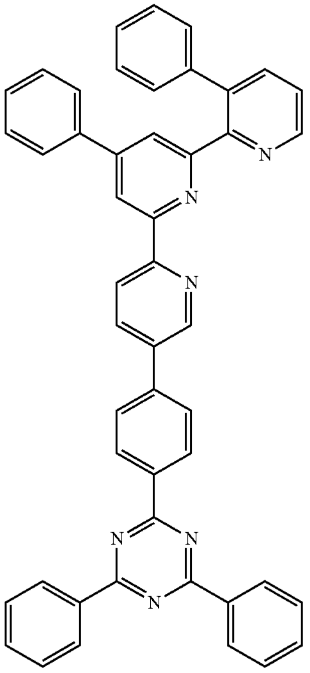

-continued
59
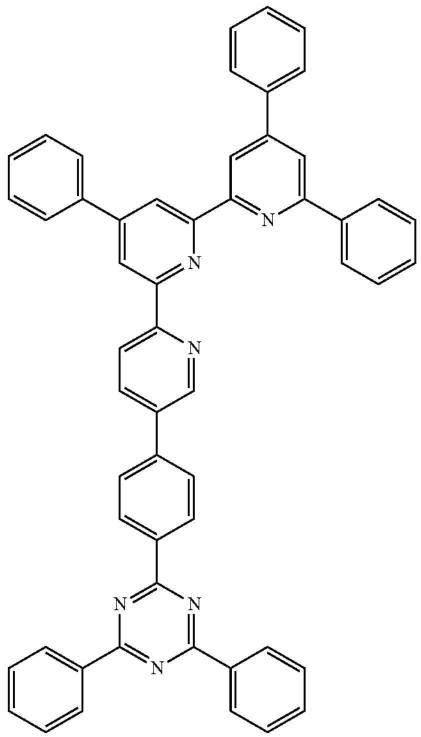
60
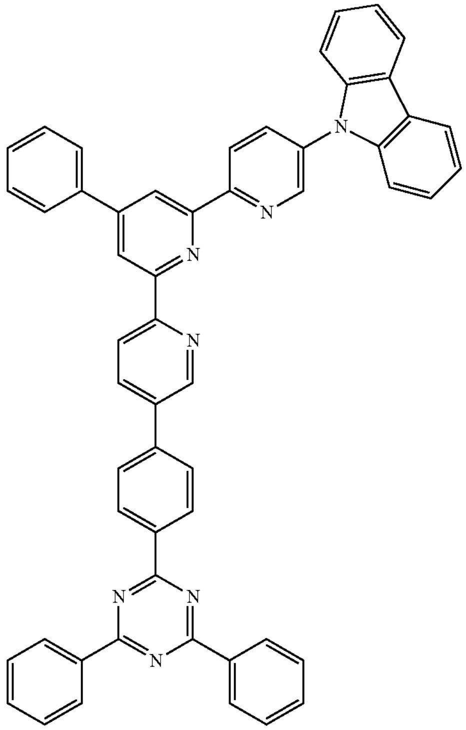
61
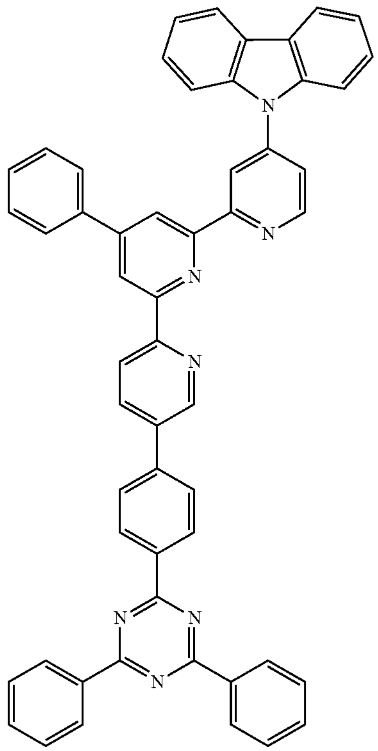
62
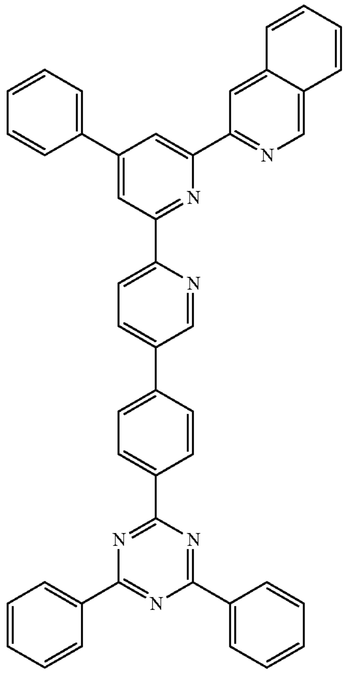

-continued
63
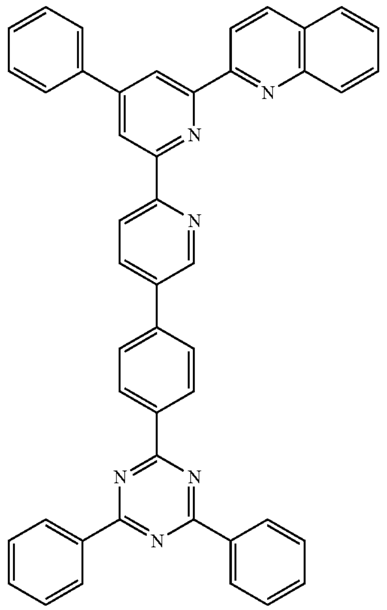
64
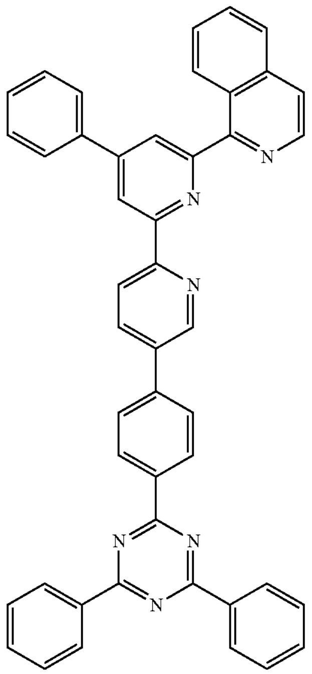
65
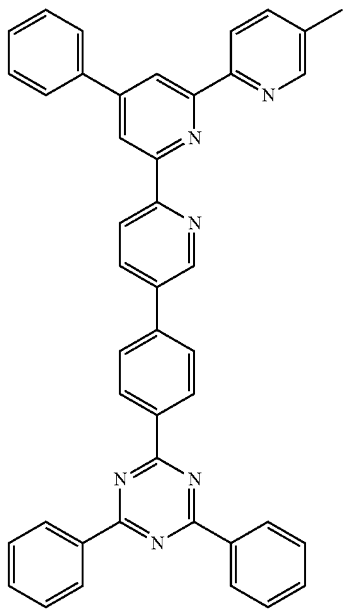
66
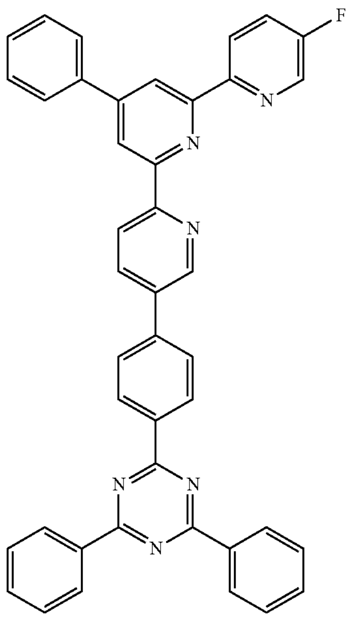

-continued
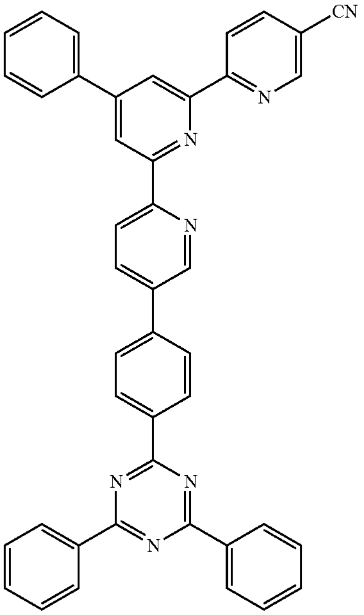
67
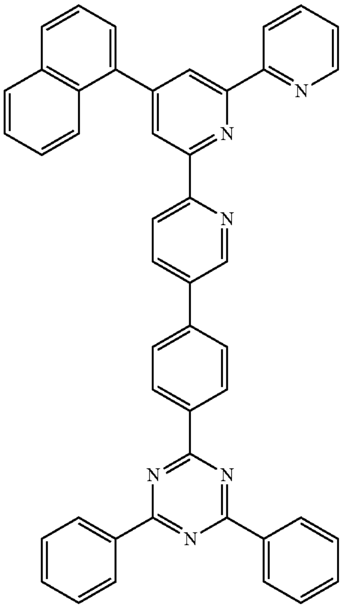
68
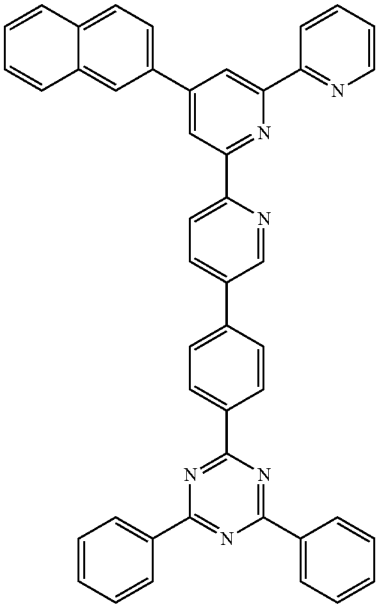
69
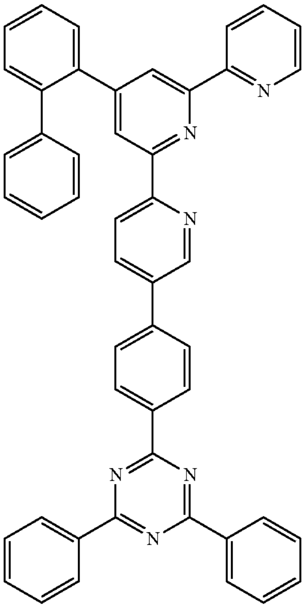
70

-continued
71
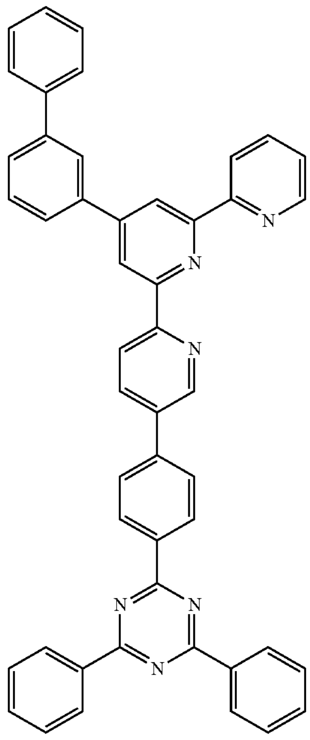
72
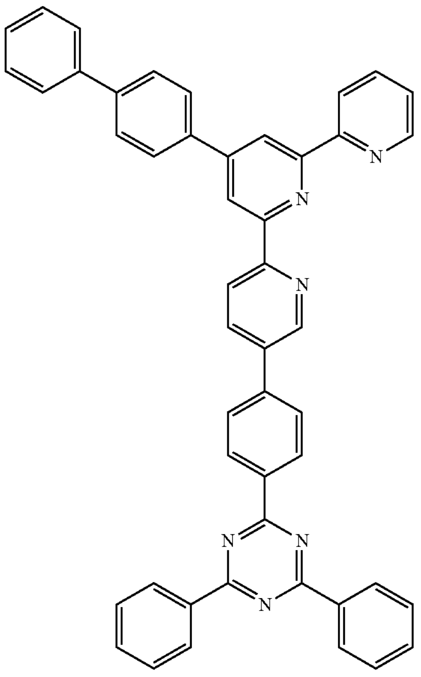
73
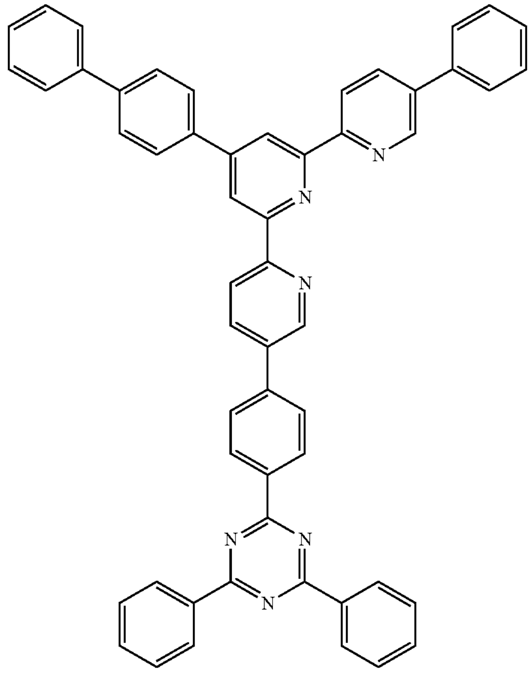
74
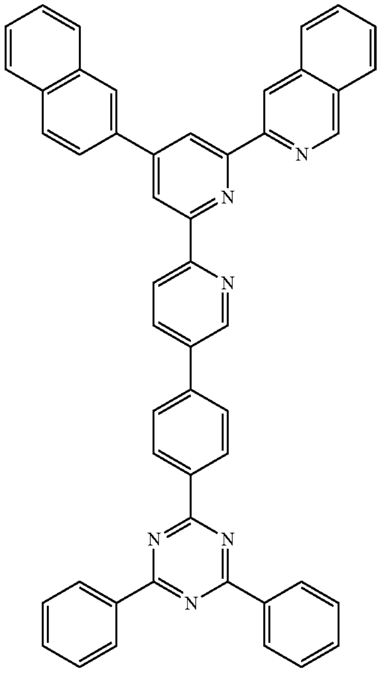

-continued
75
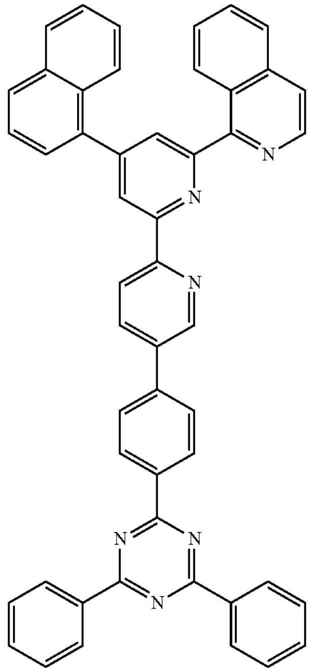
76
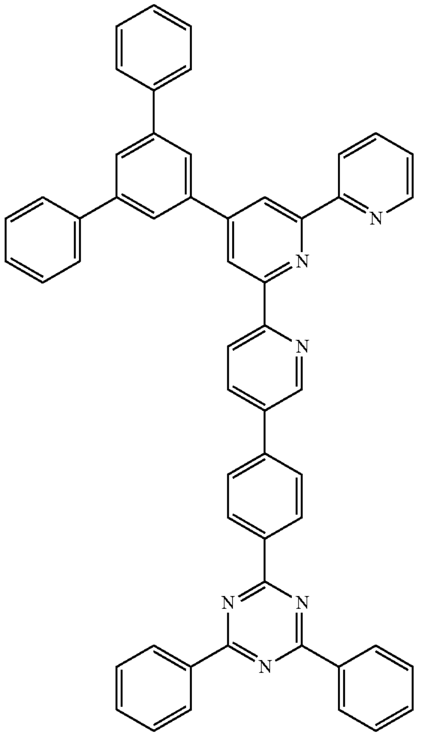
77
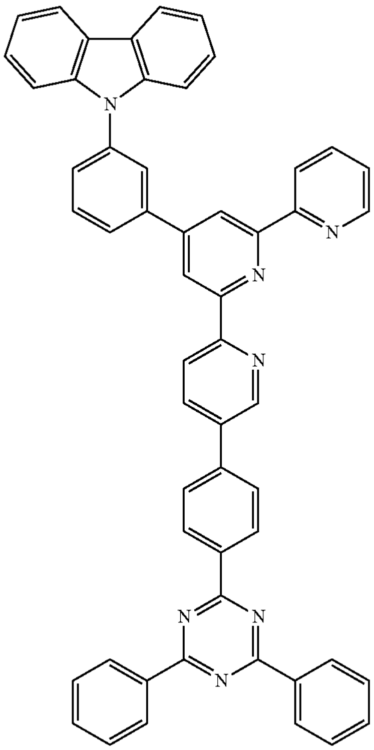
78
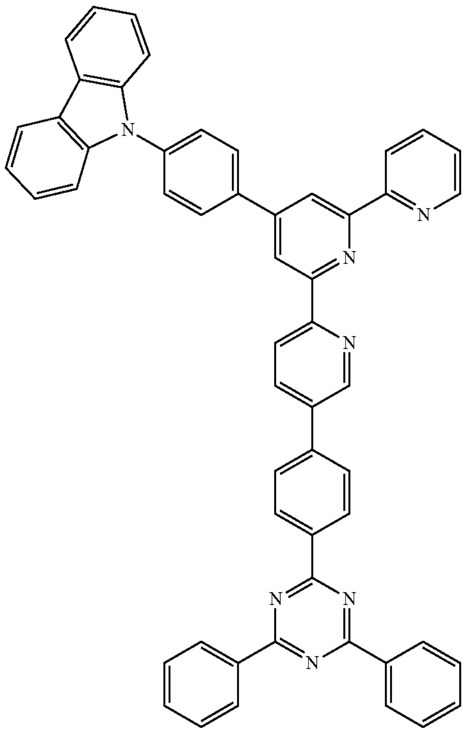

-continued
79
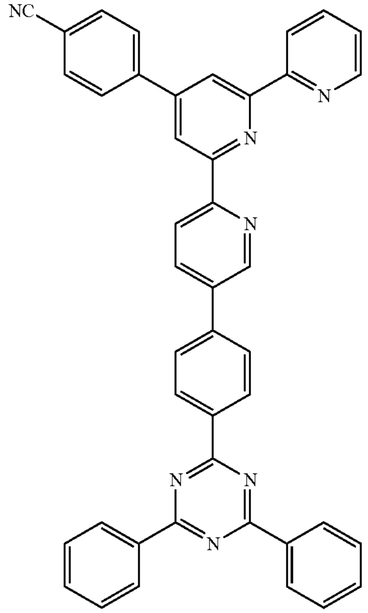
80
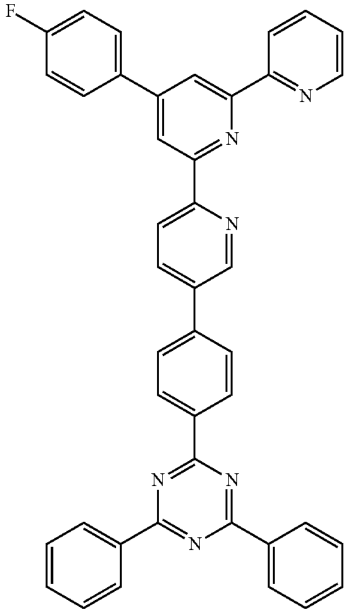
81
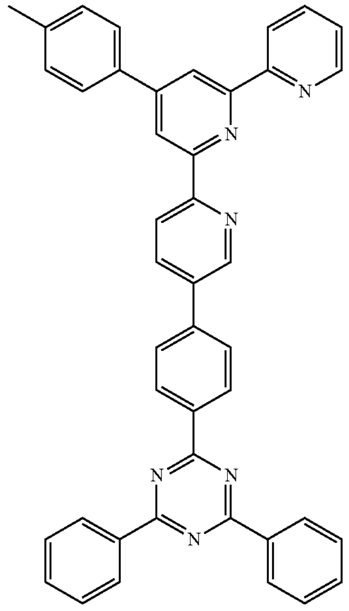
82
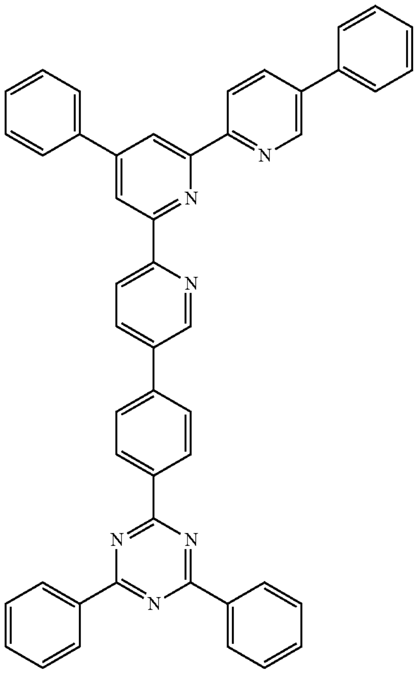

-continued
83
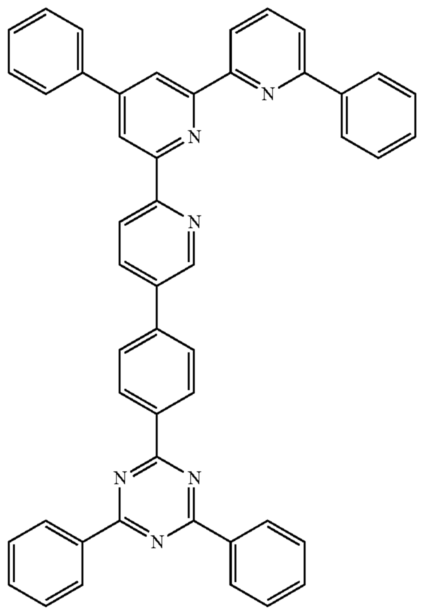
84
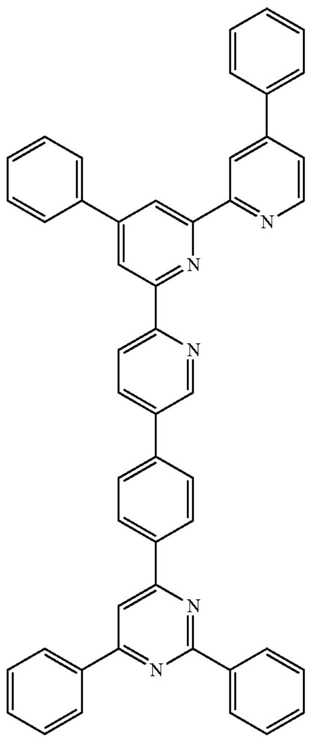
85
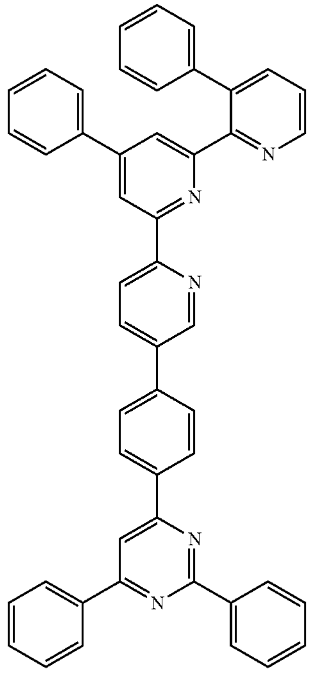
86
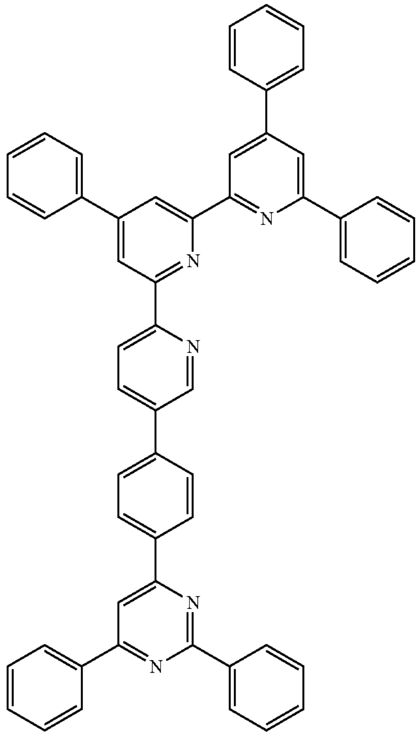

-continued
87
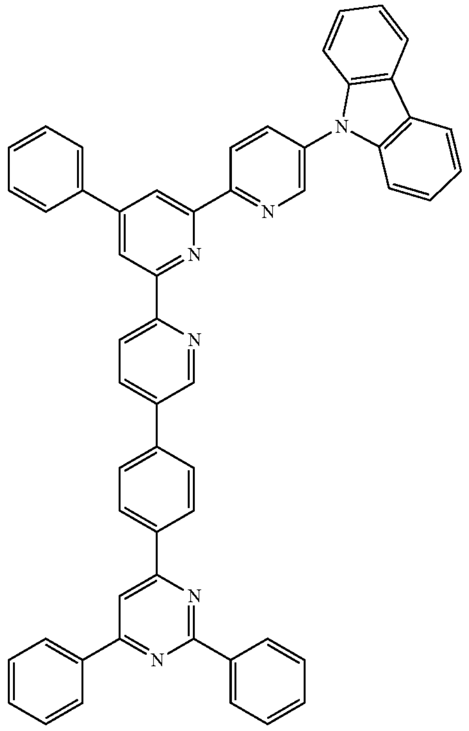
88
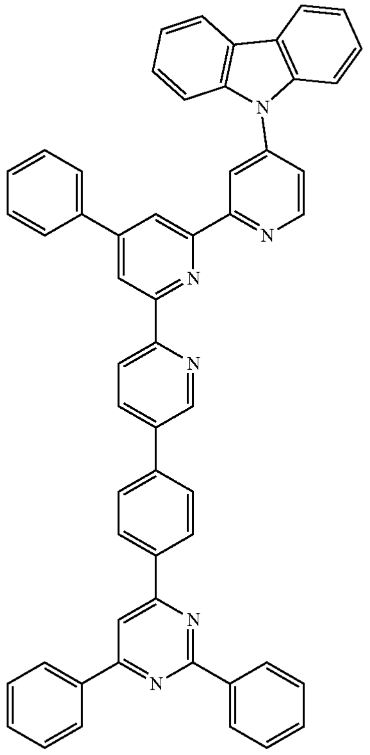
89
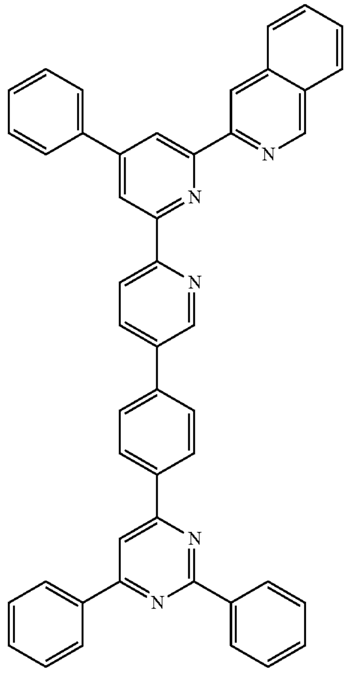
90
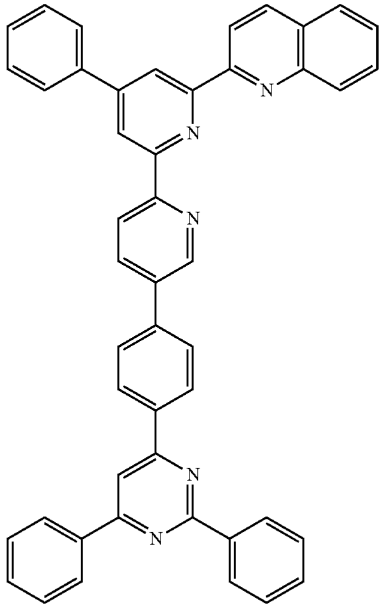

-continued
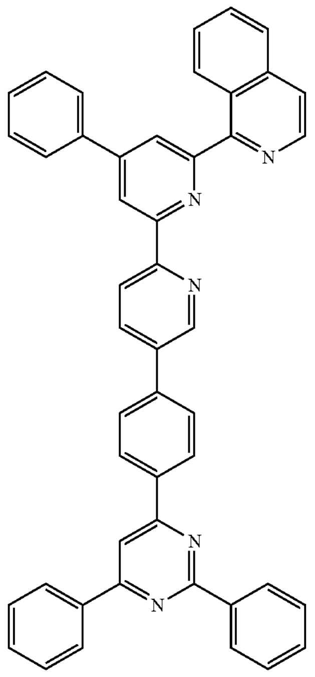
91
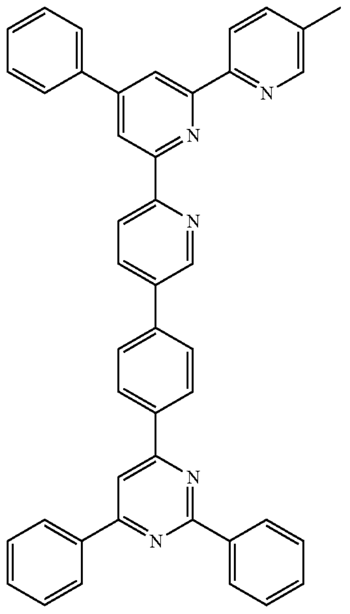
92
93
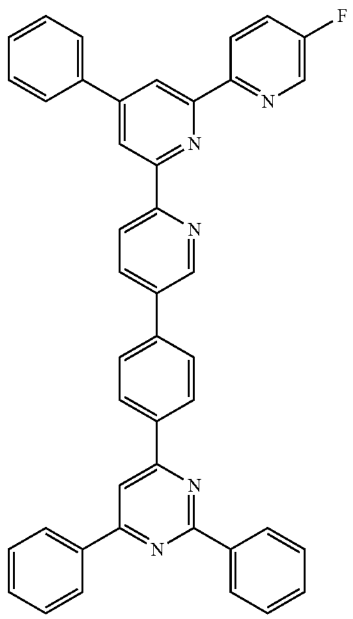
94
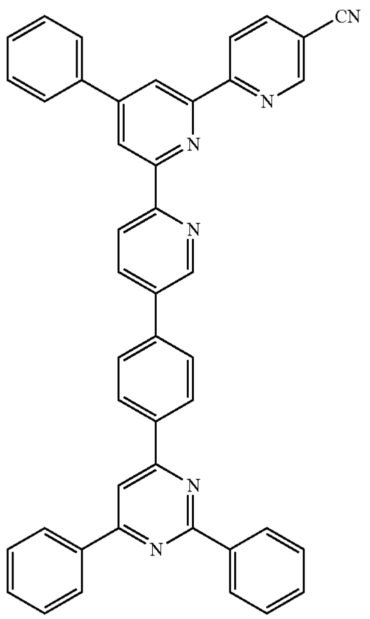

-continued
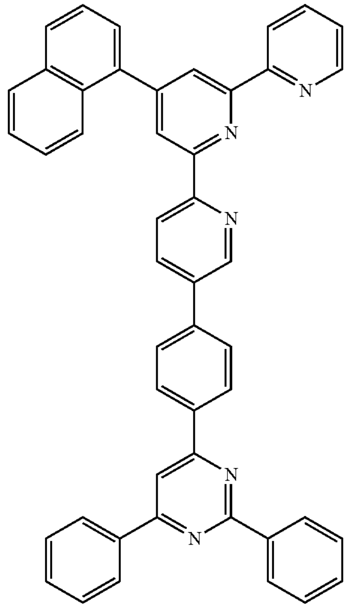
95
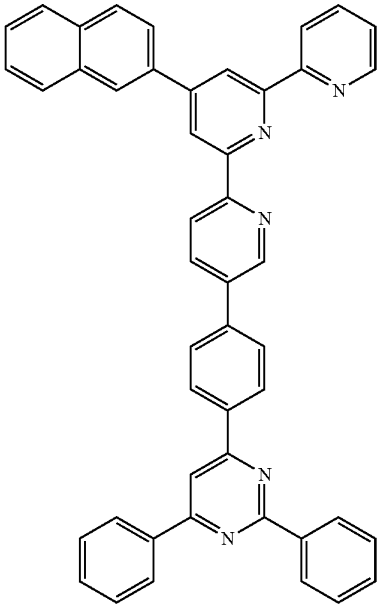
96
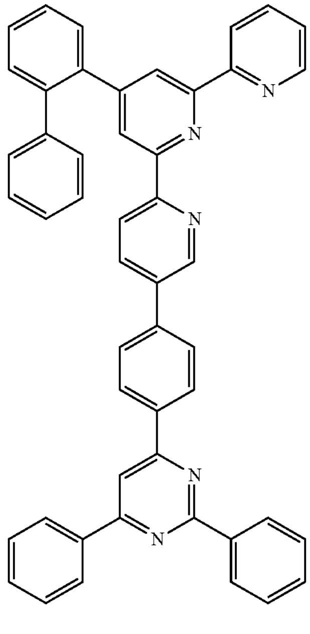
97
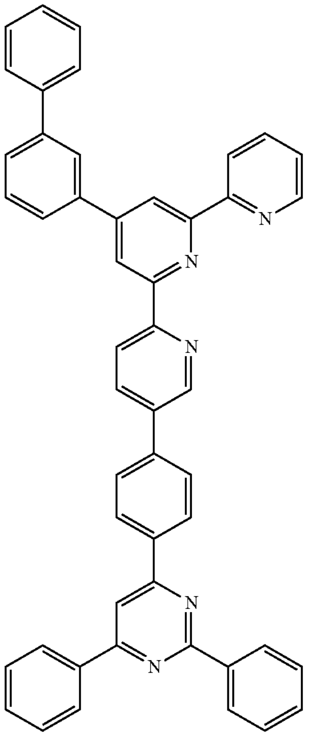
98

-continued
99
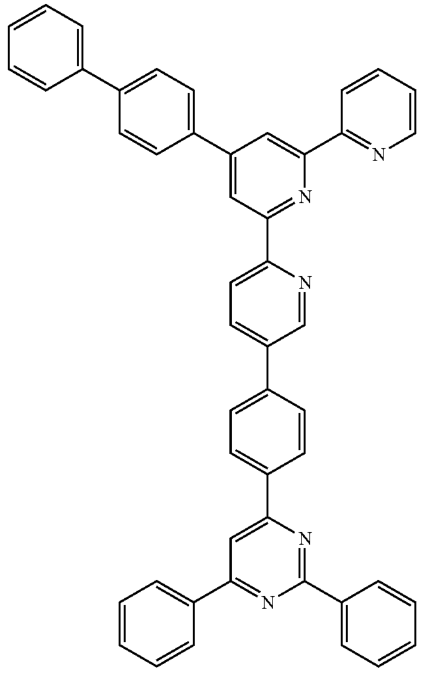
100
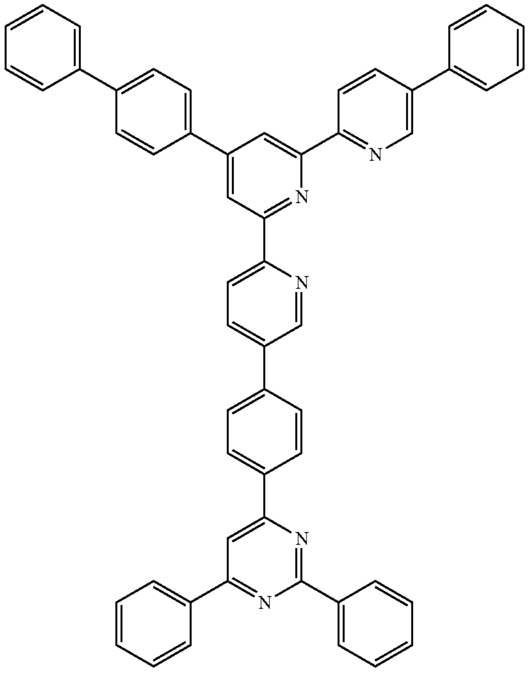
101
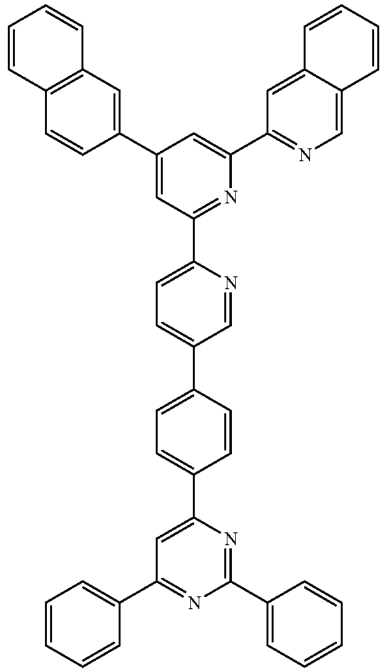
102
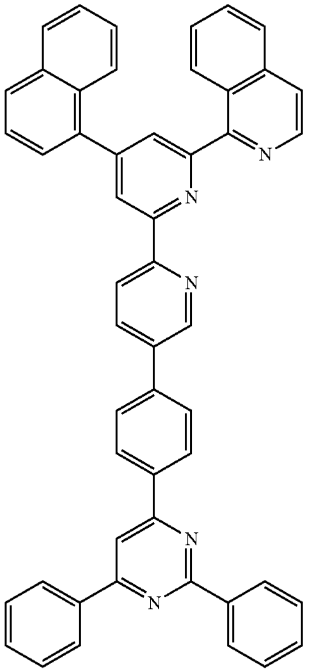

-continued
103
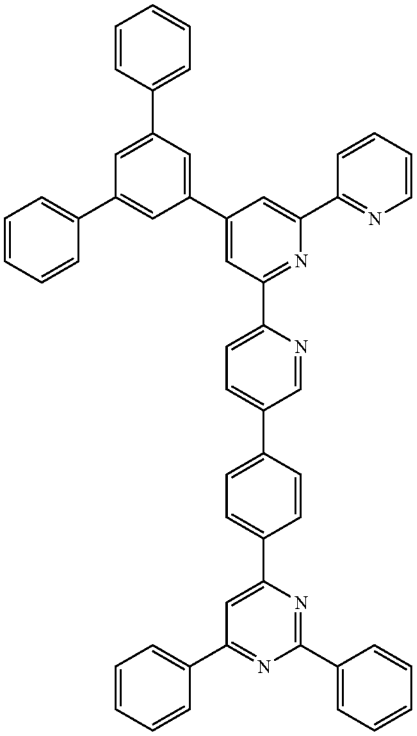
104
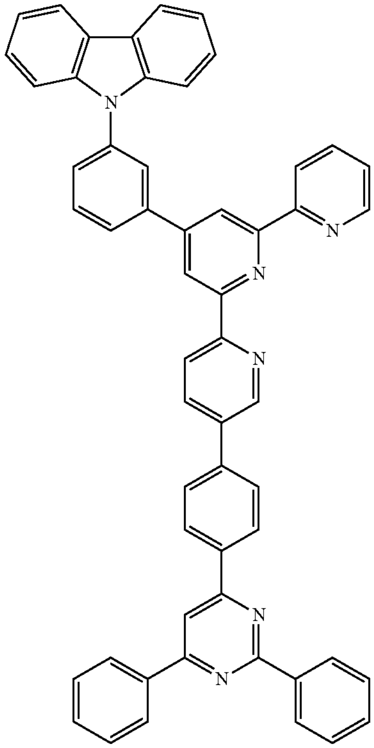
105
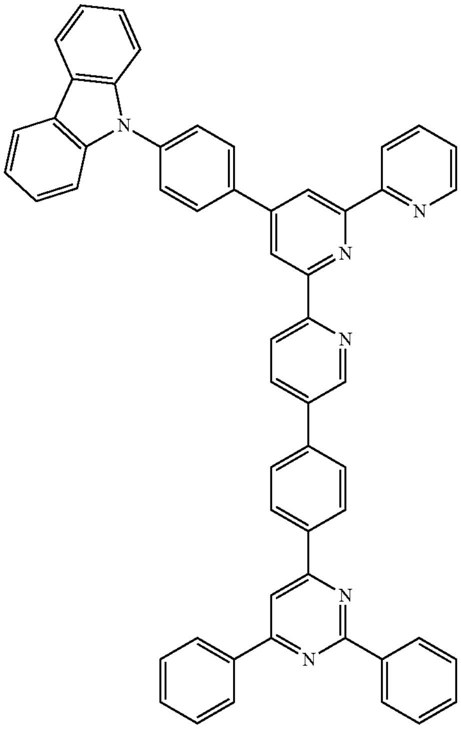
106
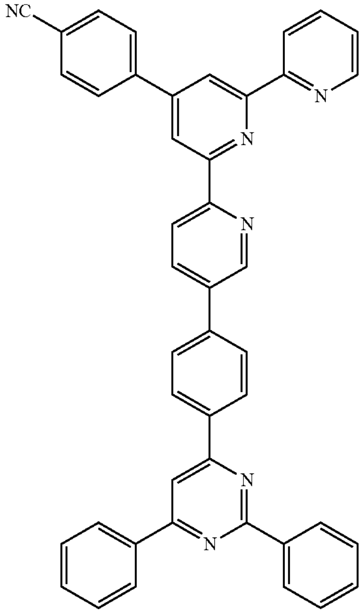

-continued
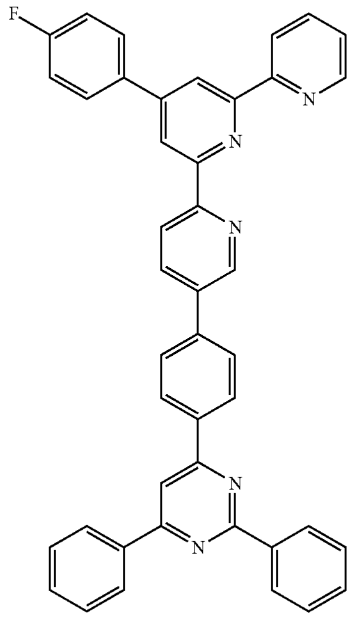
107
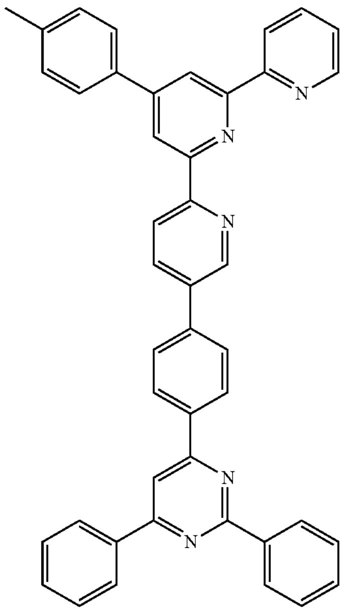
108
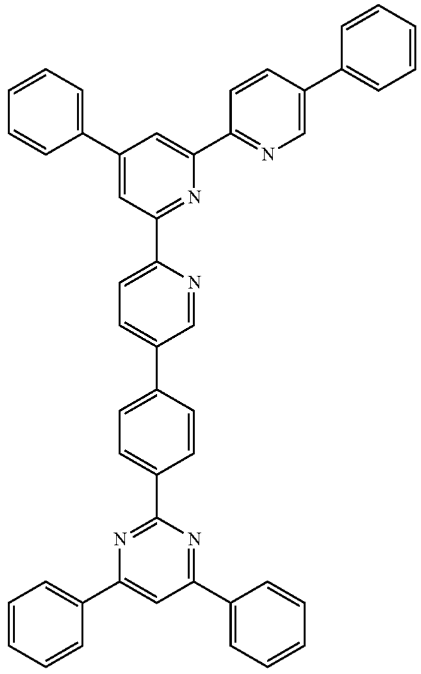
109
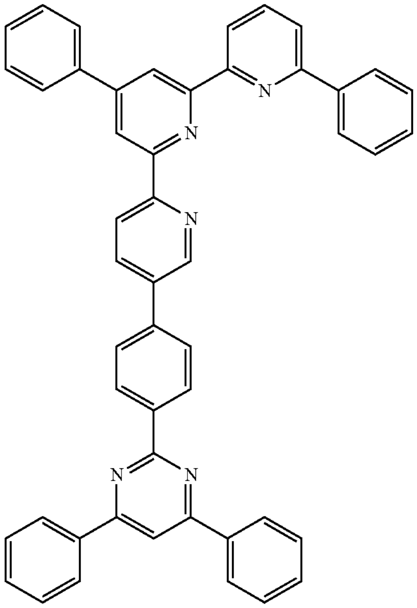
110

-continued
111
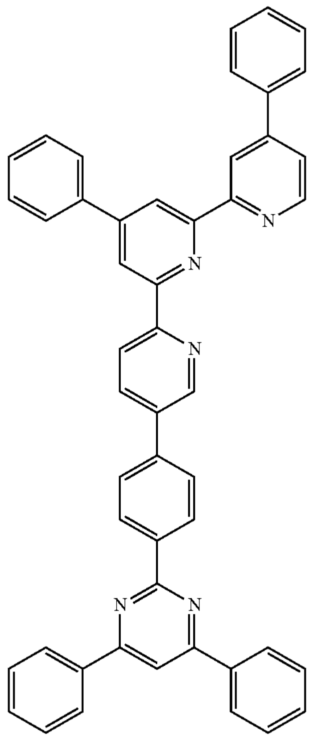
112
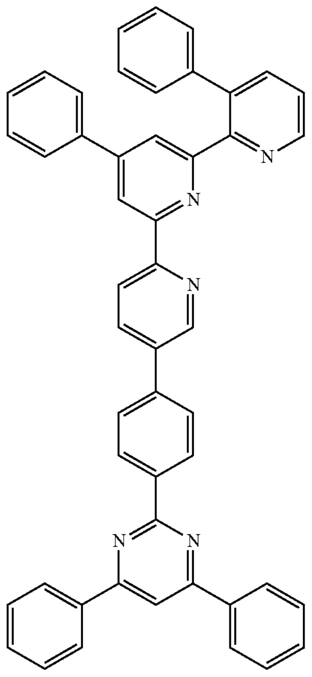
113
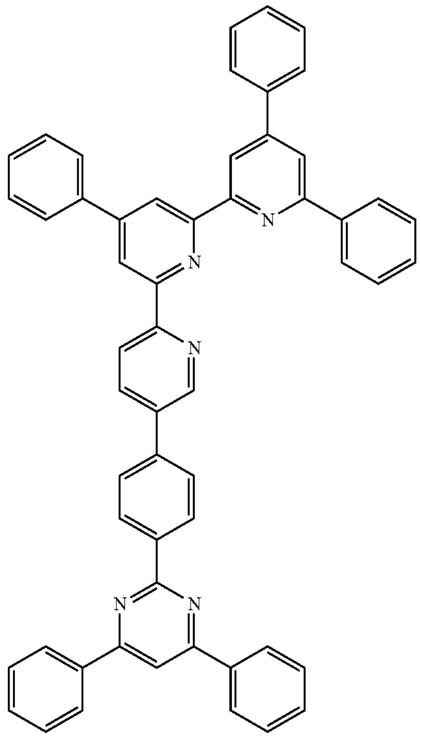
114
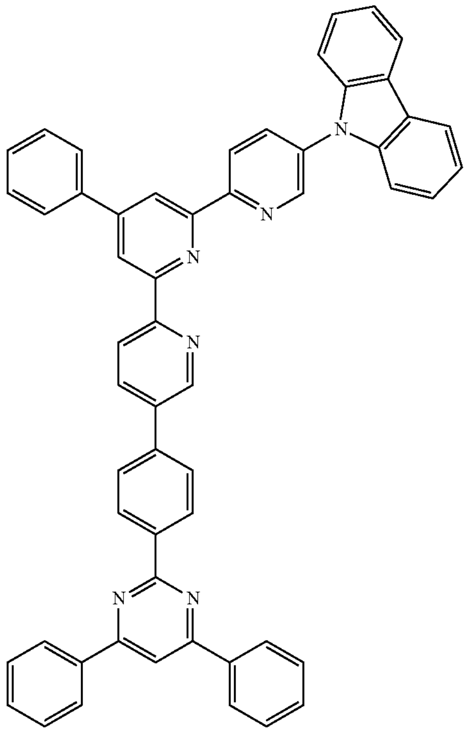

-continued
115
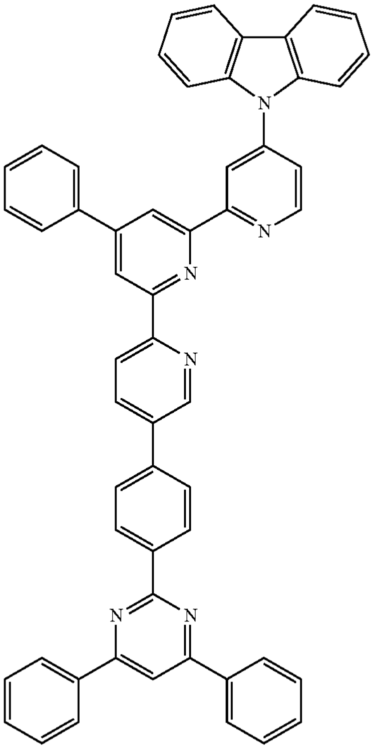
116
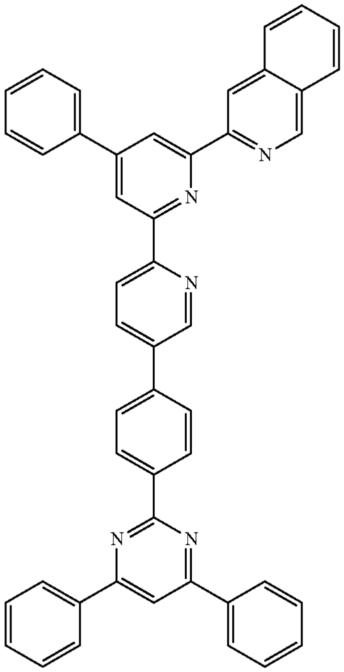
117
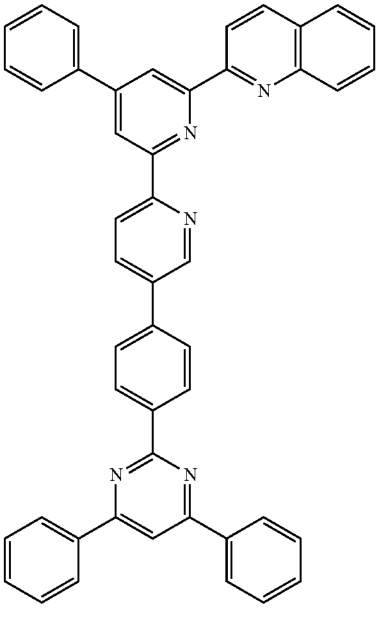
118
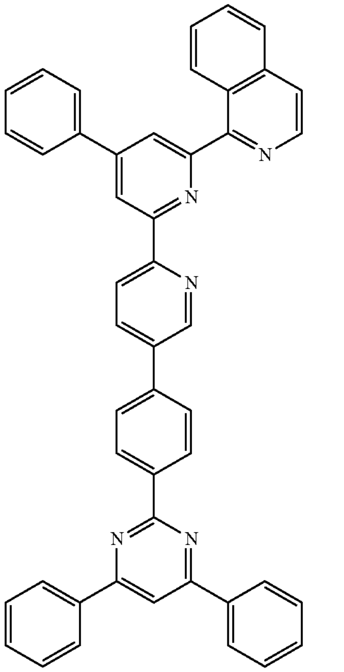

-continued
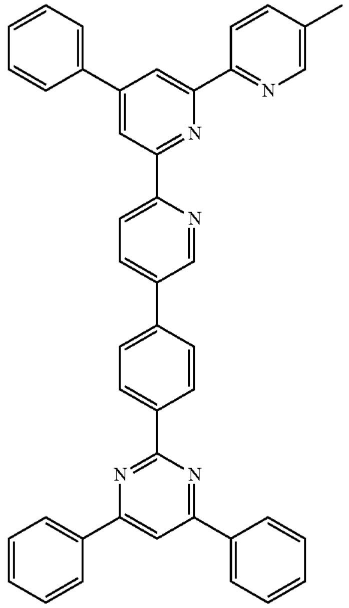
119
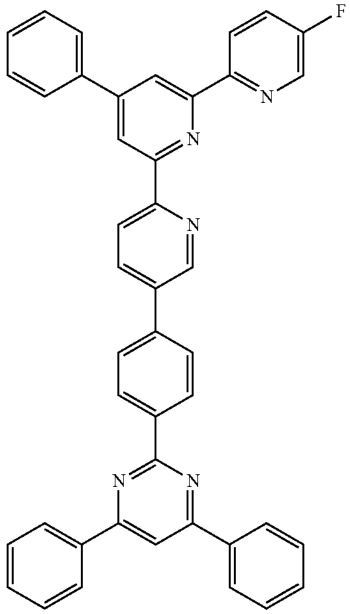
120
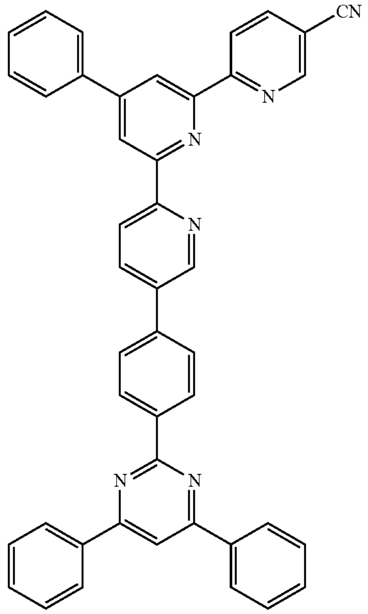
121
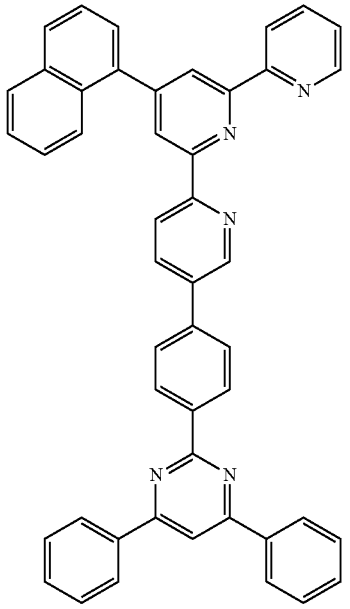
122

-continued
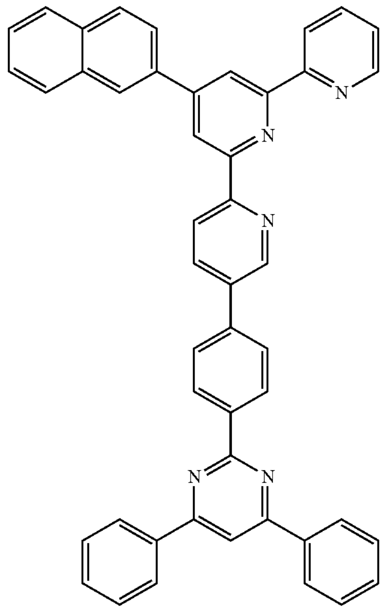
123
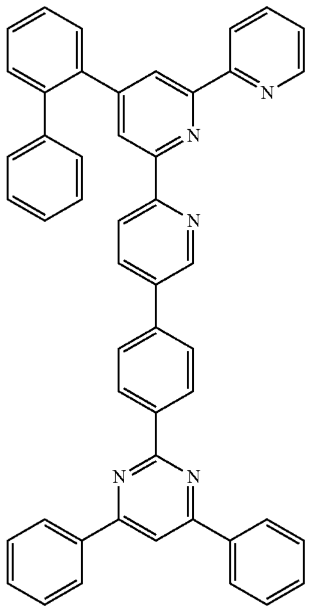
124
125
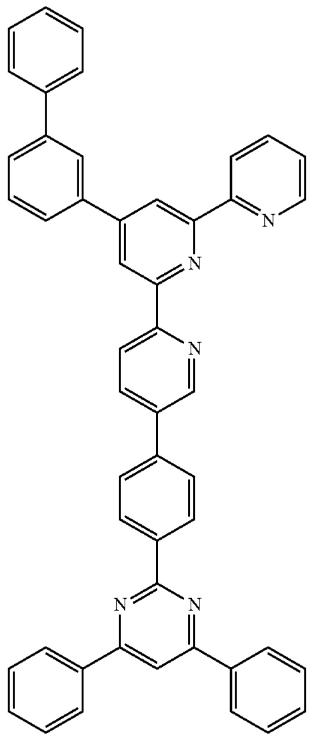
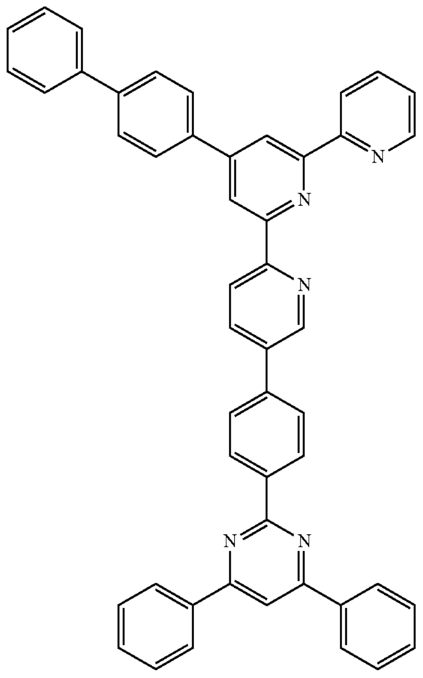
126

-continued
127
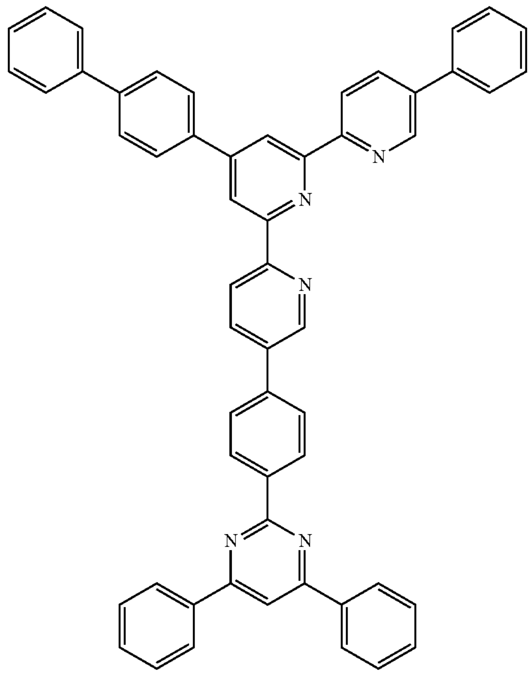
128
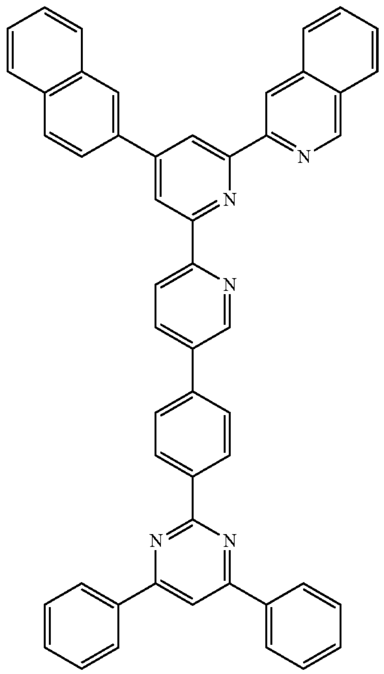
129
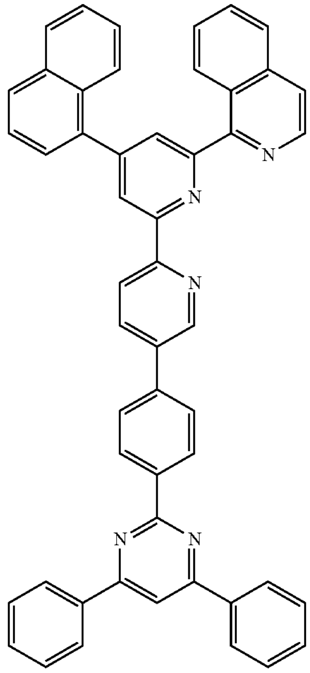
130
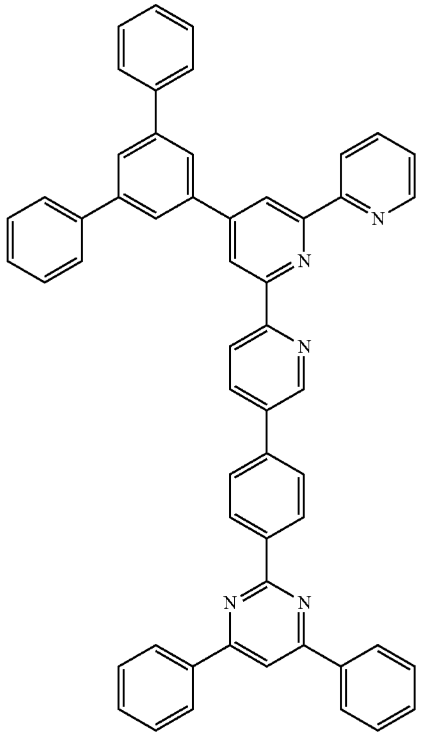

-continued
131
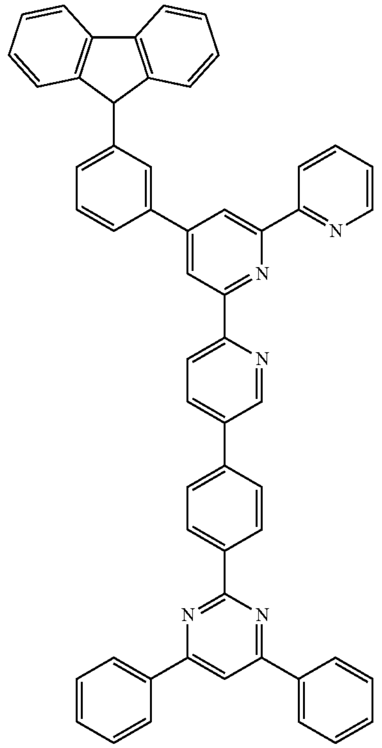
132
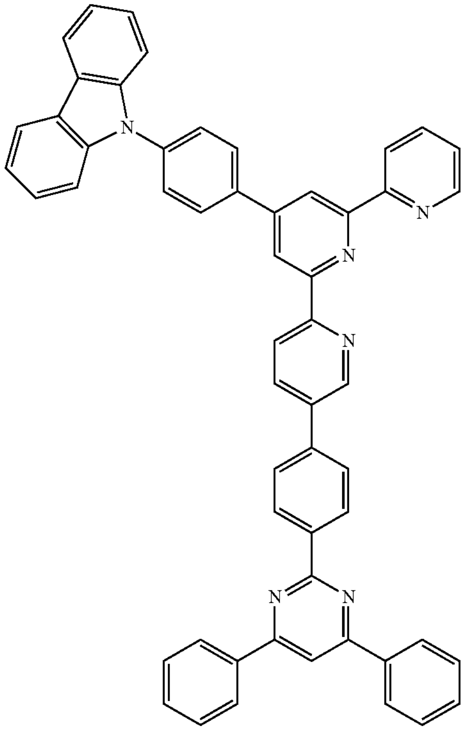
133
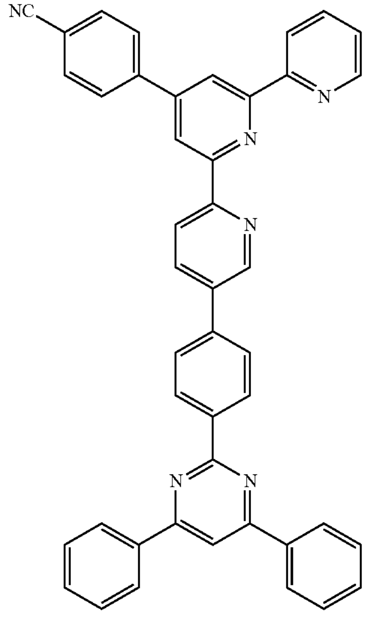
134
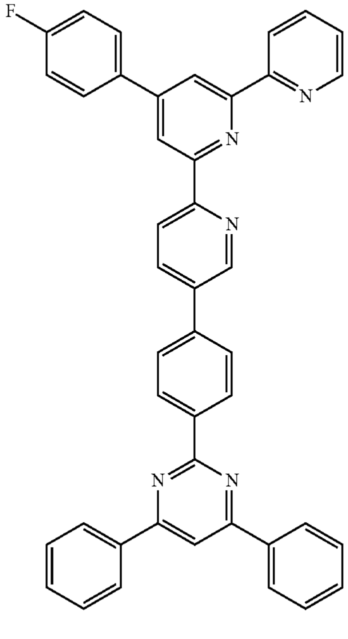

-continued
135
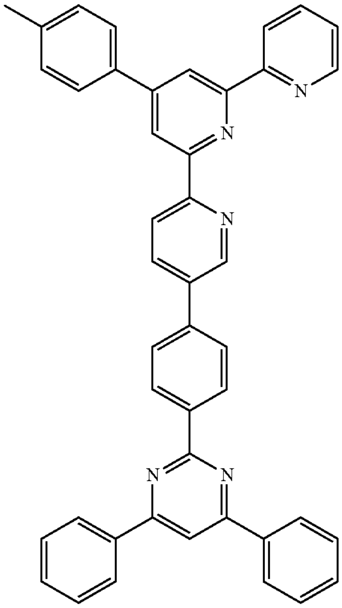
136
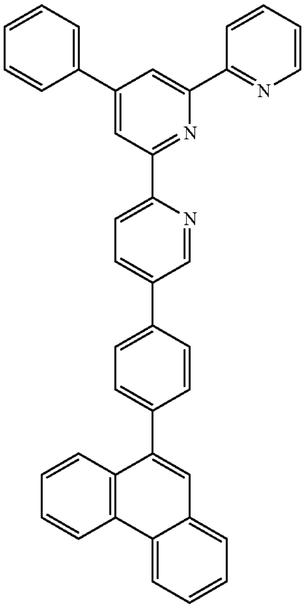
137
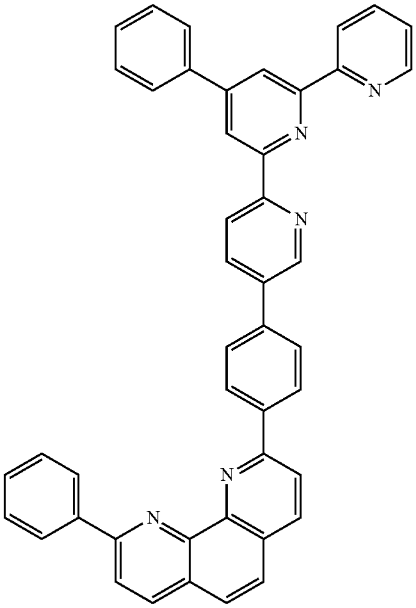
138
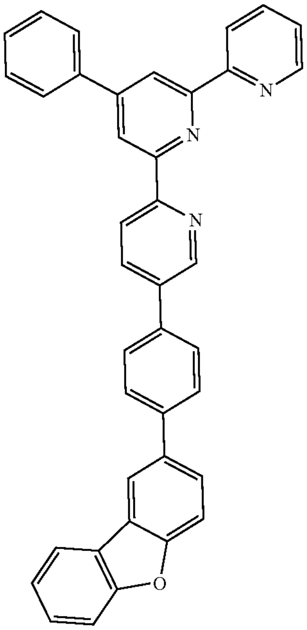

-continued
139
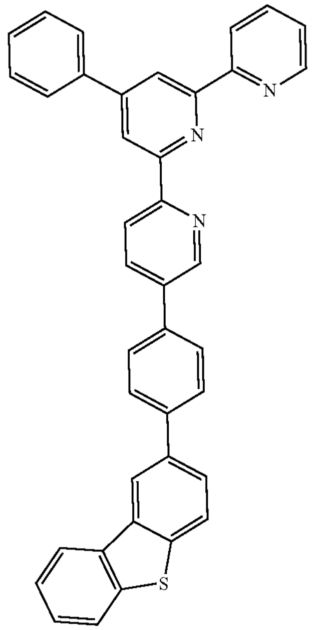
140
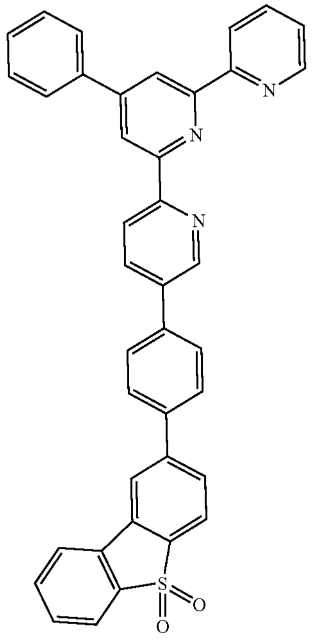
141
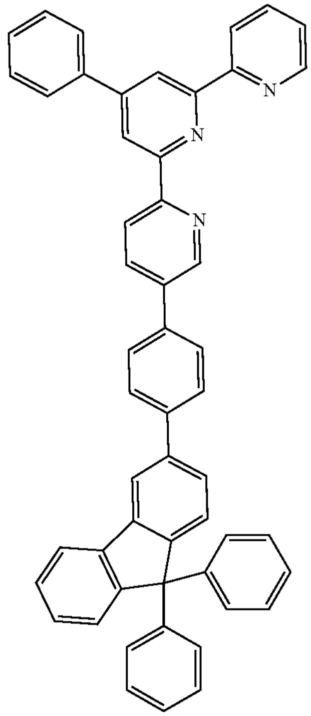
142
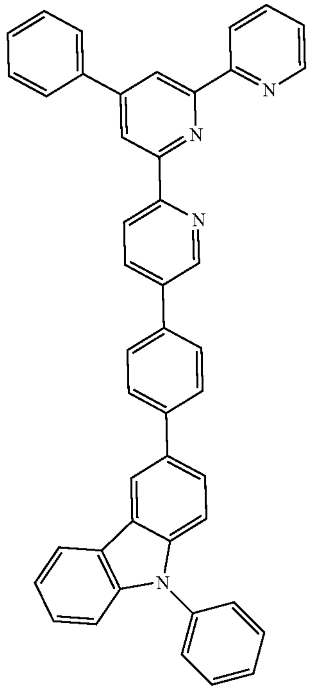

-continued
143
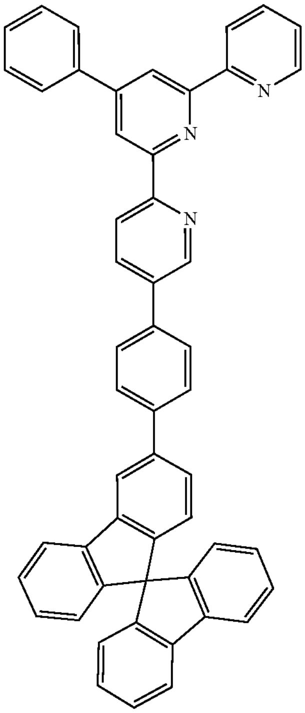
144
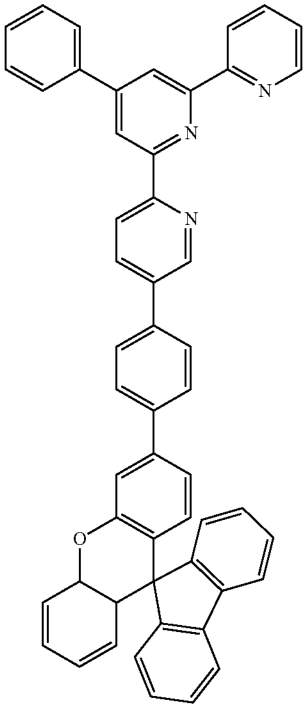
145
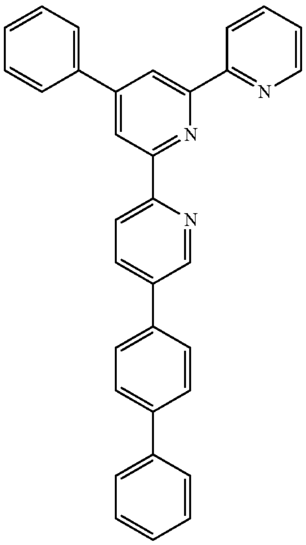
146
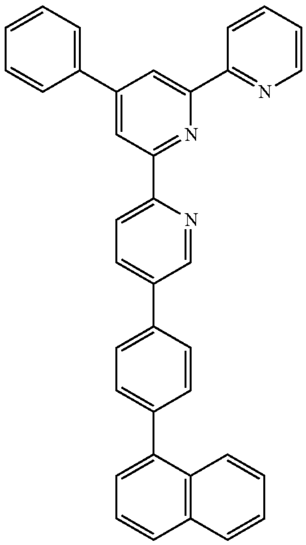

-continued
147
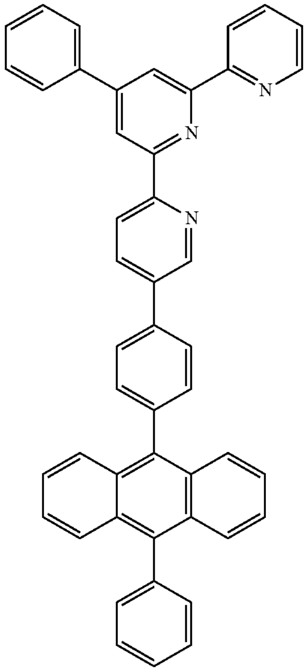
148
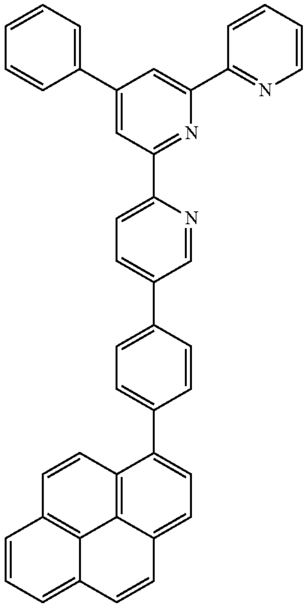
149
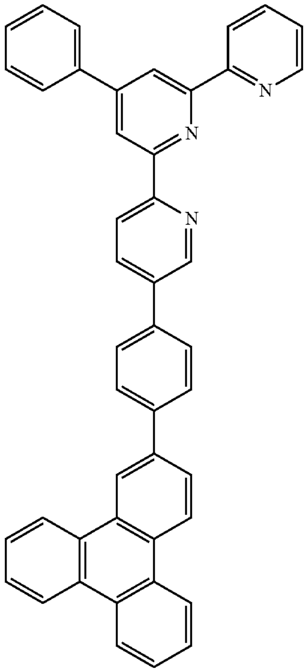
150
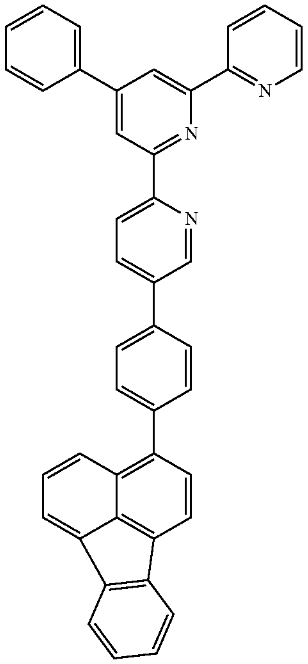

-continued
151
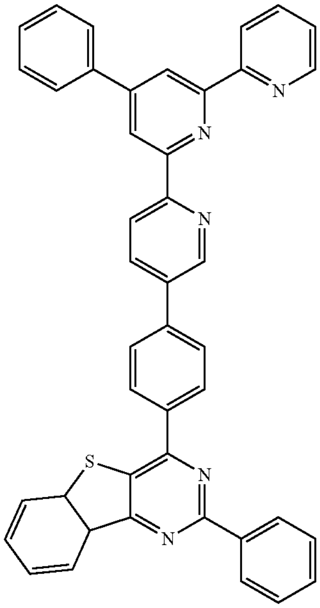
152
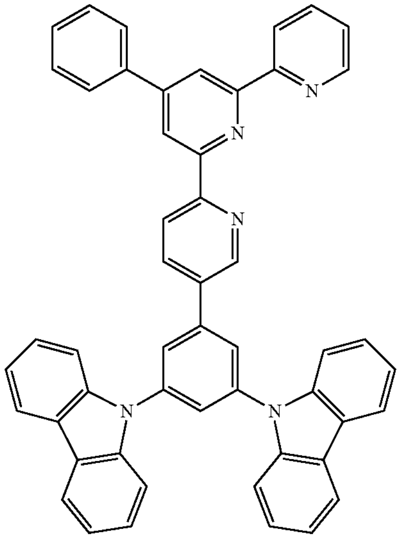
153
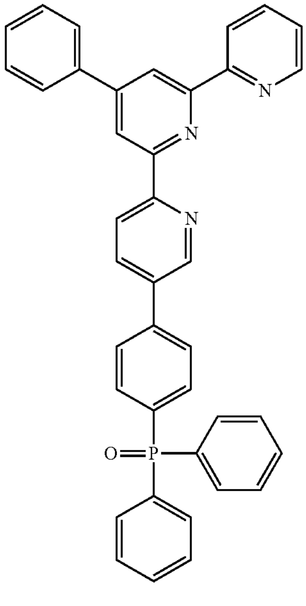
154
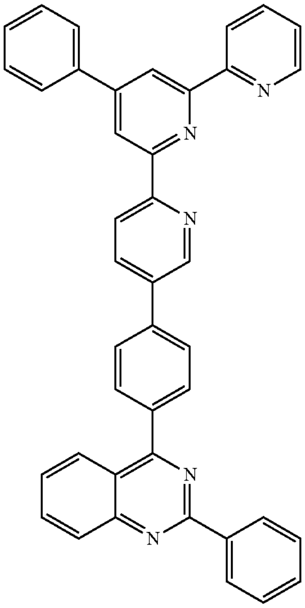

-continued
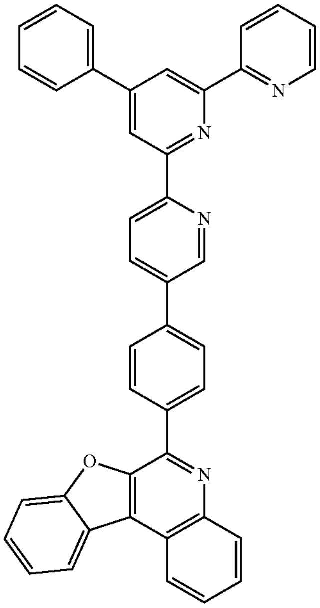
155
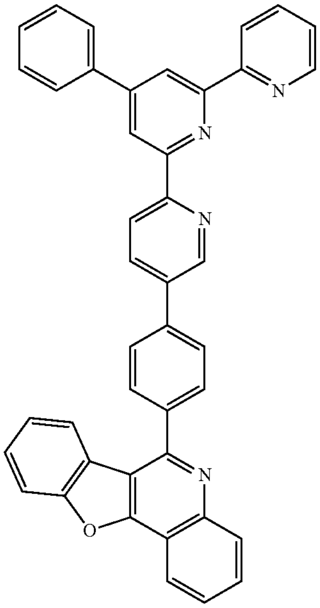
156
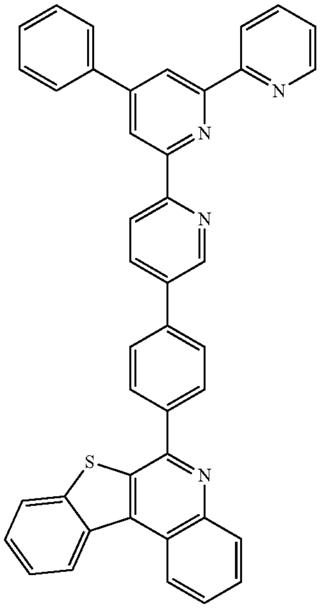
157
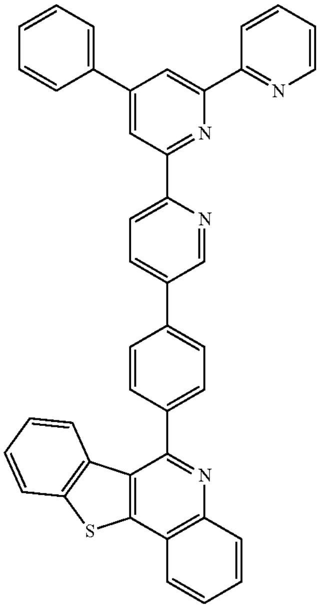
158

-continued
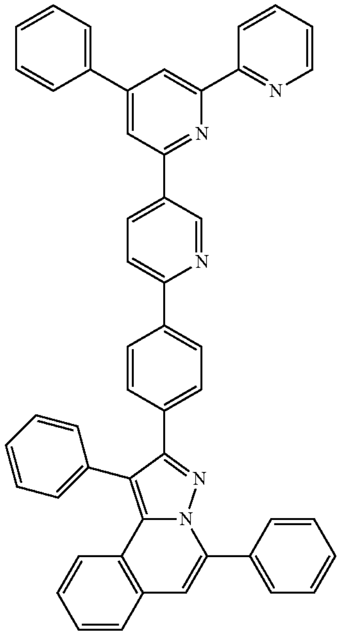
159
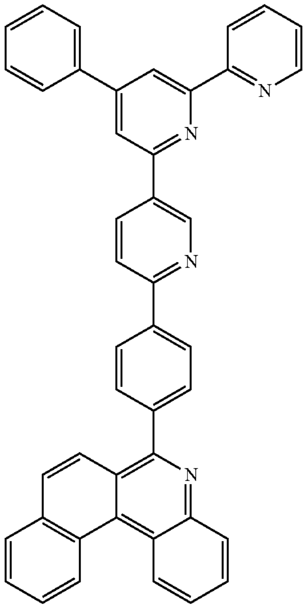
160
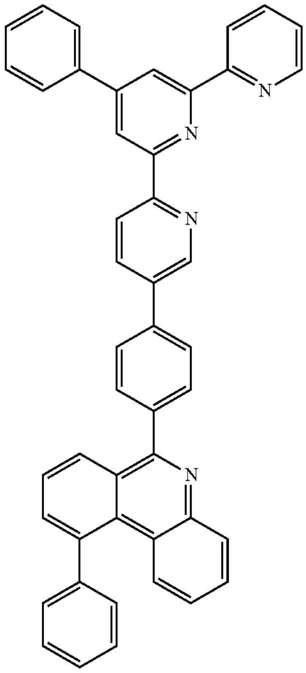
161
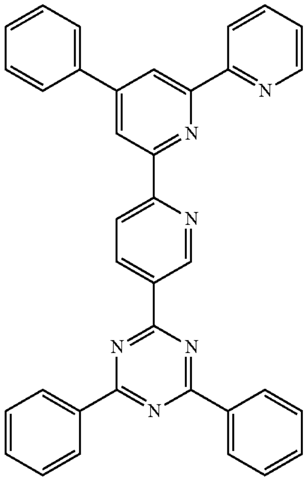
162

-continued
163
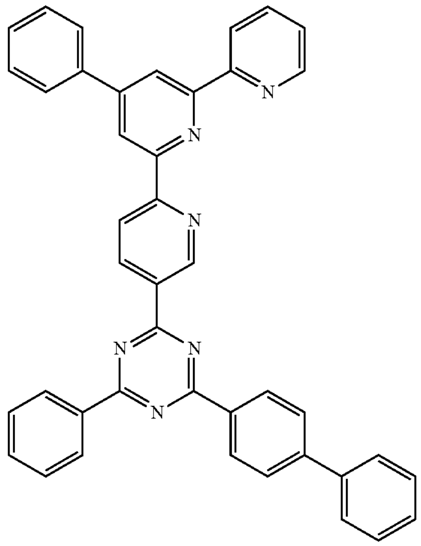
164
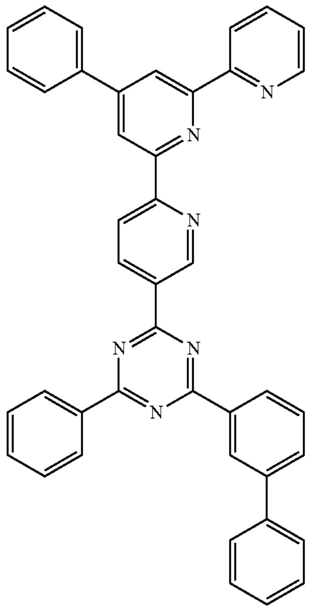
165
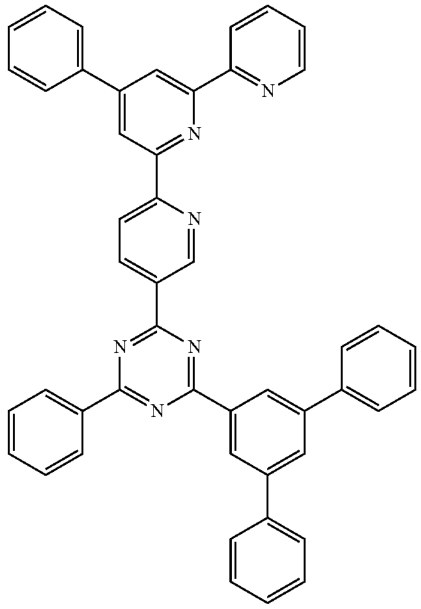
166
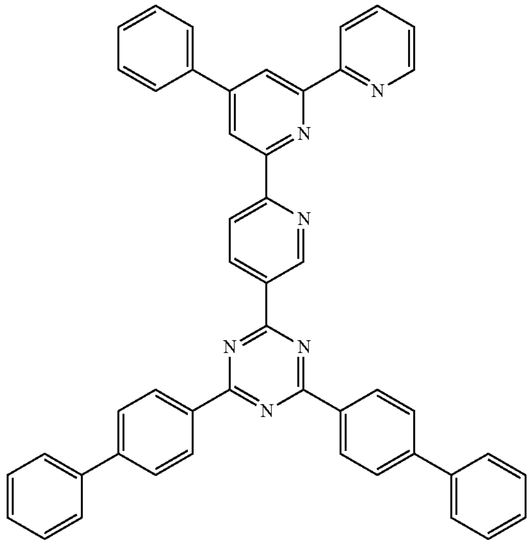

-continued
167
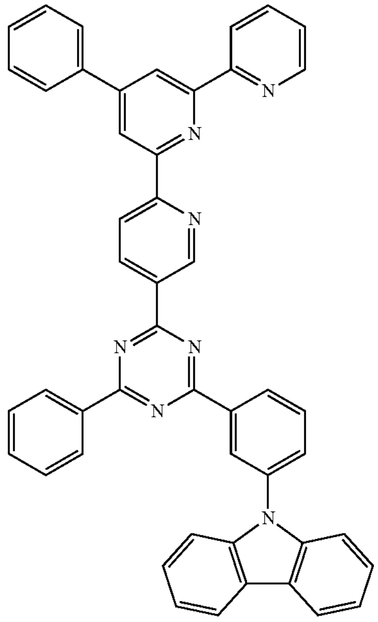
168
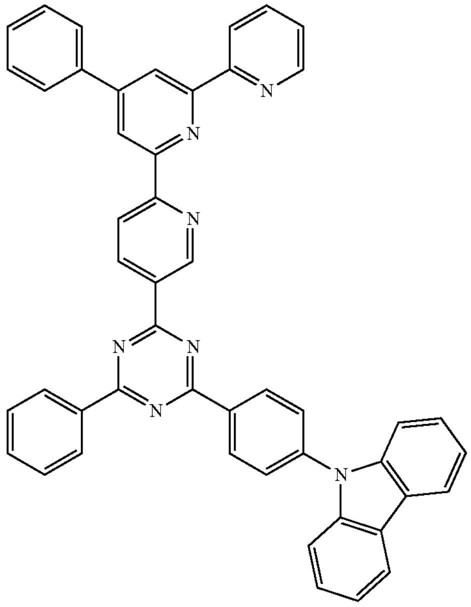
169
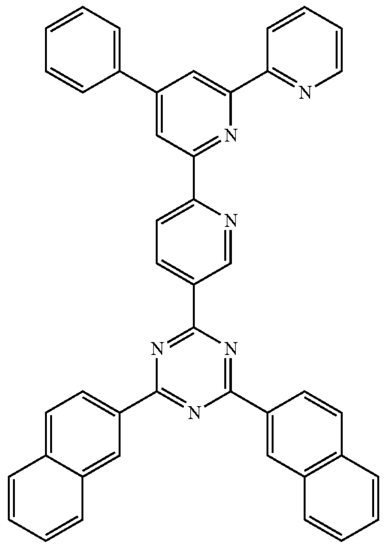
170
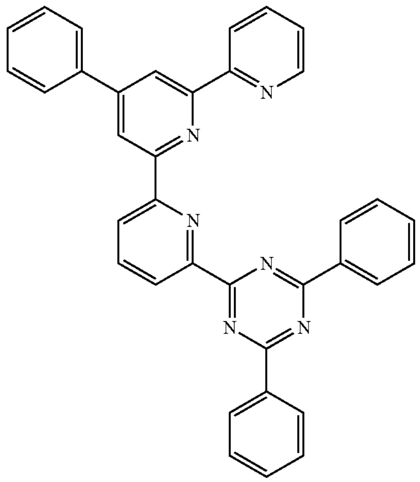

-continued
171
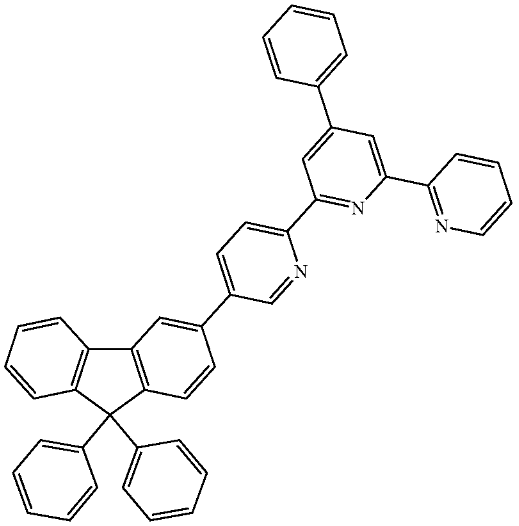
172
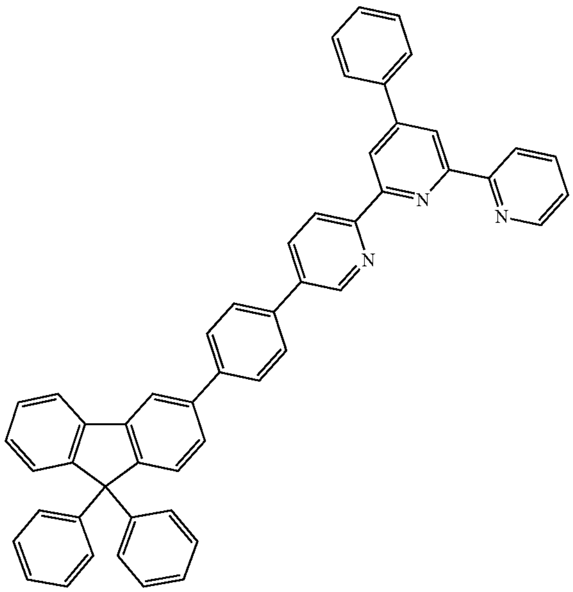
173
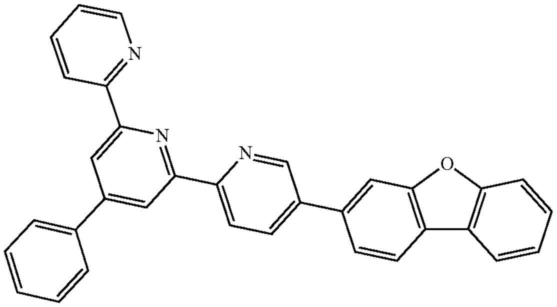
174
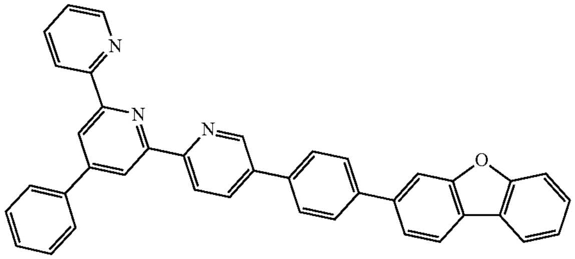
175
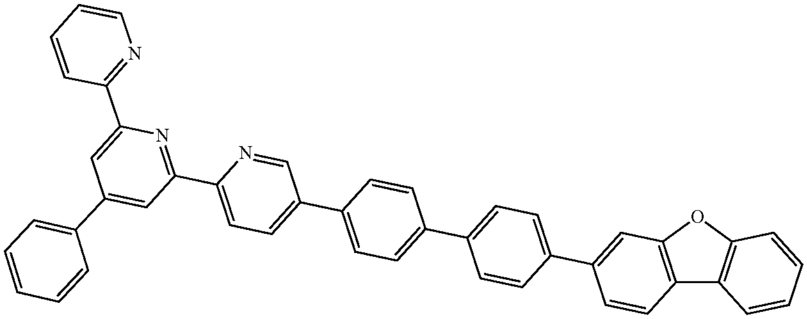
176
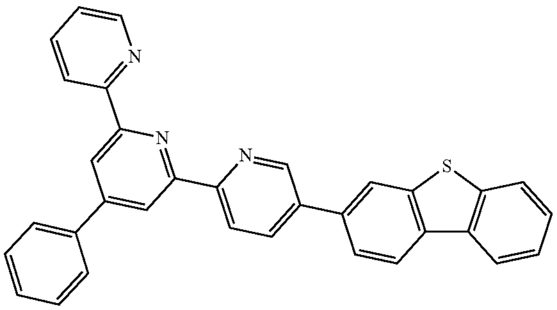
177
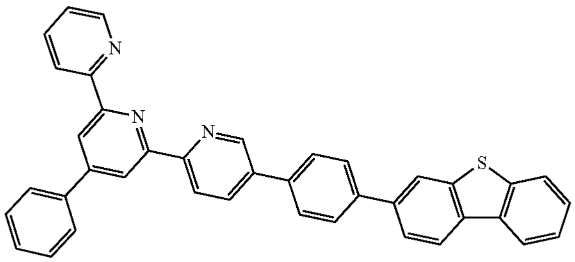

-continued
178
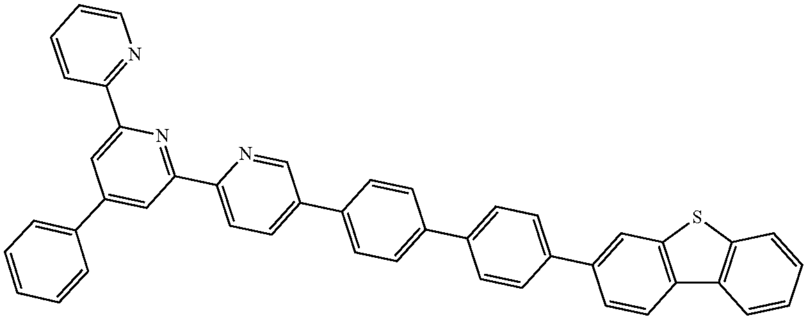
179
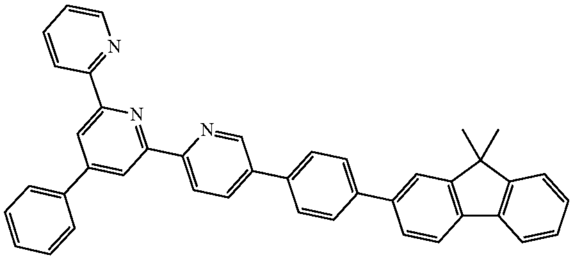
180
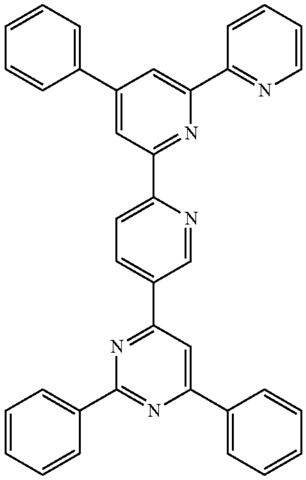
181
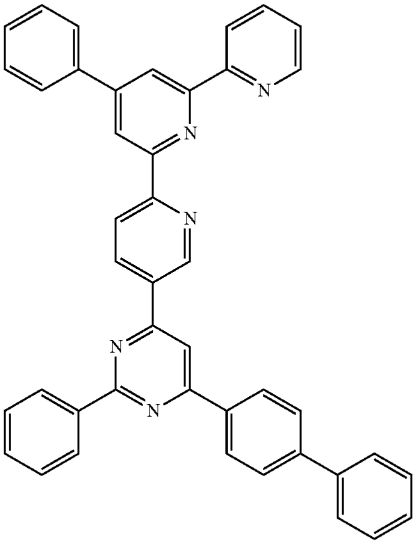
182
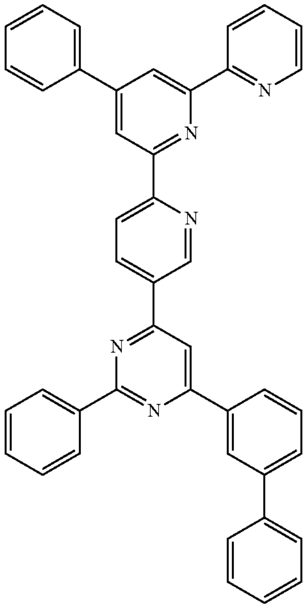

-continued
183
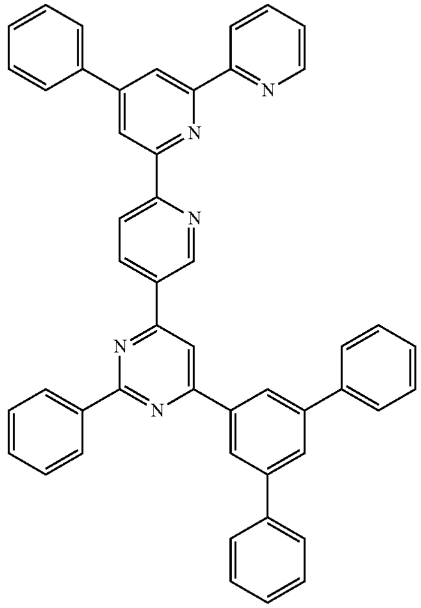
184
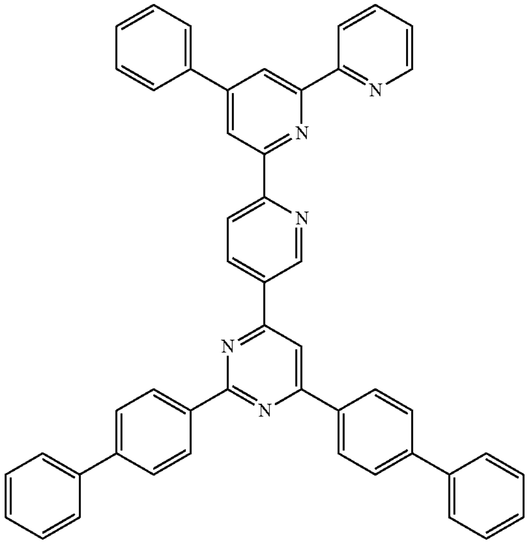
185
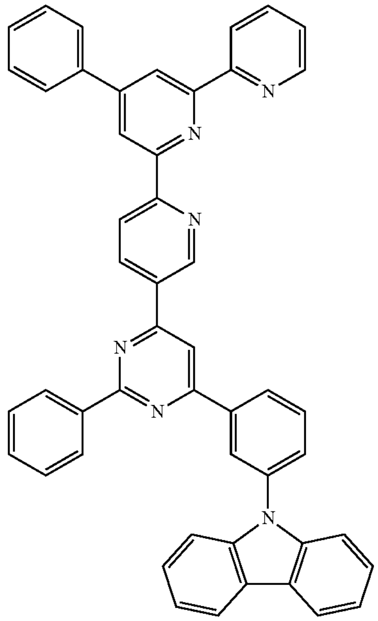
186
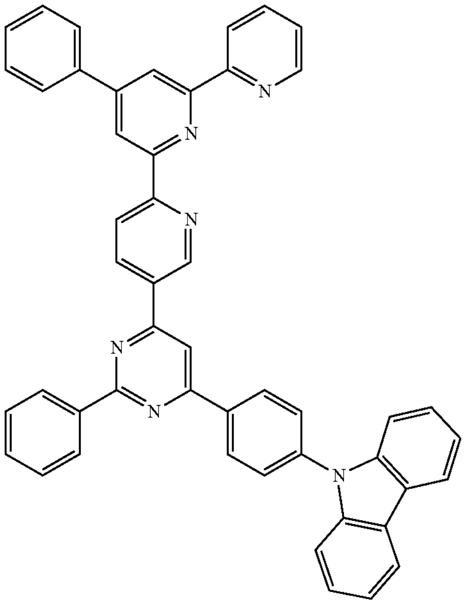

-continued
187
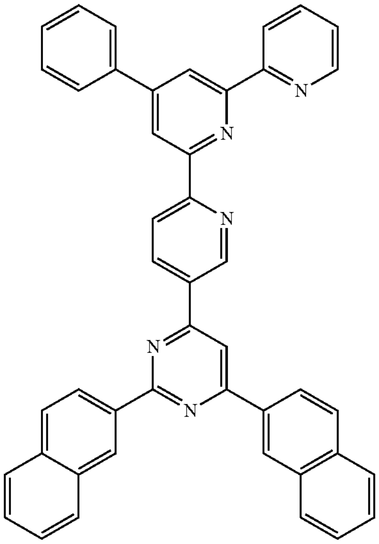
188
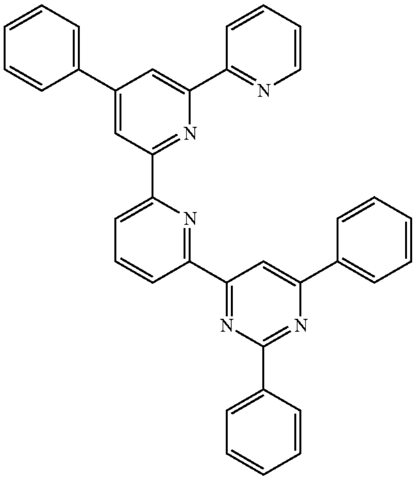
189
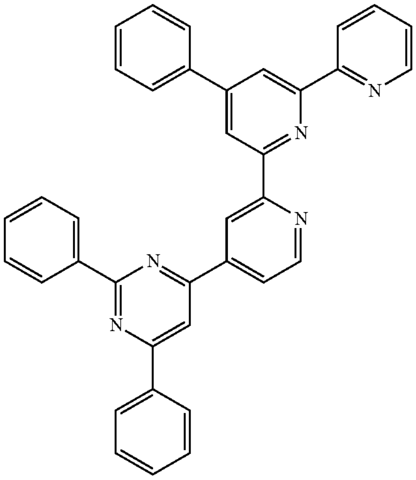
190
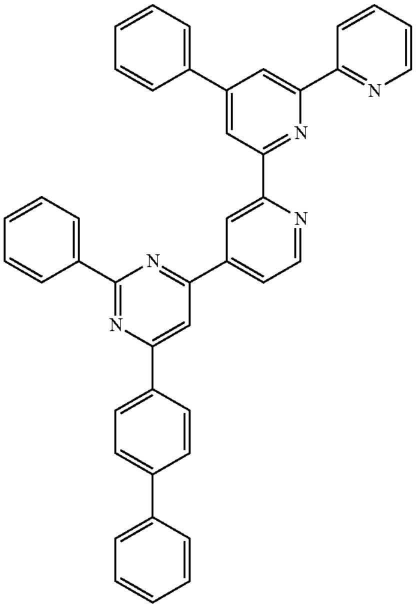

-continued
191
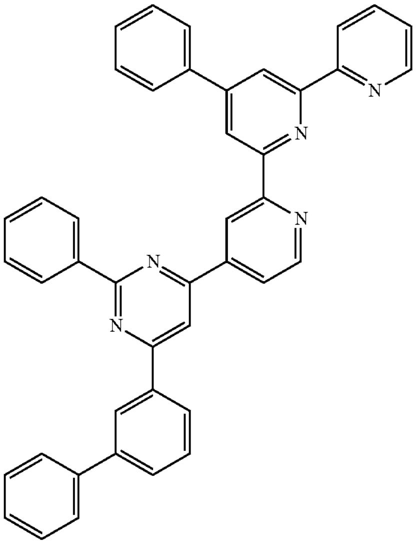
192
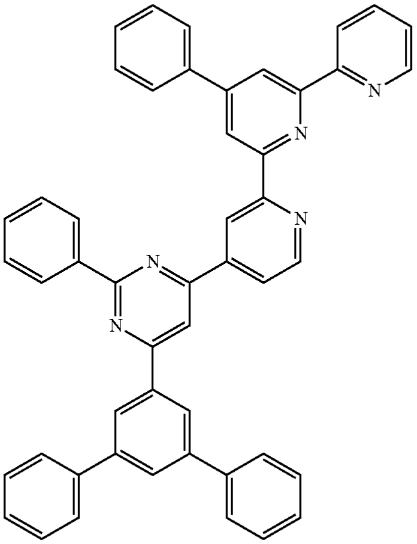
193
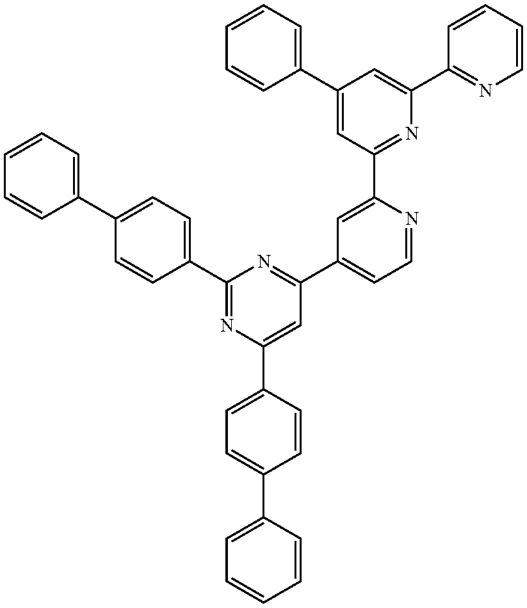
194
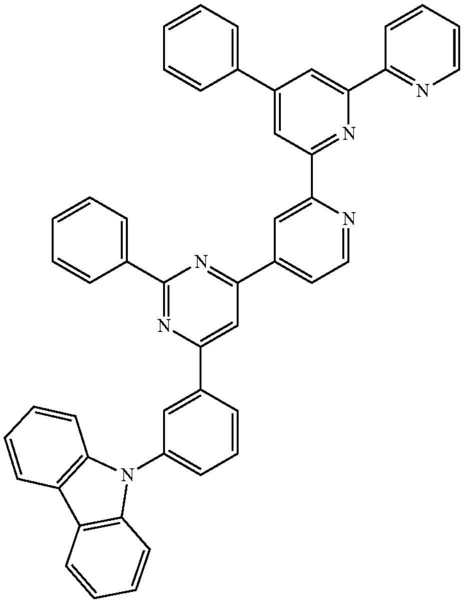

-continued
195
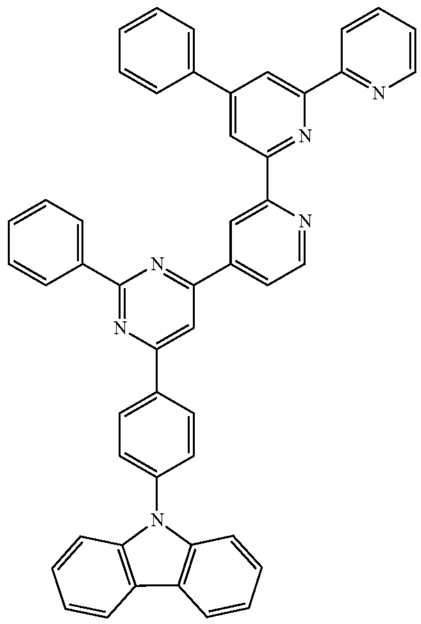
196
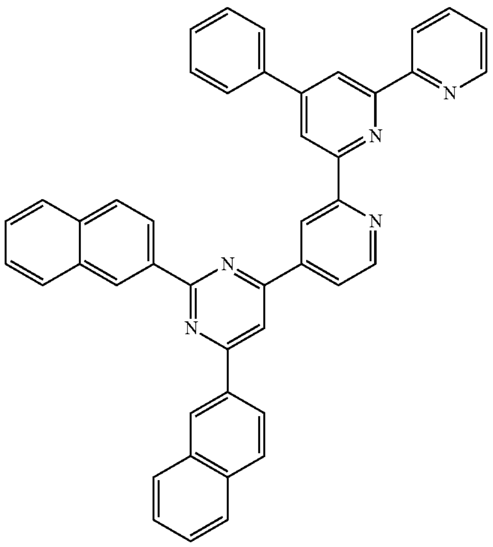
197
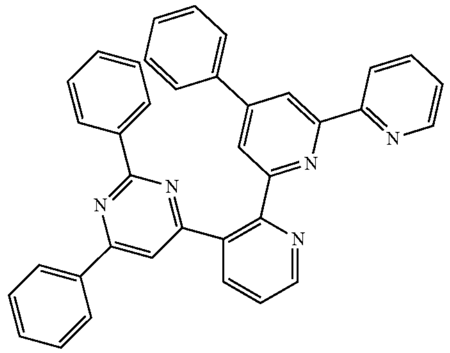
198
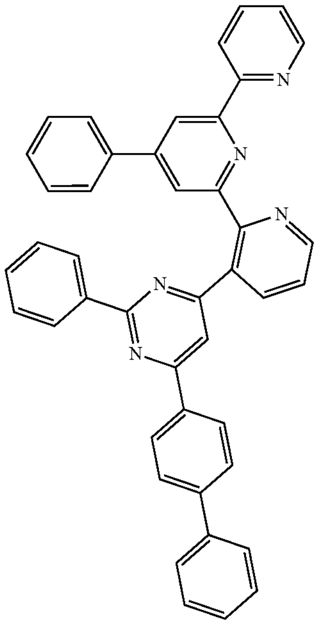

-continued
199
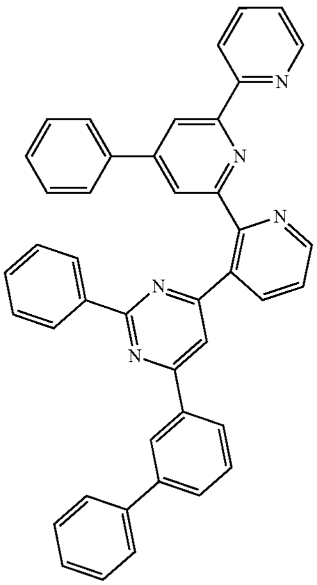
200
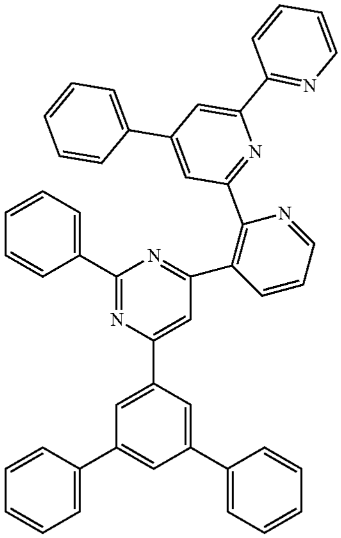
201
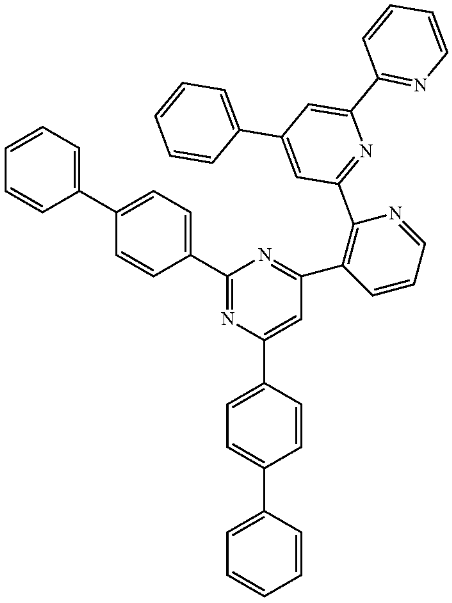
202
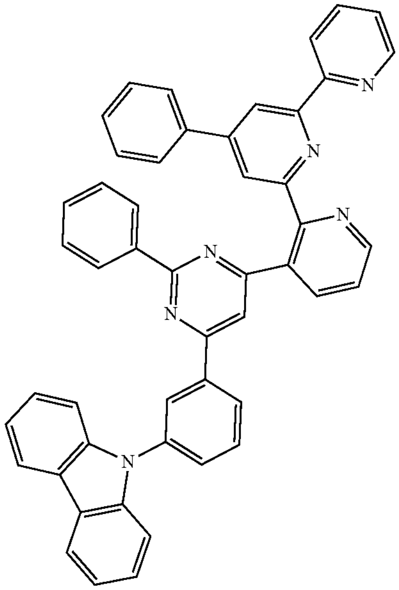

-continued
203
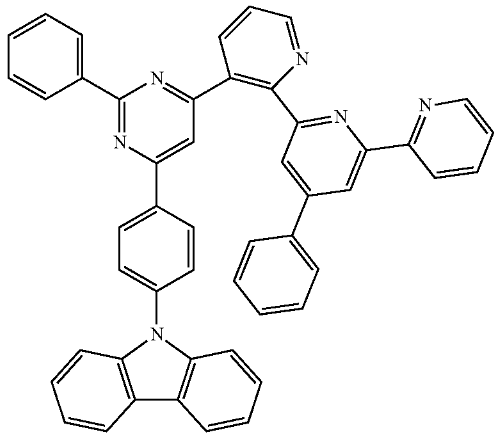
204
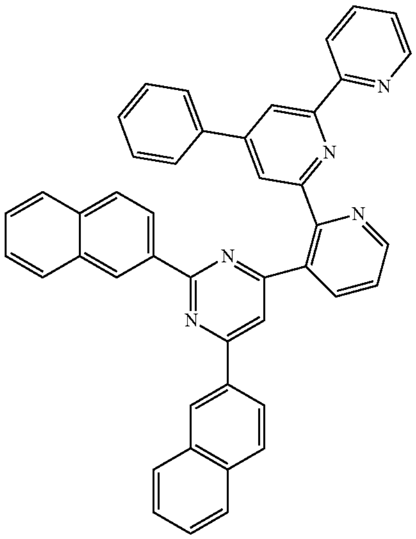
205
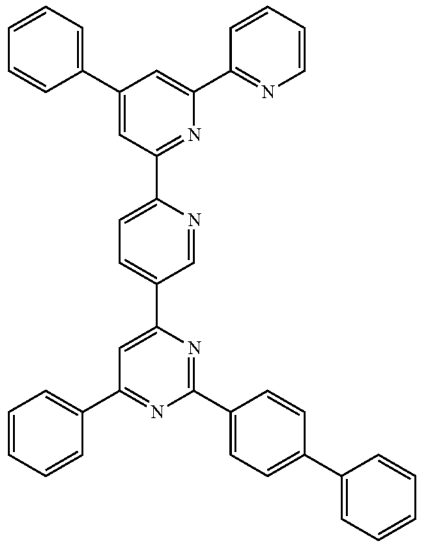
206
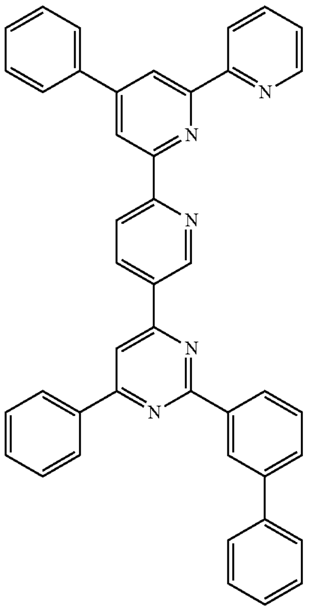

-continued
207
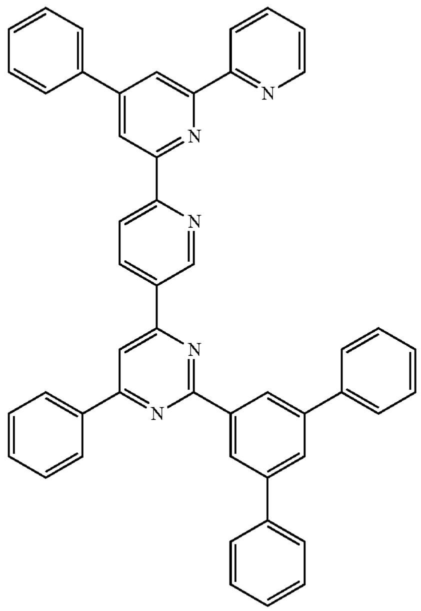
208
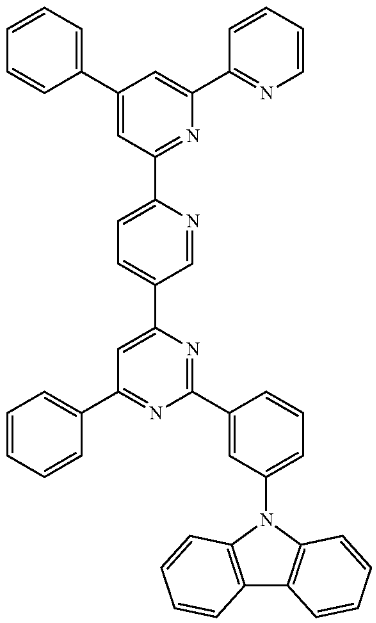
209
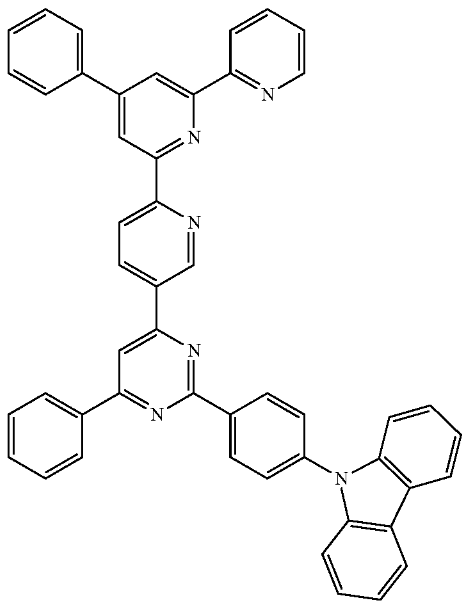
210
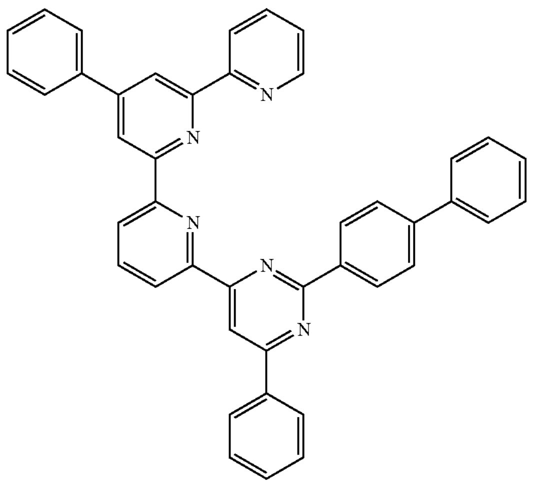

-continued
211
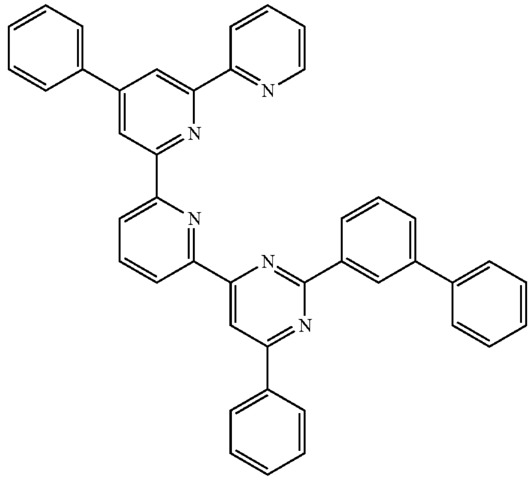
212
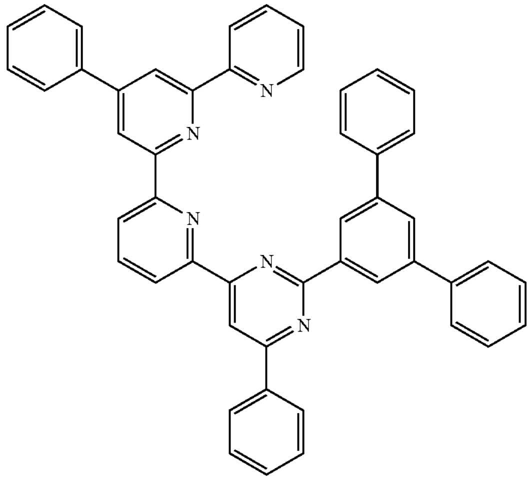
213
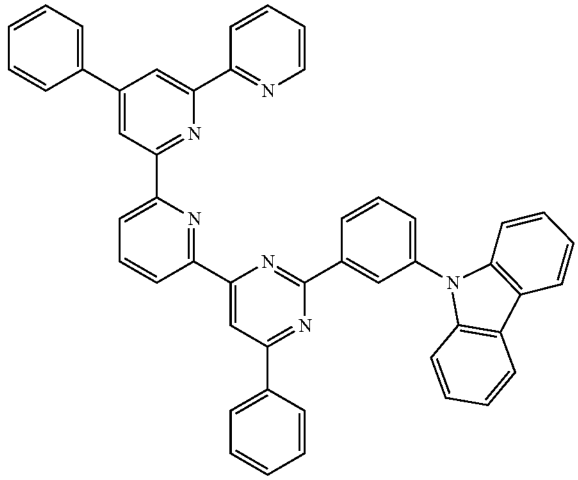
214
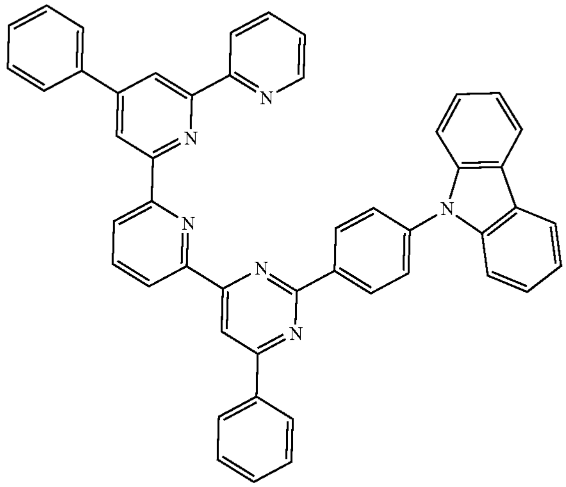
215
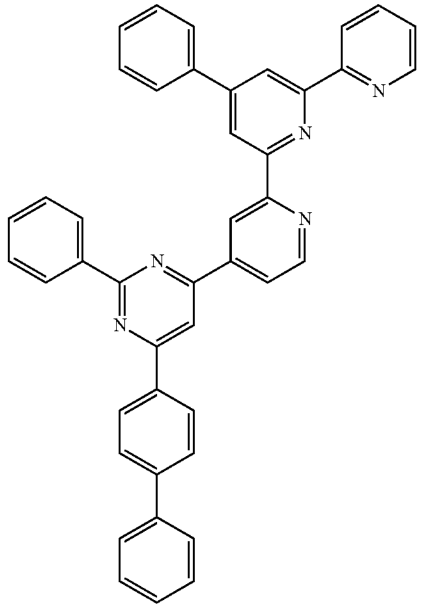
216
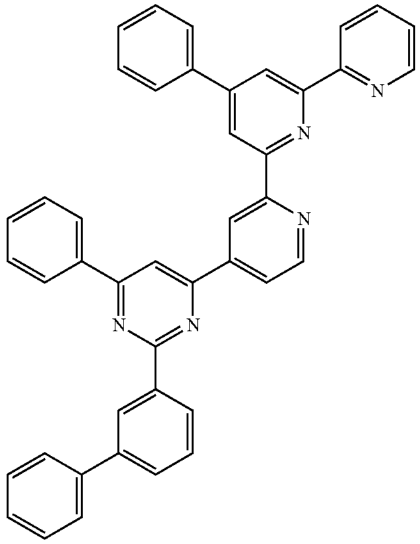

-continued
217
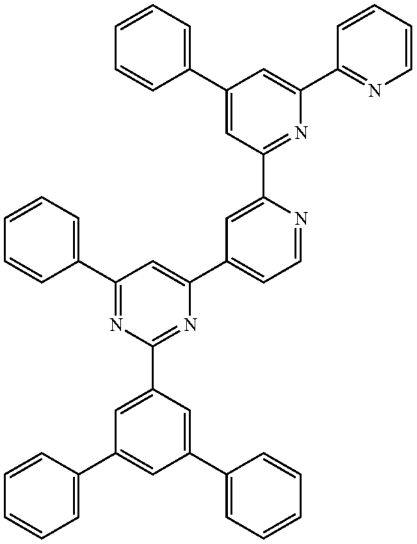
218
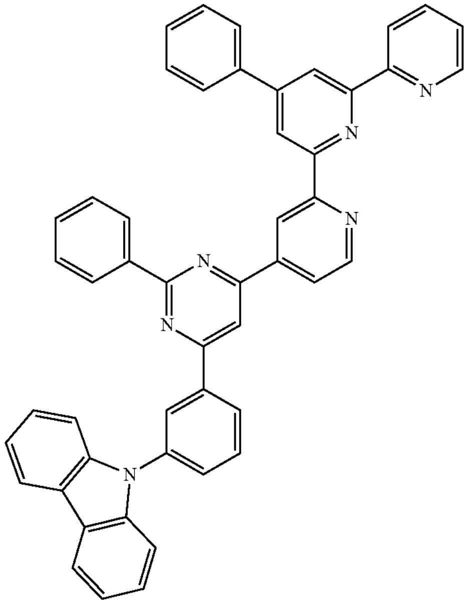
219
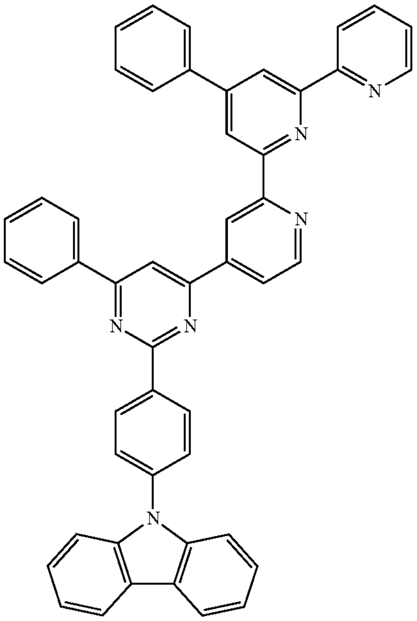
220
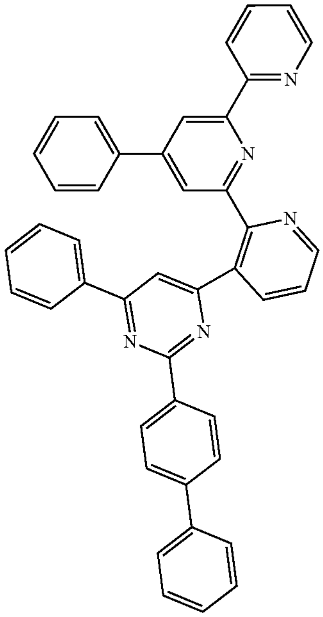

-continued
221
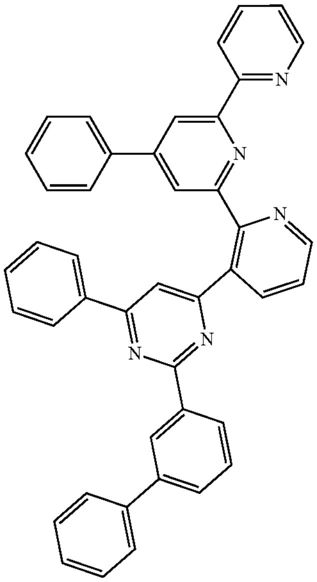
222
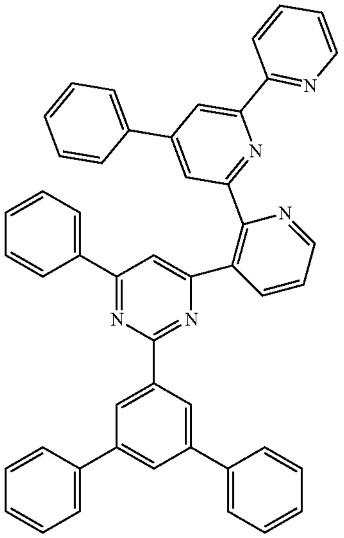
223
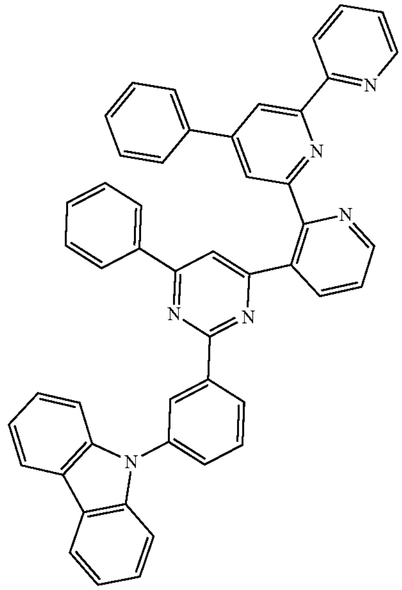
224
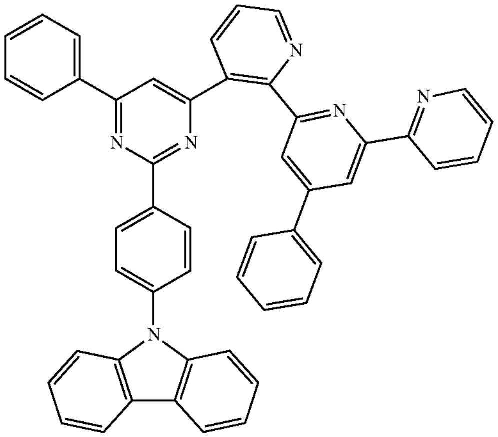

-continued
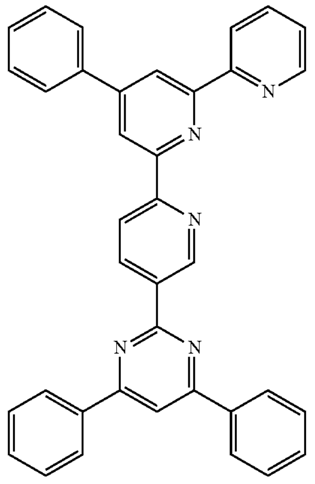
225
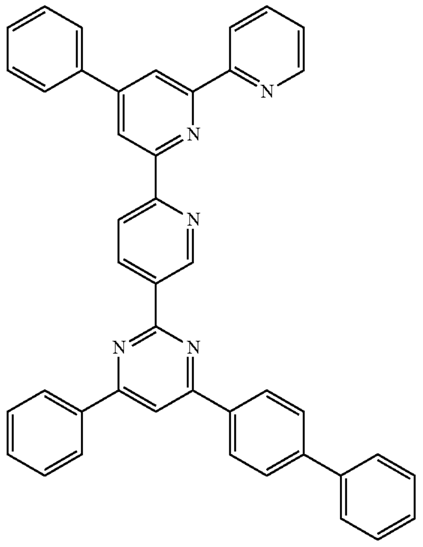
226
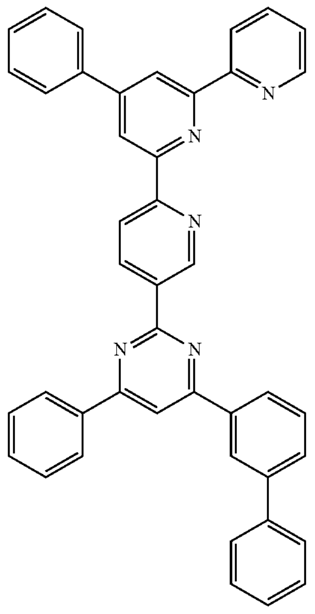
227
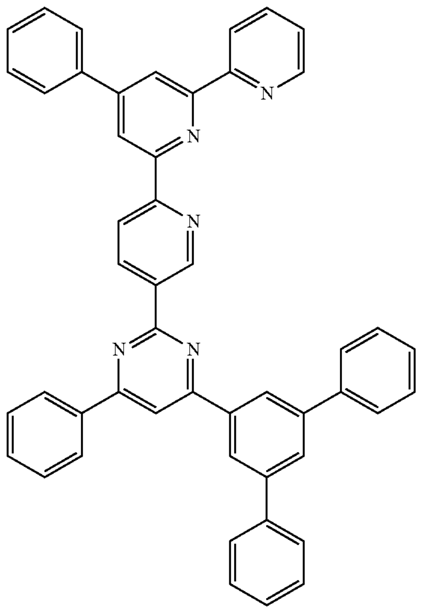
228

-continued
229
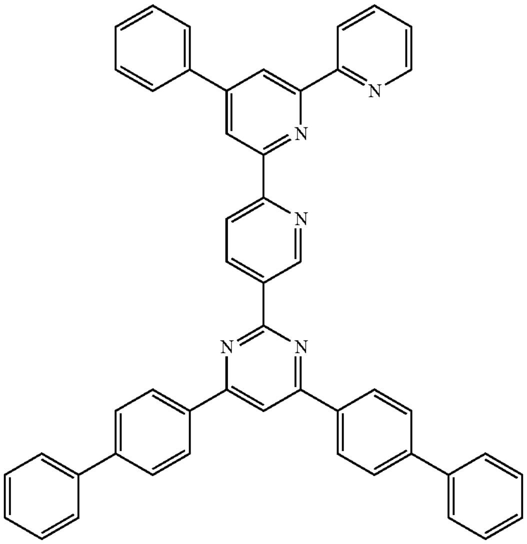
230
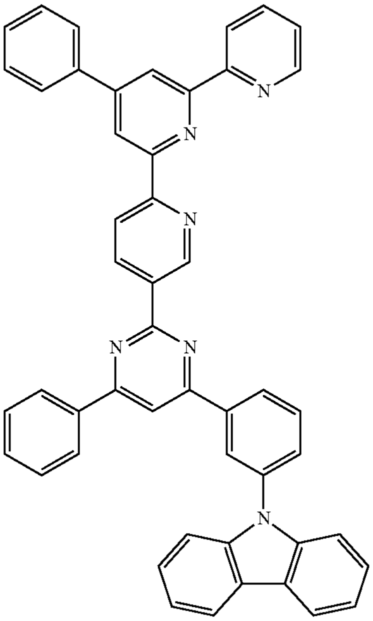
231
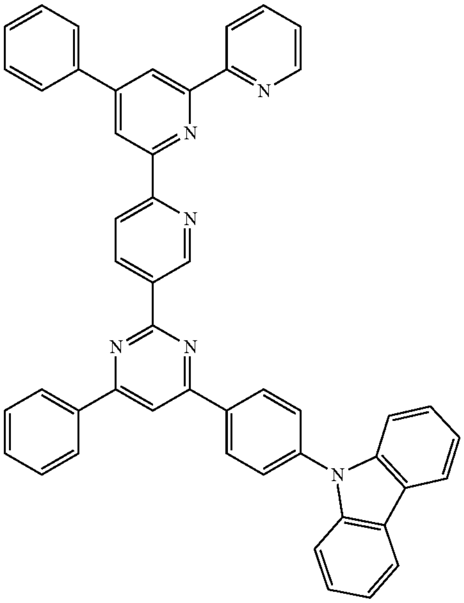
232
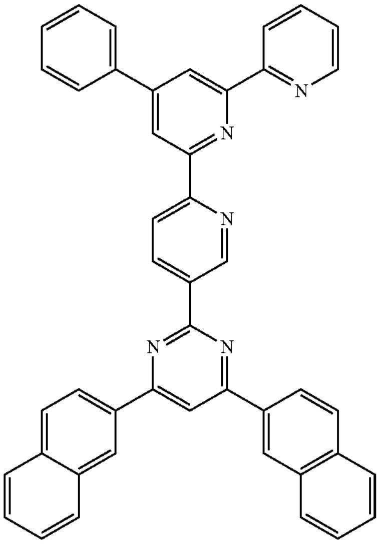

-continued
233
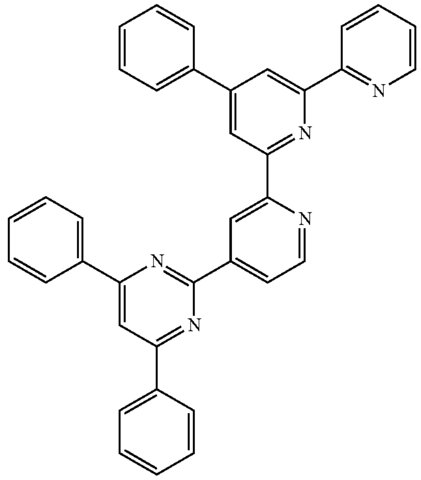
234
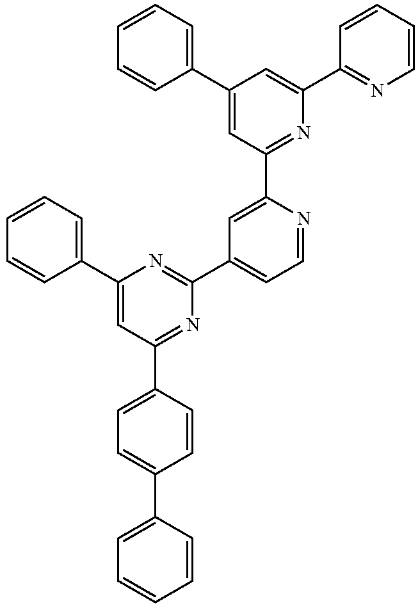
235
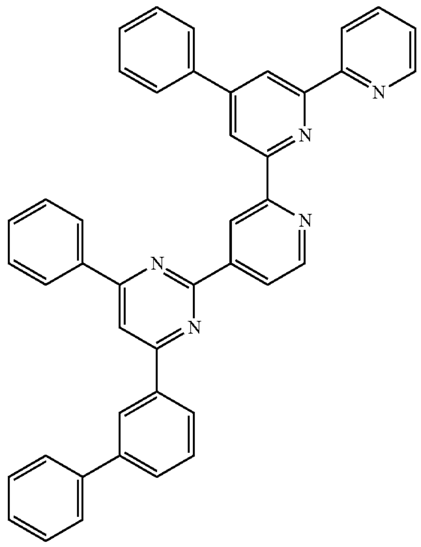
236
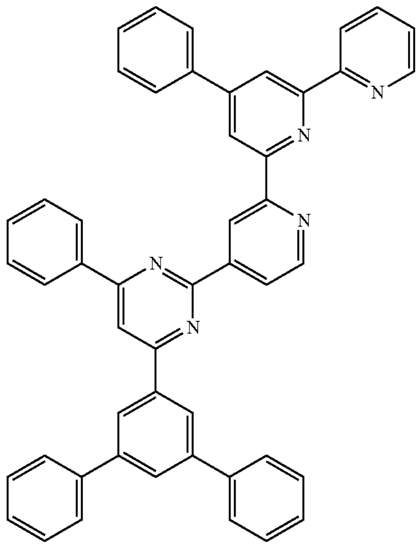

-continued
237
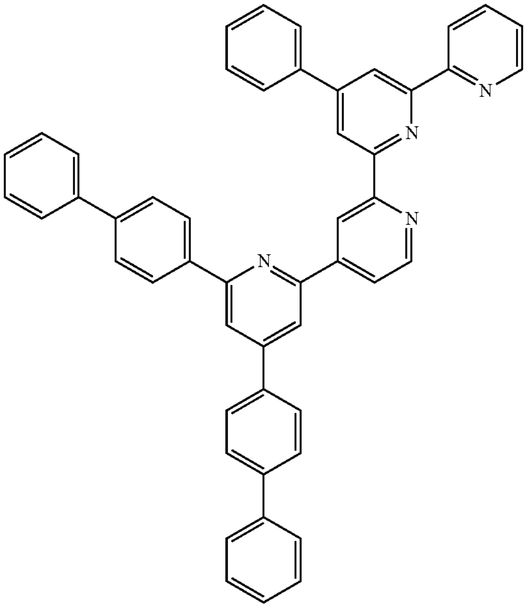
238
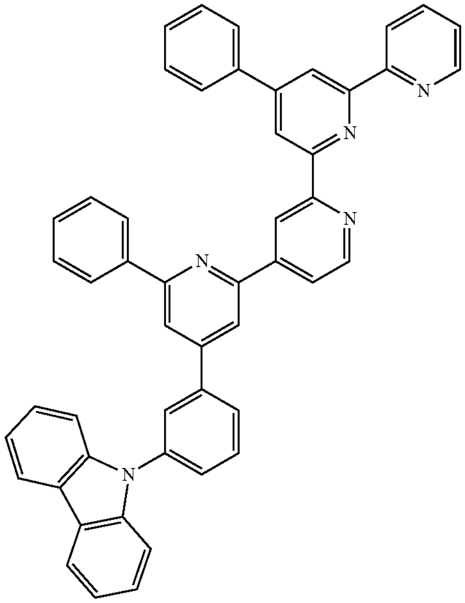
239
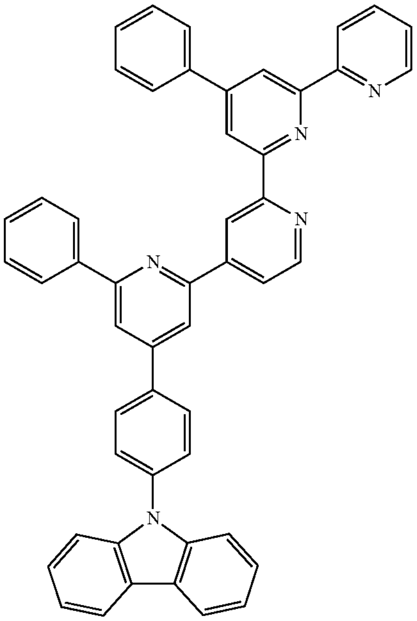
240
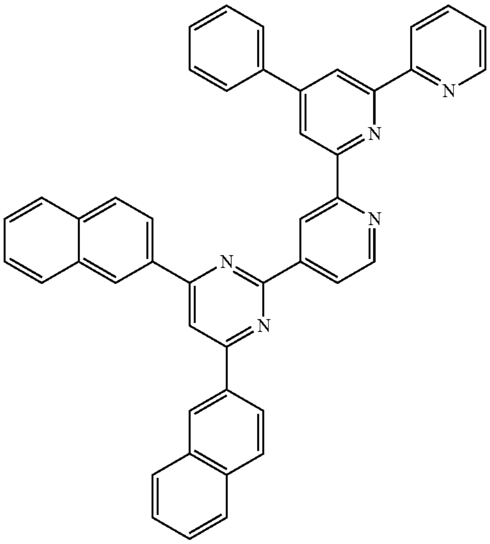

-continued
241
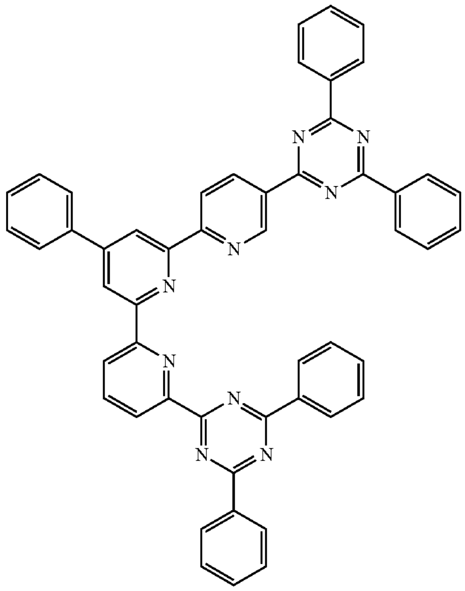
243
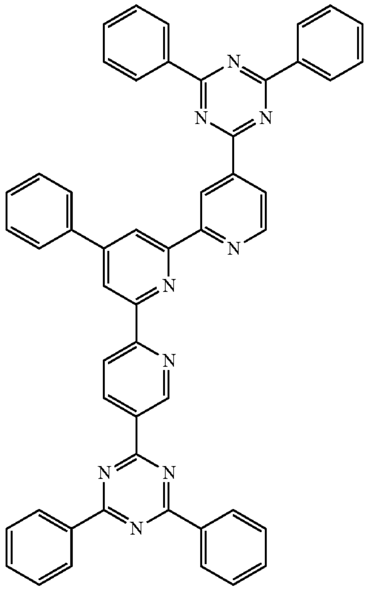
242
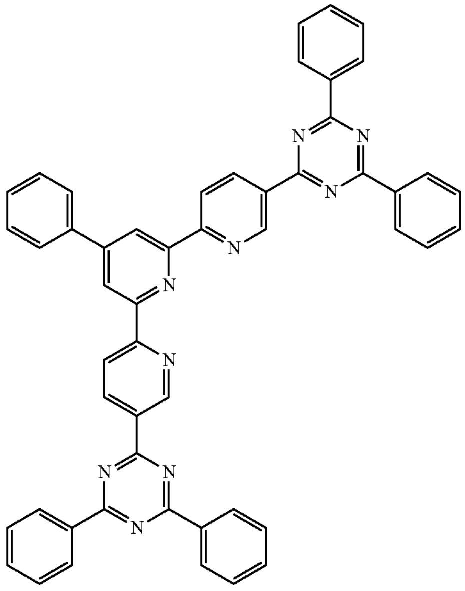
244
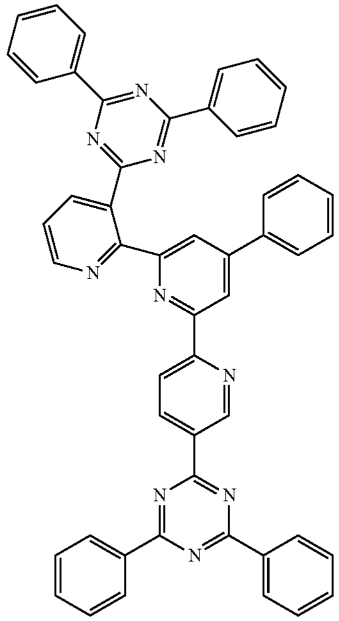

-continued
245
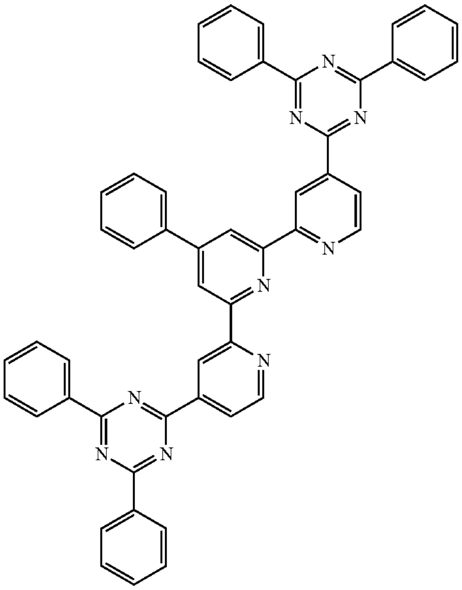
246
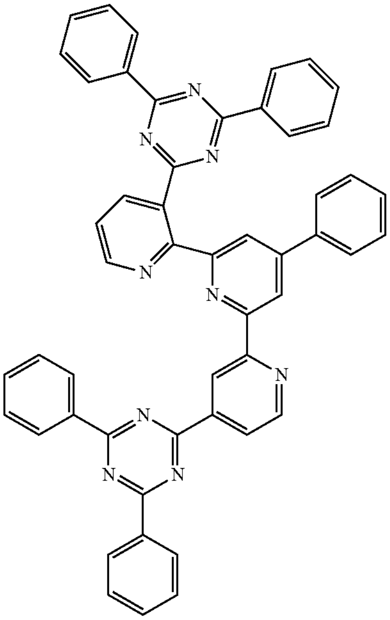
-continued
247
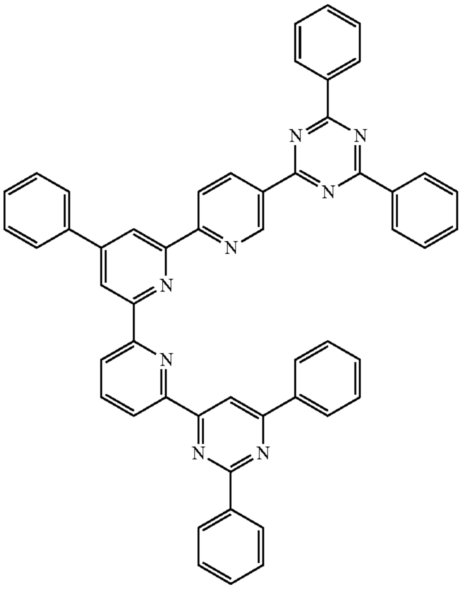
248
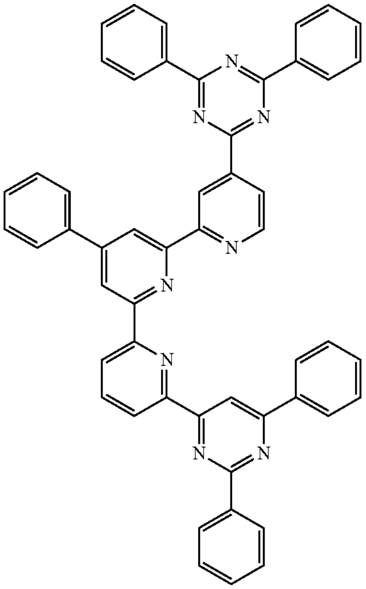

-continued
249
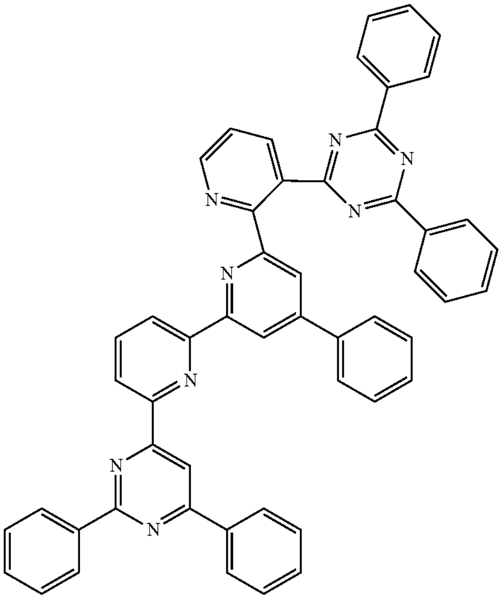
250
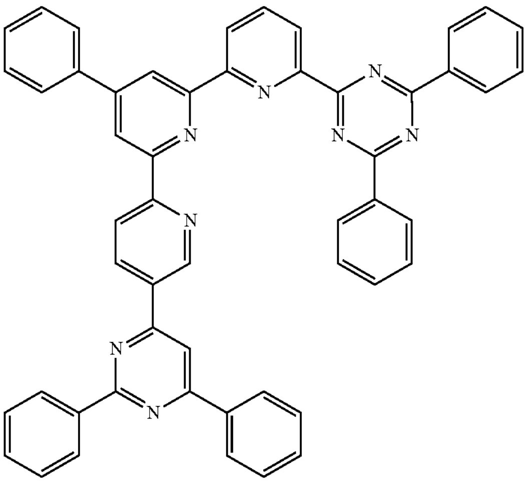
-continued
251
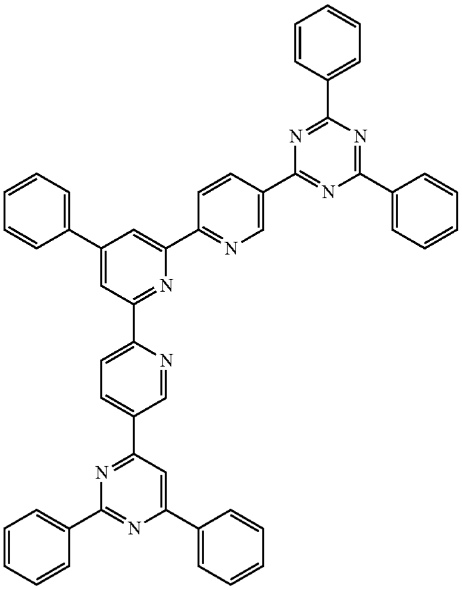
252
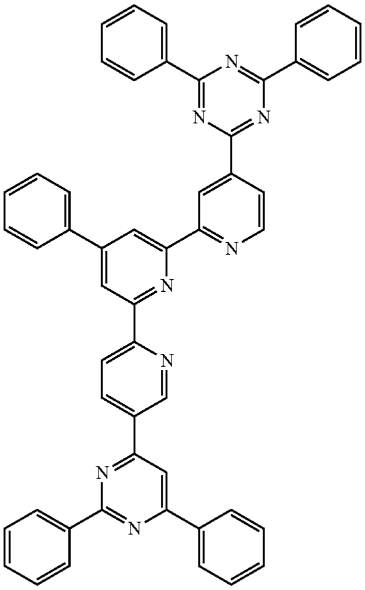

253
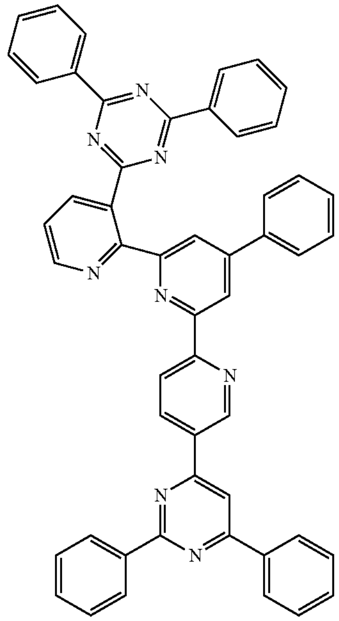
254
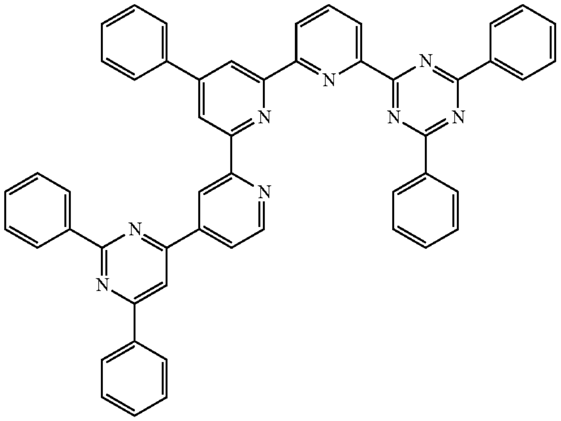
255
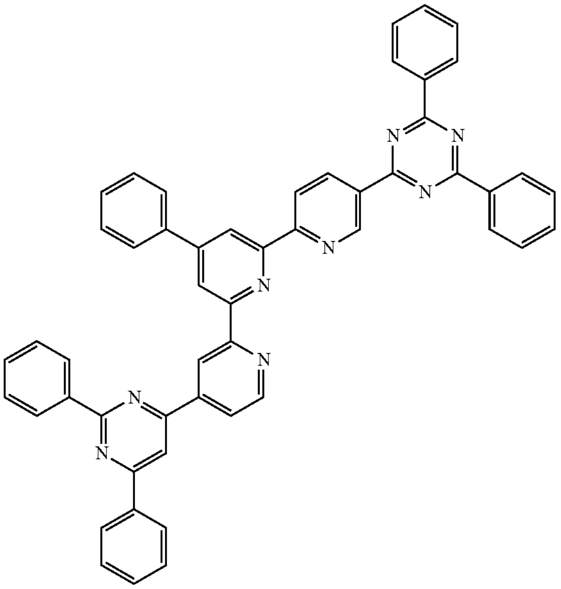
256
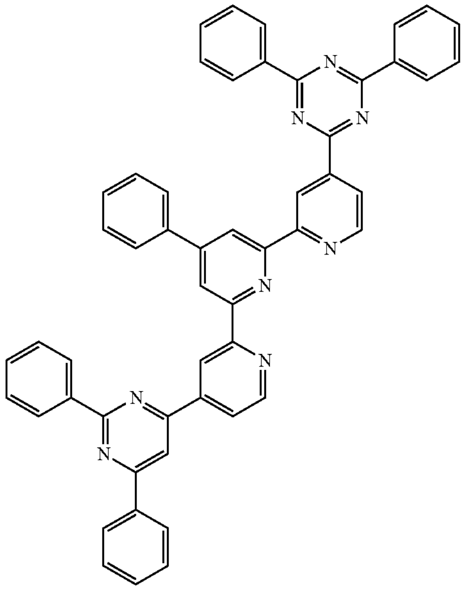

-continued
257
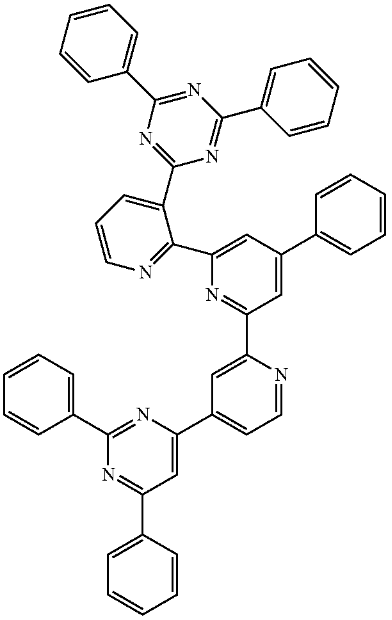
258
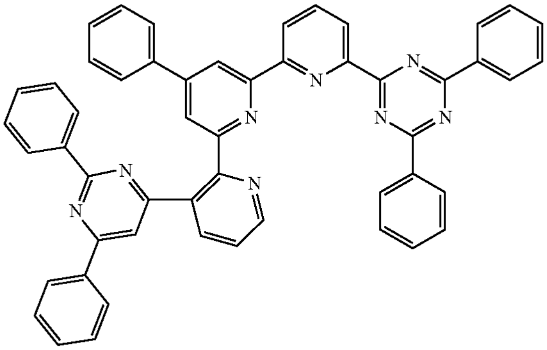
259
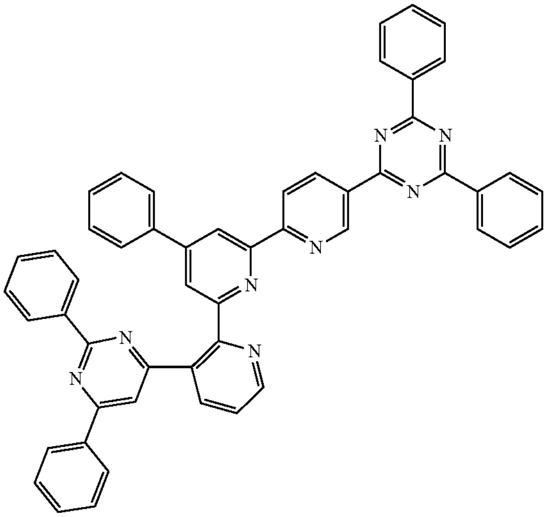
-continued
260
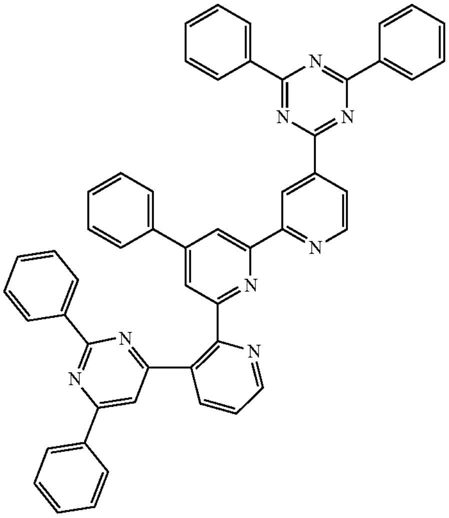
261
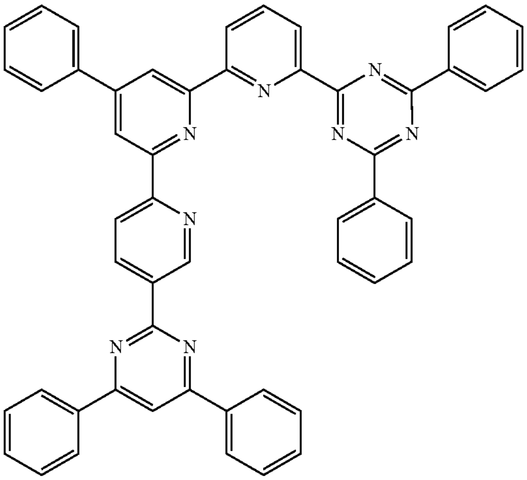
262
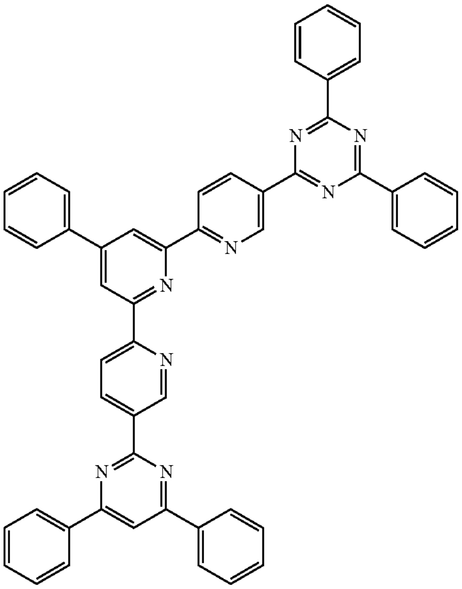

-continued
263
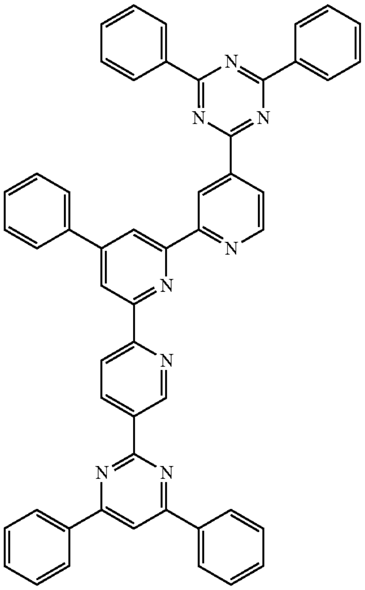
264
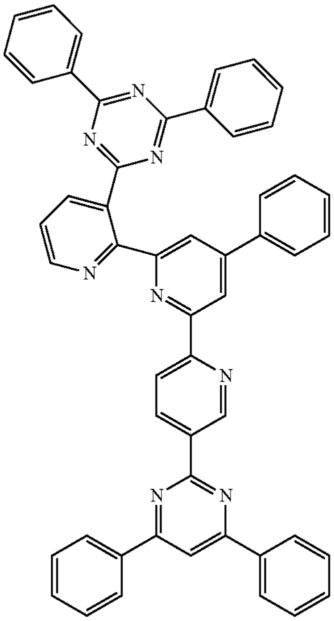
265
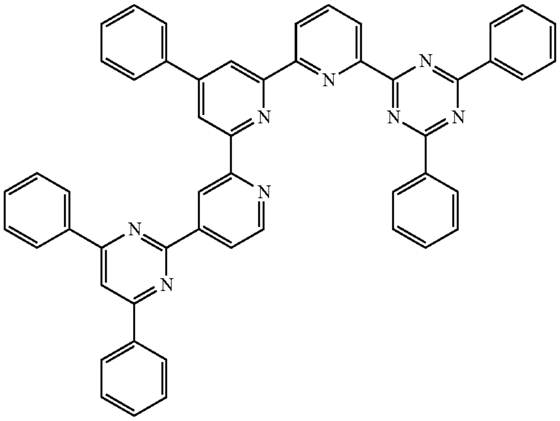
-continued
266
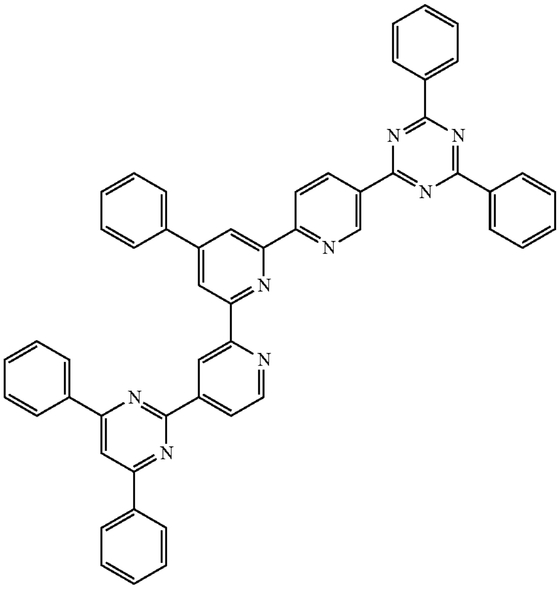
267
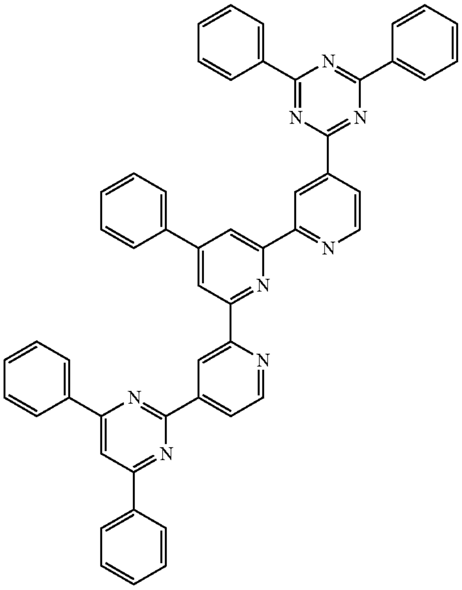

-continued
268
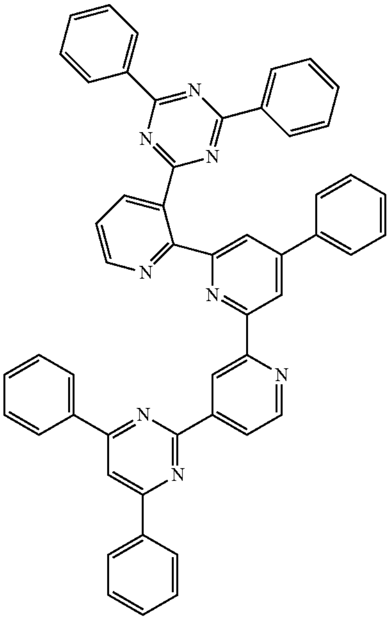
269
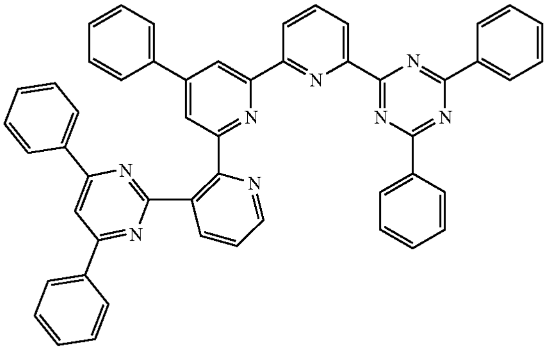
270
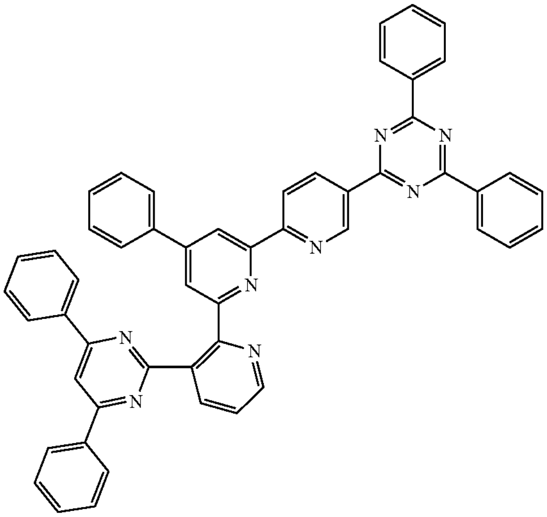
-continued
271
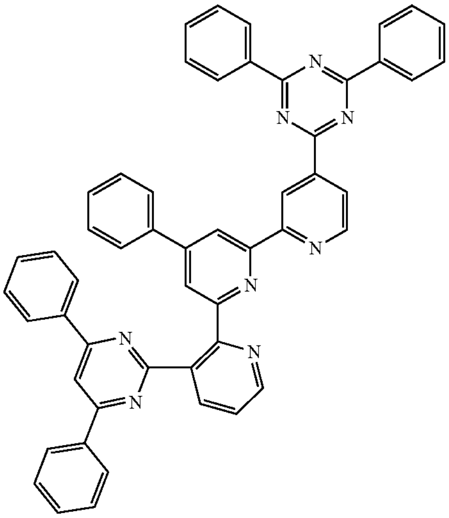
272
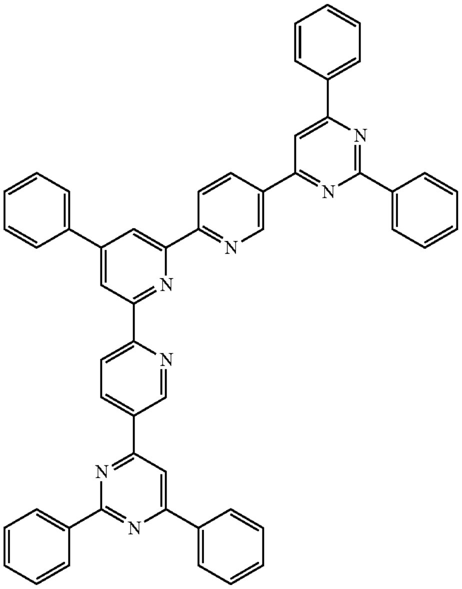

-continued
273
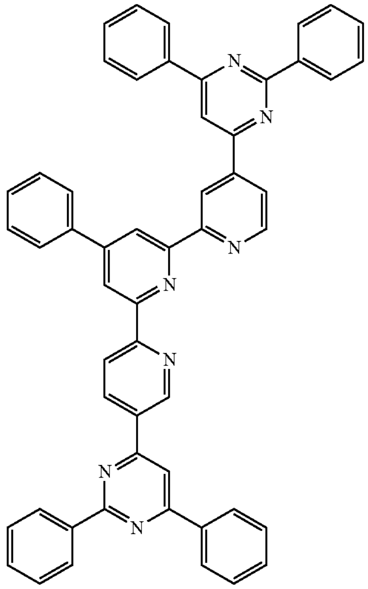
274
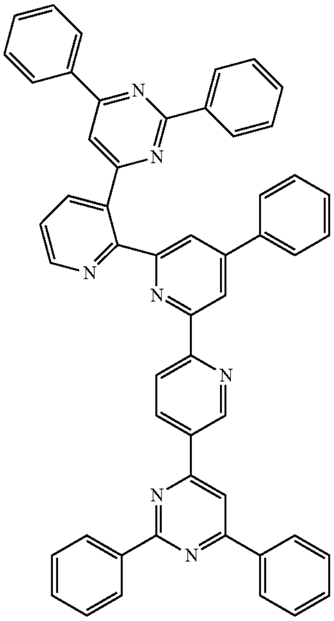
-continued
275
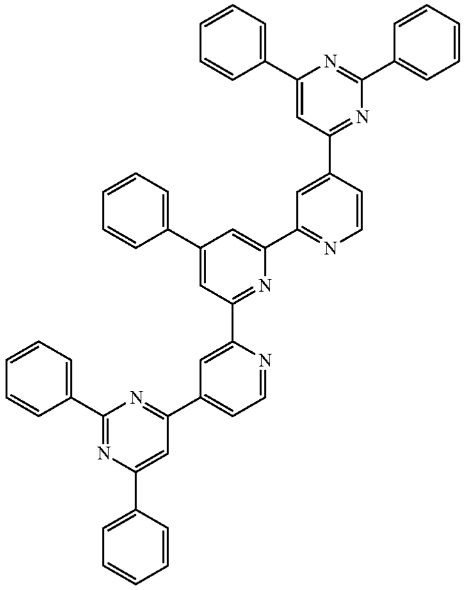
276
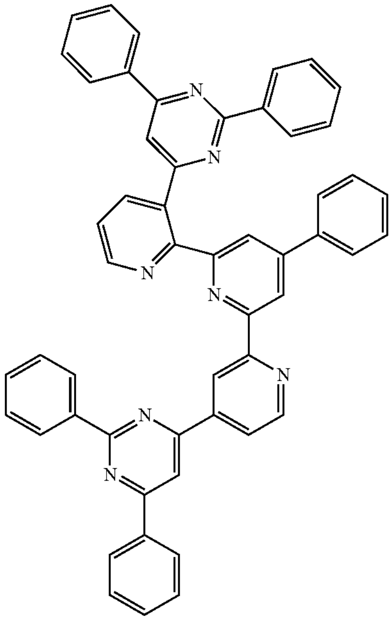

-continued
277
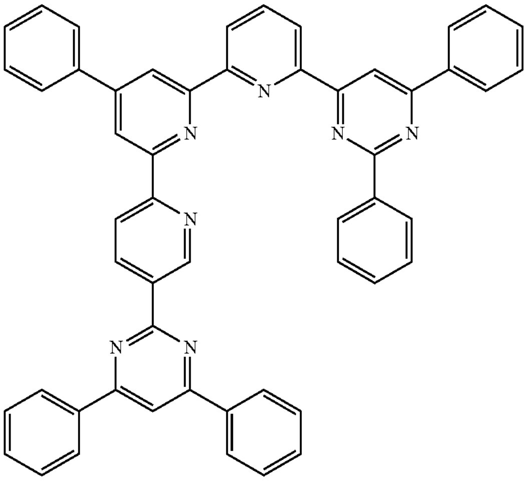
278
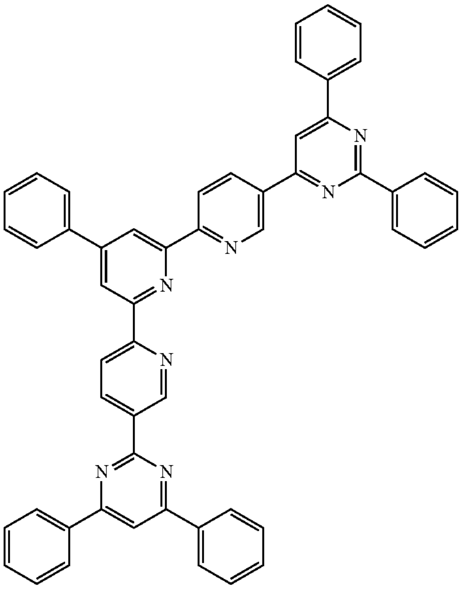
-continued
279
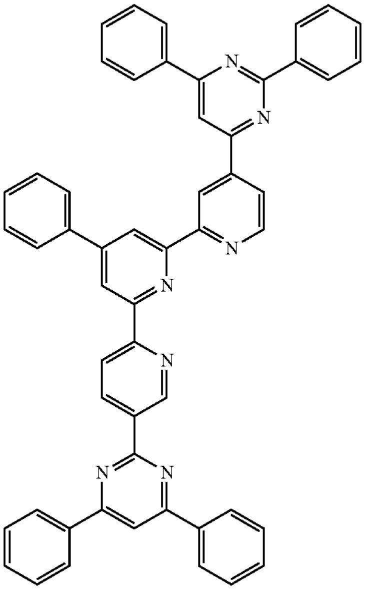
280
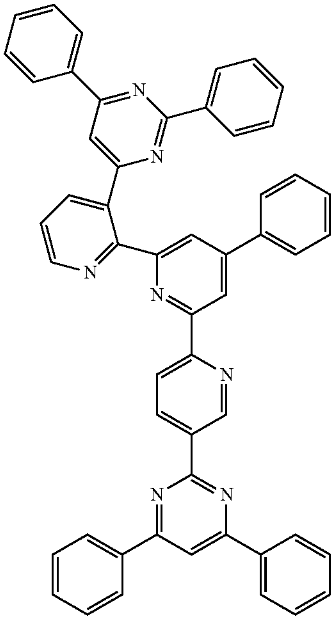
281
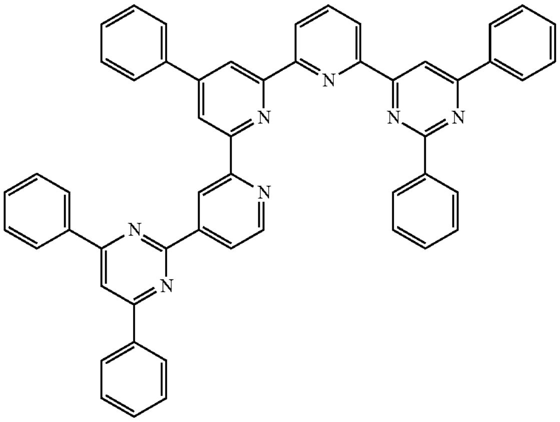

-continued
282
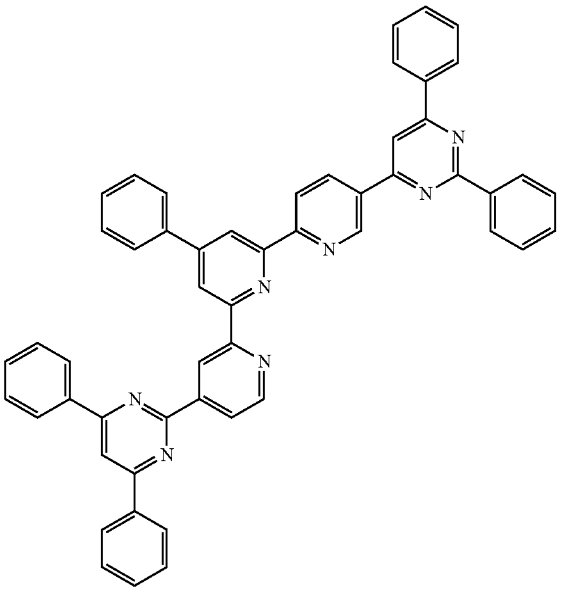
283
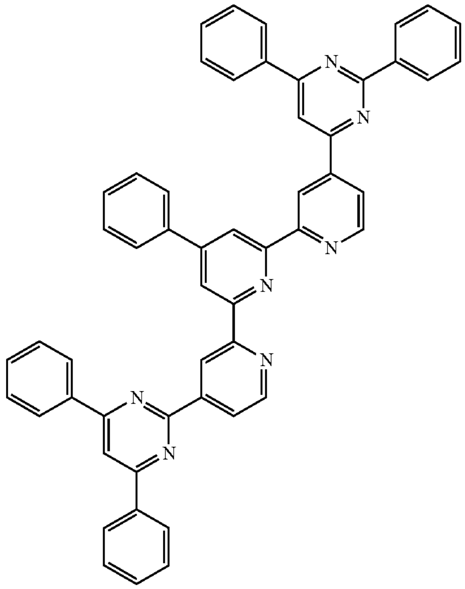
-continued
284
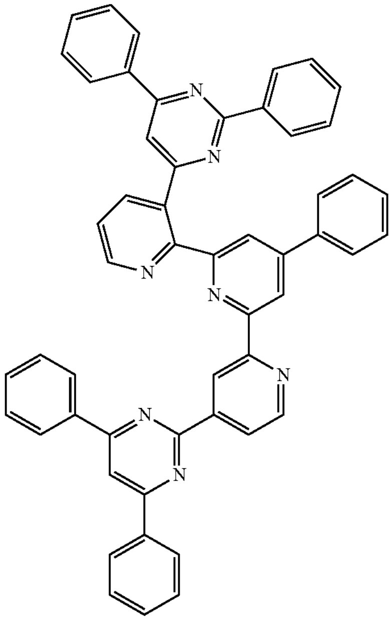
285
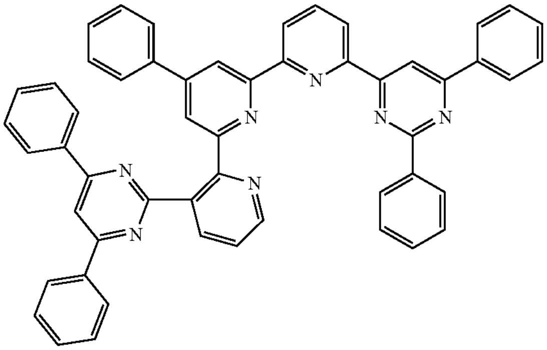
286
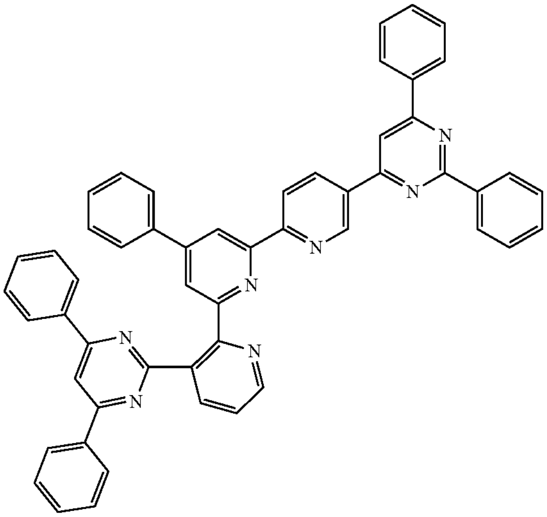

-continued
287
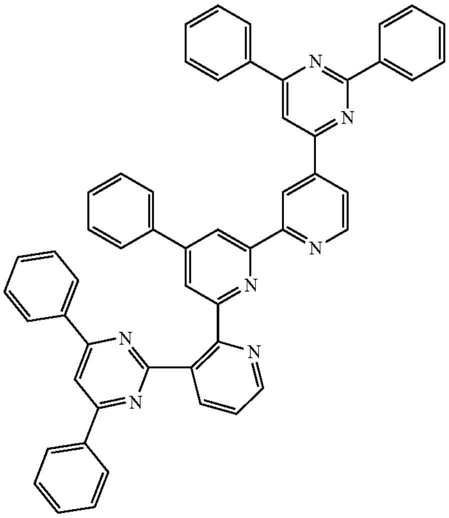
289
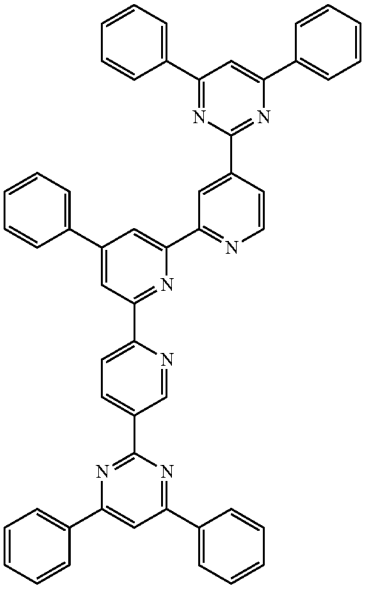
288
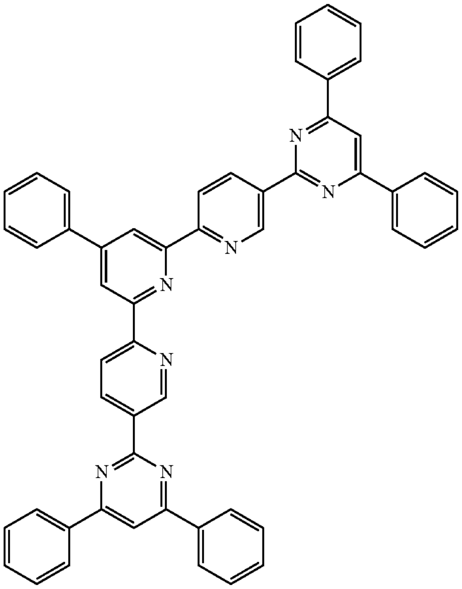
290
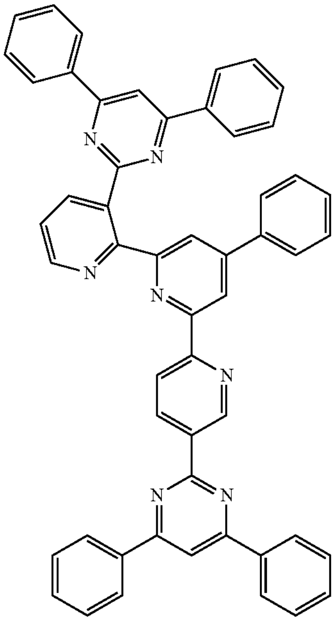

-continued
291
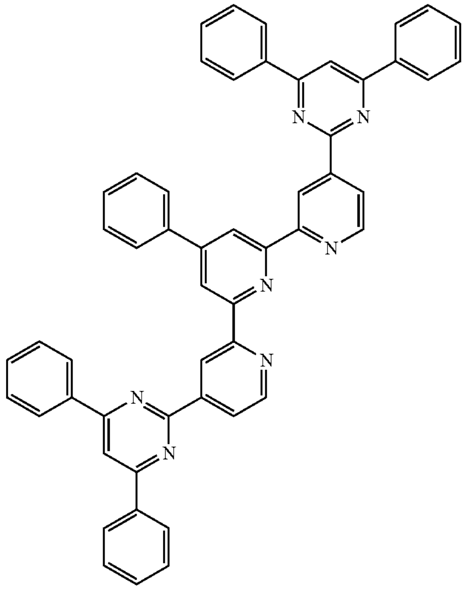
292
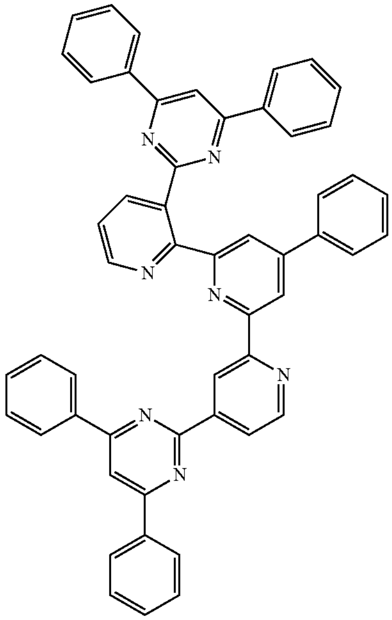
-continued
293
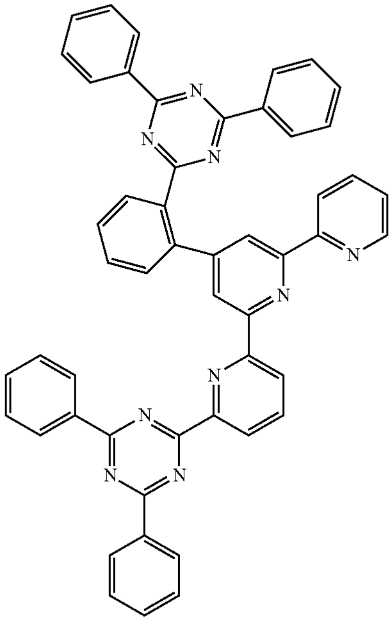
294
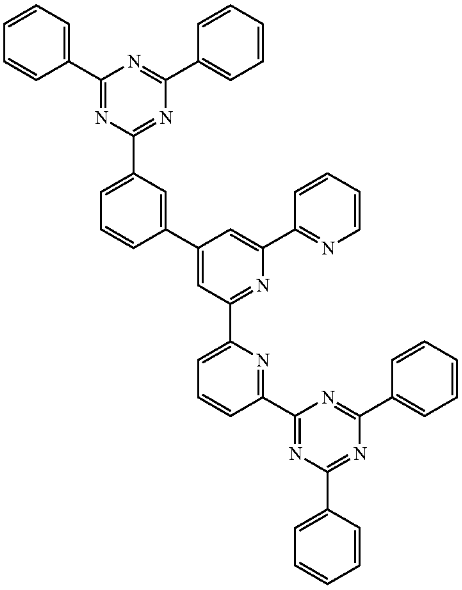

-continued
295
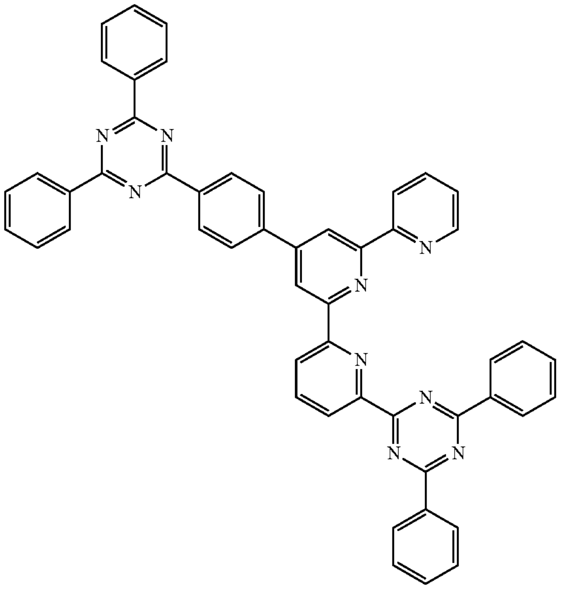
296
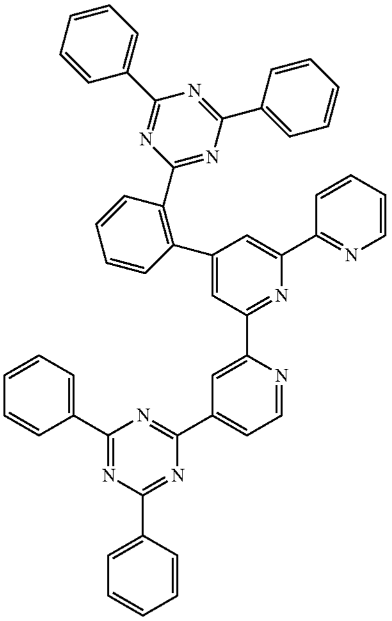
-continued
297
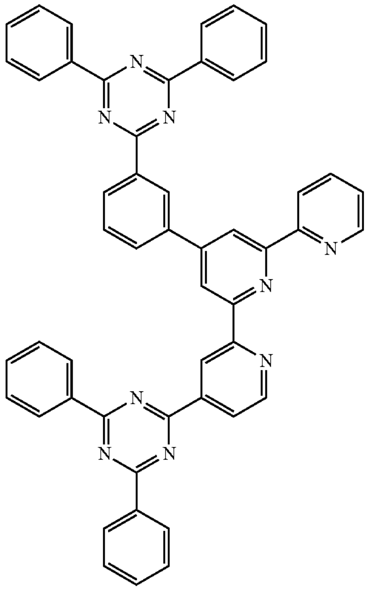
298
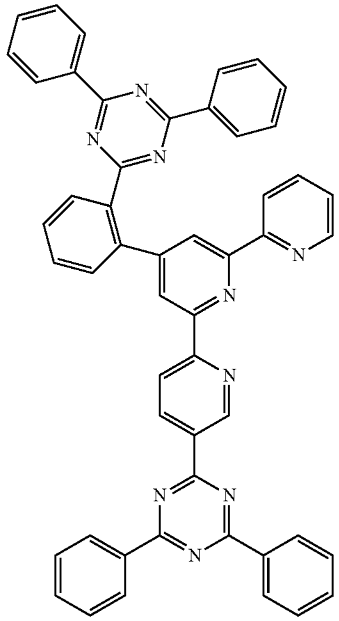

-continued
299
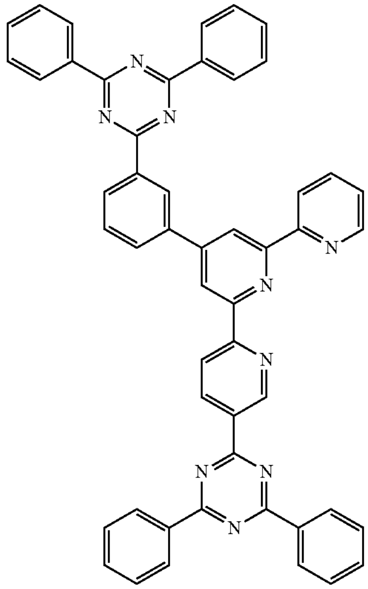
300
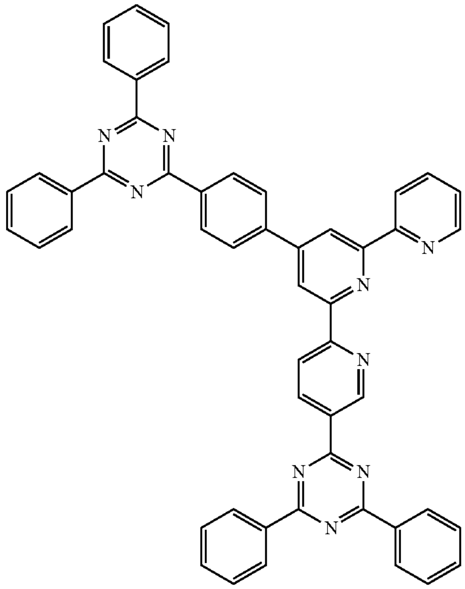
-continued
301
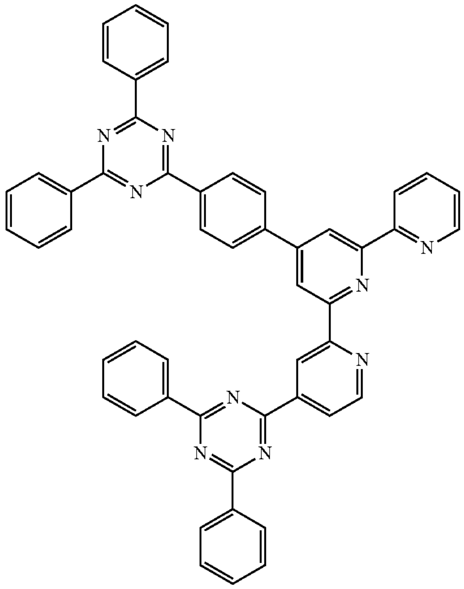
302
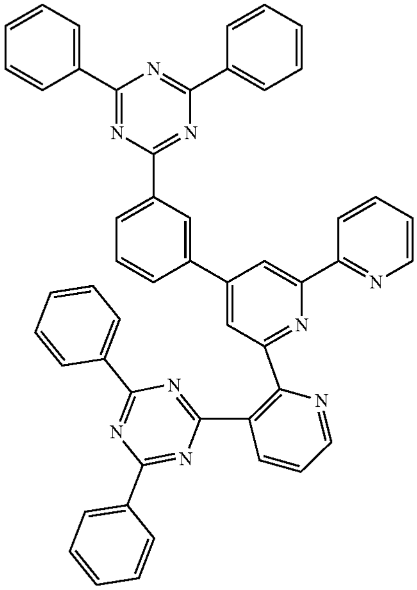

-continued
303
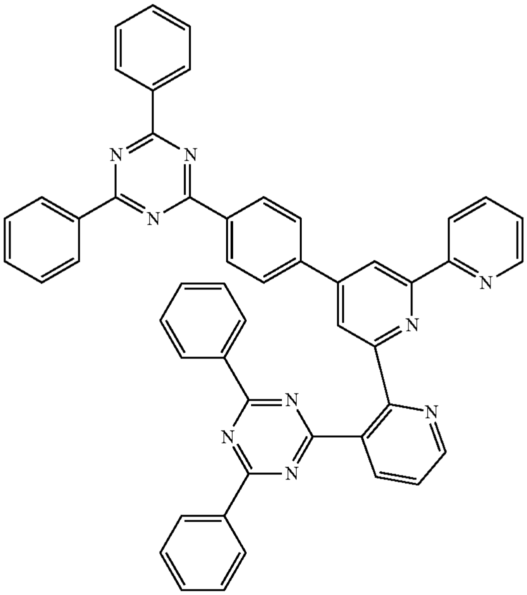
304
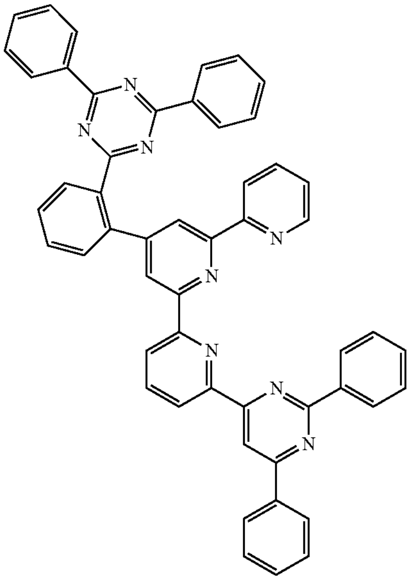
-continued
305
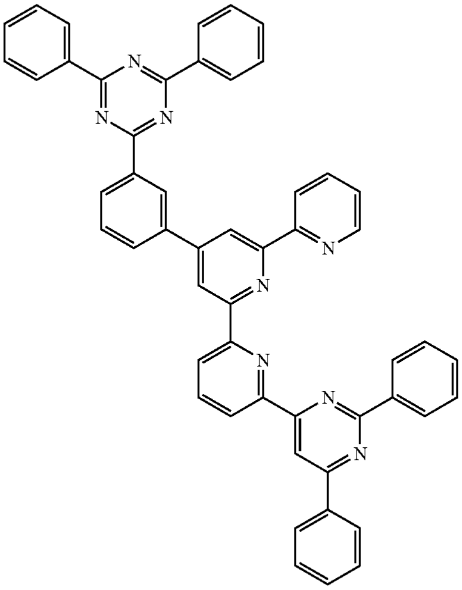
306
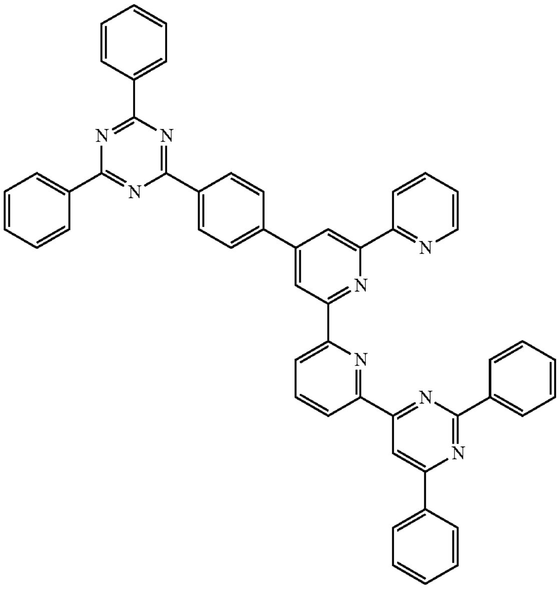

-continued
307
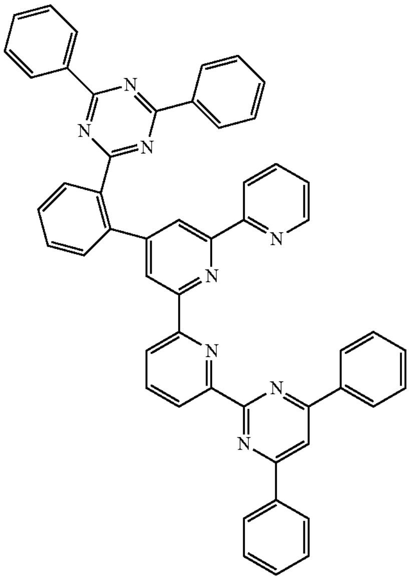
308
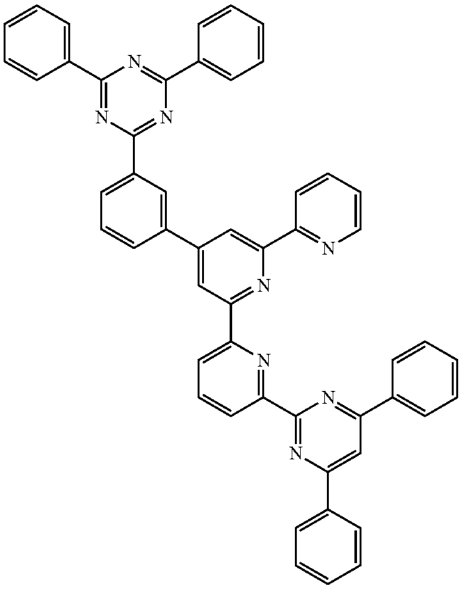
-continued
309
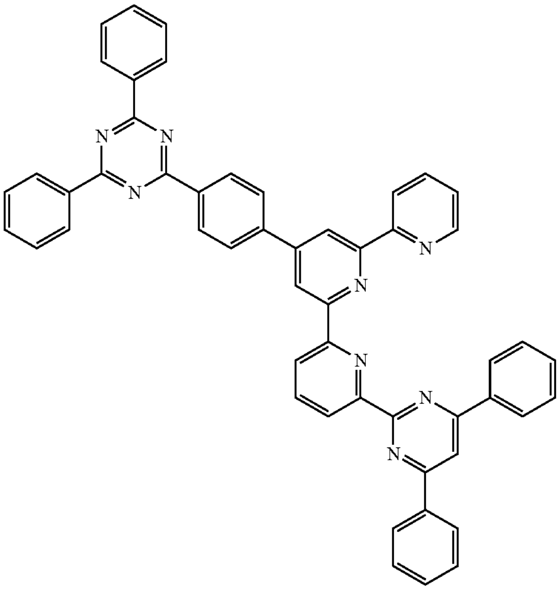
310
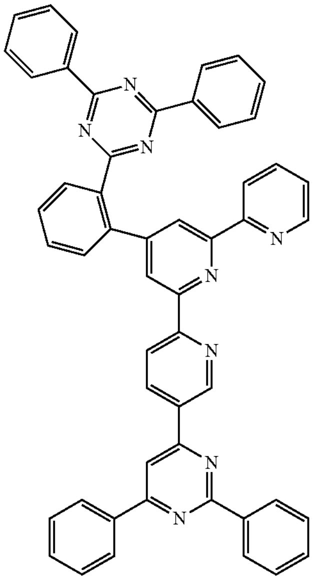

-continued
311
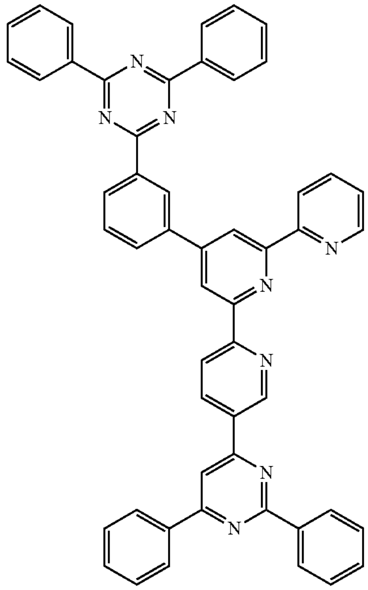
312
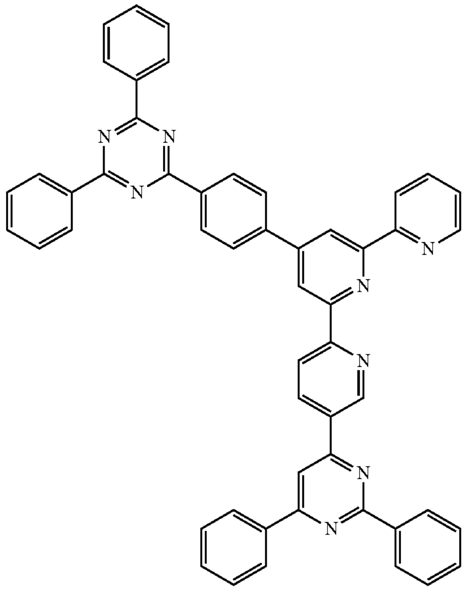
-continued
313
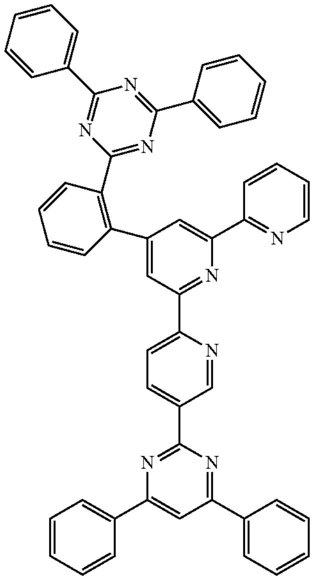
314
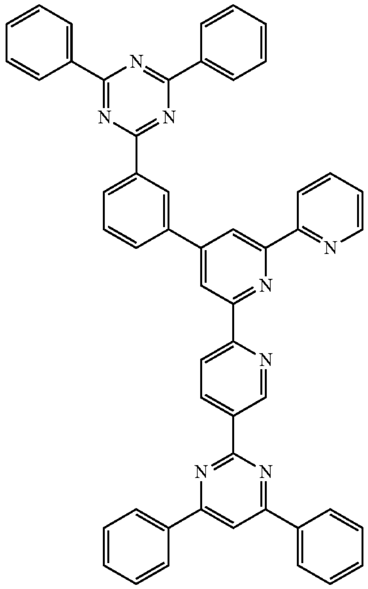

-continued
315
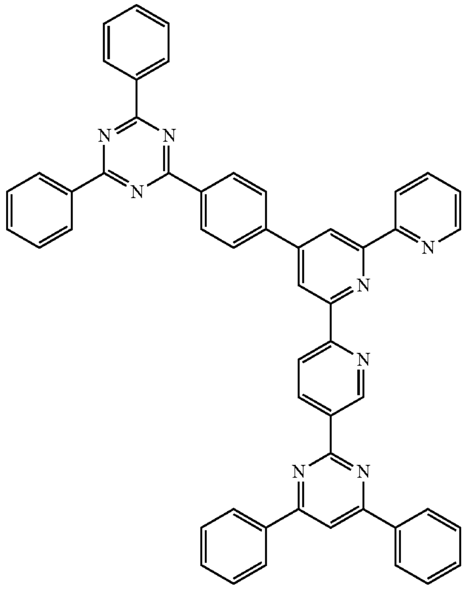
316
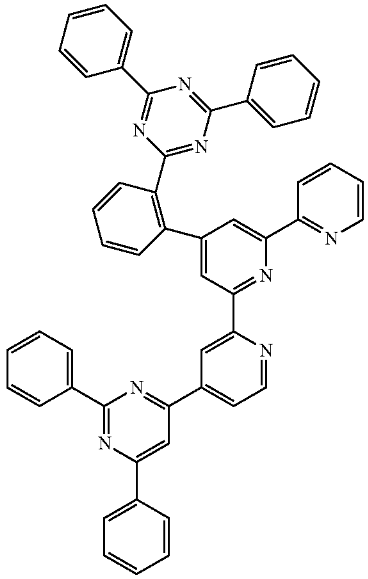
-continued
317
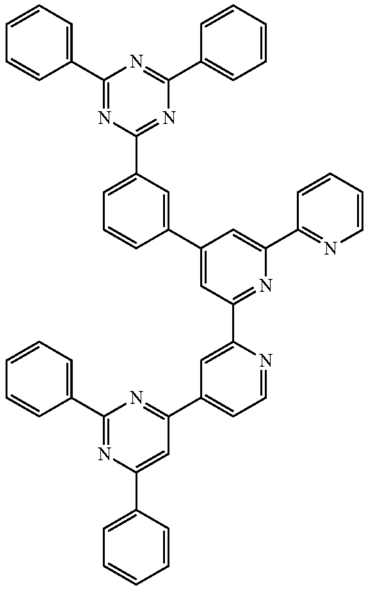
318
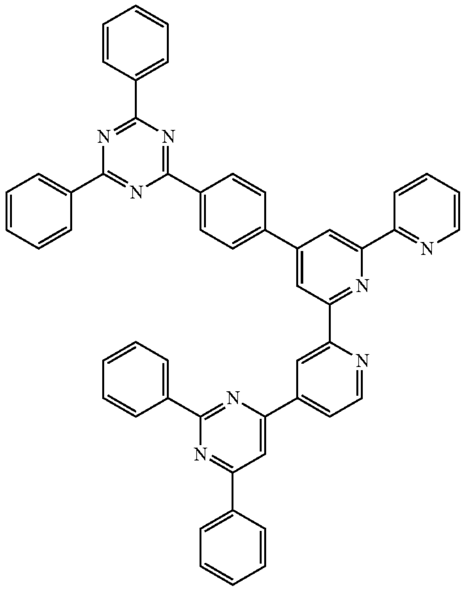

-continued
319
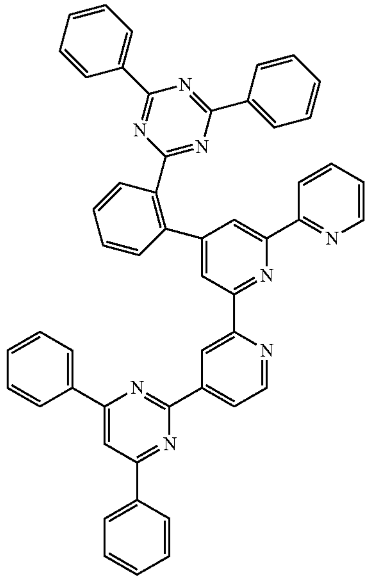
320
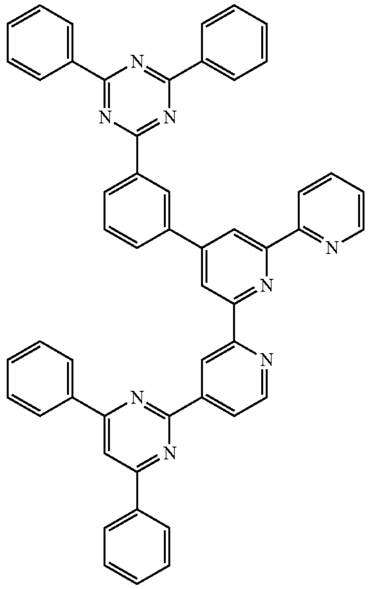
-continued
321
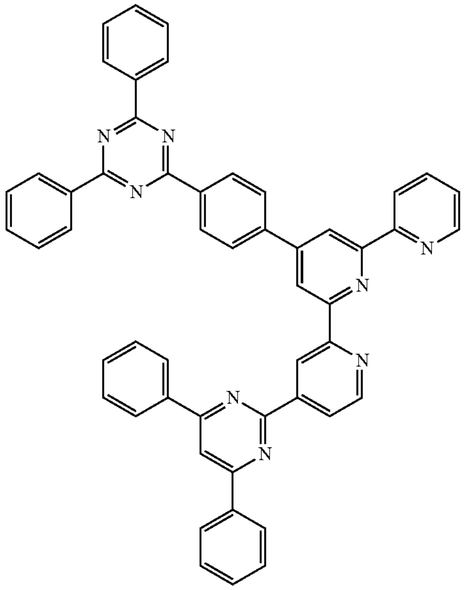
322
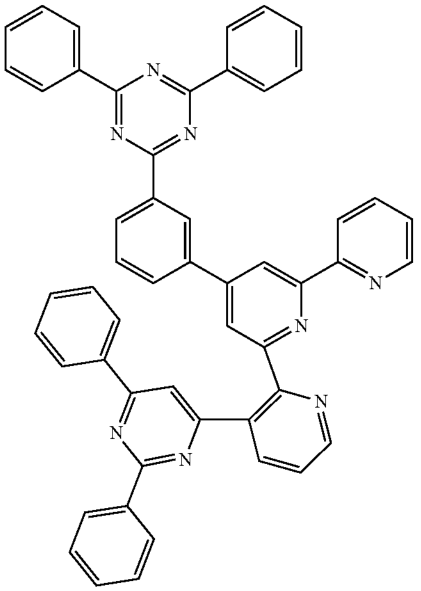

323
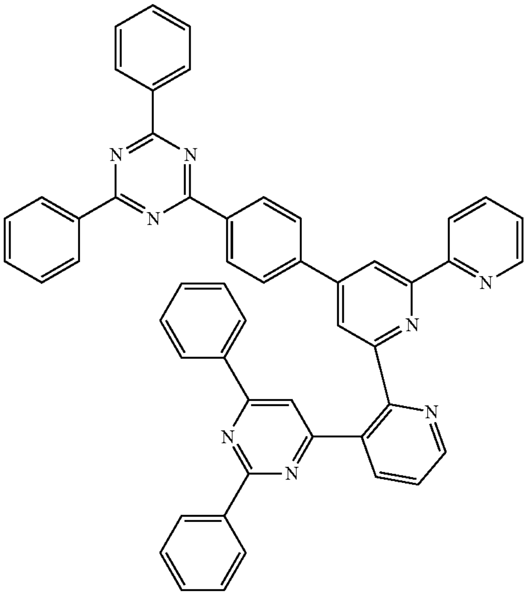
324
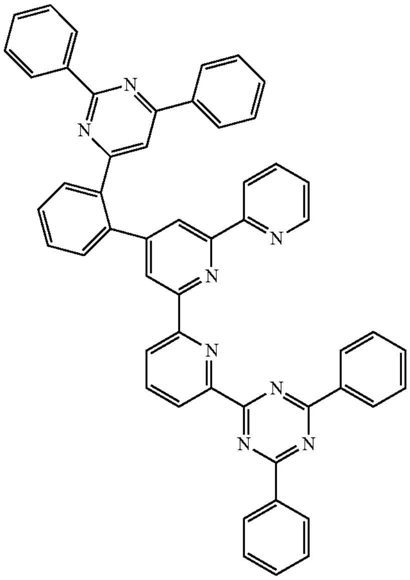
325
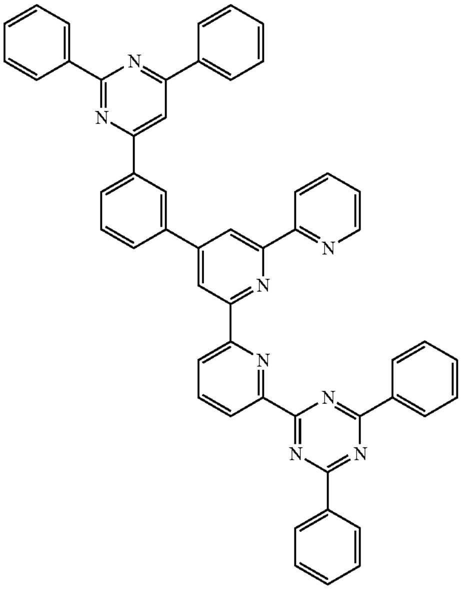
326
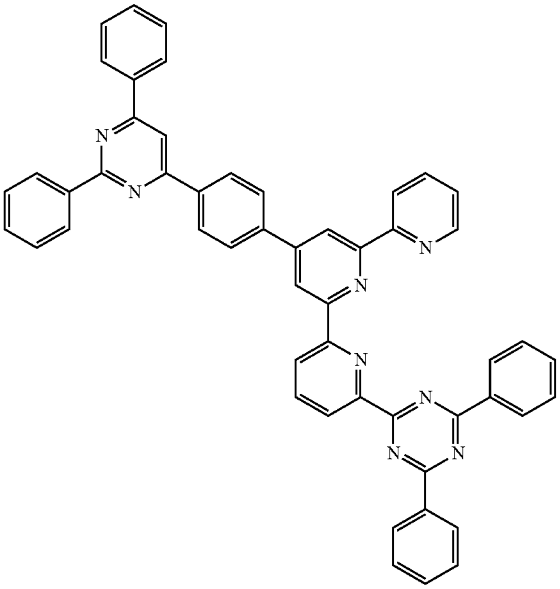

-continued
327
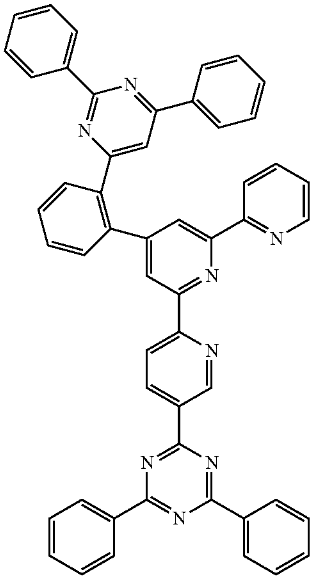
328
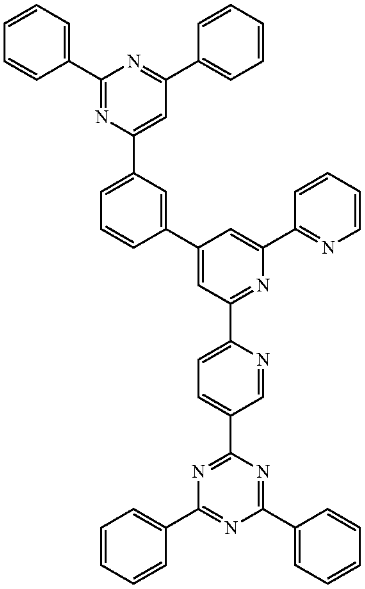
-continued
329
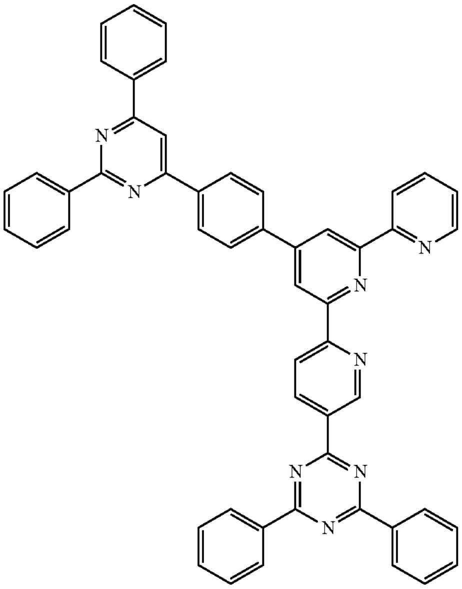
330
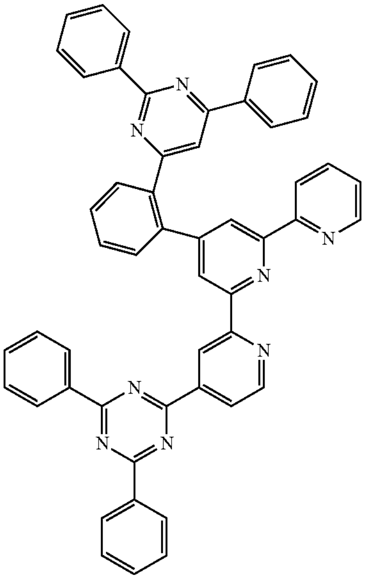

-continued
331
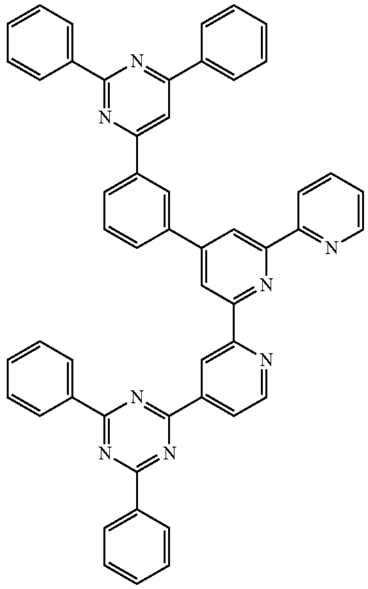
332
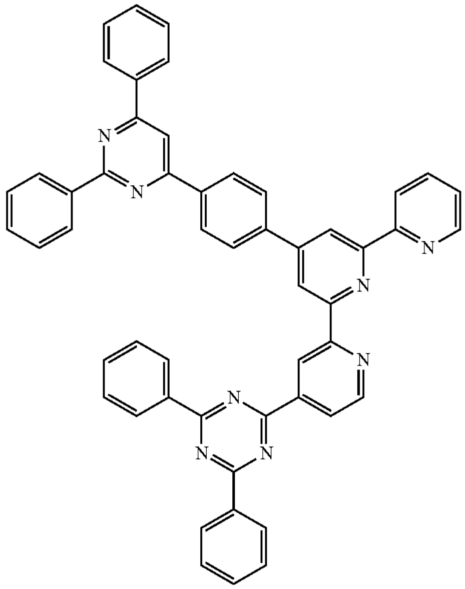
-continued
333
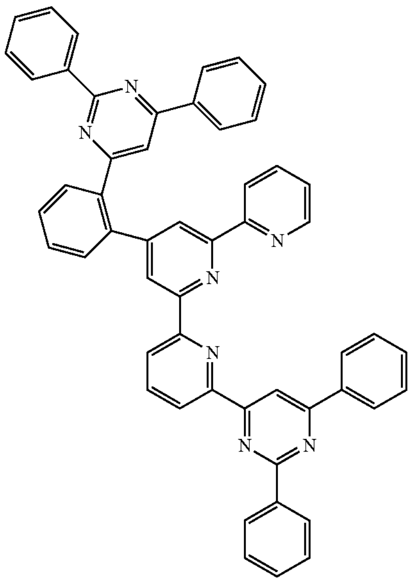
334
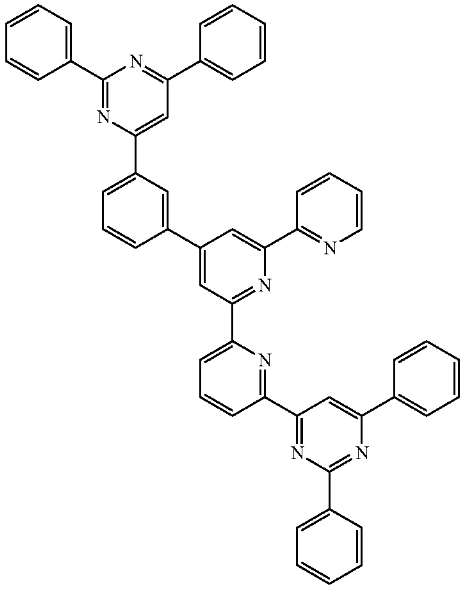

-continued
335
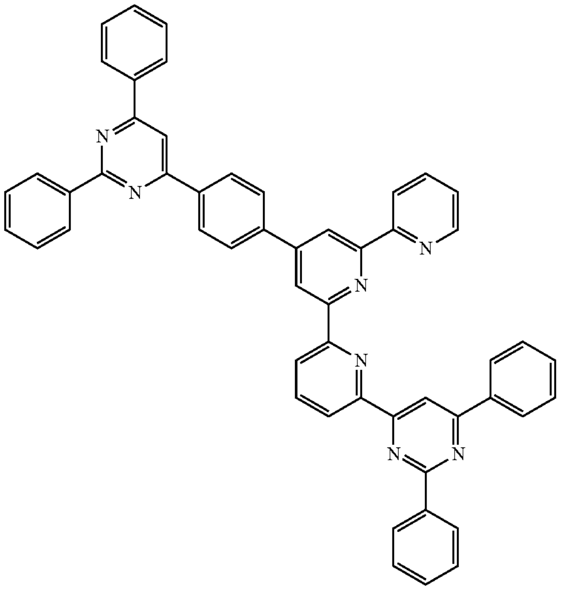
336
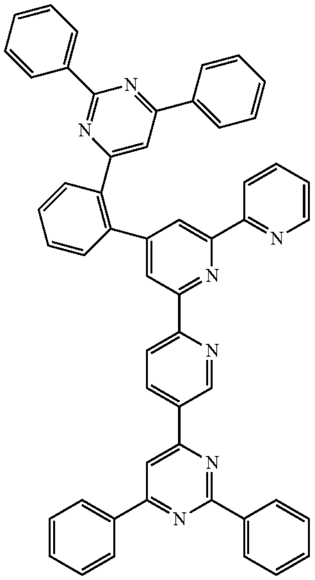
-continued
337
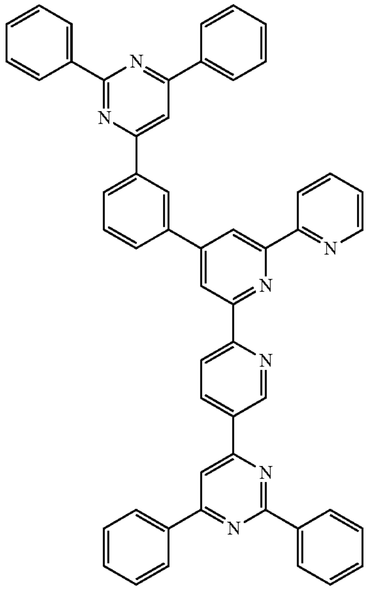
338
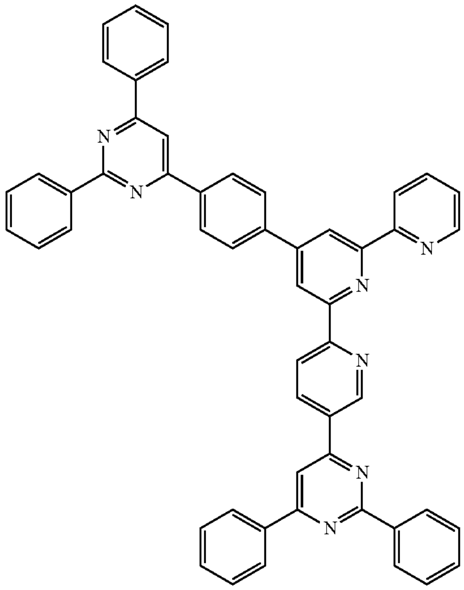

-continued
339
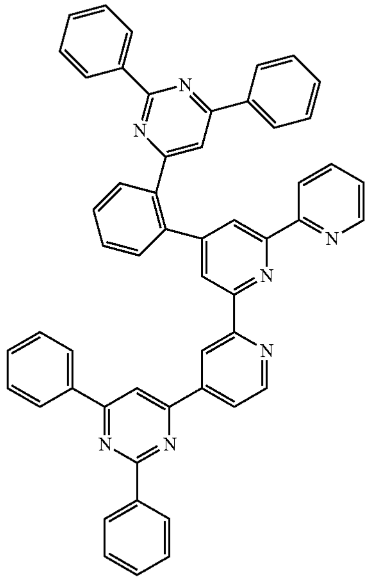
340
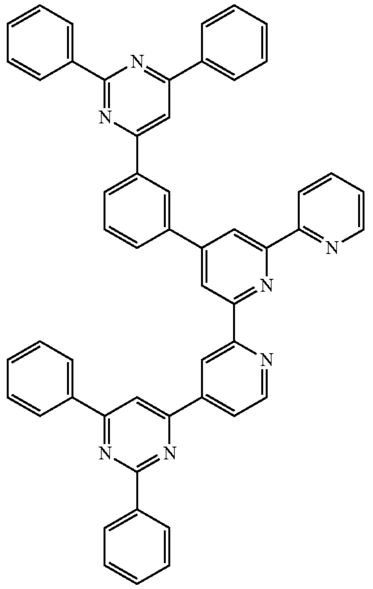
-continued
341
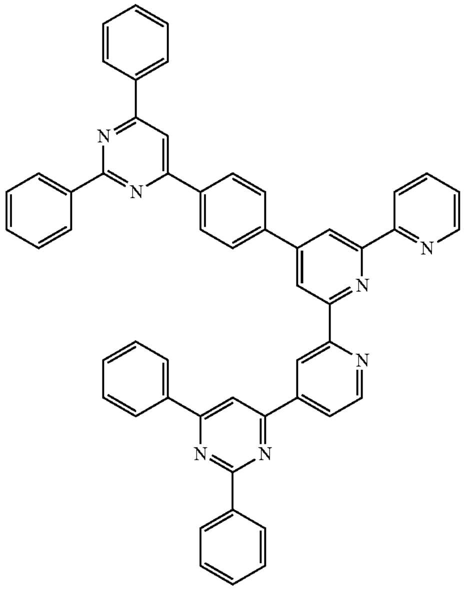
342
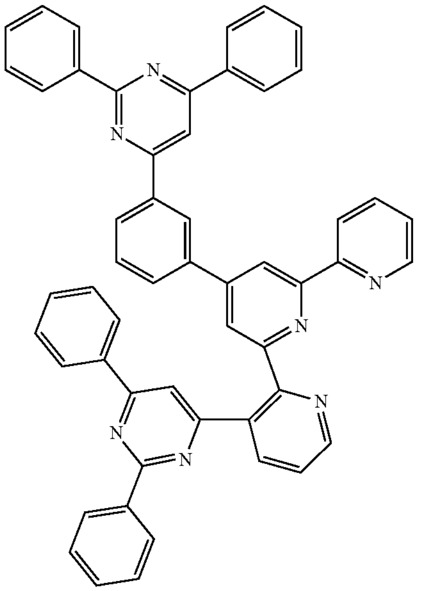

-continued
343
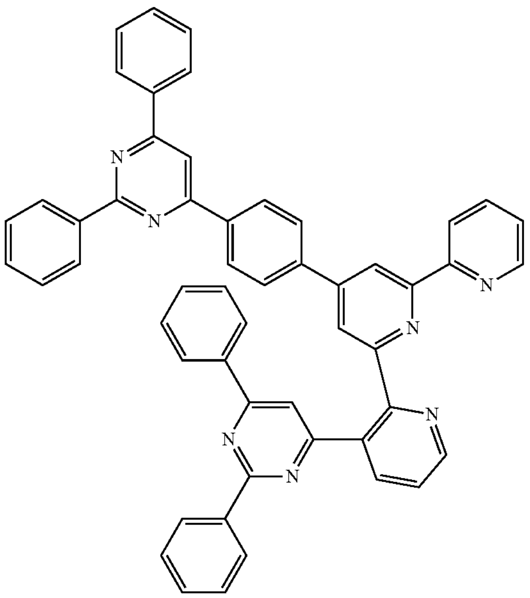
344
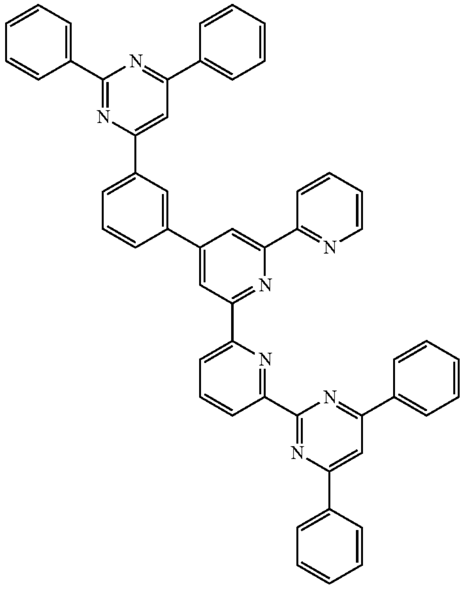
-continued
345
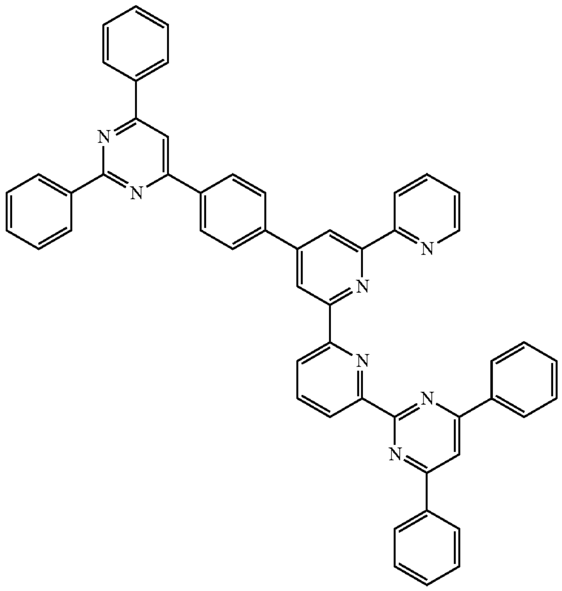
346
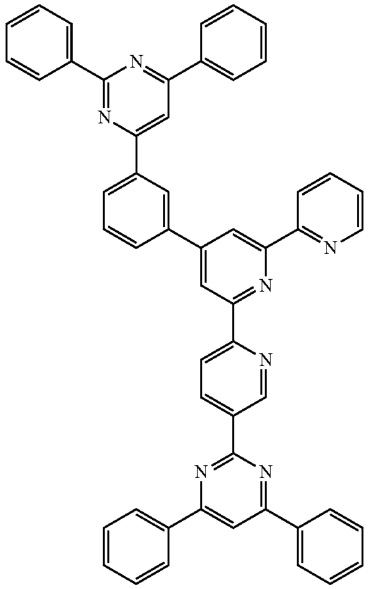

-continued
347
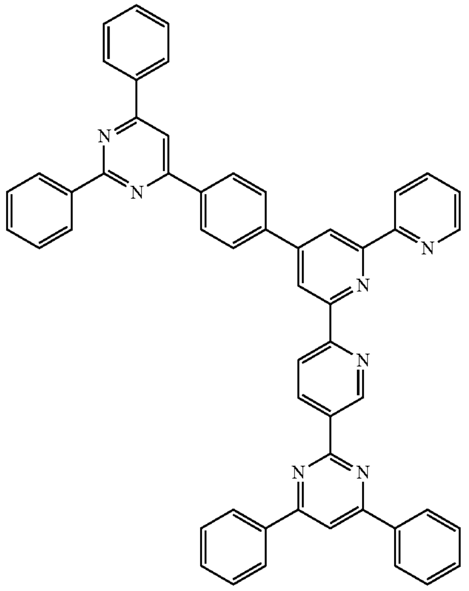
348
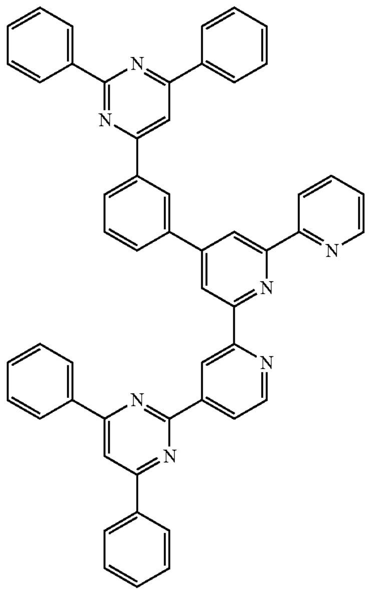
-continued
349
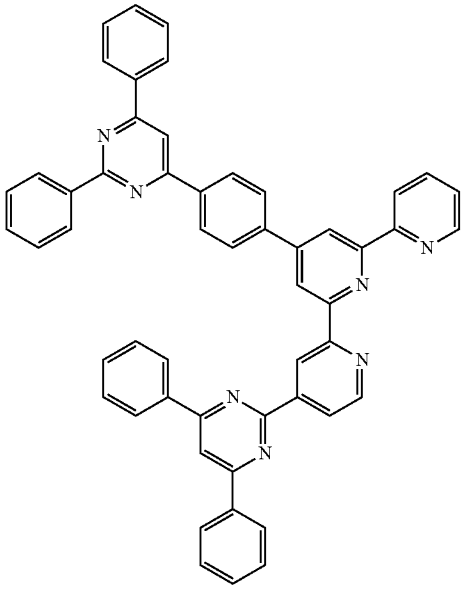
350
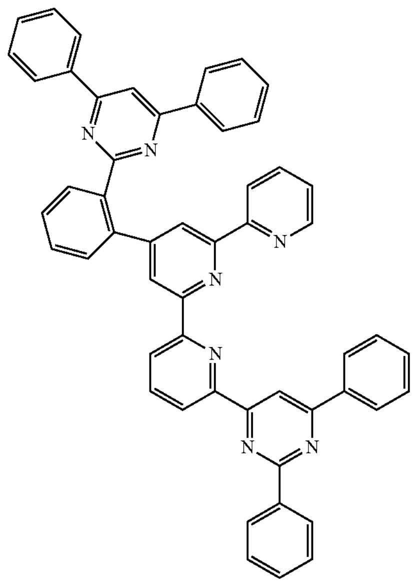

-continued
351
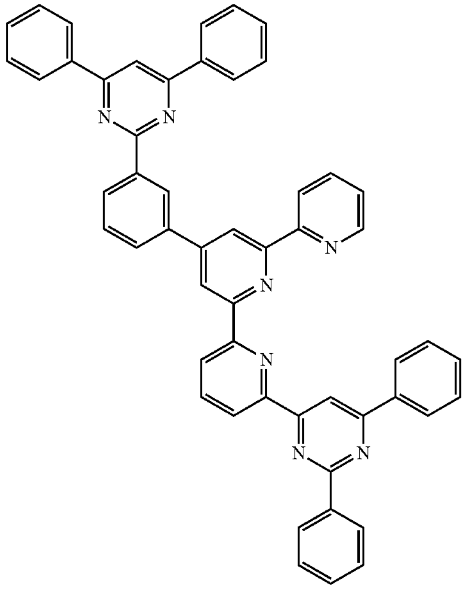
352
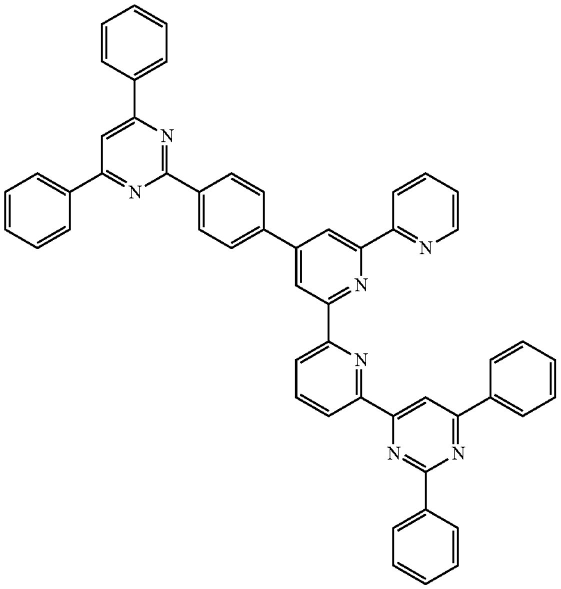
-continued
353
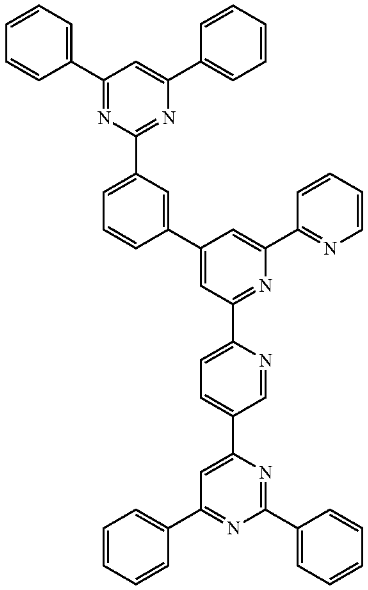
354
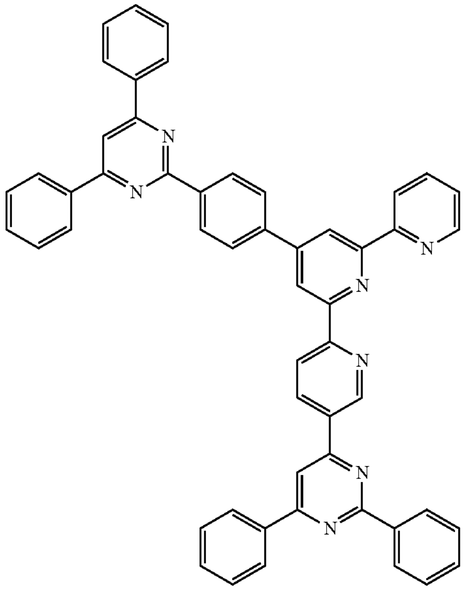

-continued
355
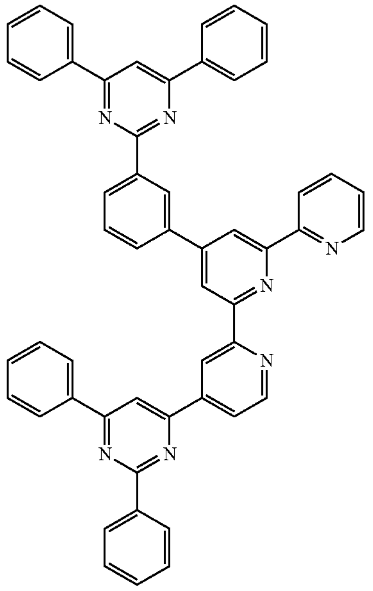
256
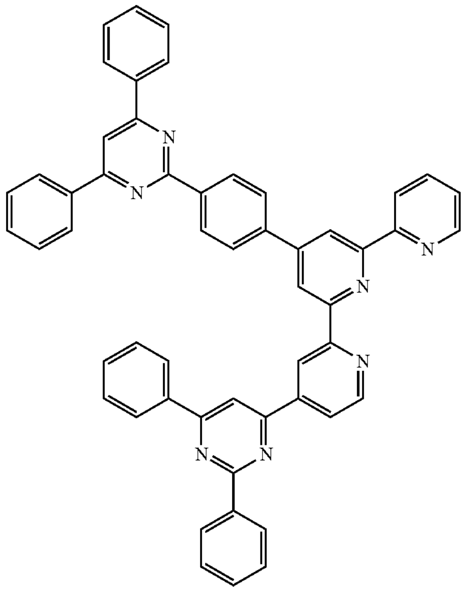
-continued
357
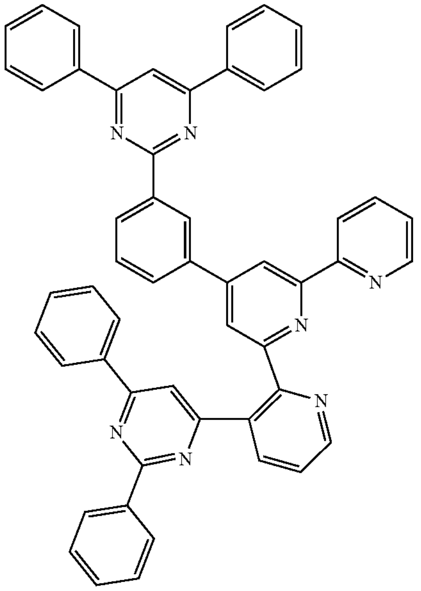
358
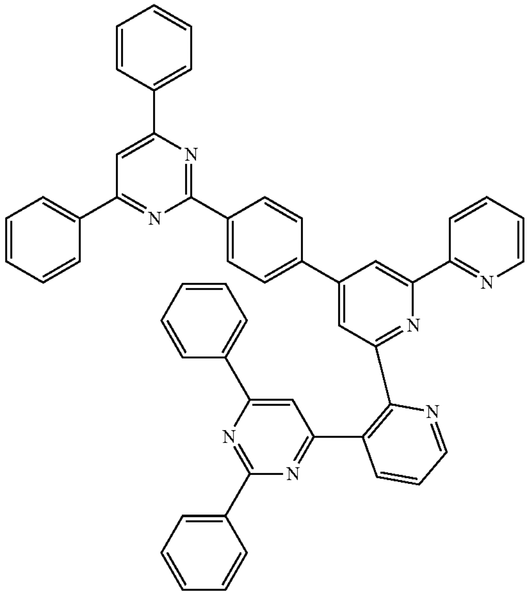

-continued
359
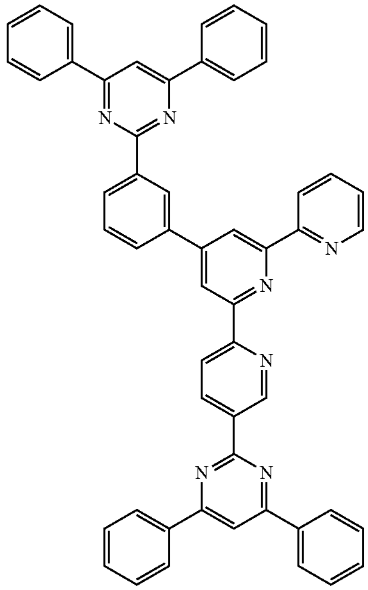
360
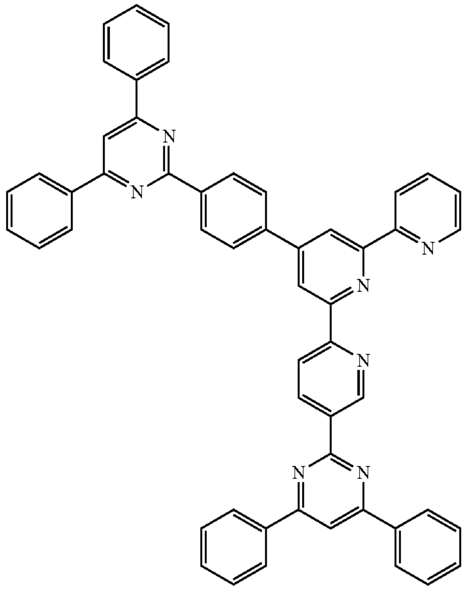
-continued
361
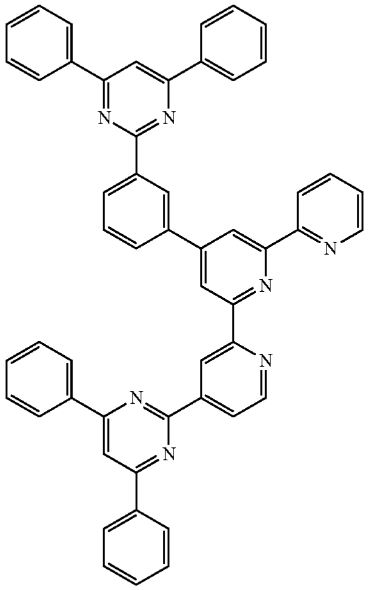
362
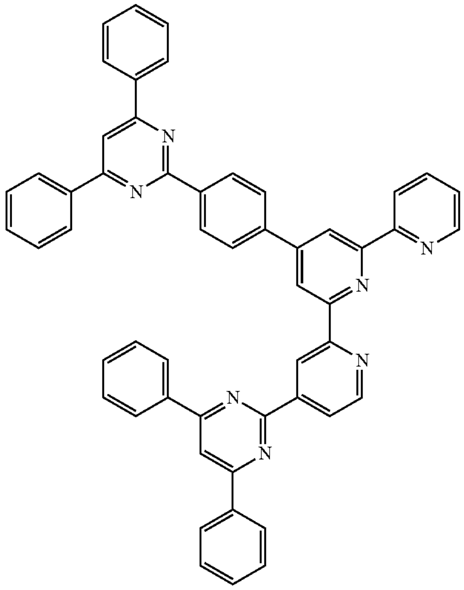

-continued
363
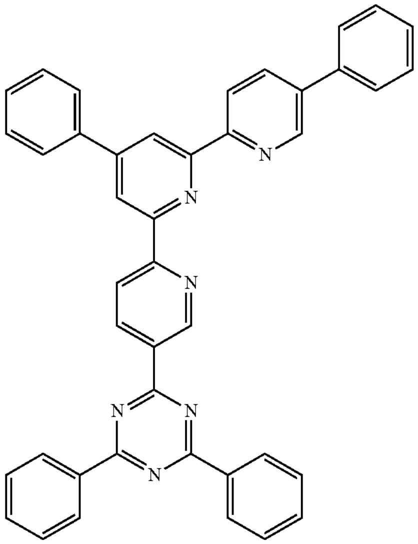
364
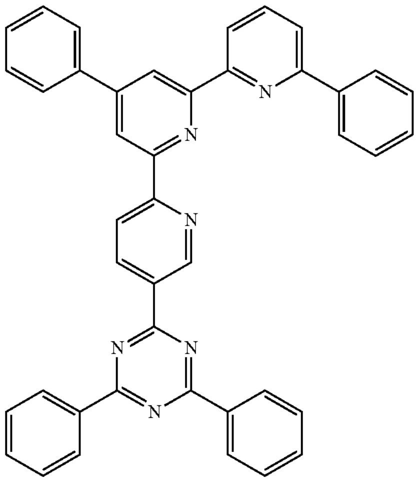
365
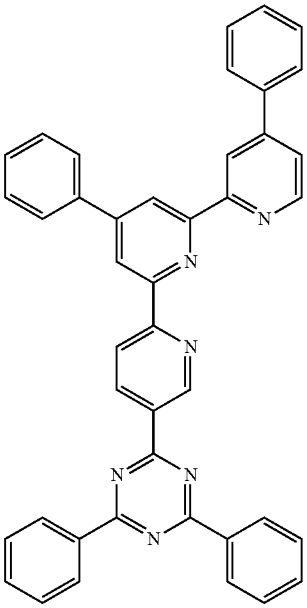
-continued
366
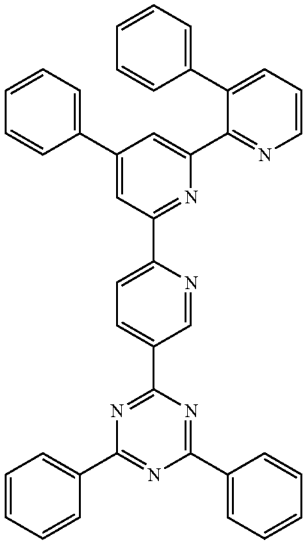
367
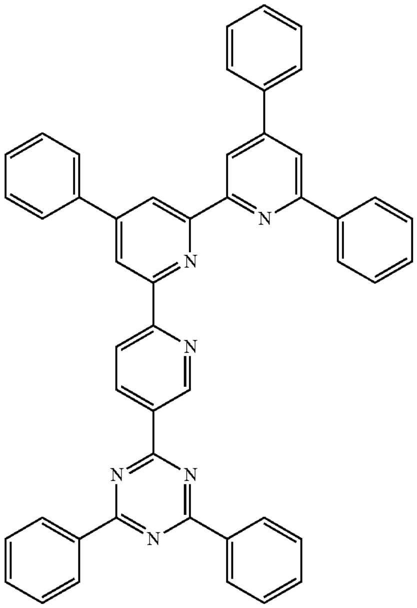

-continued
368
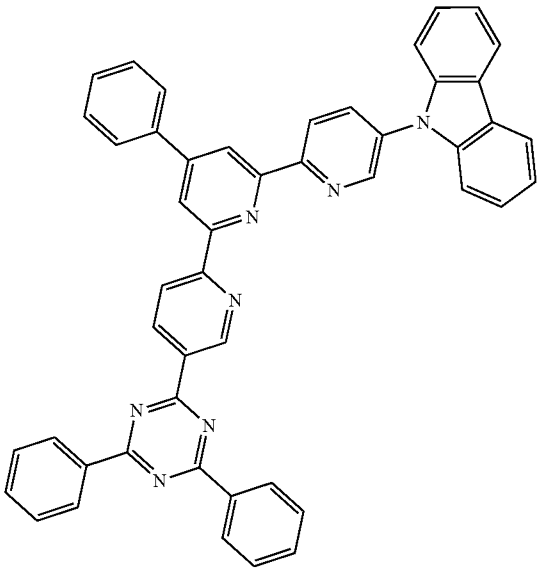
369
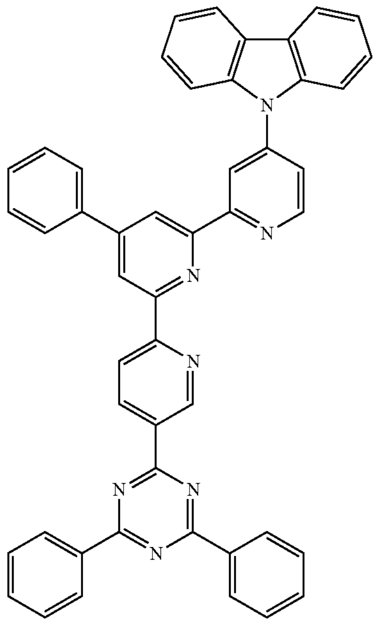
-continued
370
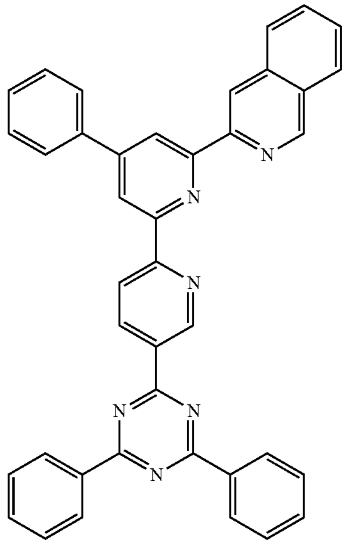
371
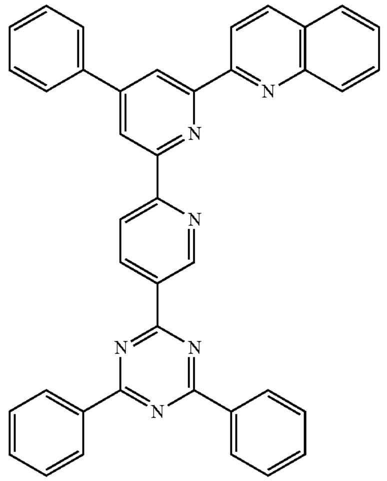
372
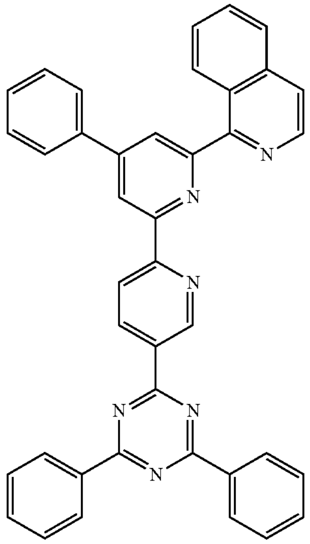

-continued
373
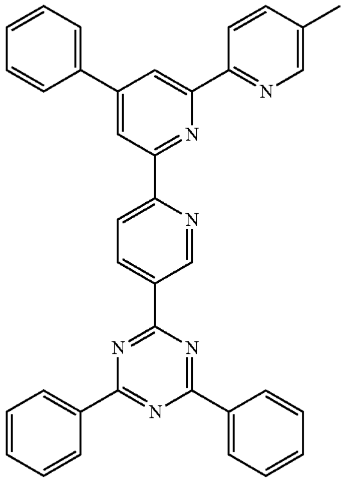
374
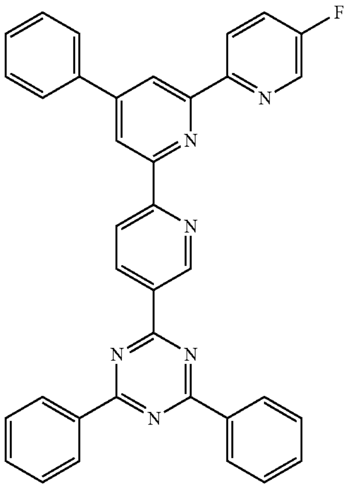
375
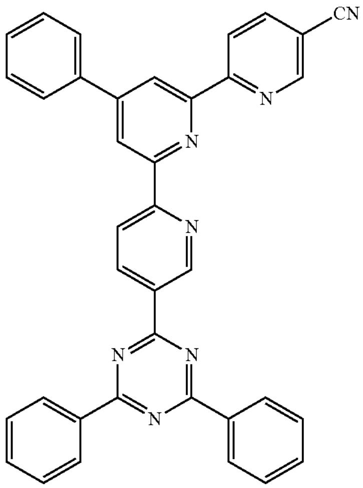
-continued
376
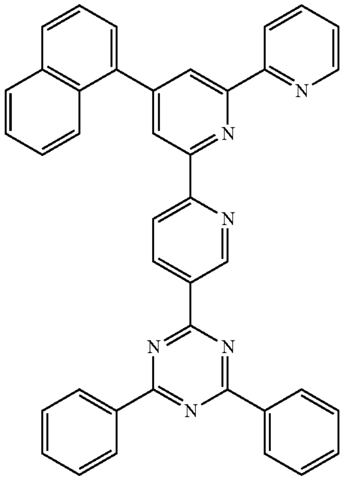
377
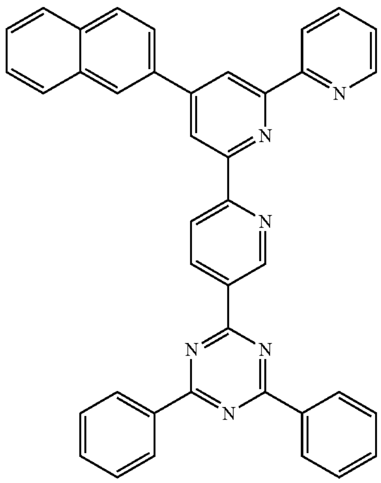
378
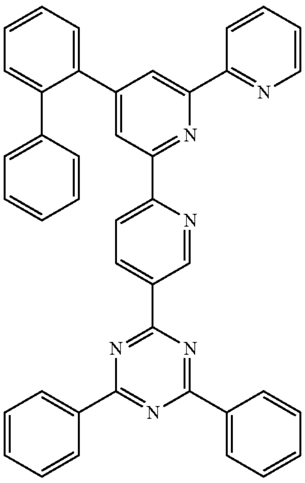

-continued
379
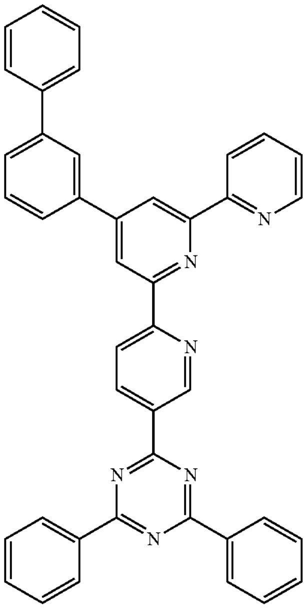
380
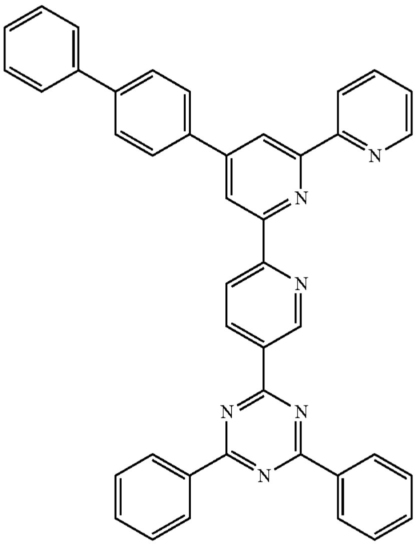
-continued
381
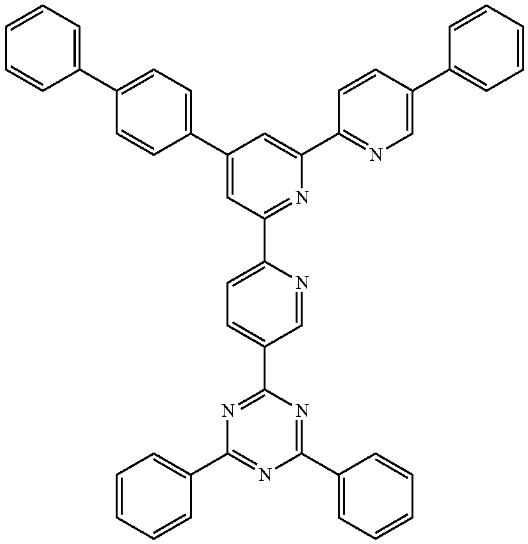
382
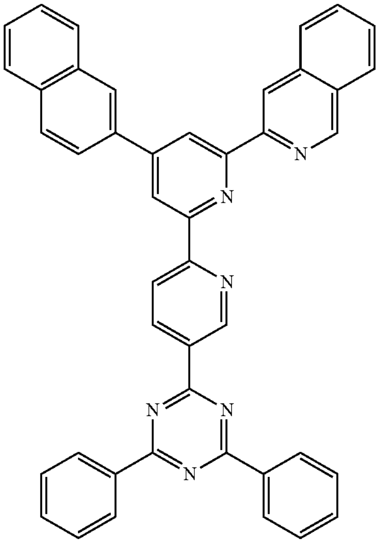
383
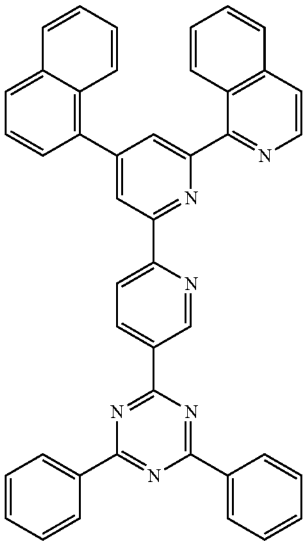

-continued
384
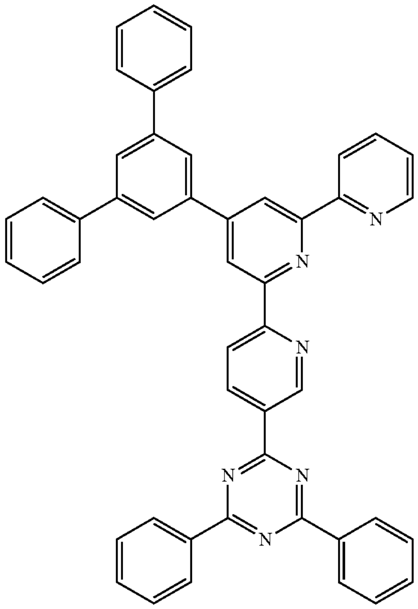
385
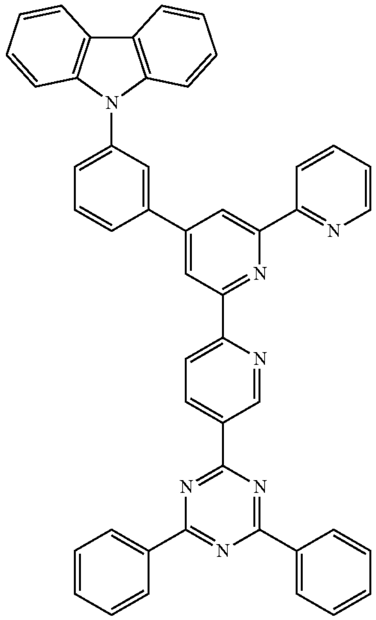
-continued
386
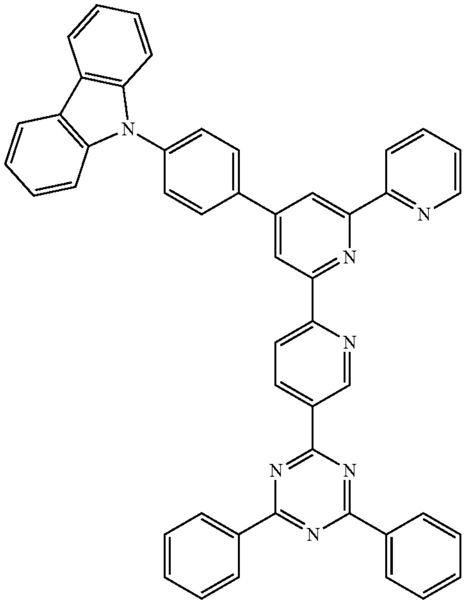
387
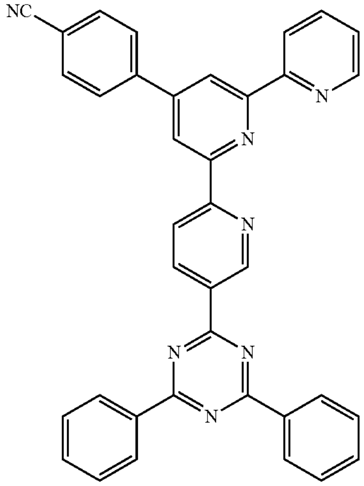
388
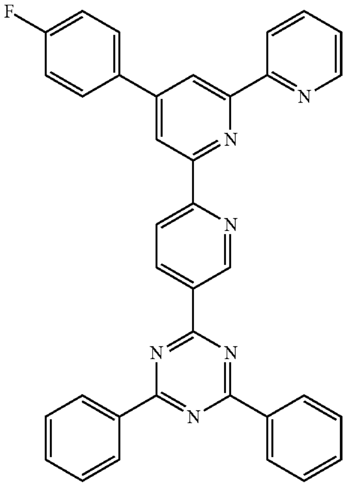

-continued
389
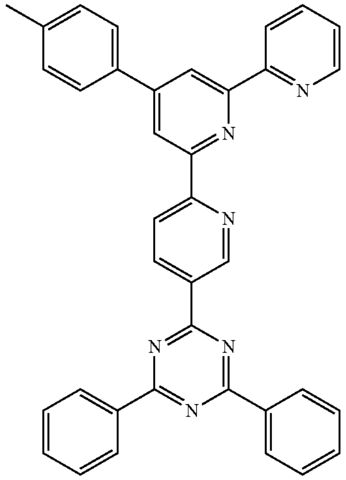
390
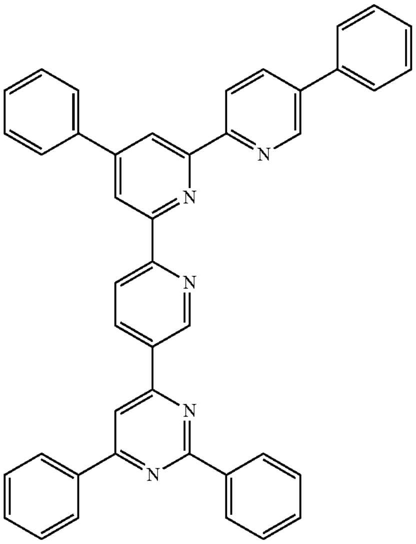
391
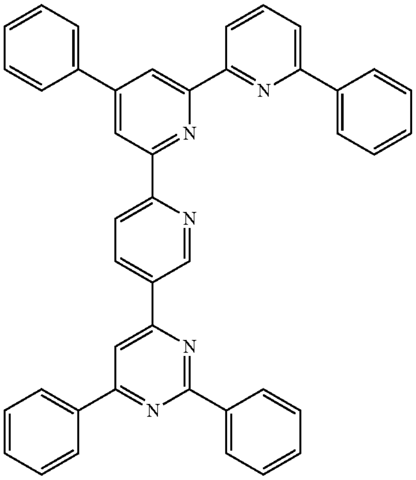
-continued
392
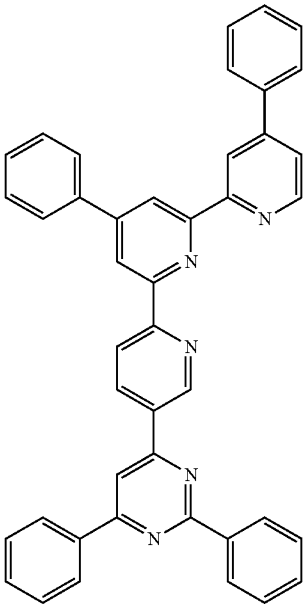
393
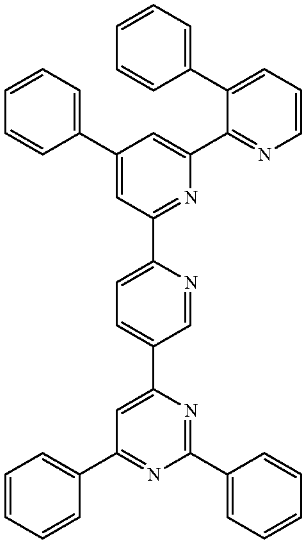

394
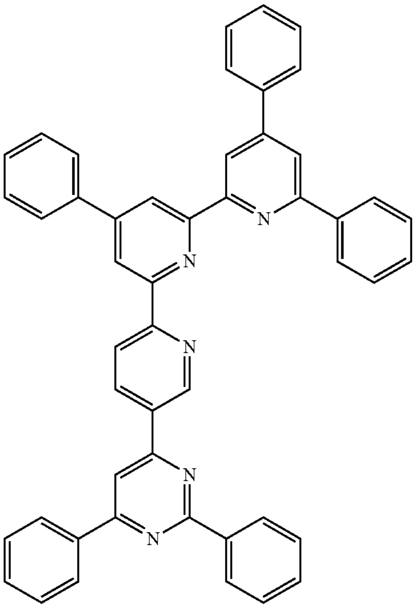
395
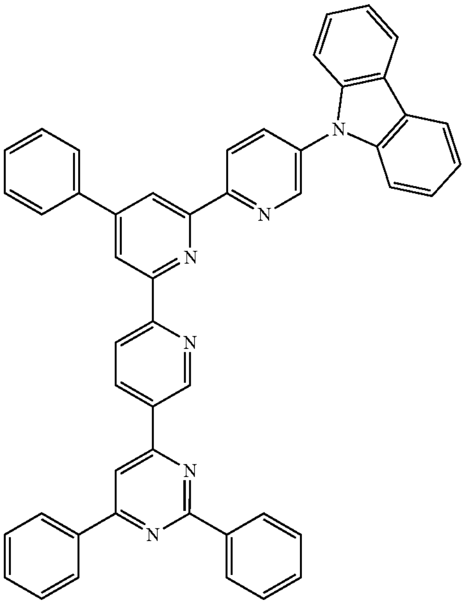
396
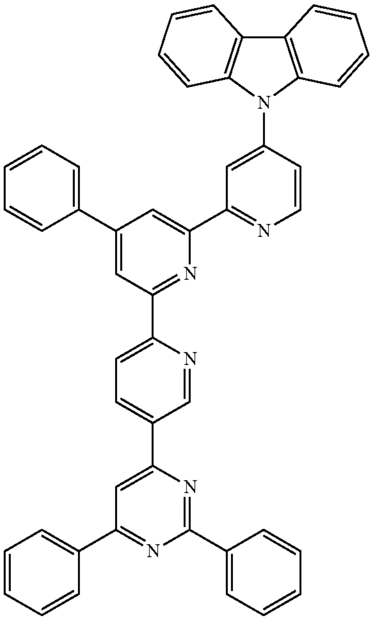
397
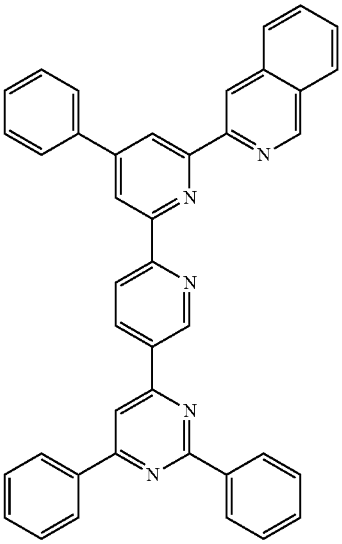
398
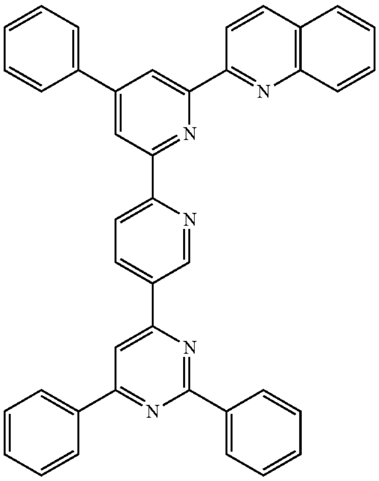

-continued
399
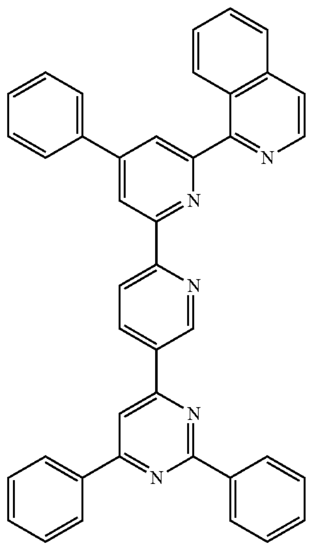
400
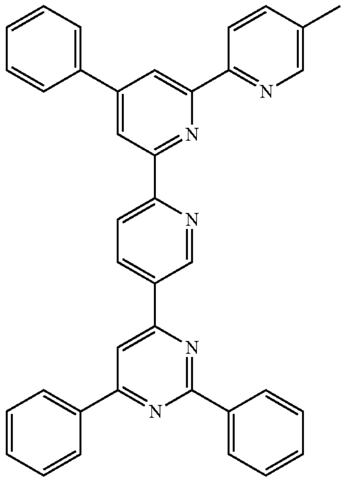
401
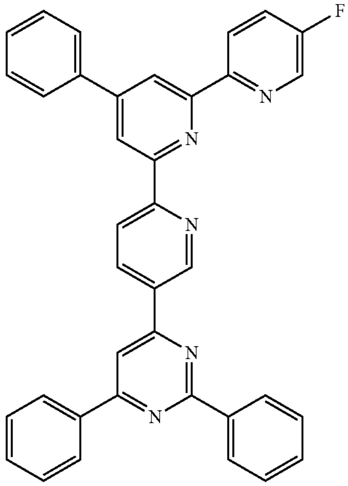
-continued
402
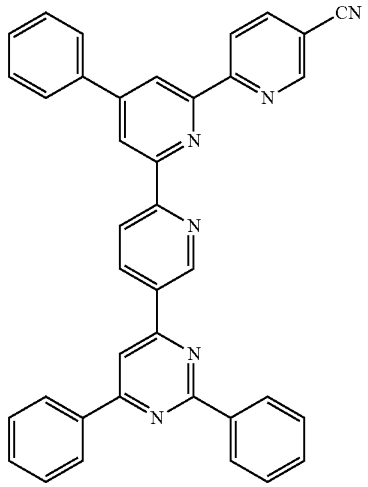
403
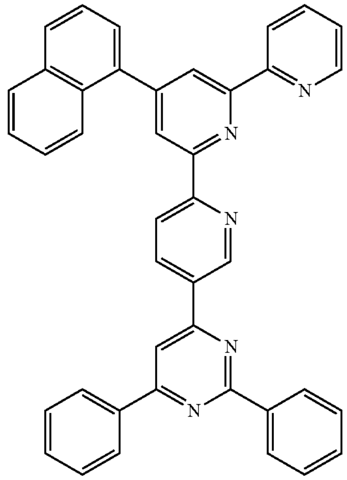
404
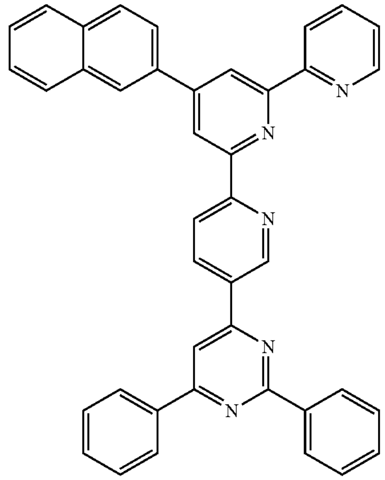

-continued
405
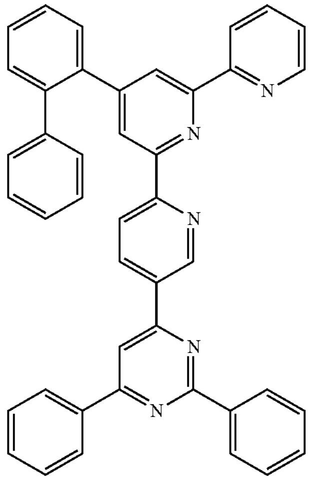
406
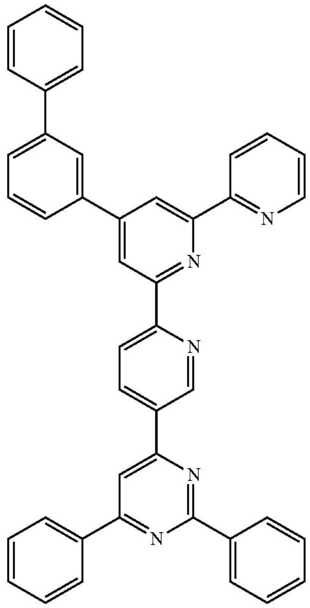
407
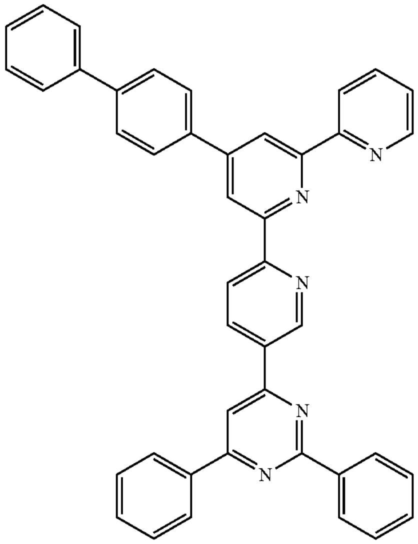
-continued
408
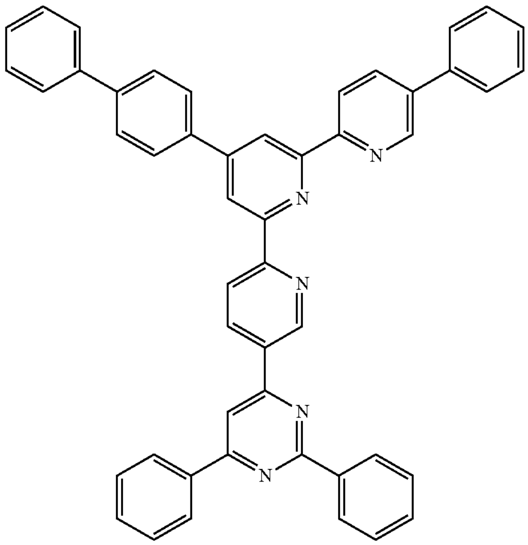
409
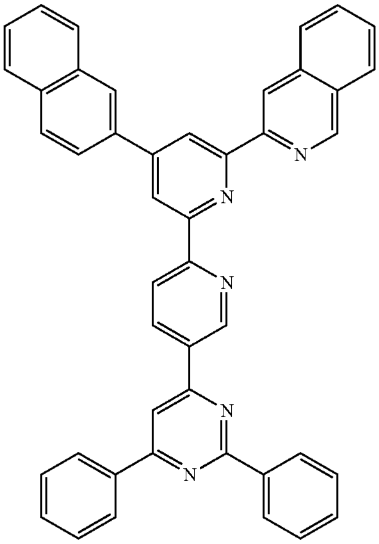
410
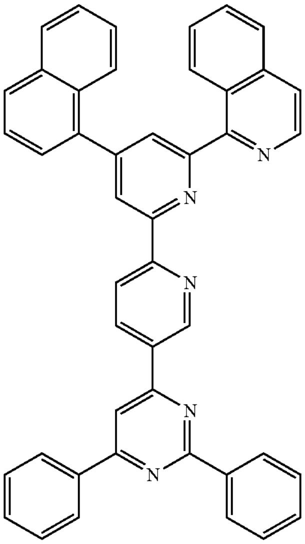

-continued
411
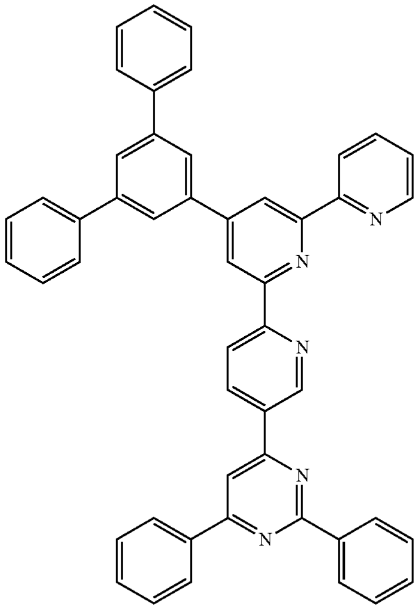
412
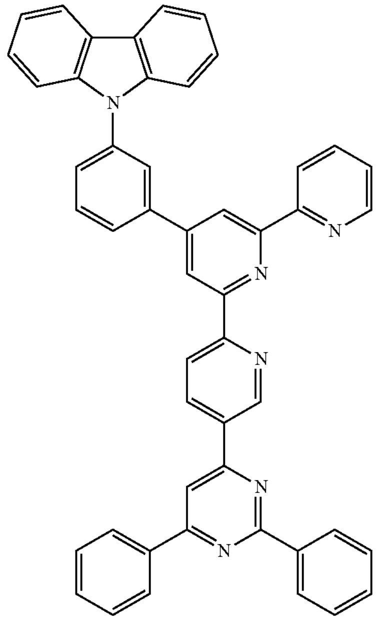
-continued
413
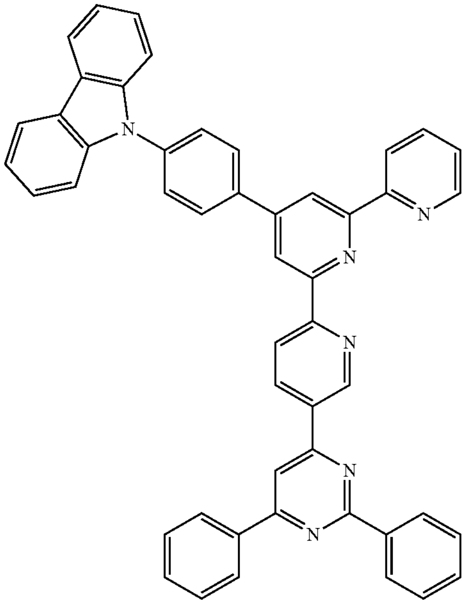
414
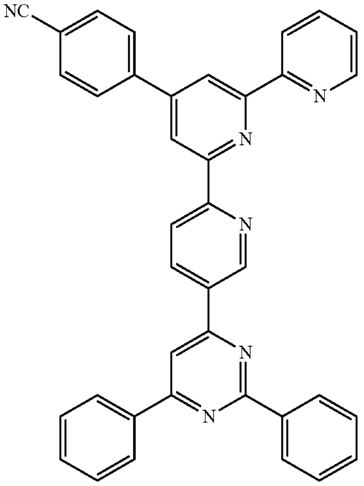
415
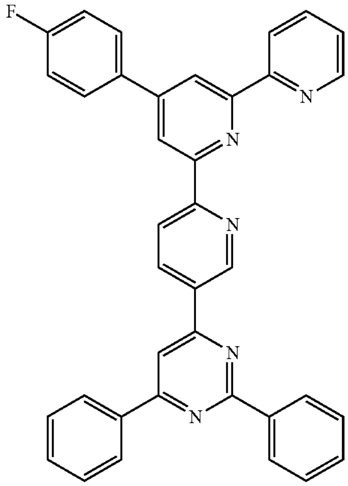

-continued
416
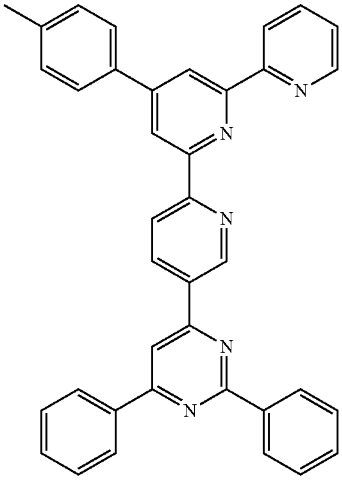
417
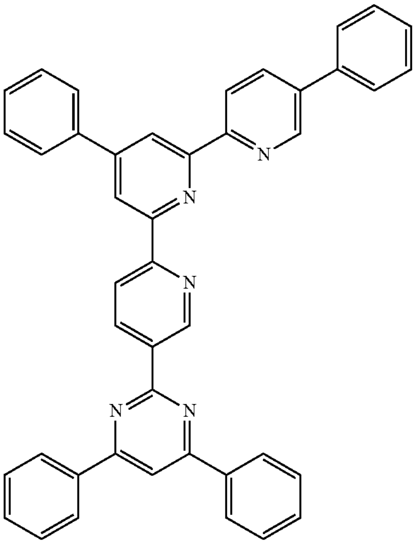
418
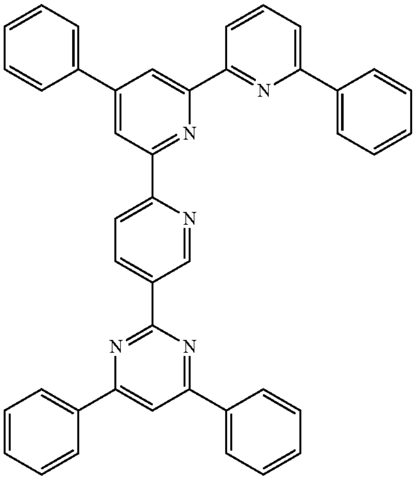
-continued
419
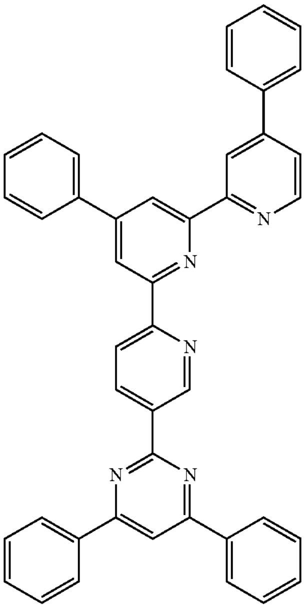
420
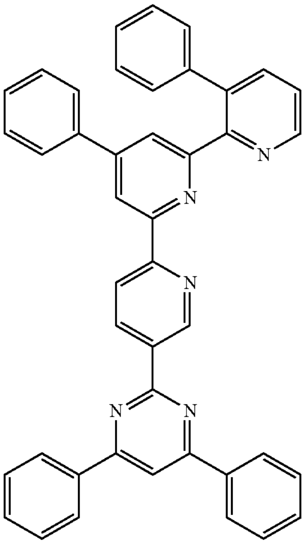

-continued
421
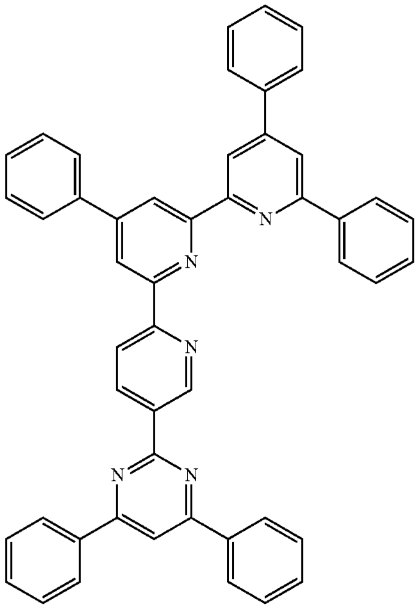
422
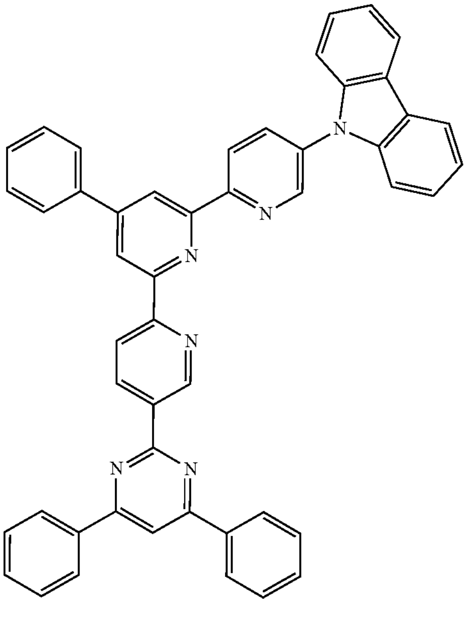
-continued
423
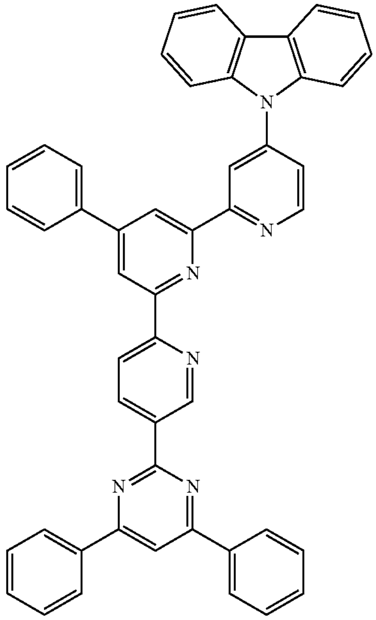
424
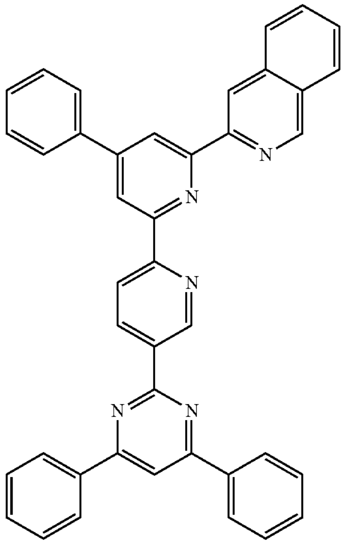
425
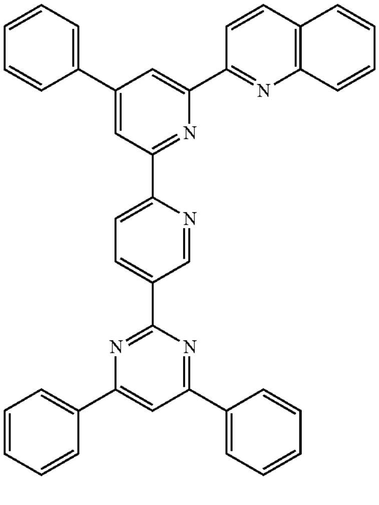

-continued
426
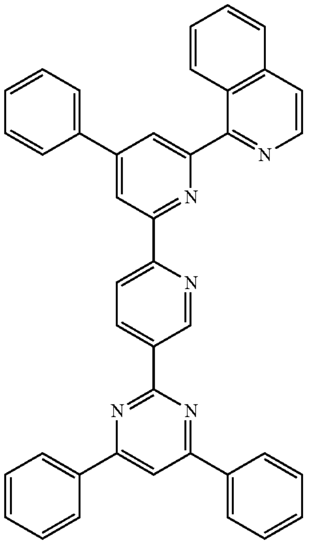
427
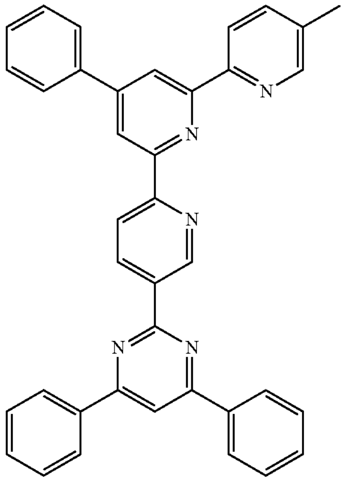
428
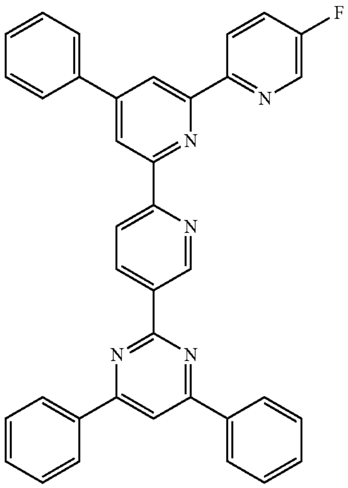
-continued
429
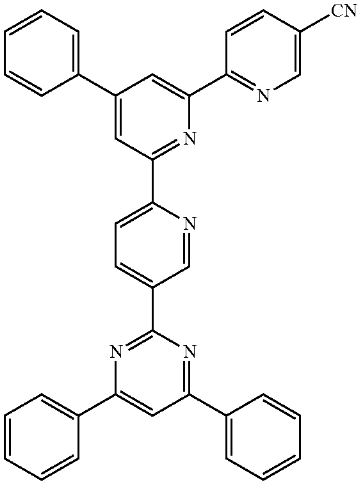
430
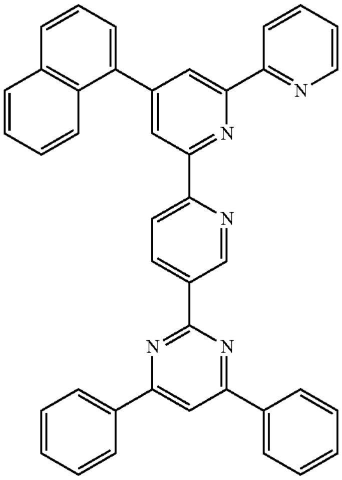
431
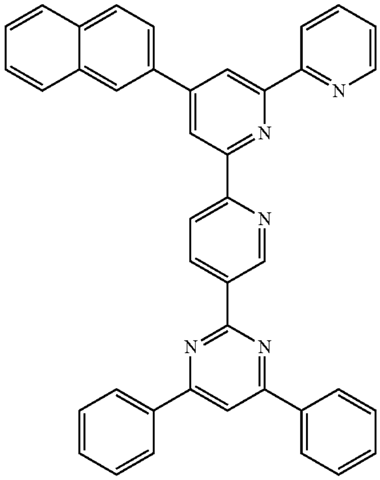

-continued
432
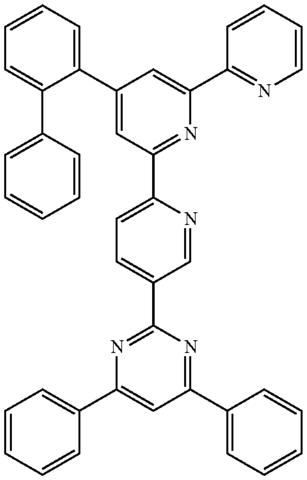
433
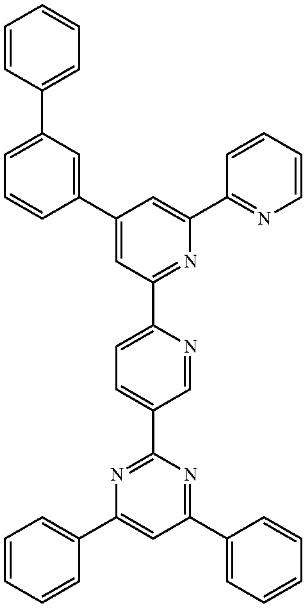
434
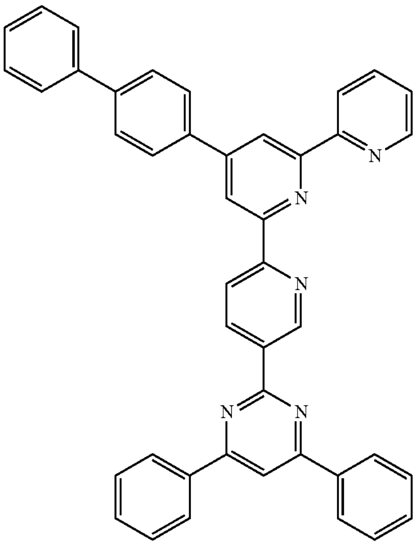
-continued
435
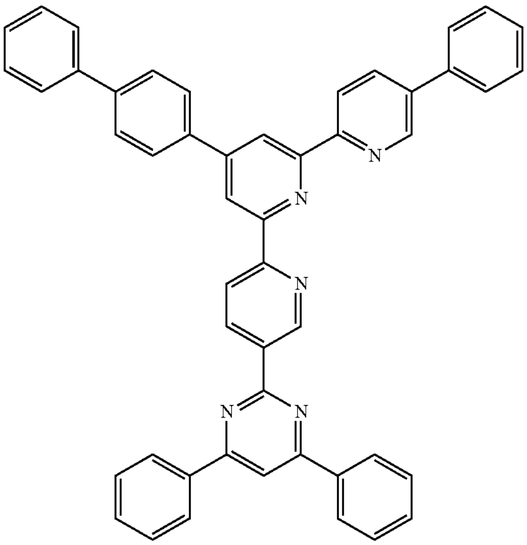
436
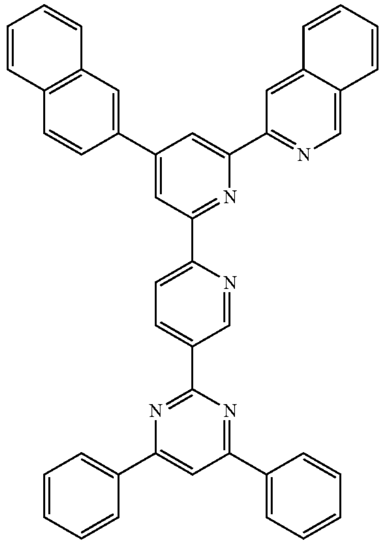
437
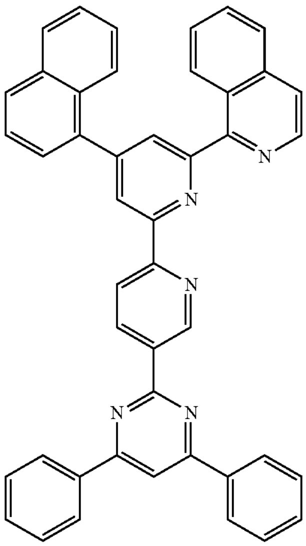

438
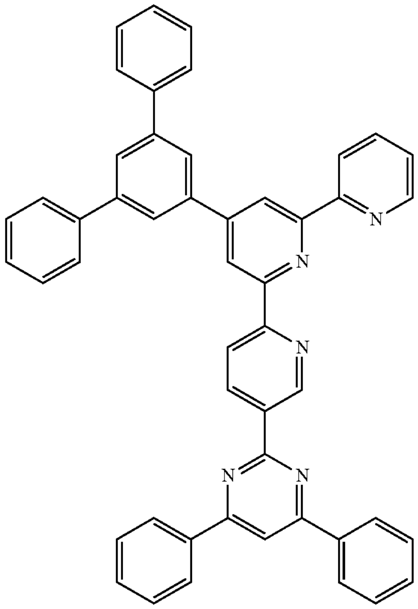
439
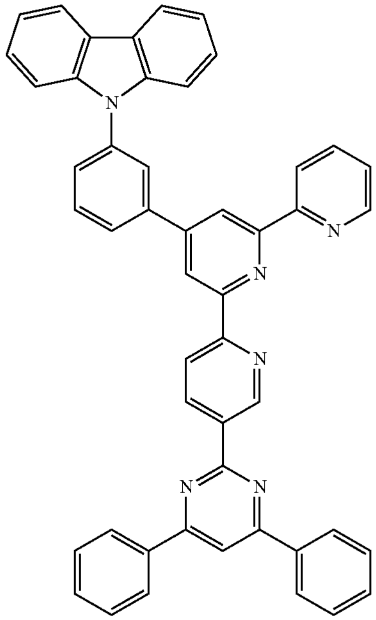
440
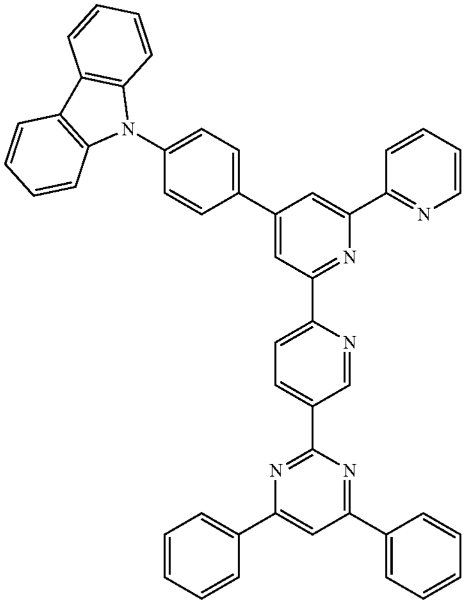
441
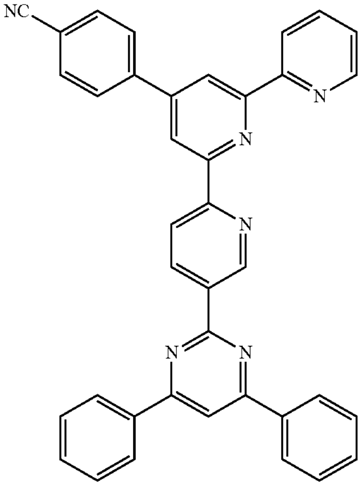
442
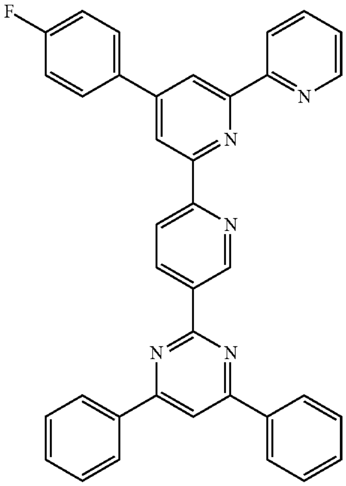

-continued
443
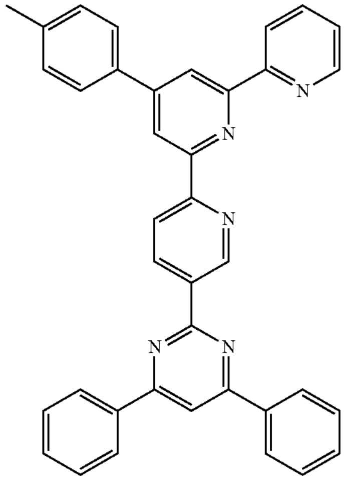
444
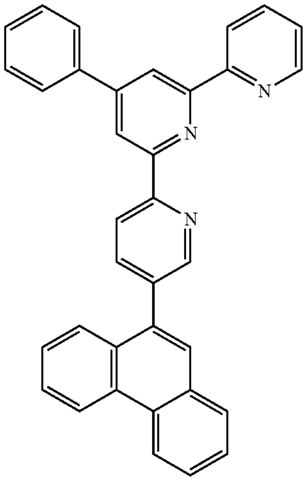
445
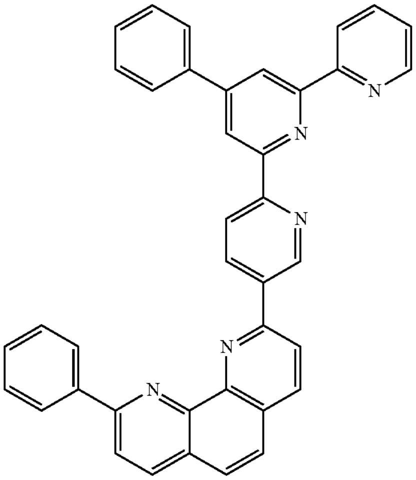
-continued
446
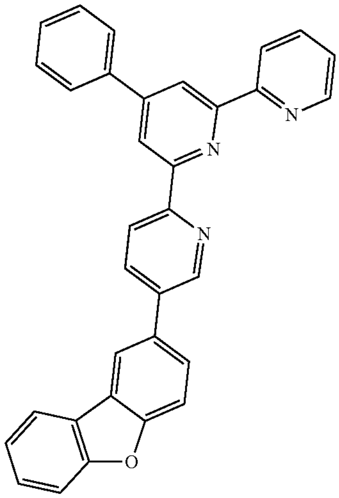
447
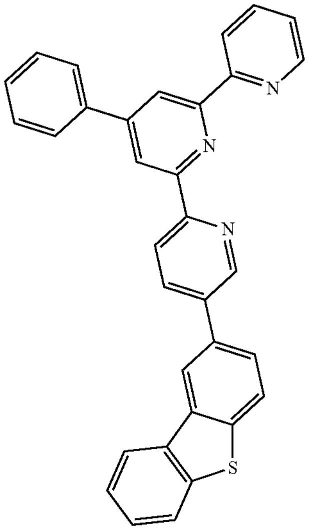
448
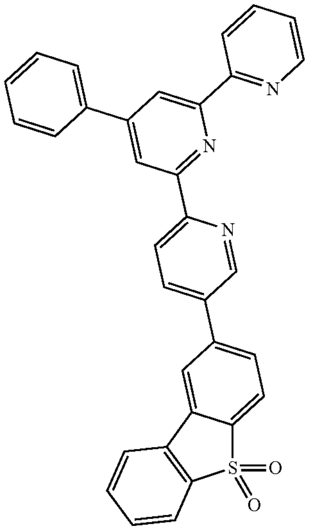

-continued
449
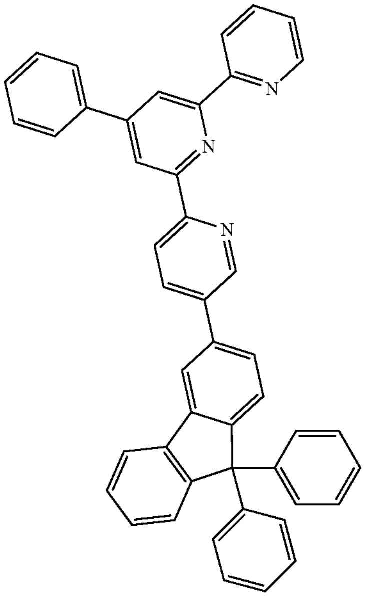
450
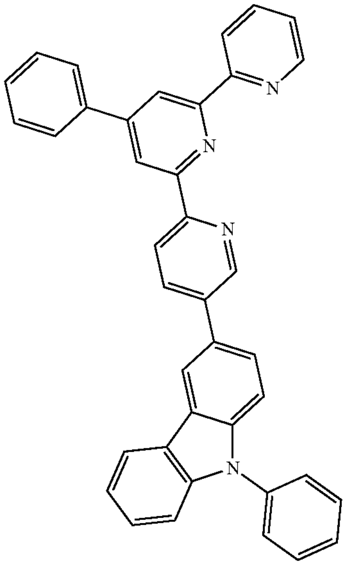
-continued
451
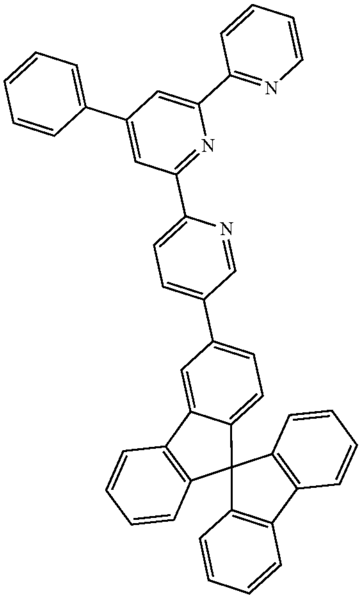
452
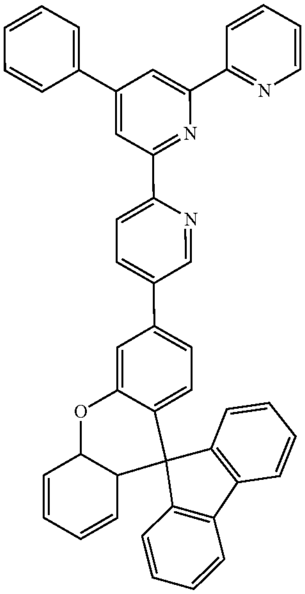
453
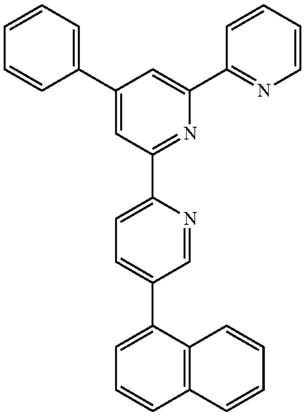

-continued
454
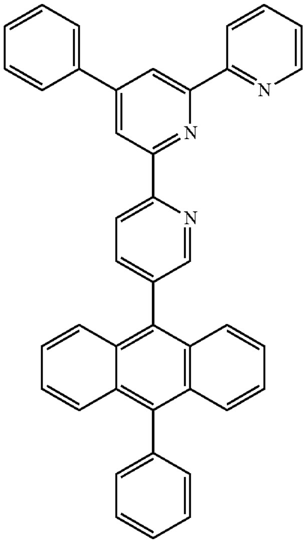
455
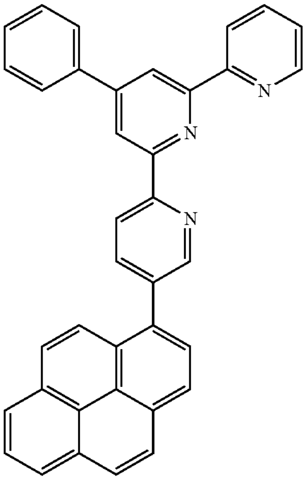
456
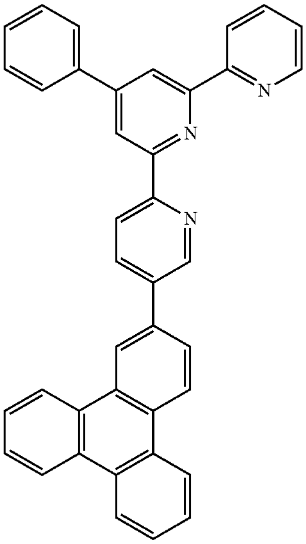
-continued
457
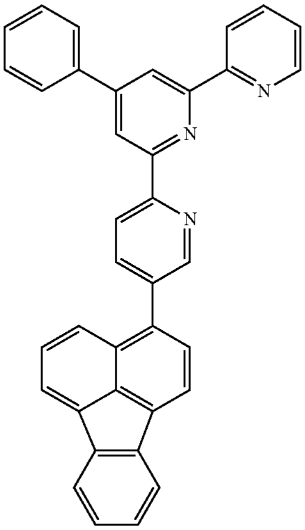
458
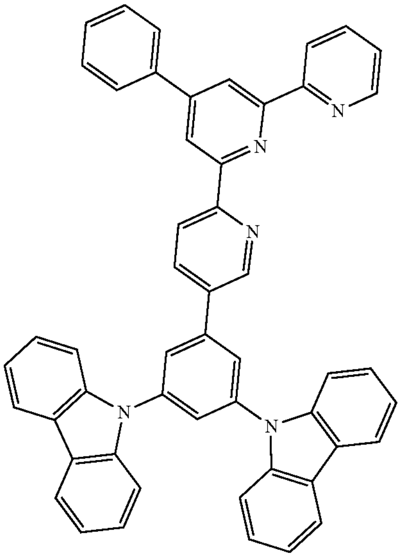

-continued
459
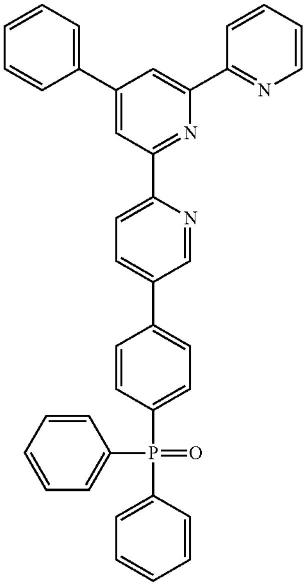
460
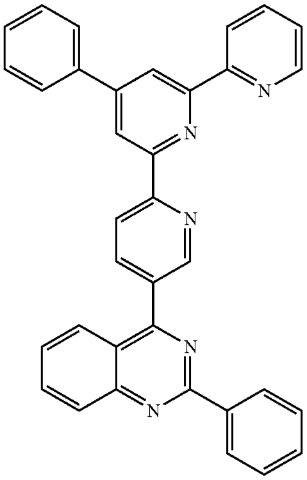
461
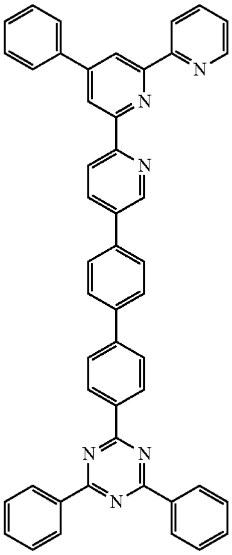
-continued
462
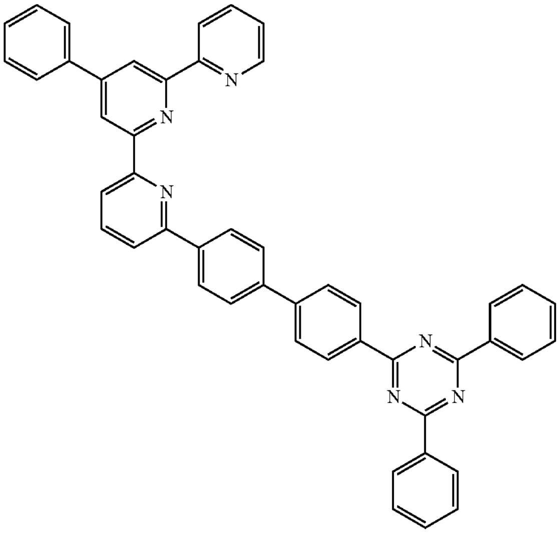
463
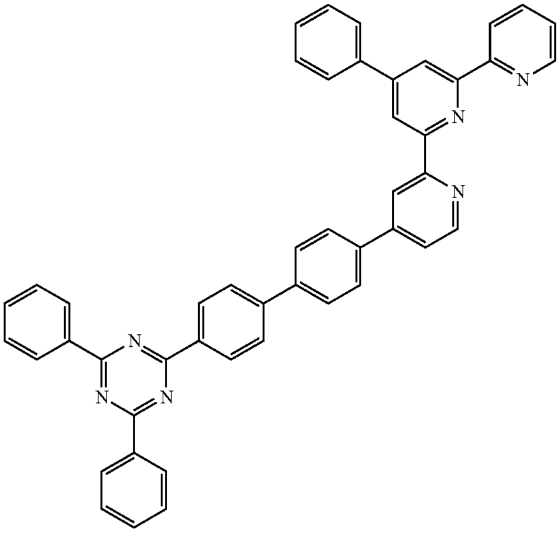
464
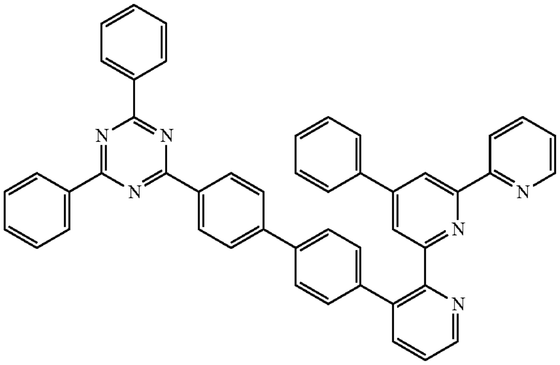

-continued
465
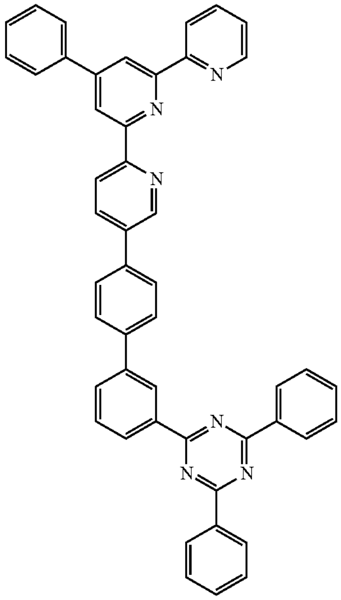
466
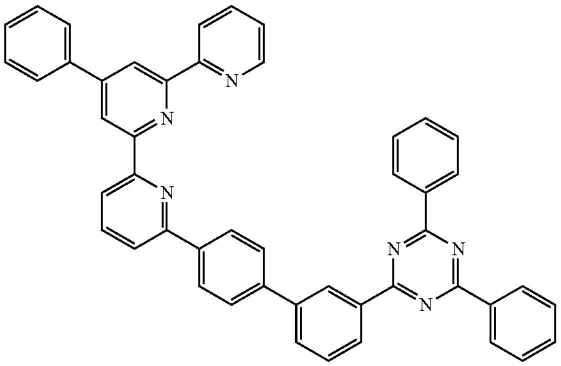
467
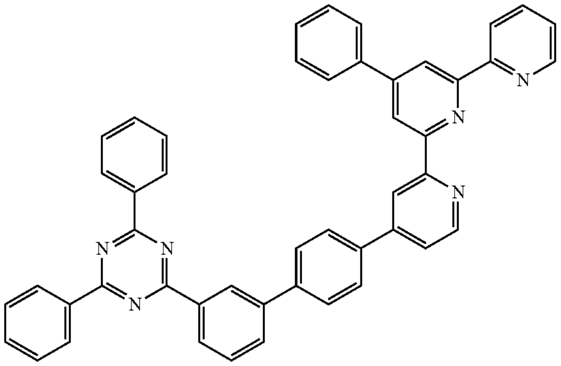
-continued
468
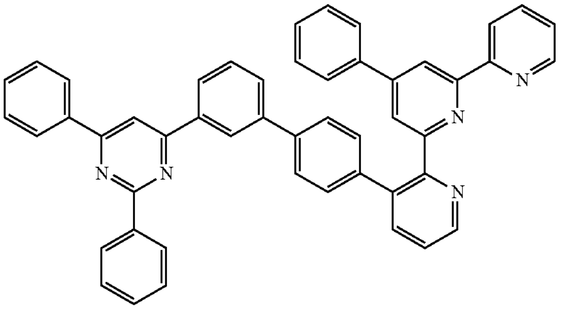
469
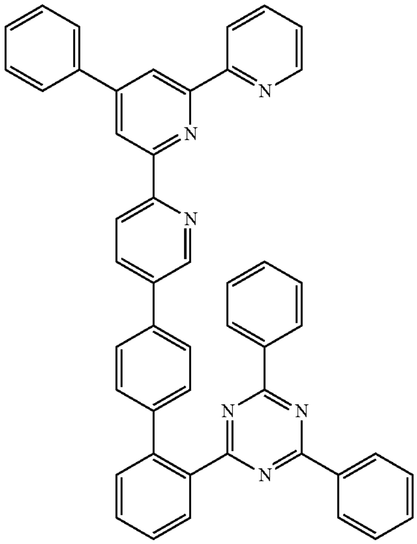
470
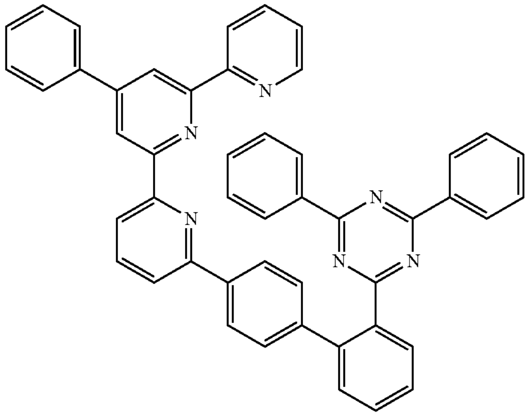

-continued
471
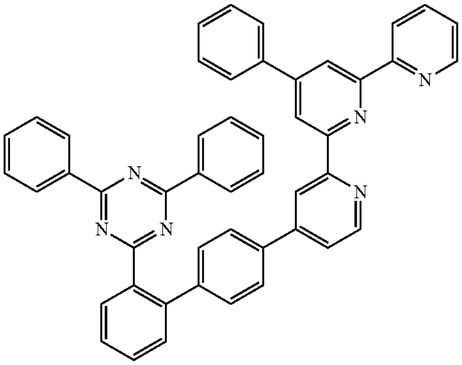
472
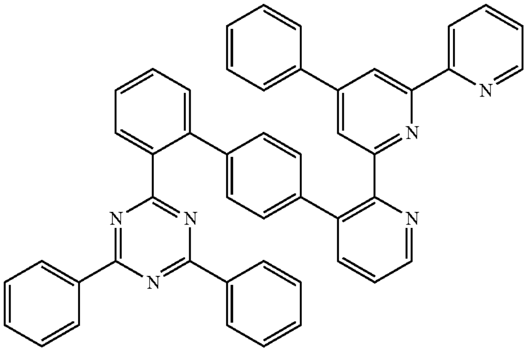
473
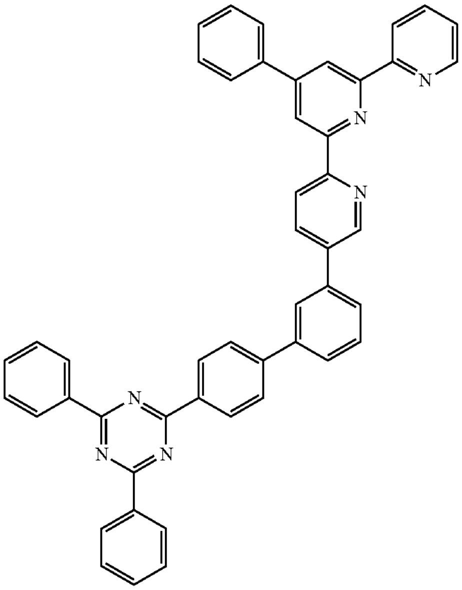
-continued
474
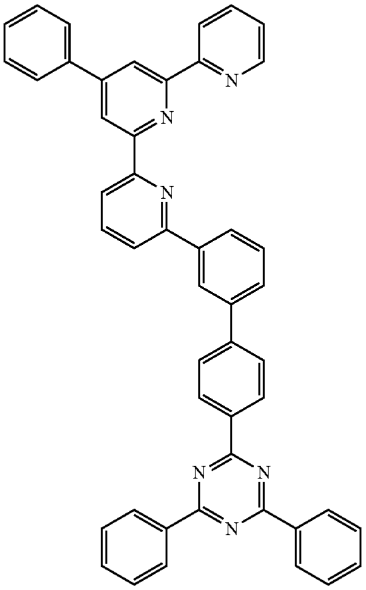
475
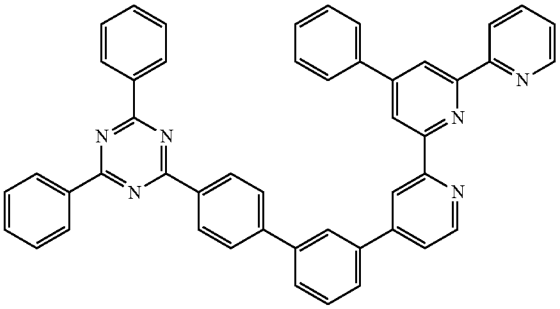
476
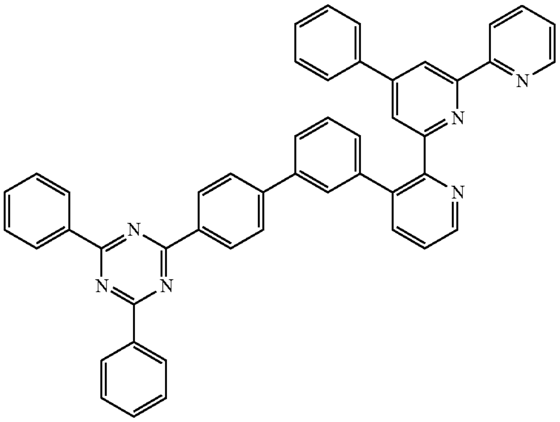

-continued
477
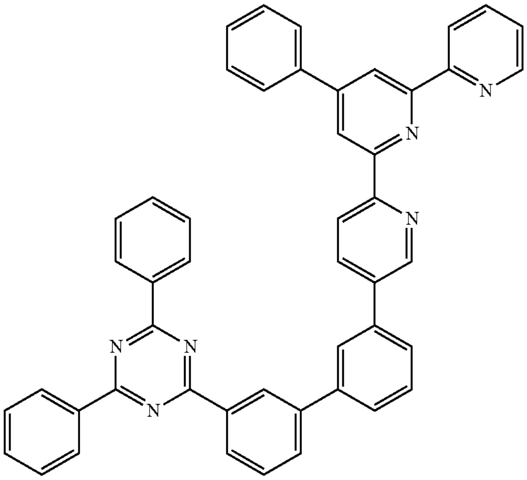
478
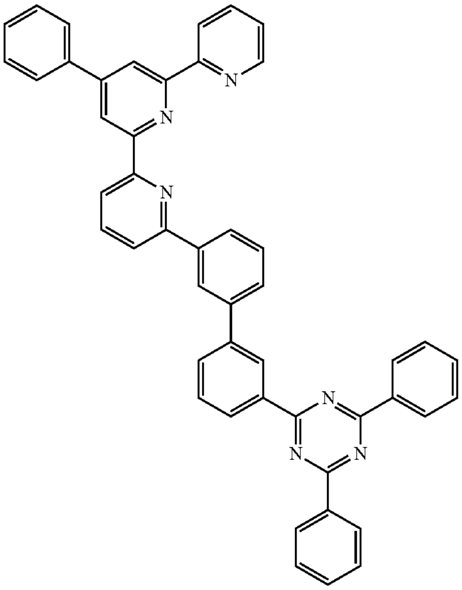
479
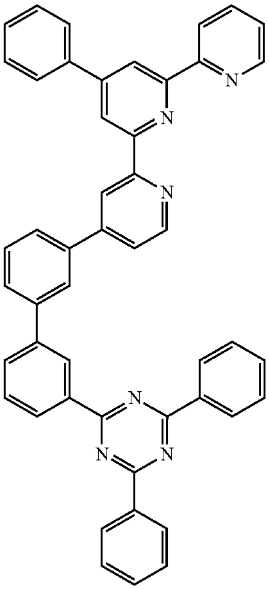
-continued
480
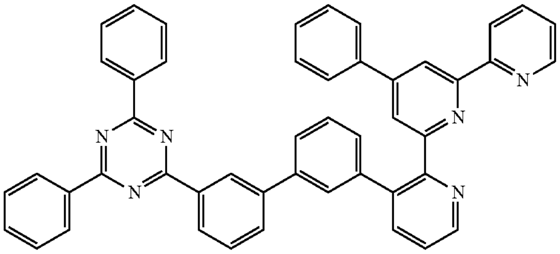
481
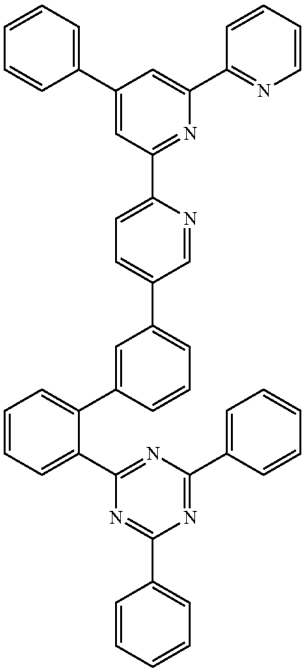
482
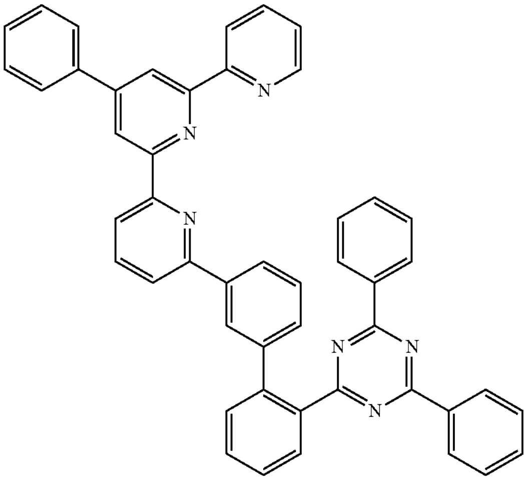

-continued
483
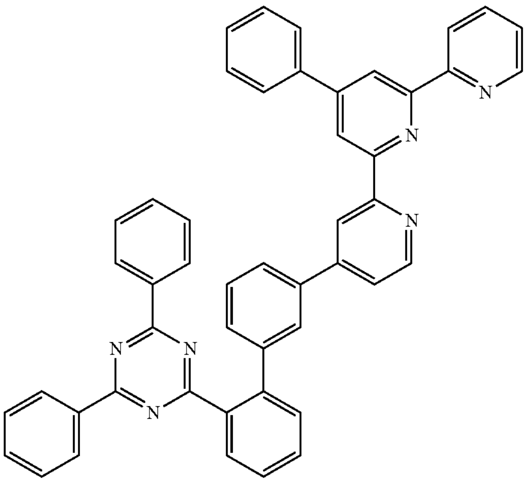
484
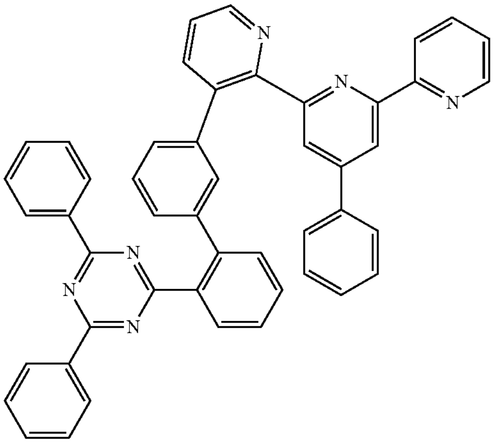
485
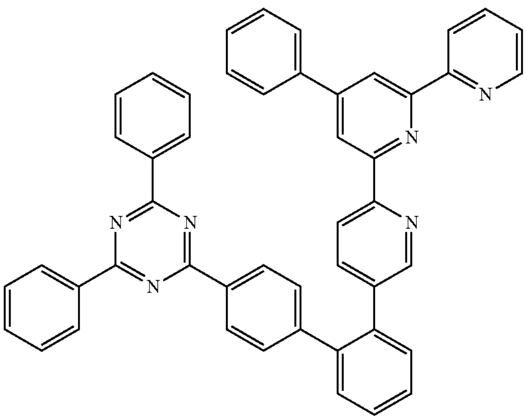
-continued
486
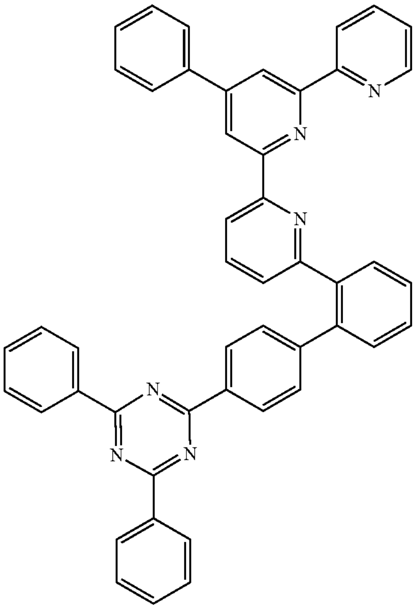
487
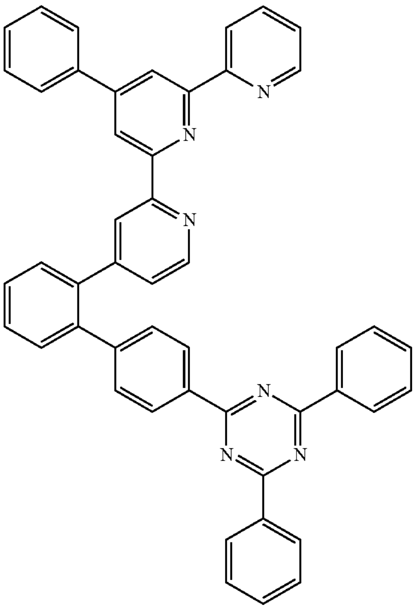

-continued
488
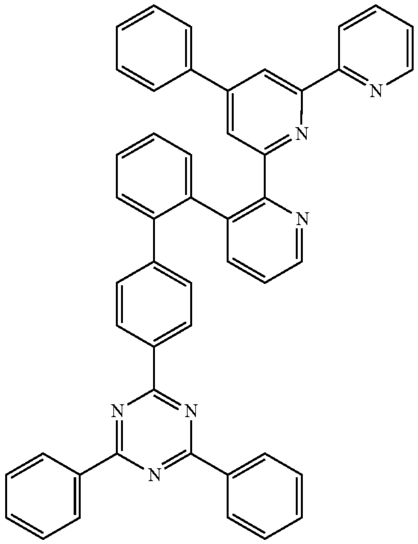
489
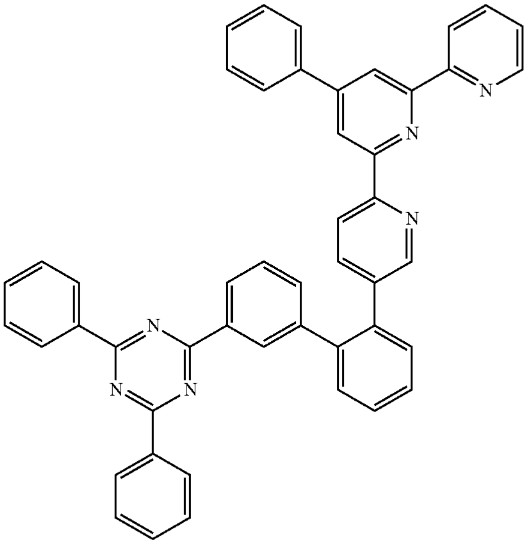
490
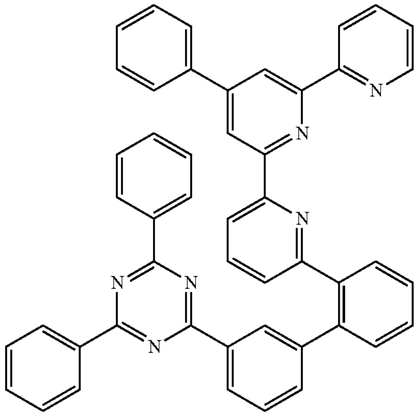
-continued
491
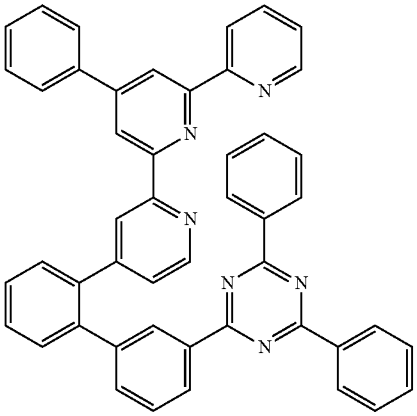
492
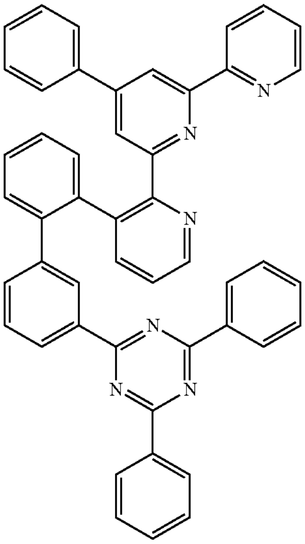
493
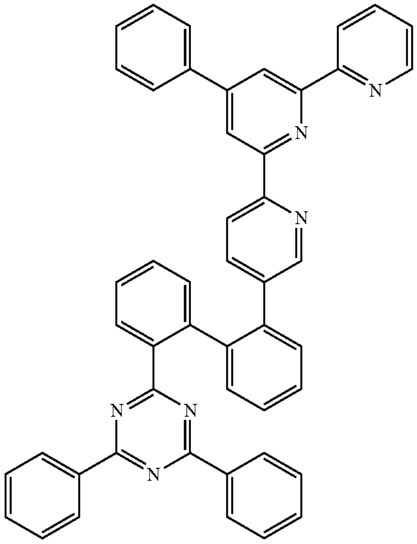

-continued
494
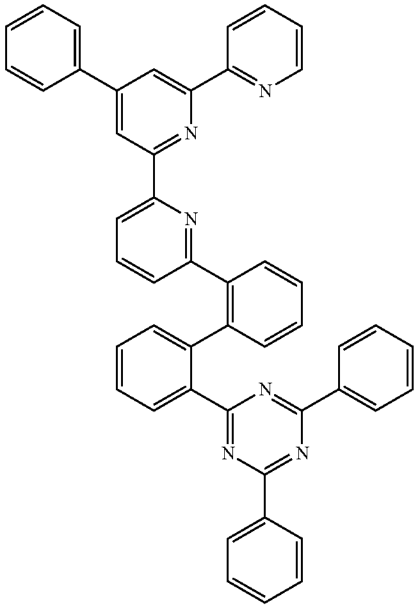
495
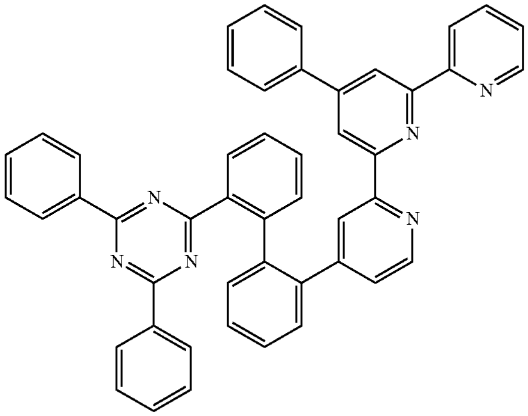
496
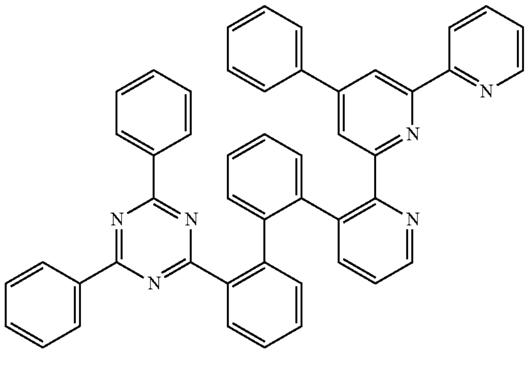
-continued
497
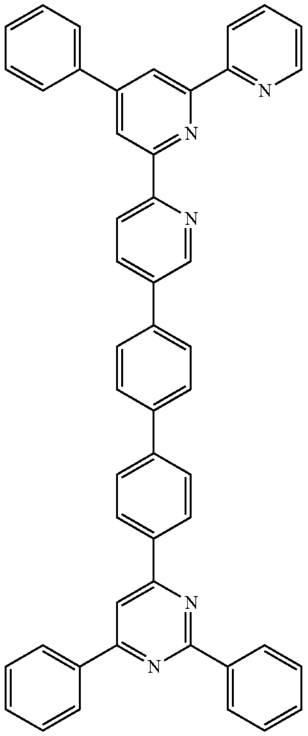
498
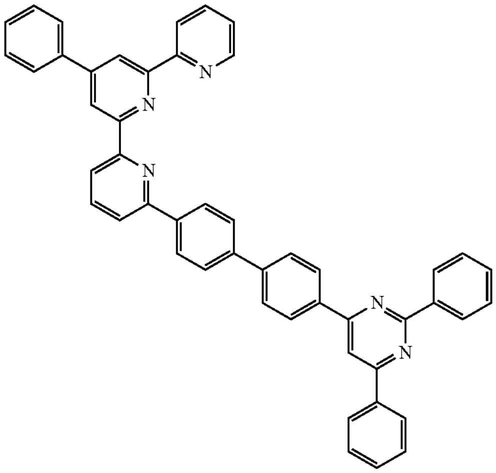

-continued
499
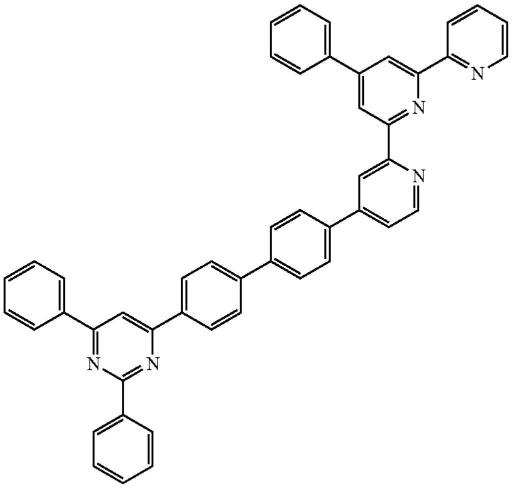
500
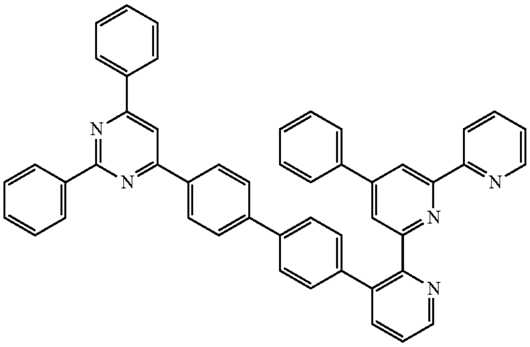
501
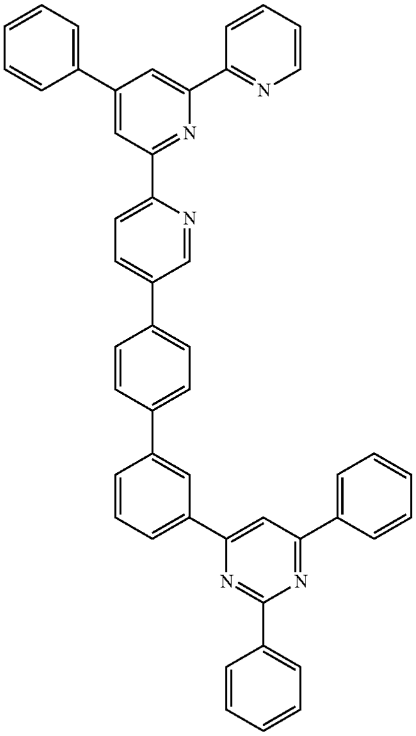
-continued
502
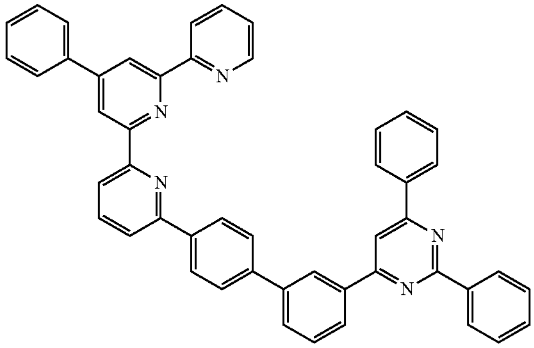
503
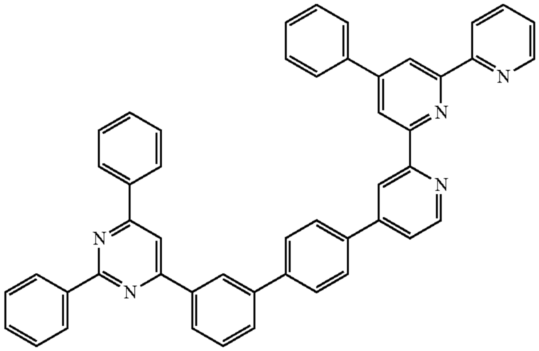
504
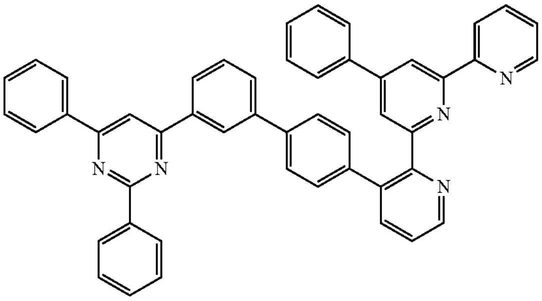
505
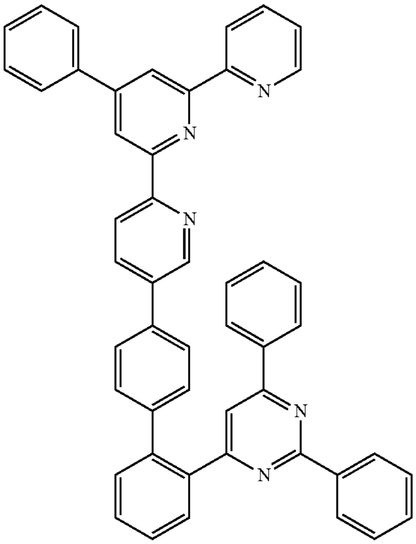

-continued
506
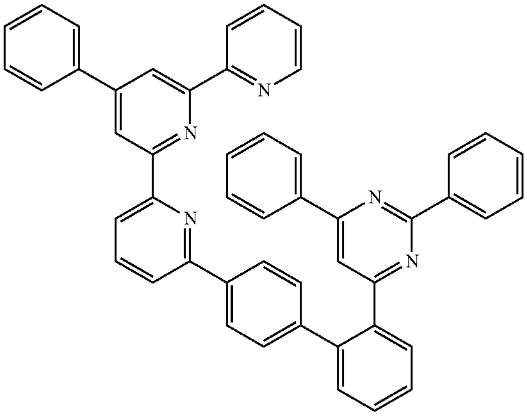
507
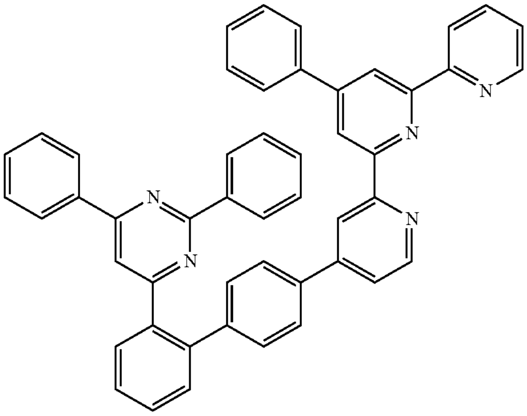
508
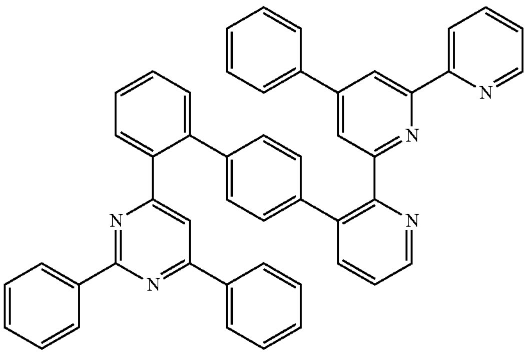
-continued
509
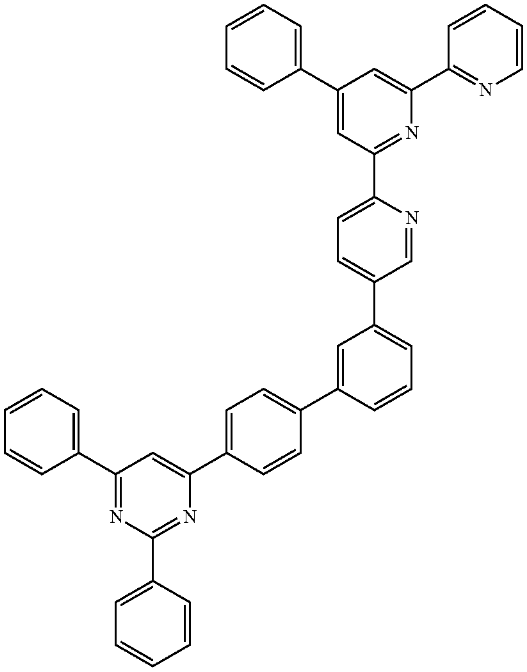
510
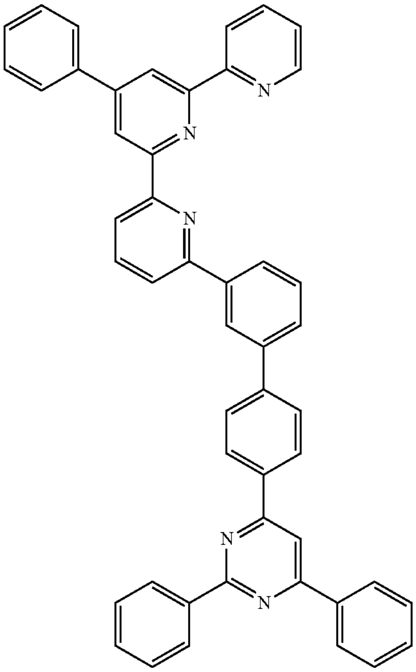

-continued
511
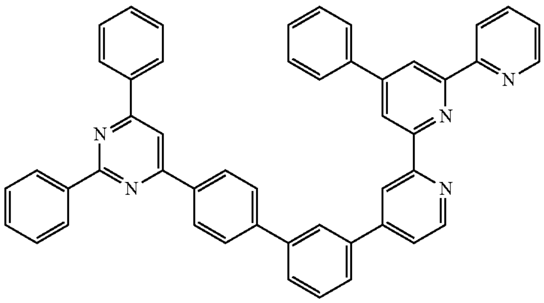
512
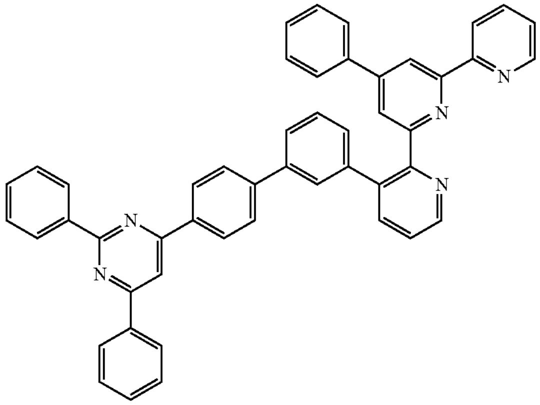
513
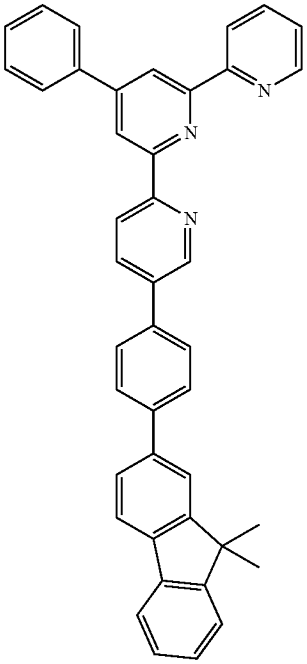
-continued
514
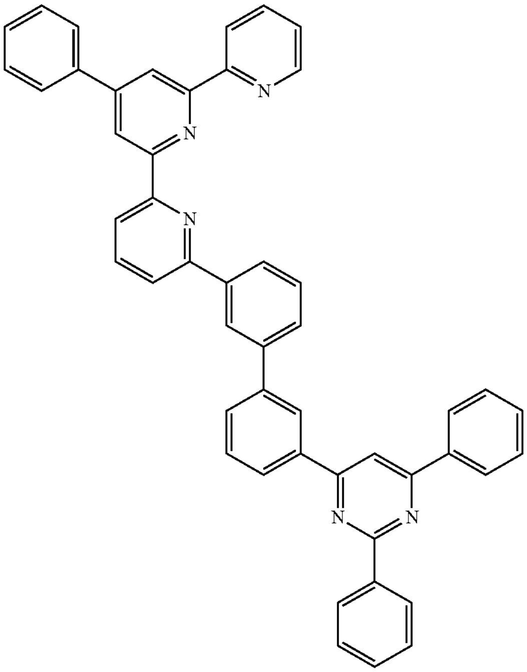
515
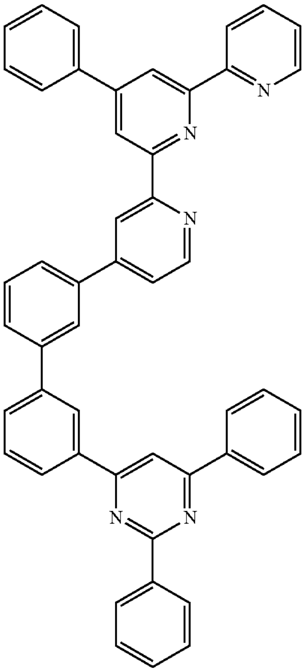
516
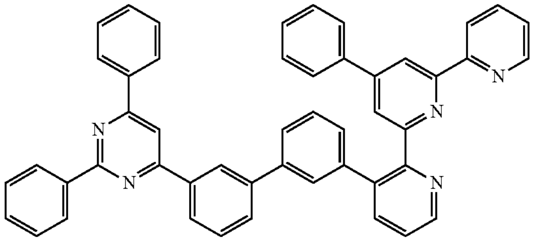

-continued
517
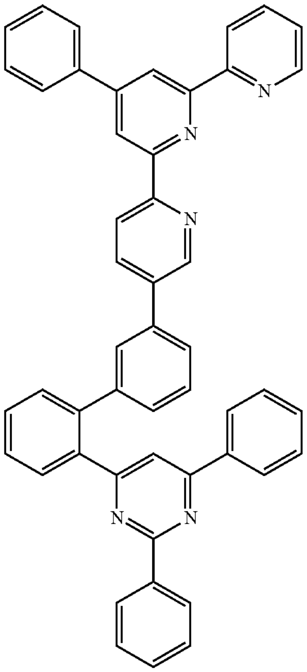
518
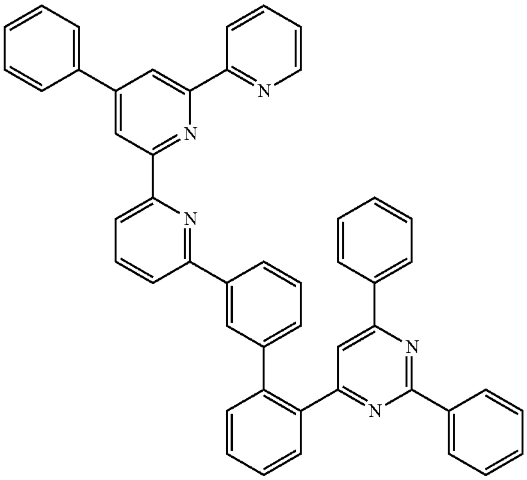
-continued
519
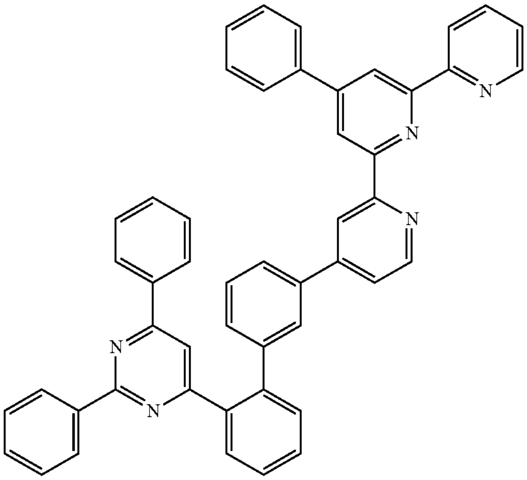
520
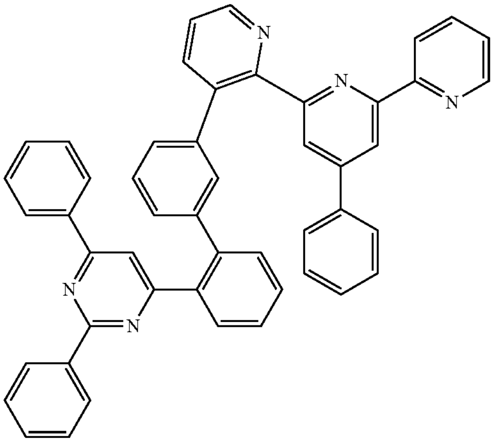
521
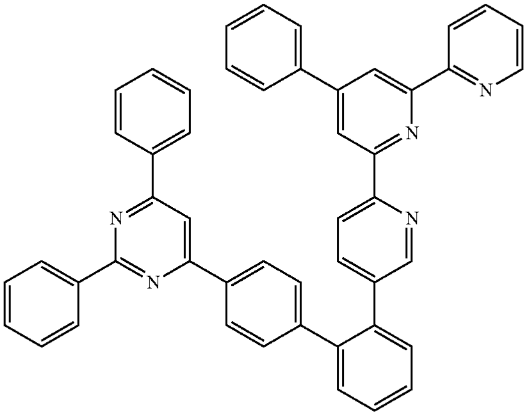

522
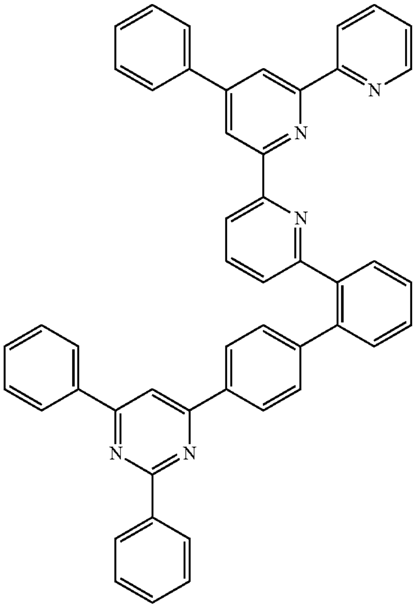
523
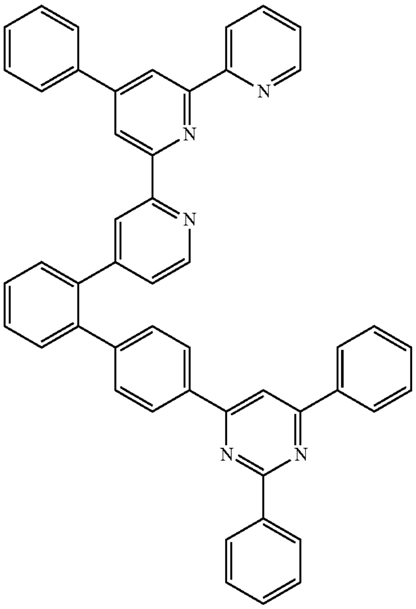
524
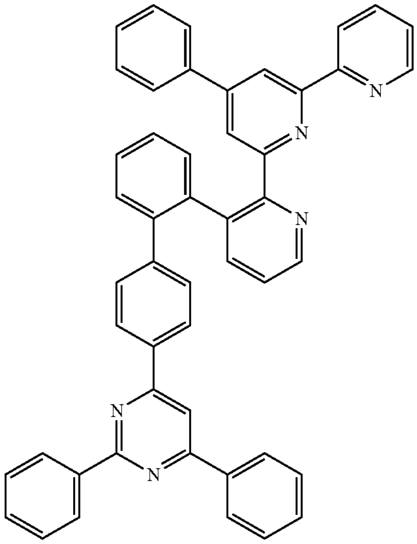
525
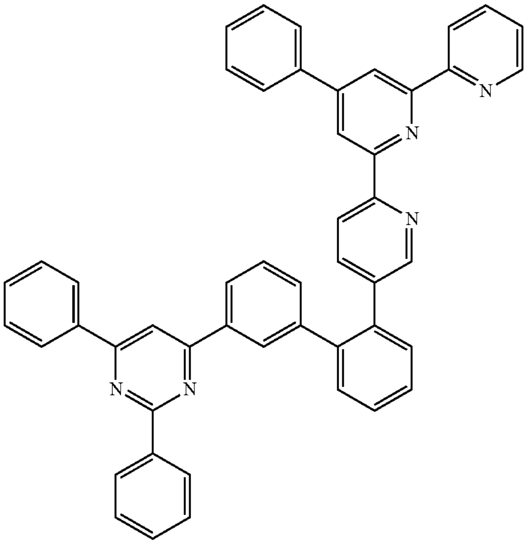
526
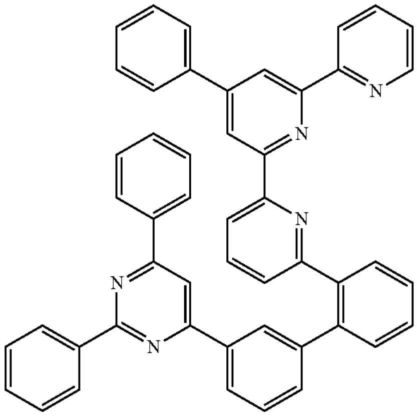

527
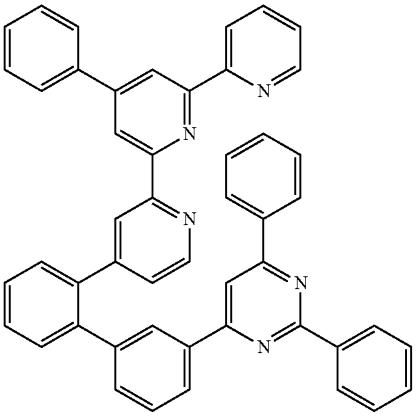
528
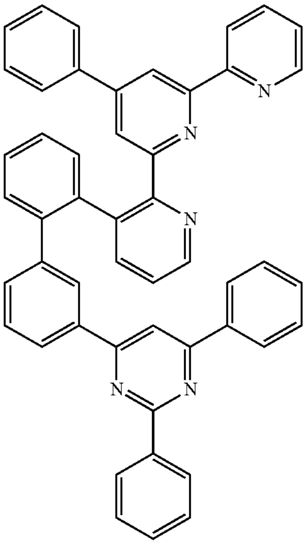
529
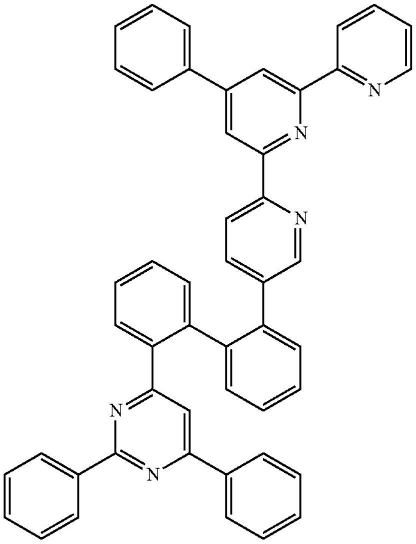
530
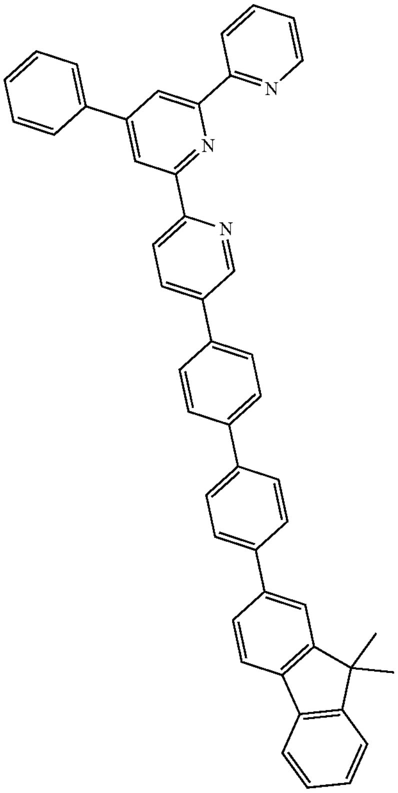
531
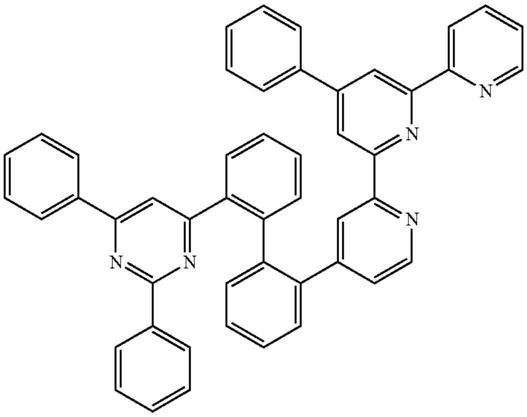
532
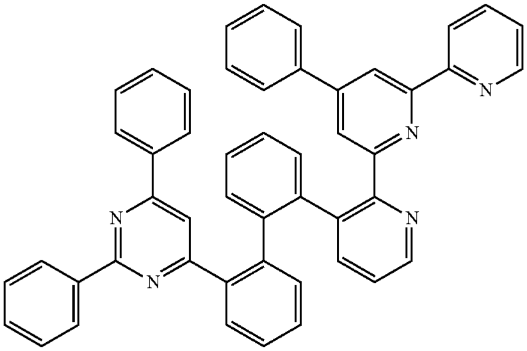

-continued
533
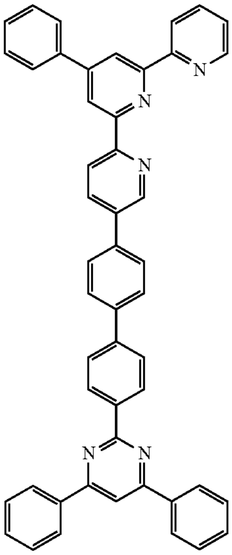
534
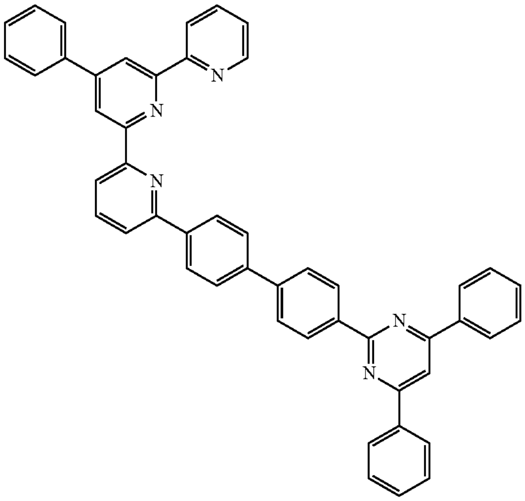
535
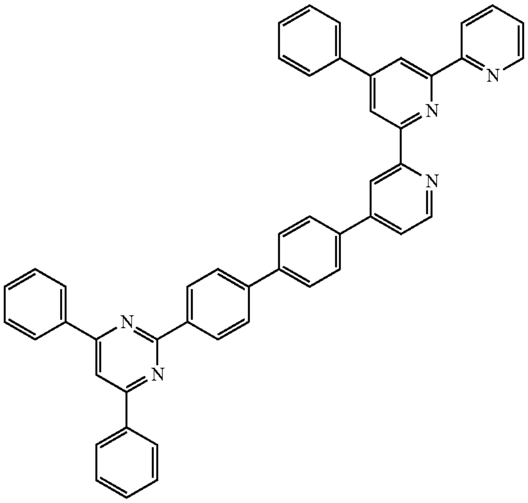
-continued
536
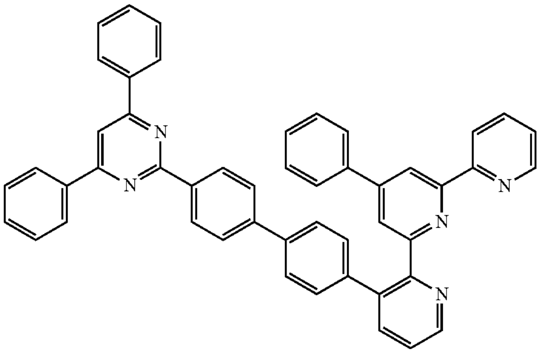
537
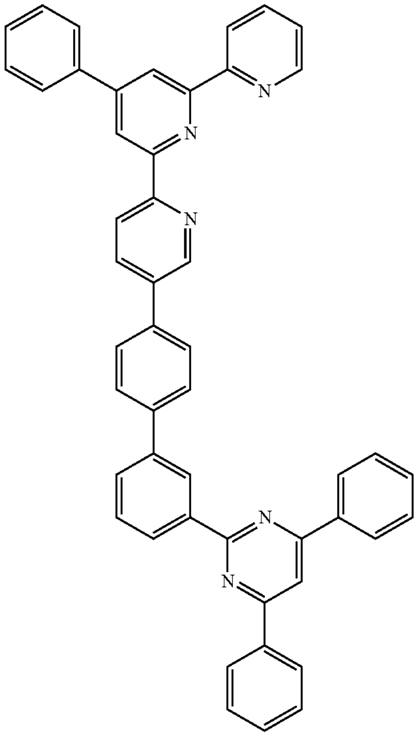
538
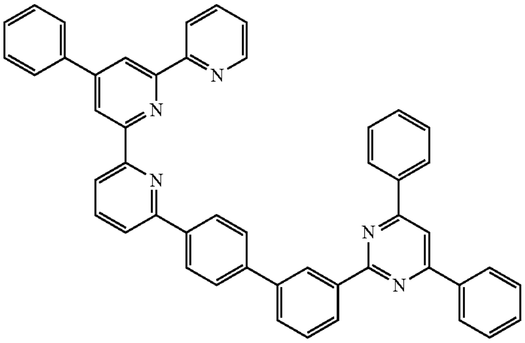

-continued
539
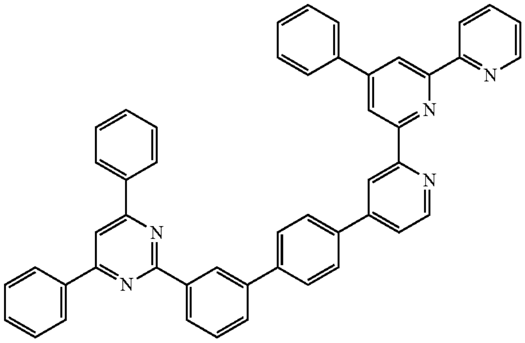
540
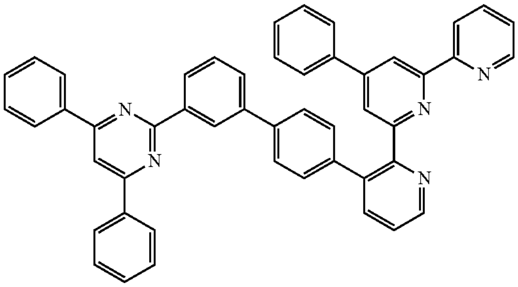
541
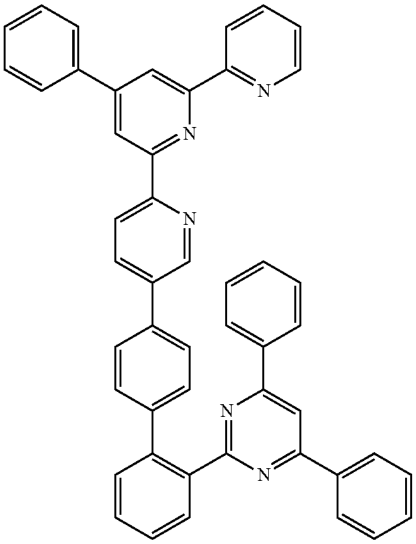
-continued
542
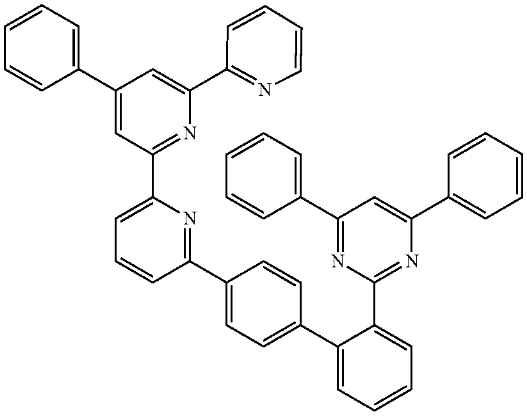
543
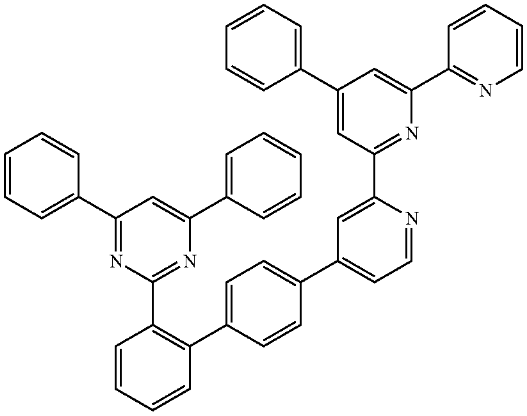
544
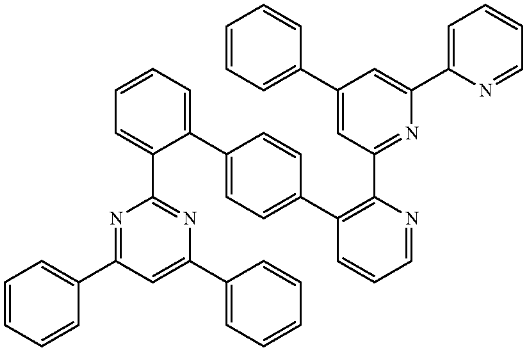

-continued
545
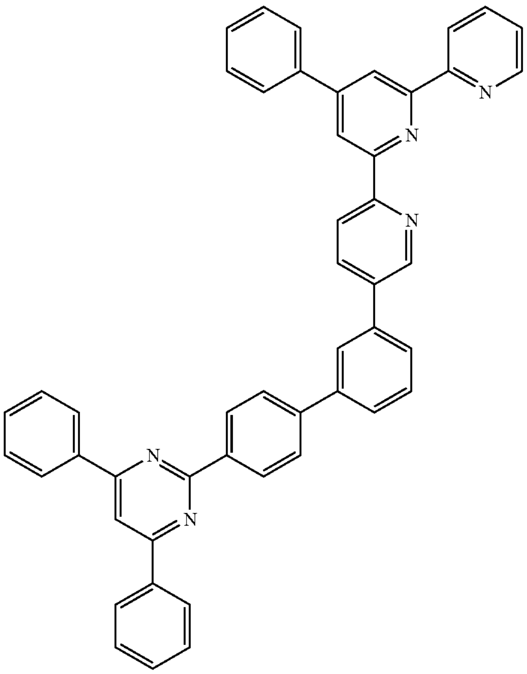
546
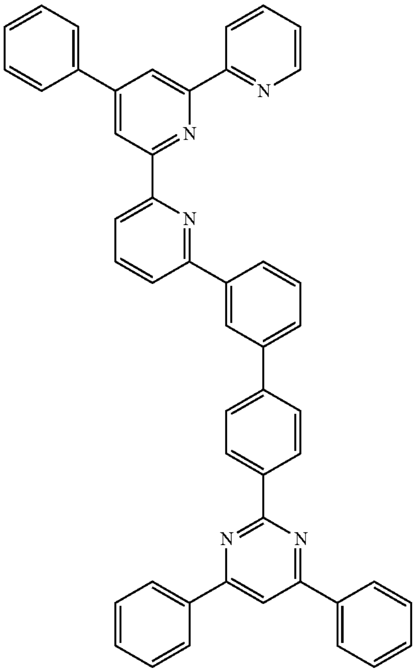
-continued
547
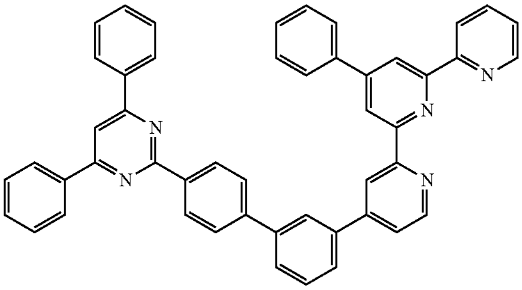
548
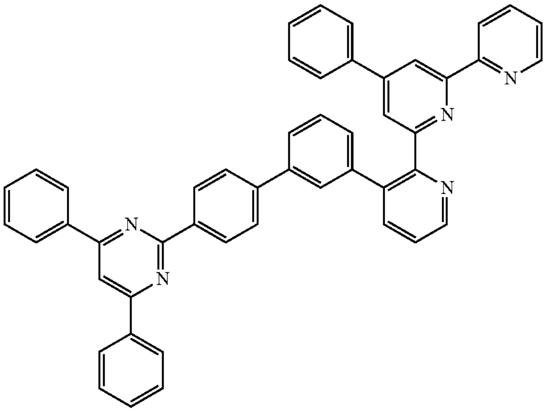
549
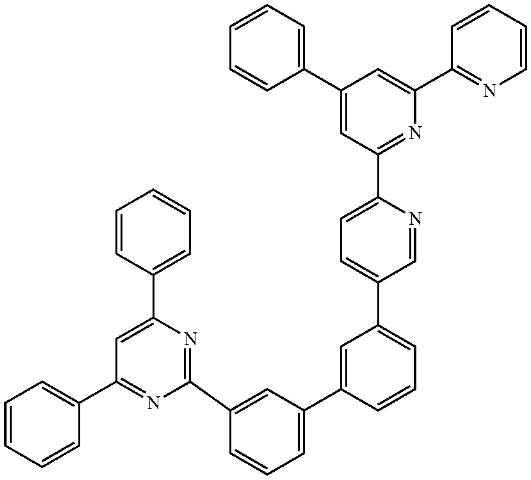

-continued
550
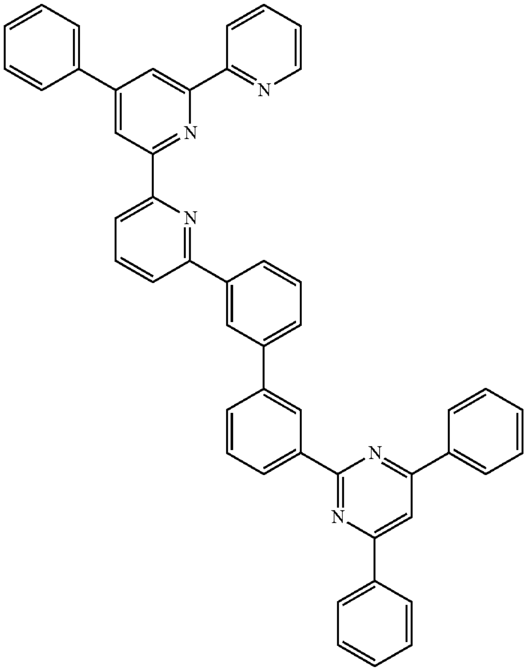
551
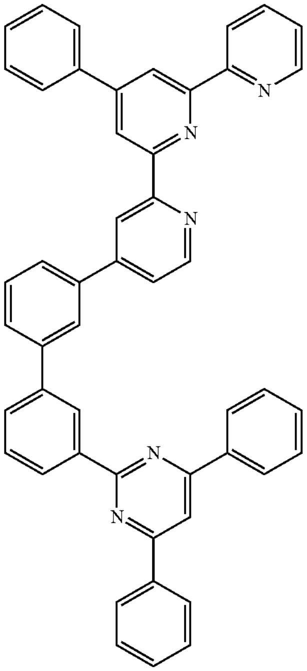
552
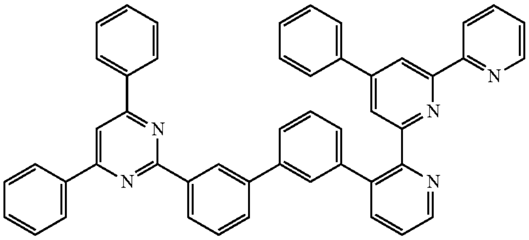
-continued
553
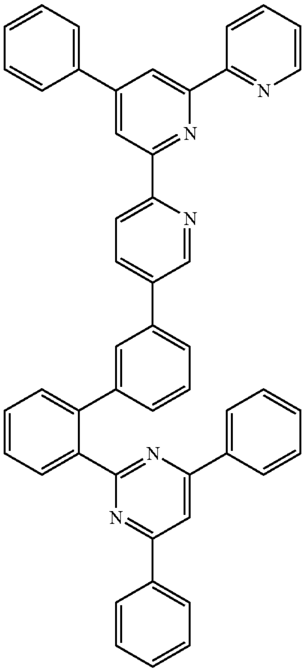
554
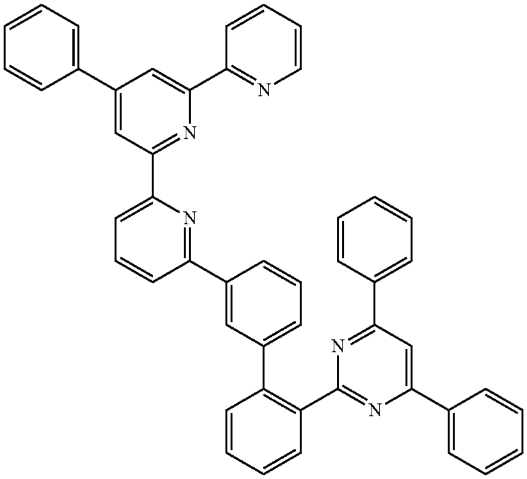

555
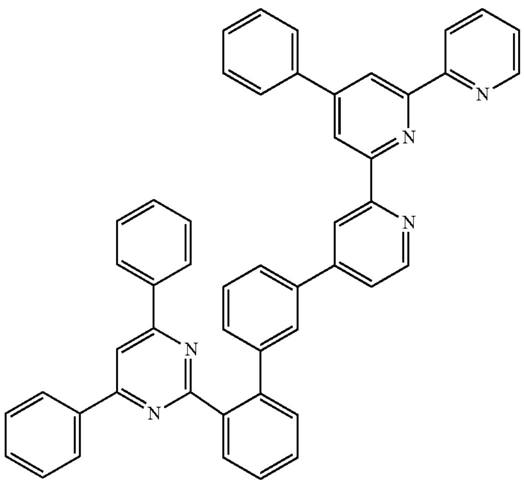
556
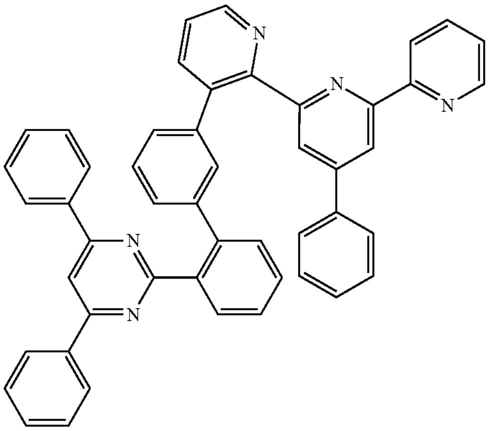
557
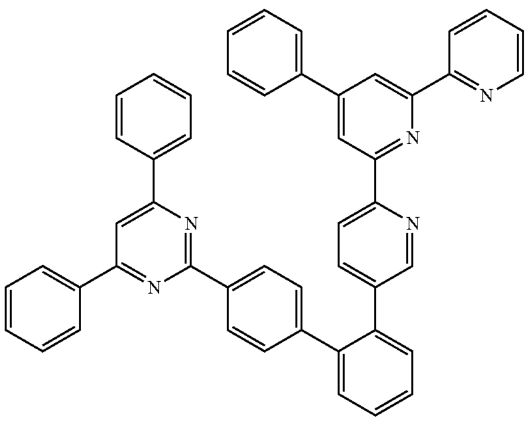
558
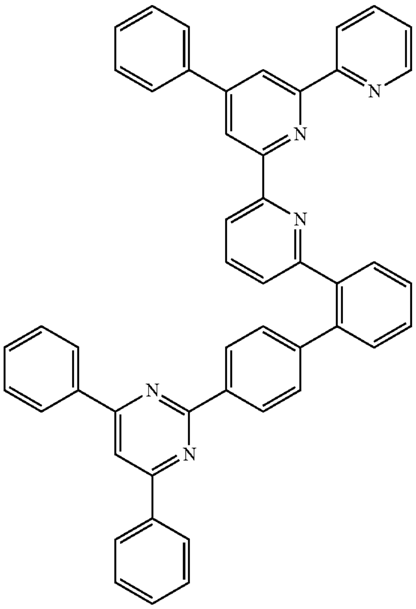
559
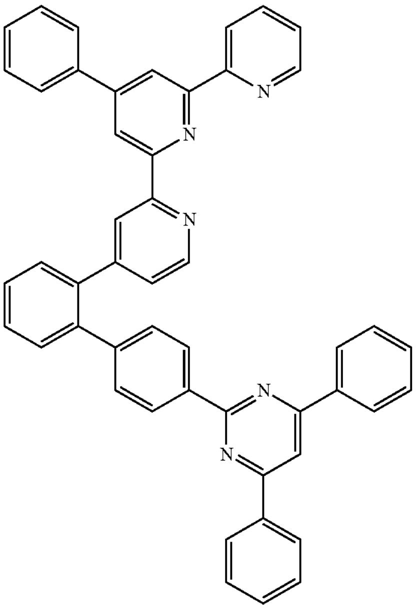

-continued
560
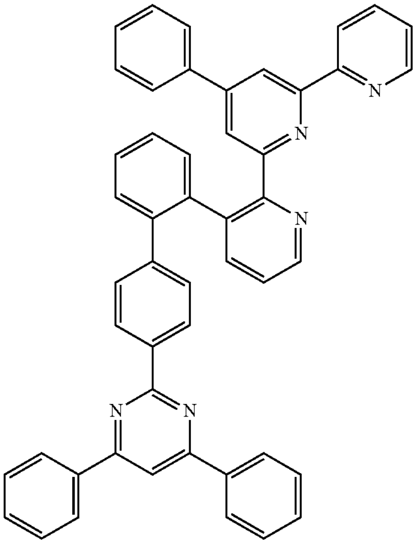
561
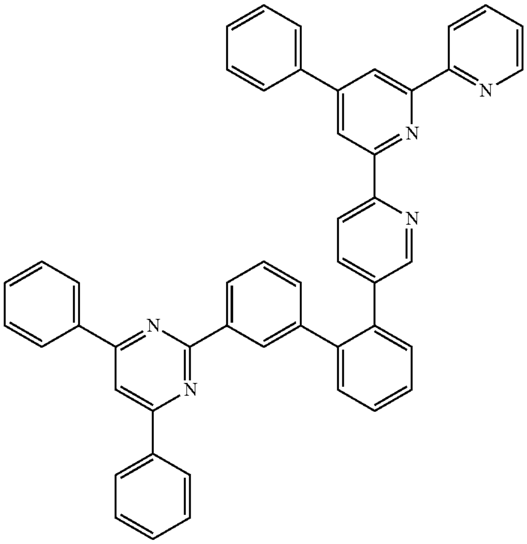
562
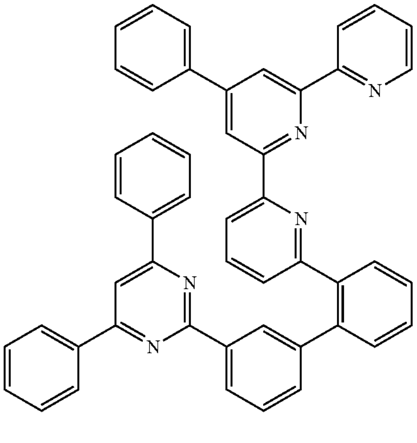
-continued
563
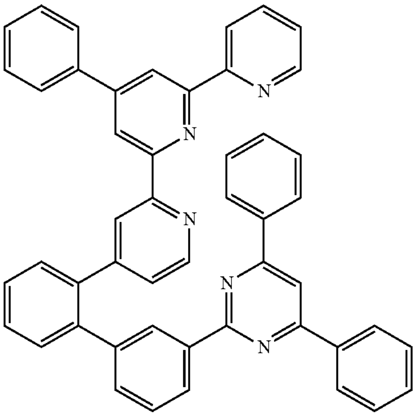
564
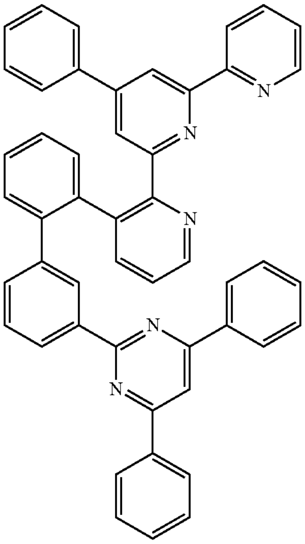
565
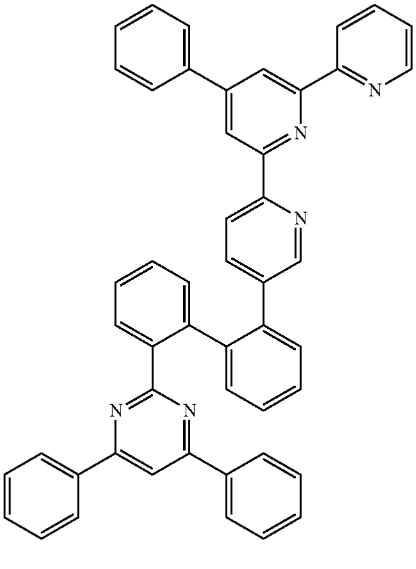

566
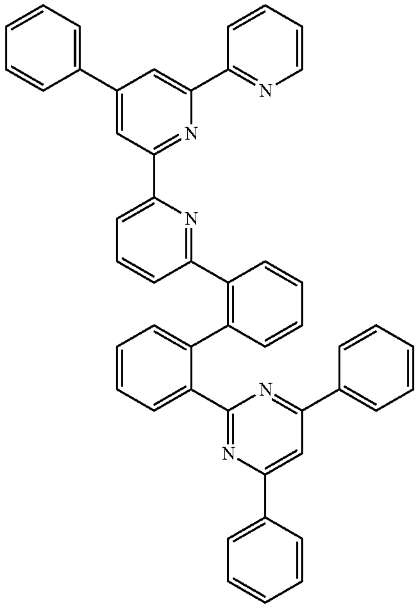
567
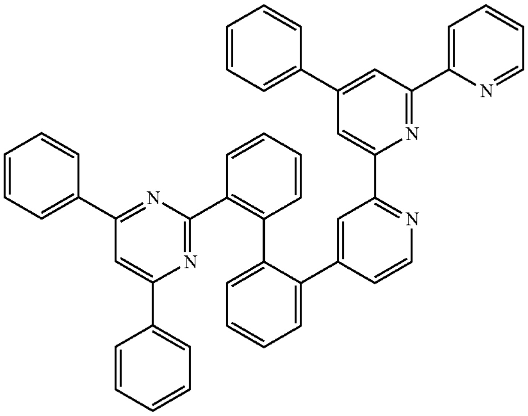
568
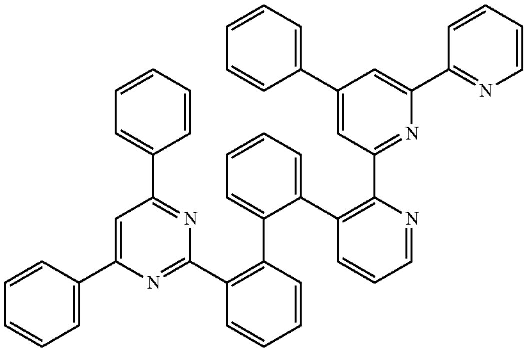
569
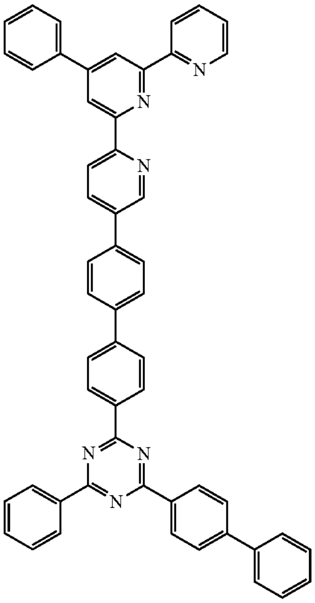
570
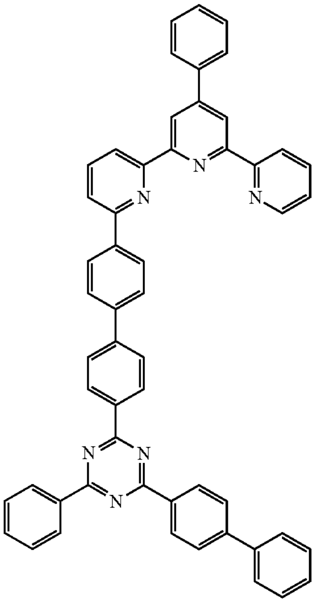

-continued
571
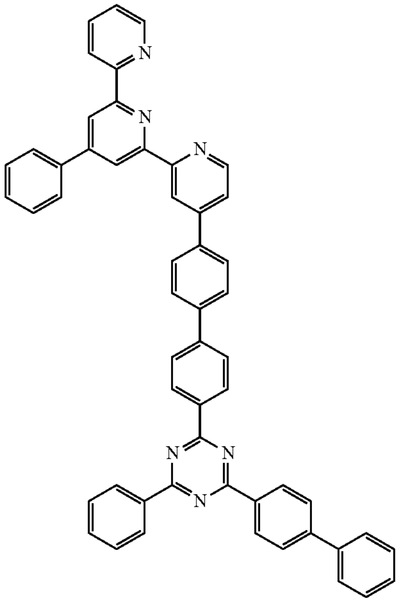
572
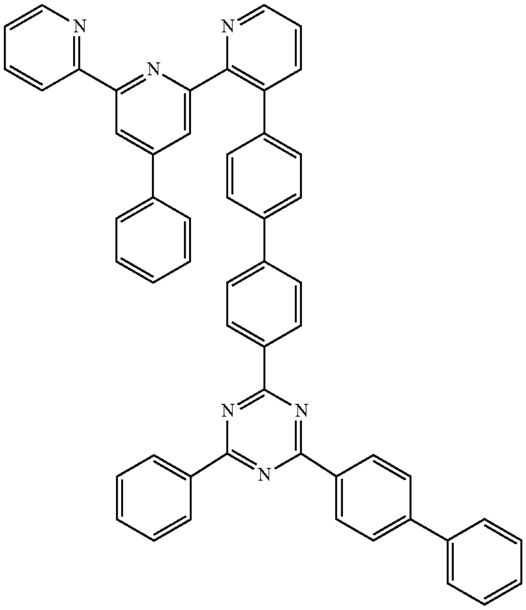
-continued
573
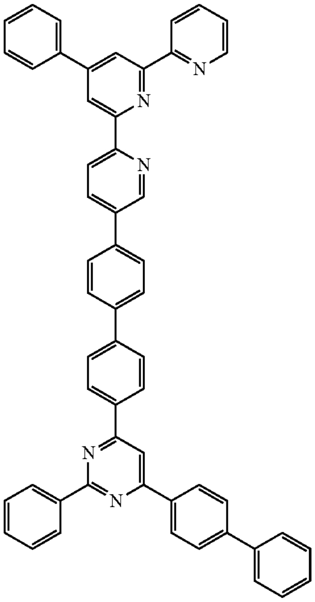
574
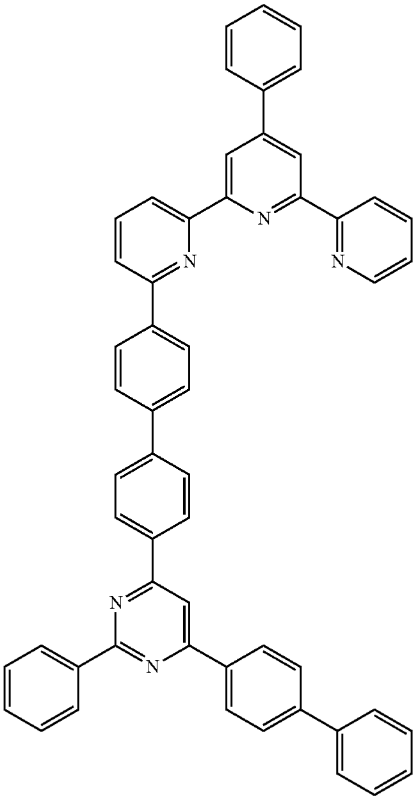

-continued
575
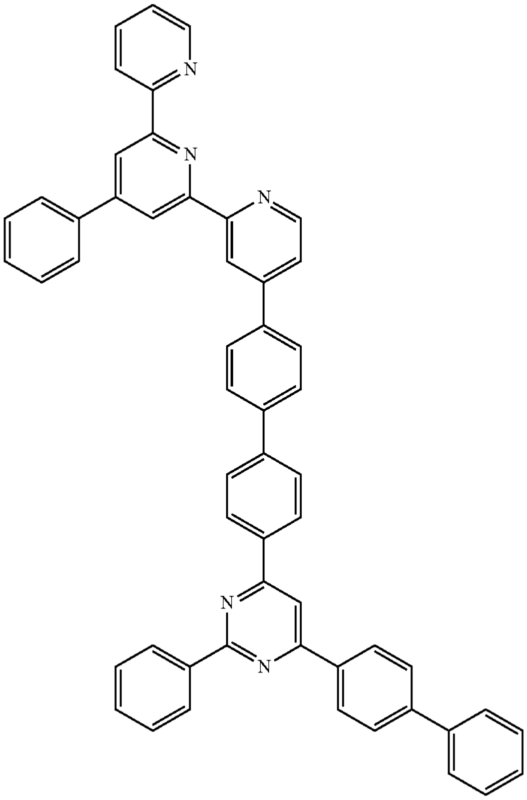
576
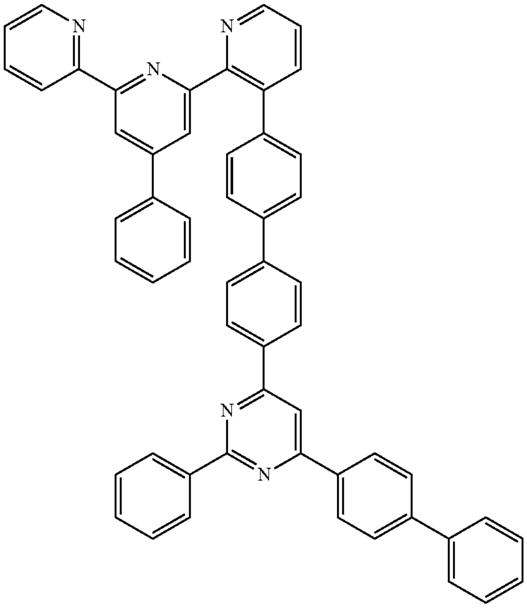
-continued
577
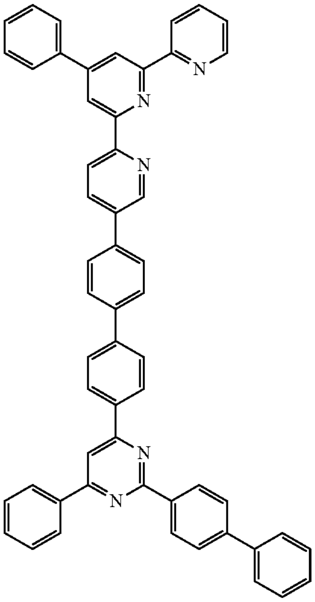
578
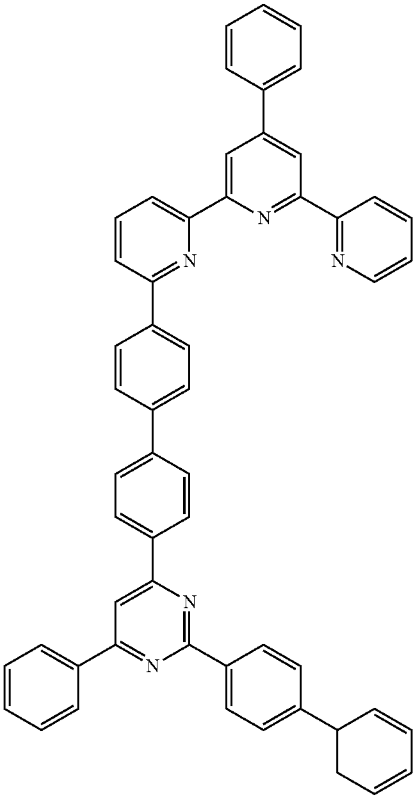

-continued
579
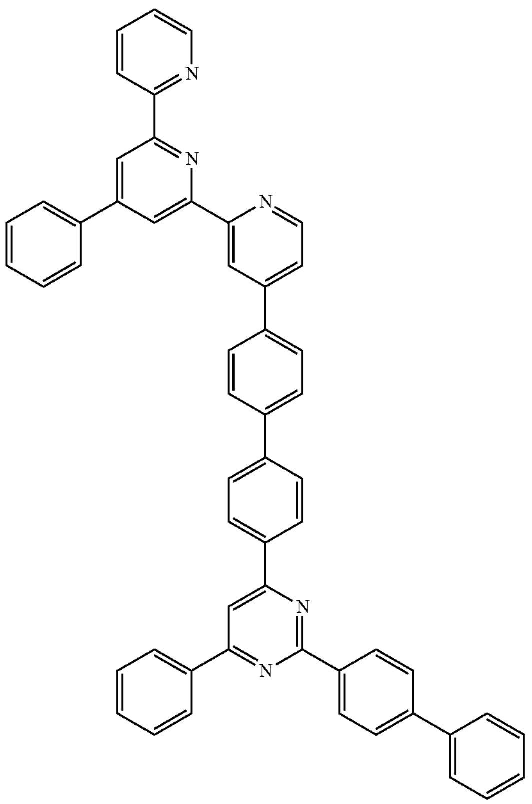
580
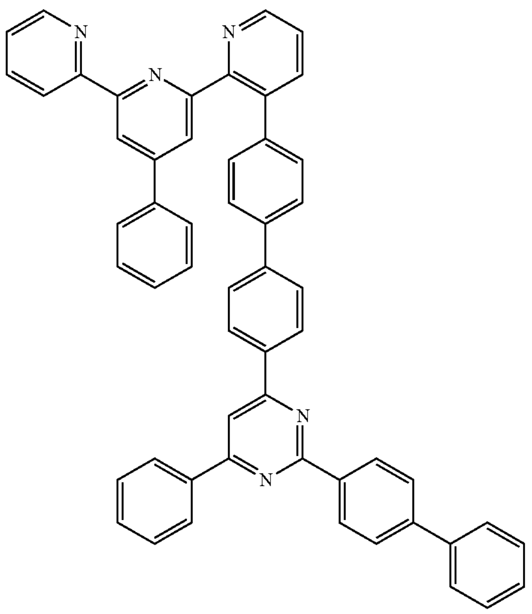
-continued
581
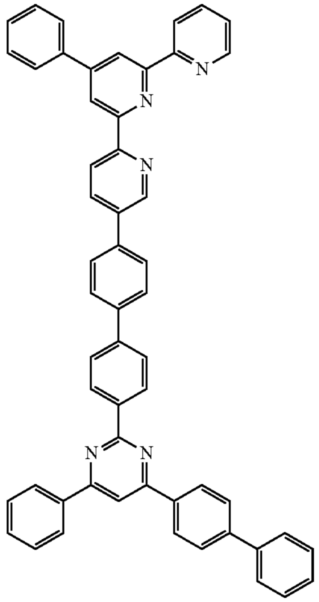
582
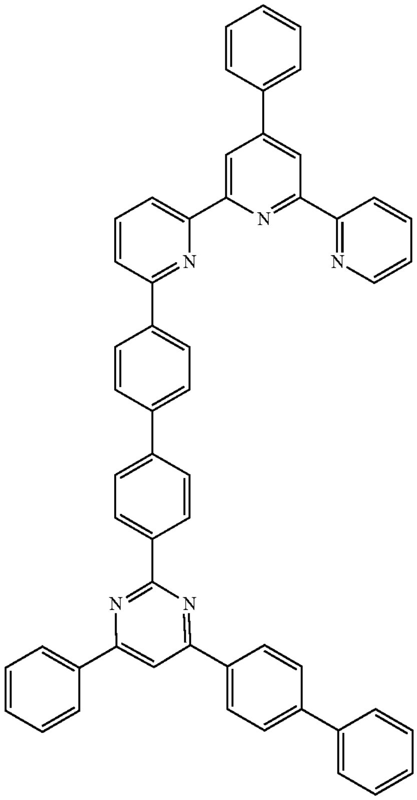

-continued
583
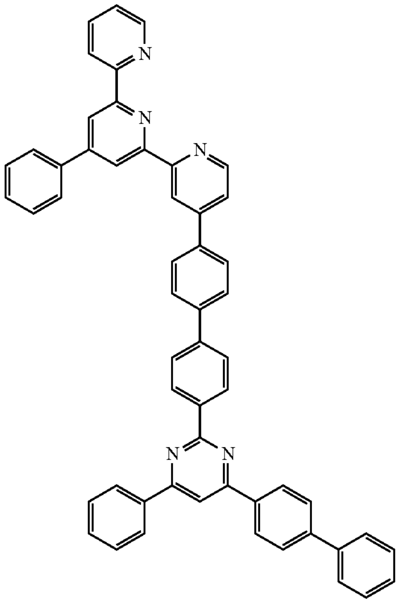
584
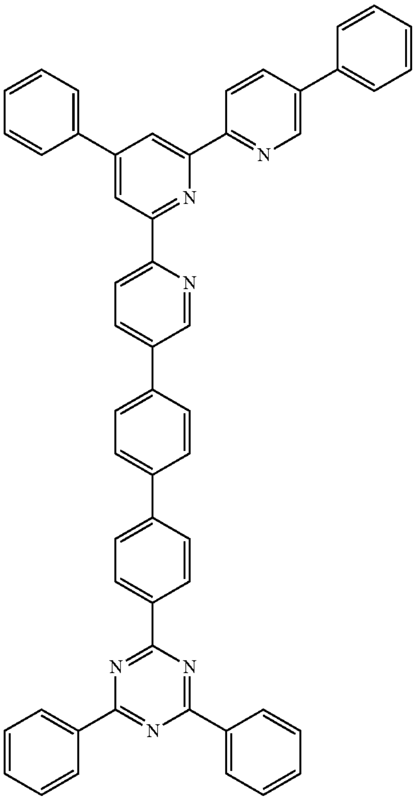
-continued
585
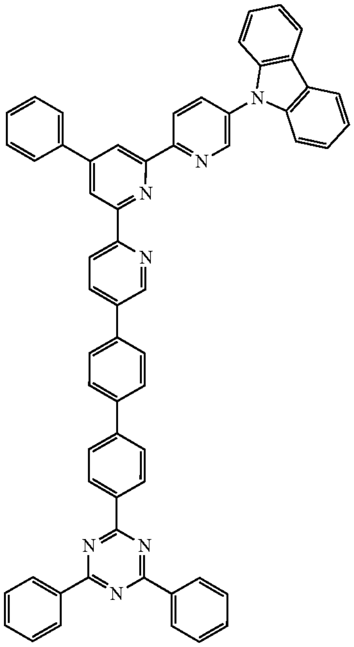
586
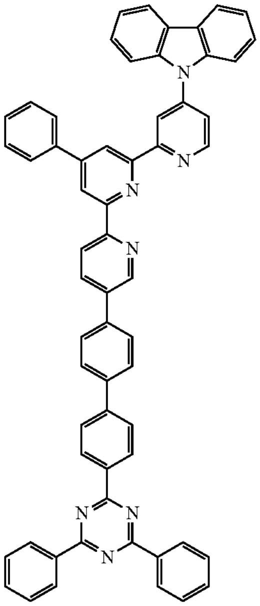

-continued
587
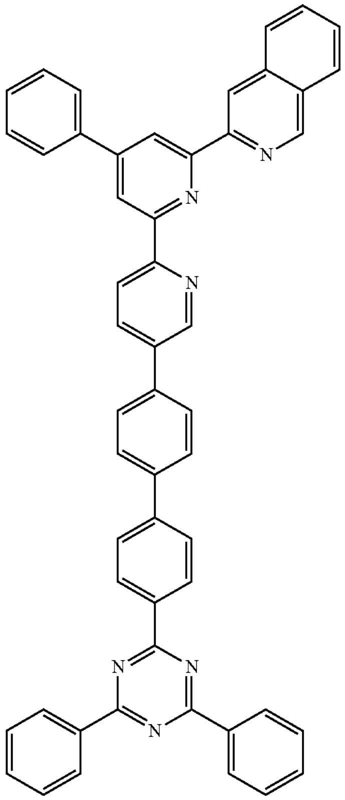
588
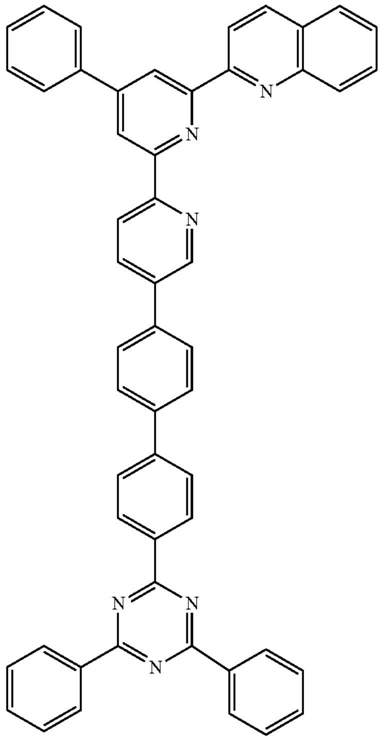
-continued
589
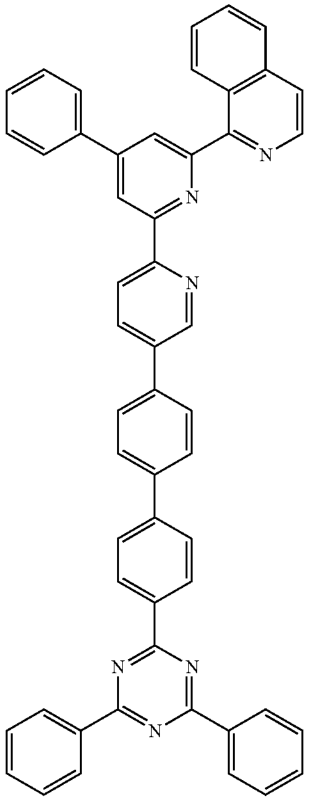
590
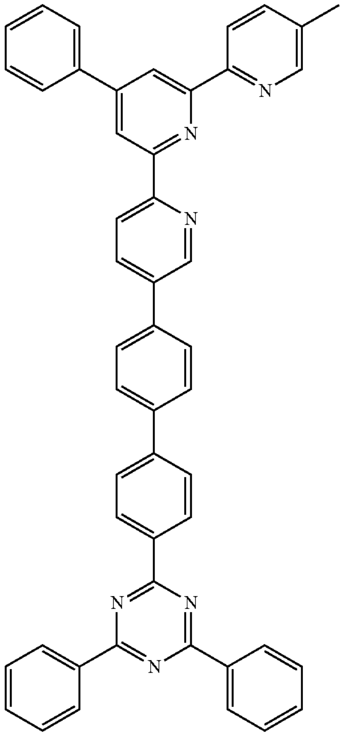

-continued
591
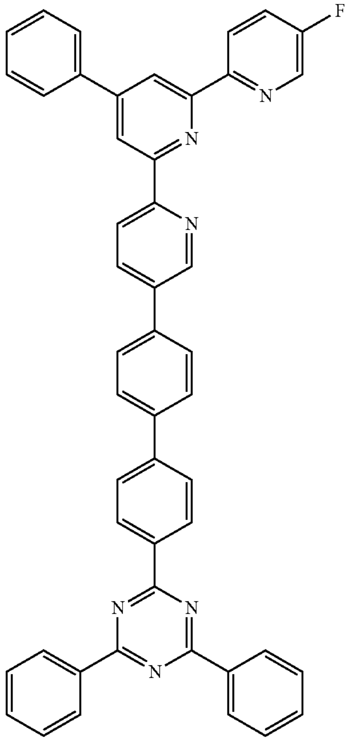
592
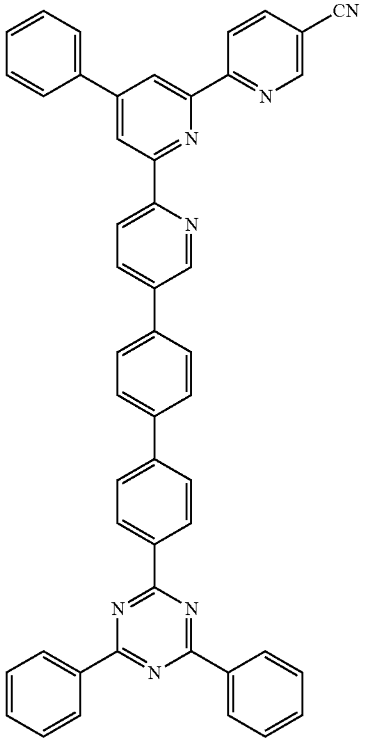
-continued
593
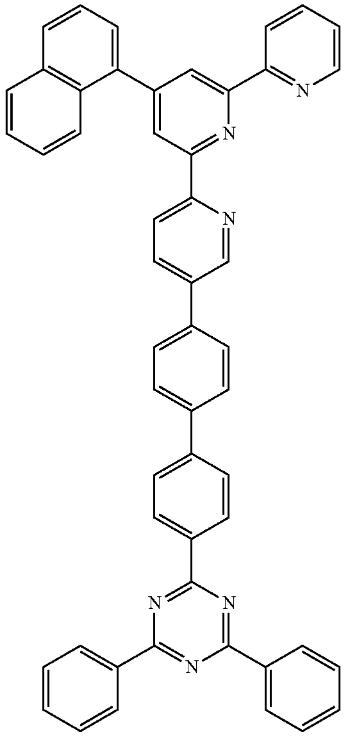
594
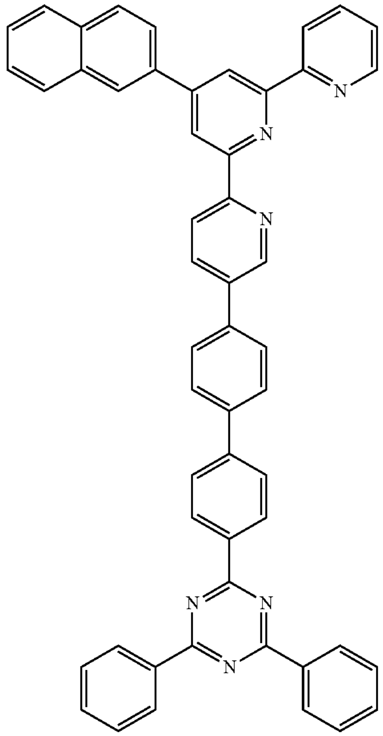

-continued
595
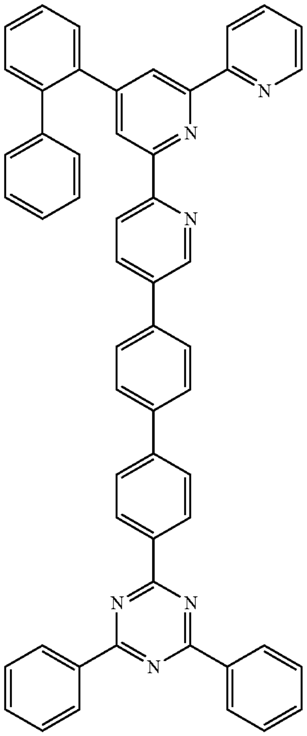
596
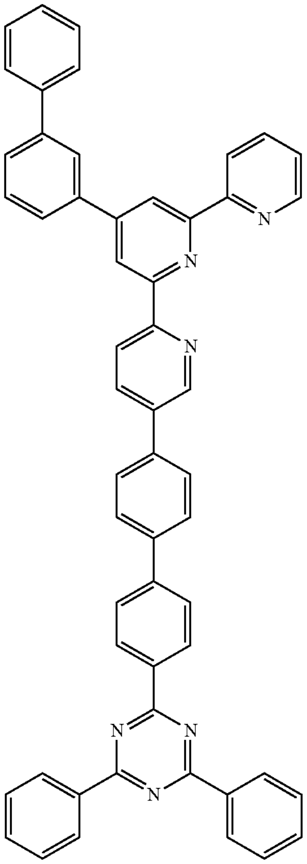
-continued
597
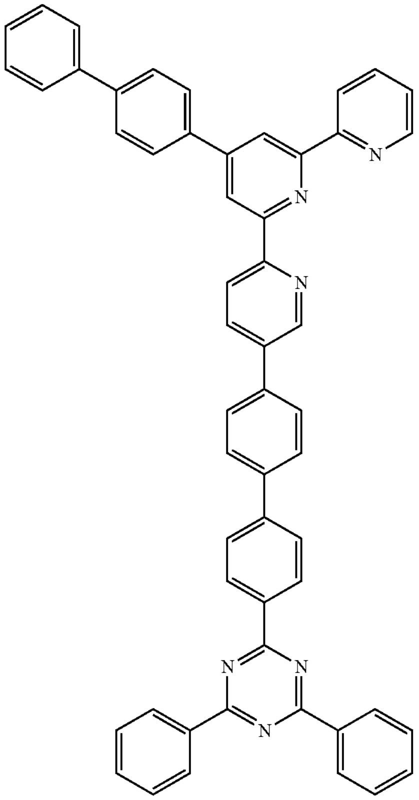
598
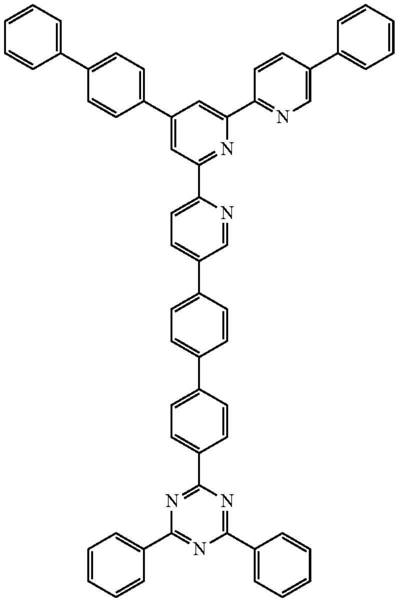

-continued
599
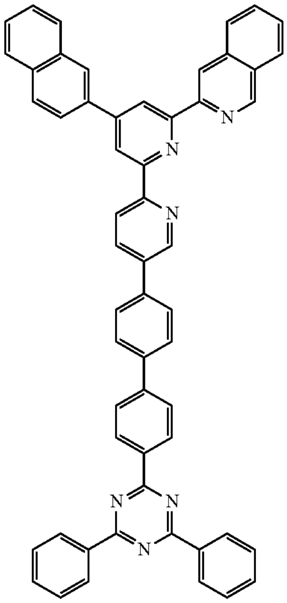
600
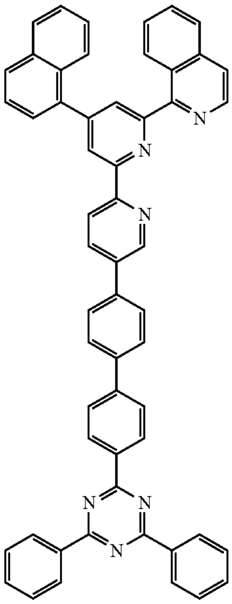
-continued
601
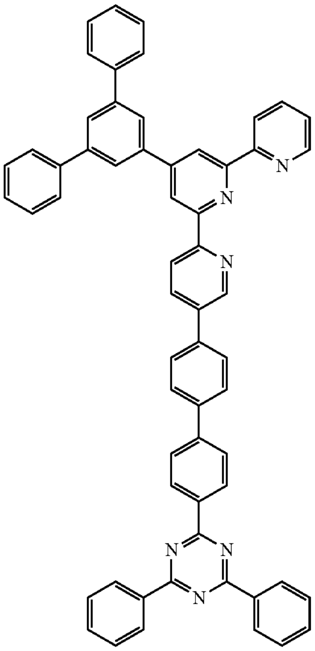
602
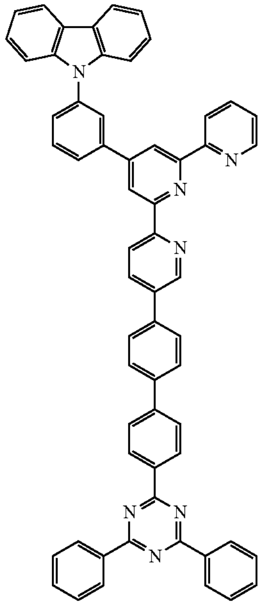

-continued
603
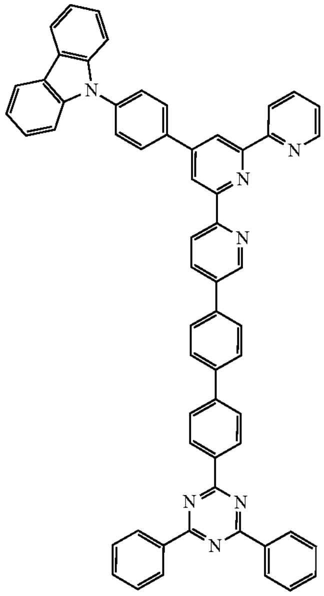
604
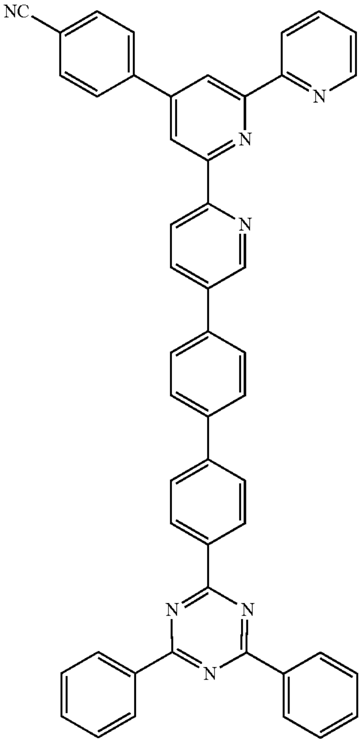
-continued
605
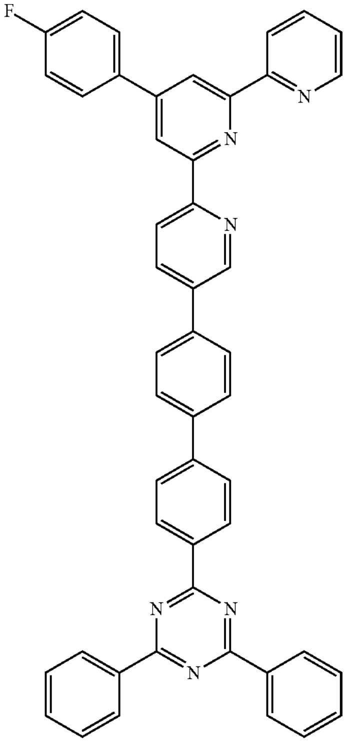
606
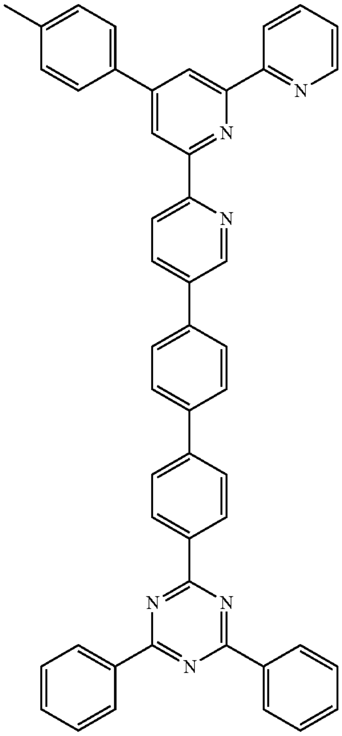

-continued
607
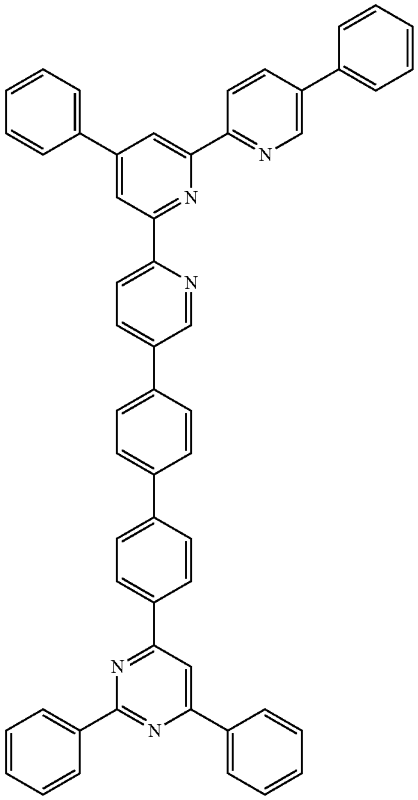
608
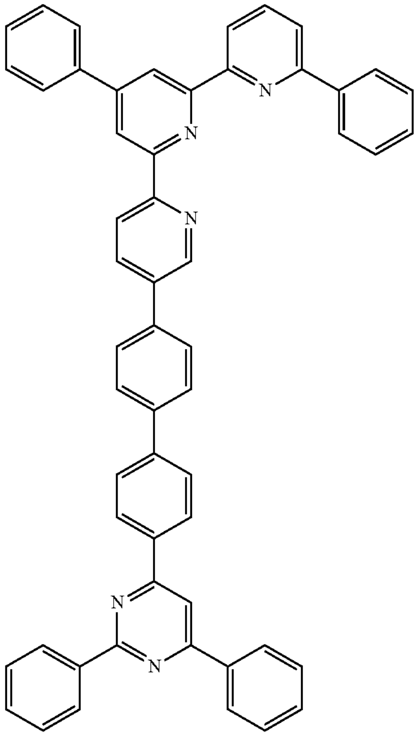
-continued
609
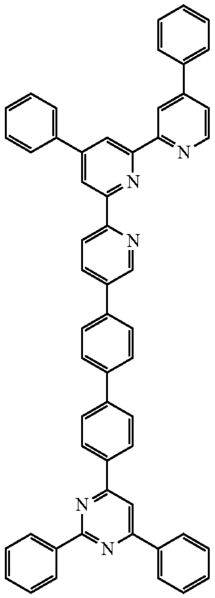
610
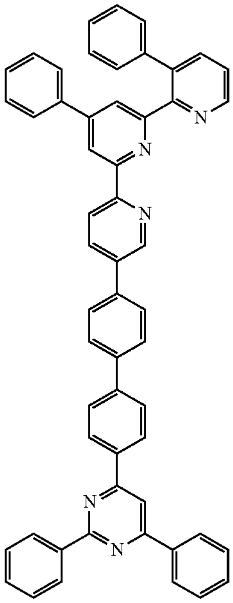

-continued
611
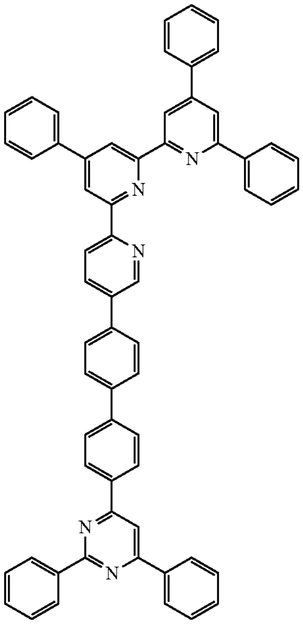
612
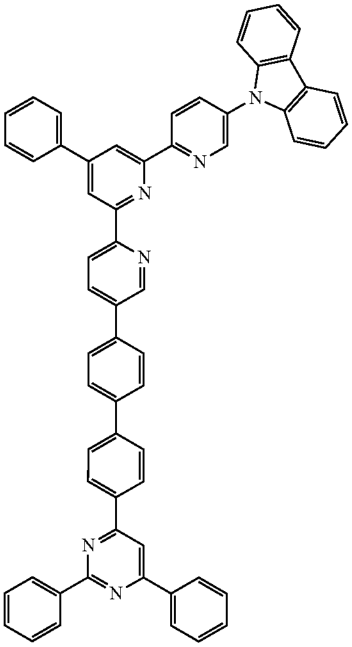
-continued
613
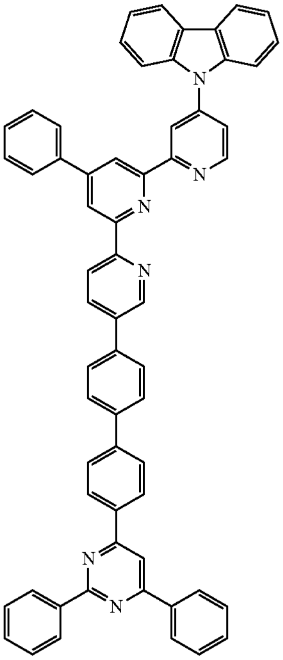
614
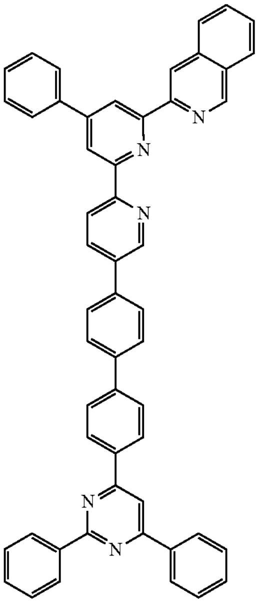

-continued
615
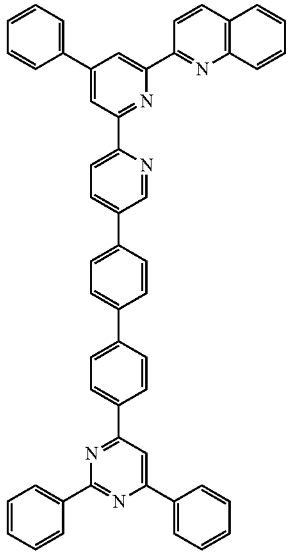
616
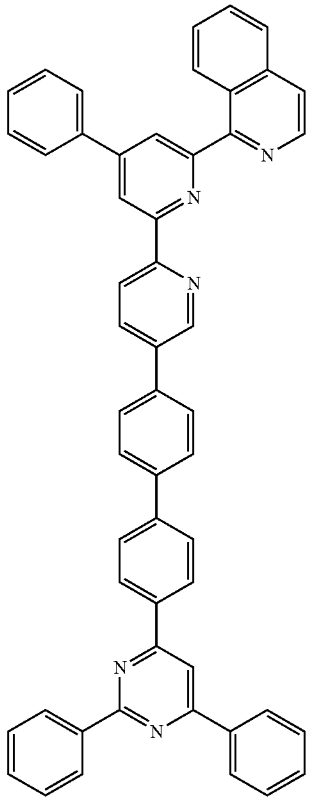
-continued
617
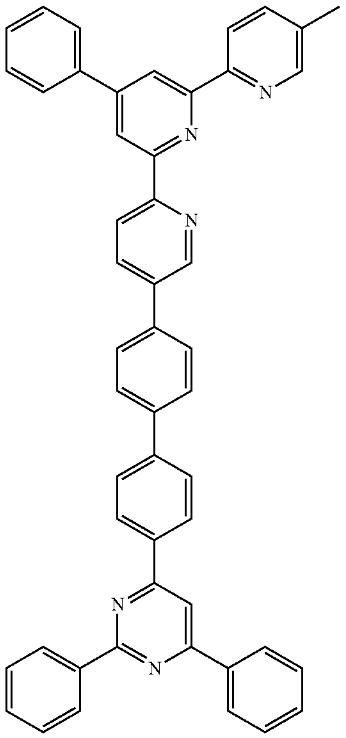
618
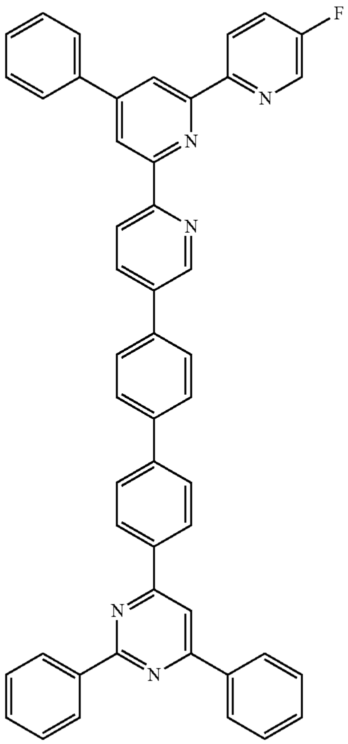

-continued
619
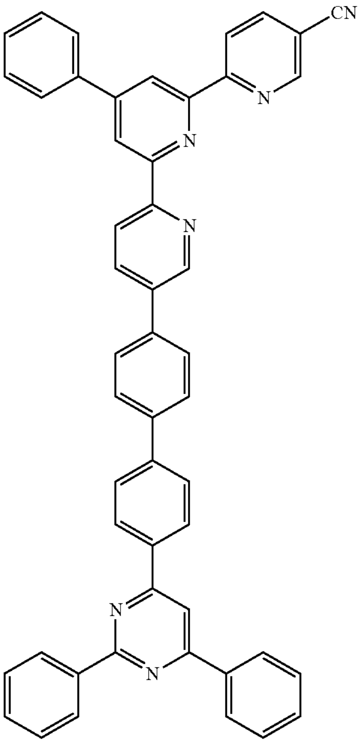
620
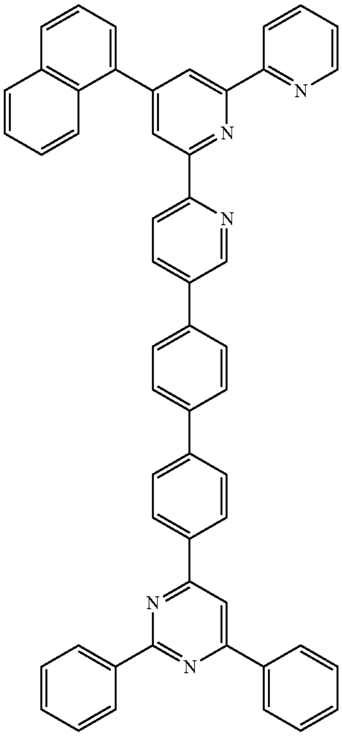
-continued
621
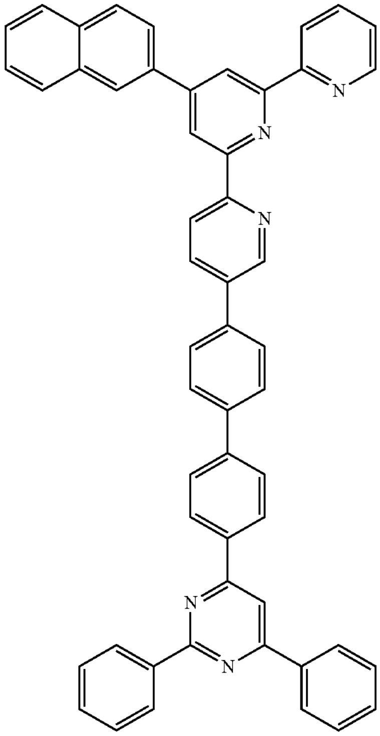
622
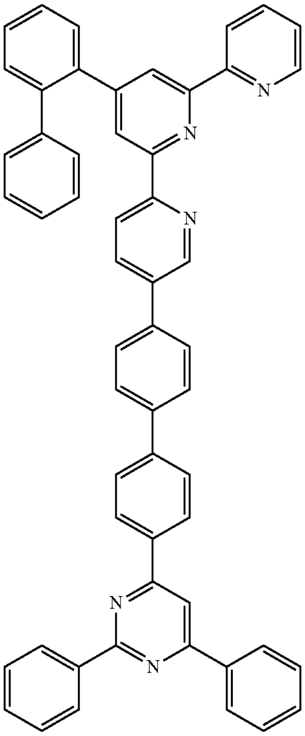

-continued
623
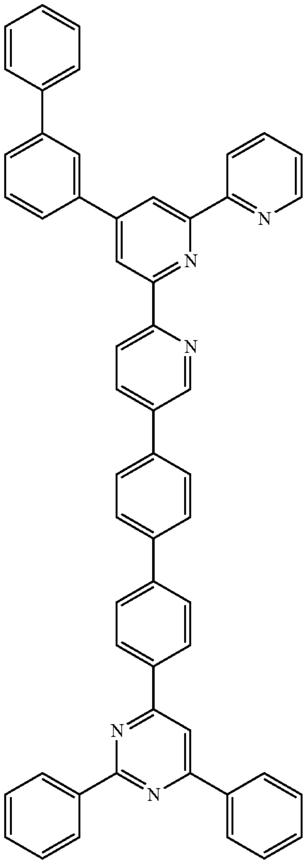
624
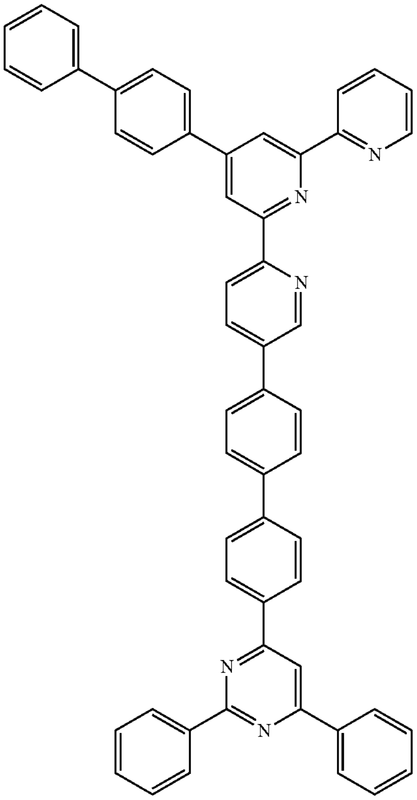
-continued
625
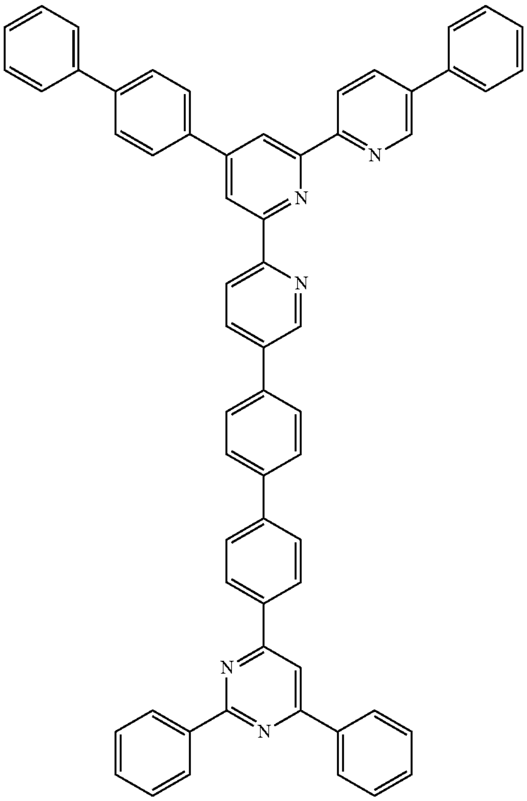
626
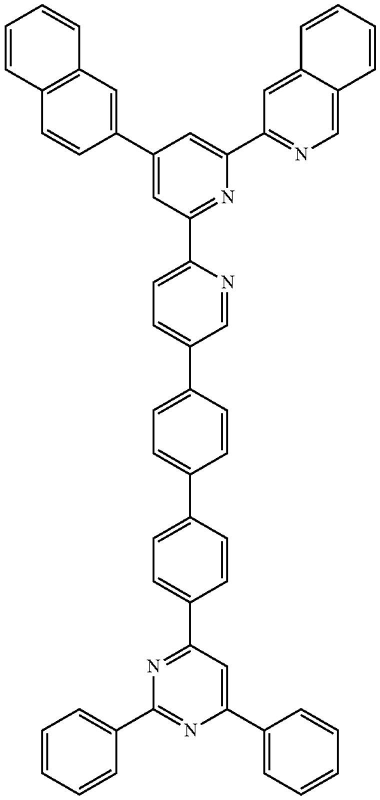

-continued
627
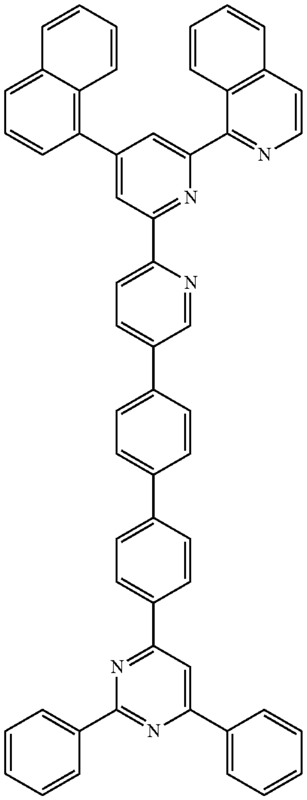
628
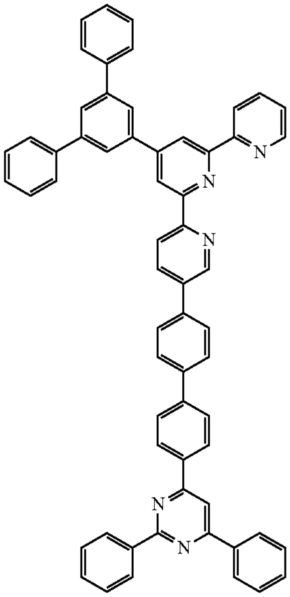
-continued
629
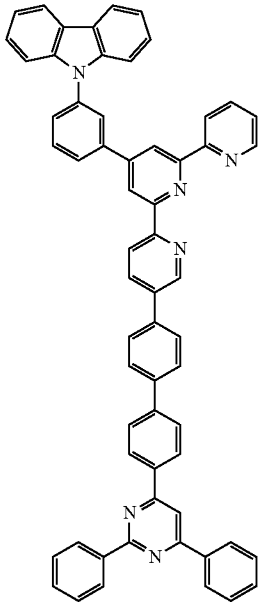
630
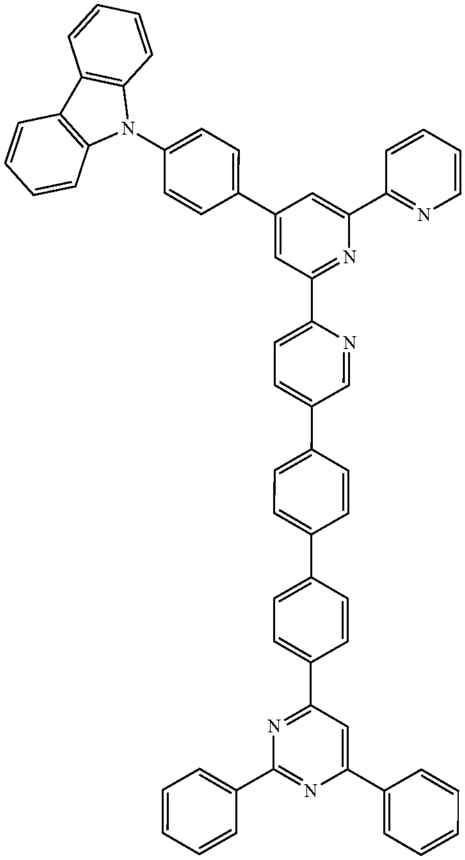

-continued
631
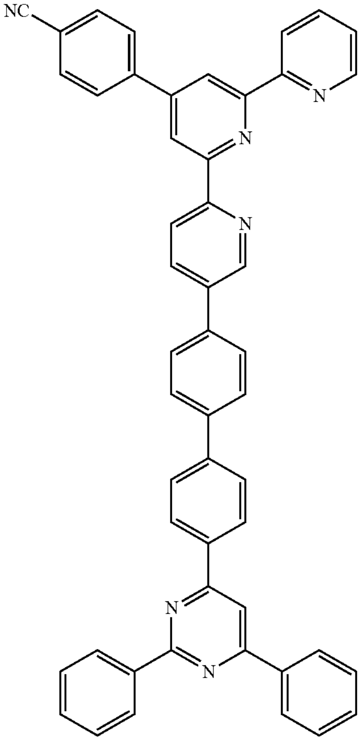
632
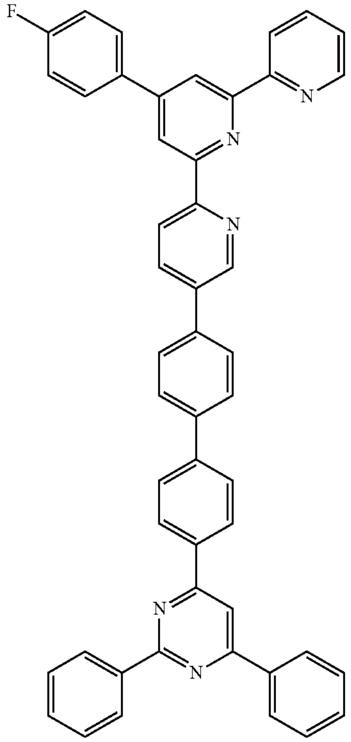
-continued
633
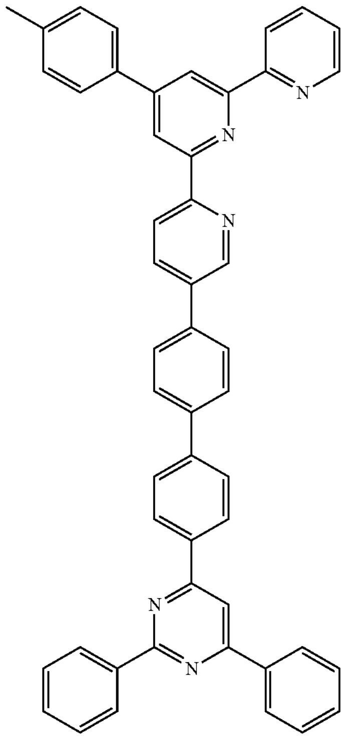
634
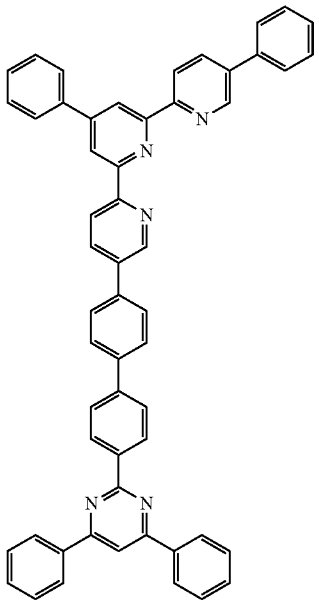

-continued
635
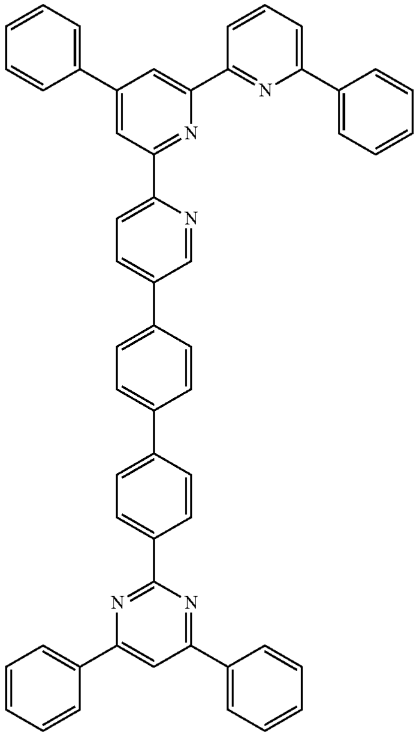
636
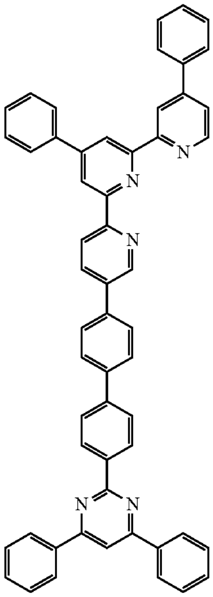
-continued
637
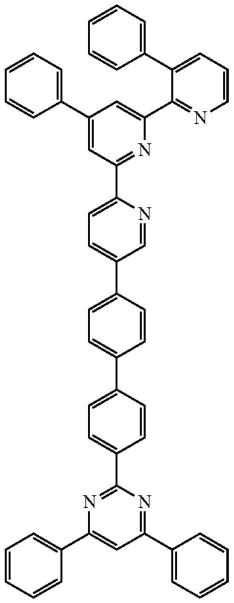
638
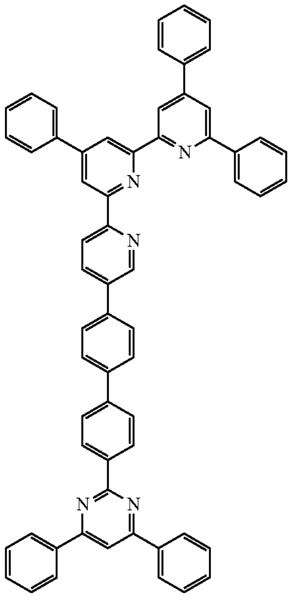

639
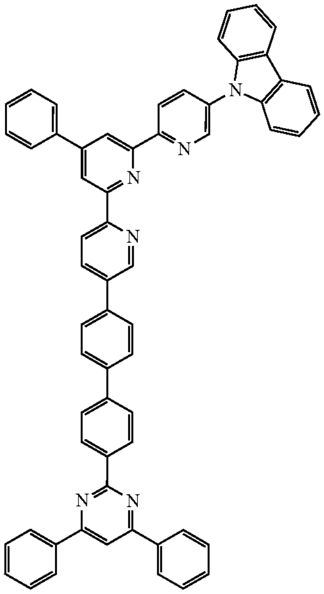
640
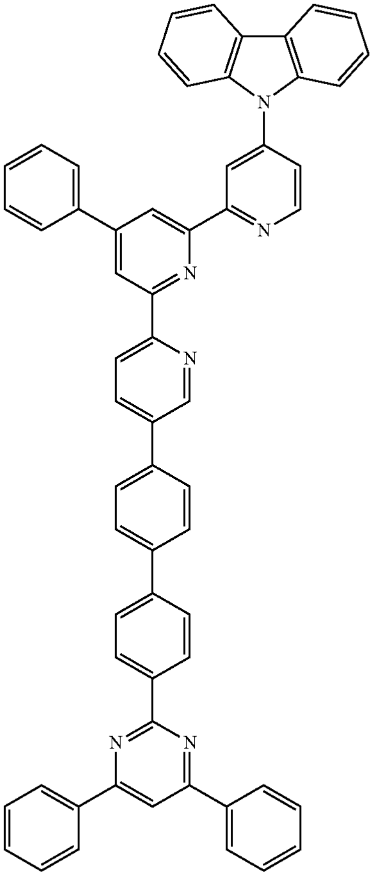
641
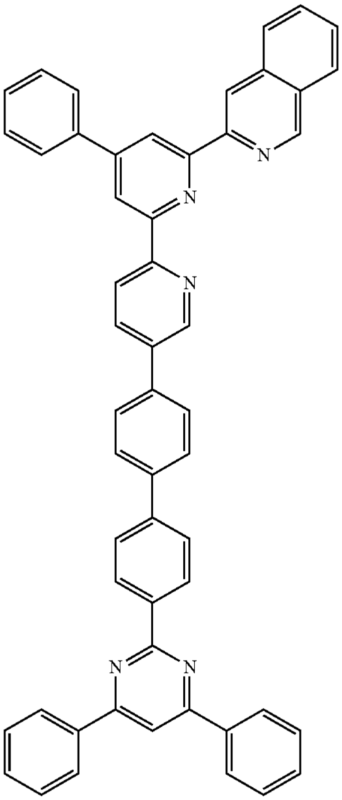
642
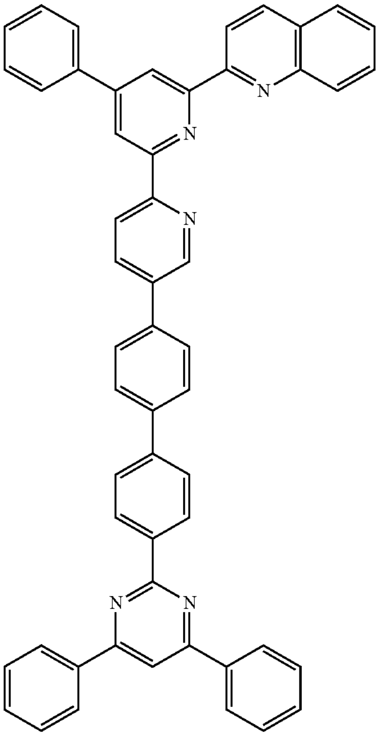

643
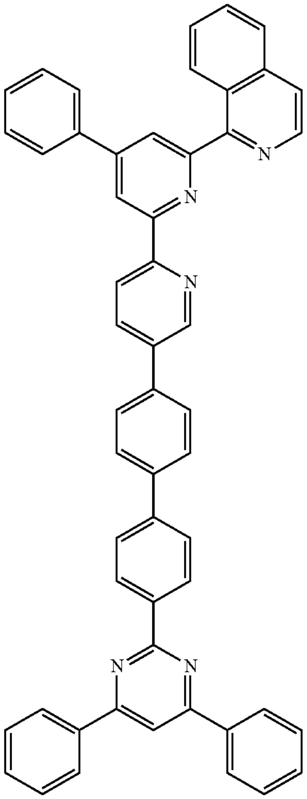
644
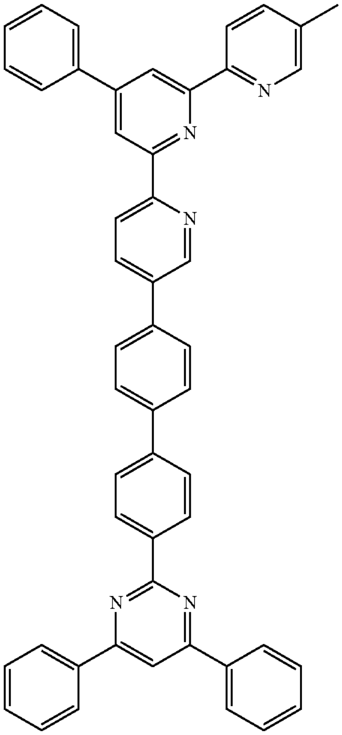
645
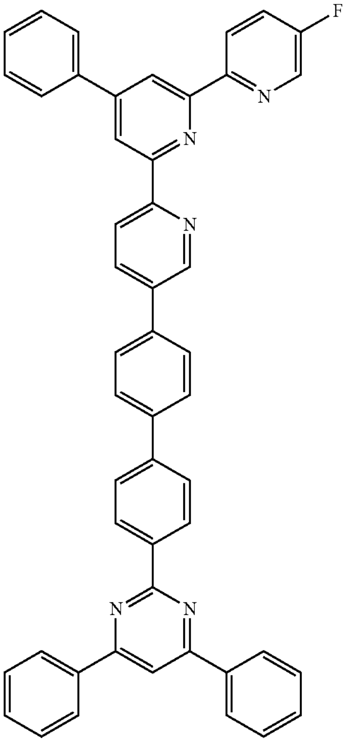
646
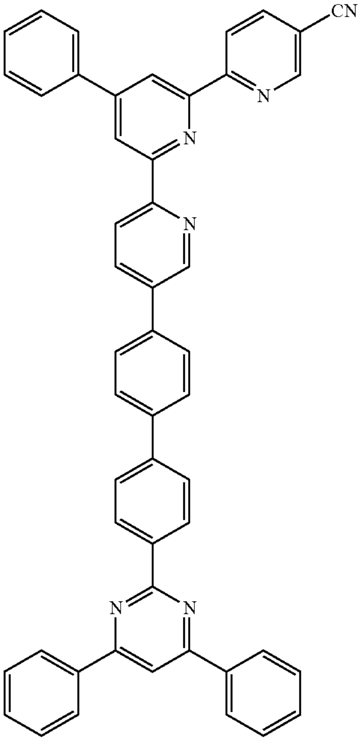

647
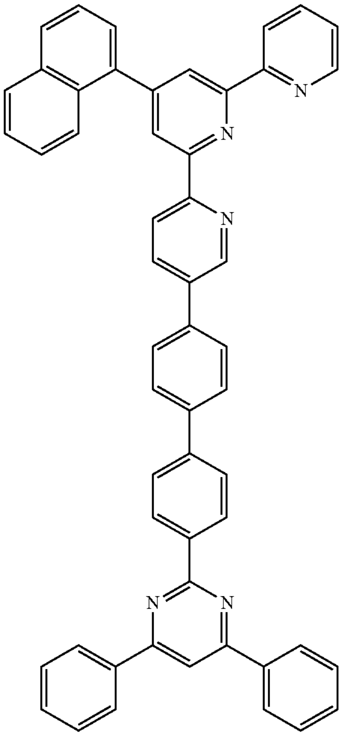
648
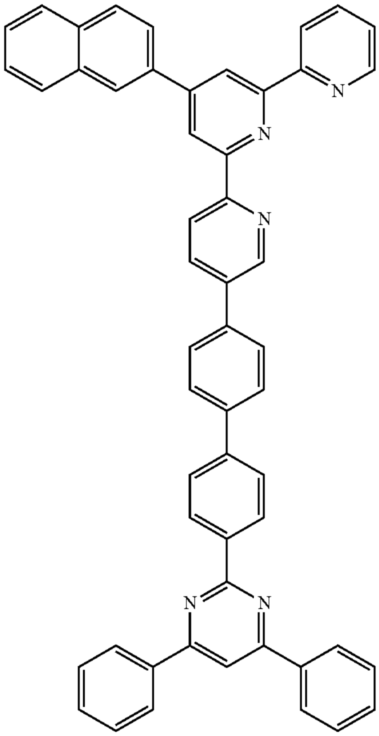
649
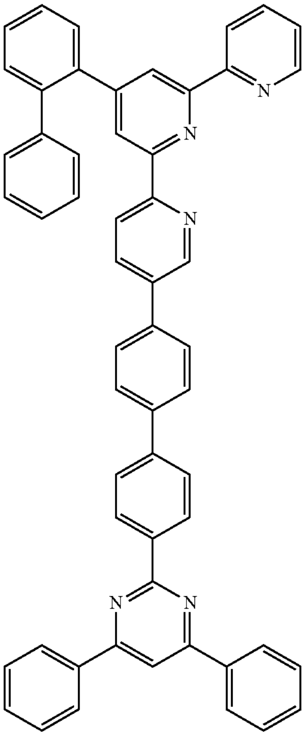
650
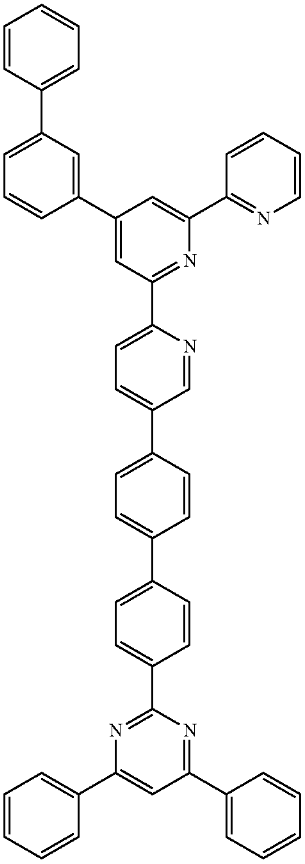

-continued
651
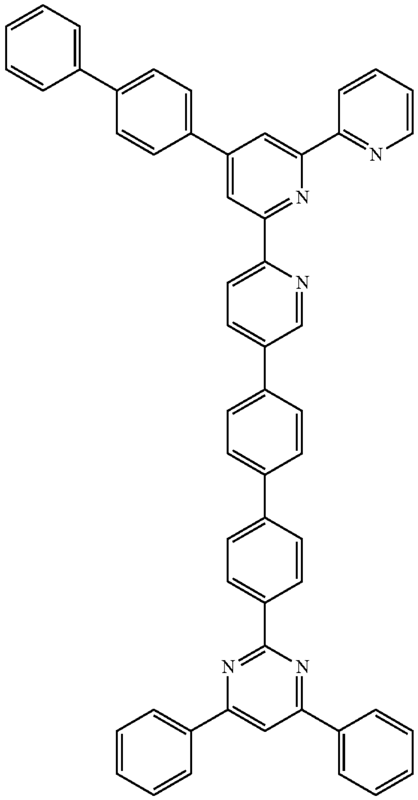
652
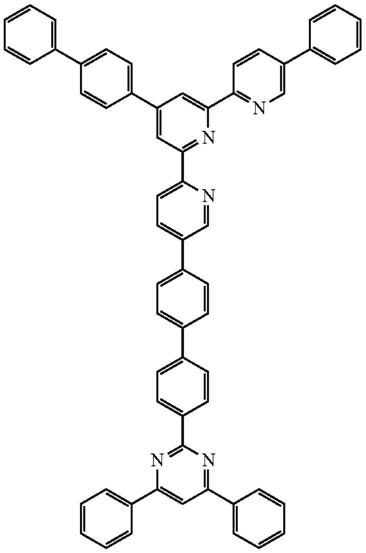
-continued
653
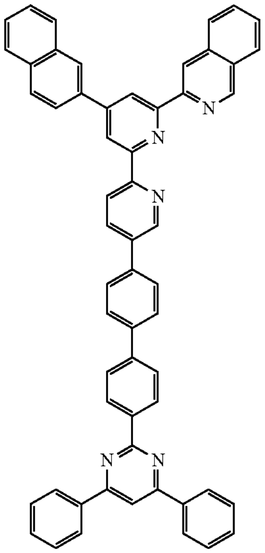
654
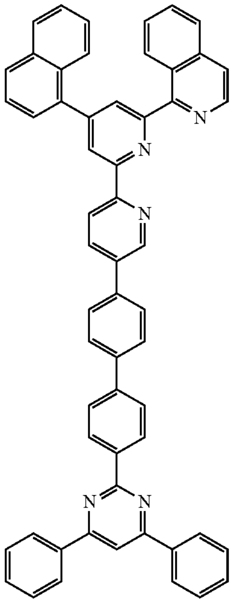

-continued
655
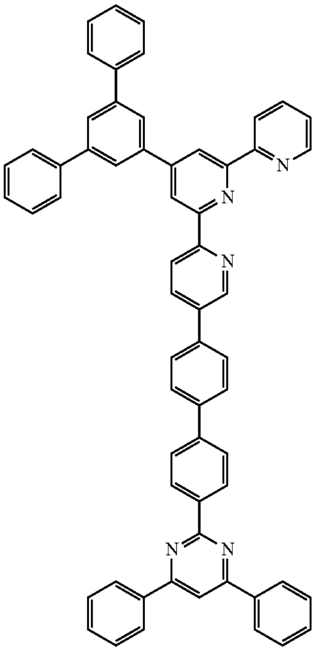
656
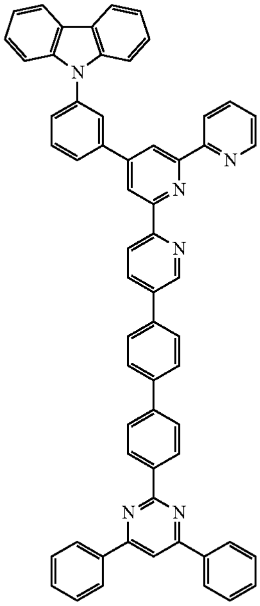
-continued
657
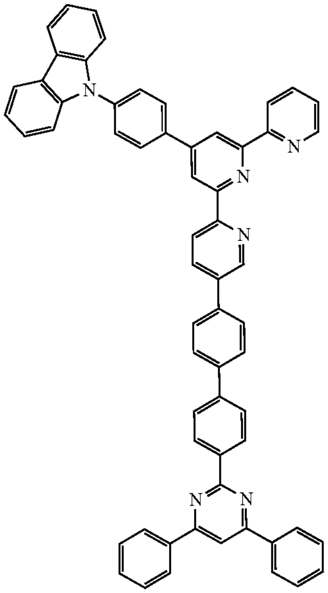
658
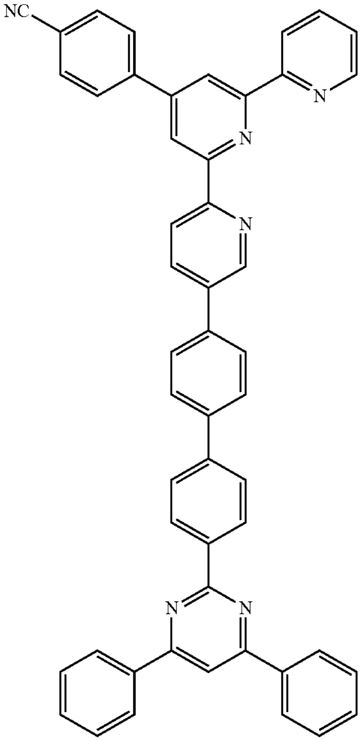

-continued
659
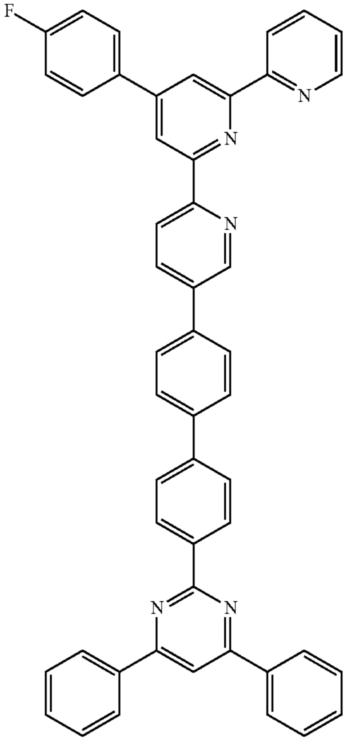
660
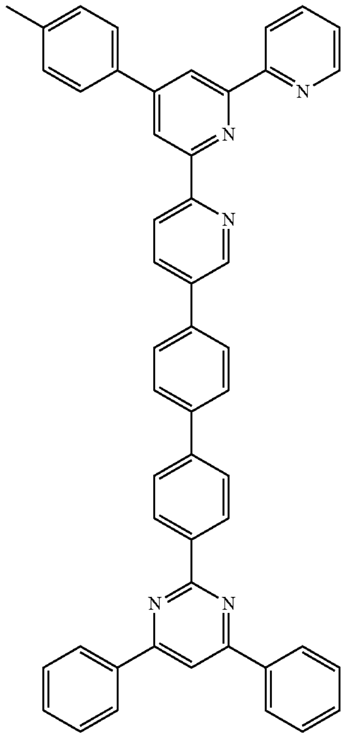
-continued
661
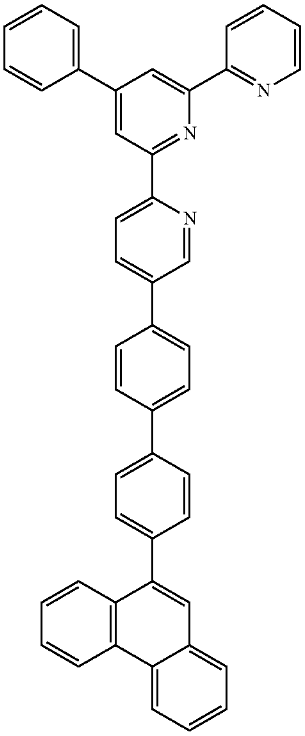
662
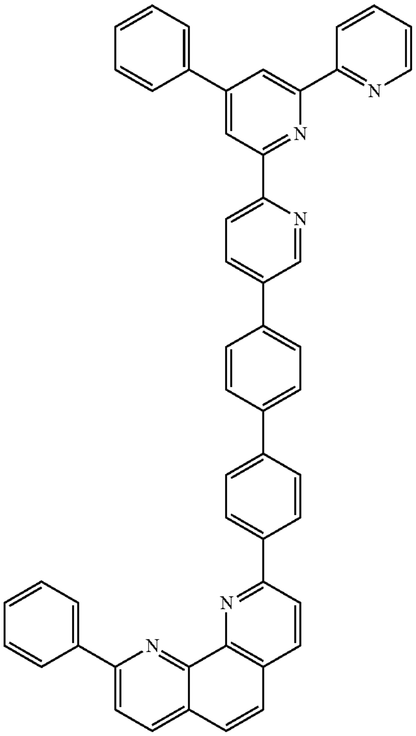

663
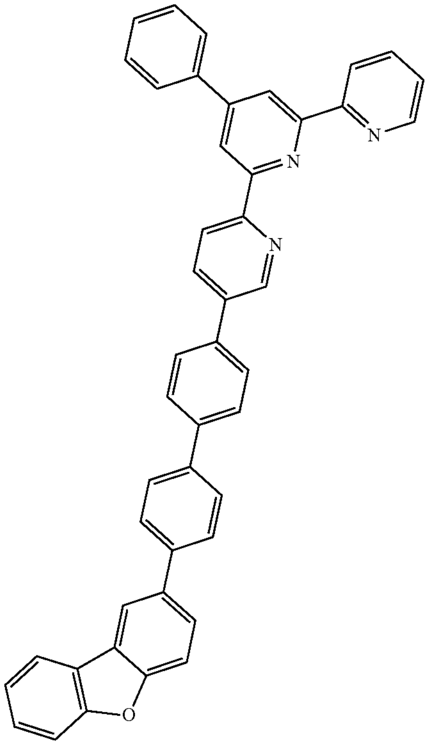
664
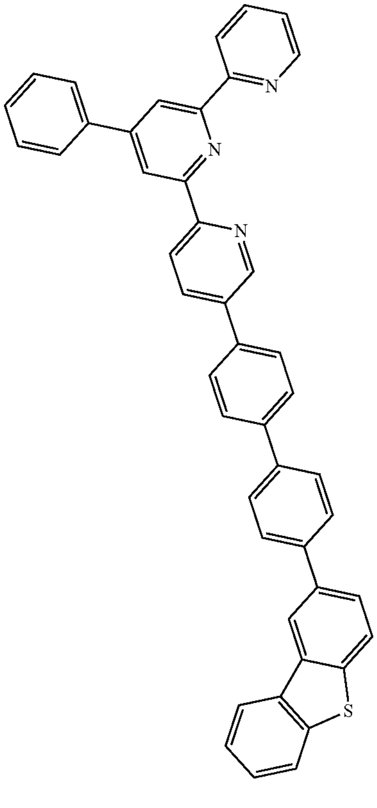
665
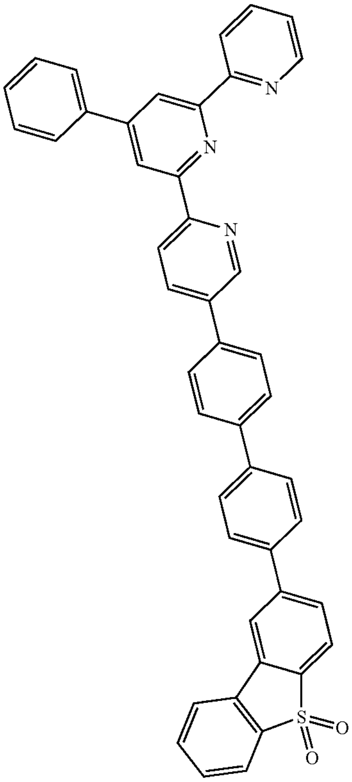
666
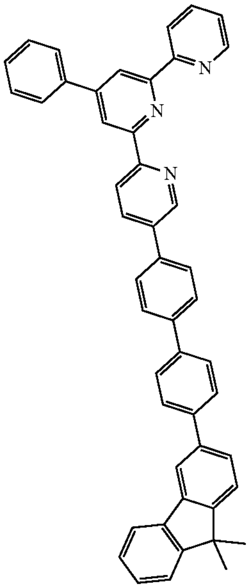

-continued
667
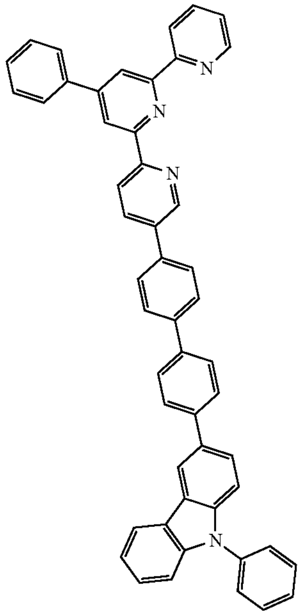
668
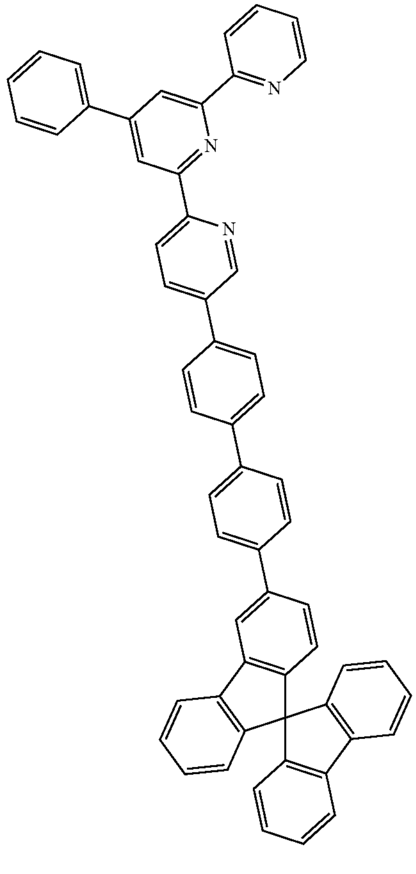
-continued
669
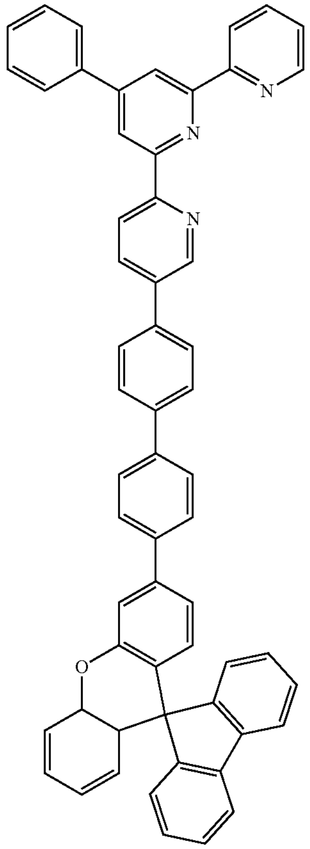
670
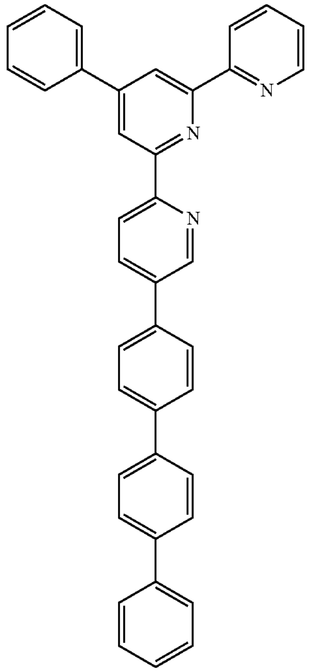

-continued
671
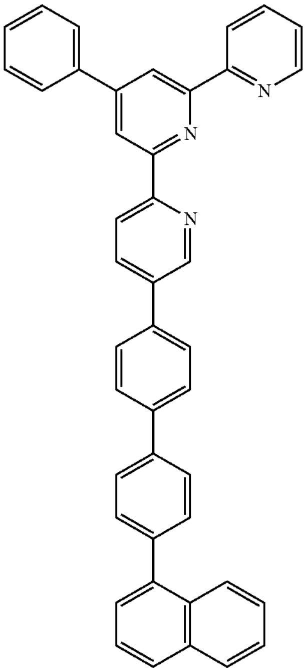
672
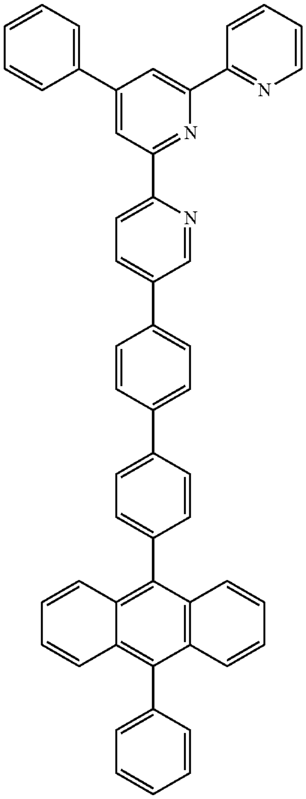
673
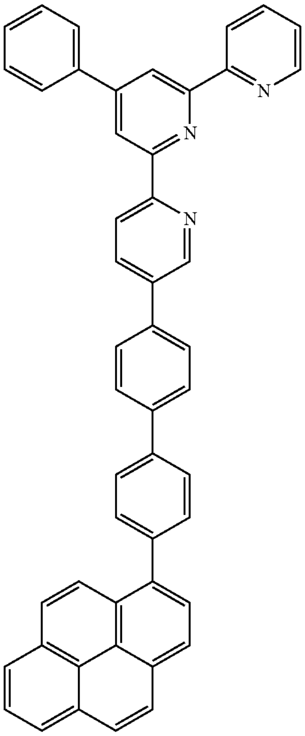
674
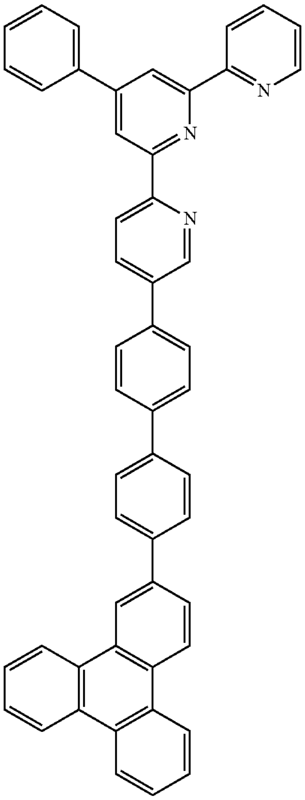

-continued

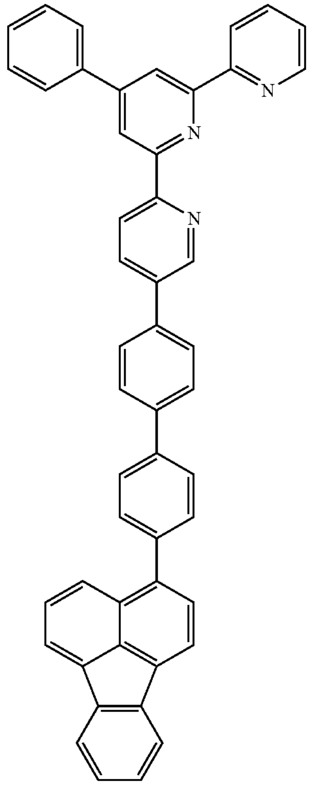

In addition, by introducing various substituents to the structure of Chemical Formula 1, compounds having unique properties of the introduced substituents may be synthesized. For example, by introducing substituents normally used as hole injection layer materials, hole transfer layer materials, light emitting layer materials, electron transfer layer materials and charge generation layer materials used for manufacturing an organic light emitting device to the core structure, materials satisfying conditions required for each organic material layer may be synthesized.

In addition, by introducing various substituents to the structure of Chemical Formula 1, the energy band gap may be finely controlled, and meanwhile, properties at interfaces between organic materials are enhanced, and material applications may become diverse.

One embodiment of the present specification provides an organic light emitting device including a first electrode; a second electrode; and an organic material layer provided between the first electrode and the second electrode, wherein the organic material layer includes one or more types of the heterocyclic compound represented by Chemical Formula 1.

In one embodiment of the present specification, the first electrode may be an anode, and the second electrode may be a cathode.

In another embodiment of the present specification, the first electrode may be a cathode, and the second electrode may be an anode.

In one embodiment of the present specification, the organic light emitting device may be a blue organic light emitting device, and the heterocyclic compound according to Chemical Formula 1 may be used as a material of the blue organic light emitting device. For example, the heterocyclic compound according to Chemical Formula 1 may be included in an electron transfer layer, a hole blocking layer or a charge generation layer of the blue organic light emitting device.

In another embodiment of the present specification, the organic light emitting device may be a green organic light emitting device, and the heterocyclic compound according to Chemical Formula 1 may be used as a material of the green organic light emitting device. For example, the heterocyclic compound according to Chemical Formula 1 may be included in an electron transfer layer, a hole blocking layer or a charge generation layer of the green organic light emitting device.

In another embodiment of the present specification, the organic light emitting device may be a red organic light emitting device, and the heterocyclic compound according to Chemical Formula 1 may be used as a material of the red organic light emitting device. For example, the heterocyclic compound according to Chemical Formula 1 may be included in an electron transfer layer, a hole blocking layer or a charge generation layer of the red organic light emitting device.

Specific descriptions on the heterocyclic compound represented by Chemical Formula 1 are the same as the descriptions provided above.

The organic light emitting device of the present specification may be manufactured using common organic light emitting device manufacturing methods and materials except that one or more of the organic material layers are formed using the heterocyclic compound described above.

The heterocyclic compound may be formed into an organic material layer through a solution coating method as well as a vacuum deposition method when manufacturing the organic light emitting device. Herein, the solution coating method means spin coating, dip coating, inkjet printing, screen printing, a spray method, roll coating and the like, but is not limited thereto.

The organic material layer of the organic light emitting device of the present specification may be formed in a single layer structure, but may be formed in a multilayer structure in which two or more organic material layers are laminated. For example, the organic light emitting device of the present disclosure may have a structure including a hole injection layer, a hole transfer layer, a light emitting layer, an electron transfer layer, an electron injection layer and the like as the organic material layer. However, the structure of the organic light emitting device is not limited thereto, and may include a smaller number of organic material layers.

In the organic light emitting device of the present specification, the organic material layer includes an electron transfer layer, and the electron transfer layer may include the heterocyclic compound of Chemical Formula 1.

In another organic light emitting device, the organic material layer includes a hole blocking layer, and the hole blocking layer may include the heterocyclic compound of Chemical Formula 1.

The organic light emitting device of the present disclosure may further include one, two or more layers selected from the group consisting of a light emitting layer, a hole injection layer, a hole transfer layer. an electron injection layer, an electron transfer layer, an electron blocking layer and a hole blocking layer.

FIG. 1 to FIG. 5 illustrate a lamination order of electrodes and organic material layers of an organic light emitting device according to one embodiment of the present specification. However, the scope of the present application is not limited to these diagrams, and structures of organic light emitting devices known in the art may also be used in the present application.

FIG. 1 illustrates an organic light emitting device in which an anode (200), an organic material layer (300) and a cathode (400) are consecutively laminated on a substrate (100). However, the structure is not limited to such a structure, and as illustrated in FIG. 2, an organic light emitting device in which a cathode, an organic material layer and an anode are consecutively laminated on a substrate may also be obtained.

FIG. 3 and FIG. 4 illustrate cases of the organic material layer being a multilayer. The organic light emitting device according to FIG. 3 includes a hole injection layer (301), a hole transfer layer (302), a light emitting layer (303), an electron transfer layer (305) and an electron injection layer (306), and the organic light emitting device according to FIG. 4 includes a hole injection layer (301), a hole transfer layer (302), a light emitting layer (303), a hole blocking layer (304), an electron transfer layer (305) and an electron injection layer (306). However, the scope of the present application is not limited to such a lamination structure, and as necessary, layers other than the light emitting layer may not be included, and other necessary functional layers may be further added.

The organic material layer including the heterocyclic compound represented by Chemical Formula 1 may further include other materials as necessary.

In addition, the organic light emitting device according to one embodiment of the present specification includes an anode, a cathode, and two or more stacks provided between the anode and the cathode, the two or more stacks each independently include a light emitting layer, a charge generation layer is included between the two or more stacks, and the charge generation layer includes the heterocyclic compound represented by Chemical Formula 1.

In addition, the organic light emitting device according to one embodiment of the present specification includes an anode, a first stack provided on the anode and including a first light emitting layer, a charge generation layer provided on the first stack, a second stack provided on the charge generation layer and including a second light emitting layer, and a cathode provided on the second stack. Herein, the charge generation layer may include the heterocyclic compound represented by Chemical Formula 1.

The organic light emitting device according to one embodiment of the present specification includes a first electrode; a first stack provided on the first electrode and including a first light emitting layer; a charge generation layer provided on the first stack; a second stack provided on the charge generation layer and including a second light emitting layer; and a second electrode provided on the second stack, wherein the charge generation layer may include the heterocyclic compound represented by Chemical Formula 1.

The organic light emitting device according to one embodiment of the present specification includes a first electrode; a second electrode; and an organic material layer provided between the first electrode and the second electrode, wherein the organic material layer includes two or more stacks, and the two or more stacks each independently include a light emitting layer, a charge generation layer is included between the two or more stacks, and the charge generation layer may include the heterocyclic compound represented by Chemical Formula 1.

The organic light emitting device according to one embodiment of the present specification includes a first electrode; a second electrode; and an organic material layer provided between the first electrode and the second electrode, wherein the organic material layer includes a first stack including a first light emitting layer; a charge generation layer provided on the first stack; and a second stack provided on the charge generation layer and including a second light emitting layer, and the charge generation layer may include the heterocyclic compound represented by Chemical Formula 1.

In the organic light emitting device according to one embodiment of the present specification, the charge generation layer includes an N-type charge generation layer, and the N-type charge generation layer includes the heterocyclic compound represented by Chemical Formula 1.

In the organic light emitting device according to one embodiment of the present specification, the charge generation layer may further include a P-type charge generation layer.

As the organic light emitting device according to one embodiment of the present specification, an organic light emitting device having a 2-stack tandem structure is illustrated in FIG. 5.

Herein, the first electron blocking layer, the first hole blocking layer, the second hole blocking layer and the like described in FIG. 5 may not be included in some cases.

In the organic light emitting device according to one embodiment of the present specification, materials other than the heterocyclic compound represented by Chemical Formula 1 are illustrated below, however, these are for illustrative purposes only and not for limiting the scope of the present application, and may be replaced by materials known in the art.

As the anode material, materials having relatively large work function may be used, and transparent conductive oxides, metals, conductive polymers or the like may be used. Specific examples of the anode material include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylene-1,2-dioxy)thiophene] (PEDOT), polypyrrole and polyaniline, and the like, but are not limited thereto.

As the cathode material, materials having relatively small work function may be used, and metals, metal oxides, conductive polymers or the like may be used. Specific examples of the cathode material include metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

As the hole injection material, known hole injection materials may be used, and for example, phthalocyanine compounds such as copper phthalocyanine disclosed in U.S. Pat. No. 4,356,429, or starburst-type amine derivatives such as tris(4-carbazoyl-9-ylphenyl)amine (TCTA), 4,4',4"-tri[phenyl(m-tolyl)amino]triphenylamine (m-MTDATA) or 1,3,5-tris[4-(3-methylphenylphenylamino)phenyl]benzene (m-MTDAPB) described in the literature [Advanced Material, 6, p. 677 (1994)], polyaniline/dodecylbenzene sulfonic acid, poly(3,4-ethylenedioxythiophene)/poly(4-styrenesulfonate), polyaniline/camphor sulfonic acid or polyaniline/poly(4-styrenesulfonate) that are conductive polymers having solubility, and the like, may be used.

As the hole transfer material, pyrazoline derivatives, arylamine-based derivatives, stilbene derivatives, triphenyldiamine derivatives and the like may be used, and low molecular or high molecular materials may also be used.

As the electron transfer material, metal complexes of oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, 8-hydroxyquinoline and derivatives thereof, and the like, may be used, and high molecular materials may also be used as well as low molecular materials.

As examples of the electron injection material, LiF is typically used in the art, however, the present application is not limited thereto.

As the light emitting material, red, green or blue light emitting materials may be used, and as necessary, two or more light emitting materials may be mixed and used. Herein, two or more light emitting materials may be used by being deposited as individual sources of supply or by being premixed and deposited as one source of supply. In addition, fluorescent materials may also be used as the light emitting material, however, phosphorescent materials may also be used. As the light emitting material, materials emitting light by bonding electrons and holes injected from an anode and a cathode, respectively, may be used alone, however, materials having a host material and a dopant material involving in light emission together may also be used.

When mixing light emitting material hosts, same series hosts may be mixed, or different series hosts may be mixed. For example, any two or more types of materials among n-type host materials or p-type host materials may be selected and used as a host material of a light emitting layer.

The organic light emitting device according to one embodiment of the present specification may be a top-emission type, a bottom-emission type or a dual-emission type depending on the materials used.

The heterocyclic compound according to one embodiment of the present specification may also be used in an organic electronic device including an organic solar cell, an organic photo conductor, an organic transistor and the like under a similar principle used in the organic light emitting device.

Hereinafter, the present specification will be described in more detail with reference to examples, however, these are for illustrative purposes only, and the scope of the present application is not limited thereto.

[Preparation Example 1] Preparation of Compound 1

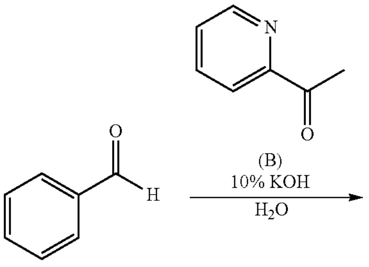

(A)

1-3

-continued

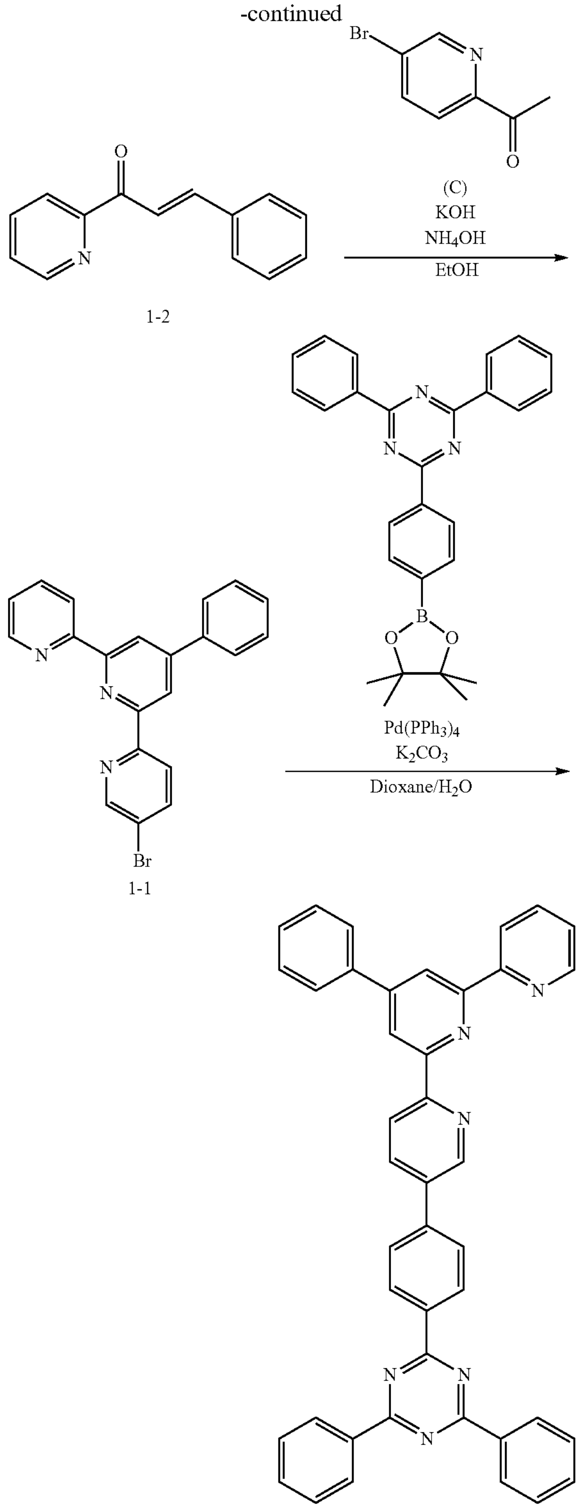

1-2

1-1

1

Preparation of Intermediate 1-2 After introducing Compound 1-3 (A) (40.0 g, 377 mmol) to $H_2O$ (2000 mL), the temperature was lowered to 0° C., and 1-(pyridin-2-yl)ethan-1-one (B) (45.7 g, 377 mmol) was introduced thereto. 10% KOH (20.0 g) was slowly introduced thereto, and then the result was stirred for 19 hours at 0° C. Produced solids were filtered, and then washed with $H_2O$:EtOH (ethanol)

(4:1). The result was purified by column chromatography using ethyl acetate and hexane as a developing solvent to obtain Intermediate 1-2 (54.3 g, yield 69%).

Preparation of Intermediate 1-1

After introducing Intermediate 1-2 (54.3 g, 259 mmol), 1-(5-bromopyridin-2-yl)ethan-1-one (C) (51.9 g, 259 mmol) and KOH (43.6 g, 777 mmol) to EtOH (1100 mL), the result was stirred for 30 minutes. $NH_4OH$ was added thereto, and then the result was stirred for 3 hours at 60° C. Produced solids were filtered, and then washed with $H_2O$:EtOH (4:1) to obtain Intermediate 1-1 (57.2 g, 57%).

Preparation of Compound 1

After introducing Intermediate 1-1 (10.0 g, 25.8 mmol), 2,4-diphenyl-6-(4-(4,4,5,5-tetramethyl-1,3,2-dioxaborolan-2-yl)phenyl)-1,3,5-triazine (D) (12.3 g, 28.3 mmol), $Pd(PPh_3)_4$ (1.49 g, 1.29 mmol) and $K_2CO_3$ (10.7 g, 77.4 mmol) to 1,4-dioxane/$H_2O$ (180 mL, 5:1), the result was stirred for 5 hours at 100° C. The result was cooled, and then produced solids were filtered to obtain Compound 1 (11.2 g, yield 71%).

Target compounds of the following Table 1 were synthesized in the same manner as in Preparation of Compound 1 except that Compounds A, B, C and D of the following Table 1 were used instead of A, B, C and D of Preparation Example 1.

TABLE 1

| Target Compound | Compound A | Compound B | Compound C |
|---|---|---|---|
| 2 | 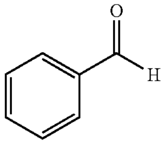 | 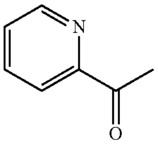 | 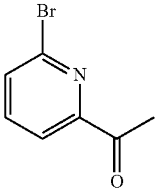 |
| 3 | 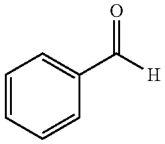 | 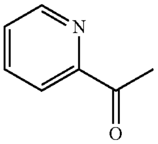 | 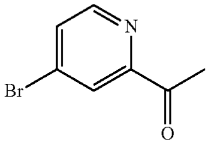 |
| 13 | 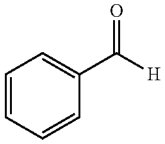 | 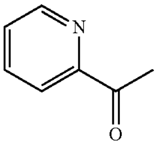 | 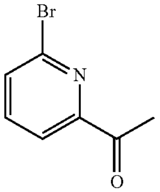 |
| 14 | 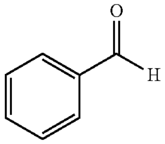 | 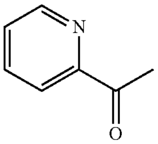 | 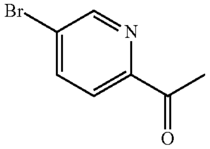 |
| 15 | 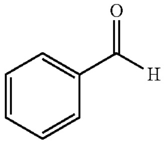 | 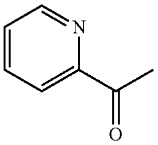 | 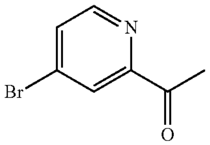 |
| 26 | 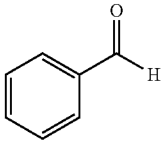 | 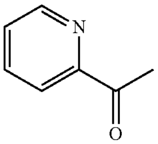 | 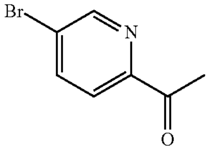 |

TABLE 1-continued
| | | | |
|---|---|---|---|
| 73 | 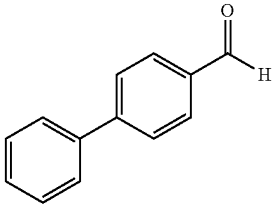 | 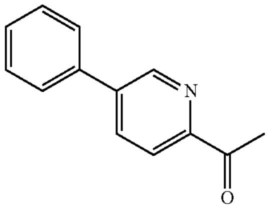 | 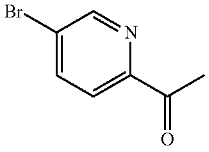 |
| 100 | 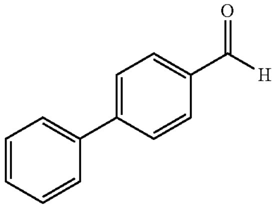 | 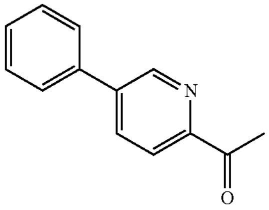 | 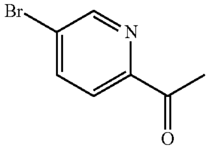 |
| 137 | 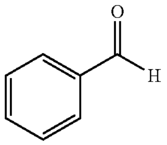 | 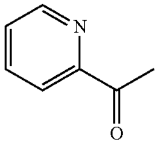 | 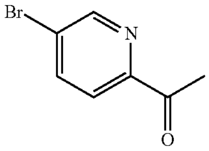 |
| 141 | 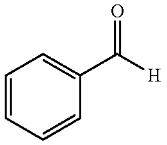 | 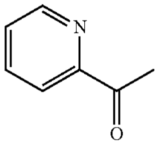 | 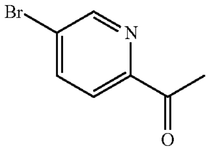 |
| 142 | 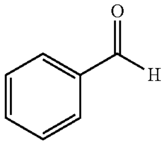 | 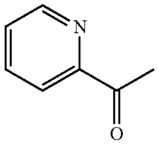 | 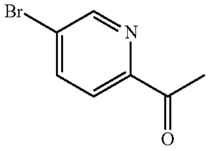 |
| 143 | 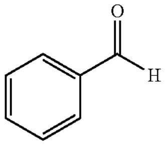 | 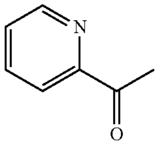 | 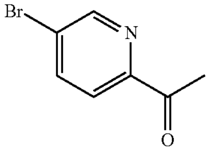 |
| 144 | 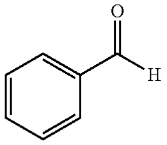 | 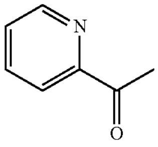 | 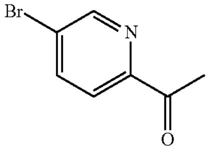 |
| 153 | 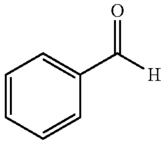 | 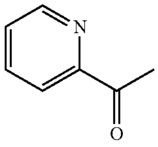 | 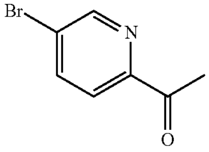 |
| 155 | 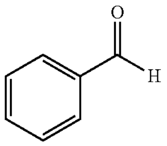 | 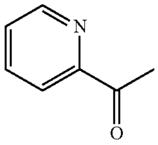 | 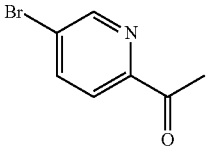 |

TABLE 1-continued
| | | | |
|---|---|---|---|
| 156 | 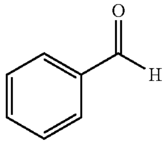 | 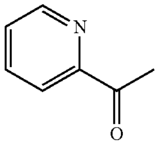 | 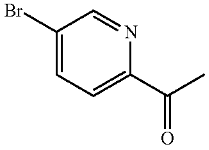 |
| 157 | 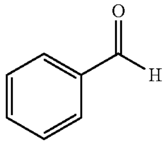 | 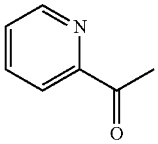 | 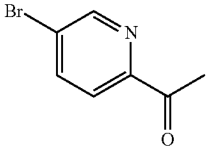 |
| 158 | 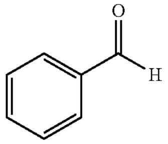 | 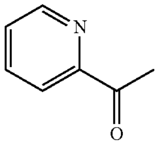 | 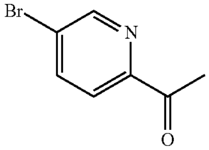 |
| 159 | 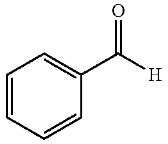 | 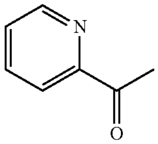 | 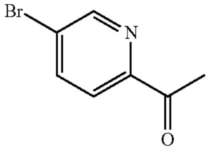 |
| 161 | 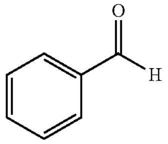 | 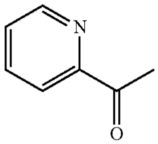 | 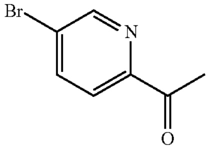 |
| 449 | 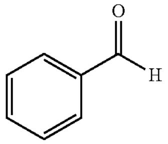 | 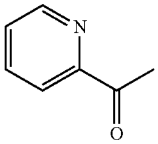 | 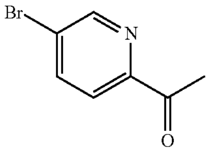 |
| 450 | 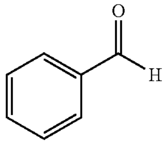 | 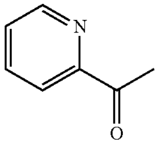 | 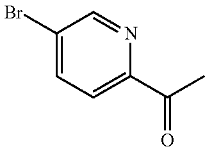 |
| 451 | 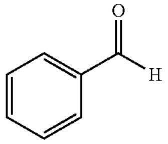 | 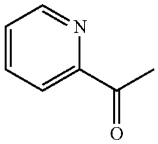 | 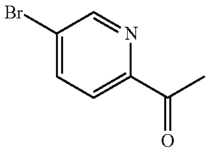 |
| 452 | 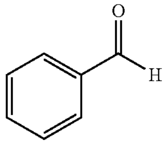 | 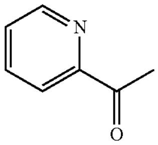 | 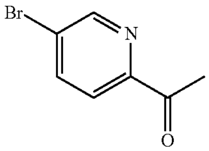 |
| 461 | 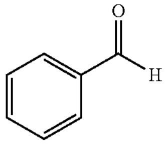 | 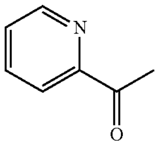 | 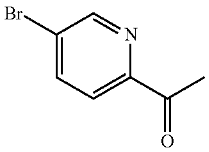 |

TABLE 1-continued
| | | | |
|---|---|---|---|
| 462 | 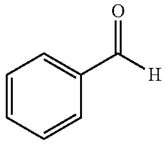 | 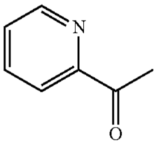 | 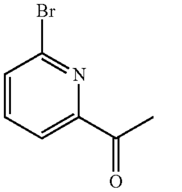 |
| 465 | 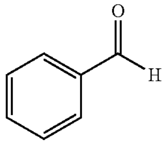 | 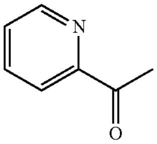 | 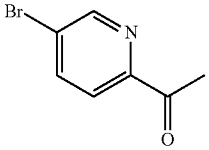 |
| 474 | 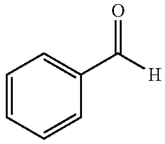 | 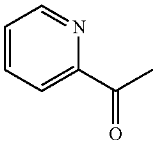 | 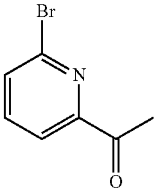 |
| 497 | 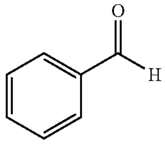 | 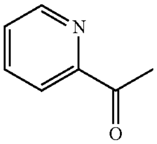 | 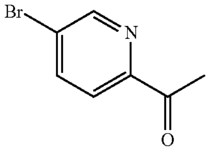 |
| 498 | 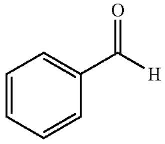 | 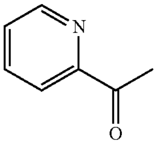 | 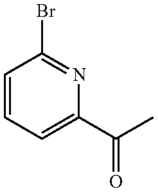 |
| 501 | 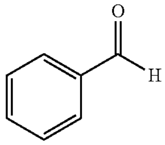 | 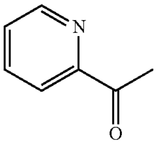 | 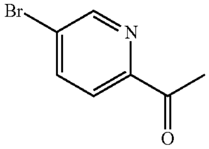 |
| 510 | 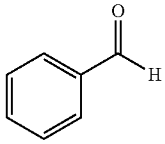 | 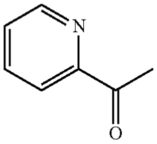 | 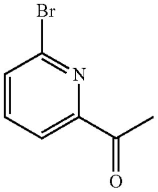 |
| 569 | 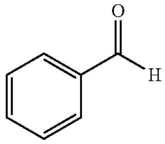 | 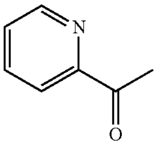 | 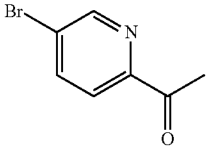 |
| 573 | 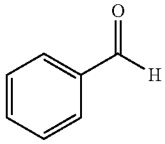 | 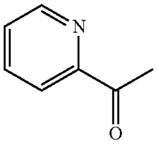 | 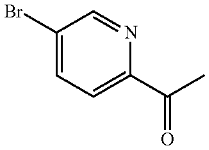 |

TABLE 1-continued
| | | | |
|---|---|---|---|
| 577 | 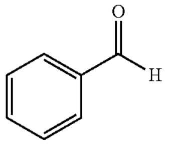 | 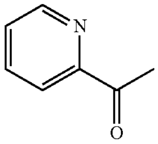 | 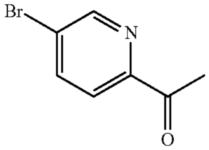 |
| Target Compound | Compound D | Yield |
|---|---|---|
| 2 | 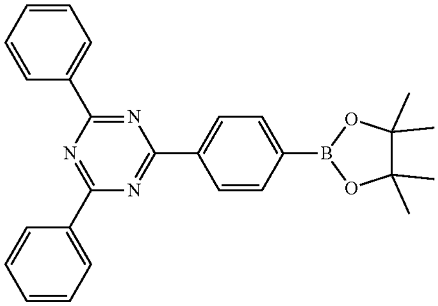 [SMILES: CC1(C)OB(c2ccc(-c3nc(-c4ccccc4)nc(-c4ccccc4)n3)cc2)OC1(C)C] | 52% |
| 3 | 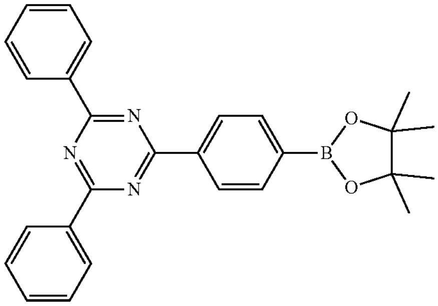 | 71% |
| 13 | 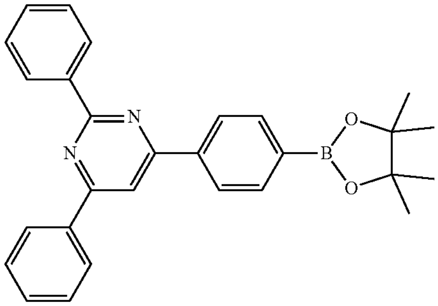 [SMILES: CC1(C)OB(c2ccc(-c3cc(-c4ccccc4)nc(-c4ccccc4)n3)cc2)OC1(C)C] | 56% |
| 14 | 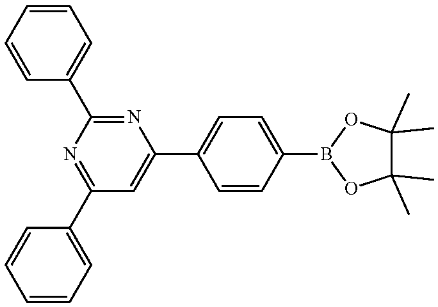 [SMILES: CC1(C)OB(c2ccc(-c3cc(-c4ccccc4)nc(-c4ccccc4)n3)cc2)OC1(C)C] | 81% |

TABLE 1-continued
| | | |
|---|---|---|
| 15 | 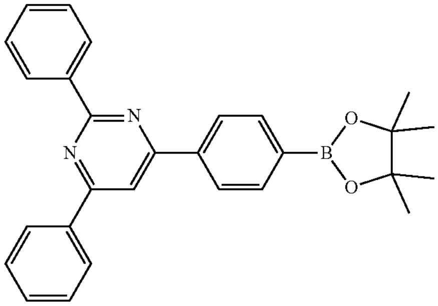 | 79% |
| 26 | 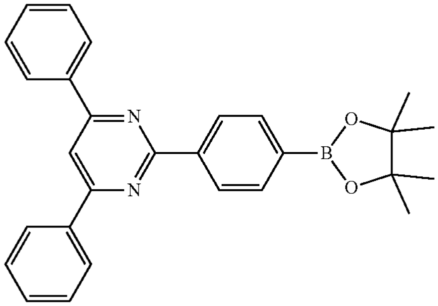 [SMILES: CC1(C)OB(c2ccc(-c3nc(-c4ccccc4)cc(-c4ccccc4)n3)cc2)OC1(C)C] | 68% |
| 73 | 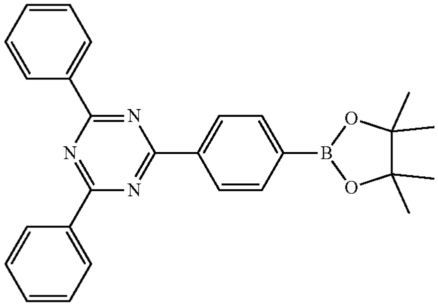 | 72% |
| 100 | 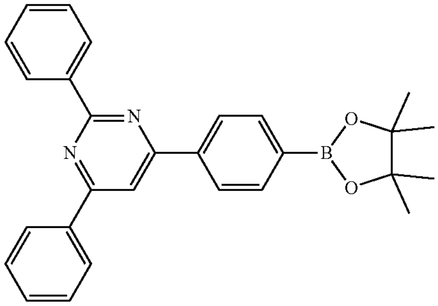 [SMILES: CC1(C)OB(c2ccc(-c3cc(-c4ccccc4)nc(-c4ccccc4)n3)cc2)OC1(C)C] | 65% |
| 137 | 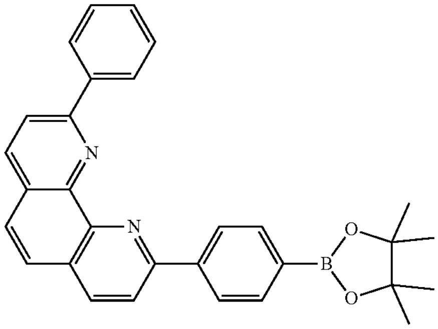 [SMILES: CC1(C)OB(c2ccc(-c3ccc4ccc5ccc(-c6ccccc6)nc5c4n3)cc2)OC1(C)C] | 59% |

TABLE 1-continued
| | | |
|---|---|---|
| 141 | 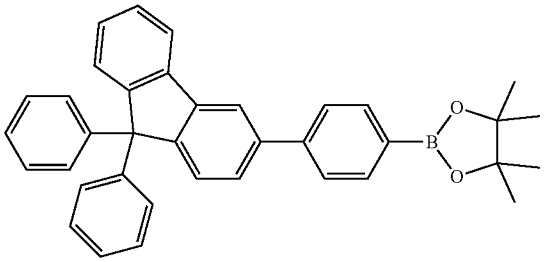 [SMILES: CC1(C)OB(c2ccc(-c3ccc4c(c3)-c3ccccc3C4(c3ccccc3)c3ccccc3)cc2)OC1(C)C] | 73% |
| 142 | 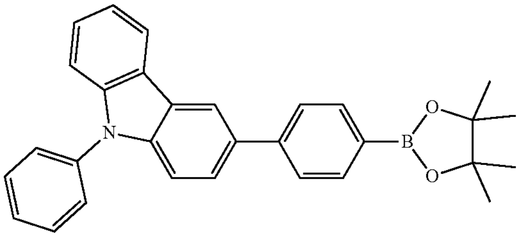 [SMILES: CC1(C)OB(c2ccc(-c3ccc4c(c3)c3ccccc3n4-c3ccccc3)cc2)OC1(C)C] | 77% |
| 143 | 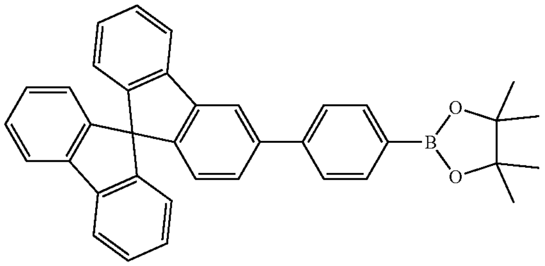 [SMILES: CC1(C)OB(c2ccc(-c3ccc4c(c3)-c3ccccc3C43c4ccccc4-c4ccccc43)cc2)OC1(C)C] | 86% |
| 144 | 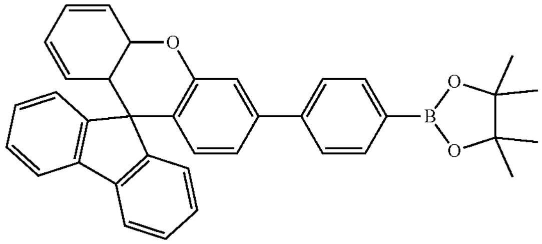 [SMILES: CC1(C)OB(c2ccc(-c3ccc4c(c3)OC3C=CC=CC3C43c4ccccc4-c4ccccc43)cc2)OC1(C)C] | 81% |
| 153 | 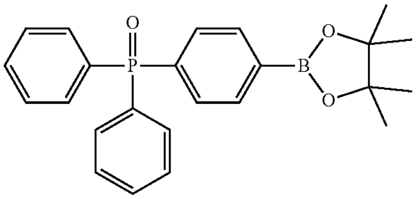 [SMILES: CC1(C)OB(c2ccc(P(=O)(c3ccccc3)c3ccccc3)cc2)OC1(C)C] | 68% |
| 155 | 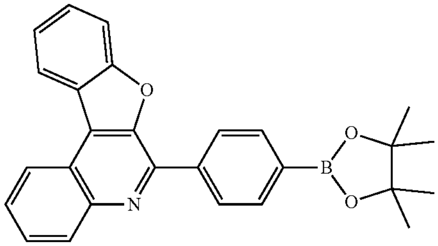 | 74% |

TABLE 1-continued
| | | |
|---|---|---|
| 156 | 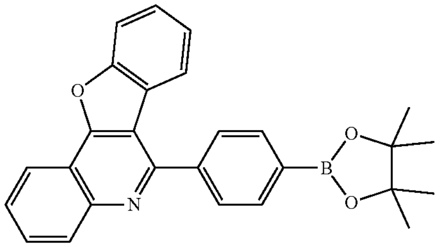 [SMILES: CC1(C)OB(c2ccc(-c3nc4ccccc4c4oc5ccccc5c34)cc2)OC1(C)C] | 74% |
| 157 | 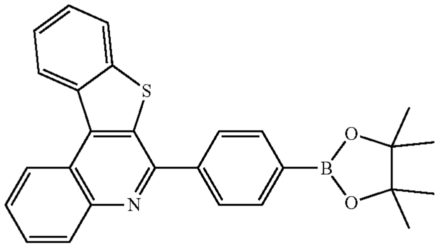 [SMILES: CC1(C)OB(c2ccc(-c3nc4ccccc4c4c3sc3ccccc34)cc2)OC1(C)C] | 79% |
| 158 | 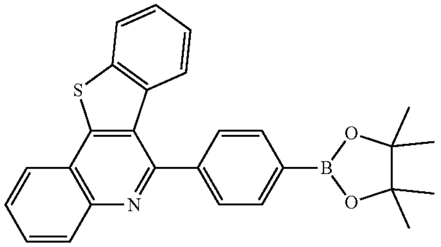 | 65% |
| 159 | 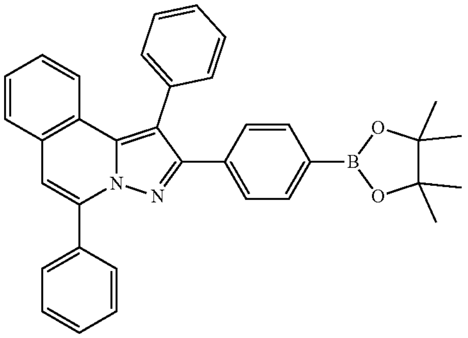 [SMILES: CC1(C)OB(c2ccc(-c3nn4c(-c5ccccc5)cc5ccccc5c4c3-c3ccccc3)cc2)OC1(C)C] | 69% |
| 161 | 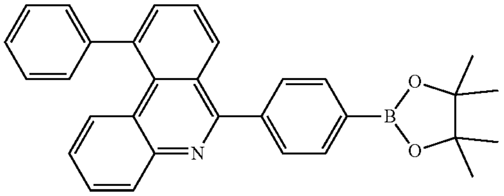 [SMILES: CC1(C)OB(c2ccc(-c3nc4ccccc4c4c(-c5ccccc5)cccc34)cc2)OC1(C)C] | 71% |
| 449 | 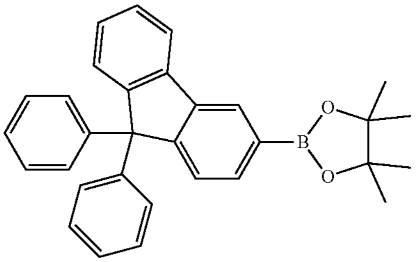 [SMILES: CC1(C)OB(c2ccc3c(c2)-c2ccccc2C3(c2ccccc2)c2ccccc2)OC1(C)C] | 65% |

TABLE 1-continued
| | | |
|---|---|---|
| 450 | 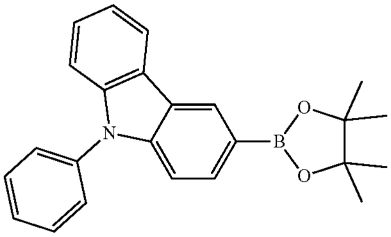 [SMILES: CC1(C)OB(c2ccc3c(c2)c2ccccc2n3-c2ccccc2)OC1(C)C] | 68% |
| 451 | 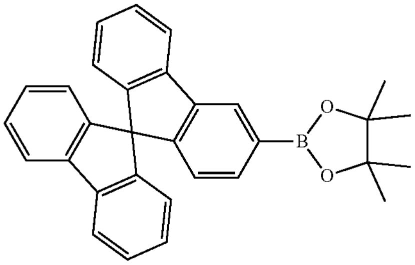 [SMILES: CC1(C)OB(c2ccc3c(c2)-c2ccccc2C32c3ccccc3-c3ccccc32)OC1(C)C] | 70% |
| 452 | 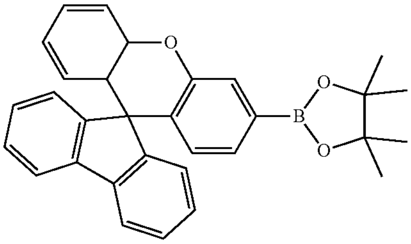 [SMILES: CC1(C)OB(c2ccc3c(c2)OC2C=CC=CC2C32c3ccccc3-c3ccccc32)OC1(C)C] | 65% |
| 461 | 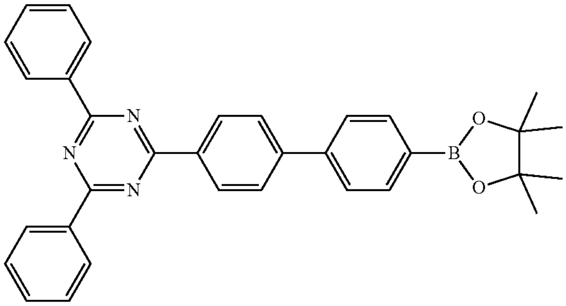 | 75% |
| 462 | 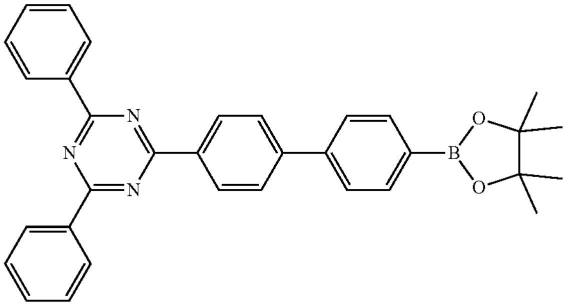 [SMILES: CC1(C)OB(c2ccc(-c3ccc(-c4nc(-c5ccccc5)nc(-c5ccccc5)n4)cc3)cc2)OC1(C)C] | 59% |

TABLE 1-continued
| | | |
|---|---|---|
| 465 | 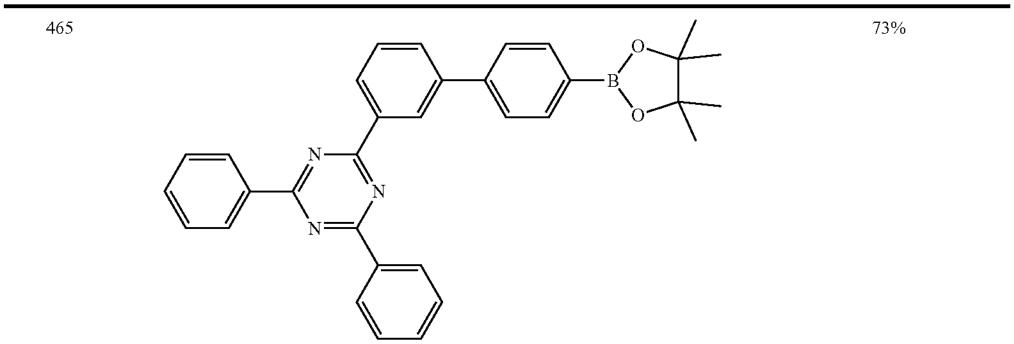 | 73% |
| 474 | 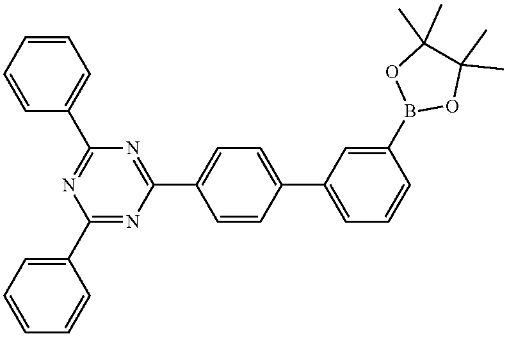 [SMILES: CC1(C)OB(c2cccc(-c3ccc(-c4nc(-c5ccccc5)nc(-c5ccccc5)n4)cc3)c2)OC1(C)C] | 51% |
| 497 | 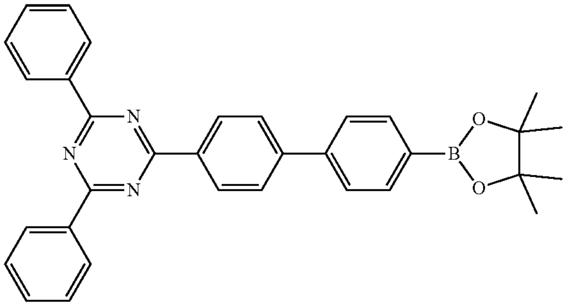 [SMILES: CC1(C)OB(c2ccc(-c3ccc(-c4nc(-c5ccccc5)nc(-c5ccccc5)n4)cc3)cc2)OC1(C)C] | 81% |
| 498 | 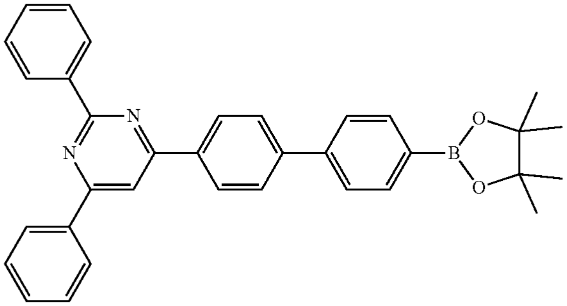 [SMILES: CC1(C)OB(c2ccc(-c3ccc(-c4cc(-c5ccccc5)nc(-c5ccccc5)n4)cc3)cc2)OC1(C)C] | 62% |
| 501 | 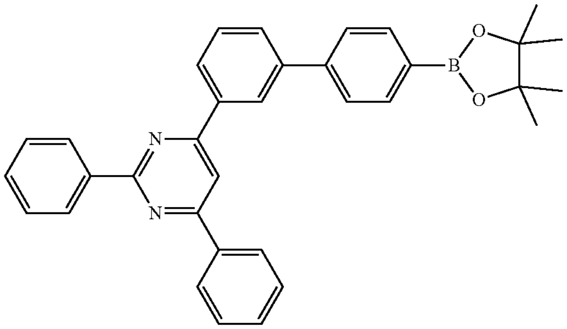 | 73% |

TABLE 1-continued
| | | |
|---|---|---|
| 510 | 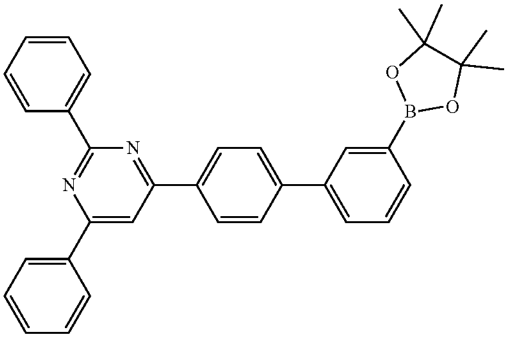 [SMILES: CC1(C)OB(c2cccc(-c3ccc(-c4cc(-c5ccccc5)nc(-c5ccccc5)n4)cc3)c2)OC1(C)C] | 50% |
| 569 | 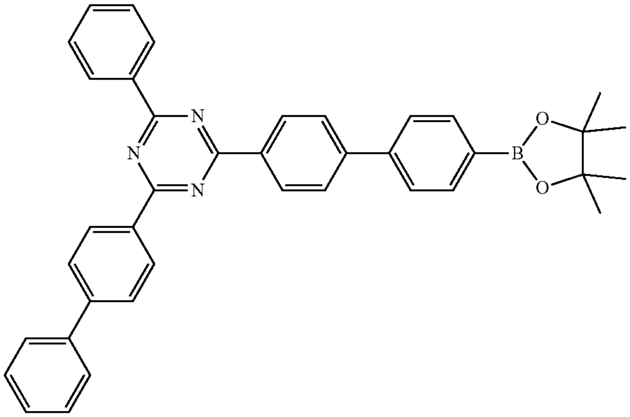 [SMILES: CC1(C)OB(c2ccc(-c3ccc(-c4nc(-c5ccccc5)nc(-c5ccc(-c6ccccc6)cc5)n4)cc3)cc2)OC1(C)C] | 72% |
| 573 | 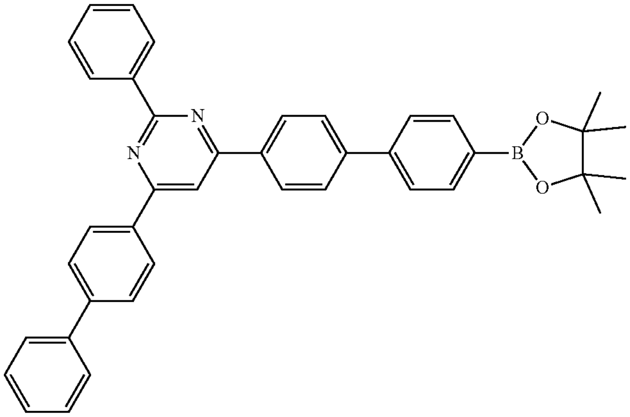 | 71% |
| 577 | 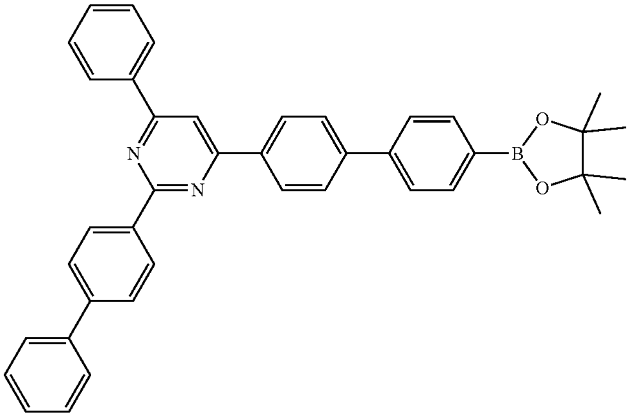 [SMILES: CC1(C)OB(c2ccc(-c3ccc(-c4cc(-c5ccccc5)nc(-c5ccc(-c6ccccc6)cc5)n4)cc3)cc2)OC1(C)C] | 68% |

[Preparation Example 2] Preparation of Compound 167

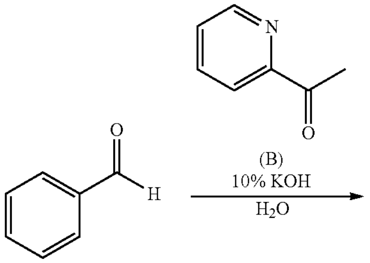

(A)

1-3

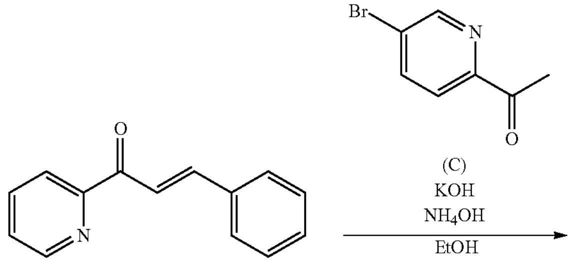

1-2

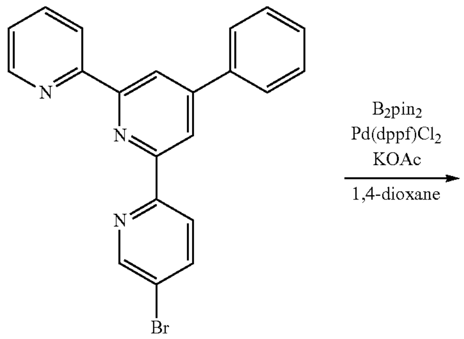

1-1

-continued

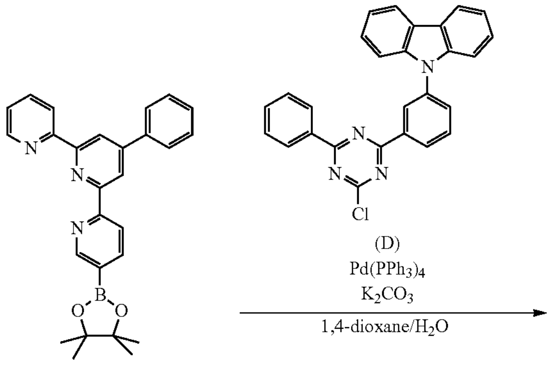

167-1

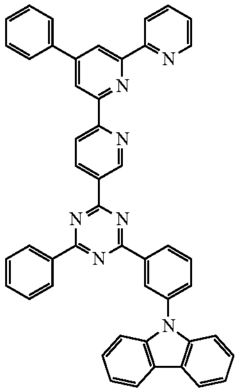

167

Preparation of Intermediate 167-1

After introducing Intermediate 1-1 (20.0 g, 51.5 mmol), bis(pinacolato)diboron) (19.6 g, 77.3 mmol), $Pd(dppf)Cl_2$ (3.77 g, 5.15 mmol) and KOAc (15.2 g, 155 mmol) to 1,4-dioxane (300 mL), the result was stirred for 3 hours at 100° C. The result was extracted with dichloromethane (DCM), and then dried with $MgSO_4$. The result was silica gel filtered and then concentrated to obtain Intermediate 167-1 (16.8 g, 75%).

Preparation of Compound 167

After introducing Intermediate 167-1 (10.0 g, 23.0 mmol), 9-(3-(4-chloro-6-phenyl-1,3,5-triazin-2-yl)phenyl)-9H-carbazole (D) (10.4 g, 24.1 mmol), $Pd(PPh_3)_4$ (1.33 g, 1.15 mmol) and $K_2CO_3$ to 1,4-dioxane/$H_2O$ (180 mL, 5:1), the result was stirred for 4 hours at 100° C. After lowering the temperature to room temperature, produced solids were filtered to obtain Compound 167 (13.8 g, 85%).

Target compounds of the following Table 2 were synthesized in the same manner as in Preparation of Compound 167 except that Compounds A, B, C and D of the following Table 2 were used instead of A, B, C and D of Preparation Example 2.

TABLE 2
| Target Compound | Compound A | Compound B | Compound C |
|---|---|---|---|
| 168 | 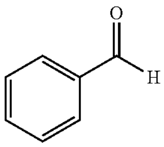 | 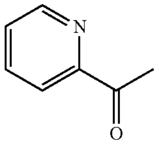 | 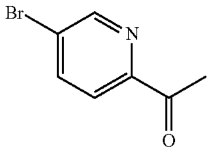 |
| 185 | 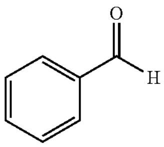 | 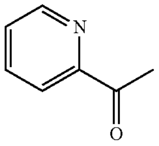 | 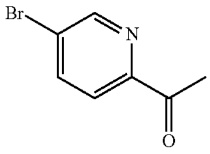 |
| 186 | 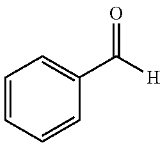 | 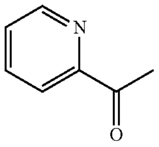 | 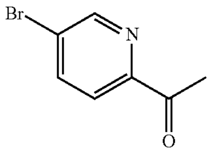 |
| 445 | 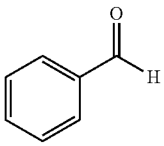 | 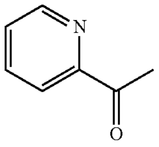 | 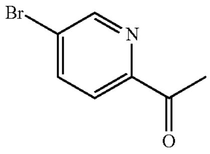 |
| Target Compound | Compound D | Yield |
|---|---|---|
| 168 | 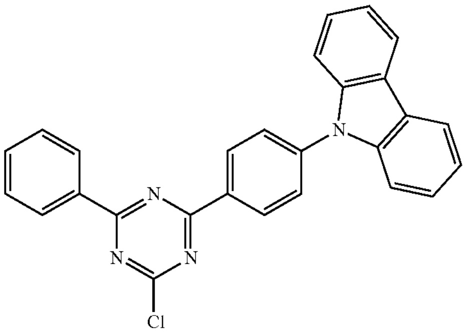 [SMILES: Clc1nc(-c2ccccc2)nc(-c2ccc(-n3c4ccccc4c4ccccc43)cc2)n1] | 63% |
| 185 | 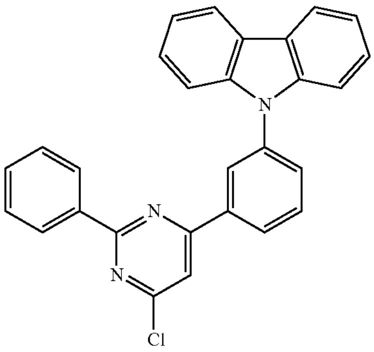 [SMILES: Clc1cc(-c2cccc(-n3c4ccccc4c4ccccc43)c2)nc(-c2ccccc2)n1] | 69% |

TABLE 2-continued

| | | |
|---|---|---|
| 186 | 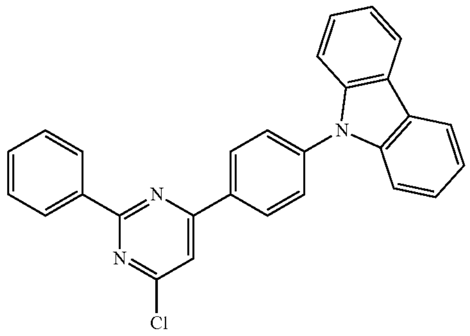 [SMILES: Clc1cc(-c2ccc(-n3c4ccccc4c4ccccc43)cc2)nc(-c2ccccc2)n1] | 57% |
| 445 | 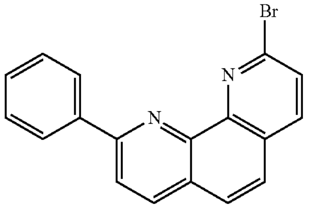 [SMILES: Brc1ccc2ccc3ccc(-c4ccccc4)nc3c2n1] | 71% |

Compounds were prepared in the same manner as in the preparation examples, and the synthesis identification results are shown in the following Table 3 and Table 4.

TABLE 3

| NO | $^1H$ NMR ($CDCl_3$, 300 Mz) |
|---|---|
| 1 | 9.18-9.14 (3H, m), 8.97-8.93 (2H, m), 8.55 (1H, s), 8.36 (4H, m), 8.00-7.96 (3H, m), 7.75 (3H, m), 7.50-7.41 (9H, m), 7.25-7.23 (3H, m) |
| 2 | 9.18-9.14 (3H, m), 8.78 (1H, d), 8.69 (2H, m), 8.55 (1H, d), 8.36 (4H, m), 7.96 (2H, m), 7.75-7.74 (3H, m), 7.50-7.37 (10H, m), 7.23 (m, 1H), 6.88 (1H, d) |
| 3 | 9.40 (1H, d), 9.18-9.14 (3H, m), 8.59-8.55 (2H, m), 8.36 (4H, m), 8.14 (1H, d), 7.96 (2H, d), 7.75-7.74 (3H, m), 7.50-7.41 (9H, m), 7.25-7.23 (3H, m) |
| 13 | 9.18-9.14 (3H, m), 8.78 (1H, d), 8.69 (2H, d), 8.55 (1H, d), 8.35-8.30 (4H, m), 7.94 (2H, d), 7.75-7.74 (3H, m), 7.55-7.37 (10H, m), 7.23 (1H, m), 6.88 (1H, d) |
| 14 | 9.18-9.14 (3H, m), 8.97-8.93 (2H, m), 8.55 (1H, d), 8.35-8.30 (4H, m), 8.23 (1H, s), 8.00-7.94 (3H, m), 7.75-7.74 (3H, m), 7.55-7.41 (9H, m), 7.25-7.23 (3H, m) |
| 15 | 9.40 (1H, s), 9.18-9.14 (3H, m), 8.59-8.55 (2H, m), 8.35-8.30 (4H, m), 8.14 (1H, d), 7.94 (2H, m), 7.85 (2H, d), 7.75-7.74 (3H, m), 7.55-7.41 (9H, m), 7.23 (1H, m) |
| 26 | 9.18-9.14 (3H, m), 8.97-8.93 (2H, m), 8.55 (1H, d), 8.23 (1H, s), 8.00-7.94 (7H, m), 7.75 (3H, m), 7.55-7.41 (9H,m), 7.25-7.23 (3H, m) |
| 73 | 9.14 (2H, s), 8.97-8.93 (4H, m), 8.36 (4H, m), 8.00-7.96 (4H, m), 7.75 (2H, d), 7.51-7.41 (14H, m), 7.25 (6H, m) |
| 100 | 9.14 (2H, s), 8.97-8.93 (4H, m), 8.35-8.30 (4H, m), 8.23 (1H, s), 8.00-7.94 (4H, m), 7.75 (2H, m), 7.55-7.41 (14H, m), 7.25 (6H, m) |
| 137 | 9.18-9.14 (3H, m), 8.97-8.93 (2H, m), 8.71-8.69 (4H, m), 8.55 (1H, d), 8.33 (2H, d), 8.20 (1H, d), 8.00 (1H, d), 7.90 (1H, d), 7.75-7.74 (3H, m), 7.55-7.41 (6H, m), 7.29-7.23 (5H, m) |
| 141 | 9.18-9.14 (3H, m), 8.97-8.93 (2H, m), 8.55 (1H, d), 8.18 (1H, s), 8.00 (1H, d), 7.90 (1H, d), 7.75-7.68 (5H, m), 7.49-7.38 (5H, m), 7.28-7.10 (16H, m) |
| 142 | 9.18-9.14 (3H, m), 8.97-8.93 (2H, m), 8.55 (1H, d), 8.30 (1H, d), 8.19-8.13 (2H, m), 8.00 (1H, d), 7.89 (1H, s), 7.75-7.74 (3H, m), 7.62-7.41 (10H, m), 7.25-7.20 (6H, m) |
| 143 | 9.18-9.14 (3H, m), 8.97-8.93 (2H, m), 8.55 (1H, d), 8.18 (1H, s), 8.00 (1H, d), 7.90-7.89 (3H, m), 7.75-7.68 (5H, m), 7.49-7.38 (7H, m), 7.28-7.23 (10H, m) |
| 144 | 9.18-9.14 (3H, m), 8.97-8.93 (2H, m), 8.55 (1H, d), 8.00 (1H, d), 7.90 (2H, d), 7.75-7.74 (3H, m), 7.55-7.01 (21H, m) |
| 153 | 9.18-9.14 (3H, m), 8.97-8.93 (2H, m), 8.55 (1H, d), 8.00-7.96 (5H, m), 7.77-7.74 (7H, m), 7.51-7.41 (9H, m), 7.23 (1H, m) |

TABLE 3-continued

| NO | $^1H$ NMR ($CDCl_3$, 300 Mz) |
|---|---|
| 155 | 9.18-9.14 (3H, m), 8.97-8.93 (2H, m), 8.69 (2H, d), 8.55 (1H, d), 8.20 (1H, d), 8.00-7.70 (8H, m), 7.54-7.25 (9H, m) |
| 156 | 9.18-9.14 (3H, m), 8.97-8.93 (2H, m), 8.69 (2H, d), 8.55 (1H, d), 8.20 (1H, d), 7.98-7.70 (8H, m), 7.54-7.25 (9H, m) |
| 157 | 9.18-9.14 (3H, m), 8.97-8.93 (2H, m), 8.69 (2H, d), 8.55 (1H, d), 8.45 (1H, d), 8.20 (1H, d), 8.00-7.70 (8H, m), 7.56-7.41 (5H, m), 7.25-7.23 (3H, m) |
| 158 | 9.18-9.14 (3H, m), 8.97-8.93 (2H, m), 8.69 (2H, d), 8.55 (1H, d), 8.45 (1H, d), 8.20 (1H, d), 7.98-7.70 (8H, m), 7.56-7.41 (5H, m), 7.25-7.23 (3H, m) |
| 159 | 9.50 (1H, s), 9.29 (1H, s), 9.18 (1H, d), 8.69-8.30 (2H, d), 8.55 (1H, d), 8.52 (1H, s), 8.20 (1H, m), 8.05-8.01 (2H, m), 7.75-7.62 (7H, m), 7.51-7.41 (11H, m), 7.23 (1H, m), 7.08 (2H, m) |
| 161 | 9.50 (1H, s), 9.29 (1H, s), 9.18 (1H, d), 8.69 (4H, s), 8.55 (1H, d), 8.52 (1H, s), 8.20 (2H, m), 7.94-7.70 (10H, m), 7.58-7.41 (8H, m), 7.23 (1H, m) |
| 167 | 9.18 (1H, d), 9.14 (2H, s), 8.97-8.93 (2H, m), 8.55 (1H, d), 8.36 (2H, m), 8.24-8.19 (3H, m), 8.00-7.94 (2H, m), 7.75-7.35 (11H, m), 7.20-7.16 (2H, m) |
| 168 | 9.18 (1H, d), 9.14 (2H, s), 8.97-8.93 (2H, m), 8.55 (1H, d), 8.36 (2H, m), 8.19 (1H, d), 8.00-7.91 (6H, m), 7.75-7.74 (3H, m), 7.58-7.35 (9H, m), 7.23-7.16 (3H, m) |
| 185 | 9.18 (1H, d), 9.14 (2H, s), 8.97-8.93 (2H, m), 8.55 (2H, d), 8.41 (1H, s), 8.35 (2H, d), 8.21 (1H, s), 8.19 (1H, d), 8.00-7.94 (2H, m), 7.80-7.35 (15H, m), 7.23-7.16 (3H, m) |
| 186 | 9.18 (1H, d), 9.14 (2H, s), 8.97-8.93 (2H, m), 8.55 (2H, d), 8.41 (1H, s), 8.35 (2H, d), 8.19 (1H, d), 8.00-7.91 (6H, m), 7.75-7.74 (3H, m), 7.58-7.35 (9H, m), 7.23-7.16 (3H, m) |
| 445 | 9.32 (1H, s), 9.18 (1H, d), 9.14 (2H, s), 8.97 (1H, d), 8.71-8.65 (2H, m), 8.55 (1H, d), 8.39-8.33 (3H, m), 8.20 (1H, d), 7.90 (1H, d), 7.75-7.74 (3H, m), 7.63-7.41 (7H, m), 7.29-7.23 (2H, m) |
| 449 | 9.18 (1H, d), 9.14 (2H, s), 8.97-8.93 (2H, m), 8.55 (1H, d), 8.18 (1H, s), 8.00 (1H, d), 7.90 (1H, d), 7.75-7.68 (5H, m), 7.55-7.10 (17H, m) |
| 450 | 9.18 (1H, d), 9.14 (2H, s), 8.97-8.93 (2H, m), 8.55 (1H, d), 8.30 (1H, d), 8.19-8.13 (2H, m), 8.00 (1H, d), 7.89 (1H, s), 7.75-7.74 (3H, m), 7.62-7.41 (10H, m), 7.23-7.20 (2H, m) |
| 451 | 9.18 (1H, d), 9.14 (2H, s), 8.97-8.93 (2H, m), 8.55 (1H, d), 8.18 (1H, s), 8.00 (1H, d), 7.90-7.89 (3H, m), 7.75-7.68 (5H, m), 7.49-7.27 (13H, m) |
| 452 | 9.18 (1H, d), 9.14 (2H, s), 8.97-8.93 (2H, m), 8.55 (1H, d), 8.00 (1H, d), 7.90 (2H, m), 7.75-7.74 (3H, m), 7.49-7.01 (17H, m) |
| 461 | 9.18 (1H, d), 9.14 (2H, s), 8.97-8.93 (2H, m), 8.55 (1H, d), 8.36 (4H, m), 8.00-7.96 (3H, m), 7.75-7.74 (3H, m), 7.50-7.41 (9H, m), 7.25-7.23 (7H, m) |

TABLE 3-continued

| NO | $^1$H NMR ($CDCl_3$, 300 Mz) |
|---|---|
| 462 | 9.18 (1H, d), 9.14 (2H, s), 8.78 (1H, d), 8.69 (2H, m), 8.55 (1H, d), 8.36 (4H, m), 7.96 (2H, m), 7.85 (2H, d), 7.75-7.74 (3H, m), 7.50-7.37 (10H, m), 7.25-7.23 (3H, m) |
| 465 | 9.18 (1H, d), 9.14 (2H, s), 8.97-8.93 (2H, m), 8.55 (1H, d), 8.38-8.36 (5H, m), 8.00-7.94 (2H, m), 7.75-7.73 (4H, m), 7.91 (1H, d), 7.50-7.41 (9H, m), 7.25-7.23 (5H, m) |
| 474 | 9.18 (1H, d), 9.14 (2H, s), 8.78 (1H, d), 8.55 (1H, d), 8.36-8.33 (6H, m), 7.96 (2H, d), 7.75-7.73 (4H, m), 7.50-7.37 (10H, m), 7.25-7.23 (3H, m), 6.88 (1H, d) |
| 497 | 9.18 (1H, d), 9.14 (2H, s), 8.97-8.93 (2H, m), 8.55 (1H, d), 8.35-8.30 (4H, m), 8.23 (1H, s), 8.00-7.94 (3H, m), 7.85 (2H ,d), 7.75-7.74 (3H, m), 7.55-7.41 (9H, m), 7.25-7.23 (5H, m) |
| 498 | 9.18 (1H, d), 9.14 (2H, s), 8.78 (1H, d), 8.69 (2H, d), 8.55 (1H, d), 8.35-8.30 (4H, m), 8.23 (1H, s), 7.94-7.85 (6H, m), 7.75-7.74 (3H, m), 7.55-7.37 (10H, m), 7.23 (1H, m), 6.88 (1H, d) |
| 501 | 9.18 (1H, d), 9.14 (2H, s), 8.97-8.93 (2H, m), 8.55 (1H, d), 8.35 (2H, d), 8.23 (1H, s), 8.00-7.94 (5H, m), 7.75-7.73 (4H, m), 7.61-7.41 (10H, m), 7.25-7.23 (5H, m) |
| 510 | 9.18 (1H, d), 9.14 (2H, s), 8.78 (1H, d), 8.55 (1H, d), 8.35-8.30 (6H, m), 8.23 (1H, s), 7.94 (2H, d), 7.85 (2H, d), 7.75-7.73 (4H, m), 7.61-7.37 (11H, m), 7.23 (1H, m), 6.88 (1H, d) |
| 569 | 9.18 (1H, d), 9.14 (2H, s), 8.97-8.93 (2H, m), 8.55 (1H, d), 8.36 (2H, d), 8.00-7.96 (5H, m), 7.75-7.74 (5H, m), 7.50-7.41 (9H, m), 7.25-7.23 (9H, m) |
| 573 | 9.18 (1H, d), 9.14 (2H, s), 8.97-8.93 (2H, m), 8.55 (1H, d), 8.35-8.23 (7H, m), 8.00 (1H, d), 7.85 (4H, m), 7.75-7.74 (5H, m), 7.50-7.41 (9H, m), 7.25-7.23 (5H, m) |
| 577 | 9.18 (1H, d), 9.14 (2H, s), 8.97-8.93 (2H, m), 8.55 (1H, d), 8.30 (2H, d), 8.23 (1H, s), 8.00-7.94 (5H, m), 7.85 (2H, d), 7.75-7.74 (5H, m), 7.55-7.41 (9H, m), 7.25-7.23 (7H, m) |

TABLE 4

| Compound | FD-MS |
|---|---|
| 1 | m/z = 616.23 (C42H28N6 = 616.72) |
| 2 | m/z = 616.23 (C42H28N6 = 616.72) |
| 3 | m/z = 616.23 (C42H28N6 = 616.72) |
| 13 | m/z = 615.24 (C43H29N5 = 615.74) |
| 14 | m/z = 615.24 (C43H29N5 = 615.74) |
| 15 | m/z = 615.24 (C43H29N5 = 615.74) |
| 26 | m/z = 615.24 (C43H29N5 = 615.74) |
| 73 | m/z = 768.30 (C54H36N6 = 768.92) |
| 100 | m/z = 767.30 (C55H37N5 = 767.93) |
| 137 | m/z = 639.24 (C45H29N5 = 639.76) |
| 141 | m/z = 701.28 (C52H35N3 = 701.87) |
| 142 | m/z = 626.24 (C45H30N4 = 626.76) |
| 143 | m/z = 699.26 (C52H33N3 = 699.85) |
| 144 | m/z = 715.26 (C52H33N3O = 715.85) |
| 153 | m/z = 585.19 (C39H28N3OP = 585.64) |
| 155 | m/z = 602.21 (C42H26N4O = 602.69) |
| 156 | m/z = 602.21 (C42H26N4O = 602.69 |
| 157 | m/z = 618.18 (C42H26N4S = 618.75) |
| 158 | m/z = 618.18 (C42H26N4S = 618.75) |
| 159 | m/z = 703.27 (C50H33N5 = 703.84) |
| 161 | m/z = 638.24 (C46H30N4 = 638.77) |
| 167 | m/z = 705.26 (C48H31N7 = 705.82) |
| 168 | m/z = 705.26 (C48H31N7 = 705.82) |
| 185 | m/z = 704.26 (C49H32N6 = 704.83) |
| 186 | m/z = 704.26 (C49H32N6 = 704.83) |
| 445 | m/z = 563.21 (C39H25N5 = 563.66) |
| 449 | m/z = 625.25 (C46H31N3 = 625.77) |
| 450 | m/z = 550.21 (C39H26N4 = 550.66) |
| 451 | m/z = 623.23 (C46H29N3 = 623.75) |
| 452 | m/z = 639.23 (C46H29N3O = 639.75) |
| 461 | m/z = 692.26 (C48H32N6 = 692.82) |

TABLE 4-continued

| Compound | FD-MS |
|---|---|
| 462 | m/z = 692.26 (C48H32N6 = 692.82) |
| 465 | m/z = 692.26 (C48H32N6 = 692.82) |
| 474 | m/z = 692.26 (C48H32N6 = 692.82) |
| 497 | m/z = 691.27 (C49H33N5 = 691.83) |
| 498 | m/z = 691.27 (C49H33N5 = 691.83) |
| 501 | m/z = 691.27 (C49H33N5 = 691.83) |
| 510 | m/z = 691.27 (C49H33N5 = 691.83) |
| 569 | m/z = 768.30 (C54H36N6 = 768.92) |
| 573 | m/z = 767.30 (C55H37N5 = 767.93) |
| 577 | m/z = 767.30 (C55H37N5 = 767.93) |

<Experimental Example 1> Manufacture of Organic Light Emitting Device

1) Manufacture of Organic Light Emitting Device

Comparative Examples 1-1 to 1-5

A transparent ITO electrode thin film obtained from glass for an OLED (manufactured by Samsung-Corning Co., Ltd.) was ultrasonic cleaned using trichloroethylene, acetone, ethanol and distilled water consecutively for 5 minutes each, stored in isopropanol, and used.

Next, an ITO substrate was installed in a substrate folder of a vacuum deposition apparatus, and the following 4,4',4"-tris(N,N-(2-naphthyl)-phenylamino)triphenylamine (2-TNATA) was introduced to a cell in the vacuum deposition apparatus.

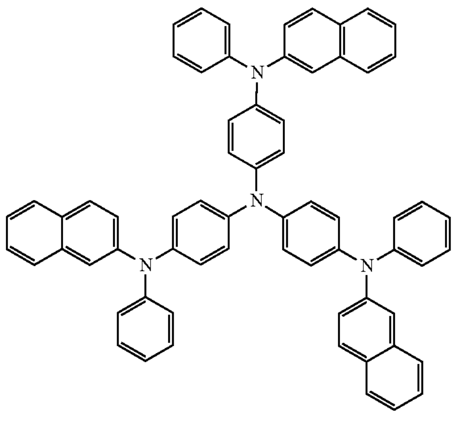

2-TNATA

Subsequently, the chamber was evacuated until the degree of vacuum therein reached $10^{-6}$ torr, and then 2-TNATA was evaporated by applying a current to the cell to deposit a hole injection layer having a thickness of 600 Å on the ITO substrate.

To another cell in the vacuum deposition apparatus, the following N,N'-bis(α-naphthyl)-N,N'-diphenyl-4,4'-diamine (NPB) was introduced, and evaporated by applying a current to the cell to deposit a hole transfer layer having a thickness of 300 Å on the hole injection laver.

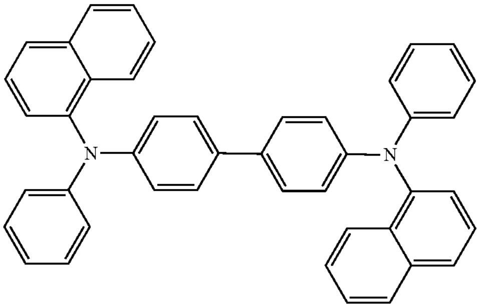

NPB

After forming the hole injection layer and the hole transfer layer as above, a blue light emitting material having a structure as below was deposited thereon as a light emitting layer. Specifically, in one side cell in the vacuum deposition apparatus, H1, a blue light emitting host material, was vacuum deposited to a thickness of 200 Å, and D1, a blue light emitting dopant material, was vacuum deposited thereon by 5% with respect to the host material.

H1

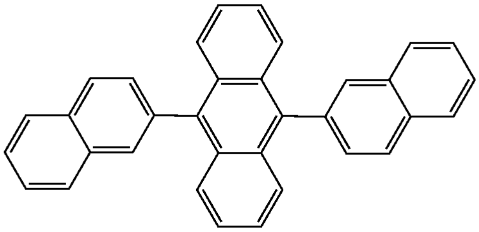

D1

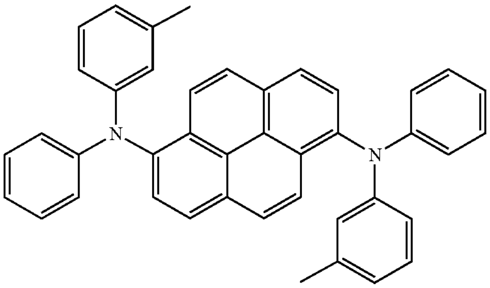

Subsequently, as an electron transfer layer, each of compounds of the following structural formulae E1 to E3, BBQB and TBQB was deposited to a thickness of 300 Å according to each comparative example.

E1

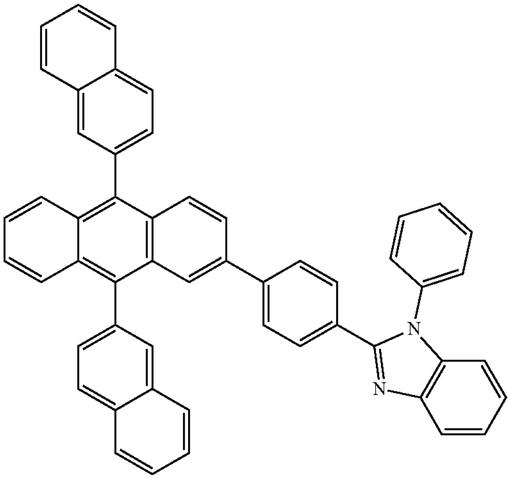

E2

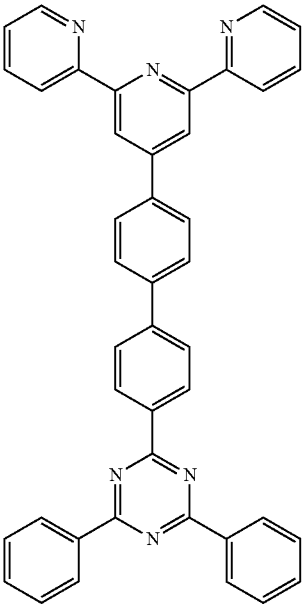

-continued

E3

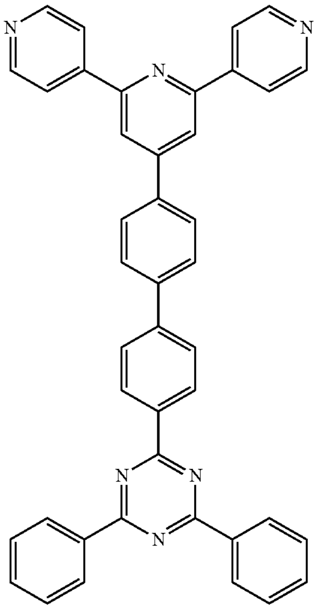

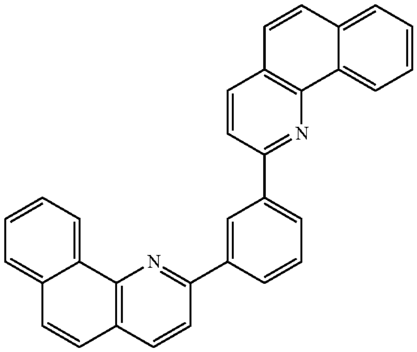

BBQB

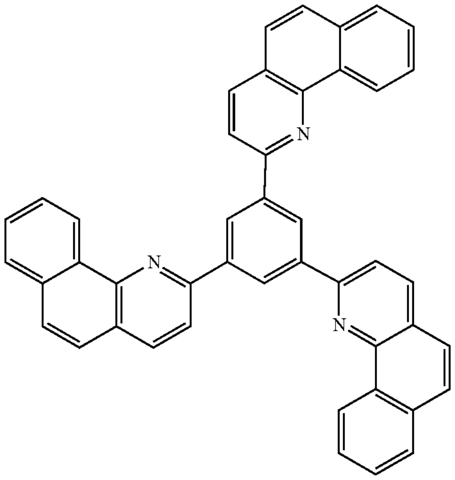

TBQB

As an electron injection layer, lithium fluoride (LiF) was deposited to a thickness of 10 Å, and an Al cathode was employed to a thickness of 1,000 Å, and as a result, an OLED was manufactured.

Examples 1-1 to 1-41

Organic electroluminescent devices of Examples 1-1 to 1-41 were manufactured in the same manner as in the comparative examples except that compounds shown in the following Table 5 were used instead of the compounds of E1 to E3, BBQB and TBQB used when forming the electron transfer layer.

Meanwhile, all the organic compounds required to manufacture the OLED were vacuum sublimation purified under $10^{-8}$ torr to $10^{-6}$ torr by each material to be used in the OLED manufacture.

2) Driving Voltage and Light Emission Efficiency of Organic Light Emitting Device For each of the organic light emitting devices manufactured as above, electroluminescent (EL) properties were measured using M7000 manufactured by McScience Inc., and with the measurement results, $T_{95}$ was measured when standard luminance was 700 cd/$m^2$ through a lifetime measurement system (M6000) manufactured by McScience Inc. Results of measuring driving voltage, light emission efficiency, external quantum efficiency and color coordinate (CIE) of the blue organic light emitting device manufactured according to the present disclosure are as shown in Table 5.

TABLE 5

| | Compound | Driving Voltage (V) | Light Emission Efficiency (cd/A) | CIE (x, y) | Lifetime ($T_{95}$) |
|---|---|---|---|---|---|
| Example 1-1 | 1 | 5.21 | 7.51 | (0.134, 0.102) | 42 |
| Example 1-2 | 2 | 5.30 | 6.96 | (0.134, 0.101) | 35 |
| Example 1-3 | 3 | 5.45 | 6.93 | (0.134, 0.101) | 38 |
| Example 1-4 | 13 | 5.20 | 6.87 | (0.134, 0.103) | 48 |
| Example 1-5 | 14 | 5.64 | 7.27 | (0.134, 0.102) | 44 |
| Example 1-6 | 15 | 5.29 | 6.44 | (0.134, 0.101) | 37 |
| Example 1-7 | 26 | 5.39 | 7.00 | (0.134, 0.102) | 33 |
| Example 1-8 | 73 | 5.28 | 6.77 | (0.134, 0.102) | 49 |
| Example 1-9 | 100 | 5.27 | 6.87 | (0.134, 0.101) | 50 |
| Example 1-10 | 137 | 5.33 | 6.70 | (0.134, 0.103) | 63 |
| Example 1-11 | 141 | 5.07 | 7.26 | (0.134, 0.101) | 28 |
| Example 1-12 | 142 | 5.31 | 7.14 | (0.134, 0.100) | 37 |
| Example 1-13 | 143 | 5.13 | 6.27 | (0.134, 0.103) | 41 |
| Example 1-14 | 144 | 5.16 | 7.33 | (0.134, 0.100) | 44 |
| Example 1-15 | 153 | 5.24 | 7.08 | (0.134, 0.100) | 54 |
| Example 1-16 | 155 | 5.08 | 6.98 | (0.134, 0.100) | 49 |
| Example 1-17 | 156 | 5.19 | 8.25 | (0.134, 0.102) | 37 |
| Example 1-18 | 157 | 5.27 | 7.18 | (0.134, 0.101) | 43 |
| Example 1-19 | 158 | 5.33 | 7.10 | (0.134, 0.102) | 44 |
| Example 1-20 | 159 | 5.06 | 8.26 | (0.134, 0.100) | 38 |
| Example 1-21 | 161 | 5.10 | 7.80 | (0.134, 0.103) | 38 |
| Example 1-22 | 167 | 5.29 | 6.77 | (0.134, 0.101) | 54 |
| Example 1-23 | 168 | 5.28 | 6.90 | (0.134, 0.102) | 53 |
| Example 1-24 | 185 | 5.28 | 6.89 | (0.134, 0.102) | 51 |
| Example 1-25 | 186 | 5.41 | 7.08 | (0.134, 0.102) | 50 |
| Example 1-26 | 445 | 5.34 | 6.58 | (0.134, 0.103) | 63 |
| Example 1-27 | 449 | 4.99 | 6.71 | (0.134, 0.101) | 29 |
| Example 1-28 | 450 | 5.30 | 6.64 | (0.134, 0.101) | 41 |
| Example 1-29 | 451 | 5.07 | 7.32 | (0.134, 0.100) | 35 |
| Example 1-30 | 452 | 5.13 | 6.77 | (0.134, 0.101) | 41 |
| Example 1-31 | 461 | 5.28 | 6.83 | (0.134, 0.101) | 30 |
| Example 1-32 | 462 | 5.23 | 6.89 | (0.134, 0.102) | 30 |
| Example 1-33 | 465 | 5.19 | 6.99 | (0.134, 0.102) | 31 |
| Example 1-34 | 474 | 5.51 | 6.86 | (0.134, 0.102) | 40 |
| Example 1-35 | 497 | 5.42 | 6.93 | (0.134, 0.101) | 37 |
| Example 1-36 | 498 | 5.26 | 6.81 | (0.134, 0.102) | 44 |
| Example 1-37 | 501 | 5.69 | 7.26 | (0.134, 0.102) | 48 |
| Example 1-38 | 510 | 5.35 | 7.27 | (0.134, 0.103) | 45 |
| Example 1-39 | 569 | 5.29 | 7.27 | (0.134, 0.102) | 44 |
| Example 1-40 | 573 | 5.68 | 7.27 | (0.134, 0.102) | 41 |
| Example 1-41 | 577 | 5.27 | 6.98 | (0.134, 0.102) | 43 |
| Comparative Example 1-1 | E1 | 5.81 | 6.02 | (0.134, 0.103) | 25 |

TABLE 5-continued

| | Compound | Driving Voltage (V) | Light Emission Efficiency (cd/A) | CIE (x, y) | Life-time ($T_{95}$) |
|---|---|---|---|---|---|
| Comparative Example 1-2 | E2 | 5.76 | 6.21 | (0.134, 0.101) | 21 |
| Comparative Example 1-3 | E3 | 5.72 | 6.22 | (0.134, 0.102) | 26 |
| Comparative Example 1-4 | BBQB | 6.11 | 5.98 | (0.134, 0.102) | 24 |
| Comparative Example 1-5 | TBQB | 5.87 | 6.52 | (0.134, 0.102) | 20 |

As seen from the results of Table 5, the organic light emitting device using the electron transfer layer material of the blue organic light emitting device of the present disclosure had lower driving voltage and significantly improved light emission efficiency and lifetime compared to Comparative Examples 1-1 to 1-5. Particularly, it was identified that Compounds 1, 144, 156, 159 and 161 were superior in all aspects of driving voltage, efficiency and lifetime.

Such a result is considered to be due to the fact that, when using the disclosed compound having proper length and strength, and flatness as an electron transfer layer, a compound in an excited state is made by receiving electrons under a specific condition, and particularly when an excited state is formed in the hetero-skeleton site of the compound, excited energy moves to a stable state before the excited hetero-skeleton site goes through other reactions, and as a result, the relatively stabilized compound is capable of efficiently transferring electrons without the compound being decomposed or destroyed. For reference, those that are stable when excited are considered to be aryl or acene-based compounds or polycyclic hetero-compounds.

In addition, when compared to Comparative Example 1-2, Example 1-1 has a more planar structure than Comparative Example 1-2 since the H—N hydrogen bond of the phenyl linking group located between azine and terpyridine substituent works strongly to prevent rotational motion of the phenyl linking group. As a result, when forming the device, n-n stacking interactions are strong between the electron transfer layer compounds facilitating electron migration. When compared to Comparative Example 1-3, Example 1-1 has a structure in which heteroatoms of terpyridine are delocalized to one side, and therefore, metal binding of lithium and the terpyridine substituent strongly occurs between the electron injection layer and the electron transfer layer preventing lithium diffusion. Accordingly, it is considered that the compound of the present disclosure has enhanced electron-transfer properties or enhances stability resulting in superiority in all aspects of driving, efficiency and lifetime.

<Experimental Example 2> Manufacture of Organic Light Emitting Device

Comparative Examples 2-1 to 2-4 and Examples 2-1 to 2-41

A transparent ITO electrode thin film obtained from glass for an OLED (manufactured by Samsung-Corning Co., Ltd.) was ultrasonic cleaned using trichloroethylene, acetone, ethanol and distilled water consecutively for 5 minutes each, stored in isopropanol, and used. Next, an ITO substrate was installed in a substrate folder of a vacuum deposition apparatus, and the following 4,4',4"-tris(N,N-(2-naphthyl)-phenylamino)triphenylamine (2-TNATA) was introduced to a cell in the vacuum deposition apparatus.

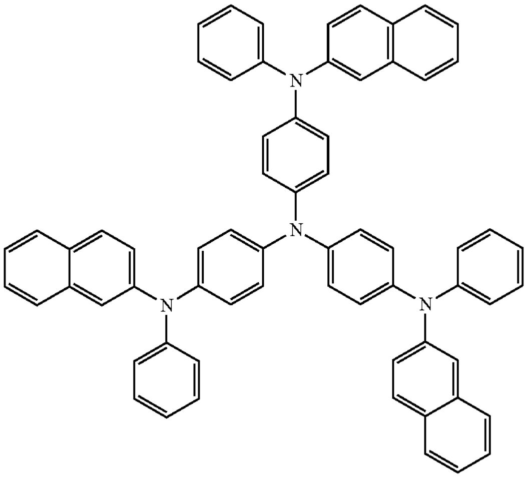

2-TNATA

Subsequently, the chamber was evacuated until the degree of vacuum therein reached $10^{-6}$ torr, and then 2-TNATA was evaporated by applying a current to the cell to deposit a hole injection layer having a thickness of 600 Å on the ITO substrate. To another cell in the vacuum deposition apparatus, the following N,N'-bis(α-naphthyl)-N,N'-diphenyl-4,4'-diamine (NPB) was introduced, and evaporated by applying a current to the cell to deposit a hole transfer layer having a thickness of 300 Å on the hole injection layer.

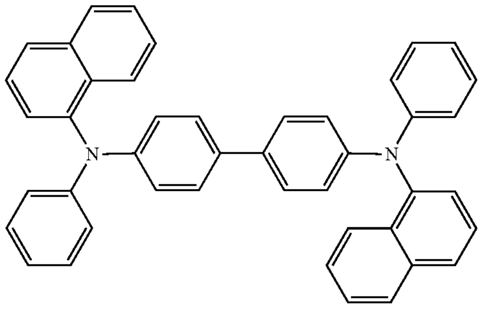

NPB

After forming the hole injection layer and the hole transfer layer as above, a blue light emitting material having a structure as below was deposited thereon as a light emitting layer. Specifically, in one side cell in the vacuum deposition apparatus, H1, a blue light emitting host material, was vacuum deposited to a thickness of 200 Å, and D1, a blue light emitting dopant material, was vacuum deposited thereon by 5% with respect to the host material.

H1
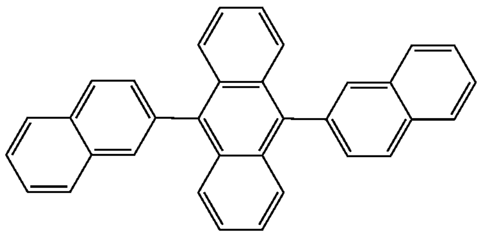
D1
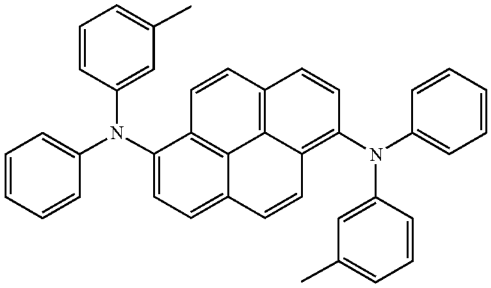
Subsequently, a hole blocking layer was formed to a thickness of 50 Å using a compound shown in the following Table 6, and then the following E1 was formed to a thickness of 250 Å as an electron transfer layer.
E1
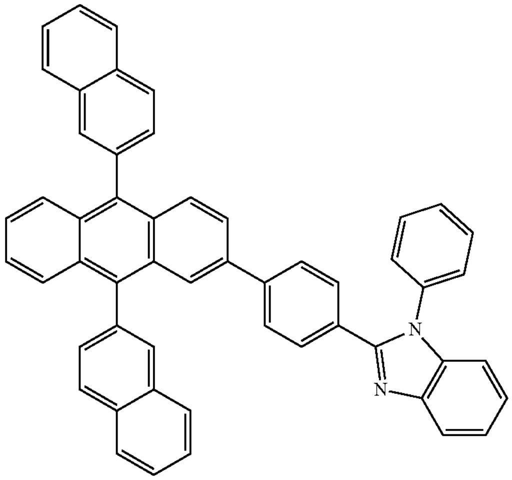
-continued
E2
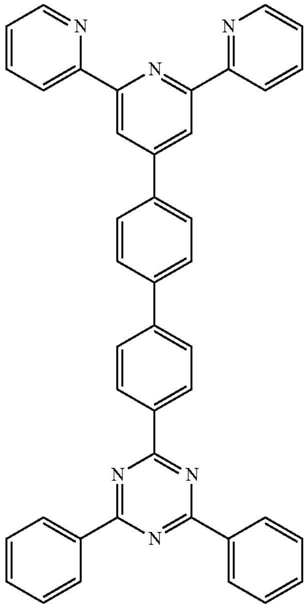
E3
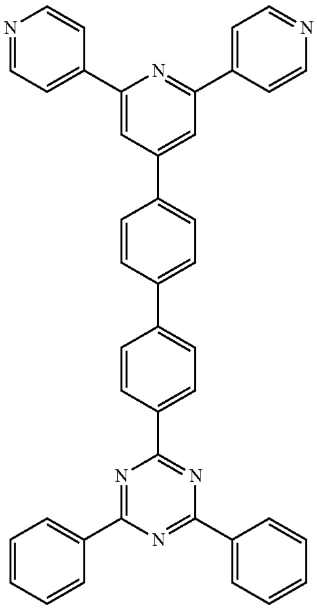
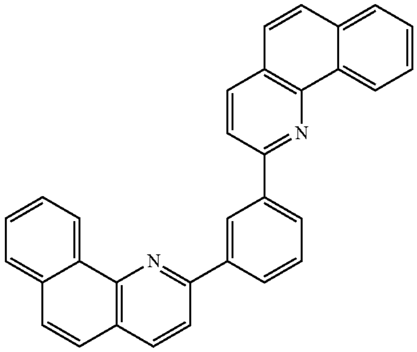
BBQB -continued

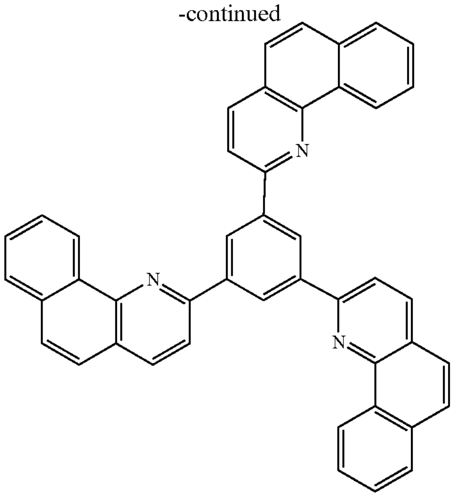

TBQB

Then, as an electron injection layer, lithium fluoride (LiF) was deposited to a thickness of 10 Å, and an Al cathode was employed to a thickness of 1,000 Å, and as a result, an OLED was manufactured. Meanwhile, all the organic compounds required to manufacture the OLED were vacuum sublimation purified under $10^{-8}$ torr to $10^{-6}$ torr by each material to be used in the OLED manufacture.

Results of measuring driving voltage, light emission efficiency, color coordinate (CIE) and lifetime of the blue organic light emitting devices manufactured according to the present disclosure in the same manner as in Experimental Example 1 are as shown in Table 6.

TABLE 6

| | Compound | Driving Voltage (V) | Light Emission Efficiency (cd/A) | CIE (x, y) | Lifetime ($T_{95}$) |
|---|---|---|---|---|---|
| Example 2-1 | 1 | 4.93 | 8.00 | (0.134, 0.102) | 43 |
| Example 2-2 | 2 | 5.28 | 6.23 | (0.134, 0.101) | 35 |
| Example 2-3 | 3 | 5.23 | 6.82 | (0.134, 0.101) | 31 |
| Example 2-4 | 13 | 5.06 | 6.57 | (0.134, 0.103) | 34 |
| Example 2-5 | 14 | 5.45 | 6.18 | (0.134, 0.102) | 26 |
| Example 2-6 | 15 | 5.50 | 6.79 | (0.134, 0.101) | 29 |
| Example 2-7 | 26 | 5.20 | 7.47 | (0.134, 0.102) | 28 |
| Example 2-8 | 73 | 5.04 | 7.27 | (0.134, 0.102) | 49 |
| Example 2-9 | 100 | 5.14 | 6.33 | (0.134, 0.101) | 36 |
| Example 2-10 | 137 | 5.20 | 6.69 | (0.134, 0.103) | 41 |
| Example 2-11 | 141 | 5.06 | 6.64 | (0.134, 0.101) | 25 |
| Example 2-12 | 142 | 5.45 | 6.95 | (0.134, 0.100) | 39 |
| Example 2-13 | 143 | 5.23 | 7.39 | (0.134, 0.103) | 41 |
| Example 2-14 | 144 | 4.95 | 6.91 | (0.134, 0.100) | 37 |
| Example 2-15 | 153 | 5.50 | 6.49 | (0.134, 0.100) | 54 |
| Example 2-16 | 155 | 5.34 | 6.46 | (0.134, 0.100) | 48 |
| Example 2-17 | 156 | 5.13 | 6.32 | (0.134, 0.102) | 37 |
| Example 2-18 | 157 | 5.09 | 6.67 | (0.134, 0.101) | 54 |
| Example 2-19 | 158 | 5.35 | 6.18 | (0.134, 0.102) | 37 |
| Example 2-20 | 159 | 5.43 | 8.13 | (0.134, 0.100) | 44 |
| Example 2-21 | 161 | 5.30 | 6.76 | (0.134, 0.103) | 33 |
| Example 2-22 | 167 | 5.26 | 6.33 | (0.134, 0.101) | 29 |
| Example 2-23 | 168 | 4.95 | 6.21 | (0.134, 0.102) | 33 |
| Example 2-24 | 185 | 5.31 | 6.33 | (0.134, 0.102) | 36 |
| Example 2-25 | 186 | 5.56 | 6.59 | (0.134, 0.102) | 32 |
| Example 2-26 | 445 | 5.44 | 6.36 | (0.134, 0.103) | 49 |
| Example 2-27 | 449 | 5.15 | 6.51 | (0.134, 0.101) | 54 |
| Example 2-28 | 450 | 5.22 | 6.55 | (0.134, 0.101) | 39 |
| Example 2-29 | 451 | 5.37 | 6.12 | (0.134, 0.100) | 35 |
| Example 2-30 | 452 | 5.43 | 6.24 | (0.134, 0.101) | 37 |
| Example 2-31 | 461 | 5.07 | 6.32 | (0.134, 0.101) | 28 |

TABLE 6-continued

| | Compound | Driving Voltage (V) | Light Emission Efficiency (cd/A) | CIE (x, y) | Lifetime ($T_{95}$) |
|---|---|---|---|---|---|
| Example 2-32 | 462 | 5.52 | 6.43 | (0.134, 0.102) | 37 |
| Example 2-33 | 465 | 5.20 | 6.21 | (0.134, 0.102) | 37 |
| Example 2-34 | 474 | 5.31 | 6.73 | (0.134, 0.102) | 49 |
| Example 2-35 | 497 | 5.24 | 6.74 | (0.134, 0.101) | 37 |
| Example 2-36 | 498 | 5.40 | 6.55 | (0.134, 0.102) | 41 |
| Example 2-37 | 501 | 5.26 | 6.26 | (0.134, 0.102) | 44 |
| Example 2-38 | 510 | 5.19 | 7.12 | (0.134, 0.103) | 31 |
| Example 2-39 | 569 | 5.11 | 6.14 | (0.134, 0.102) | 37 |
| Example 2-40 | 573 | 5.07 | 6.51 | (0.134, 0.102) | 28 |
| Example 2-41 | 577 | 5.02 | 6.44 | (0.134, 0.102) | 37 |
| Comparative Example 2-1 | E2 | 5.56 | 6.18 | (0.134, 0.101) | 25 |
| Comparative Example 2-2 | E3 | 5.84 | 6.07 | (0.134, 0.102) | 22 |
| Comparative Example 2-3 | BBQB | 6.11 | 6.20 | (0.134, 0.102) | 23 |
| Comparative Example 2-4 | TBQB | 6.31 | 6.27 | (0.134, 0.102) | 28 |

As seen from the results of Table 6, the organic electroluminescent device using the hole blocking layer material of the blue organic electroluminescent device of the present disclosure had lower driving voltage and significantly improved light emission efficiency and lifetime compared to Comparative Examples 2-1 to 2-4.

<Experimental Example 3> Manufacture of Organic Light Emitting Device

Comparative Examples 3-1 to 3-5 and Examples 3-1 to 3-41

1) Manufacture of Organic Light Emitting Device

A glass substrate on which ITO was coated as a thin film to a thickness of 1,500 Å was cleaned with distilled water ultrasonic waves. After the cleaning with distilled water was finished, the substrate was ultrasonic cleaned with solvents such as acetone, methanol and isopropyl alcohol, then dried, and UVO treatment was conducted for 5 minutes using UV in a UV cleaner. After that, the substrate was transferred to a plasma cleaner (PT), and after conducting plasma treatment under vacuum for ITO work function and residual film removal, the substrate was transferred to a thermal deposition apparatus for organic deposition.

On the transparent ITO electrode (anode), organic materials were formed in a 2-stack white organic light emitting device (WOLED) structure. As for the first stack, TAPC was thermal vacuum deposited first to a thickness of 300 Å to form a hole transfer layer. After forming the hole transfer layer, a light emitting layer was thermal vacuum deposited thereon as follows. As the light emitting layer, TCz1, a host, was doped with FIrpic, a blue phosphorescent dopant, by 8%, and deposited to 300 Å. An electron transfer layer was formed to 400 Å using TmPyPB (1,3,5-tris(3-pyridyl-3-phenyl)benzene), and a charge generation layer having a thickness of 100 Å was formed thereon using E1, E2, E3, BBQB and TBQB as the comparative examples and compounds described in the following Table 7 as the examples and doping $Cs_2CO_3$ thereto by 20%.

As for the second stack, $MoO_3$ was thermal vacuum deposited first to a thickness of 50 Å to form a hole injection layer. A hole transfer layer, a common layer, was formed to 100 Å by doping $MoO_3$ to TAPC by 20%, and then depositing TAPC to 300 Å. A light emitting layer was formed thereon by doping $Ir(ppy)_3$, a green phosphorescent dopant, to TCz1, a host, by 8%, and depositing the result to 300 Å, and then an electron transfer layer was formed to 600 Å using TmPyPB. Lastly, an electron injection layer was formed on the electron transfer layer by depositing lithium fluoride (LiF) to a thickness of 10 Å, and then a cathode was formed on the electron injection layer by depositing an aluminum (Al) cathode to a thickness of 1,200 Å, and as a result, an organic light emitting device was manufactured.

Meanwhile, all the organic compounds required to manufacture the OLED were vacuum sublimation purified under $10^{-8}$ torr to $10^{-6}$ torr for each material to be used in the OLED manufacture.

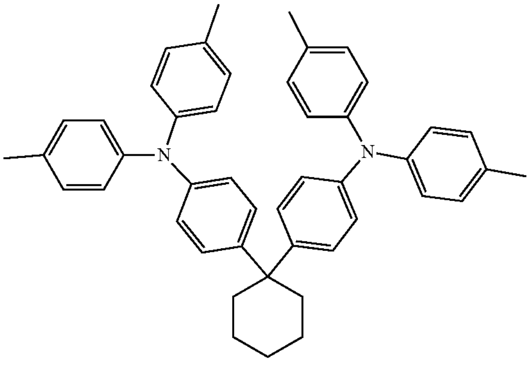

TAPC

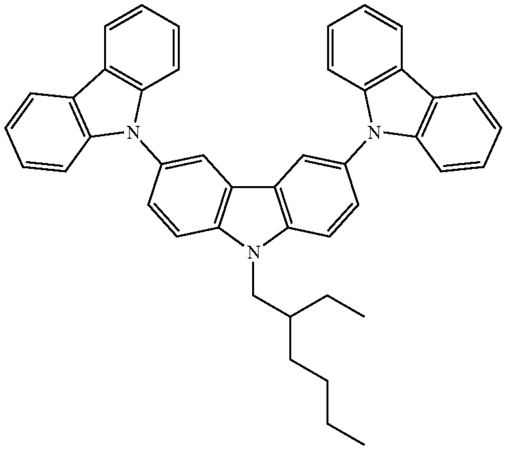

TCz1

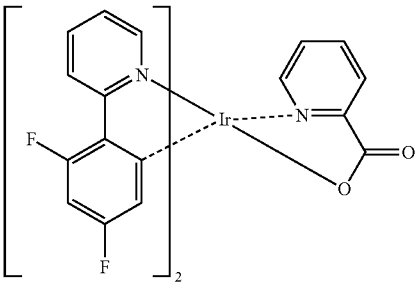

FIrpic

-continued

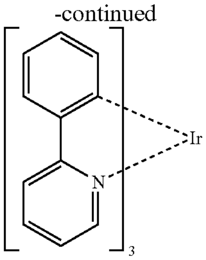

Ir(ppy)3

E1

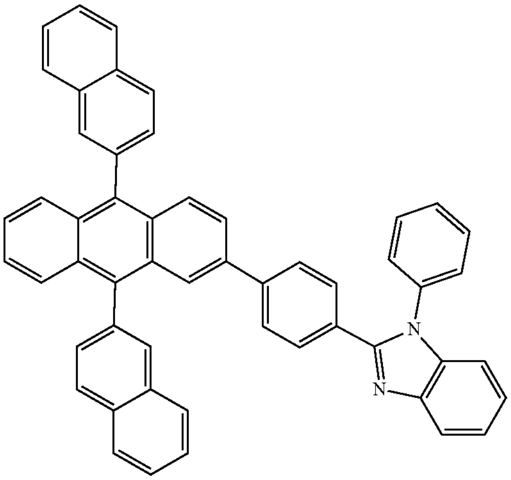

E2

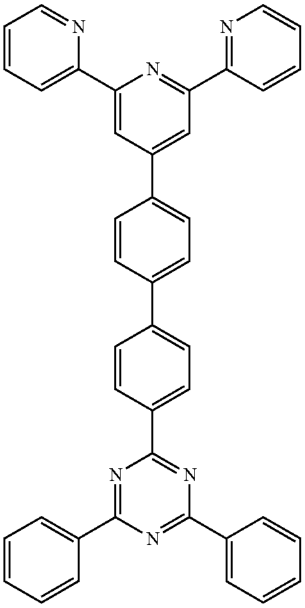

-continued

E3

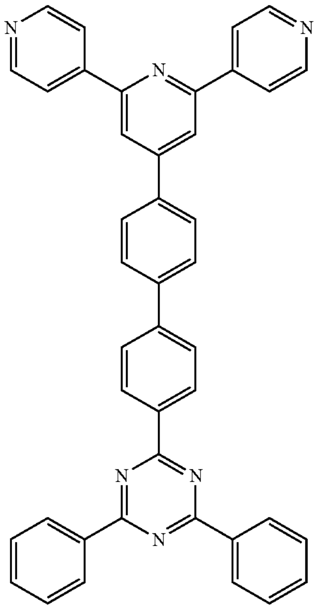

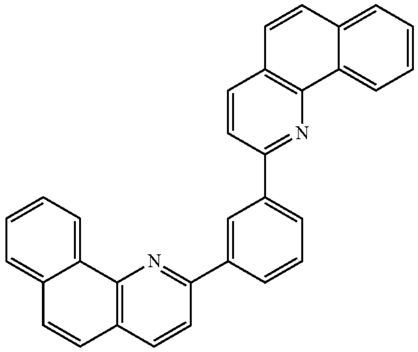

BBQB

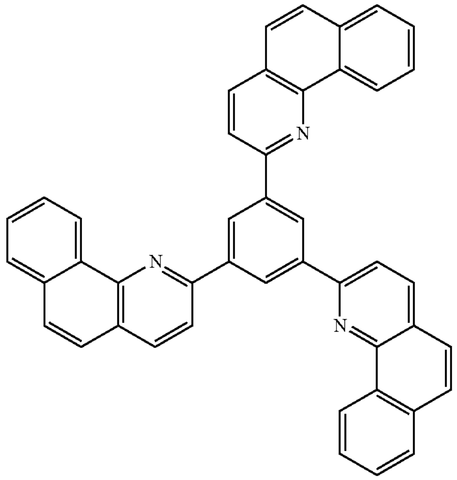

TBQB

2) Driving Voltage and Light Emission Efficiency of Organic Light Emitting Device For each of the organic light emitting devices manufactured as above, electroluminescent (EL) properties were measured using M7000 manufactured by McScience Inc., and with the measurement results, $T_{95}$ was measured when standard luminance was 3,500 cd/m$^2$ through a lifetime measurement system (M6000) manufactured by McScience Inc. Results of measuring driving voltage, light emission efficiency, external quantum efficiency and color coordinate (CIE) of the white organic light emitting device manufactured according to the present disclosure are as shown in the following Table 7.

TABLE 7

| | Compound | Driving Voltage (V) | Light Emission Efficiency (cd/A) | CIE (x, y) | Lifetime ($T_{95}$) |
|---|---|---|---|---|---|
| Example 3-1 | 1 | 5.31 | 66.67 | (0.218, 0.427) | 59 |
| Example 3-2 | 2 | 5.34 | 66.16 | (0.220, 0.431) | 55 |
| Example 3-3 | 3 | 5.31 | 65.13 | (0.220, 0.431) | 49 |
| Example 3-4 | 13 | 5.24 | 67.07 | (0.200, 0.421) | 55 |
| Example 3-5 | 14 | 5.00 | 65.48 | (0.228, 0.436) | 51 |
| Example 3-6 | 15 | 5.15 | 67.26 | (0.243, 0.442) | 52 |
| Example 3-7 | 26 | 5.19 | 65.21 | (0.221, 0.433) | 58 |
| Example 3-8 | 73 | 5.32 | 66.97 | (0,208, 0.415) | 57 |
| Example 3-9 | 100 | 5.31 | 67.07 | (0.233, 0.433) | 58 |
| Example 3-10 | 137 | 4.96 | 67.54 | (0.238, 0.438) | 73 |
| Example 3-11 | 141 | 5.10 | 67.09 | (0.225, 0.429) | 49 |
| Example 3-12 | 142 | 5.35 | 66.35 | (0.209, 0.415) | 43 |
| Example 3-13 | 143 | 5.16 | 65.03 | (0.231, 0.440) | 48 |
| Example 3-14 | 144 | 5.19 | 67.03 | (0.211, 0.419) | 45 |
| Example 3-15 | 153 | 5.28 | 69.28 | (0.209, 0.419) | 71 |
| Example 3-16 | 155 | 5.12 | 67.19 | (0.207, 0.409) | 56 |
| Example 3-17 | 156 | 5.10 | 65.21 | (0,208, 0.415) | 46 |
| Example 3-18 | 157 | 5.31 | 64.26 | (0.214, 0.420) | 50 |
| Example 3-19 | 158 | 5.37 | 67.20 | (0.224, 0.429) | 51 |
| Example 3-20 | 159 | 5.10 | 64.48 | (0.221, 0.434) | 44 |
| Example 3-21 | 161 | 5.14 | 67.35 | (0.212, 0.422) | 42 |
| Example 3-22 | 167 | 5.33 | 66.97 | (0.228, 0.418) | 51 |
| Example 3-23 | 168 | 5.32 | 67.10 | (0.231, 0.420) | 41 |
| Example 3-24 | 185 | 5.31 | 67.09 | (0.219, 0.411) | 48 |
| Example 3-25 | 186 | 5.16 | 64.28 | (0.219, 0.411) | 58 |
| Example 3-26 | 445 | 4.98 | 67.53 | (0.210, 0.412) | 73 |
| Example 3-27 | 449 | 5.22 | 64.09 | (0.218, 0.421) | 57 |
| Example 3-28 | 450 | 5.34 | 66.84 | (0.209, 0.432) | 52 |
| Example 3-29 | 451 | 5.15 | 65.30 | (0.231, 0.418) | 41 |
| Example 3-30 | 452 | 5.17 | 66.96 | (0.243, 0.442) | 47 |
| Example 3-31 | 461 | 5.32 | 67.03 | (0.205, 0.411) | 55 |
| Example 3-32 | 465 | 5.26 | 67.09 | (0.243, 0.442) | 58 |
| Example 3-33 | 474 | 5.22 | 67.19 | (0.209, 0.419) | 53 |
| Example 3-34 | 497 | 5.25 | 67.06 | (0.210, 0.420) | 46 |
| Example 3-35 | 498 | 5.22 | 66.13 | (0.231, 0.419) | 43 |
| Example 3-36 | 501 | 5.29 | 67.01 | (0.229, 0.420) | 50 |
| Example 3-37 | 510 | 5.20 | 69.43 | (0.224, 0.423) | 55 |
| Example 3-38 | 569 | 5.16 | 65.16 | (0.220, 0.424) | 52 |
| Example 3-39 | 573 | 5.20 | 64.02 | (0.221, 0.430) | 50 |
| Example 3-40 | 577 | 5.25 | 66.95 | (0.220, 0.429) | 48 |
| Example 3-41 | 462 | 5.30 | 67.18 | (0.221, 0.430) | 49 |
| Comparative Example 3-1 | E1 | 8.56 | 57.61 | (0.212, 0.430) | 26 |
| Comparative Example 3-2 | E2 | 7.45 | 55.11 | (0.220, 0,431) | 29 |
| Comparative Example 3-3 | E3 | 8.11 | 58.90 | (0.222, 0,429) | 27 |
| Comparative Example 3-4 | BBQB | 7.47 | 56.55 | (0.221, 0,431) | 28 |
| Comparative Example 3-5 | TBQB | 8.31 | 55.91 | (0.220, 0.429) | 31 |

As seen from the results of Table 7, the organic light emitting device using the charge generation layer material of the 2-stack white organic light emitting device of the present disclosure had lower driving voltage and improved light emission efficiency compared to Comparative Examples 3-1 to 3-5. Particularly, it was identified that Compounds 1, 14, 137 and 445 were significantly superior in all aspects of driving voltage, efficiency and lifetime.

Such a result is considered to be due to the fact that the compound of the present disclosure used as an N-type charge generation layer formed with the disclosed skeleton having proper length and strength, and flatness and a proper hetero-compound capable of binding to metals forms a gap state in the N-type charge generation layer by doping an alkali metal or an alkaline earth metal thereto, and electrons produced from a P-type charge generation layer are readily injected into an electron transfer layer through the gap state produced in the N-type charge generation layer. Accordingly, the P-type charge generation layer may favorably inject and transfer electrons to the N-type charge generation layer, and as a result, driving voltage was lowered, and efficiency and lifetime were improved in the organic light emitting device.

In addition, by the core structure of the present application having a substituent at two places and thereby combining an electron-deficient substituent and an aryl or acene-based substituent, the electron-deficient substituent readily receives electrons from the electron injection layer, and the aryl or acene-based substituent stabilizes the molecule itself and transfers the supplied electrons to the light emitting layer, which enhances device properties.

The invention claimed is:

1. An organic light emitting device comprising:

a first electrode;

a second electrode; and an organic material layer provided between the first electrode and the second electrode, wherein the organic material layer includes an electron transfer layer, a hole blocking layer or a charge generation layer, at least one of the electron transfer layer, the hole blocking layer and the charge generation layer includes one or more types of a heterocyclic compound represented by the following Chemical Formula 1:

[Chemical Formula 1]

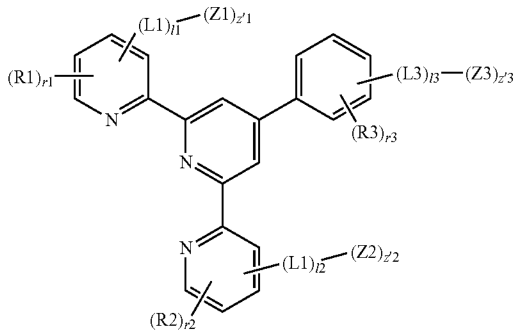

wherein, in Chemical Formula 1,

R1 is hydrogen; or deuterium,

R2 is hydrogen; deuterium; or a phenyl group, or a plurality of R2s bond to each other to form a benzene ring, R3 is hydrogen; deuterium; or a phenyl group, or a plurality of R3s bond to each other to form a benzene ring, L1 to L3 are the same as or different from each other, and each independently a direct bond; a phenylene group; or a biphenylene group, Z1 is —P(═O)(R104')(R105'); a phenyl group unsubstituted or substituted with an aryl group or a heterocyclic group; a biphenyl group; a terphenyl group; a naphthyl group; an anthracenyl group; a phenanthrenyl group unsubstituted or substituted with an aryl group; a pyrenyl group; a fluorenyl group unsubstituted or substituted with an alkyl group or an aryl group; a fluoranthenyl group; a pyrimidine group unsubstituted or substituted with an aryl group; a triazine group unsubstituted or substituted with an aryl group; a quinazolinyl group unsubstituted or substituted with an aryl group; a carbazole group unsubstituted or substituted with an aryl group; a phenanthrolinyl group unsubstituted or substituted with an aryl group; a phenanthridinyl group unsubstituted or substituted with an aryl group; a benzophenanthridinyl group; a dibenzofuran group; a dibenzothiophene group; dibenzosulfolane; spiro[fluorene-9,9'-xanthene]; a benzo[4,5]thieno[3,2-d]pyrimidyl group unsubstituted or substituted with an aryl group; a benzofuro[2,3-c]quinolinyl group; a benzofuro[3,2-c]quinolinyl group; a benzothieno[2,3-c]quinolinyl group; a benzothieno[3,2-c]quinolinyl group; or a pyrazolo[5,1-a]isoquinolinyl group unsubstituted or substituted with an aryl group, and R104' and R105' are each independently an aryl group, Z2 and Z3 are the same as or different from each other, and each independently hydrogen; deuterium; a halogen group; a cyano group; a methyl group; a pyrimidine group unsubstituted or substituted with an aryl group; a triazine group unsubstituted or substituted with an aryl group; or a carbazole group, R104 and R105 are each independently a phenyl group, r1 and r2 are each an integer of 1 to 3, r3 is an integer of 1 to 4, l1 to l3 and z'1 to z'3 are each independently an integer of 1 to 5, and when r1 to r3, l1 to l3 and z'1 to z'3 are each 2 or greater, substituents in the parentheses are the same as or different from each other.

2. The organic light emitting device of claim 1, wherein Chemical Formula 1 is represented by any one of the following Chemical Formulae 1-1 to 1-4:

[Chemical Formula 1-1]

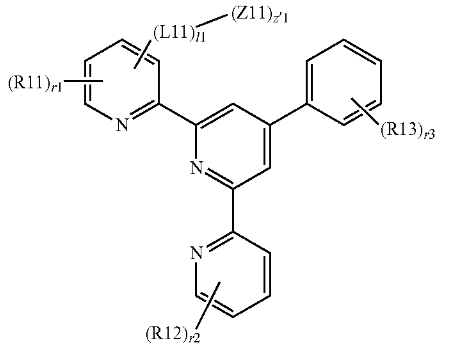

[Chemical Formula 1-2]

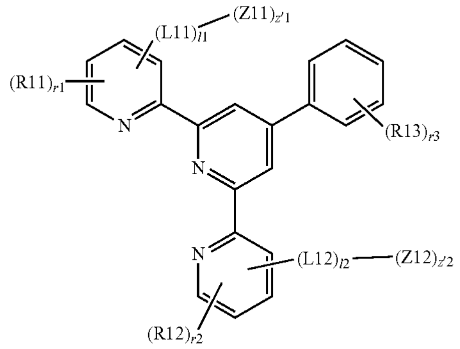

-continued

[Chemical Formula 1-3]

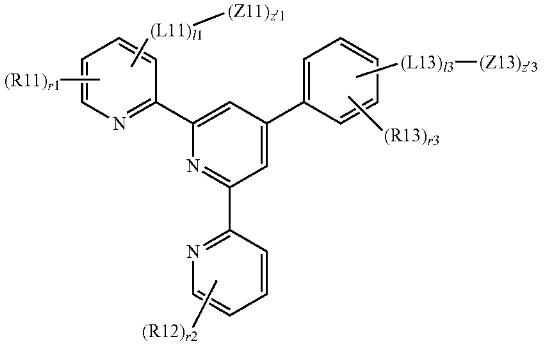

[Chemical Formula 1-4]

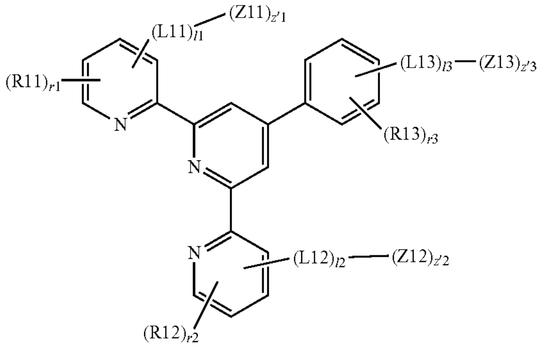

in Chemical Formulae 1-1 to 1-4, r1 to r3, l1 to l3 and z'1 to z'3 have the same definitions as in Chemical Formula 1, R11 is hydrogen; or deuterium, R12 is hydrogen; deuterium; or a phenyl group, or a plurality of R12s bond to each other to form a benzene ring, R13 is hydrogen; deuterium; or a phenyl group, or a plurality of R13s bond to each other to form a benzene ring, L11 to L13 are the same as or different from each other, and each independently a direct bond; a phenylene group; or a biphenylene group, Z11 is —P(═O)R(104')(R105'); a phenyl group unsubstituted or substituted with an aryl group or a heterocyclic group; a biphenyl group; a terphenyl group; a naphthyl group; an anthracenyl group; a phenanthrenyl group unsubstituted or substituted with an aryl group; a pyrenyl group; a fluorenyl group unsubstituted or substituted with an alkyl group or an aryl group; a fluoranthenyl group; a pyrimidine group unsubstituted or substituted with an aryl group; a triazine group unsubstituted or substituted with an aryl group; a quinazolinyl group unsubstituted or substituted with an aryl group; a carbazole group unsubstituted or substituted with an aryl group; a phenanthrolinyl group unsubstituted or substituted with an aryl group; a phenanthridinyl group unsubstituted or substituted with an aryl group; a benzophenanthridinyl group; a dibenzofuran group; a dibenzothiophene group; dibenzosulfolane; spiro[fluorene-9,9'-xanthene]; a benzo[4,5]thieno[3,2-d]pyrimidyl group unsubstituted or substituted with an aryl group; a benzofuro[2,3-c]quinolinyl group; a benzofuro[3,2-c]quinolinyl group; a benzothieno[2,3-c]quinolinyl group; a benzothieno[3,2-c]quinolinyl group; or a pyrazolo[5,1-a]isoquinolinyl group unsubstituted or substituted with an aryl group, and R104' and R105' are each independently an aryl group, Z12 and Z13 are the same as or different from each other, and each independently a halogen group; a cyano group; a methyl group; a pyrimidine group unsubstituted or substituted with an aryl group; a triazine group unsubstituted or substituted with an aryl group; or a carbazole group, and R104 and R105 are each independently a phenyl group.

3. The organic light emitting device of claim 1, wherein Chemical Formula 1 is represented by any one of the following compounds:

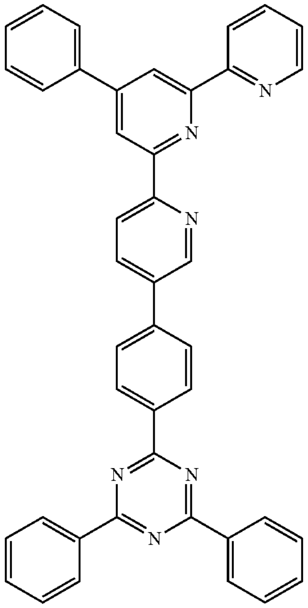

1

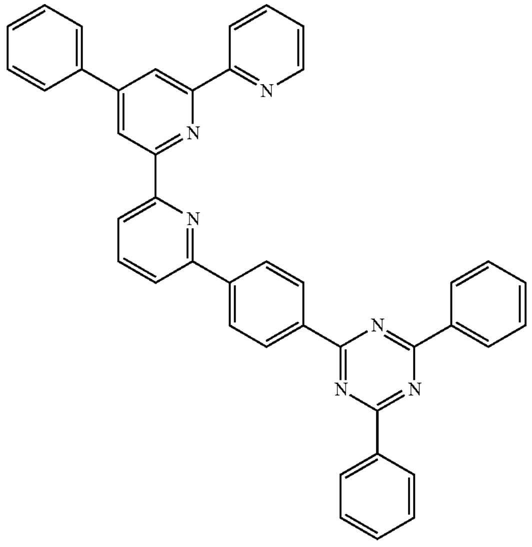

2

-continued
3
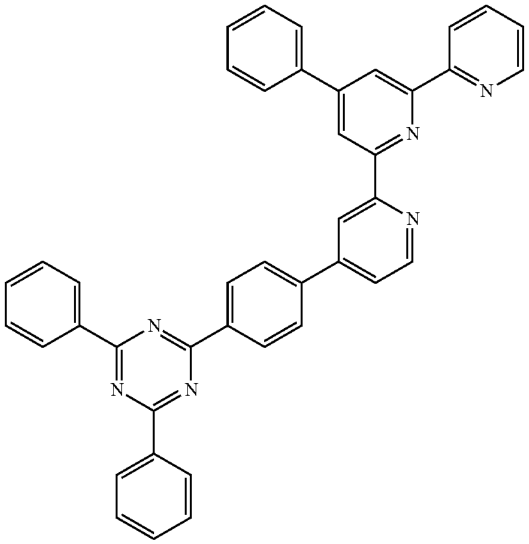
4
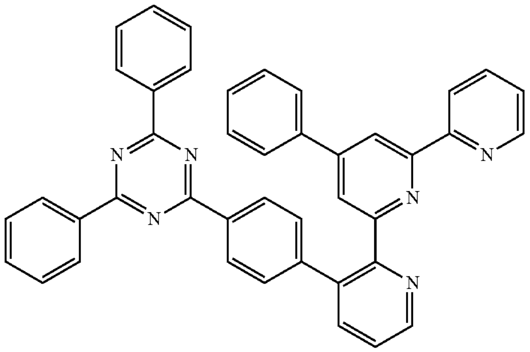
5
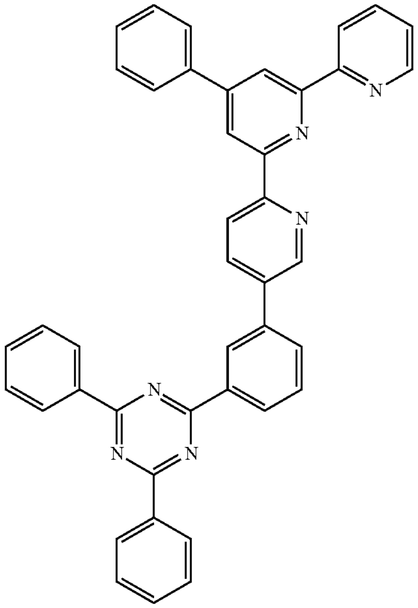
6
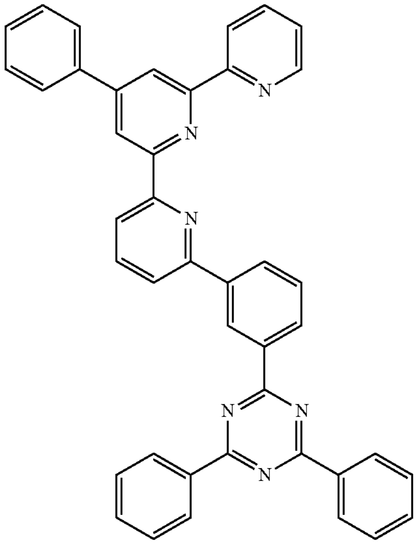
7
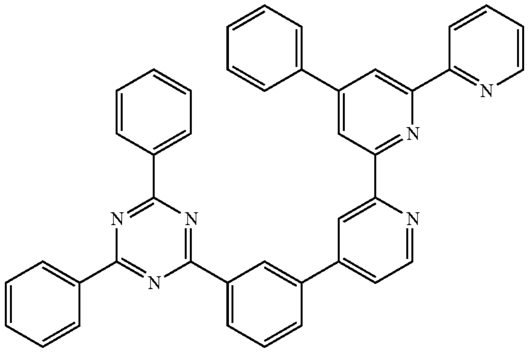
8
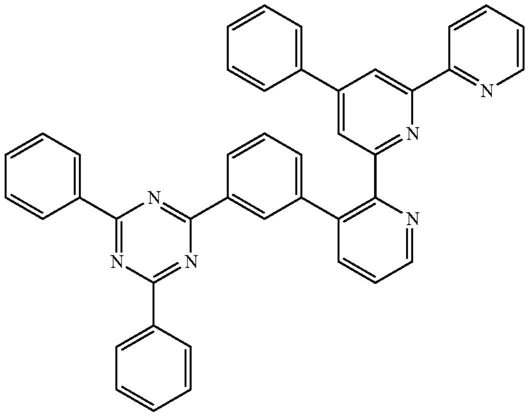

-continued
9
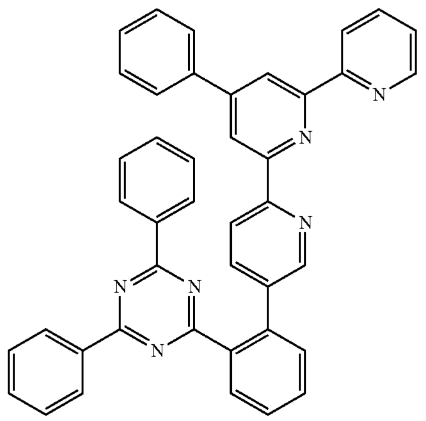
10
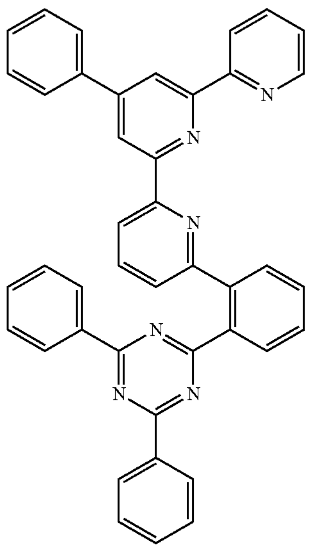
11
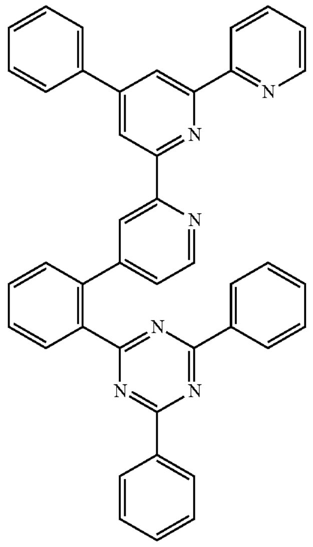
12
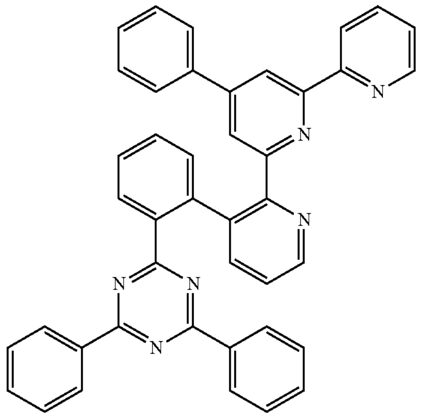

-continued
13
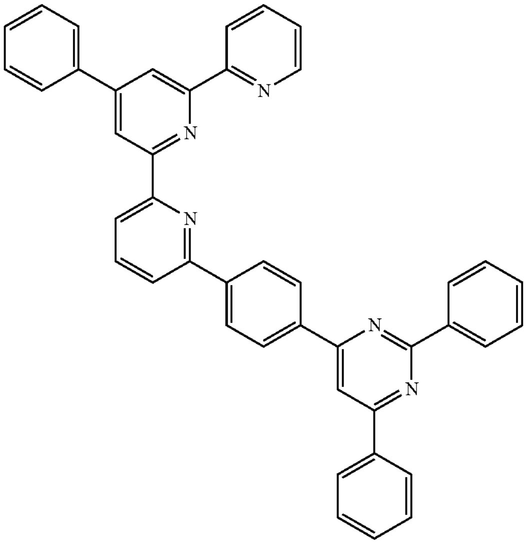
14
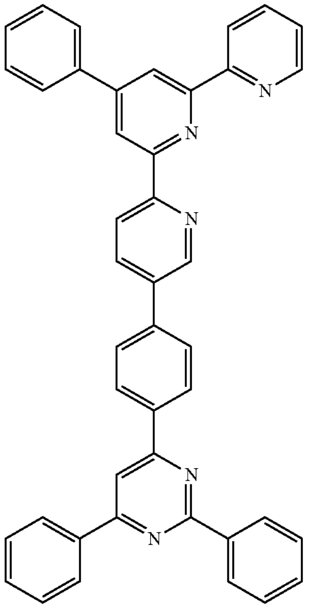
15
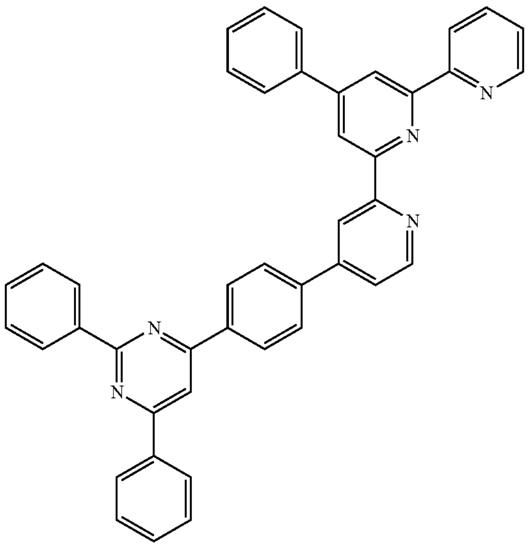
16
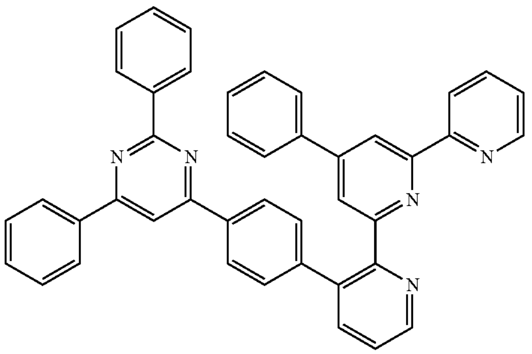

-continued
17
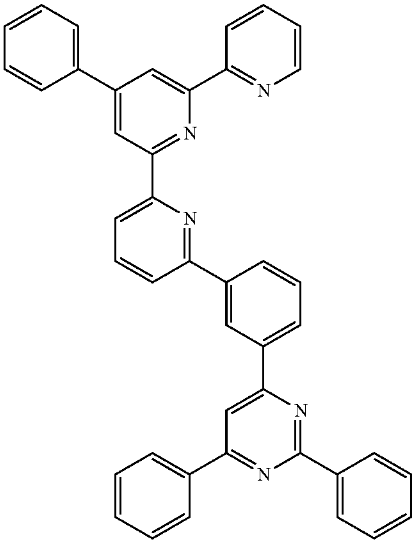
18
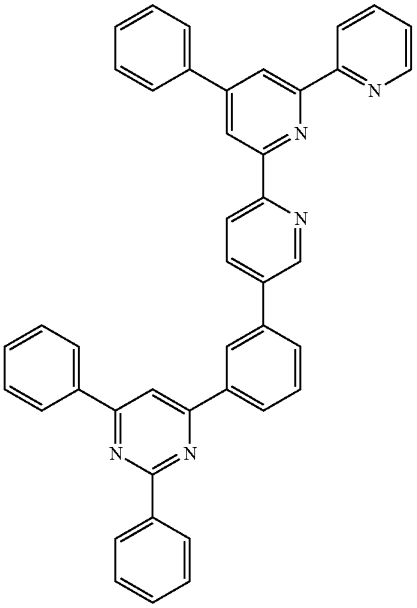
19
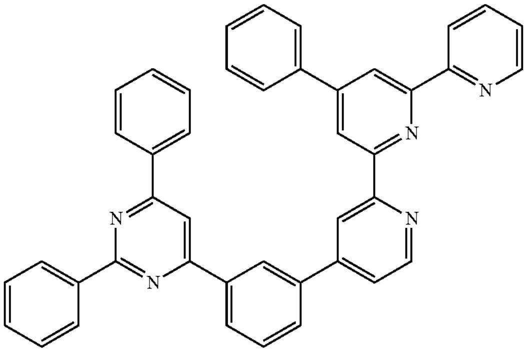
20
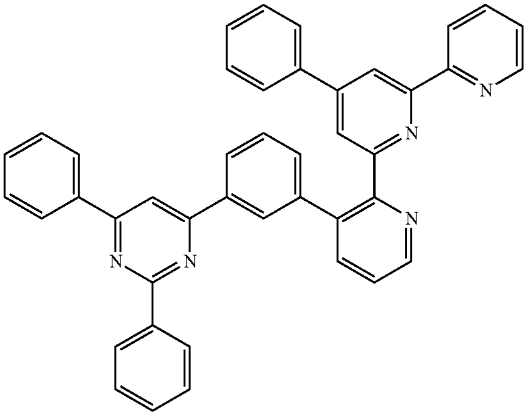
21
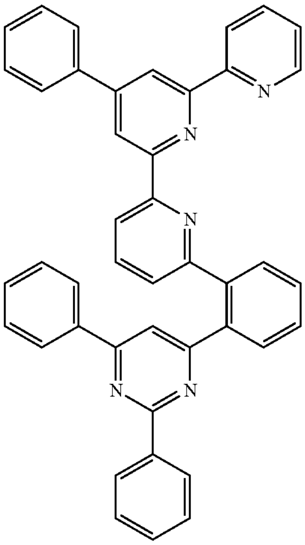
22
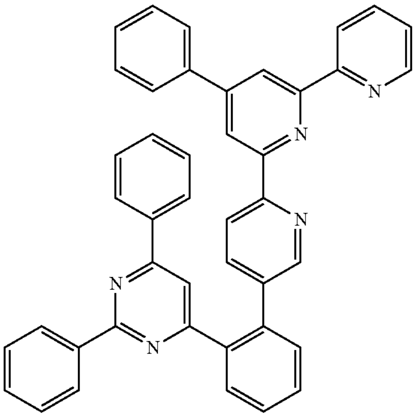

-continued
23
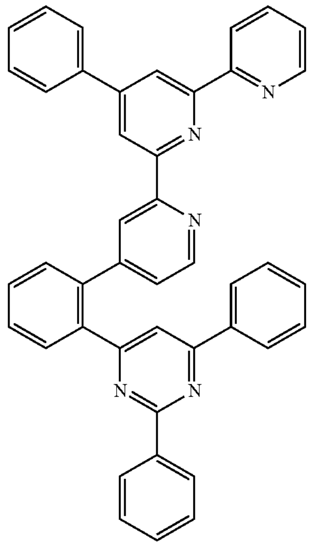
24
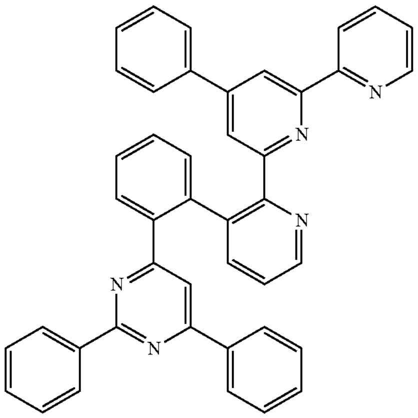
25
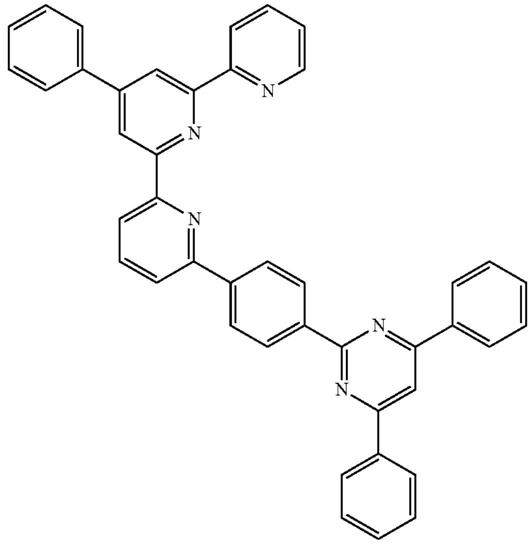
26
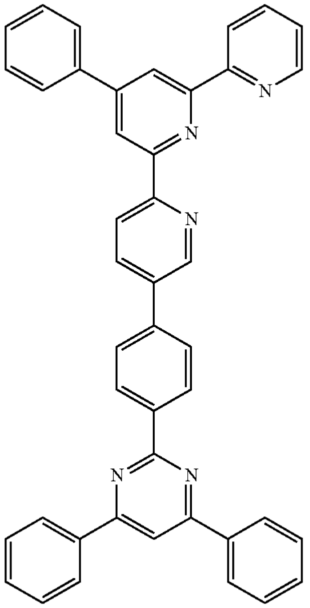

-continued
27
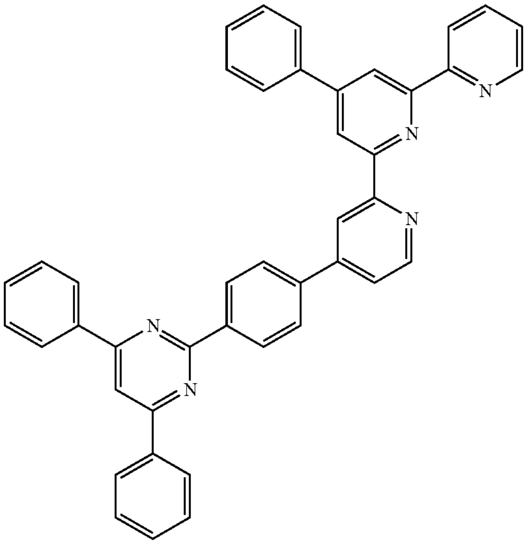
28
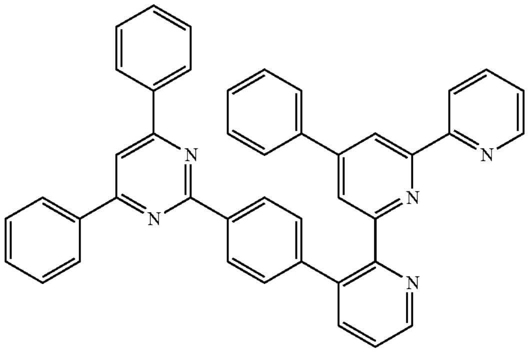
29
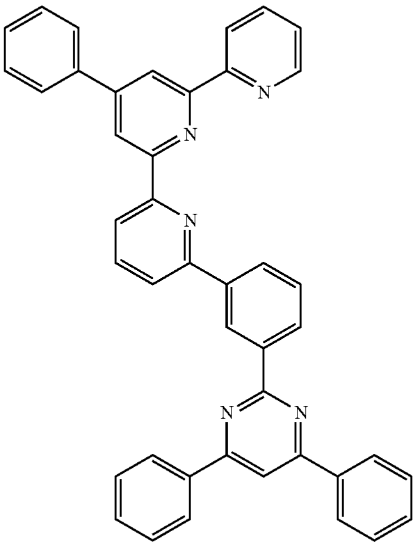
30
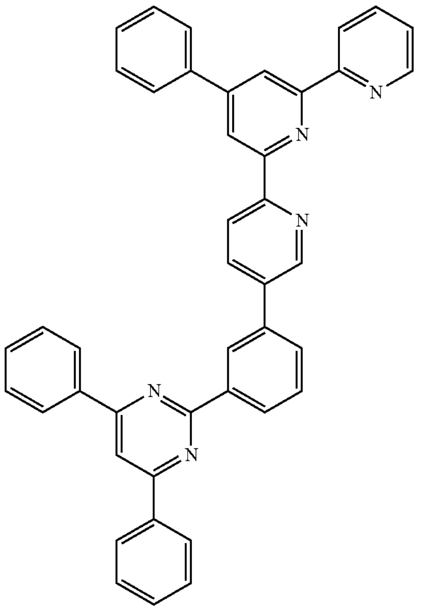
31
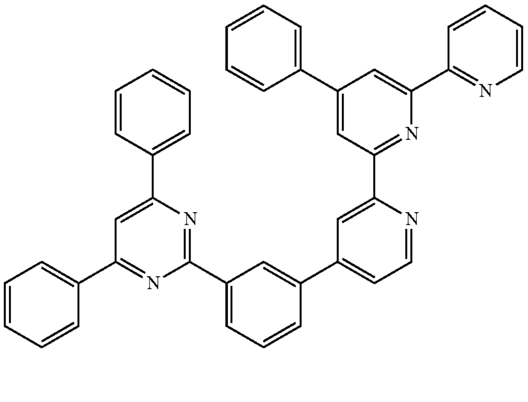
32
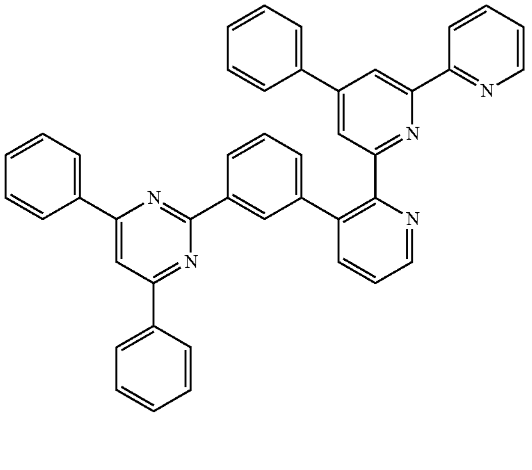

-continued
33
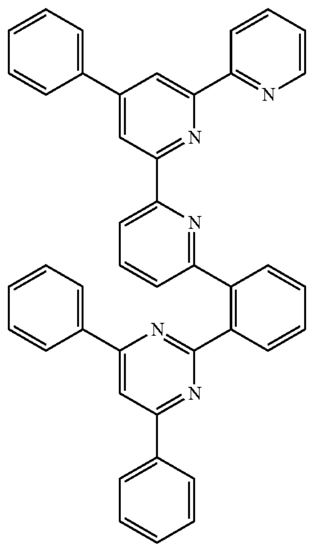
34
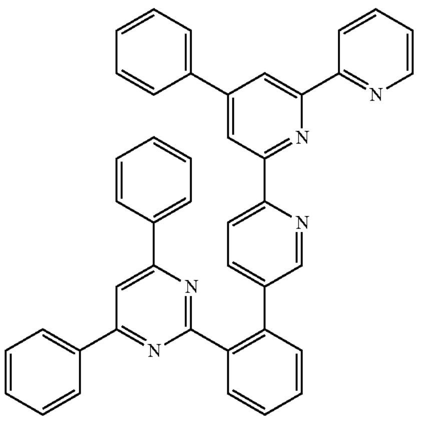
35
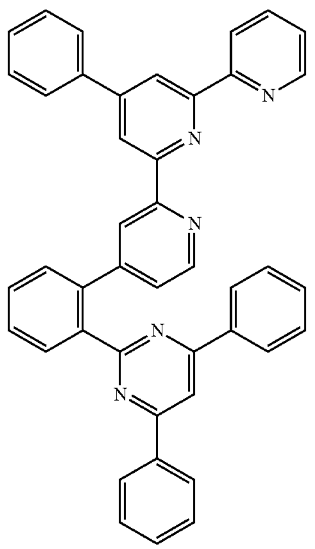
36
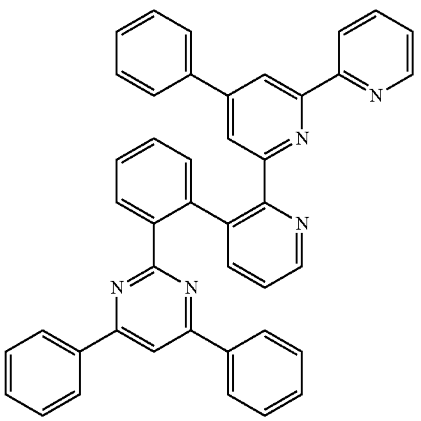

-continued
37
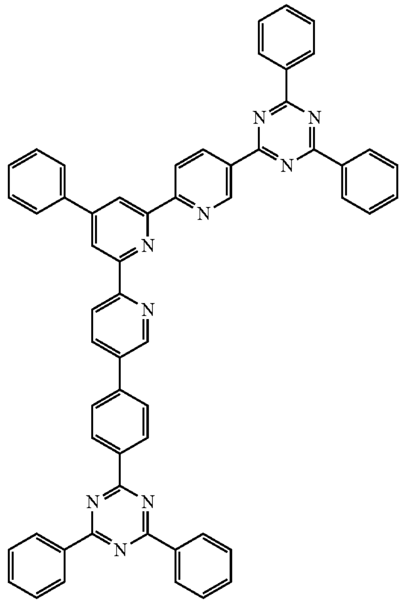
38
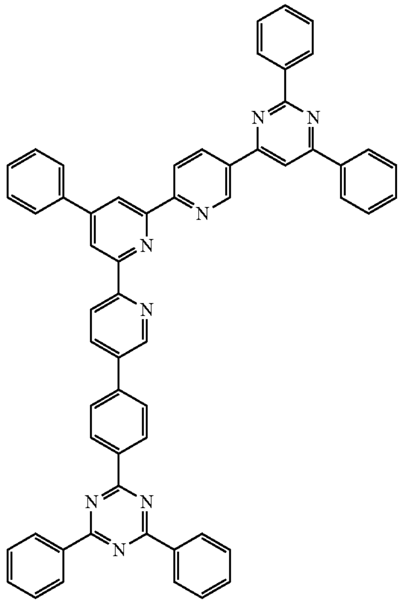
39
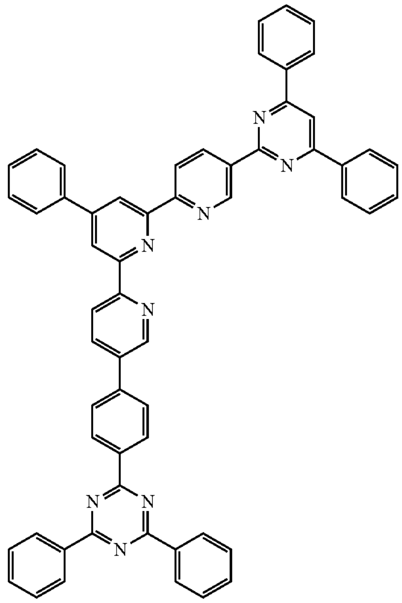
40
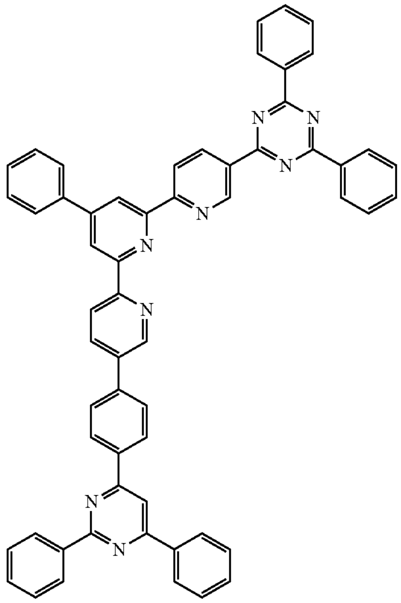

-continued
41
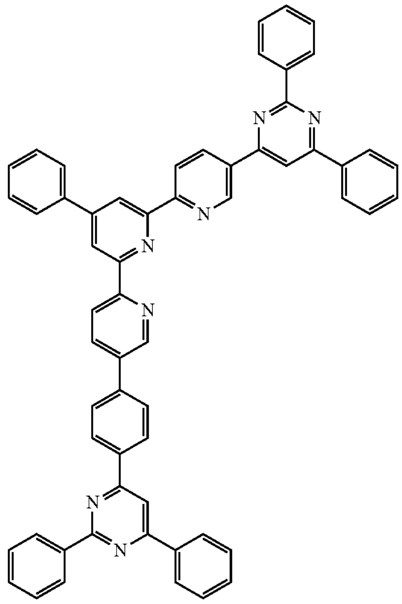
42
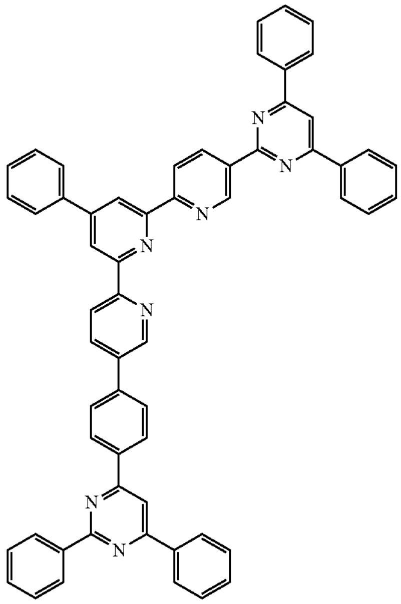
43
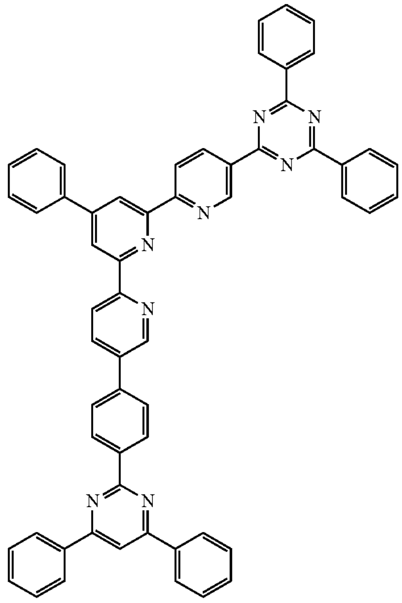
44
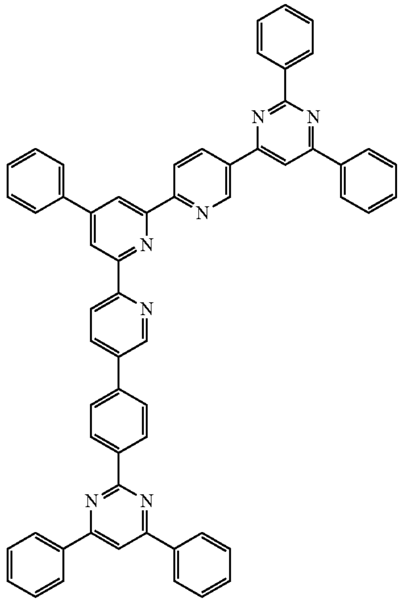

-continued
45
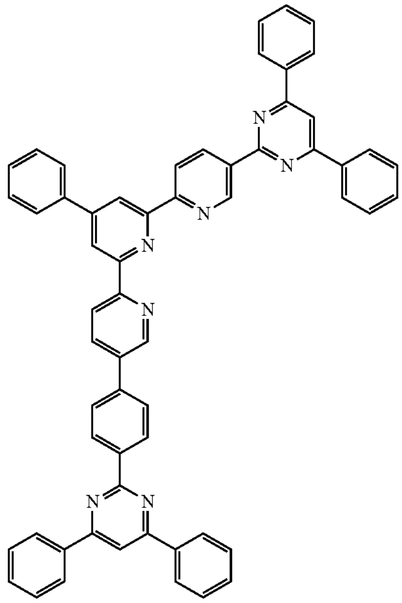
46
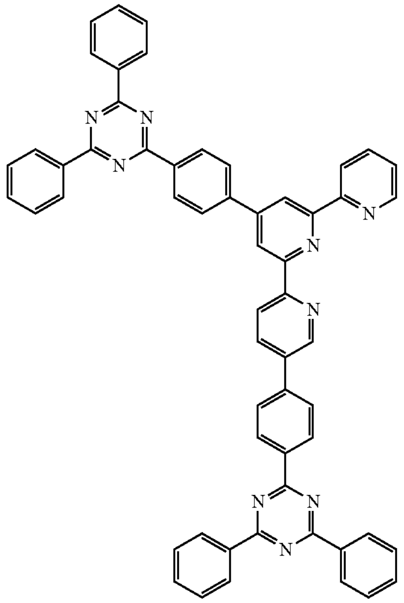
47
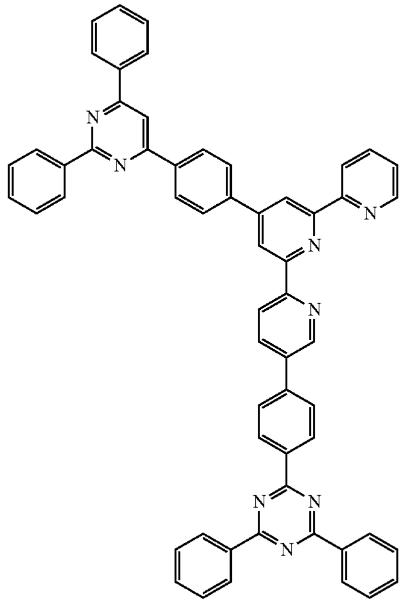
48
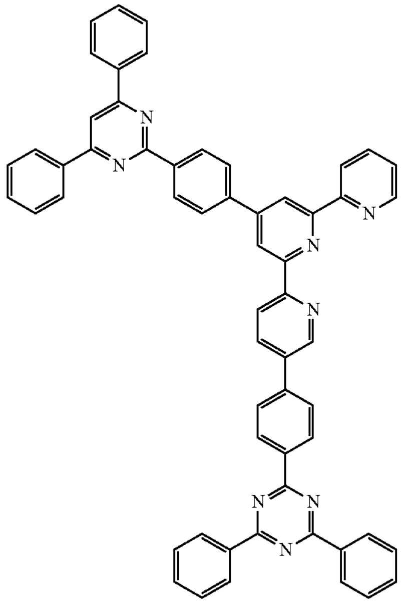

-continued
49
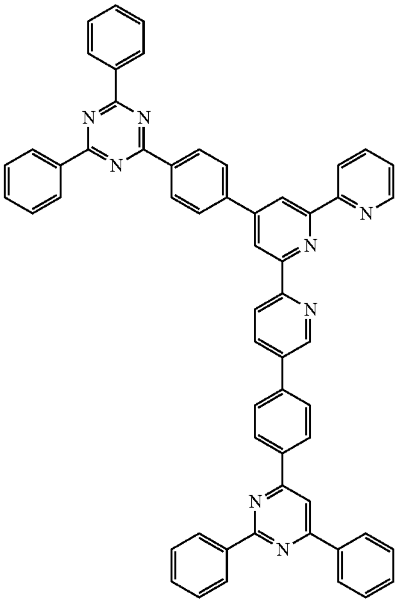
50
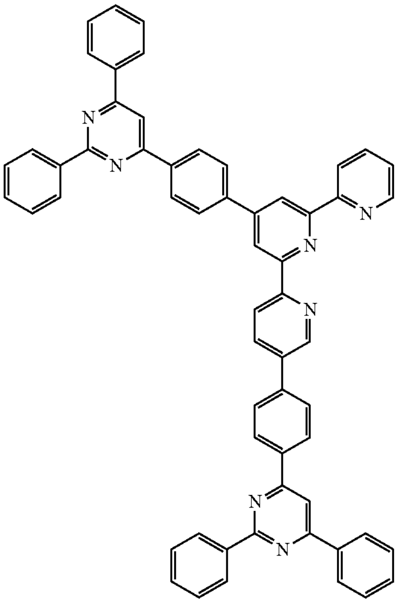
51
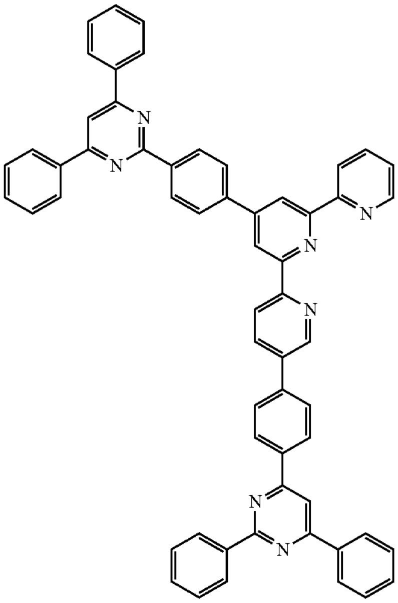
52
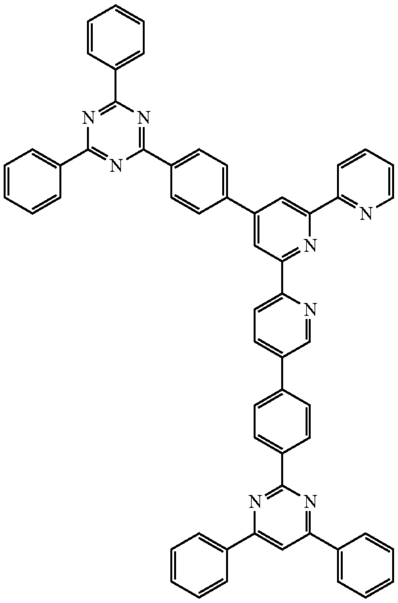

-continued
53
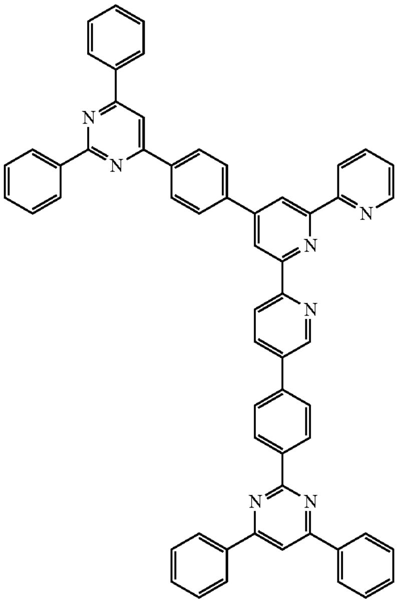
54
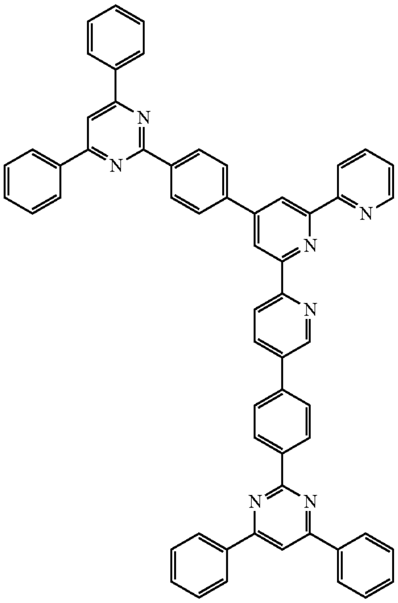
55
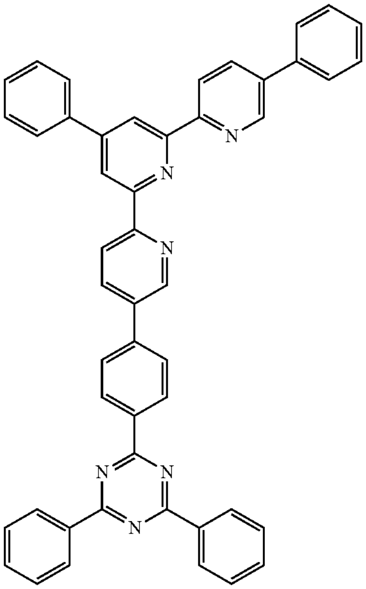
56
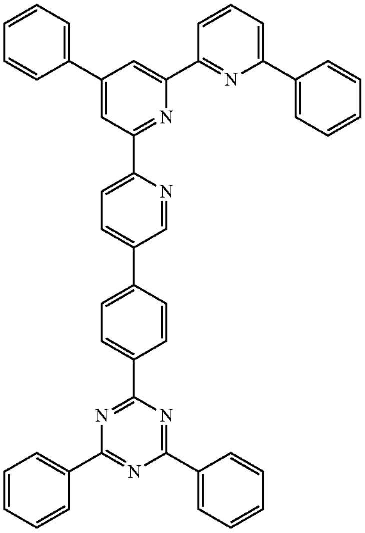

-continued
57
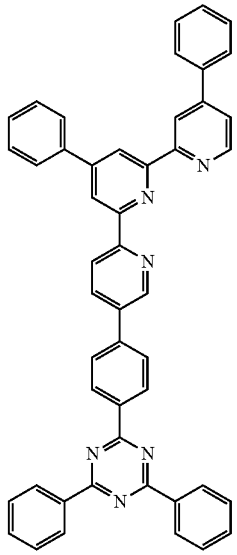
58
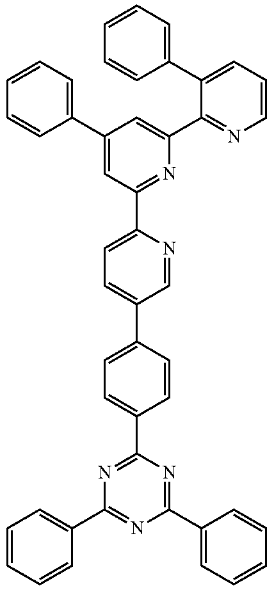
59
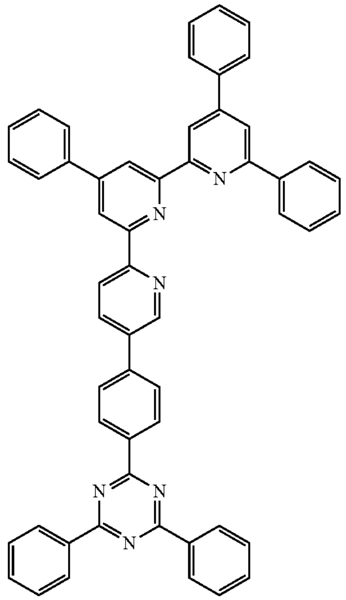
60
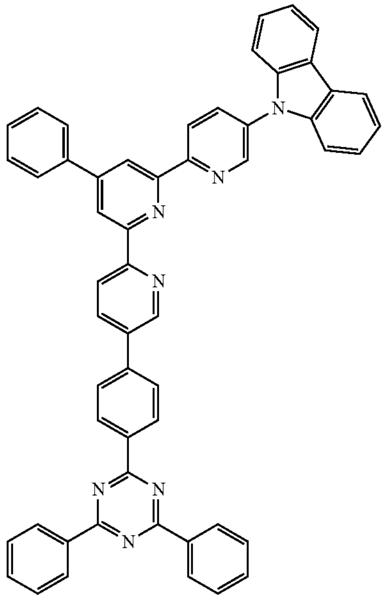

-continued
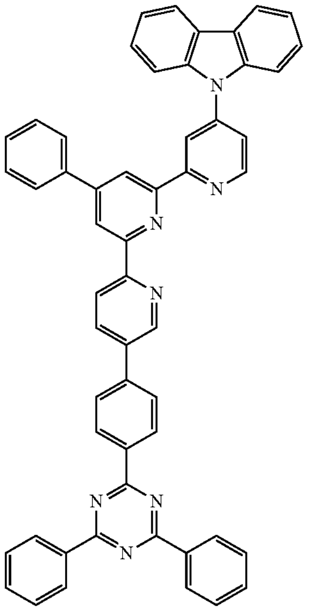
61
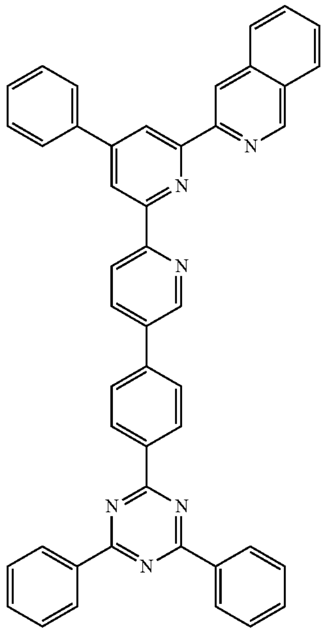
62
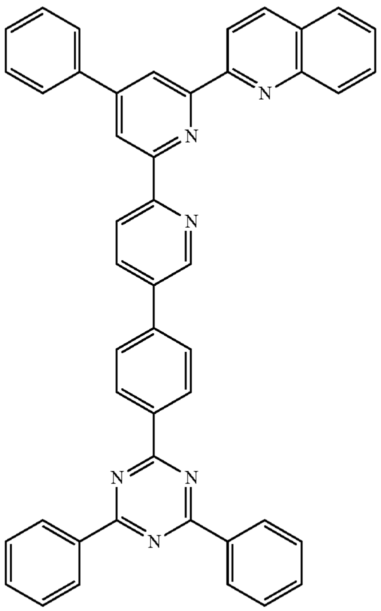
63
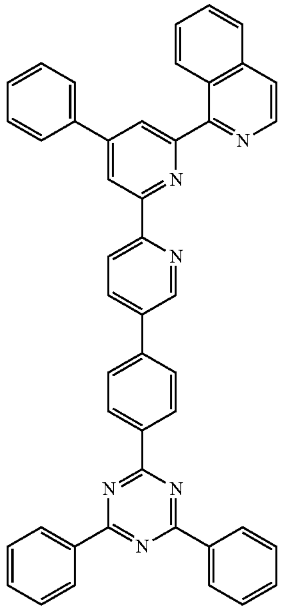
64

-continued
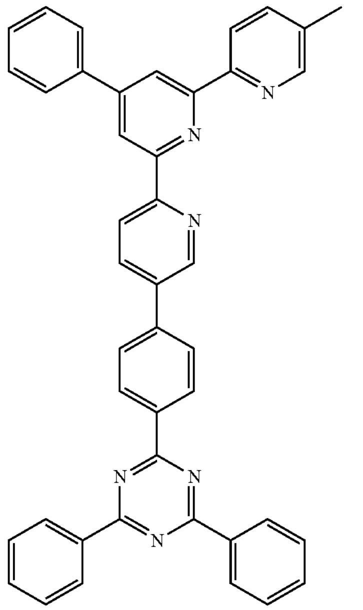
65
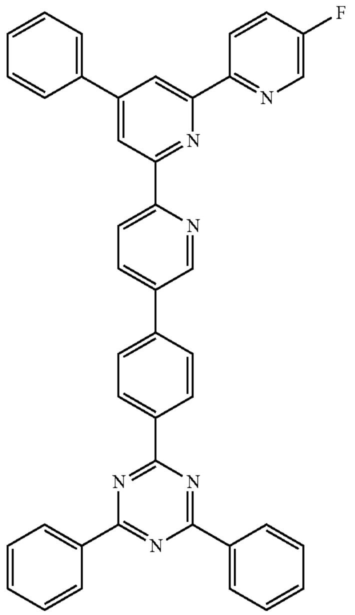
66
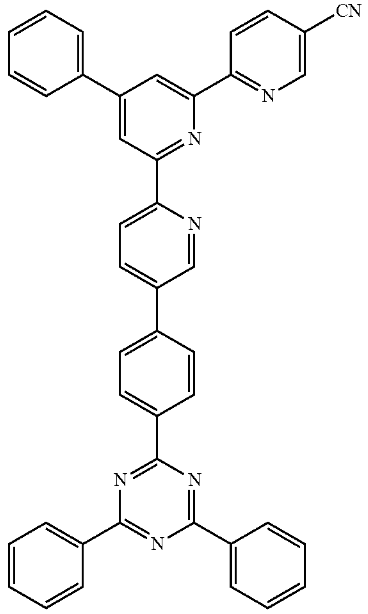
67
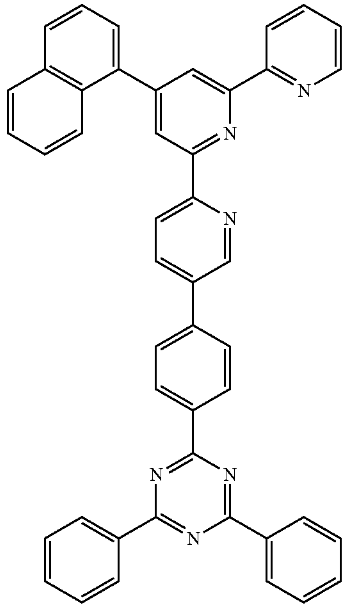
68

-continued
69
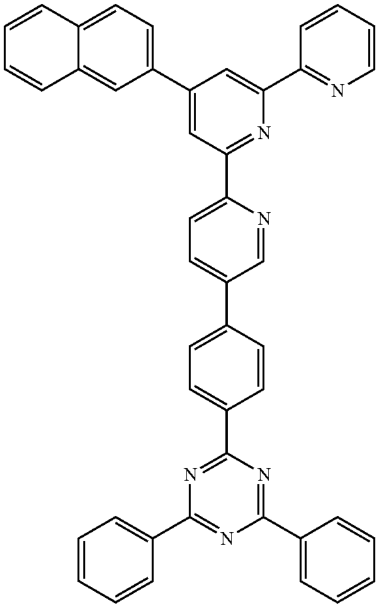
70
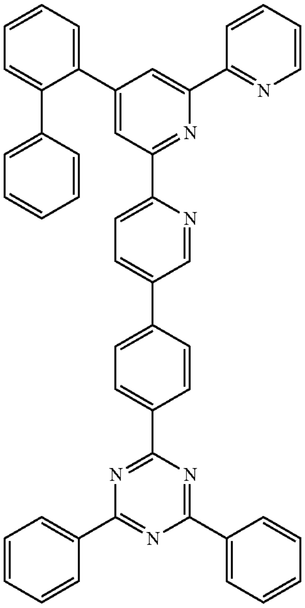
71
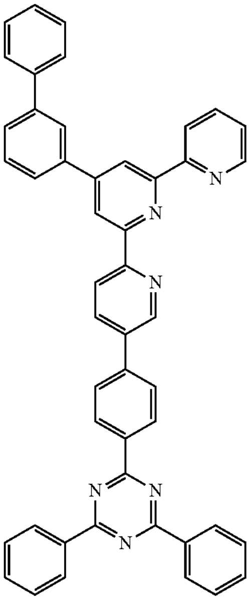
72
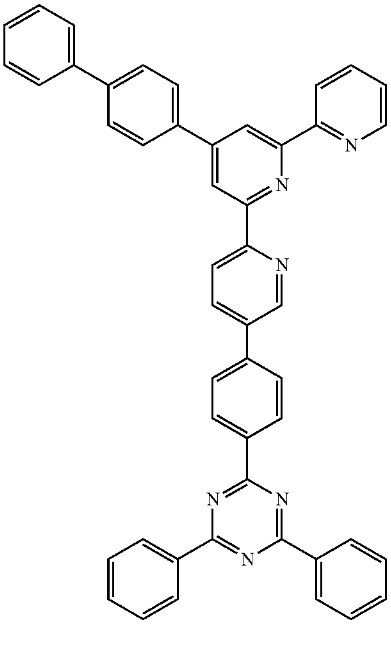

-continued
73
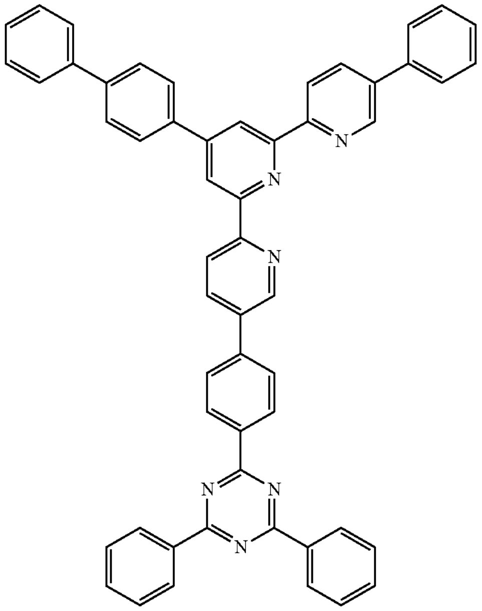
74
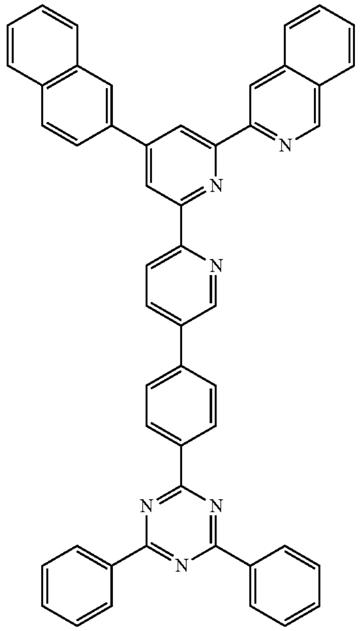
75
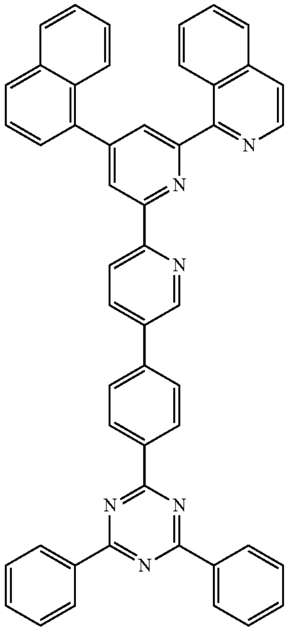
76
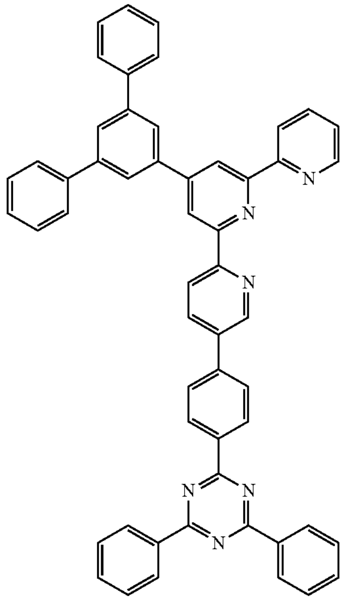

-continued
77
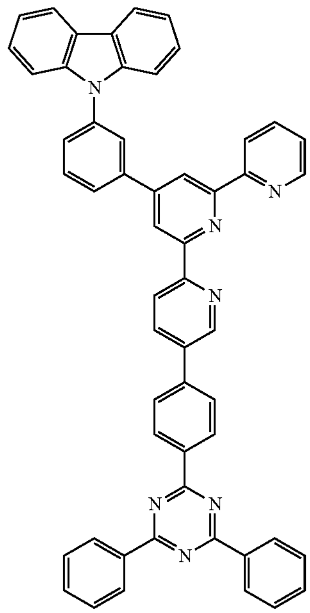
78
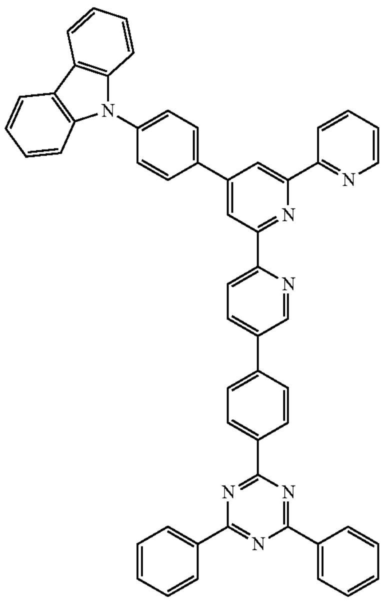
79
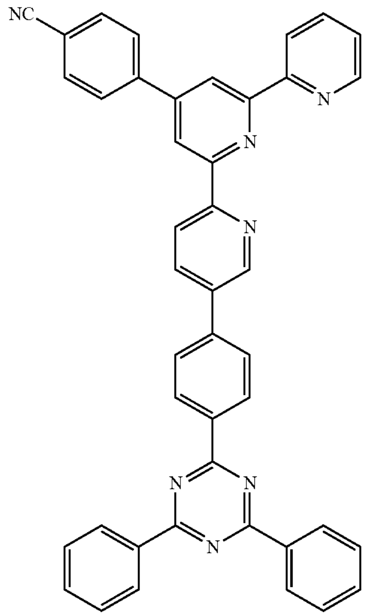
80
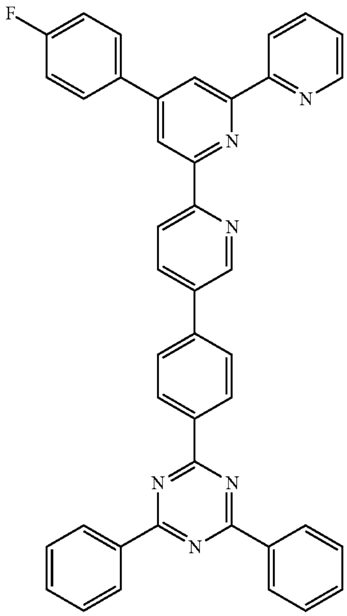

-continued
81
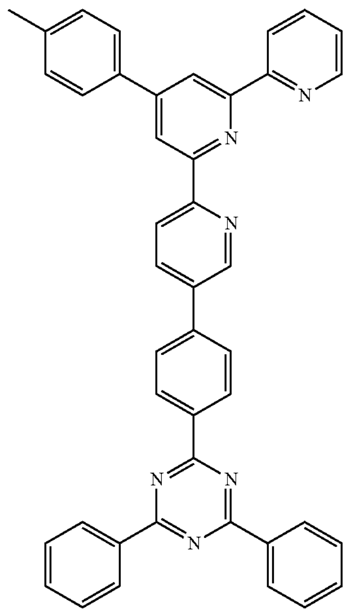
82
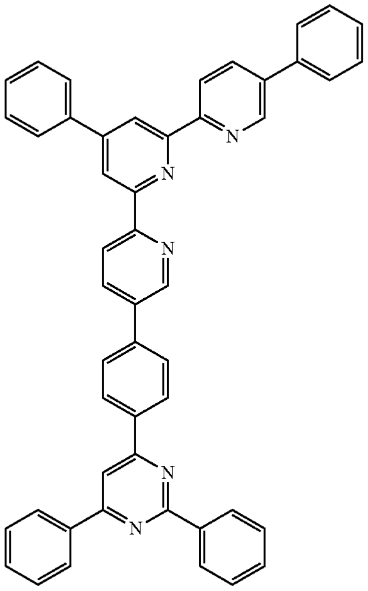
83
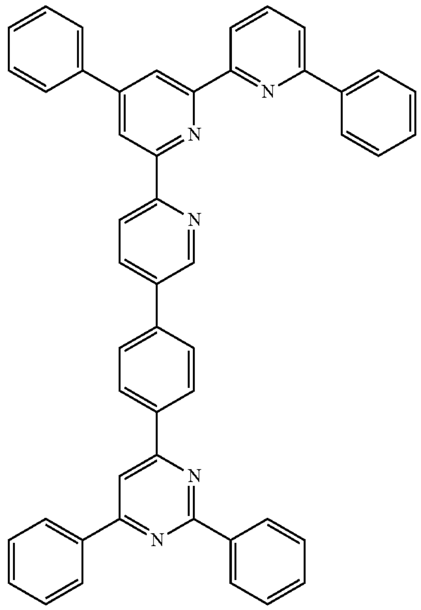
84
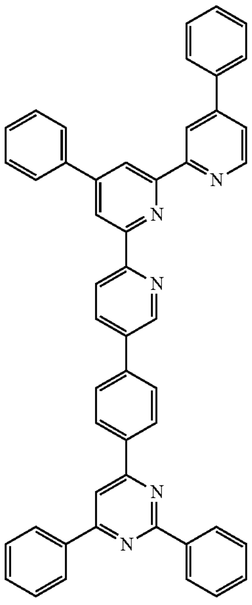

-continued
85
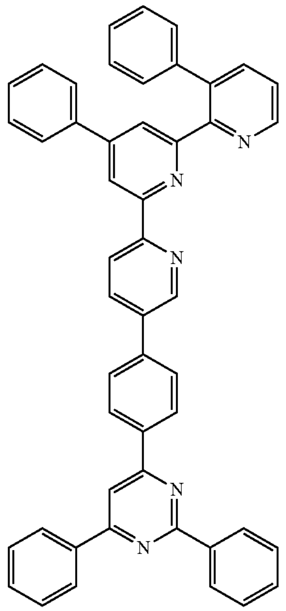
86
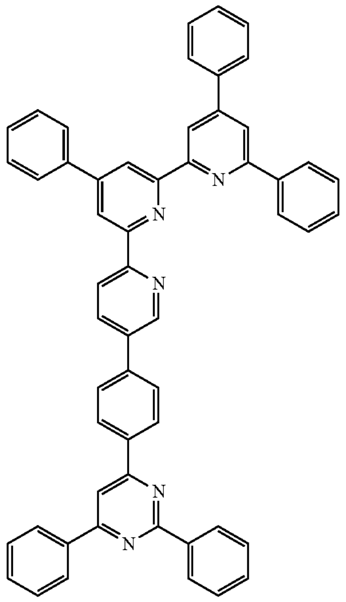
87
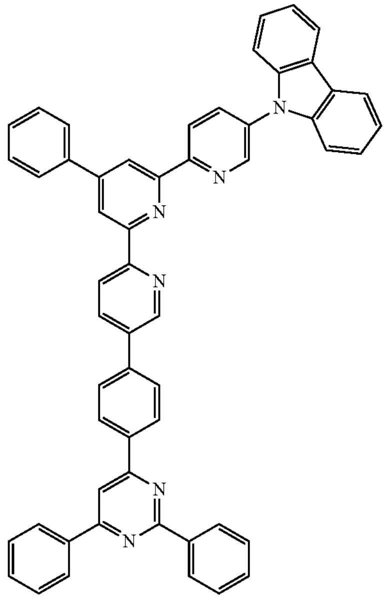
88
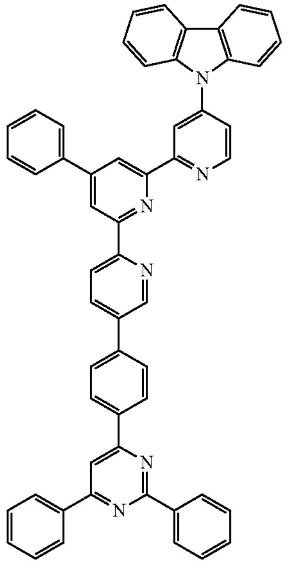

-continued
89
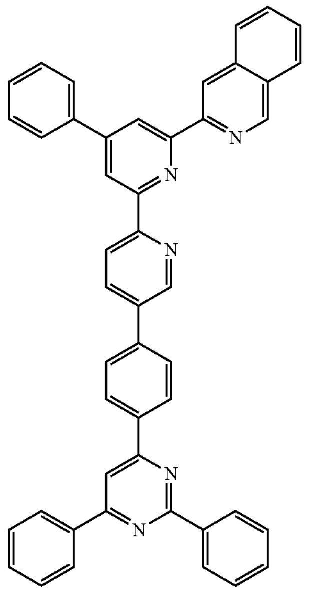
90
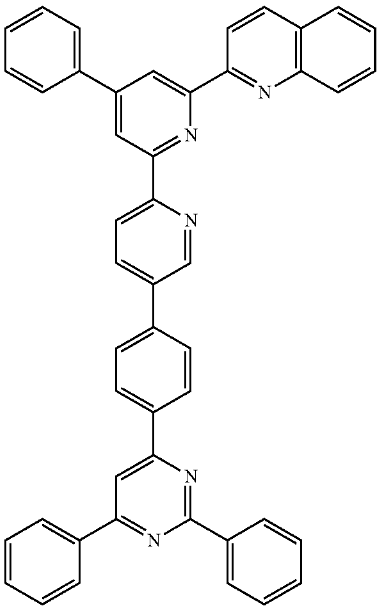
91
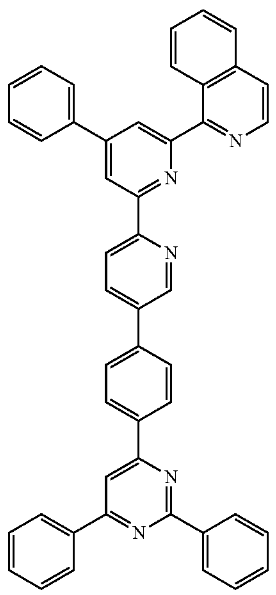
92
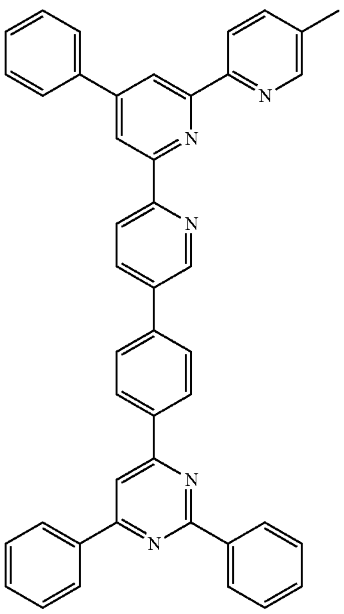

-continued
93
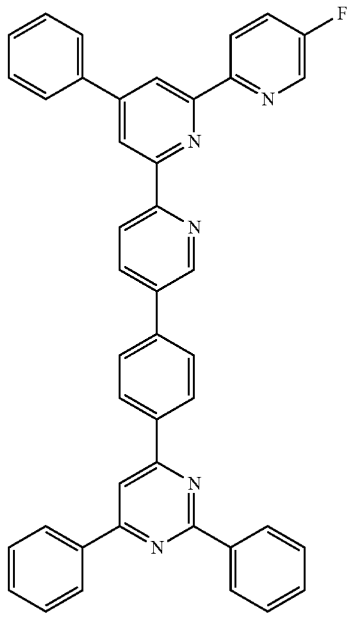
94
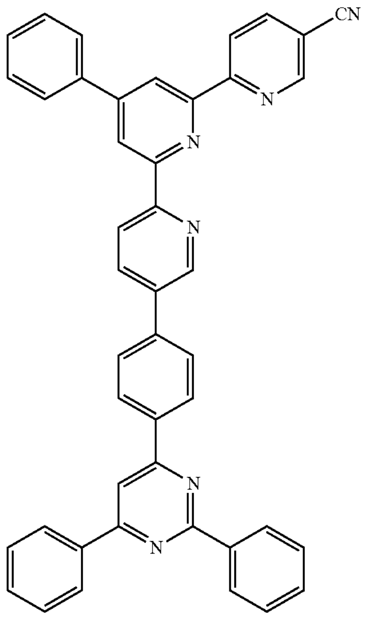
95
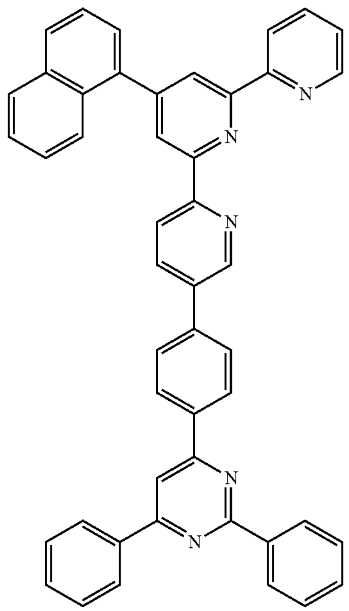
96
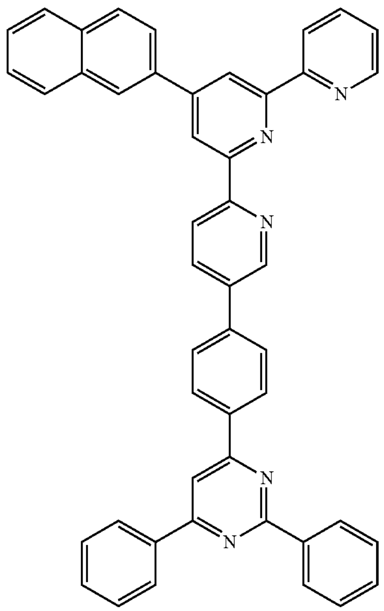

-continued
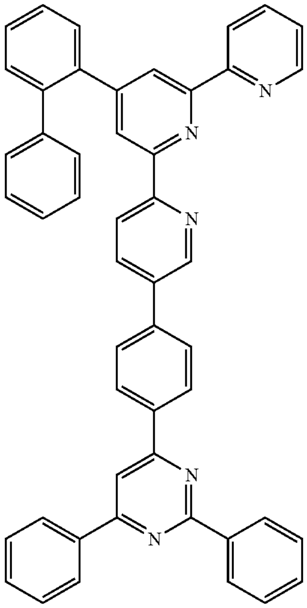
97
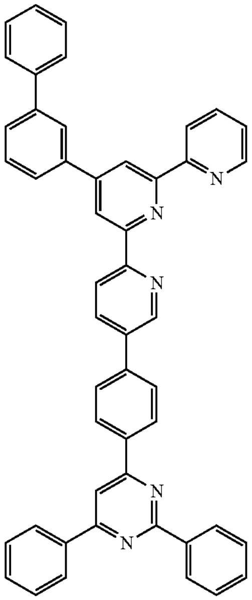
98
99
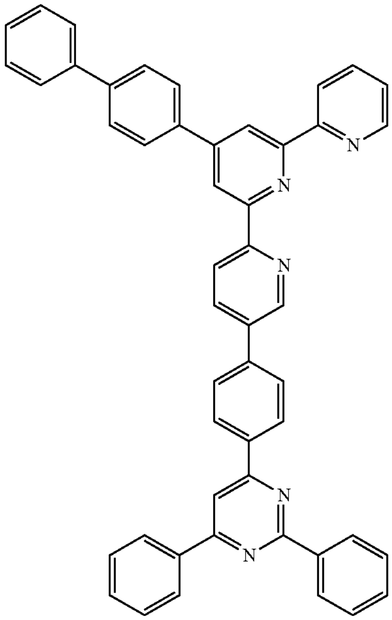
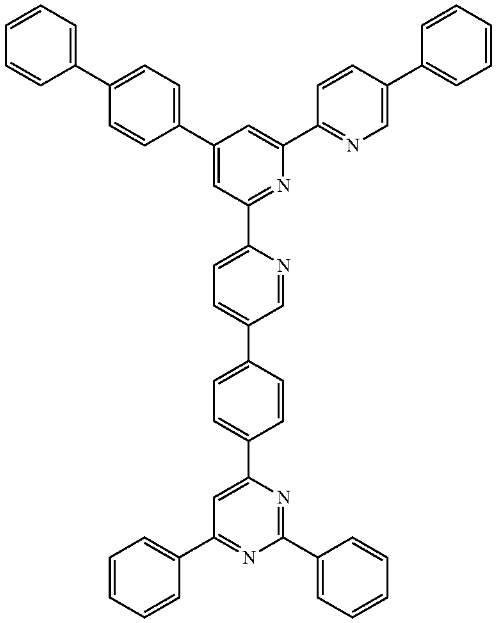
100

-continued
101
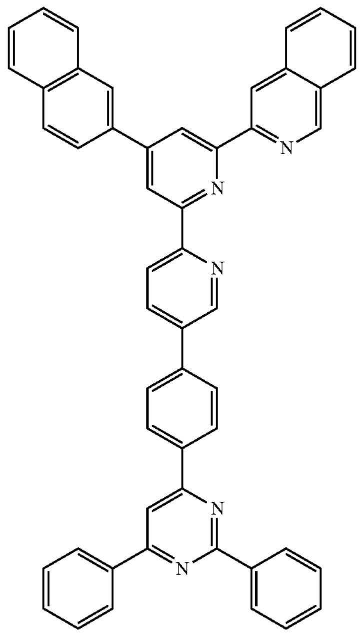
102
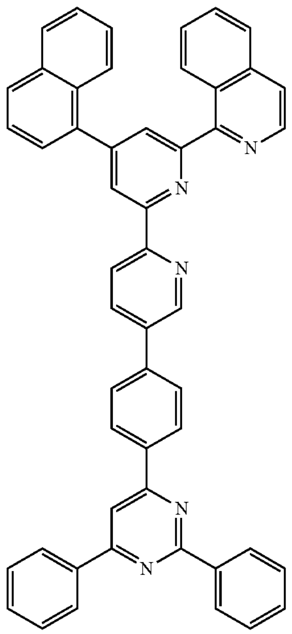
103
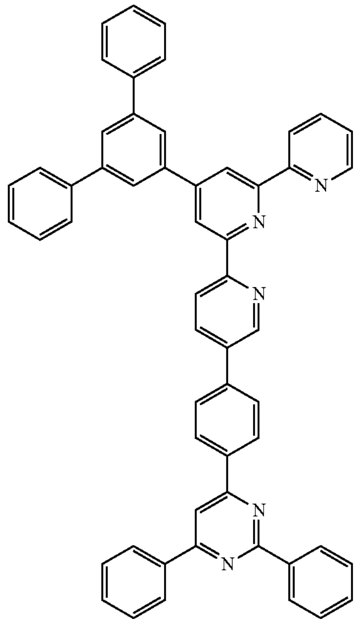
104
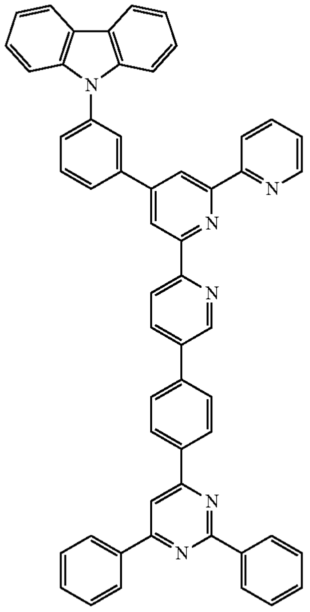

-continued
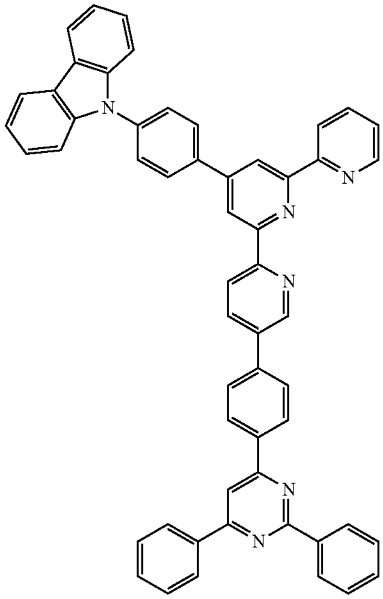
105
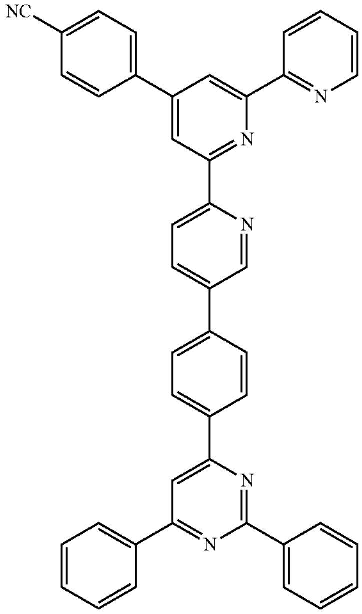
106
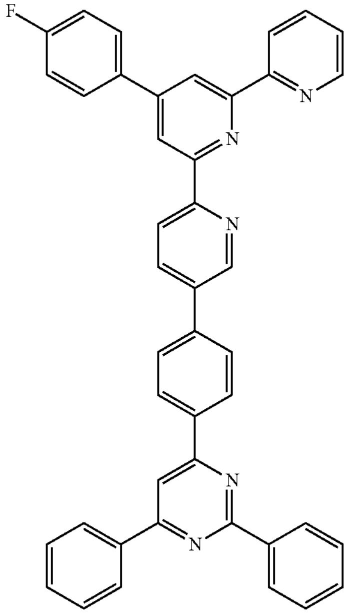
107
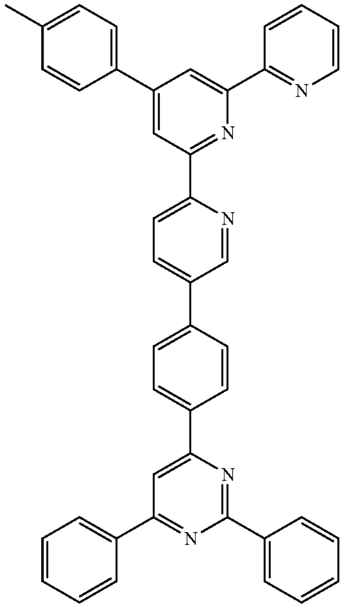
108

-continued
109
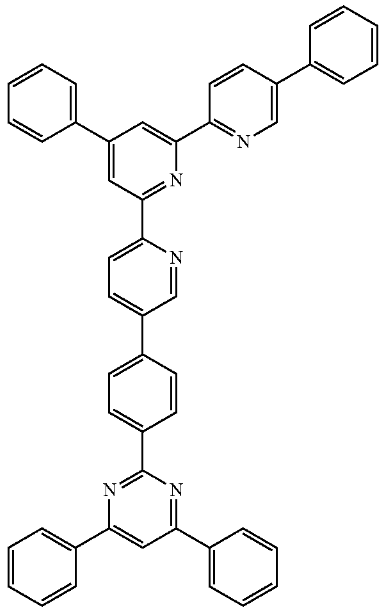
110
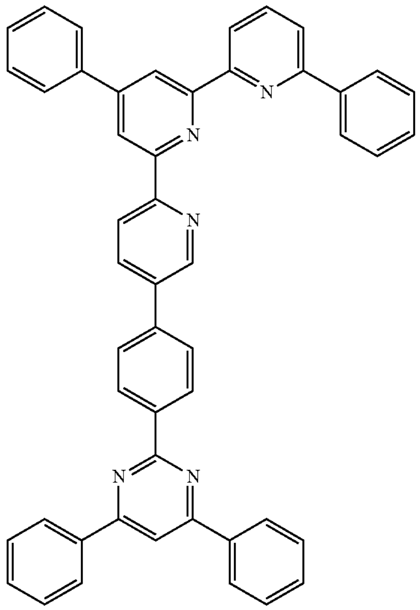
111
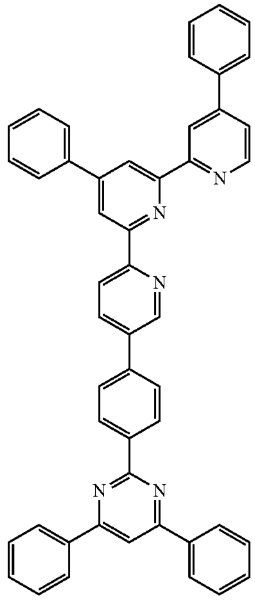
112
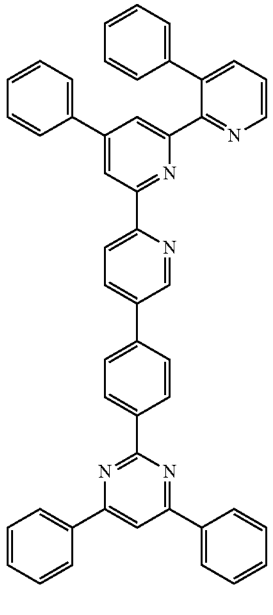

-continued
113
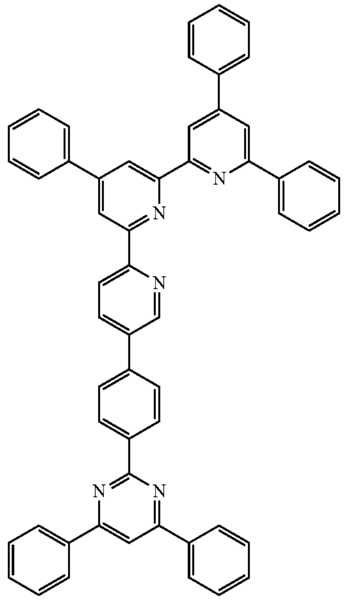
114
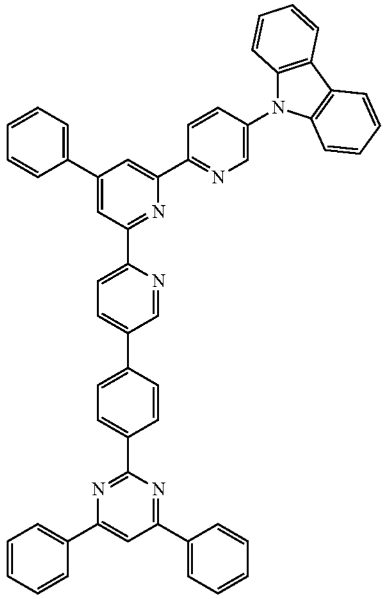
115
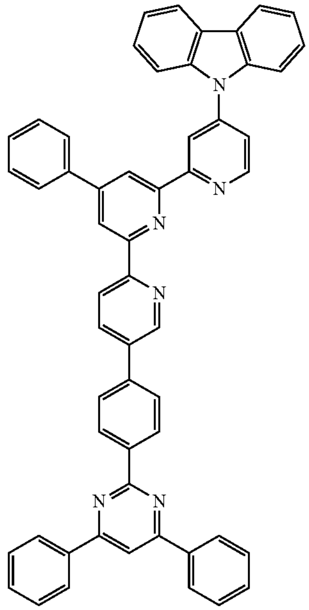
116
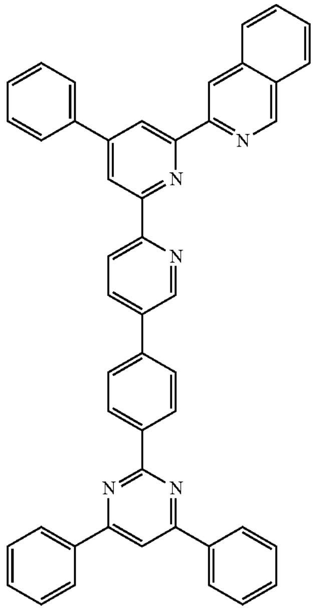

-continued
117
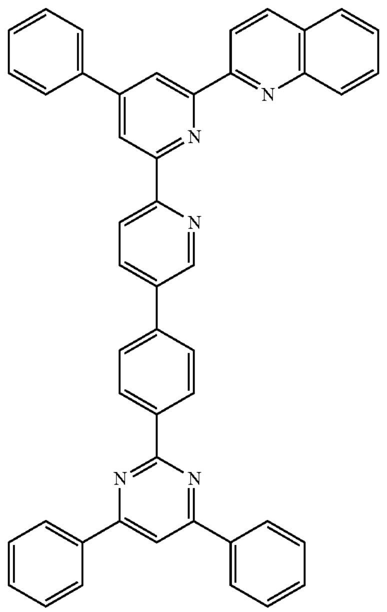
118
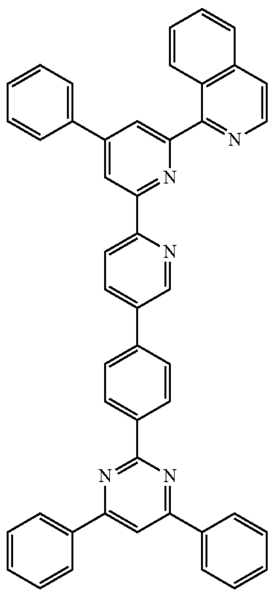
119
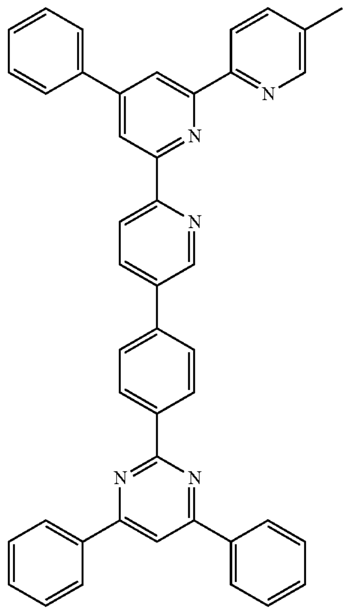
120
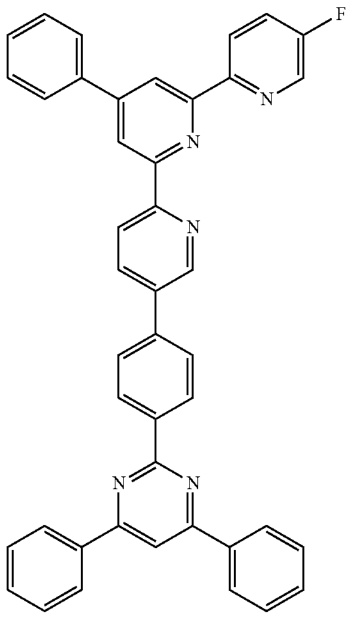

-continued
121
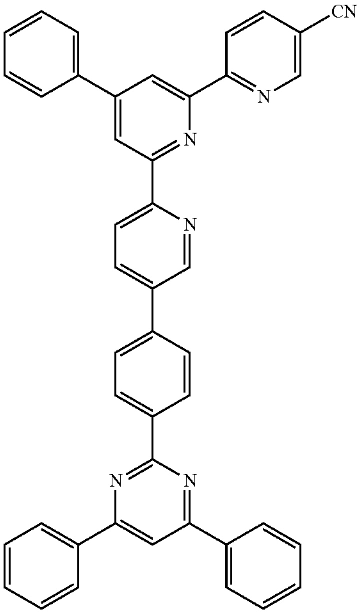
122
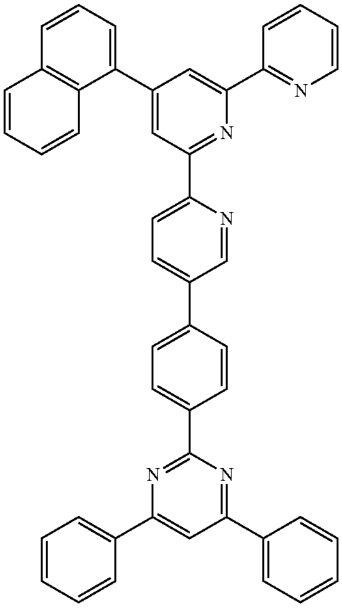
123
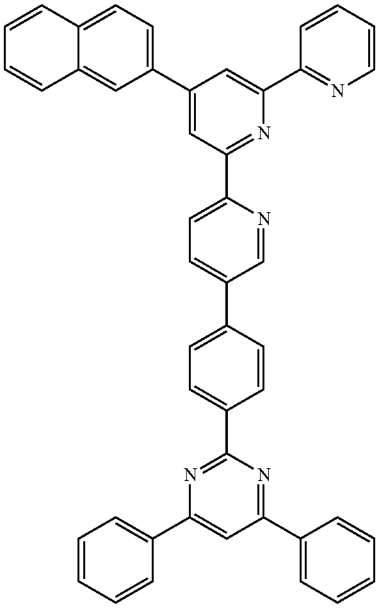
124
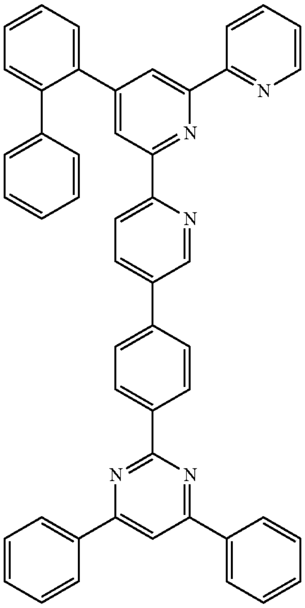

-continued
125
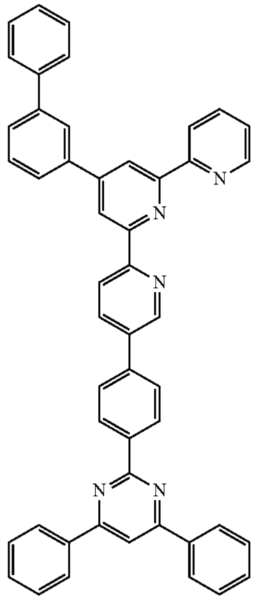
126
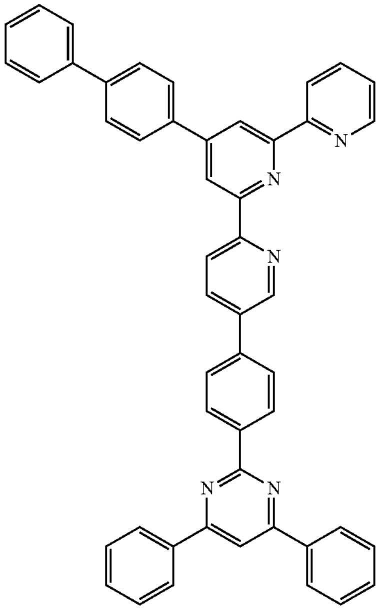
127
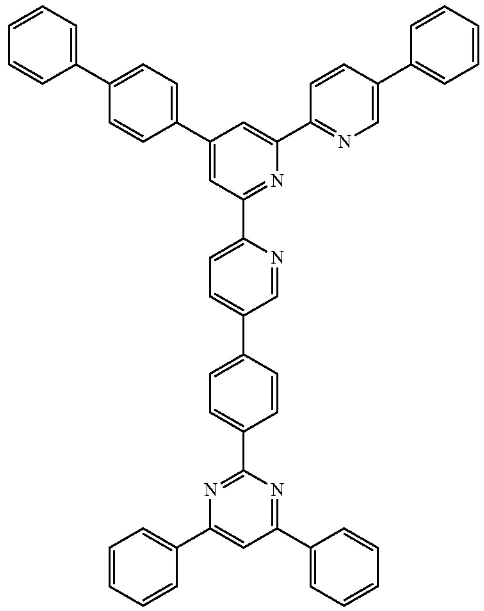
128
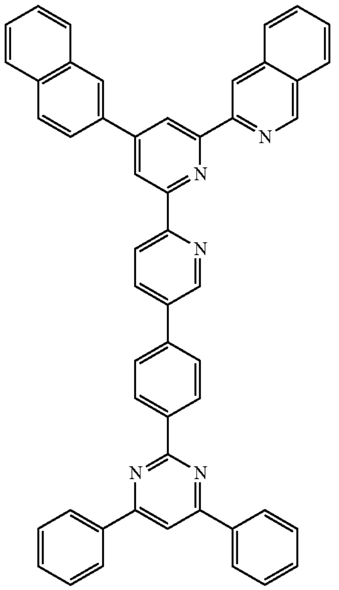

-continued
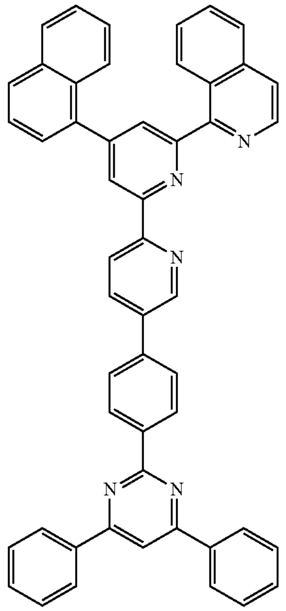
129
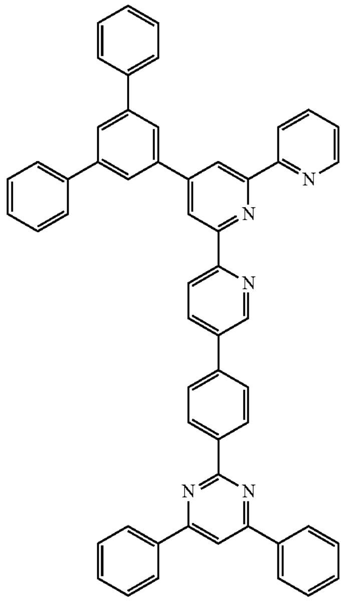
130
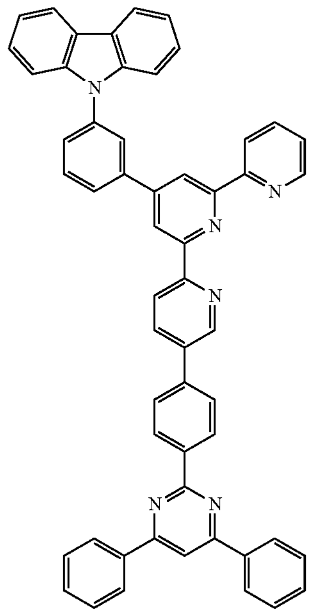
131
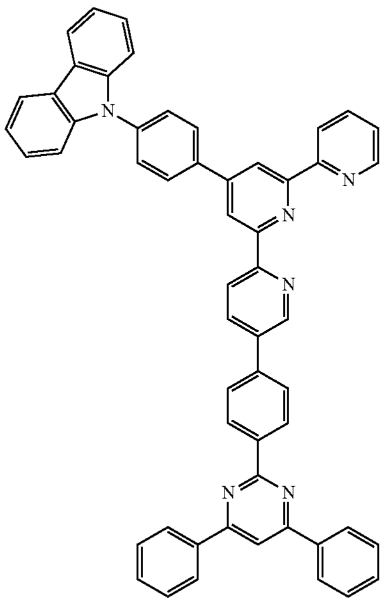
132

-continued
133
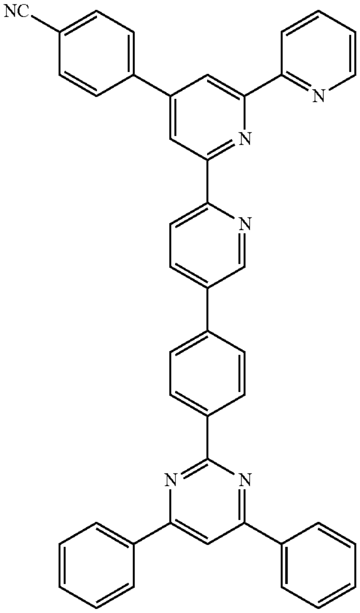
134
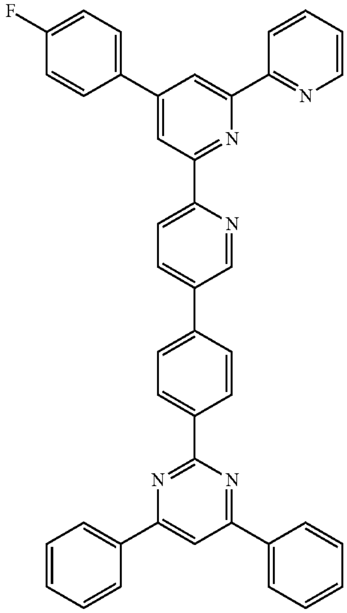
135
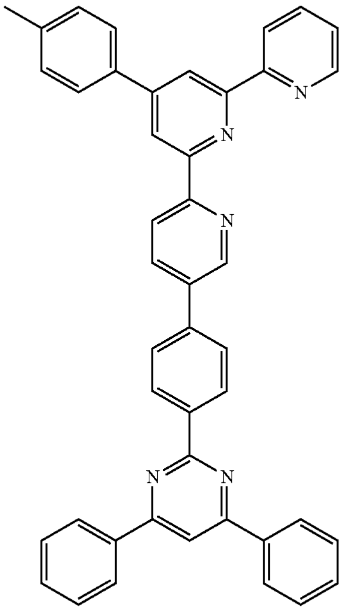
136
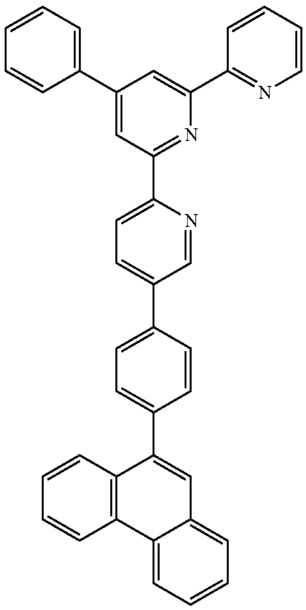

-continued
137
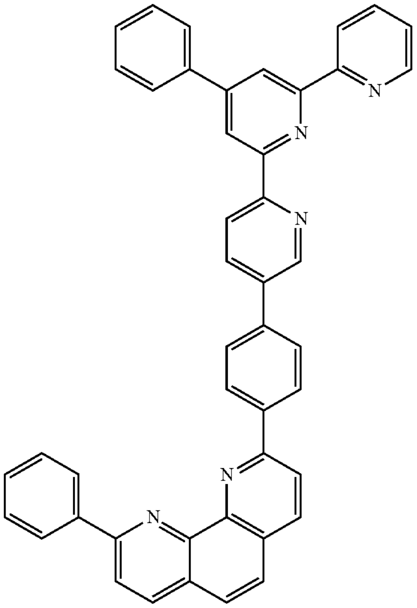
138
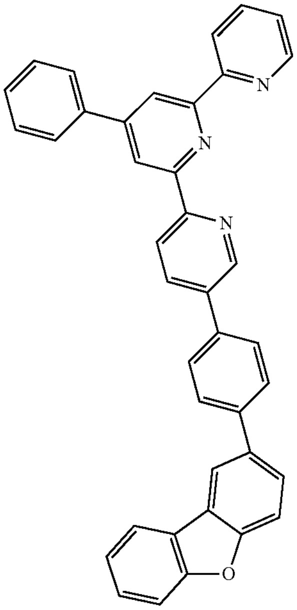
139
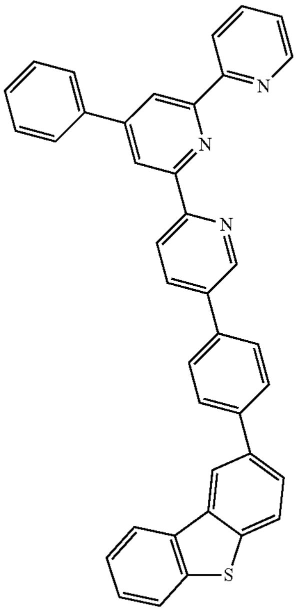
140
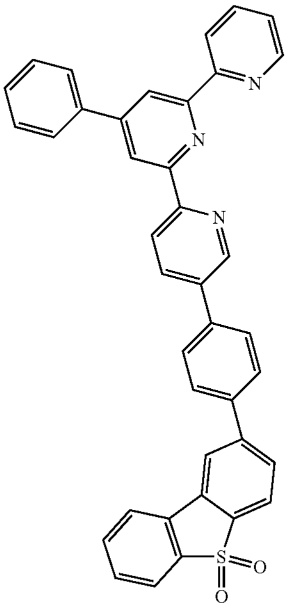

-continued
141
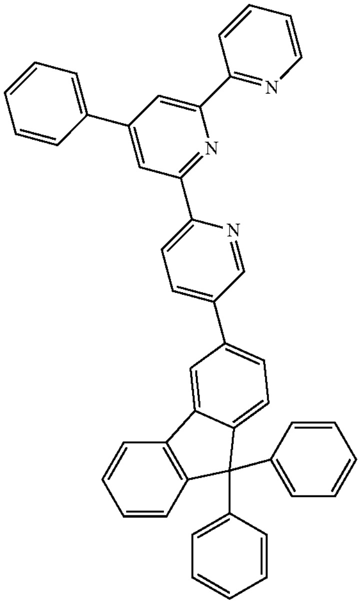
142
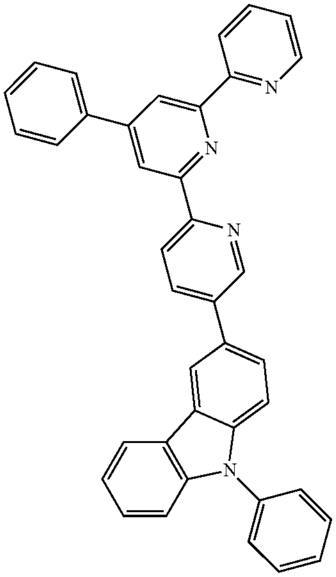
143
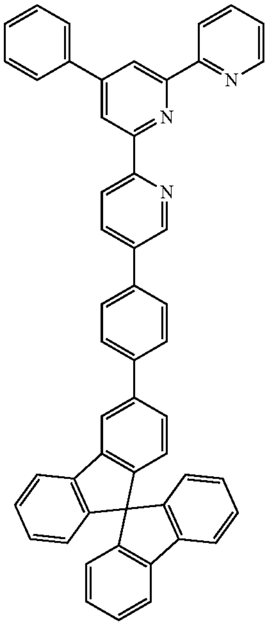
144
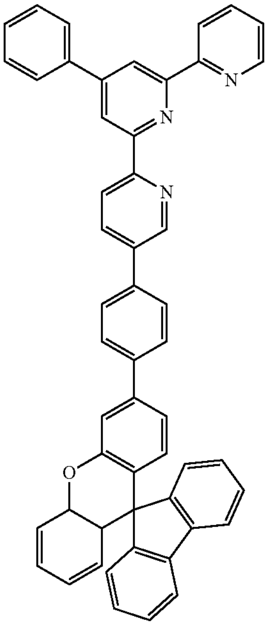

-continued
145
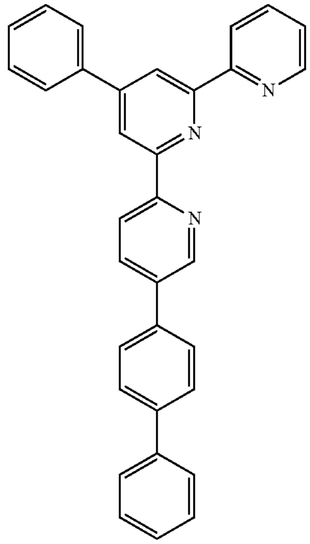
146
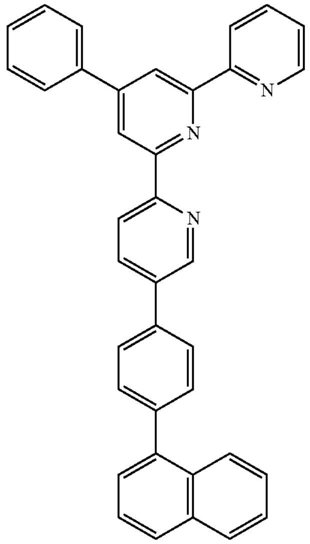
147
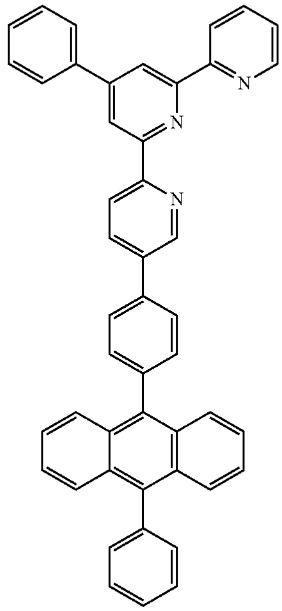
148
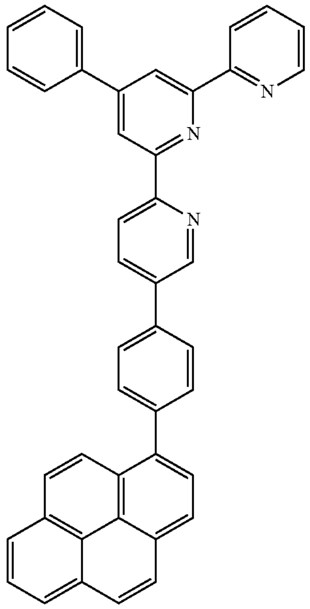

-continued
150
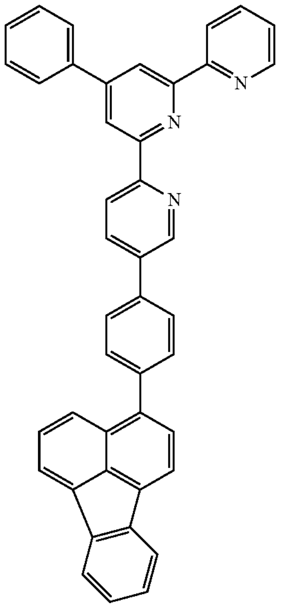
151
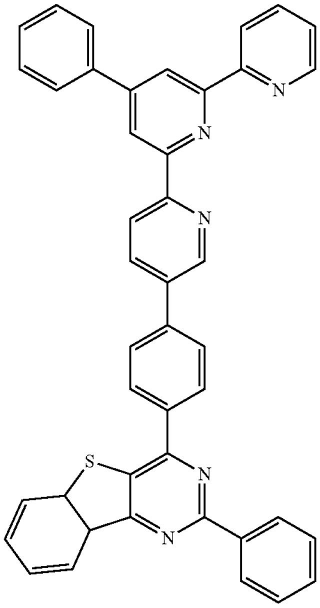
152
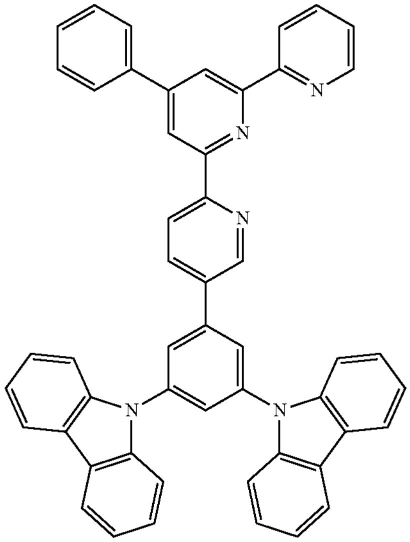

-continued
153
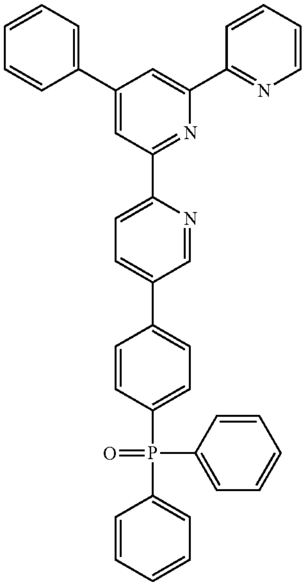
154
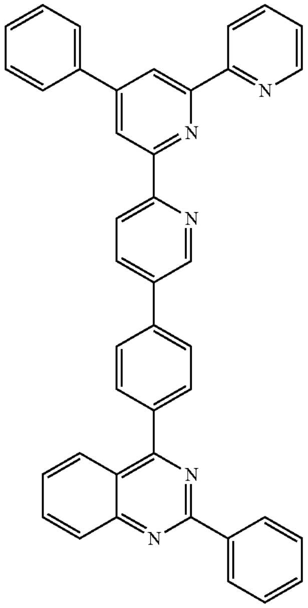
155
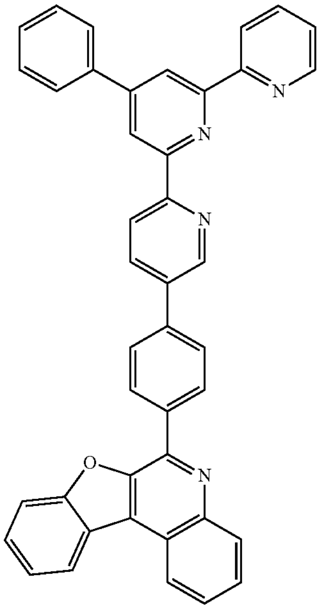
156
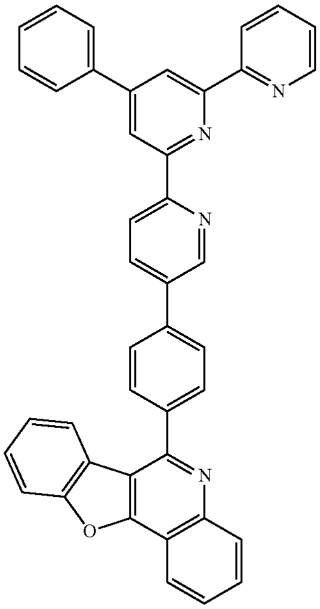

-continued
157
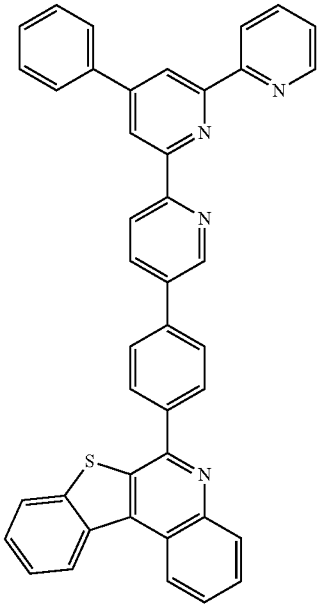
158
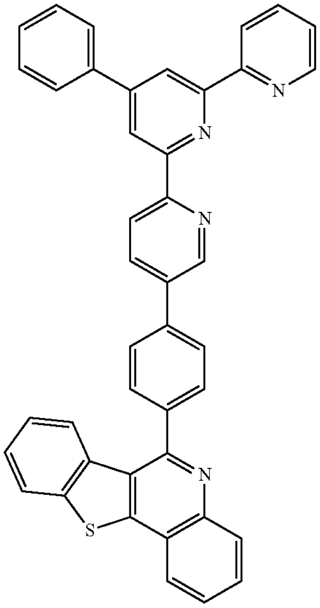
159
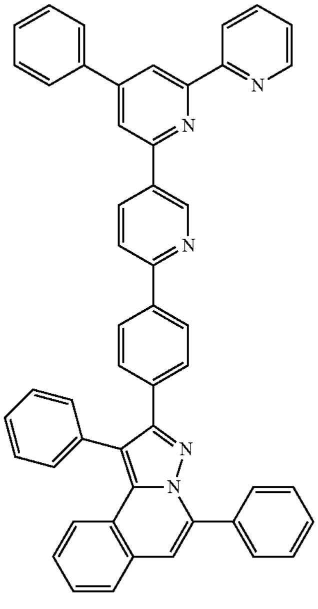
160
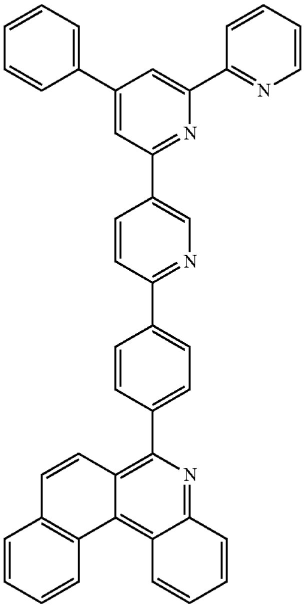

-continued
161
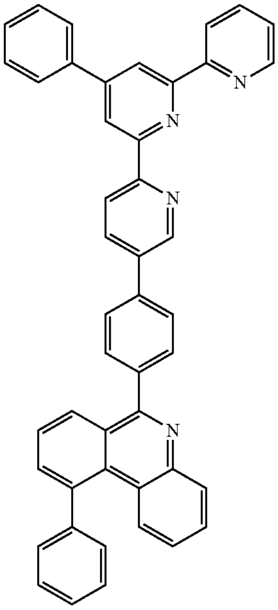
162
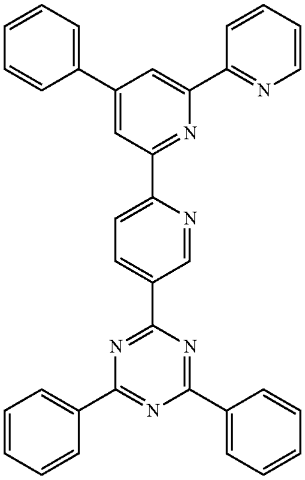
163
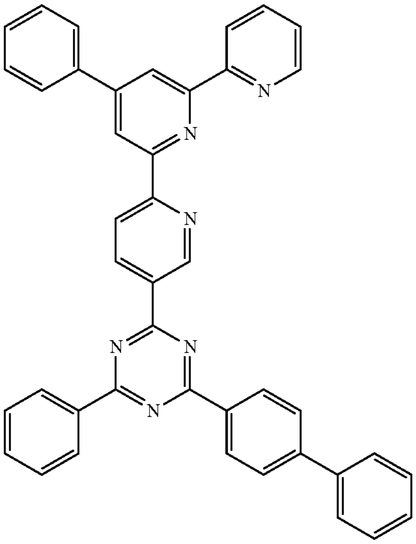
164
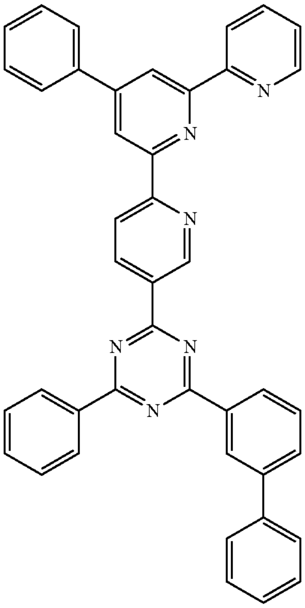

-continued
165
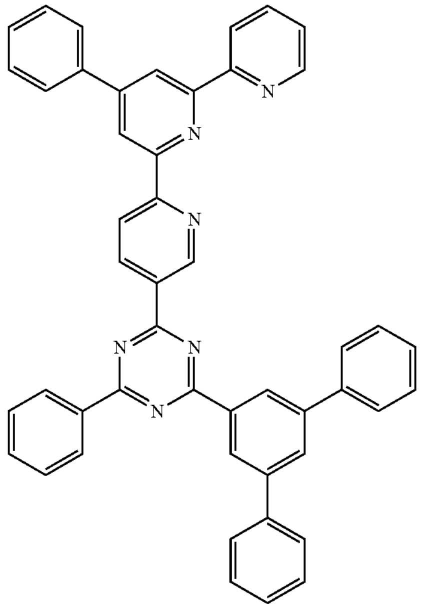
166
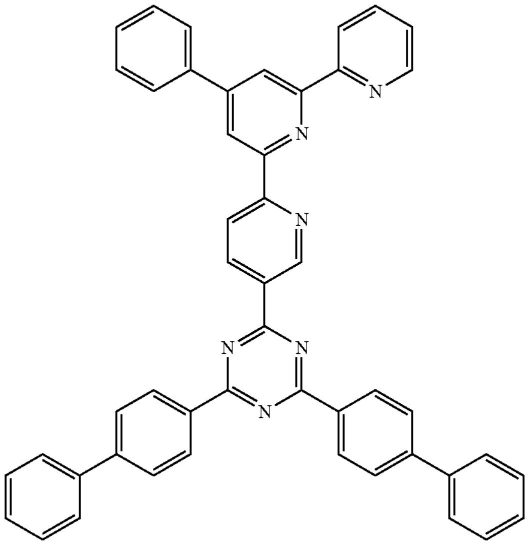
167
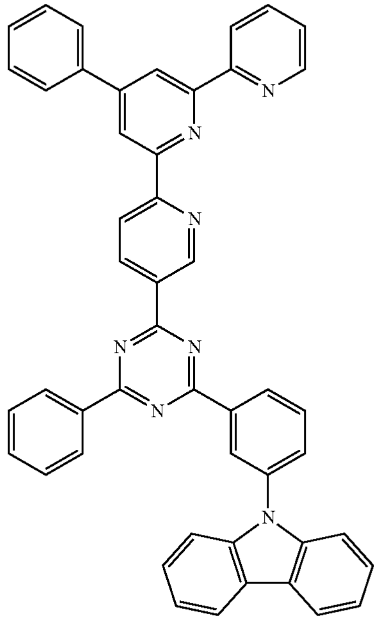
168
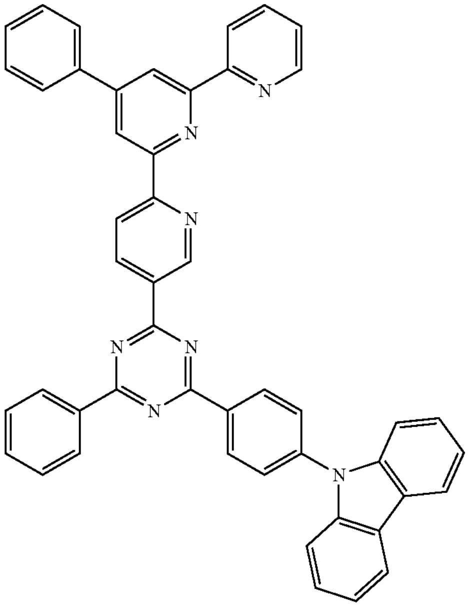

-continued
169
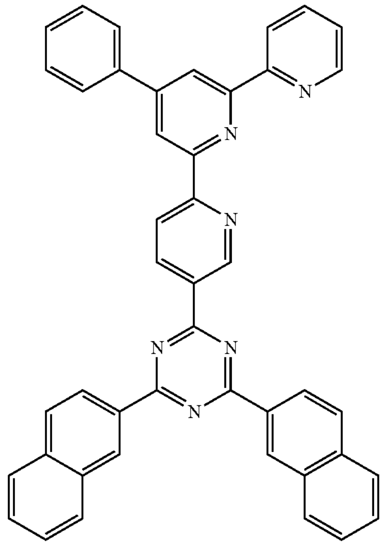
170
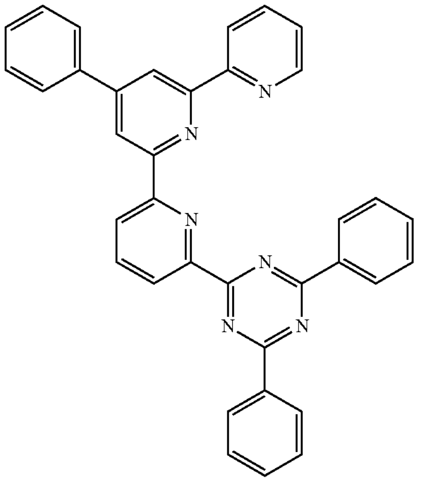
171
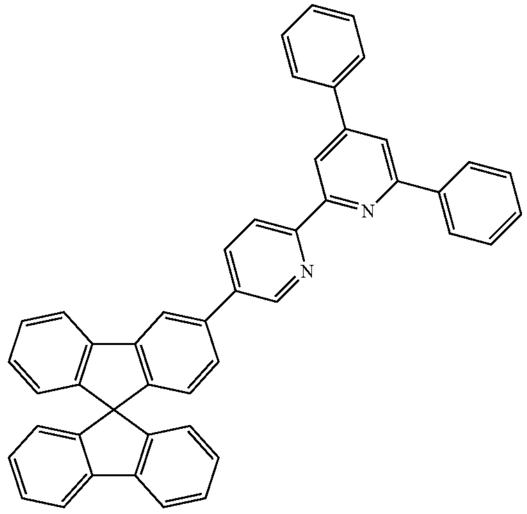
172
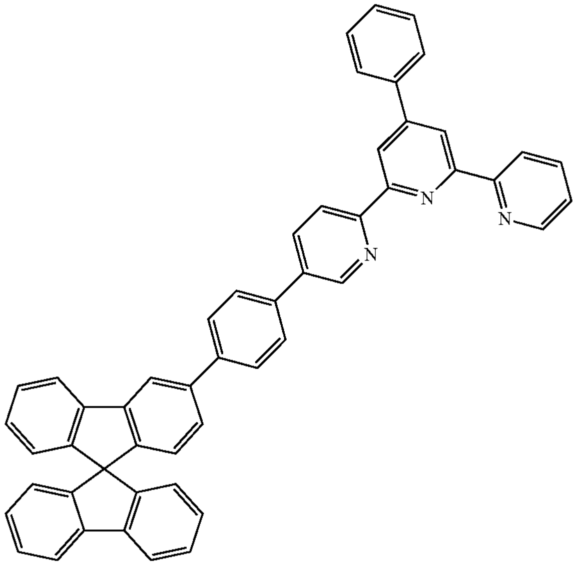
173
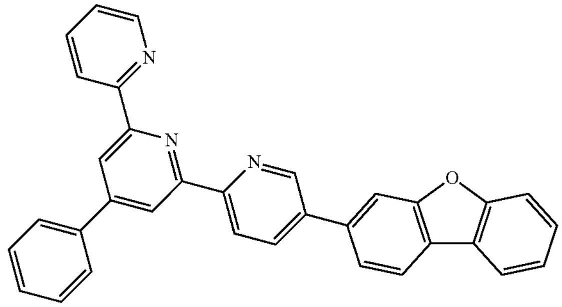
174
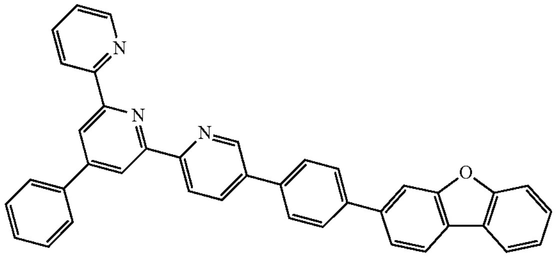

-continued
175
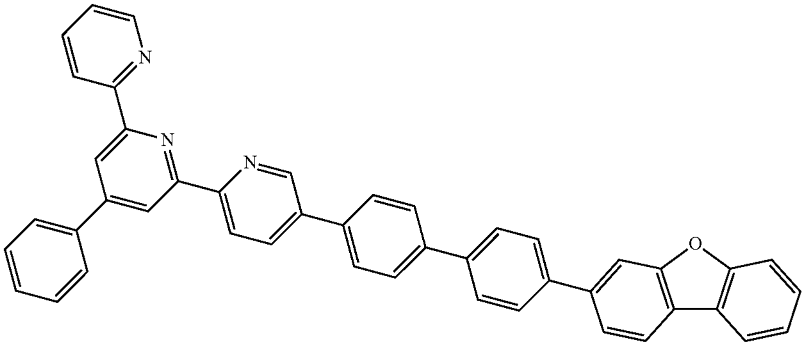
176
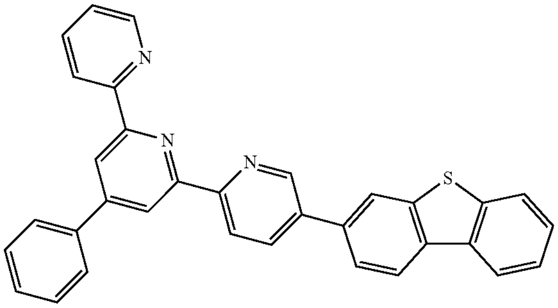
177
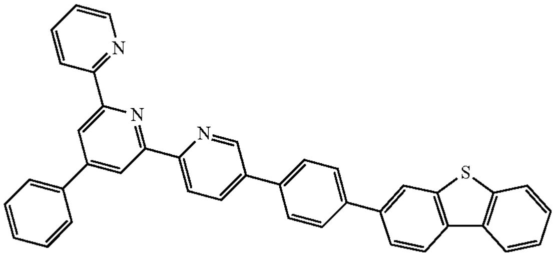
178
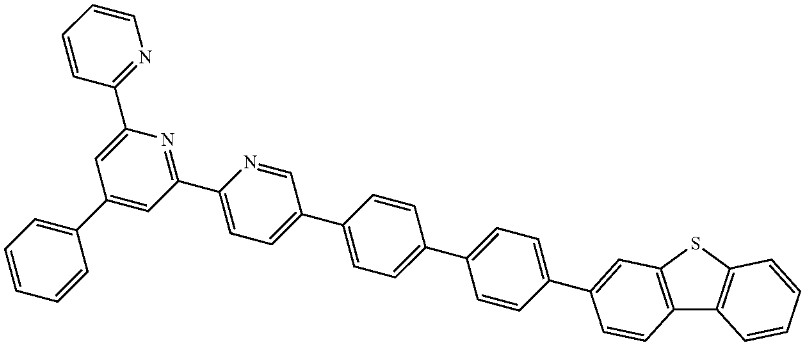
179
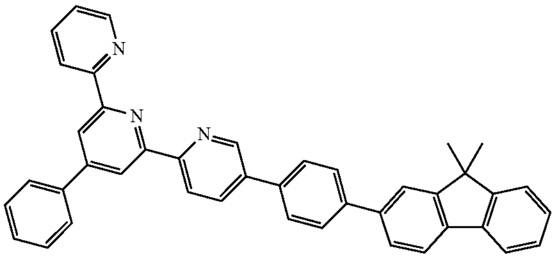
180
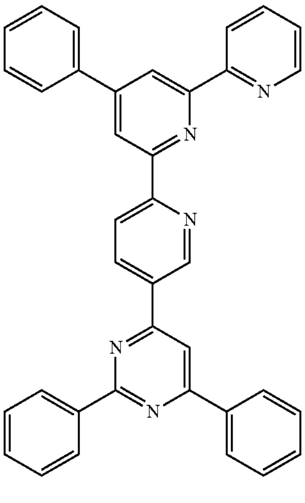

-continued
181
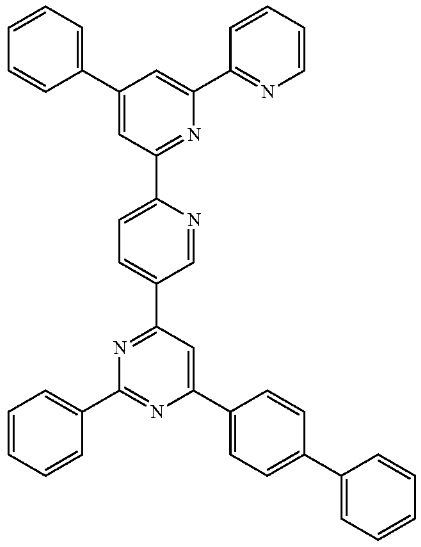
182
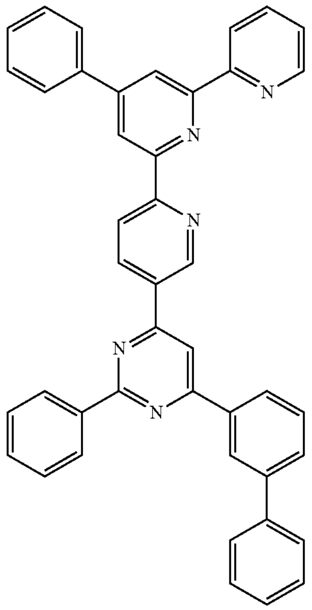
183
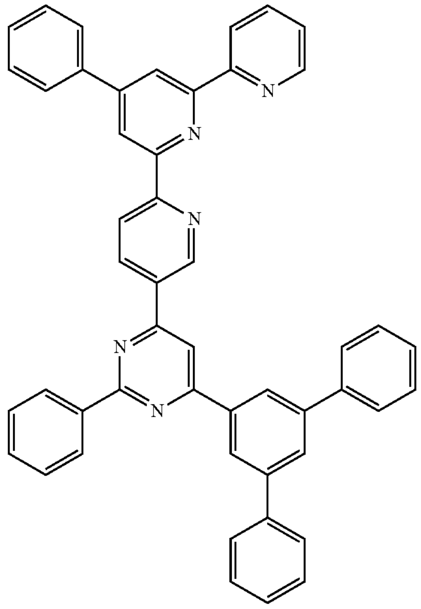
184
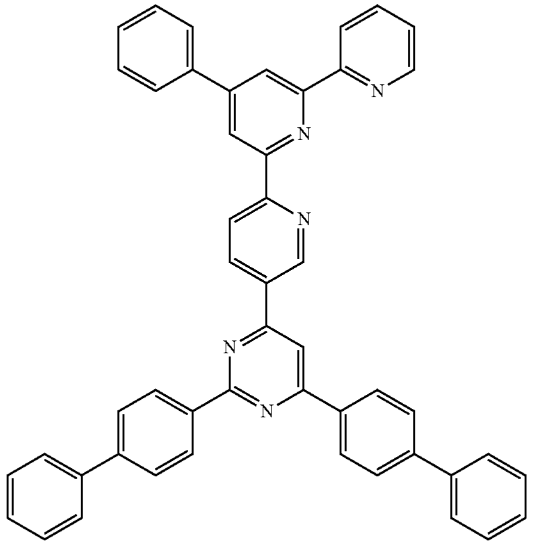

-continued
185
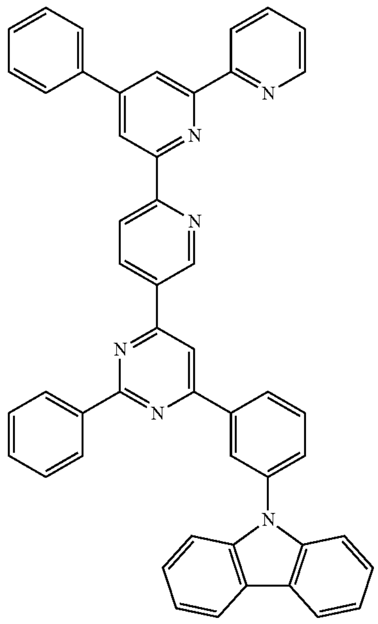
186
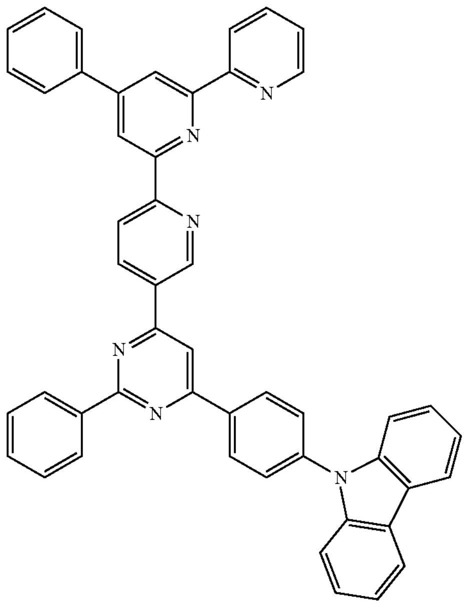
187
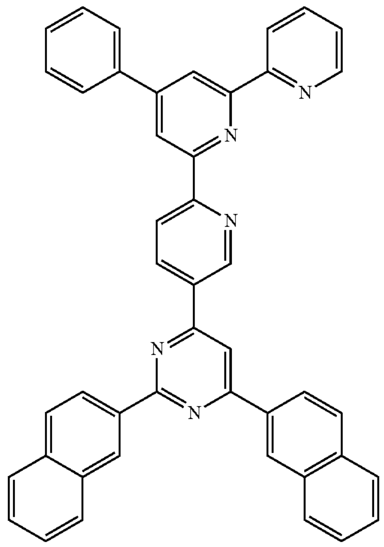
188
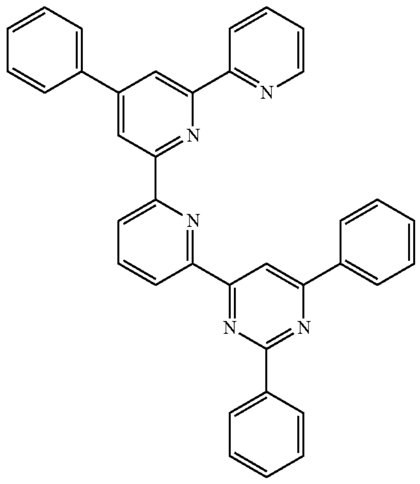

-continued
189
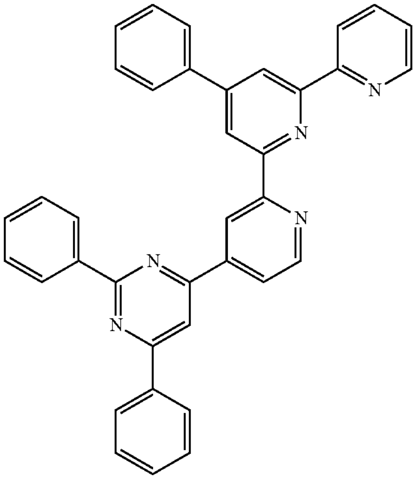
190
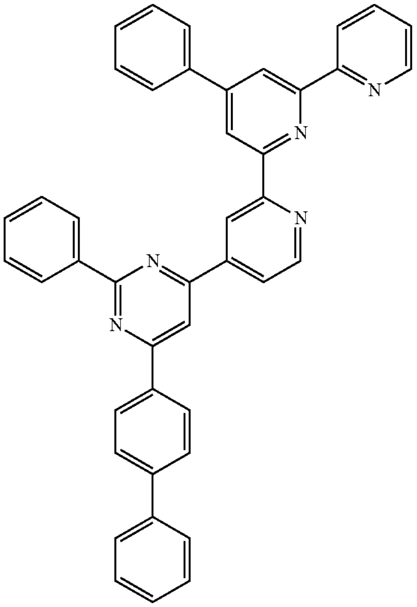
191
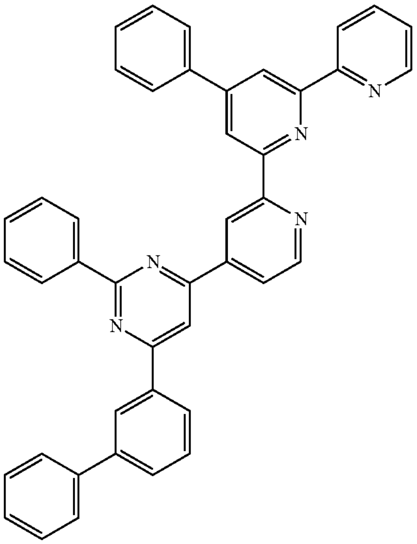
192
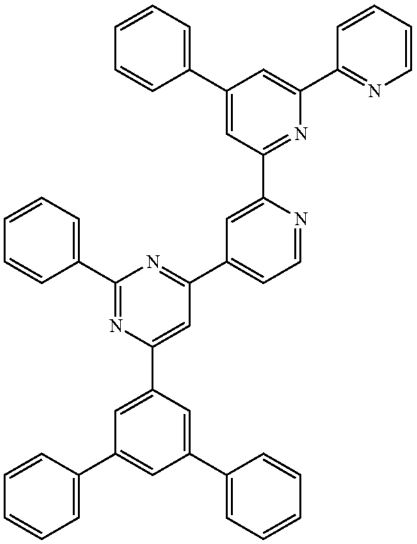

-continued
193
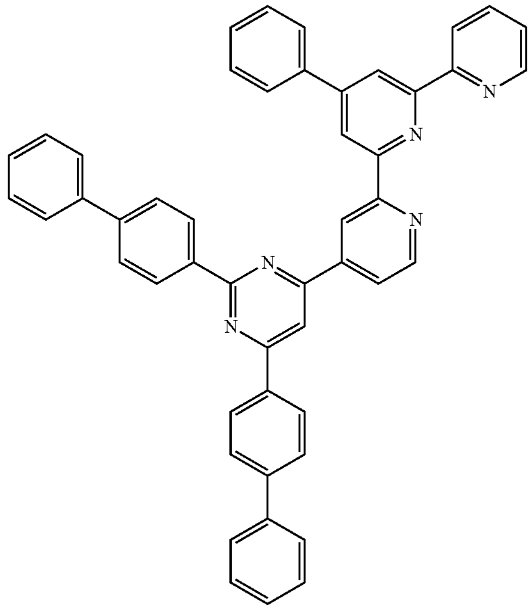
194
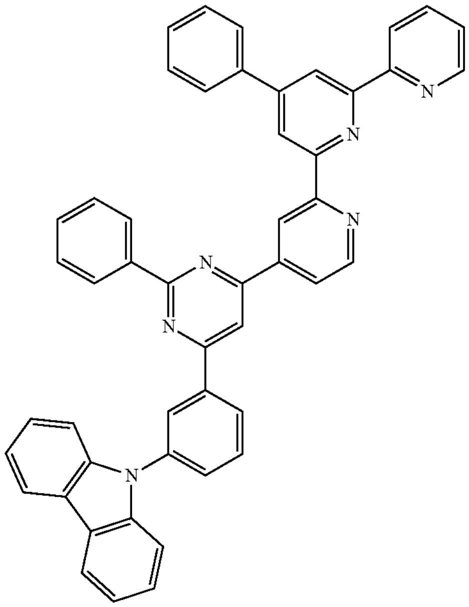
195
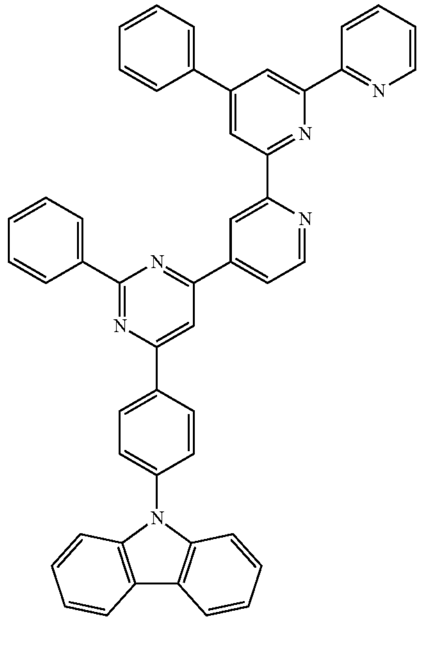
196
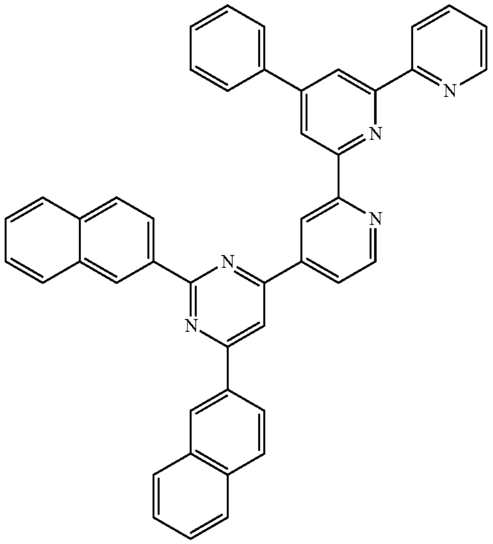

-continued
197
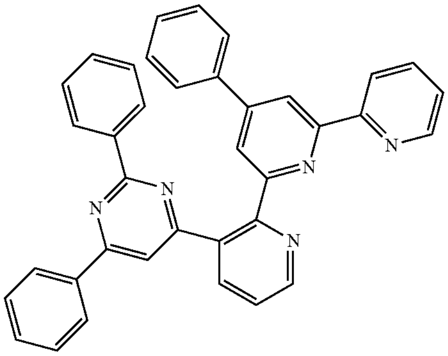
198
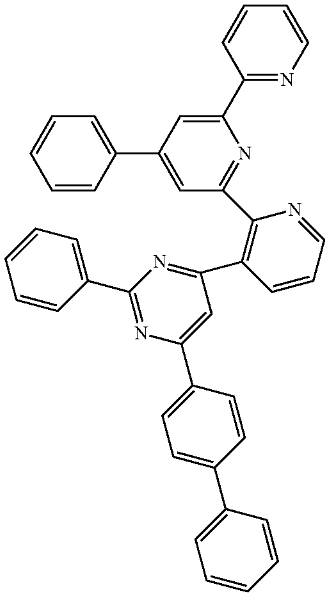
199
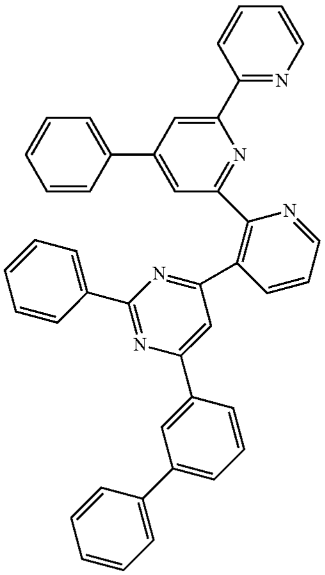
200
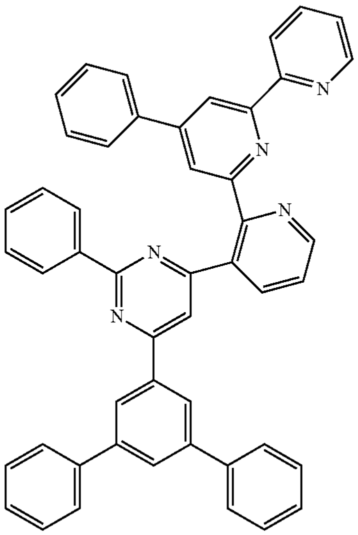

-continued
201
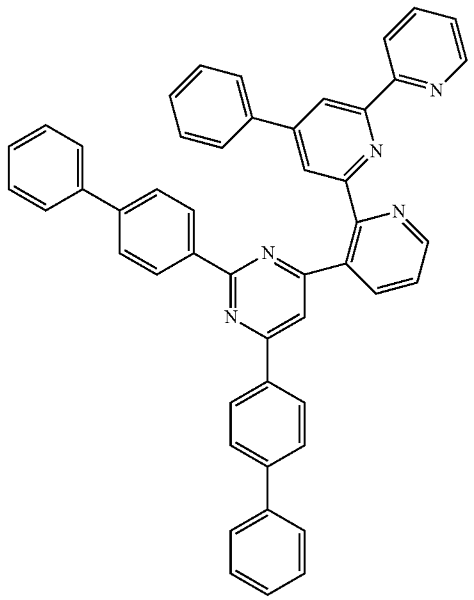
202
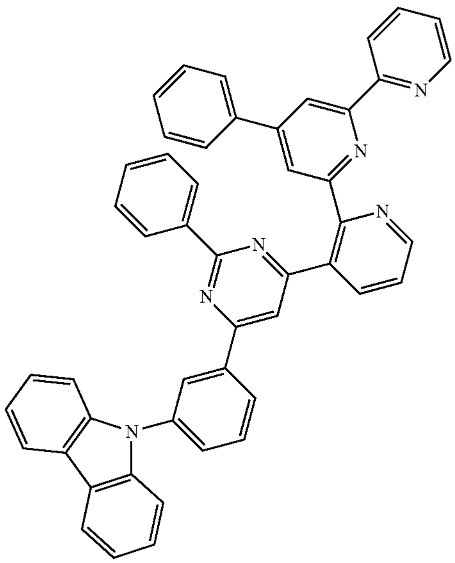
203
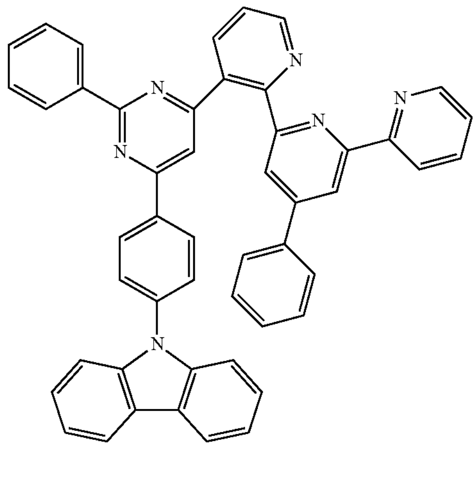
204
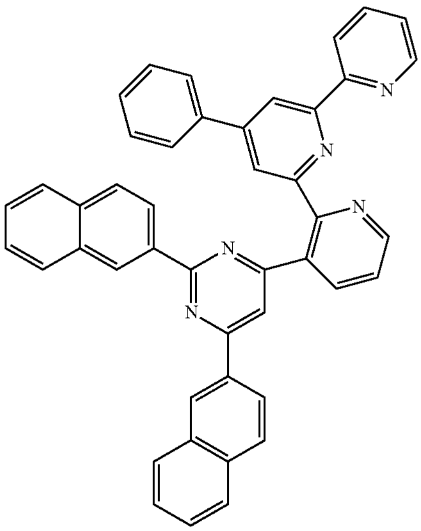

-continued
205
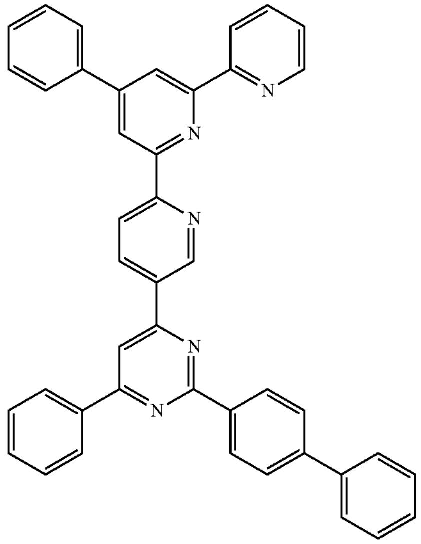
206
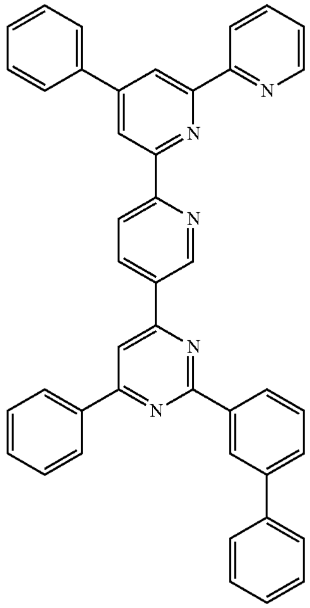
207
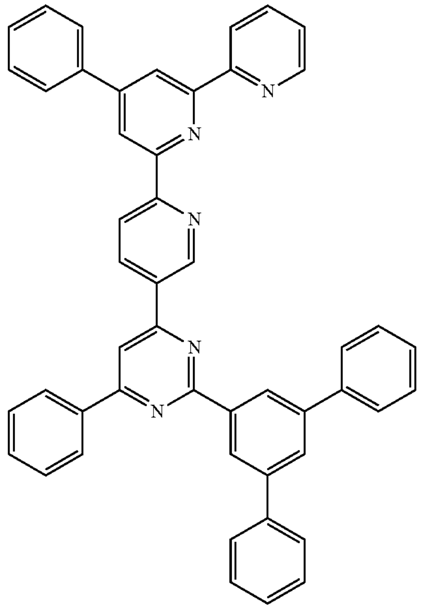
208
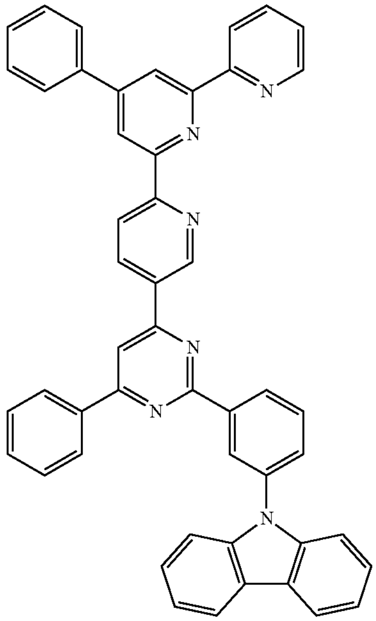

-continued
209
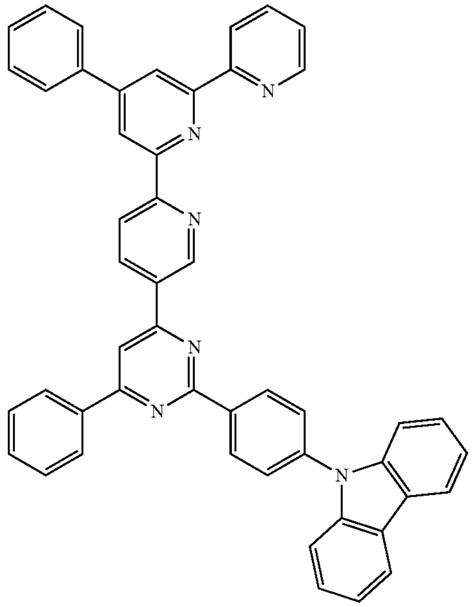
210
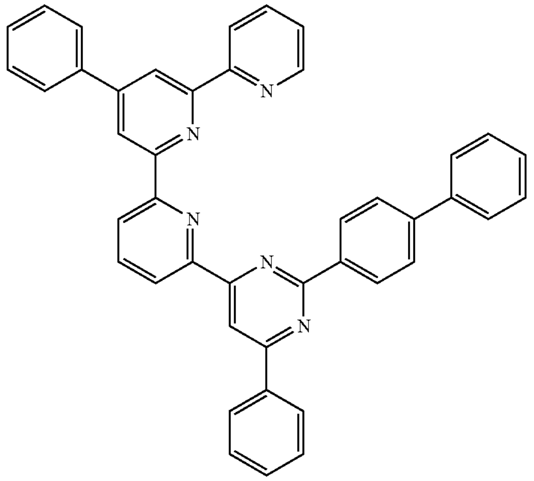
211
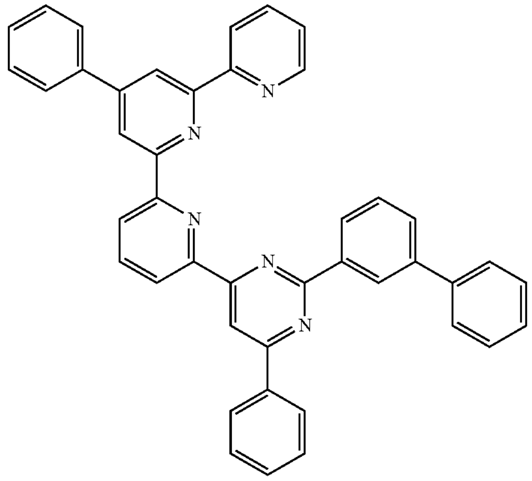
212
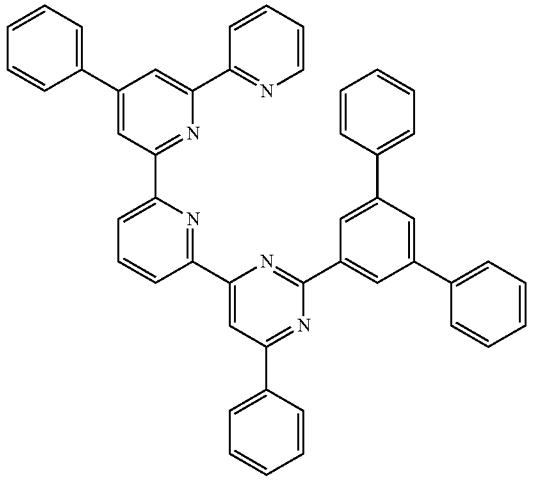
213
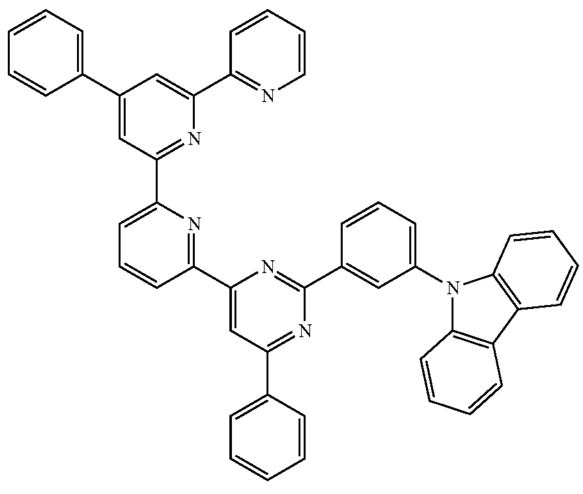
214
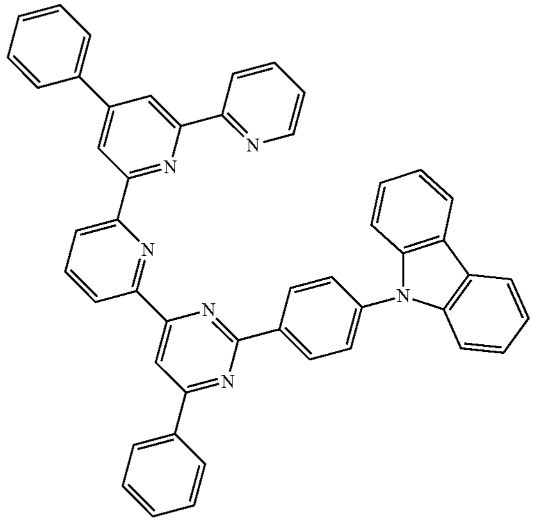

-continued
215
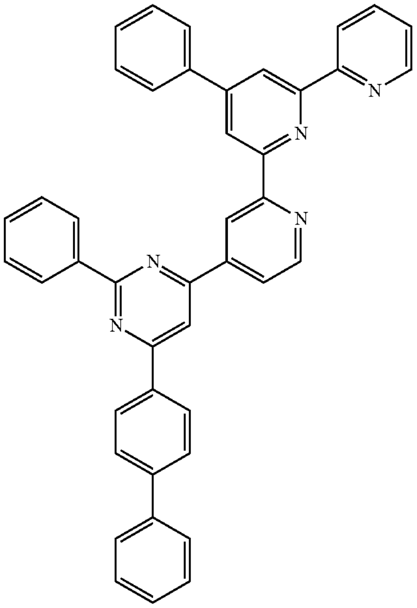
216
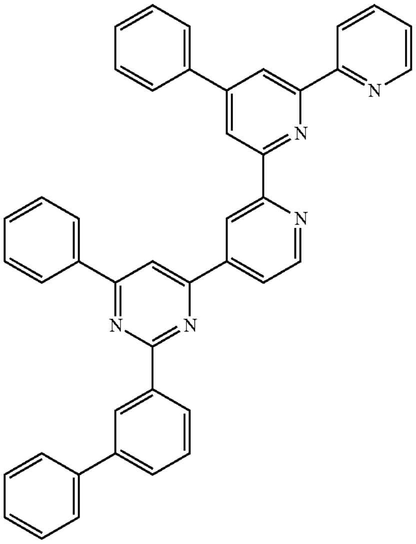
217
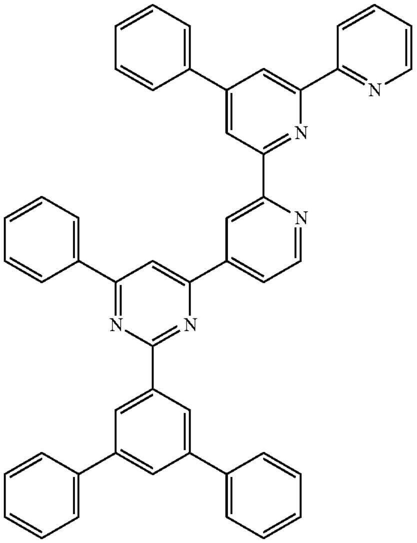
218
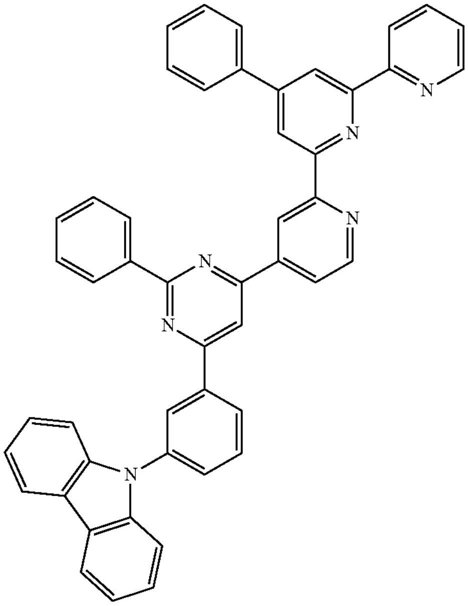

-continued
219
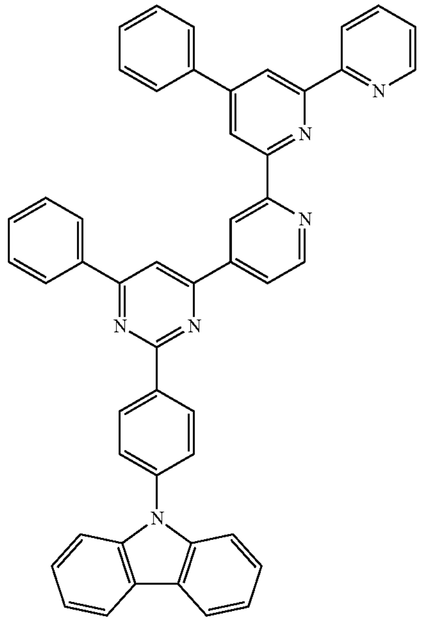
220
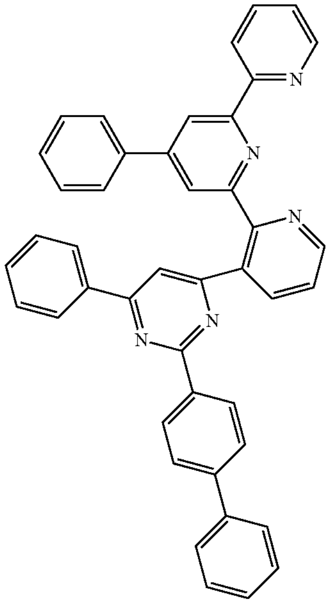
221
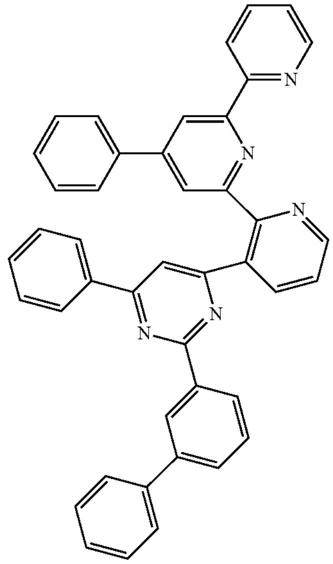
222
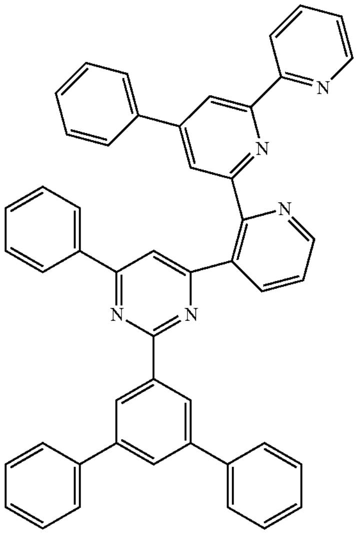

-continued
223
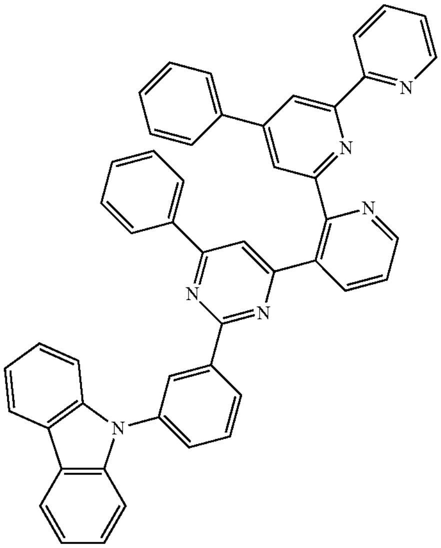
224
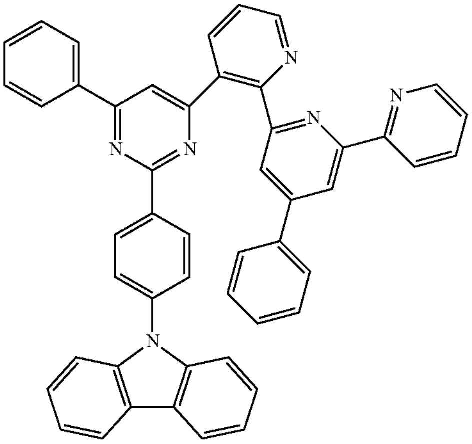
225
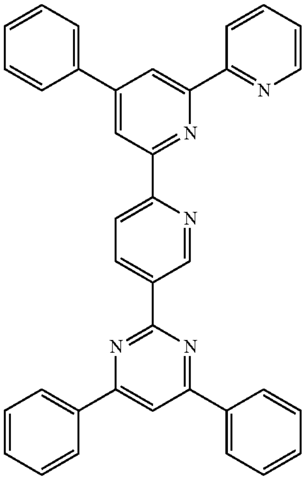
226
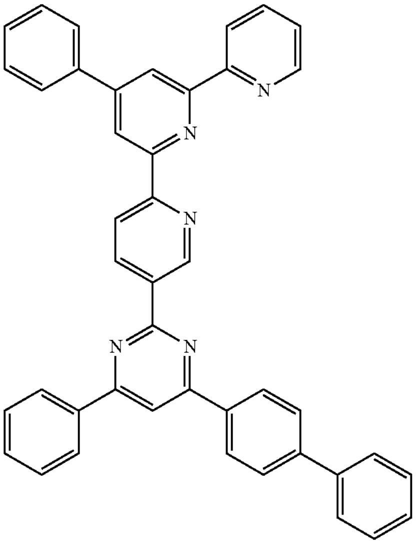

-continued
227
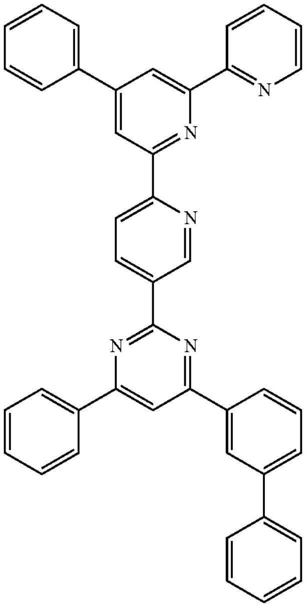
228
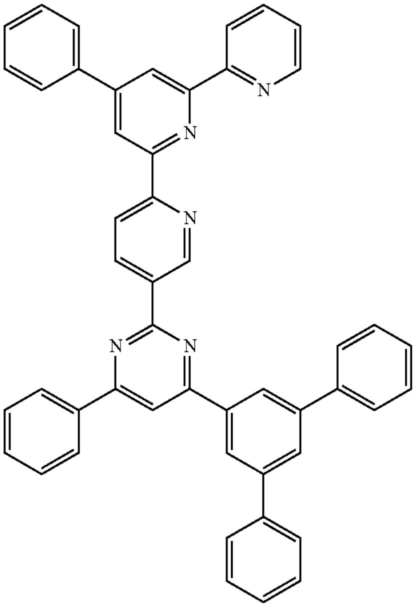
229
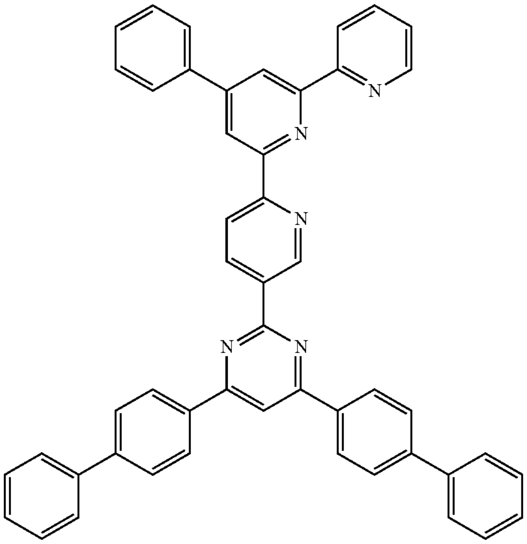
230
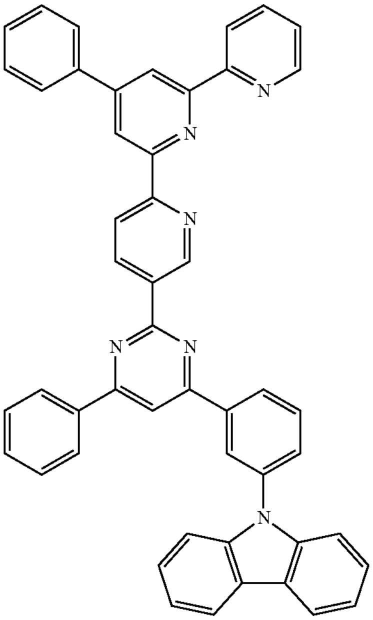

-continued
231
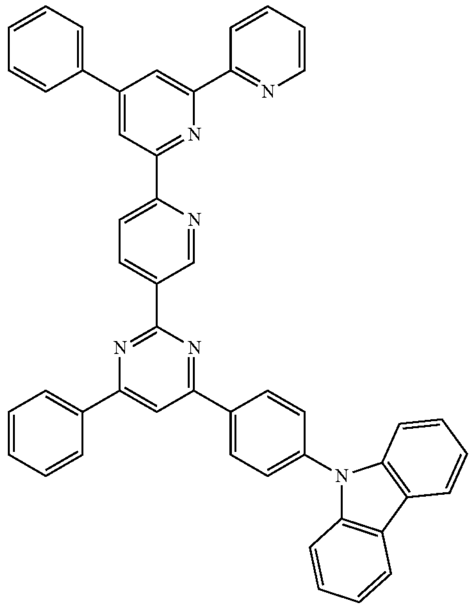
232
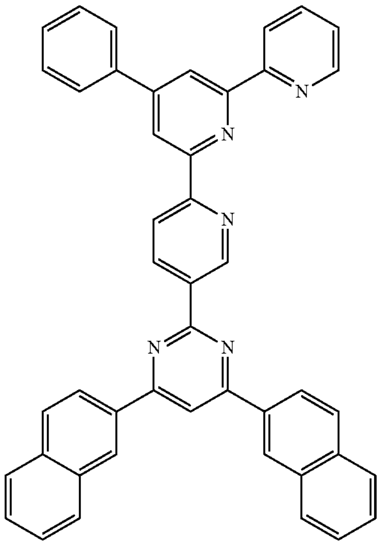
233
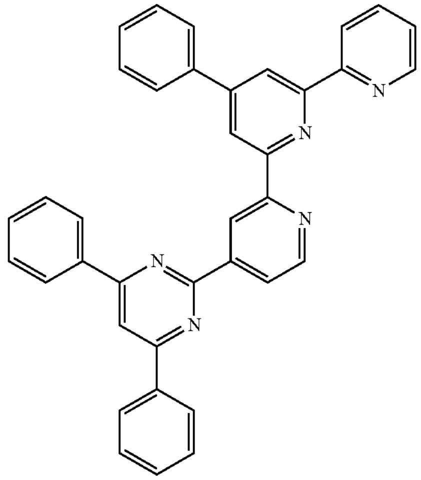
234
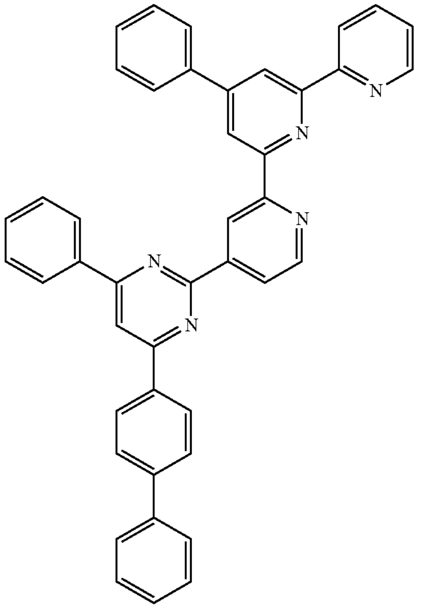

-continued
235
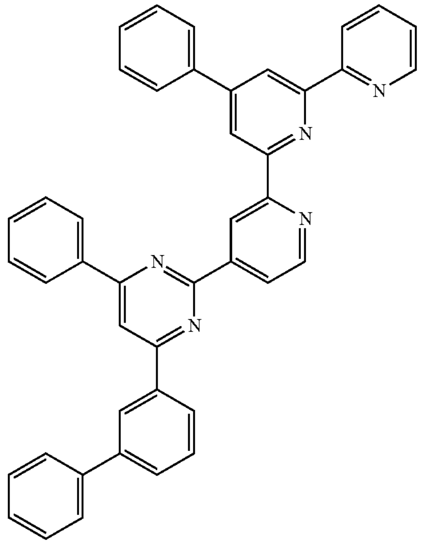
236
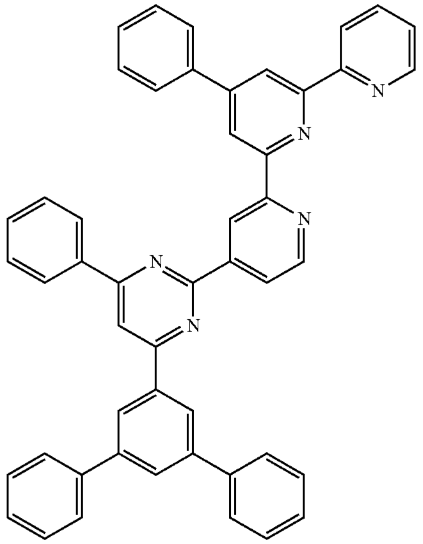
237
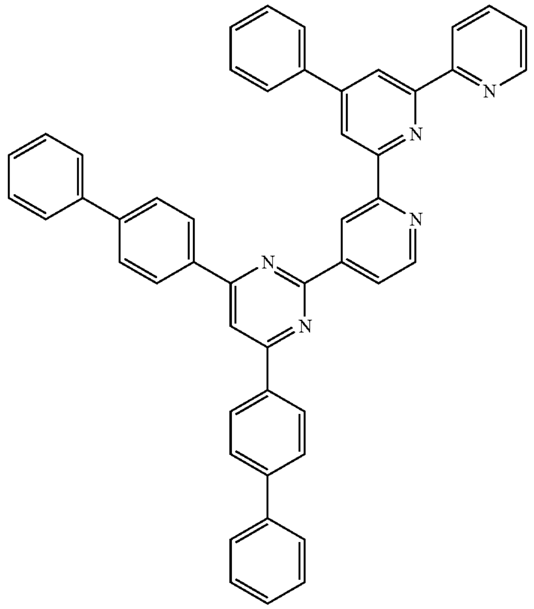
238
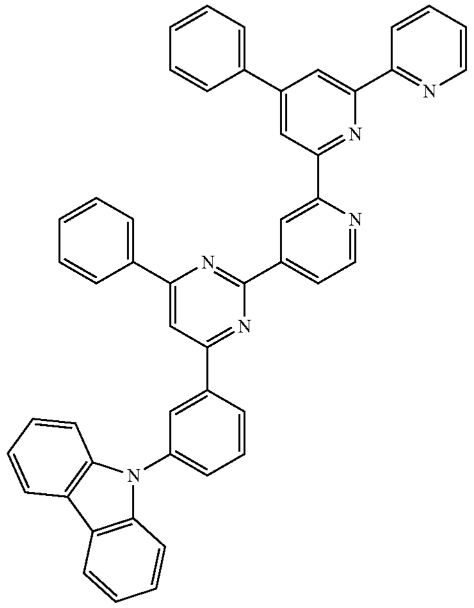

-continued
239
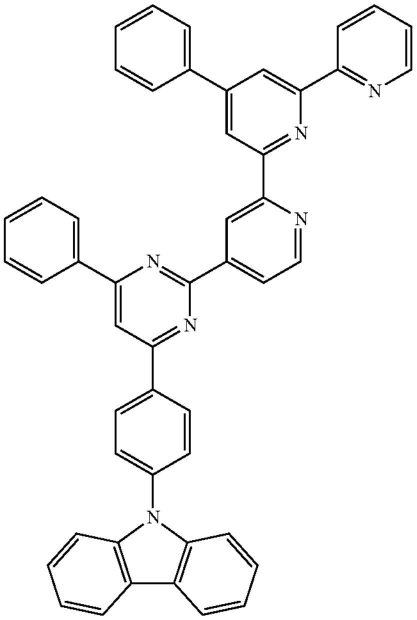
240
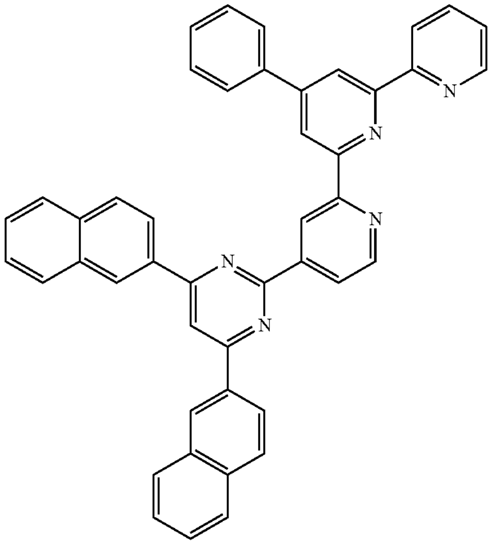
-continued
241
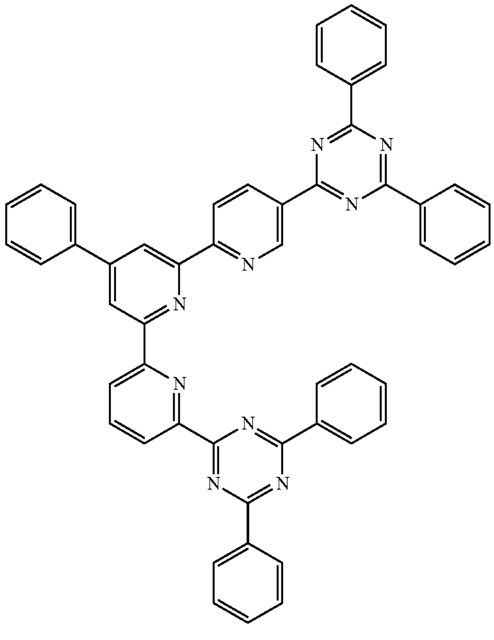
242
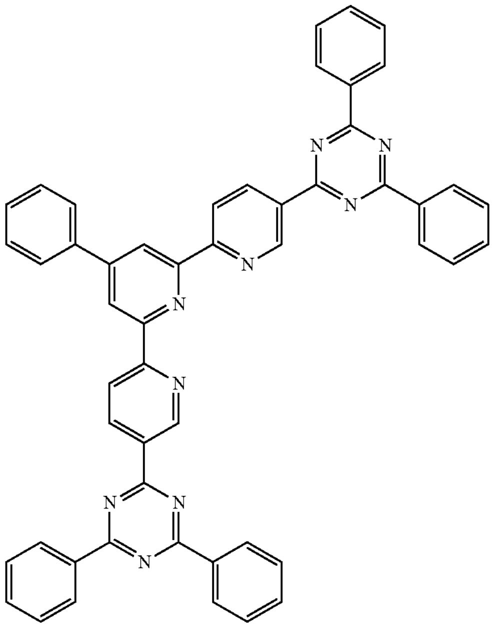

243
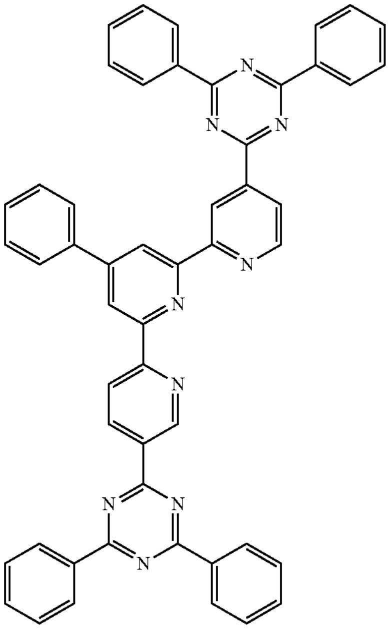
244
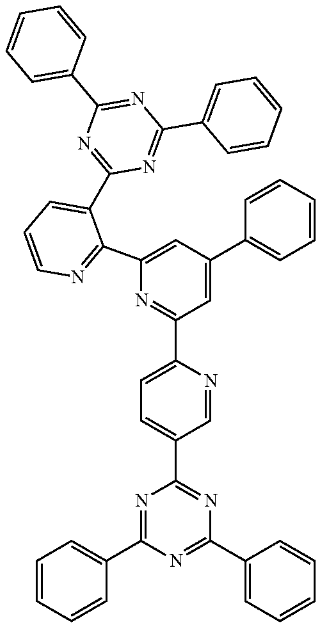
245
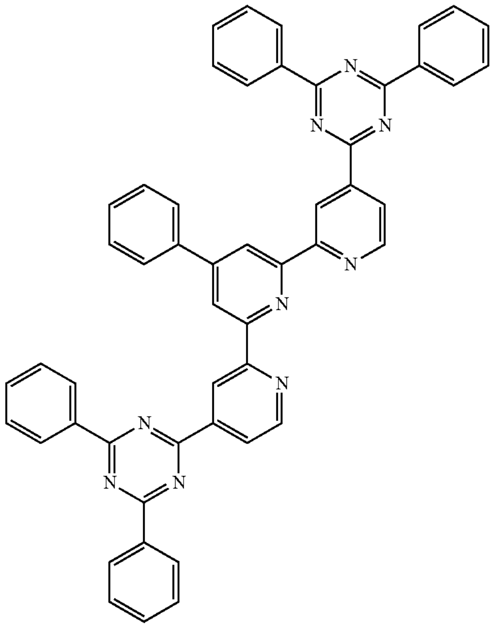
246
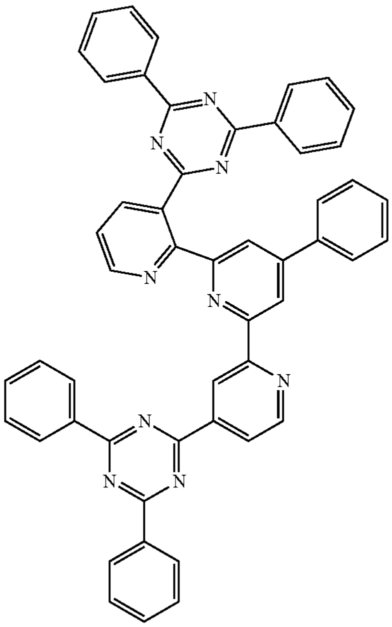

-continued
247
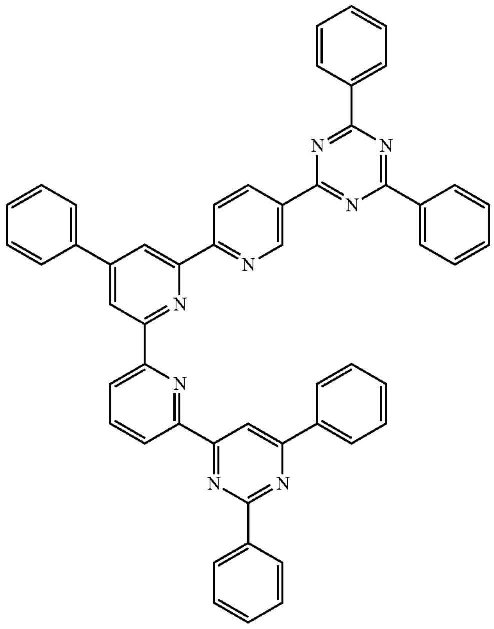
248
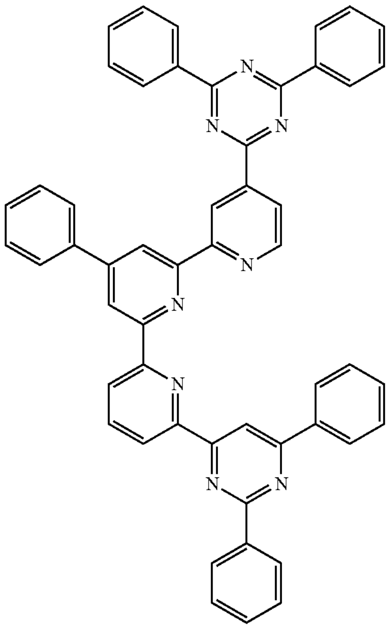
-continued
249
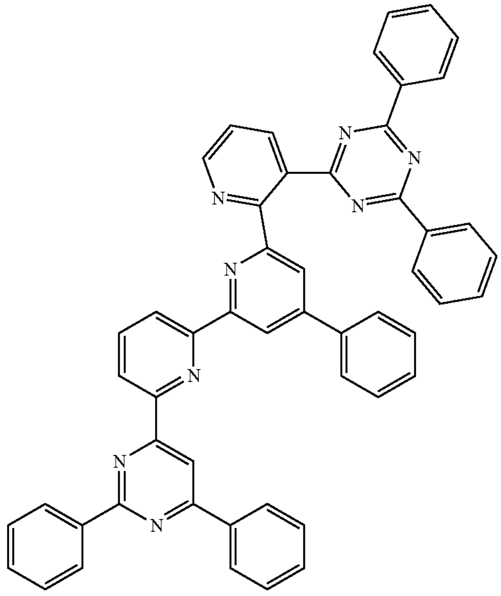
250
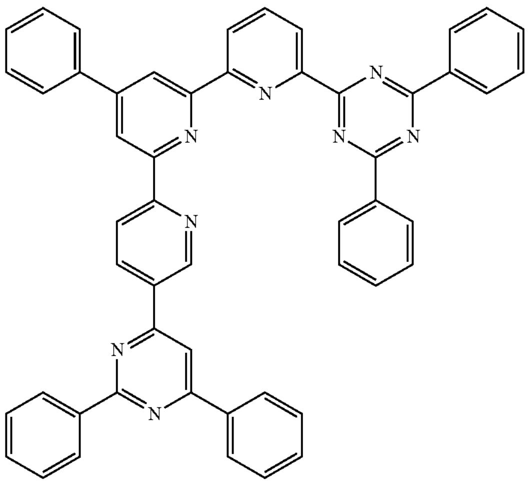

251
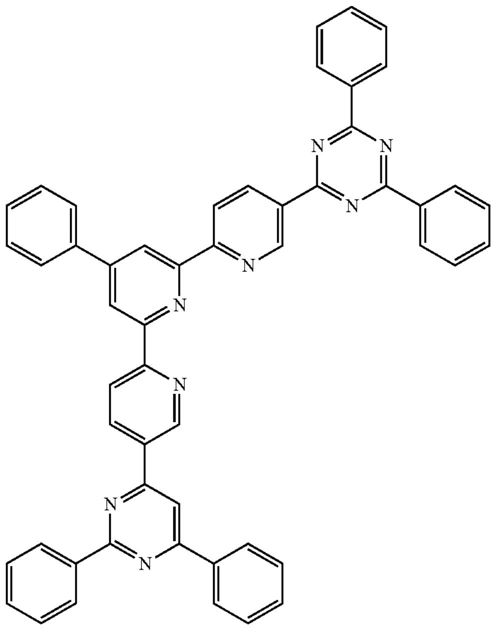
252
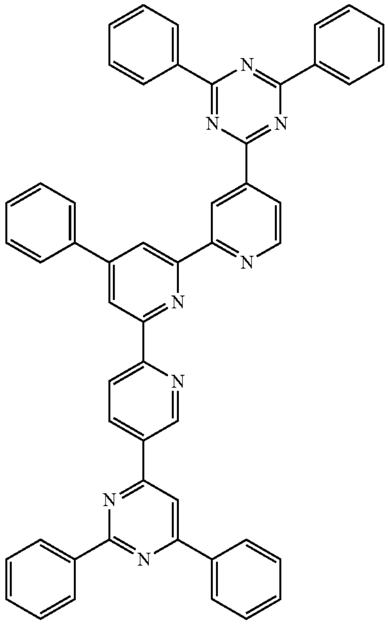
253
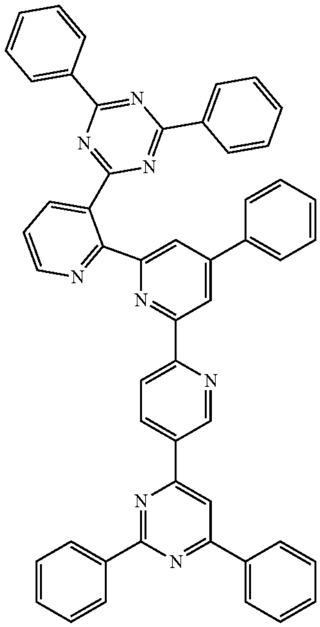
254
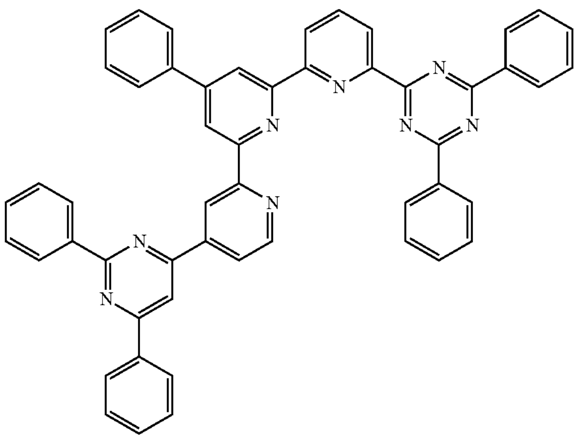

-continued
255
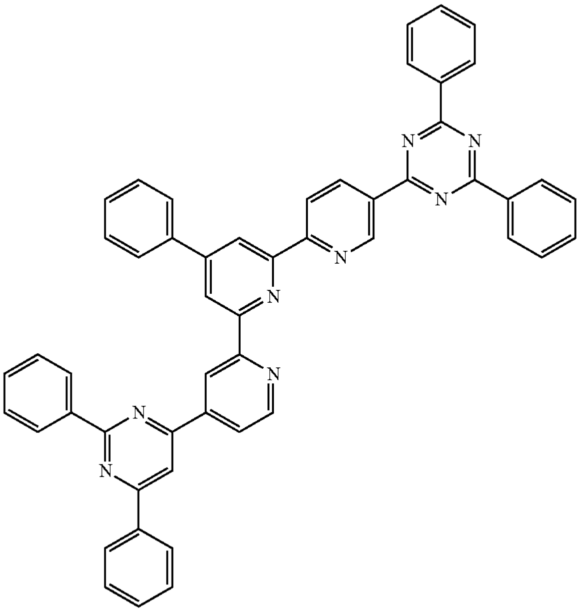
256
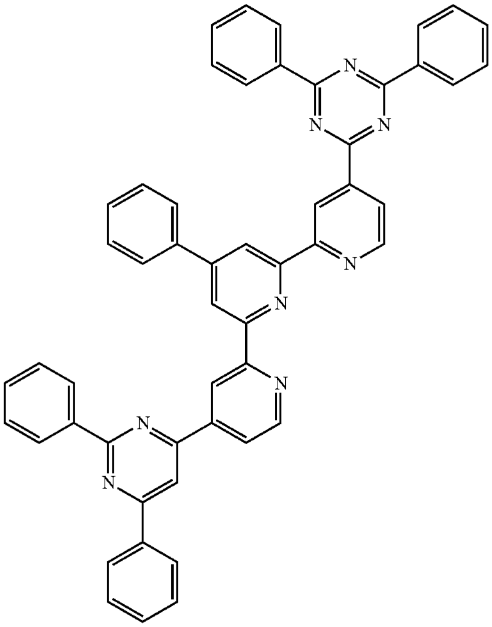
-continued
257
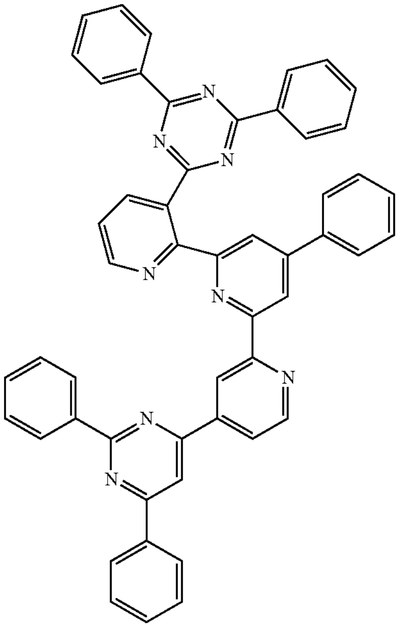
258
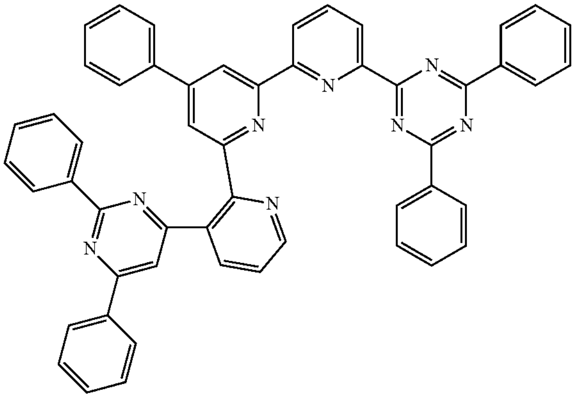
259
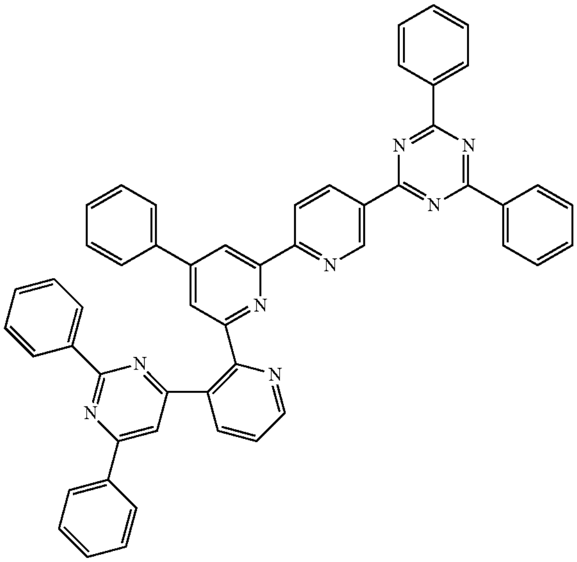

-continued
260
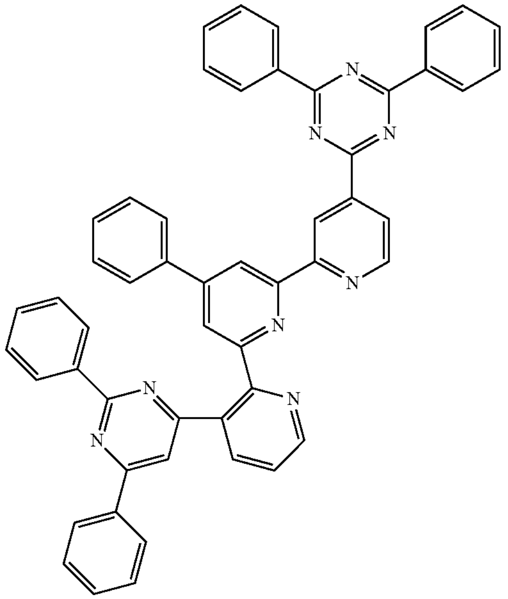
261
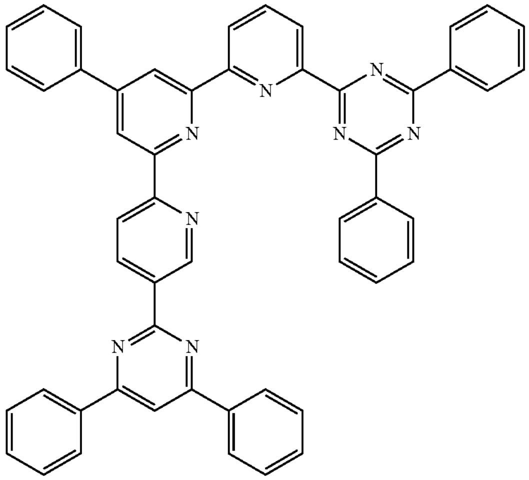
-continued
262
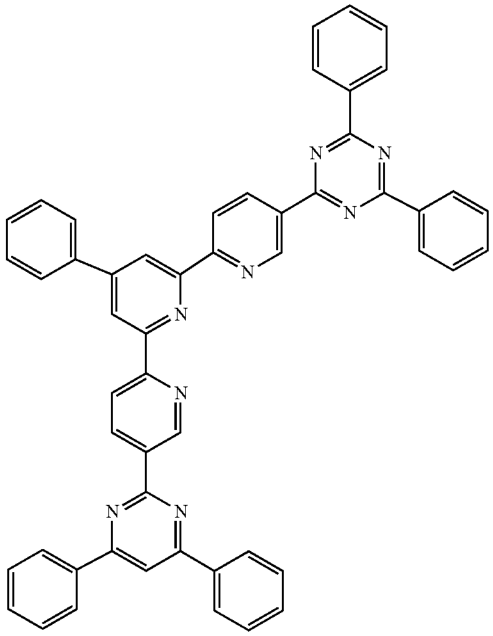
263
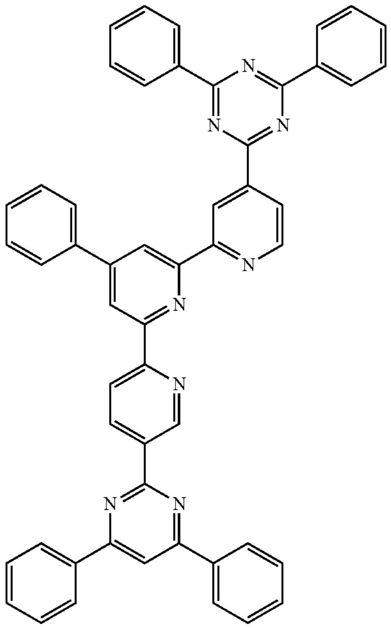

-continued
264
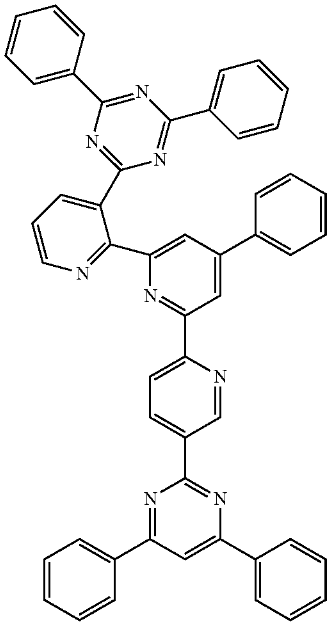
265
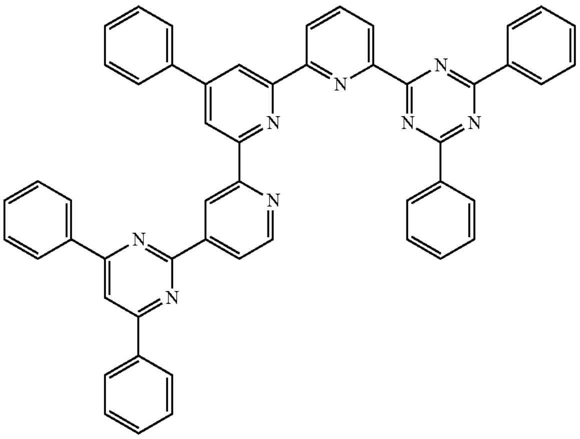
-continued
266
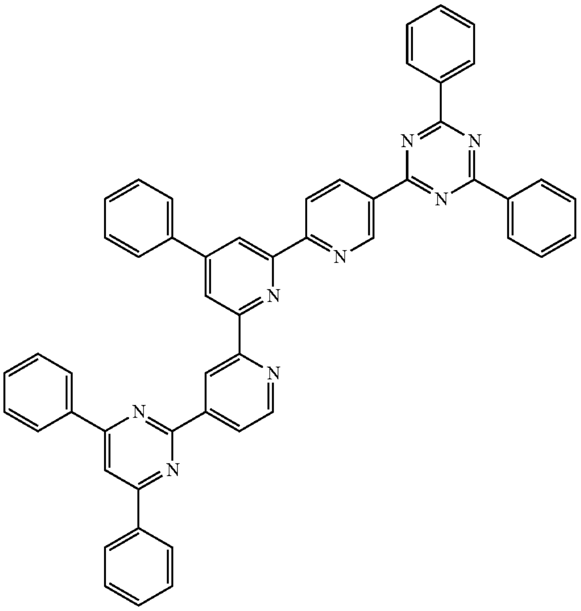
267
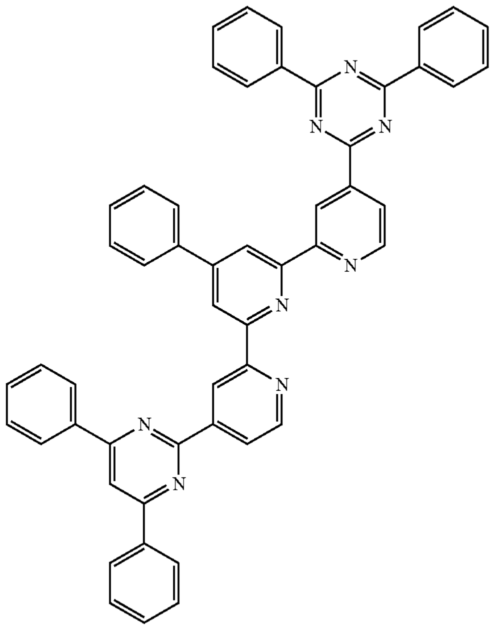

-continued
268
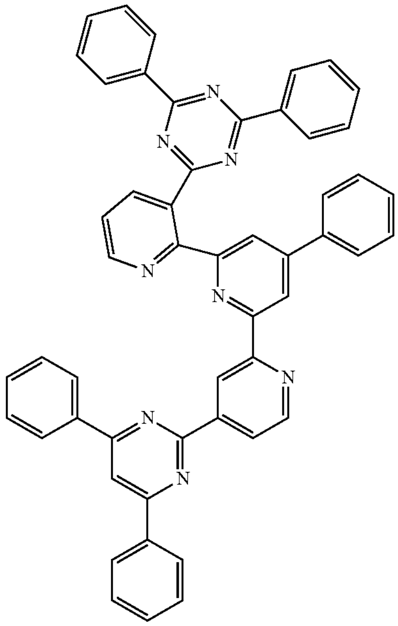
269
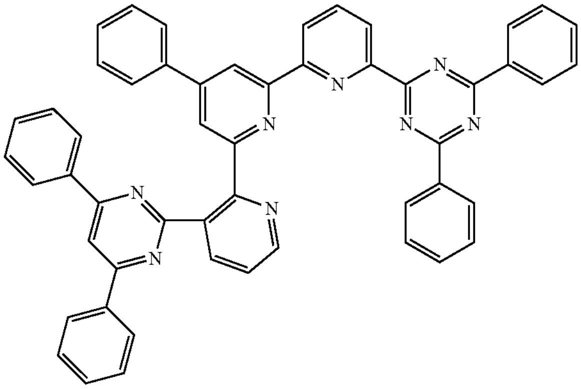
270
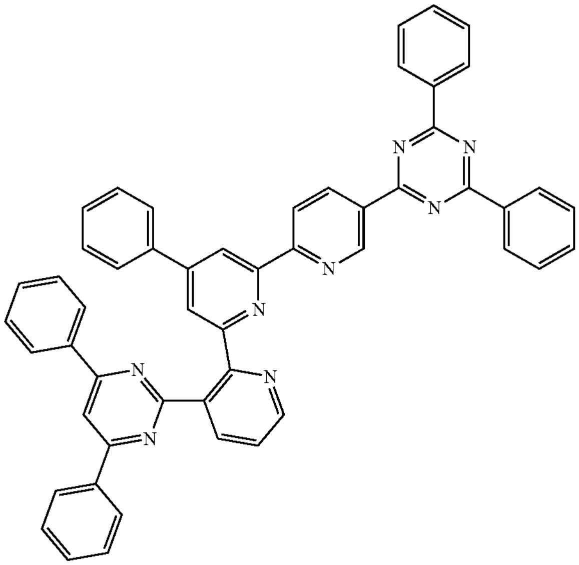
-continued
271
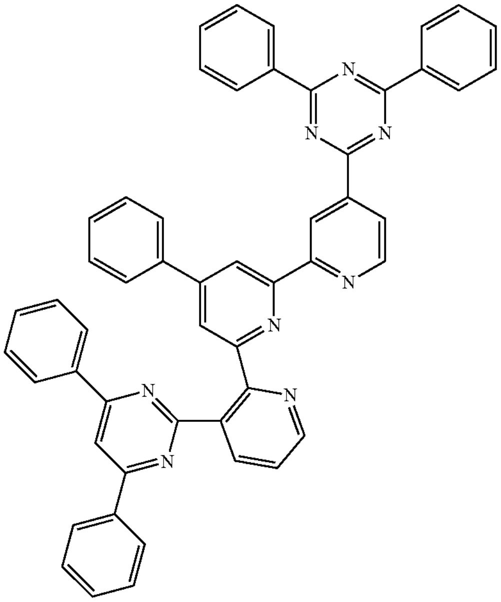
272
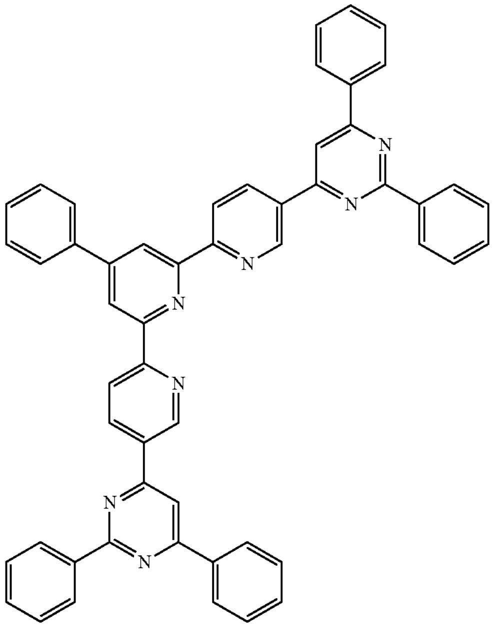

273
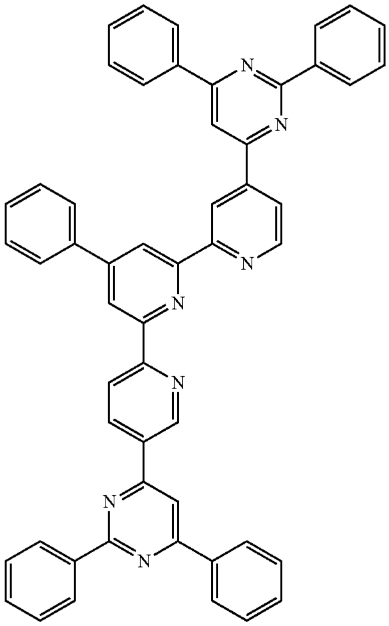
275
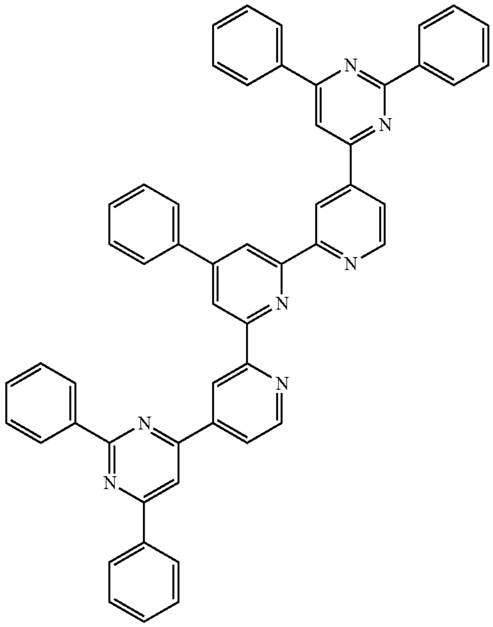
274
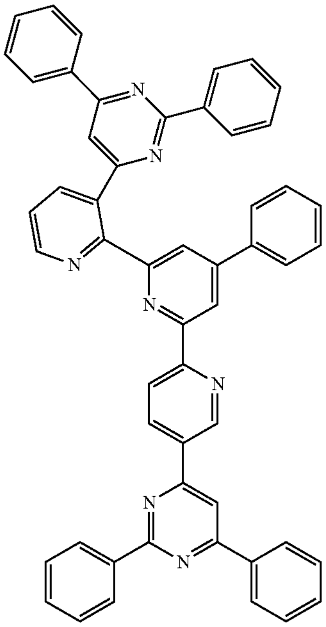
276
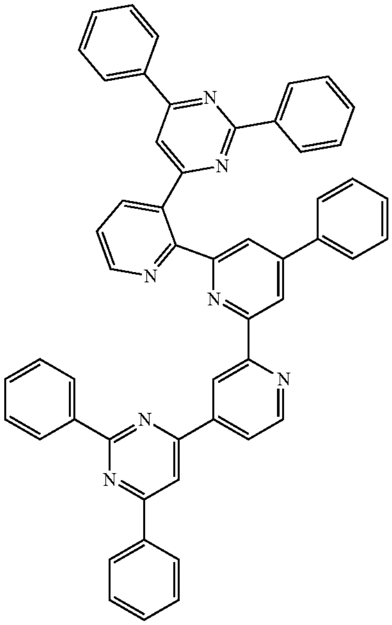

277
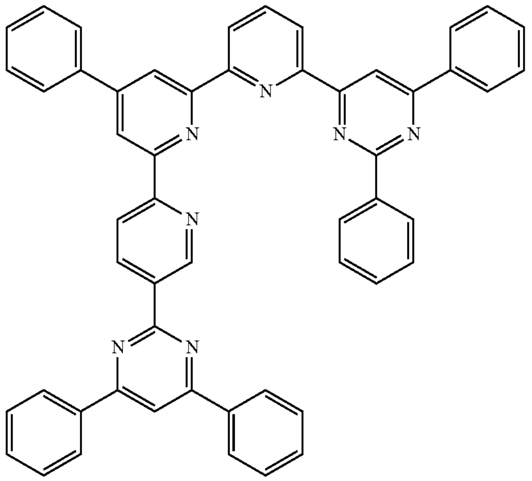
278
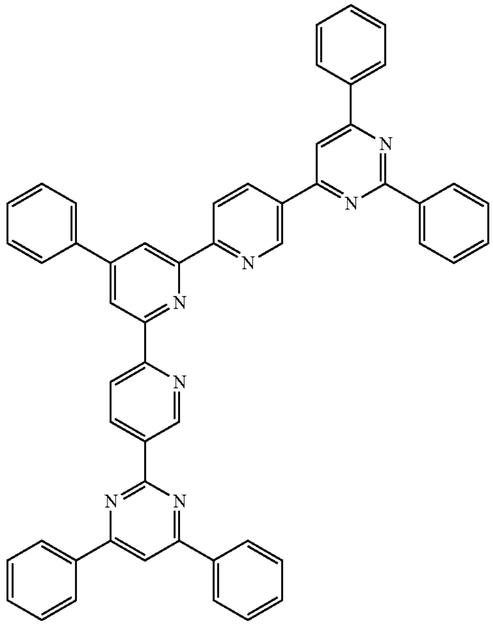
279
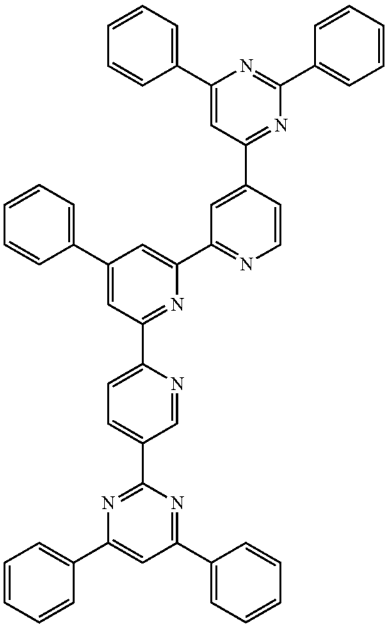
280
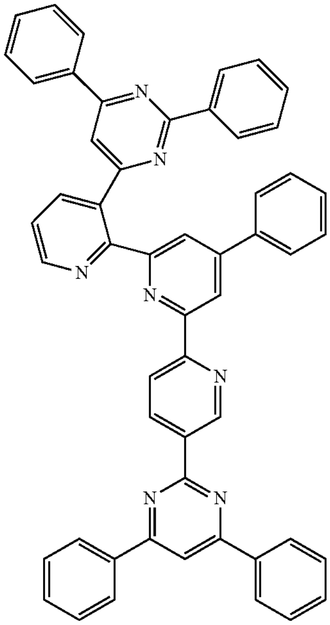

-continued
281
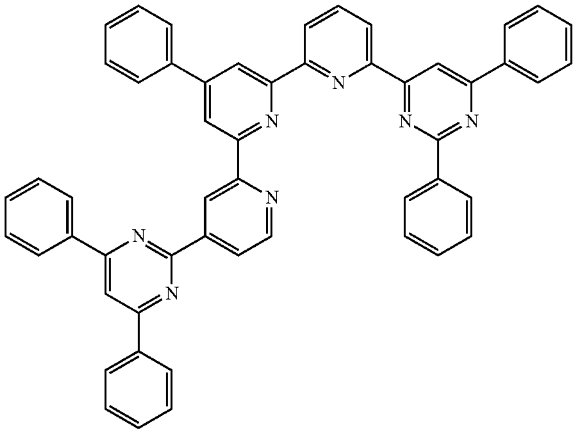
282
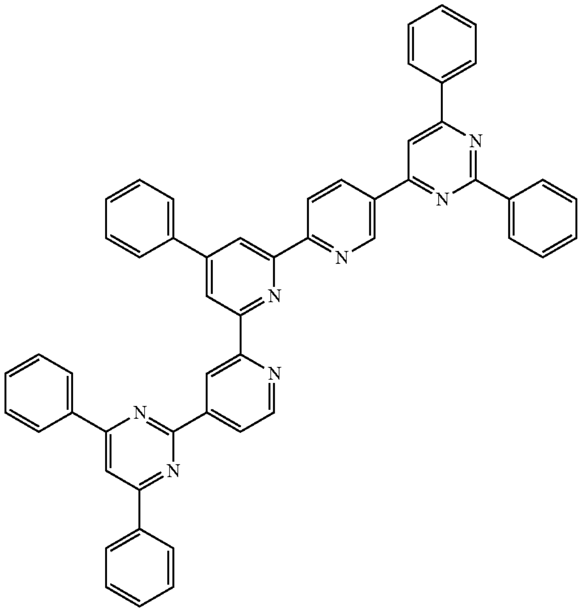
-continued
283
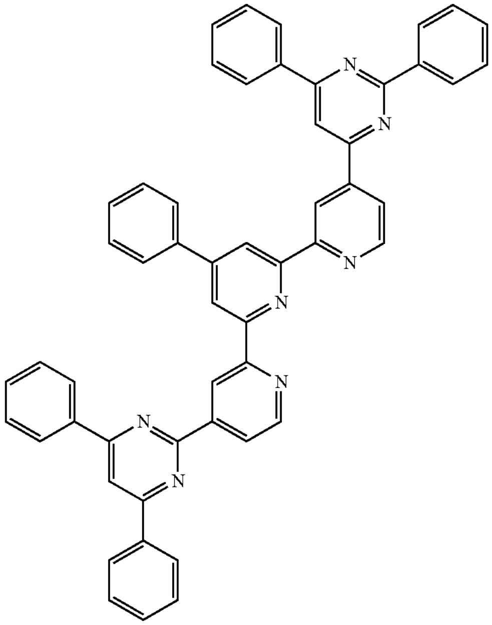
284
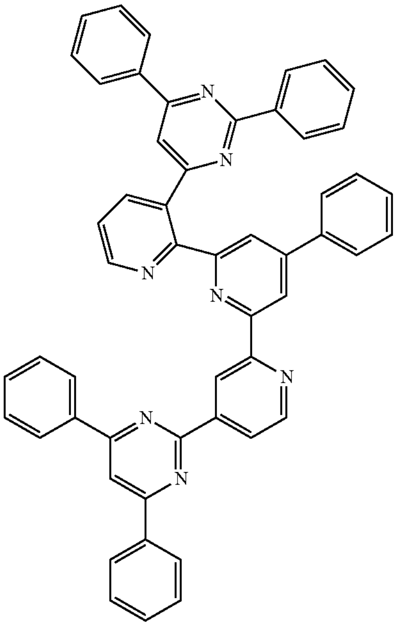
285
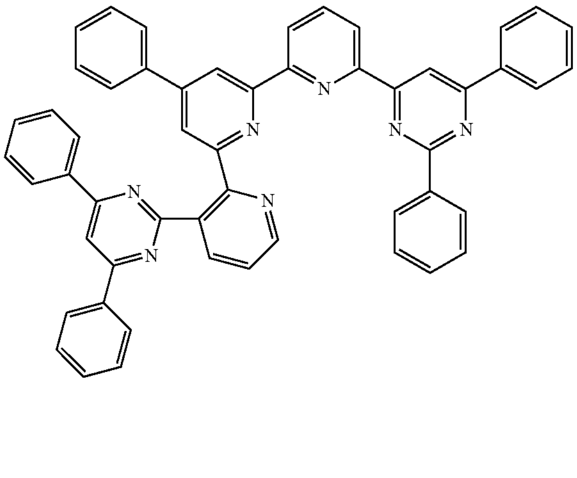

-continued
286
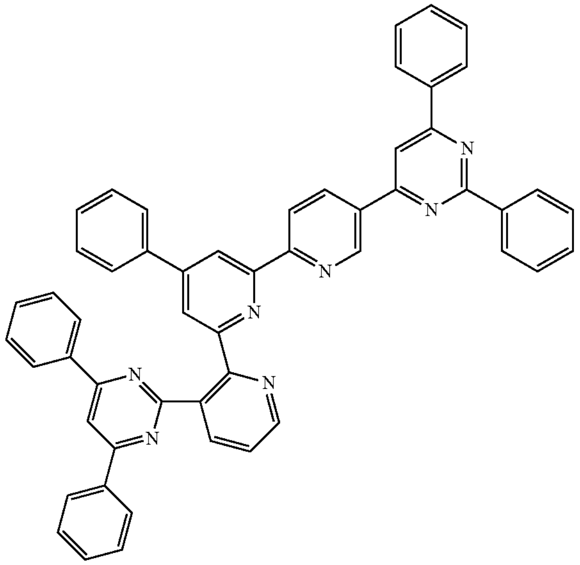
287
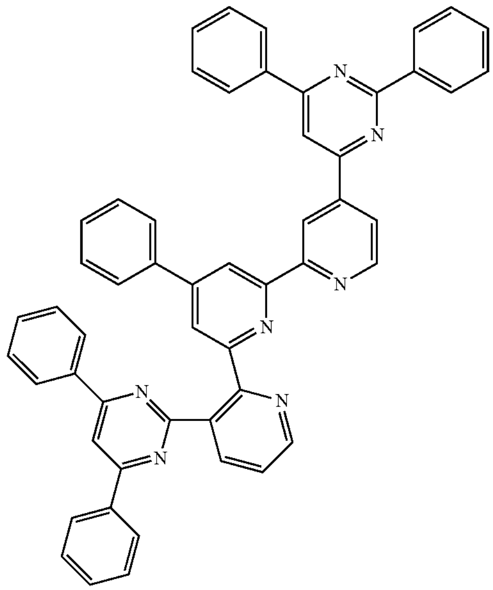
-continued
288
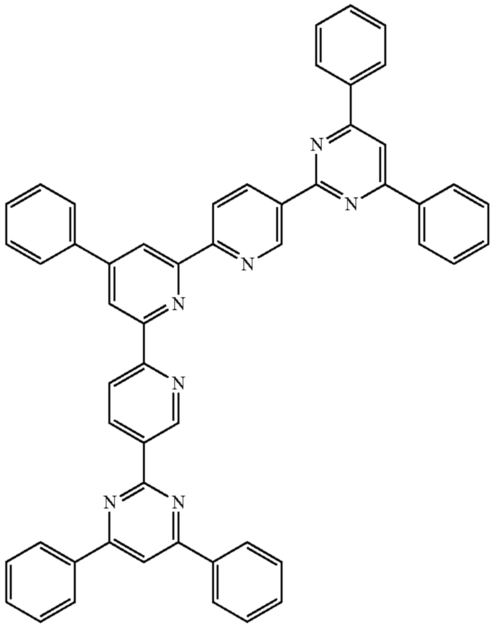
289
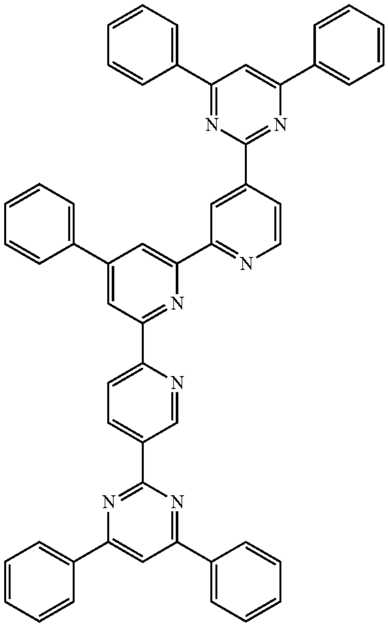

-continued
290
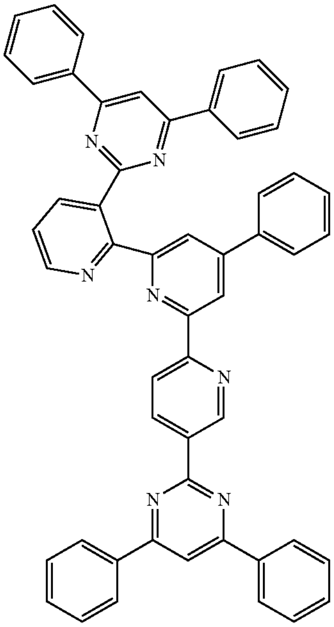
291
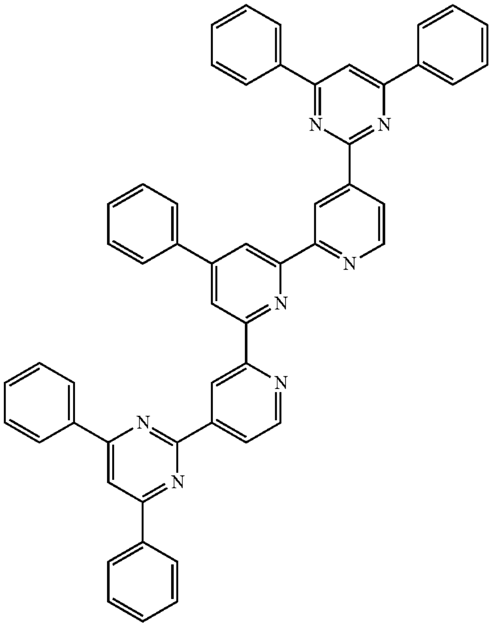
-continued
292
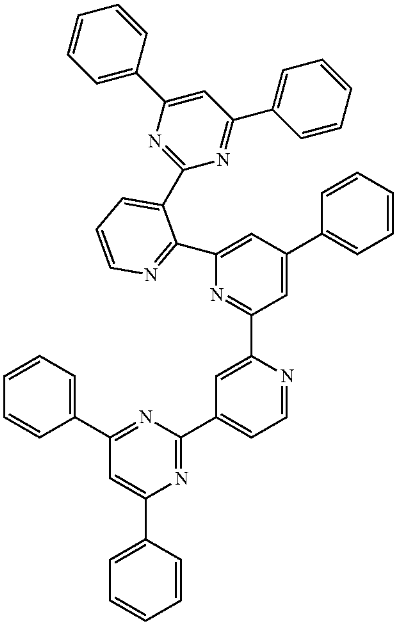
293
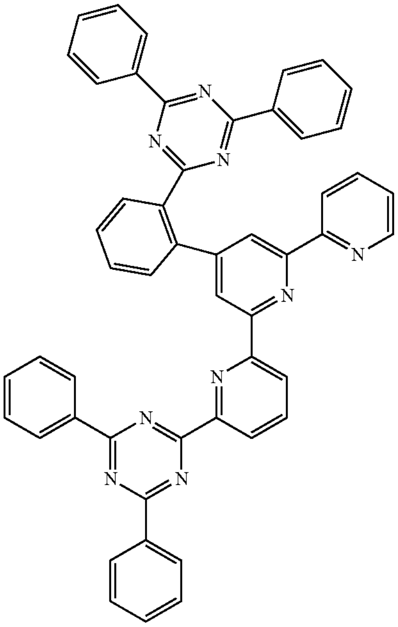

294
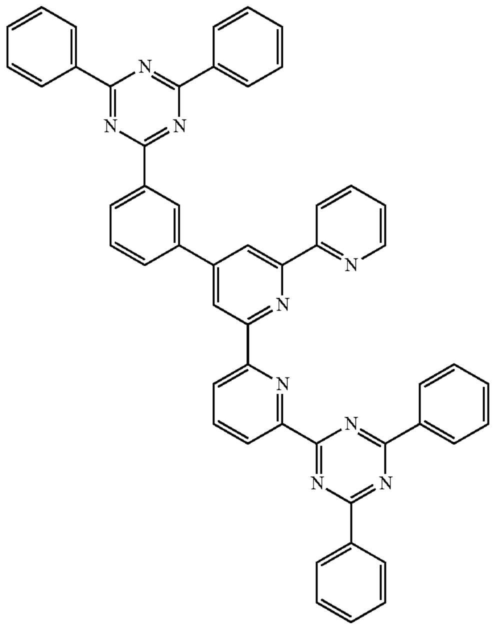
295
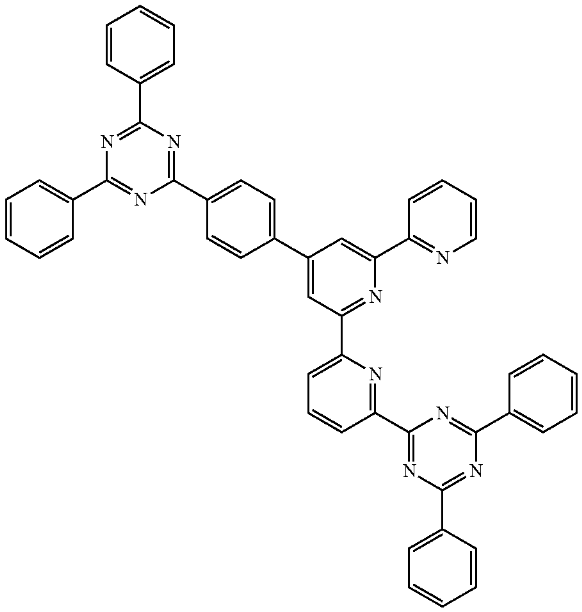
296
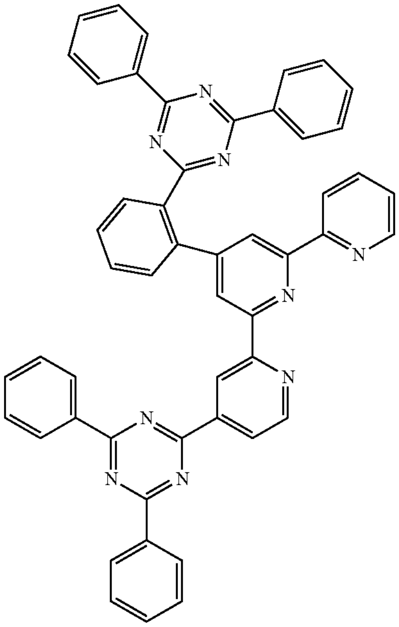
297
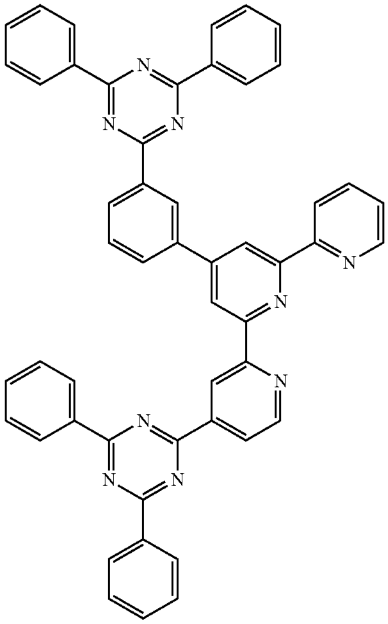

-continued
298
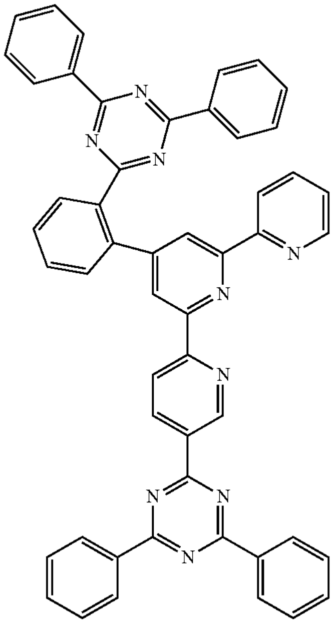
299
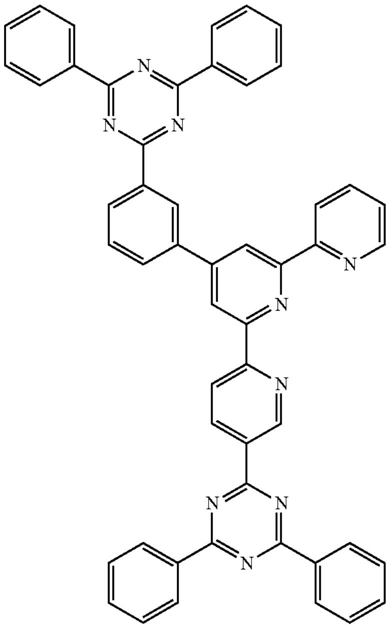
-continued
300
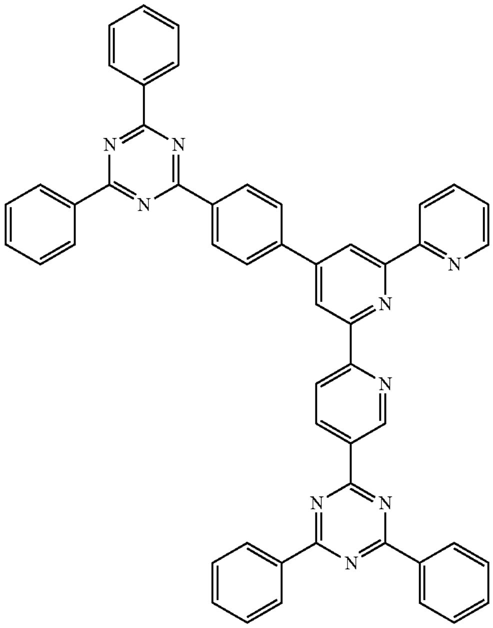
301
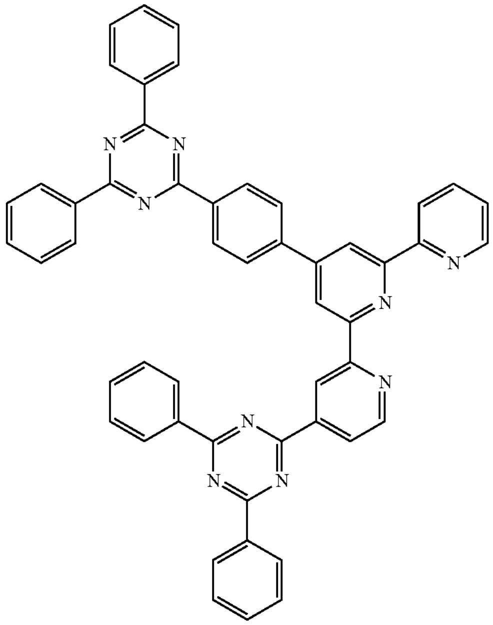

-continued
302
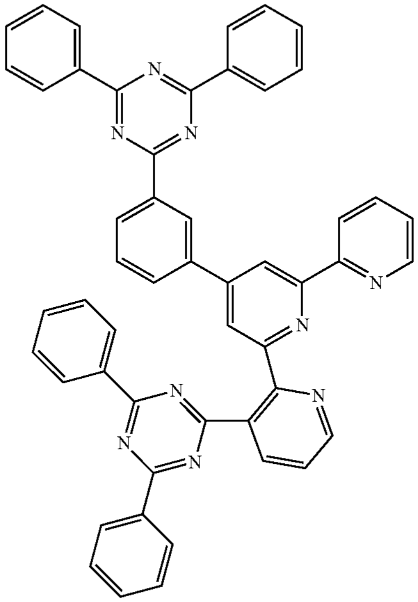
303
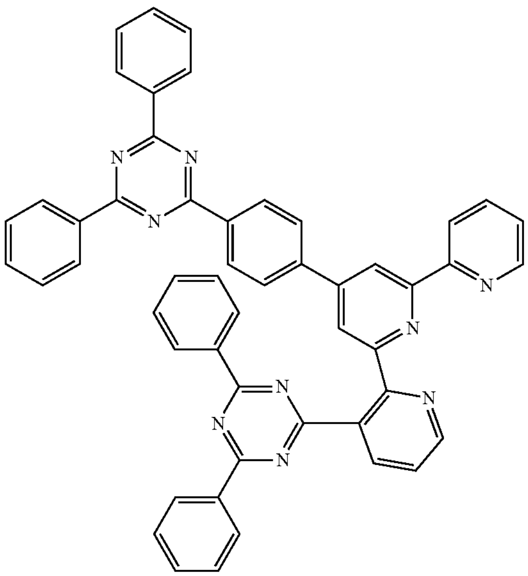
-continued
304
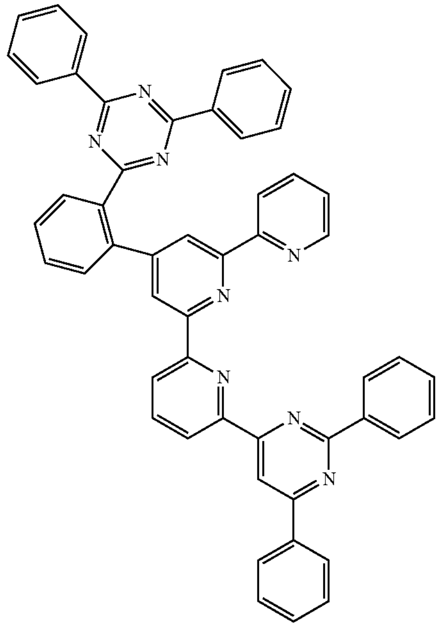
305
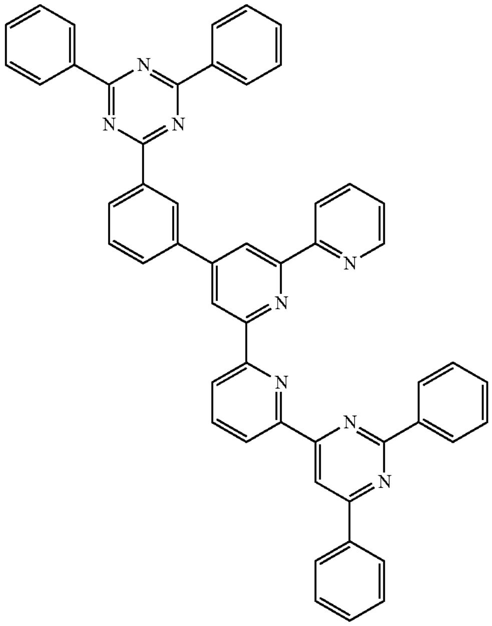

-continued
306
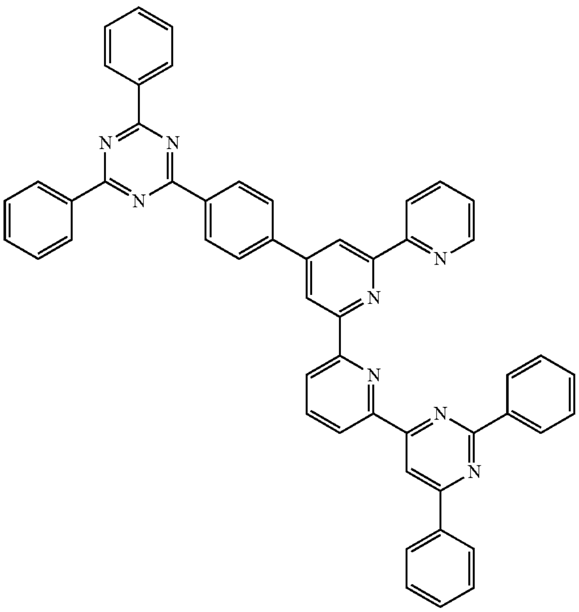
307
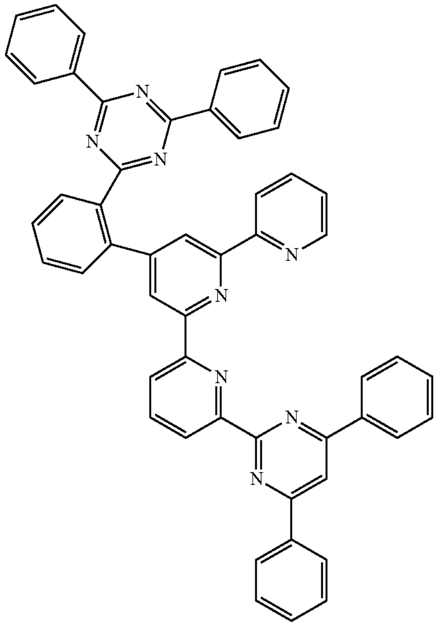
-continued
308
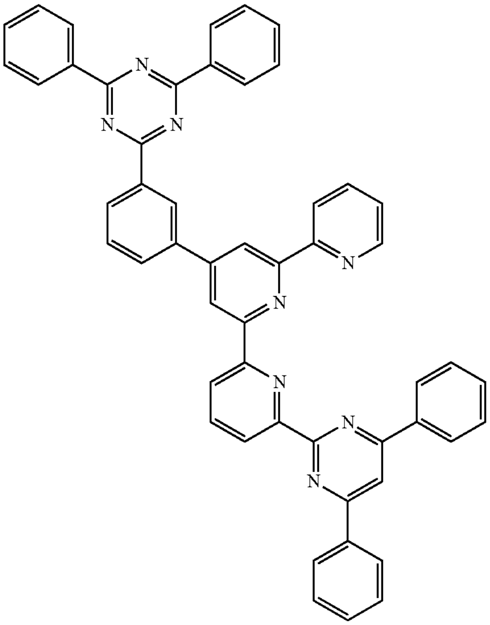
309
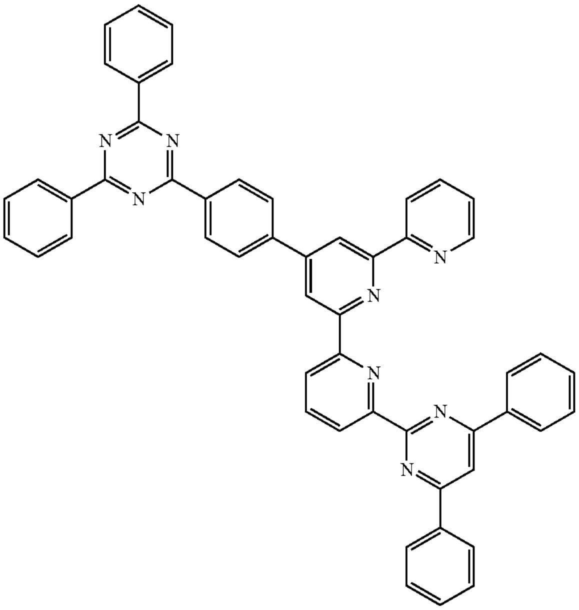

-continued
310
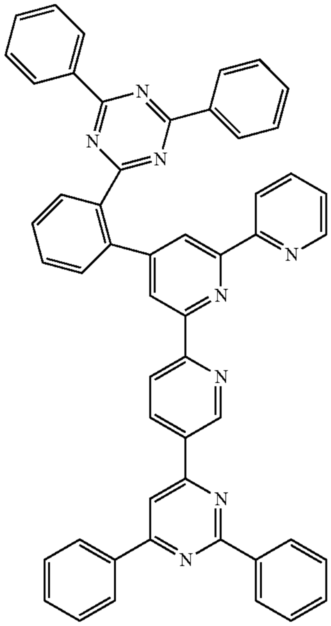
311
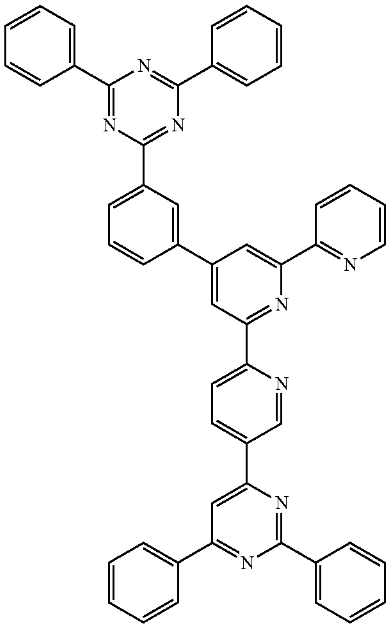
-continued
312
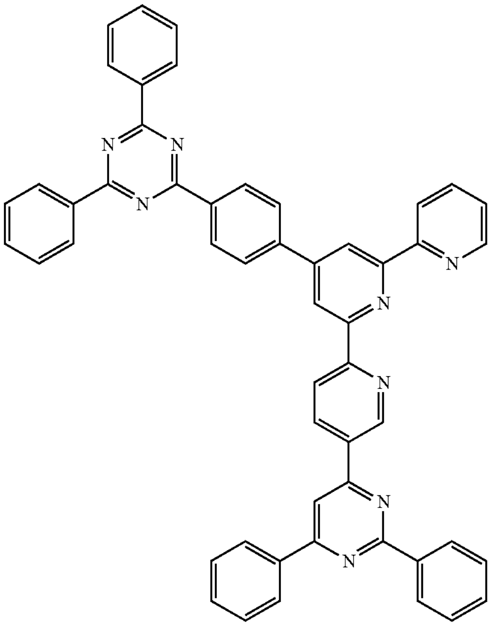
313
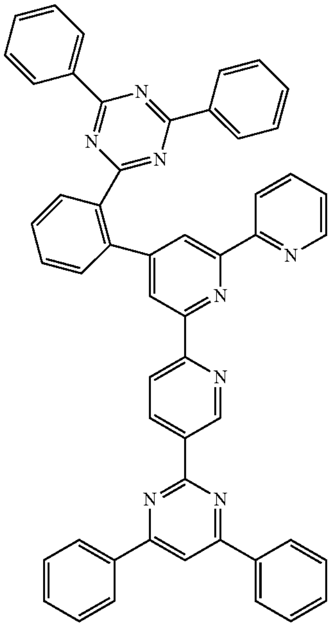

-continued
314
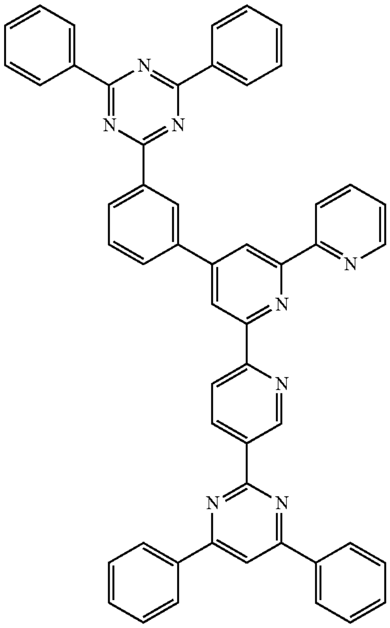
315
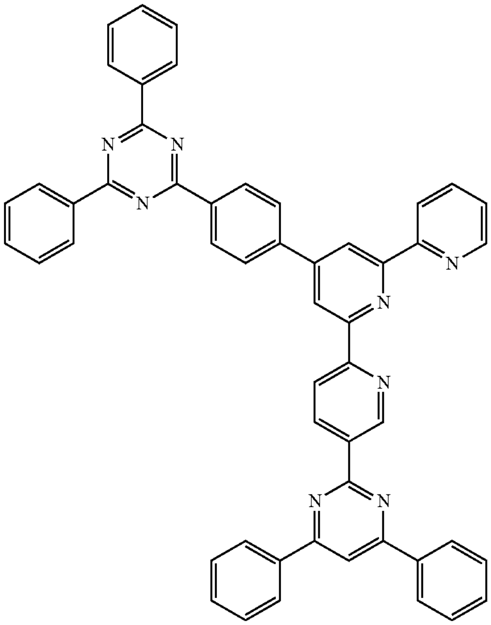
-continued
316
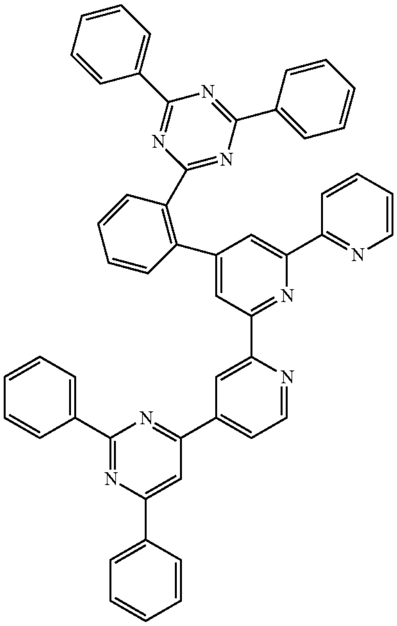
317
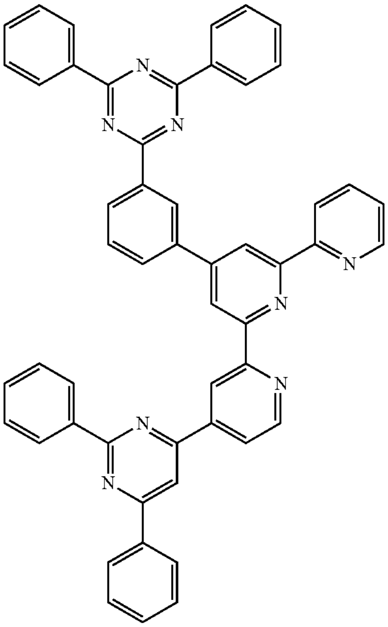

-continued
318
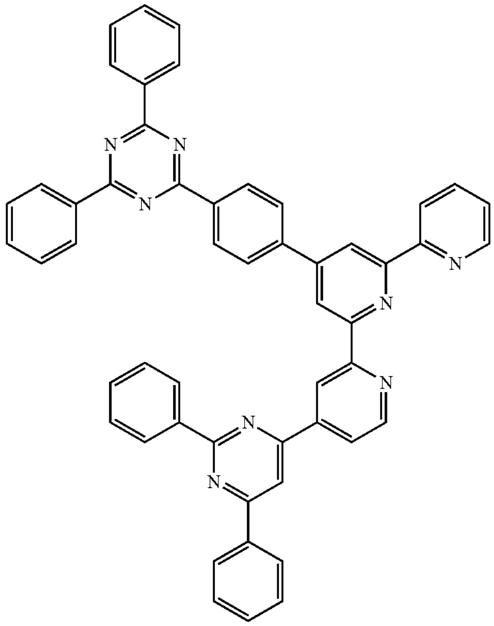
319
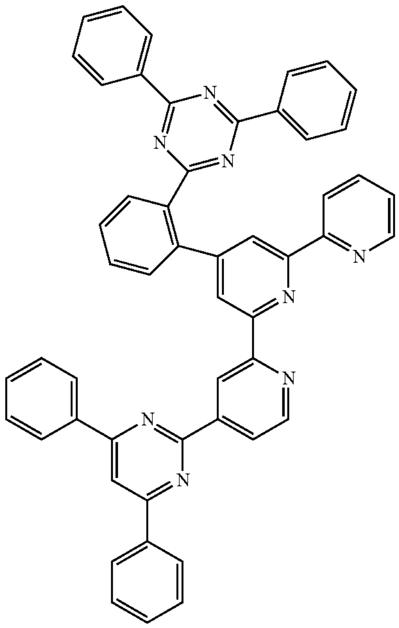
-continued
320
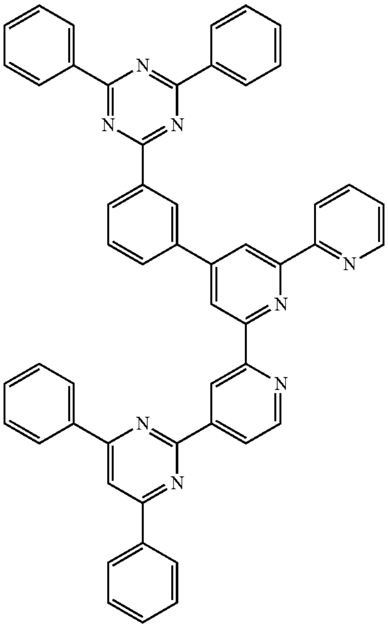
321
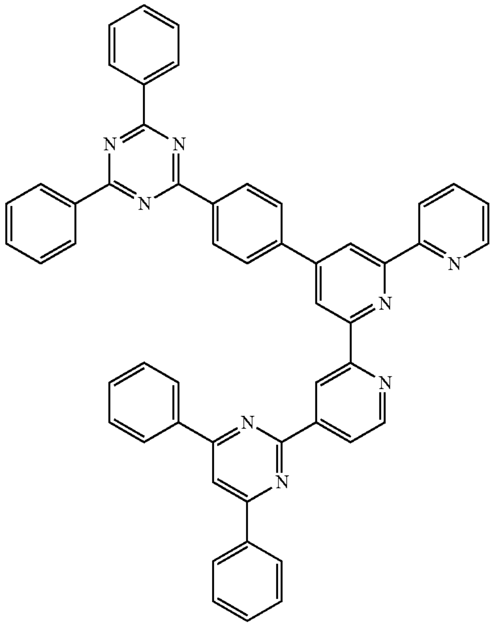

-continued
322
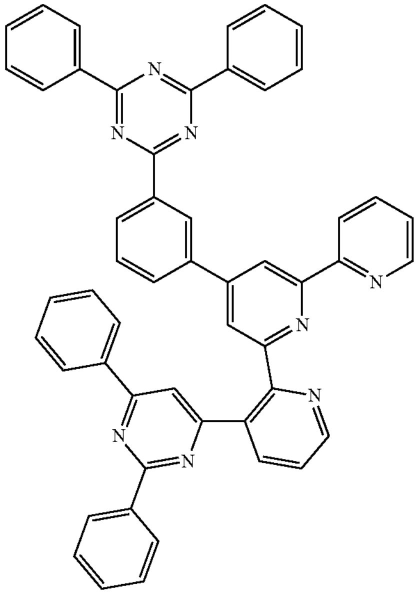
323
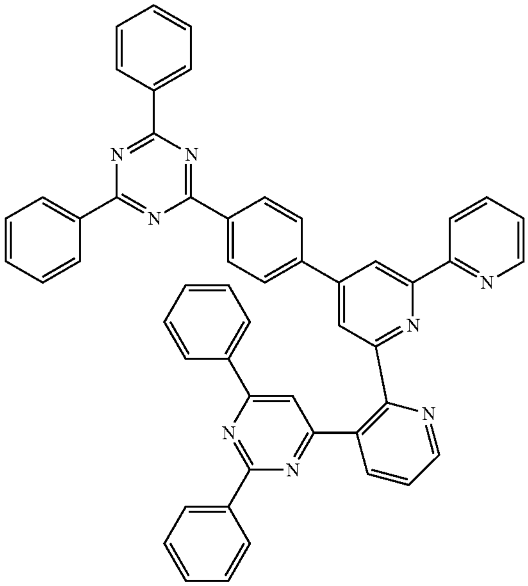
-continued
324
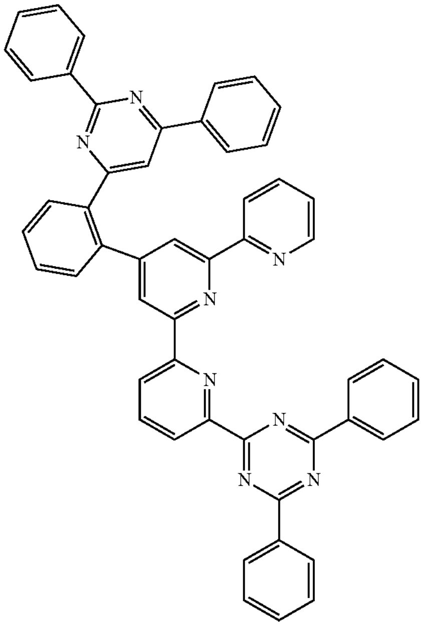
325
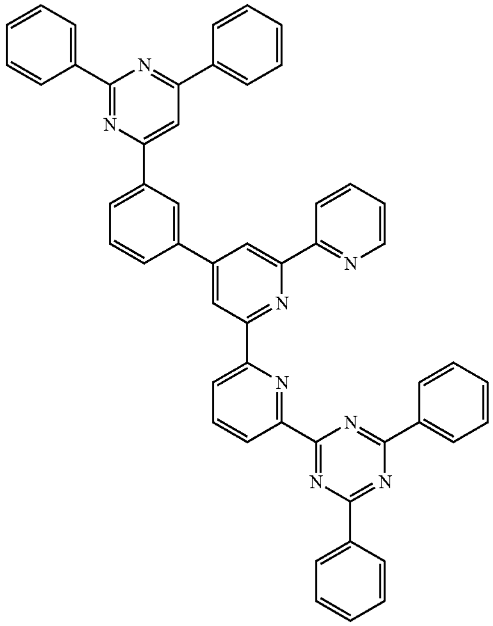

-continued
326
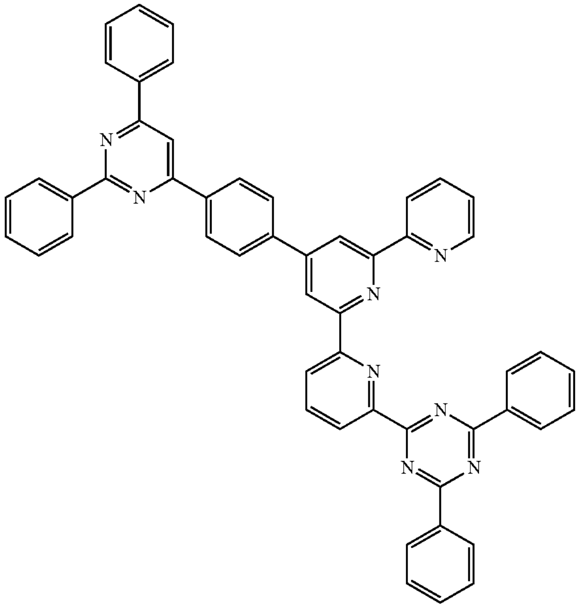
327
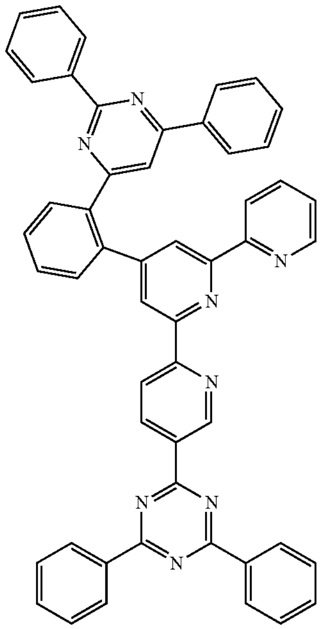
-continued
328
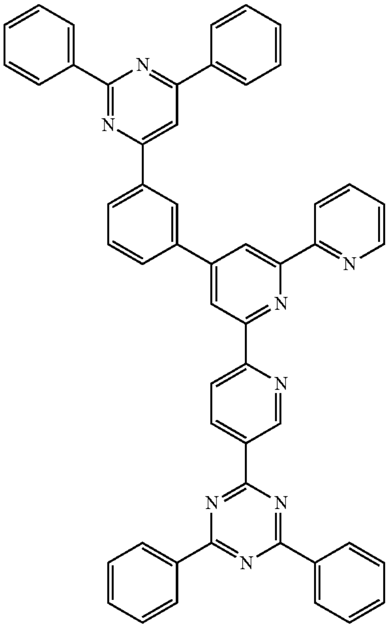
329
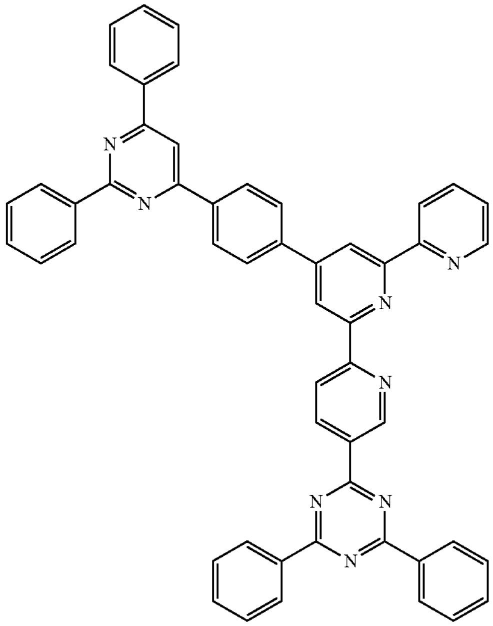

-continued
330
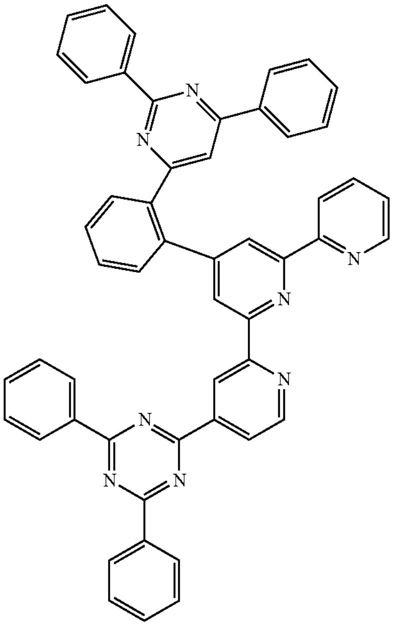
332
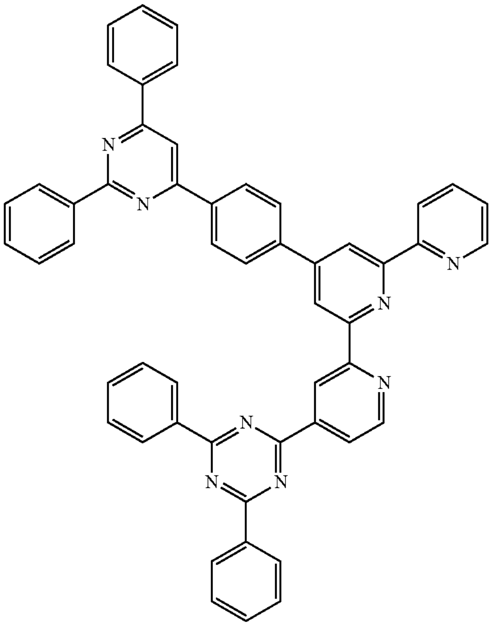
331
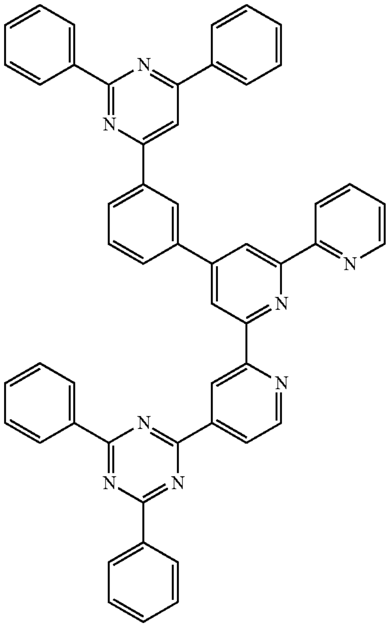
333
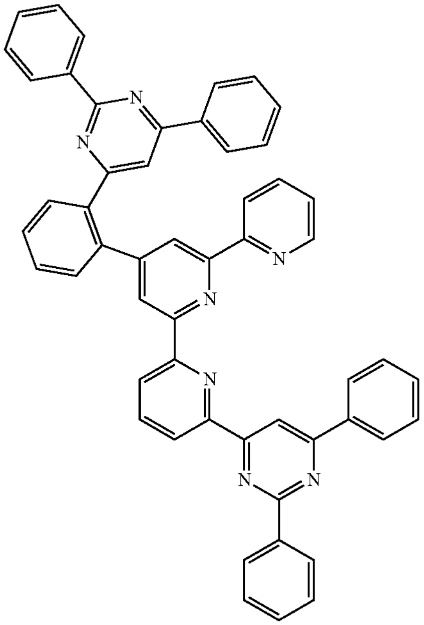

-continued
334
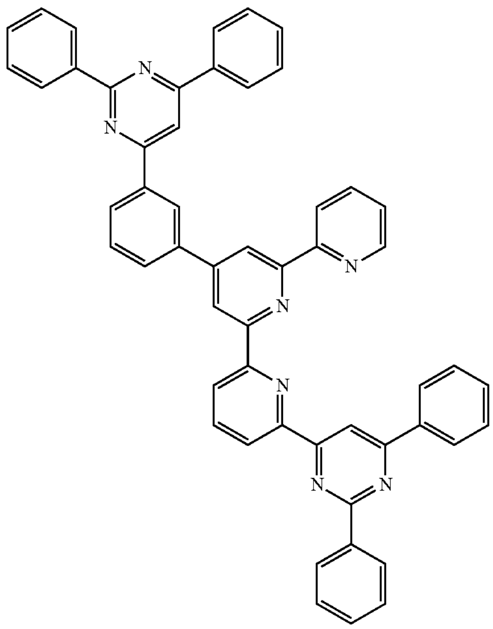
-continued
336
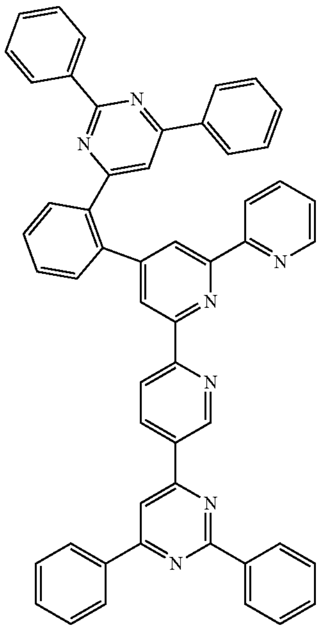
335
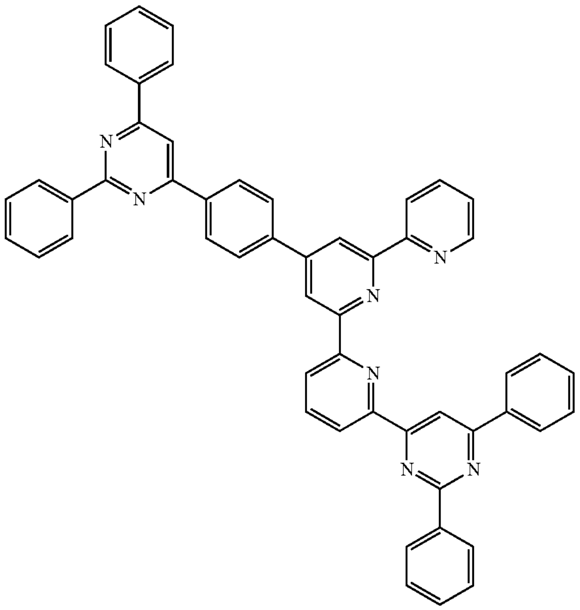
337
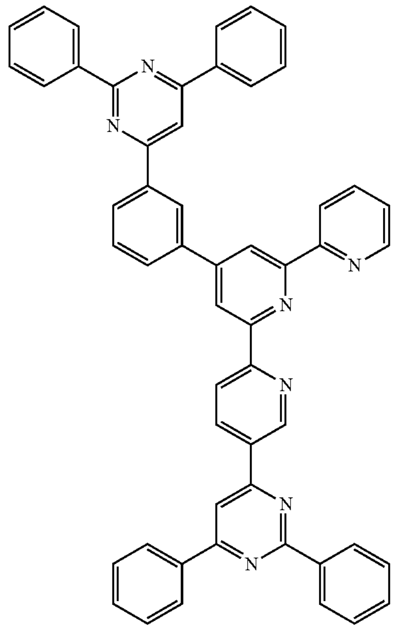

-continued
338
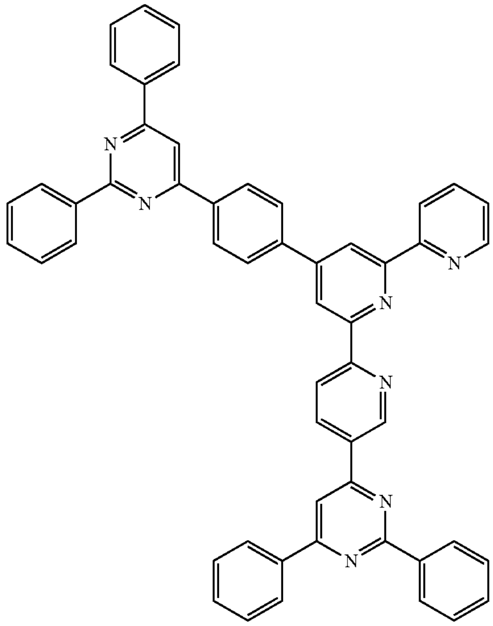
340
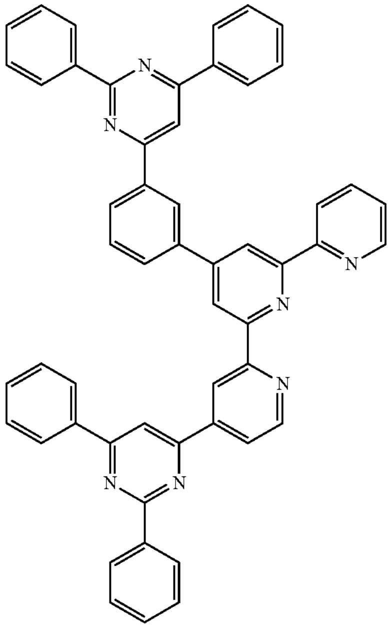
339
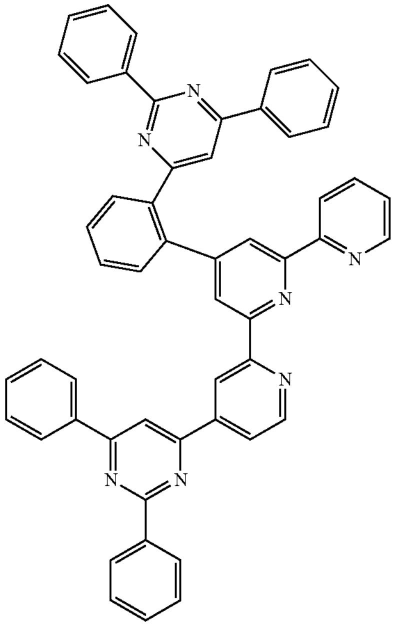
341
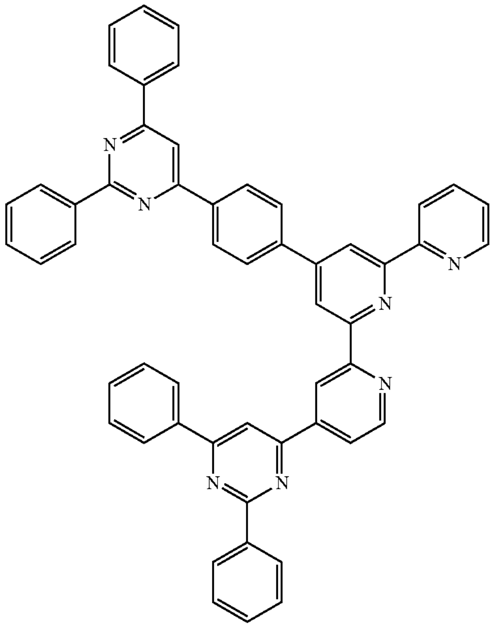

-continued
342
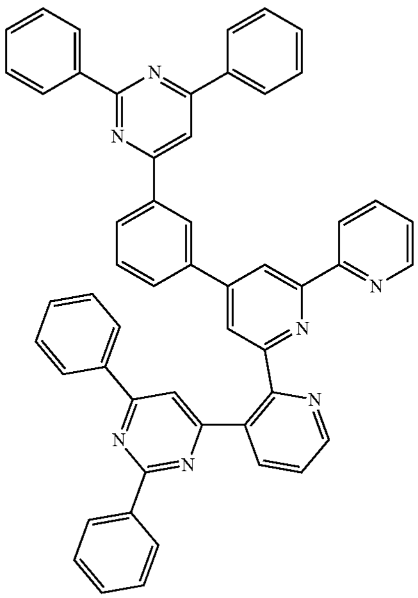
343
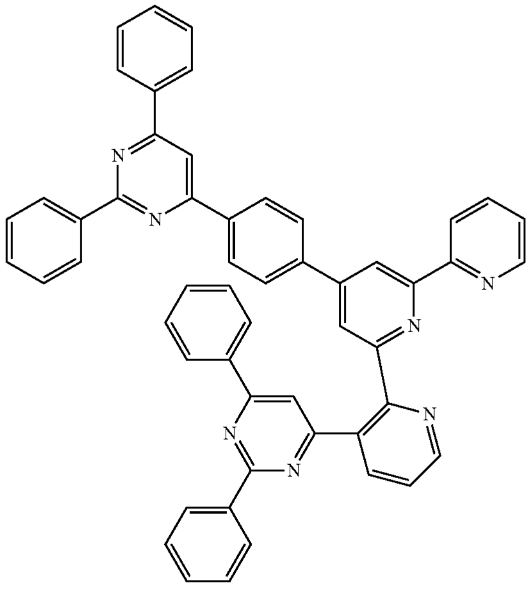
-continued
344
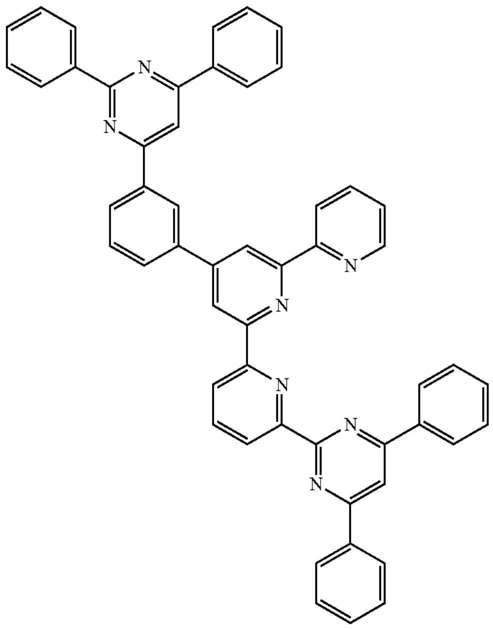
345
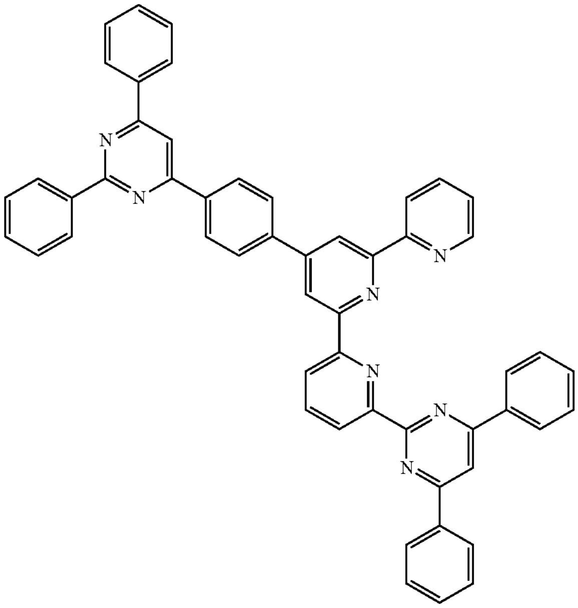

-continued
346
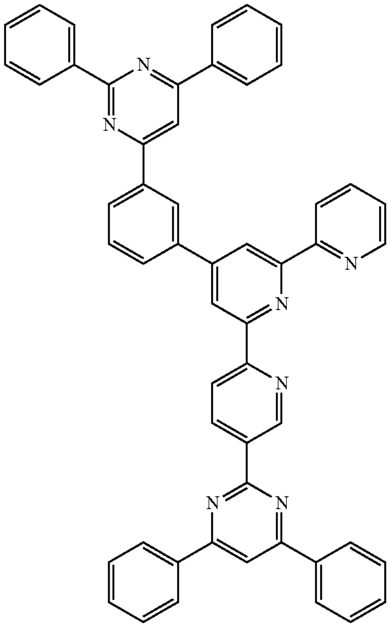
347
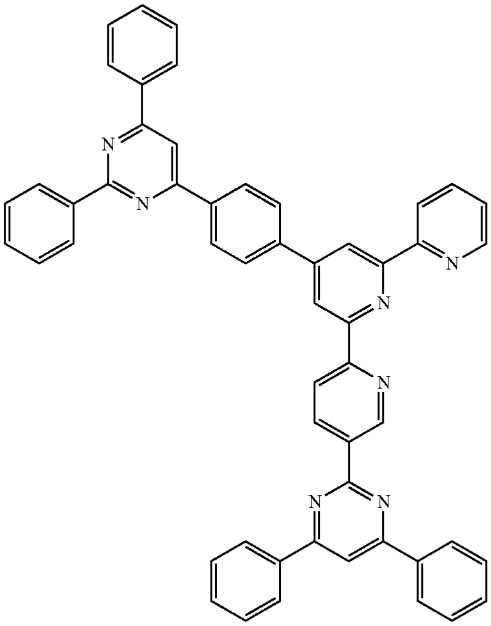
-continued
348
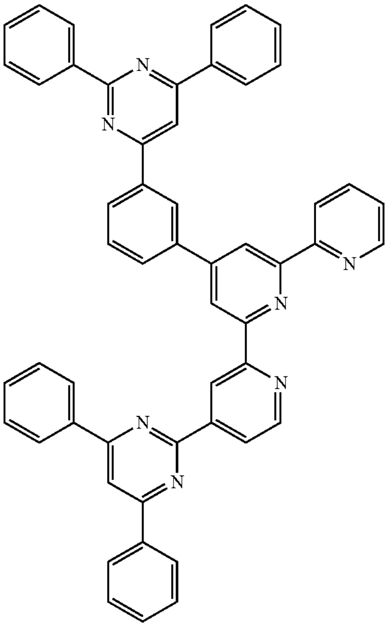
349
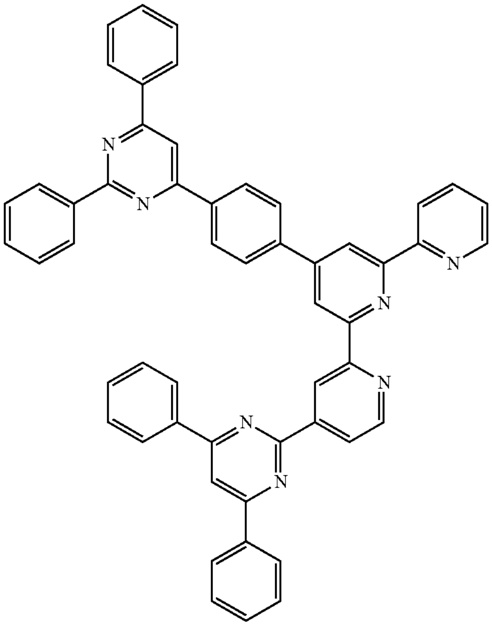

-continued
350
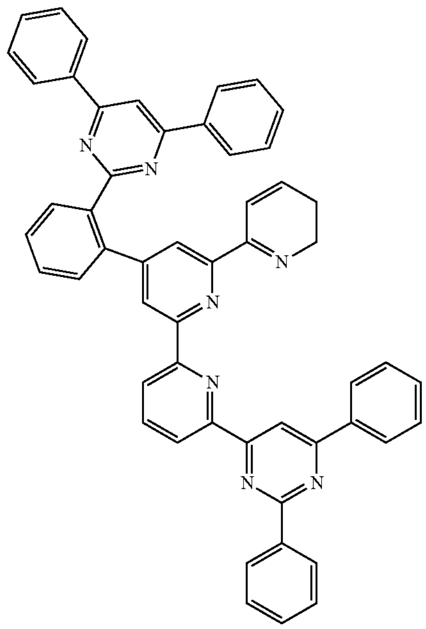
351
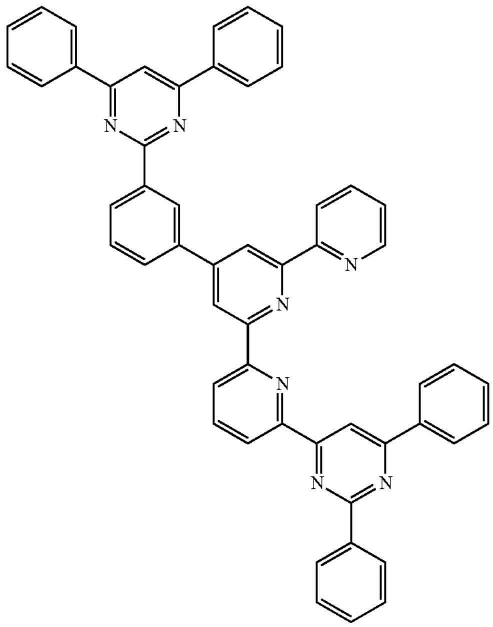
-continued
352
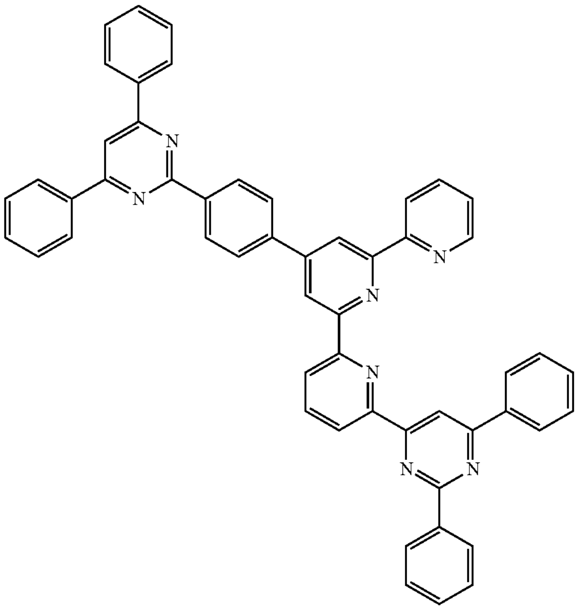
353
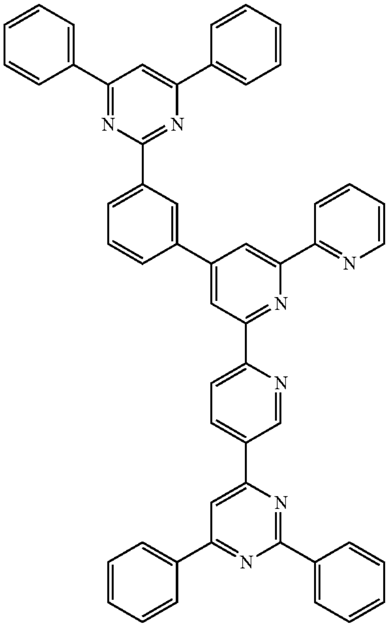

-continued
354
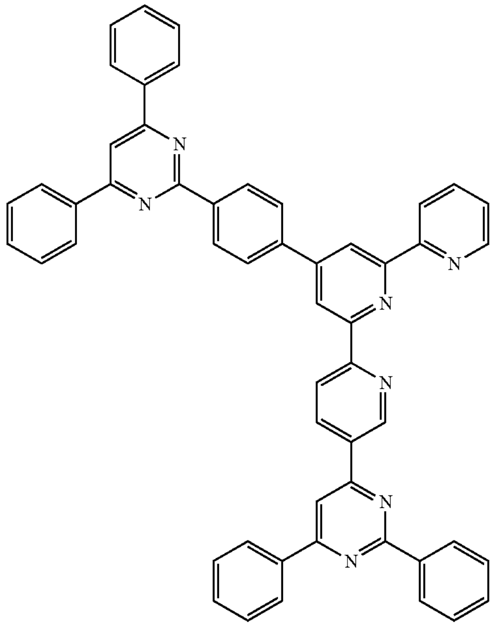
355
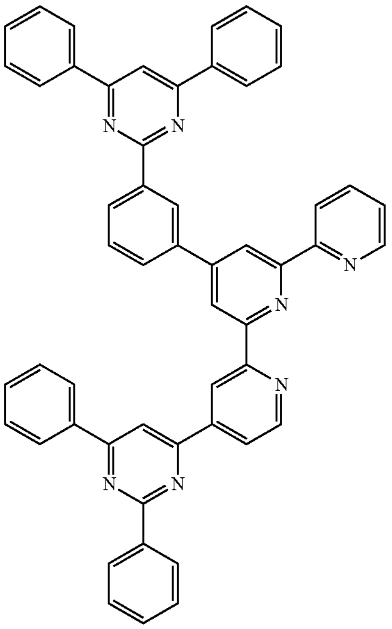
-continued
356
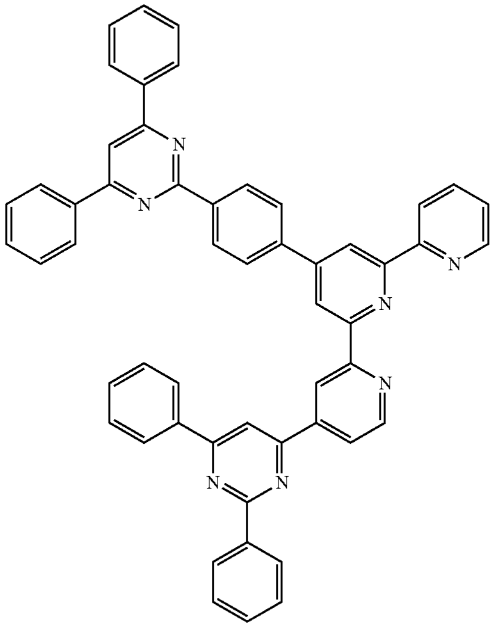
357
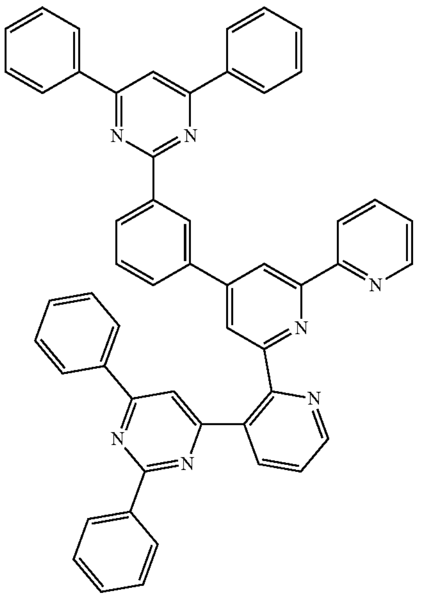

-continued
358
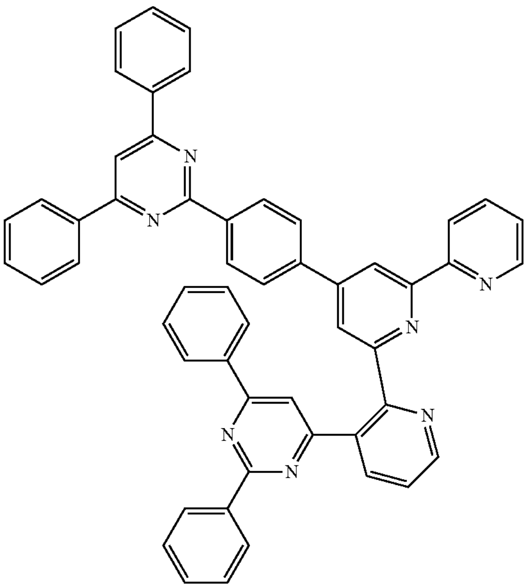
359
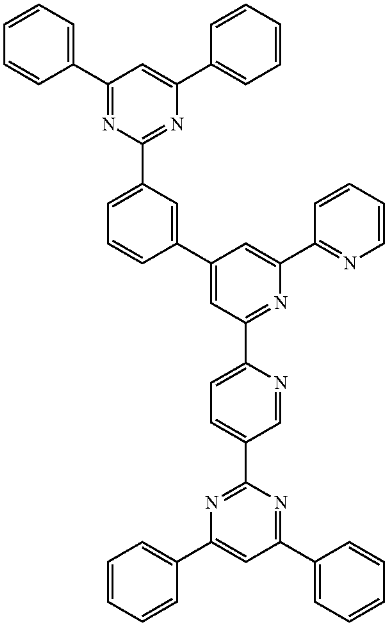
-continued
360
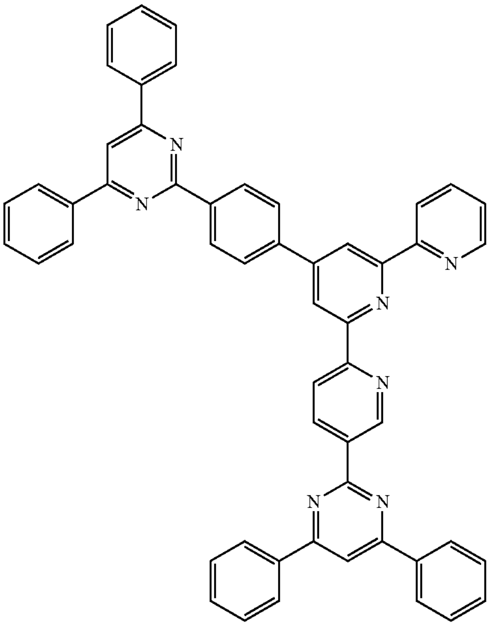
361
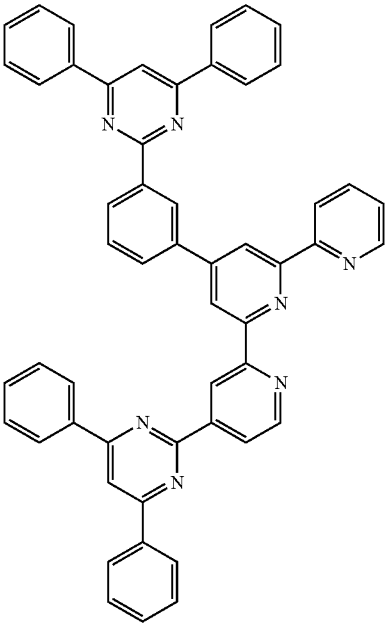

-continued
362
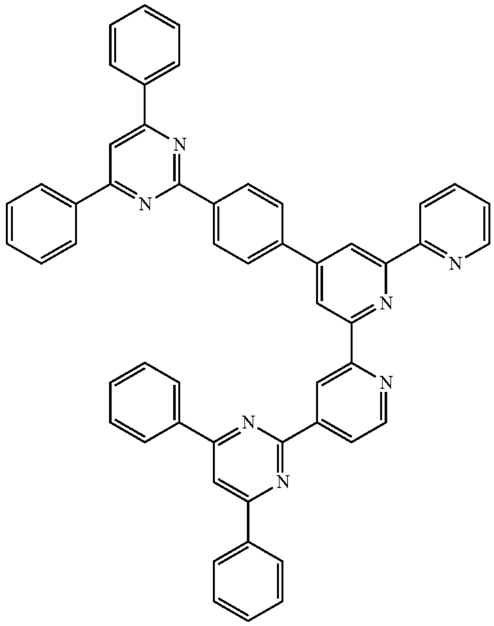
363
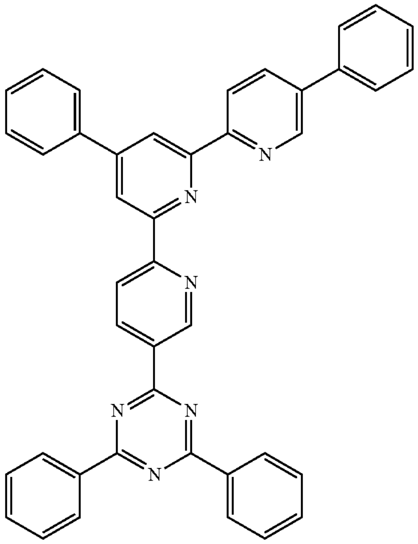
364
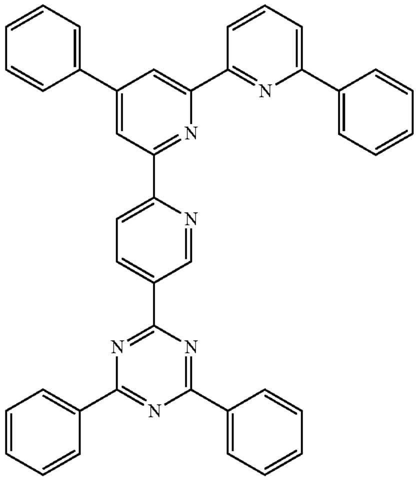
-continued
365
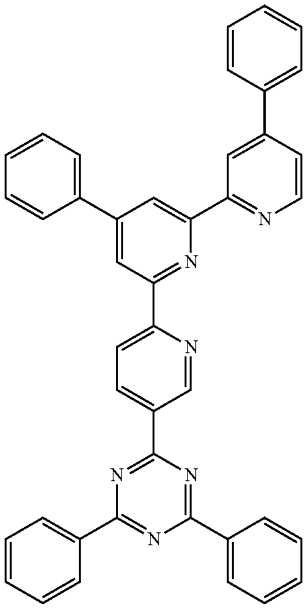
366
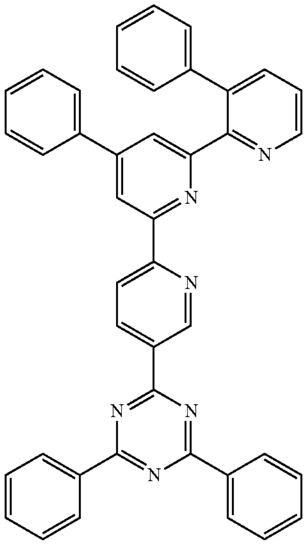

-continued
367
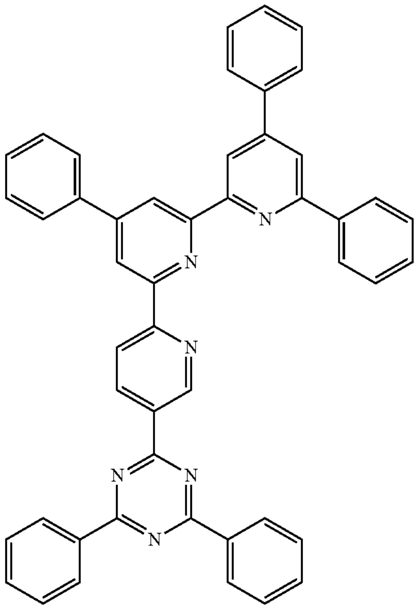
368
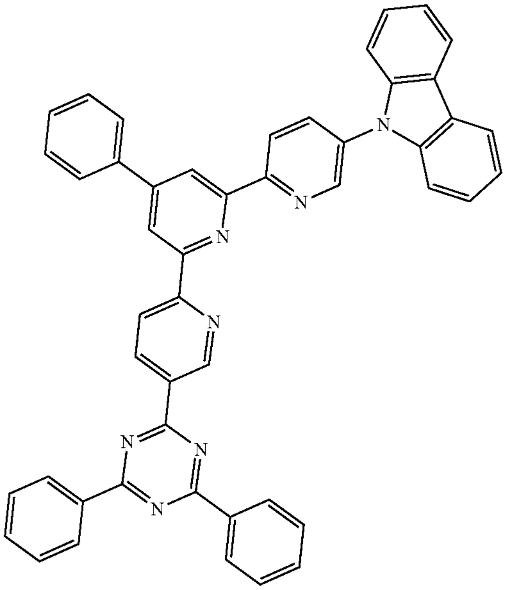
-continued
369
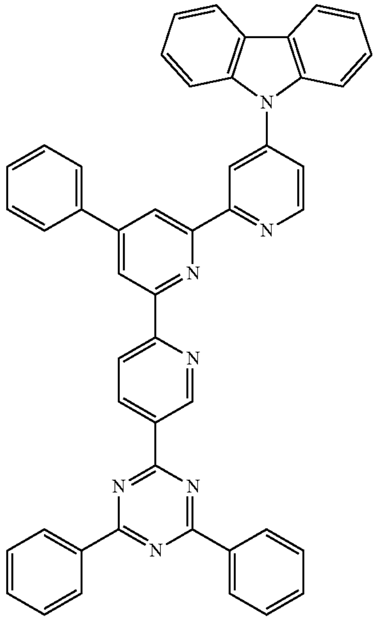
370
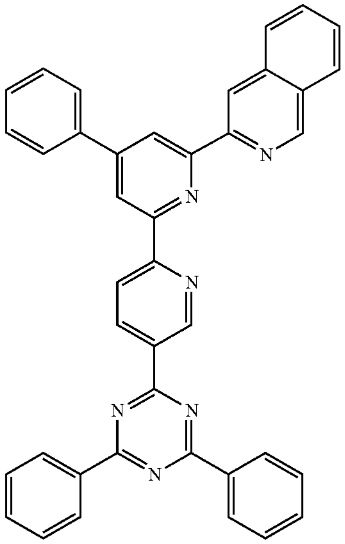
371
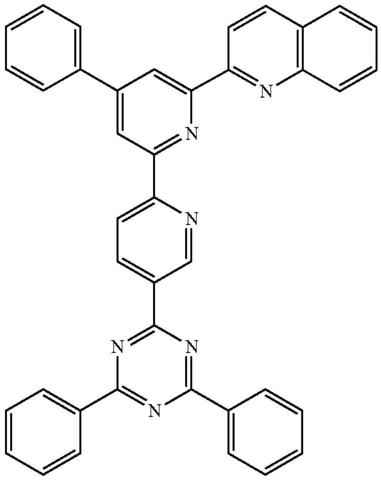

-continued
372
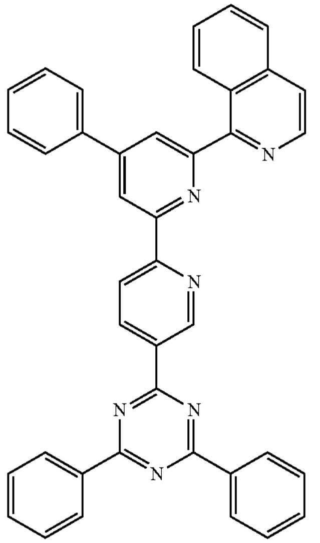
373
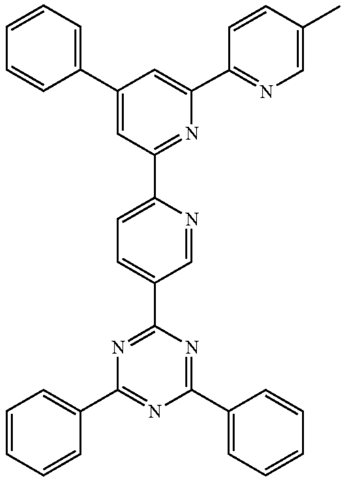
374
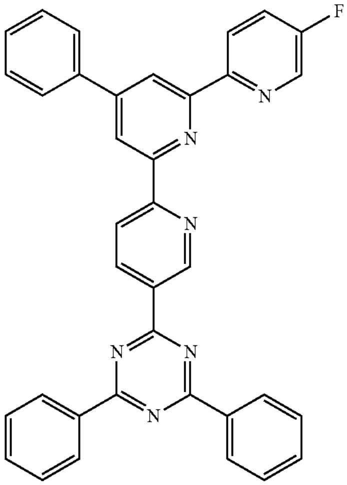
-continued
375
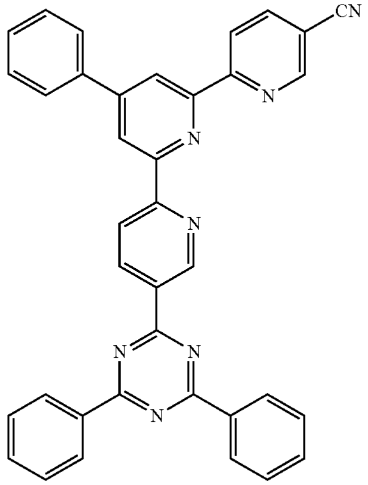
376
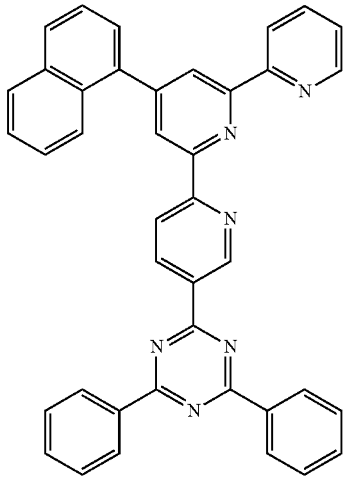
377
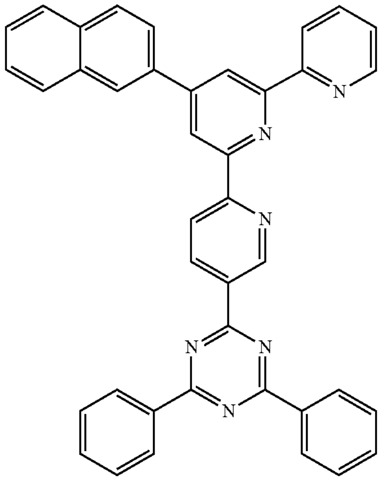

-continued
378
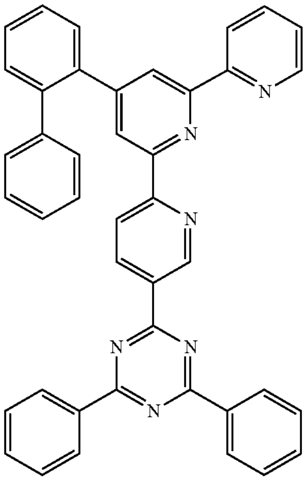
379
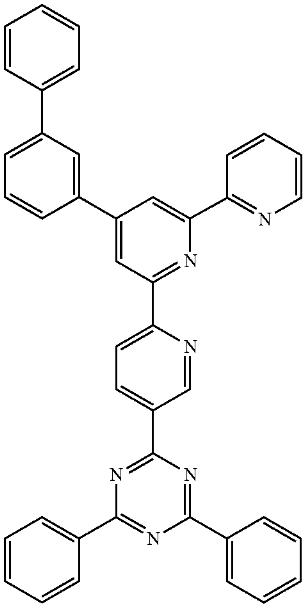
380
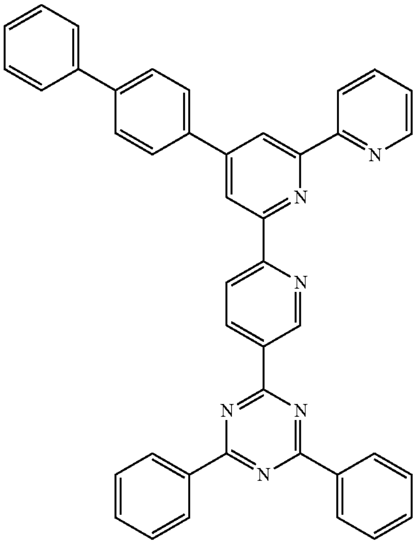
-continued
381
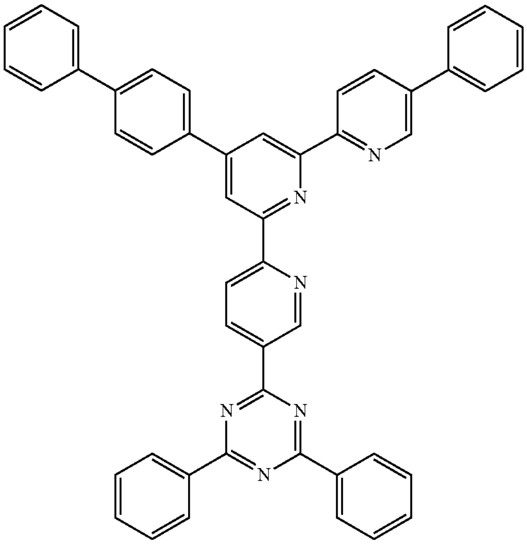
382
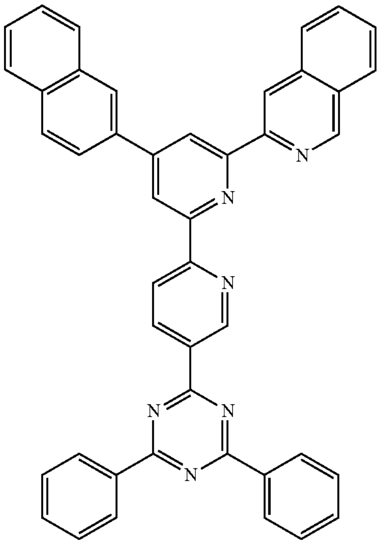
383
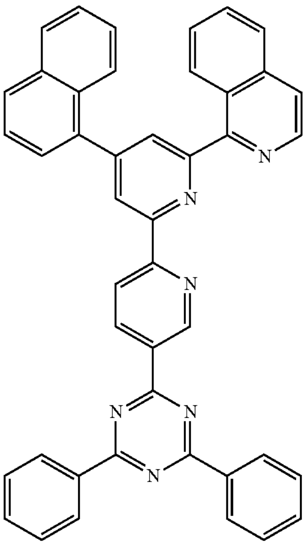

-continued
384
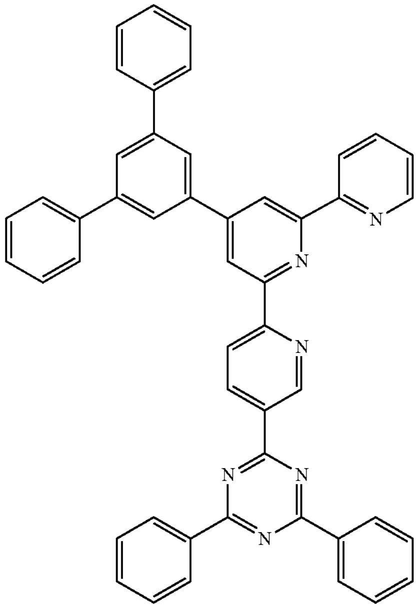
385
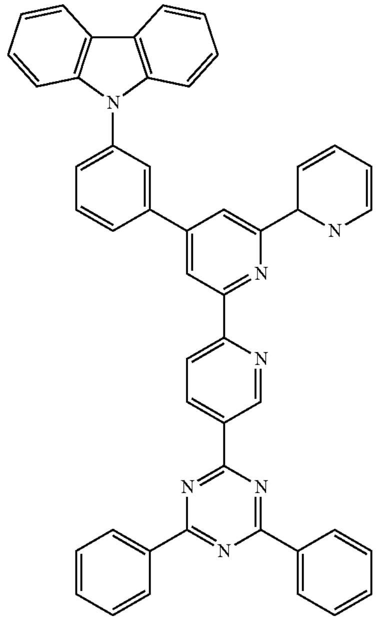
-continued
386
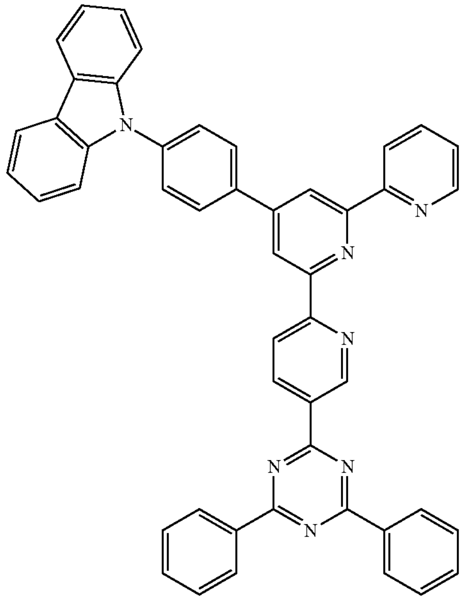
387
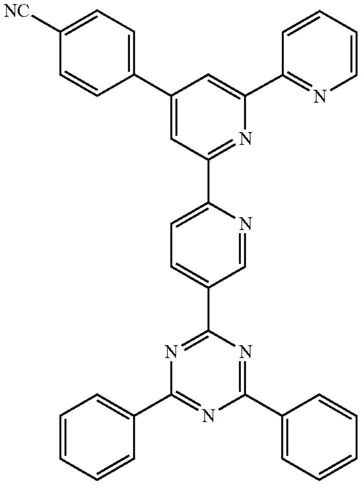
388
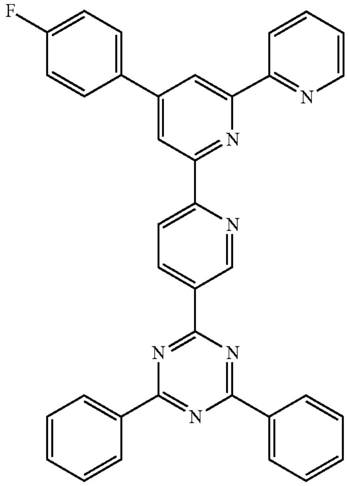

-continued
389
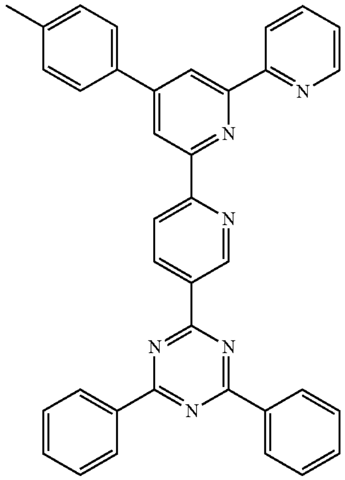
390
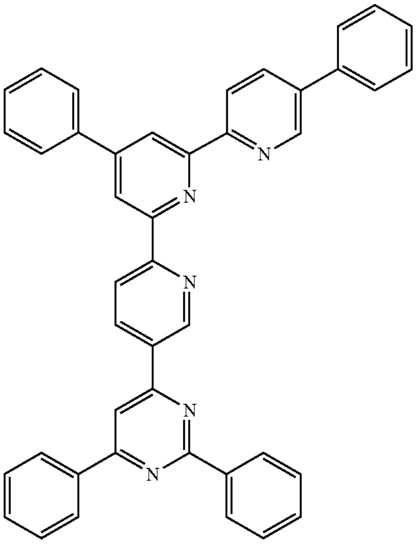
391
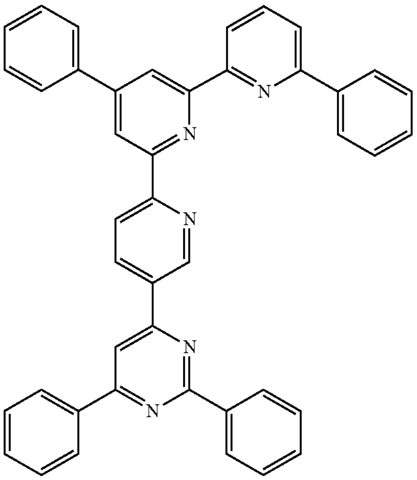
-continued
392
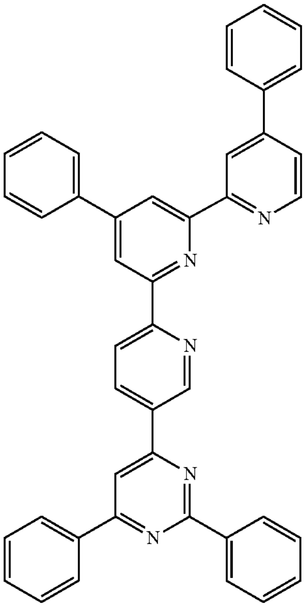
393
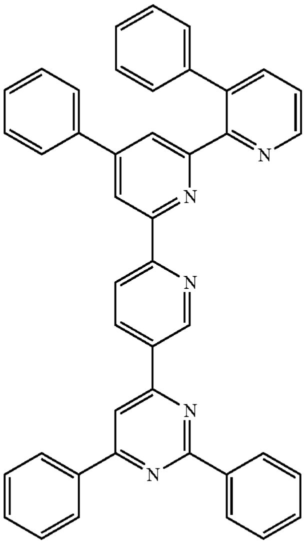

-continued
394
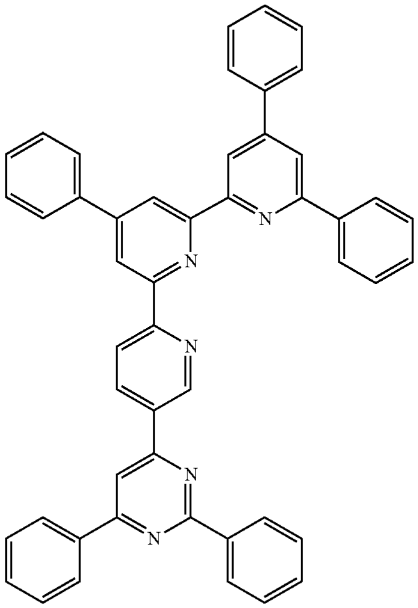
395
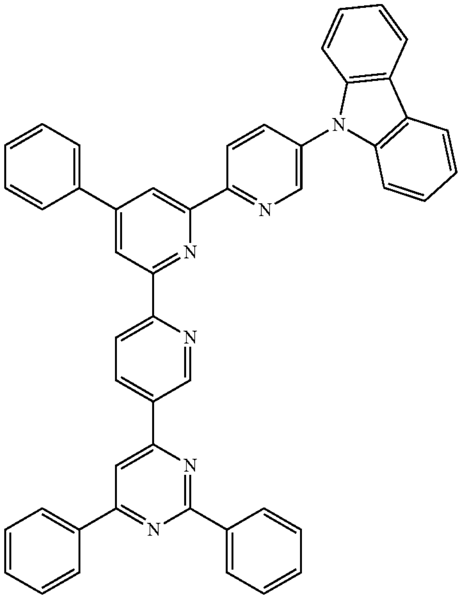
-continued
396
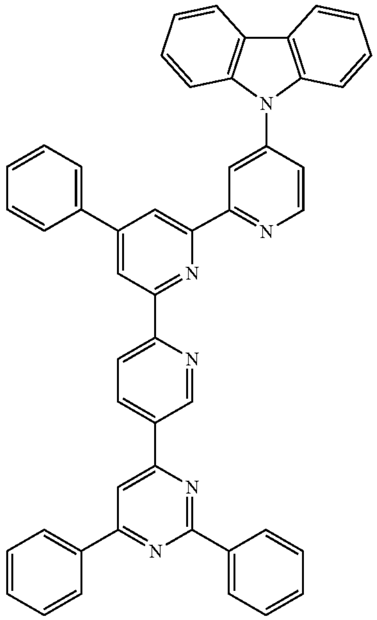
397
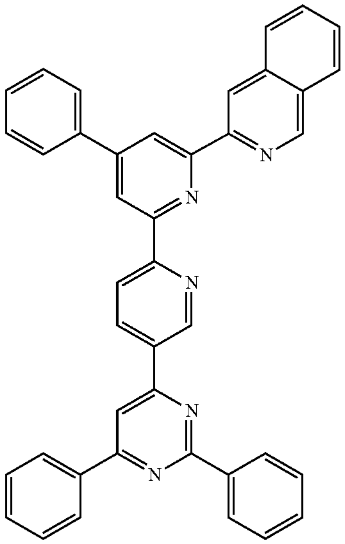
398
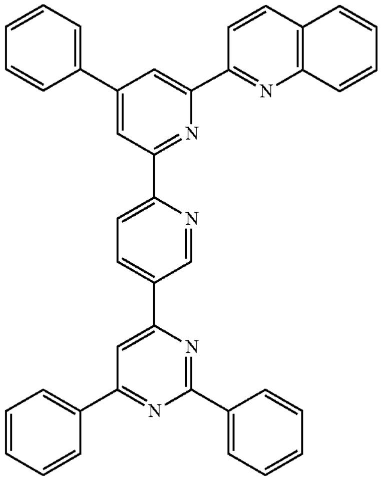

-continued
399
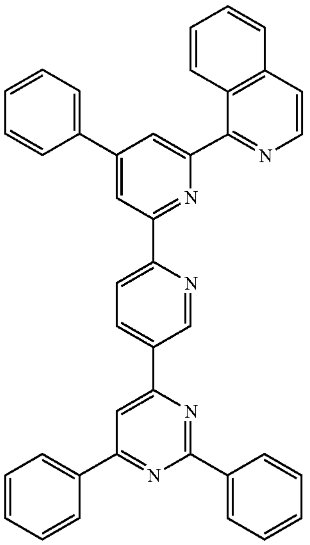
400
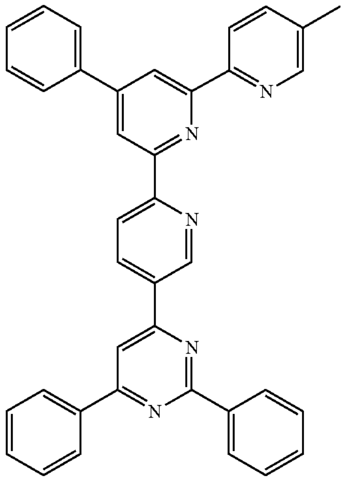
401
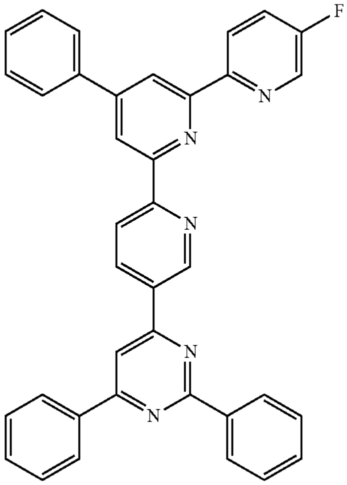
-continued
402
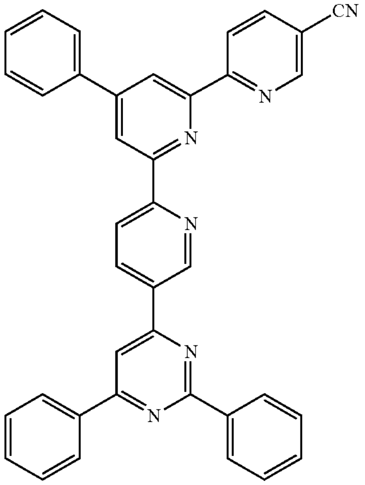
403
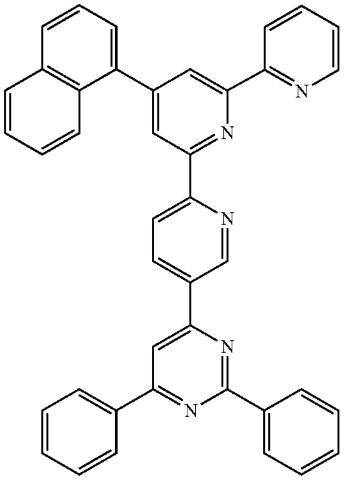
404
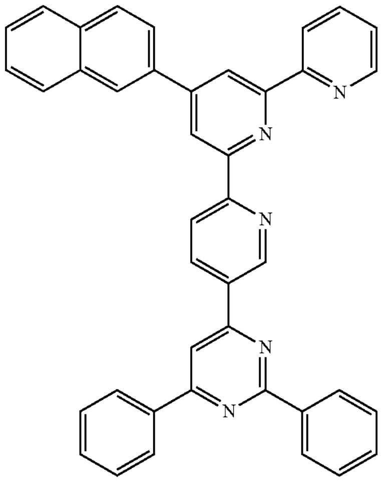

-continued
405
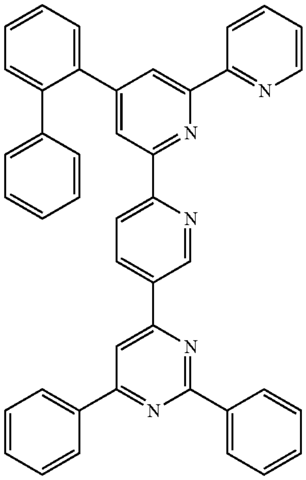
406
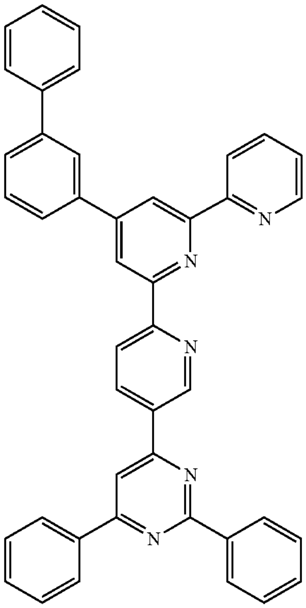
407
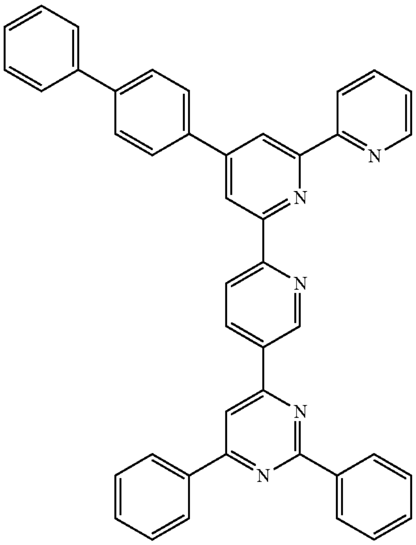
-continued
408
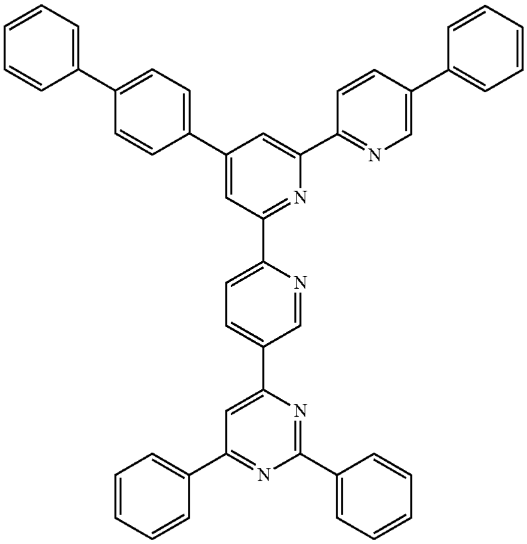
409
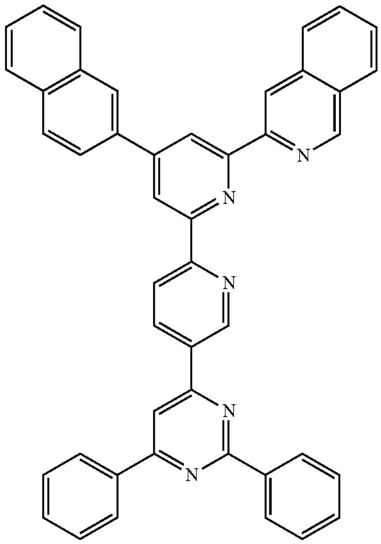
410
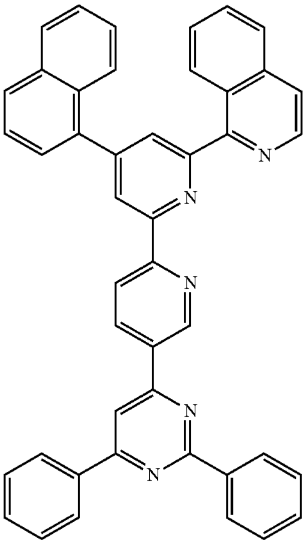

-continued
411
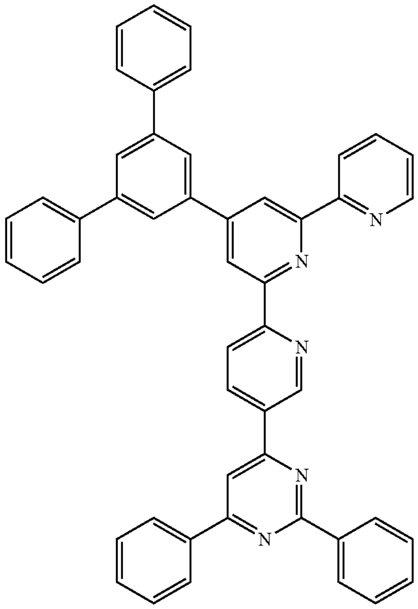
412
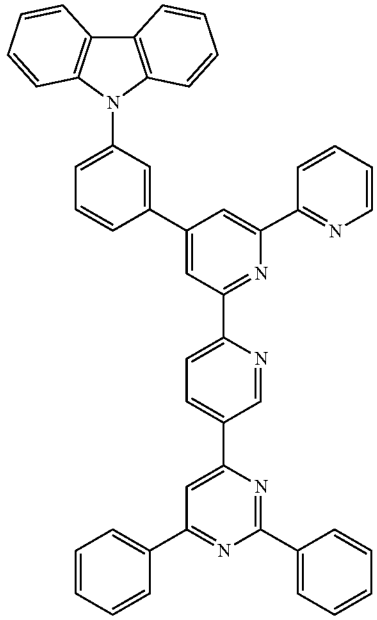
-continued
413
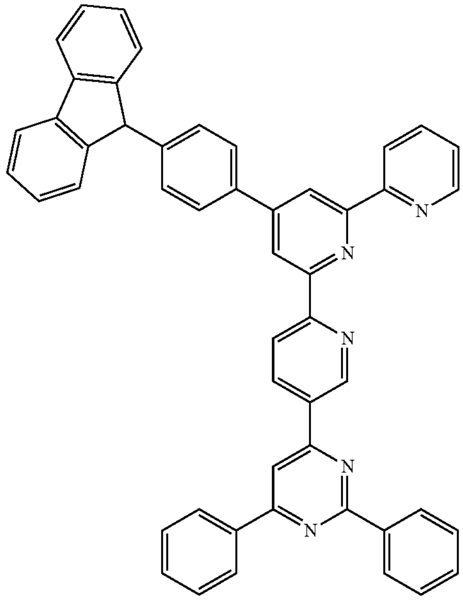
414
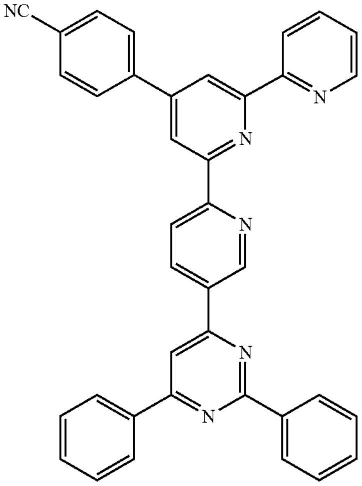
415
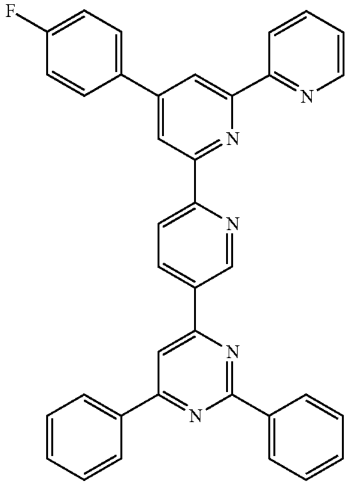

-continued
416
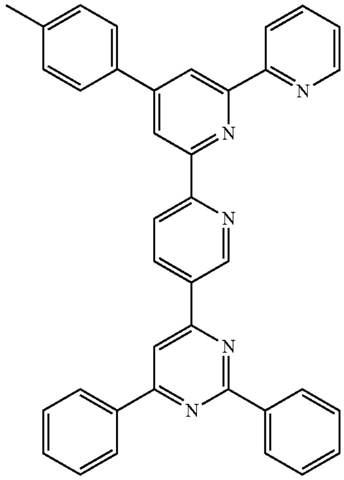
417
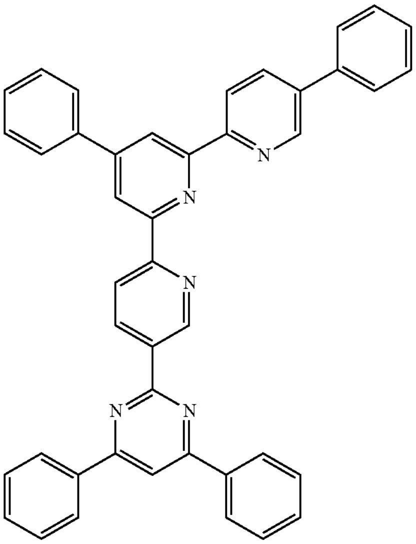
418
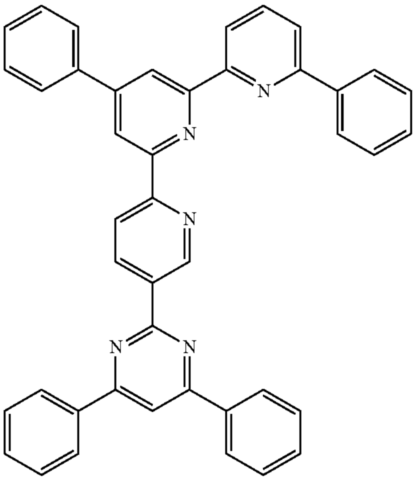
-continued
419
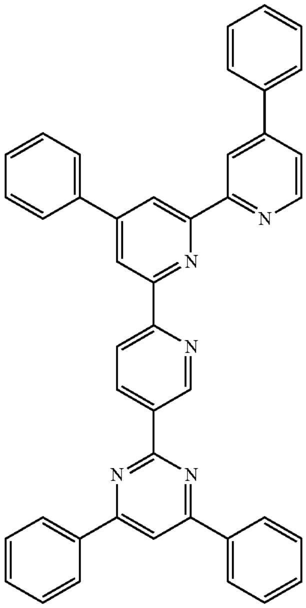
420
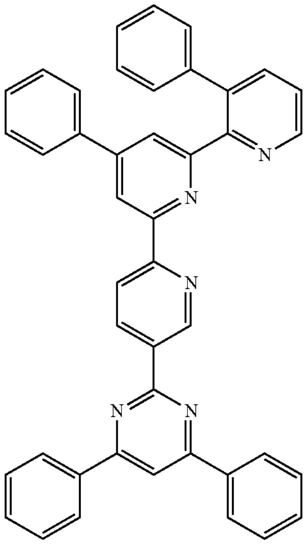

-continued
421
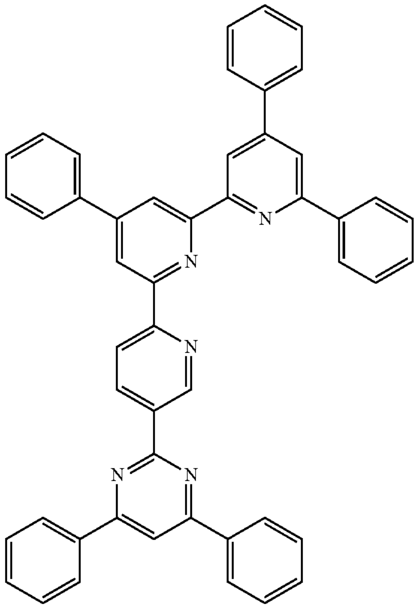
422
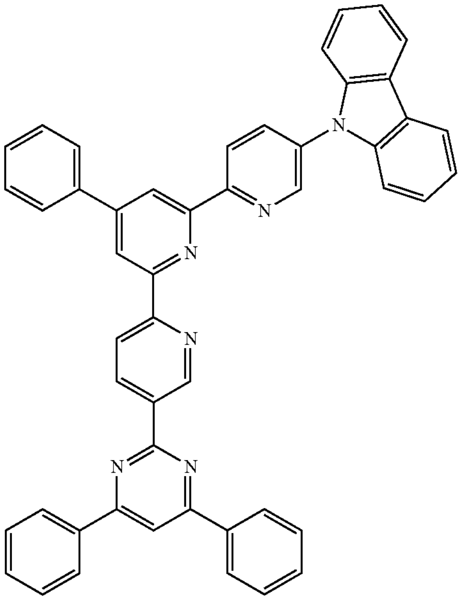
-continued
423
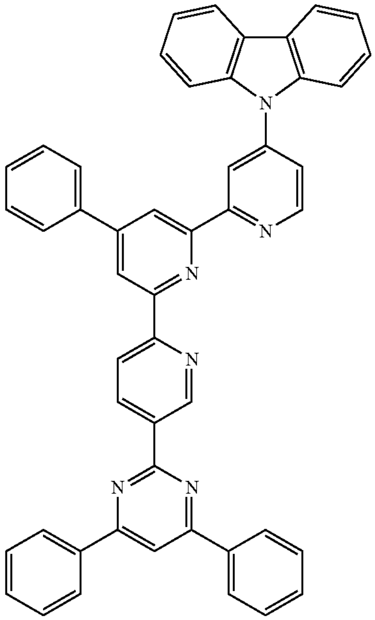
424
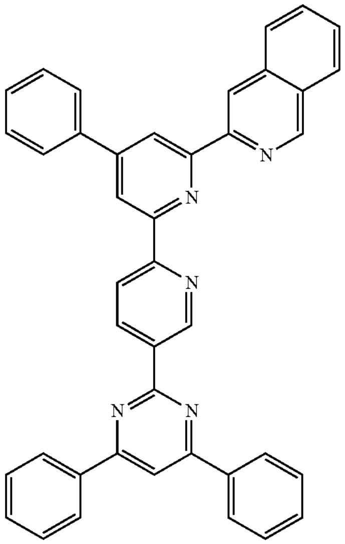
425
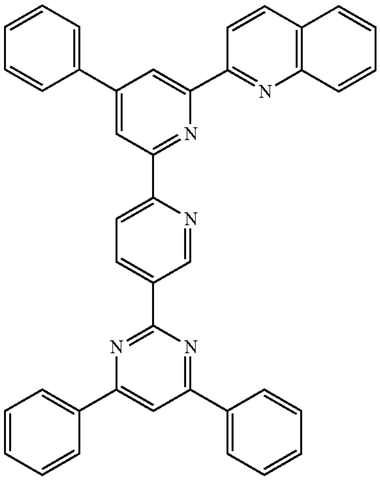

-continued
426
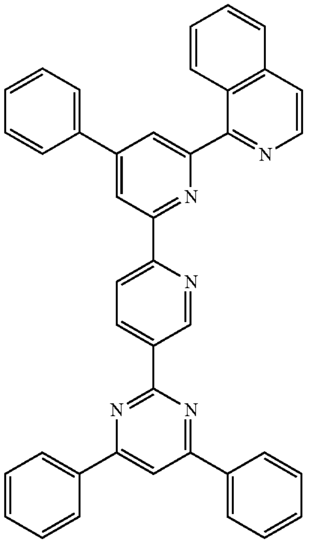
427
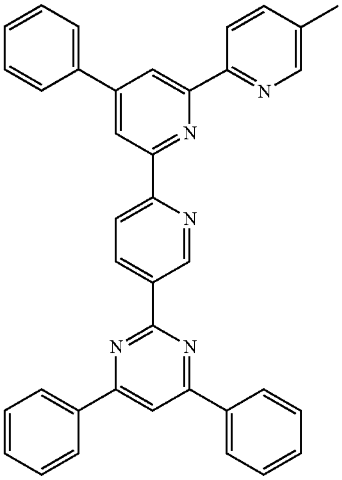
428
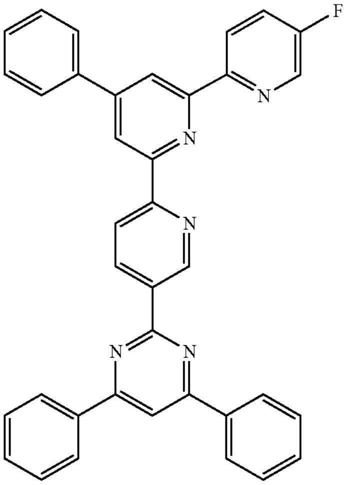
-continued
429
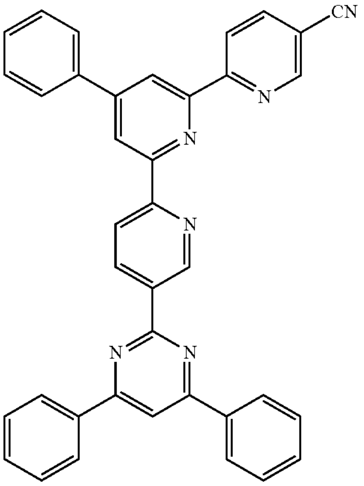
430
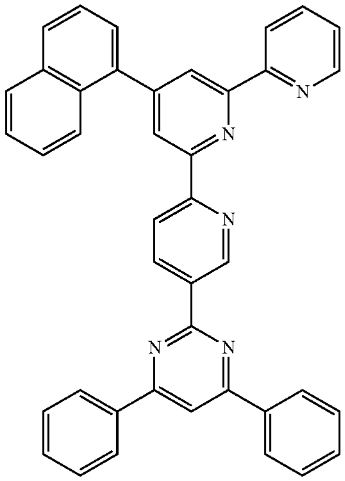
431
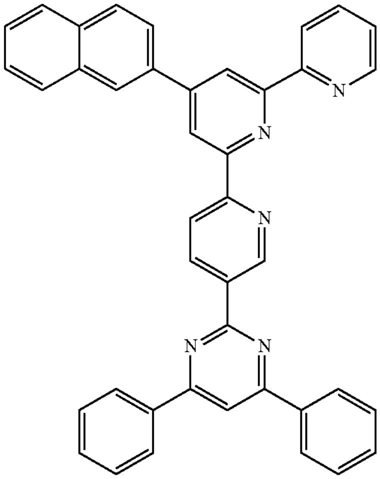

-continued
432
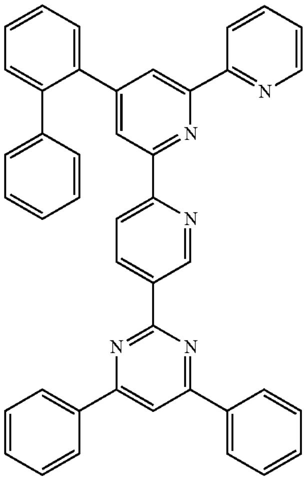
433
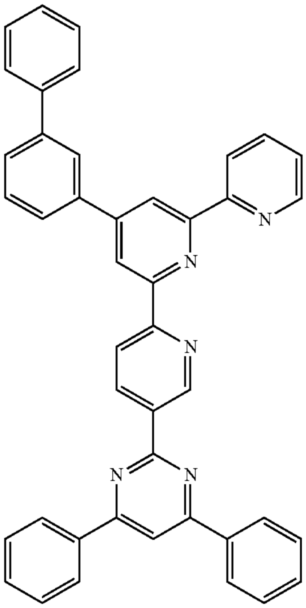
434
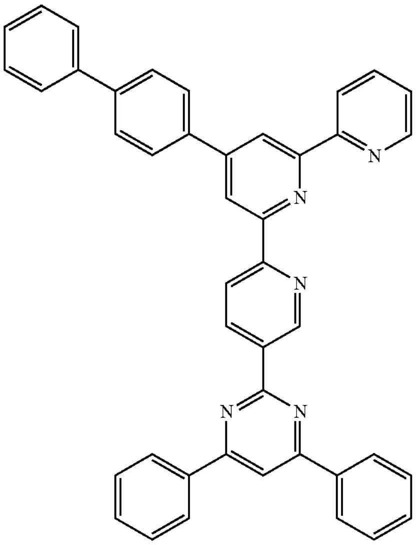
-continued
435
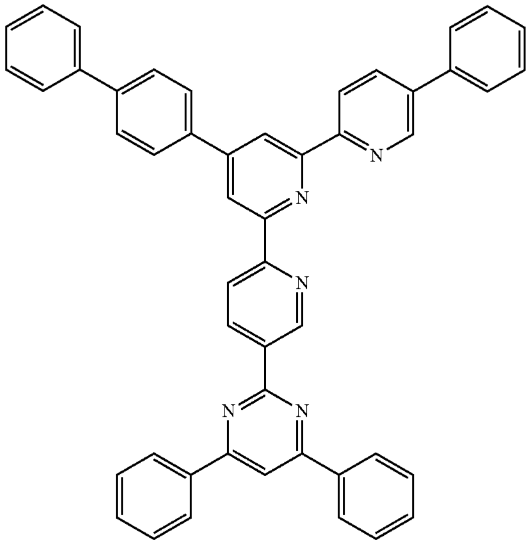
436
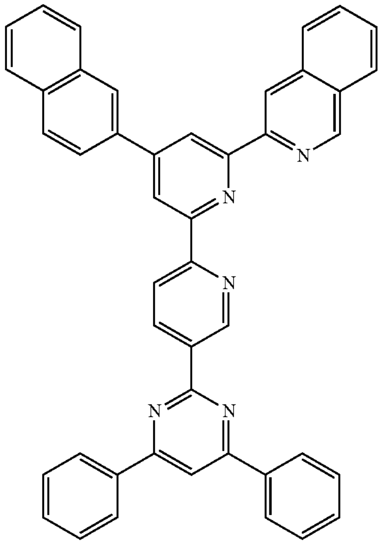
437
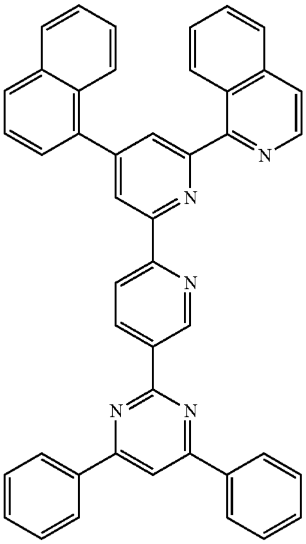

-continued
438
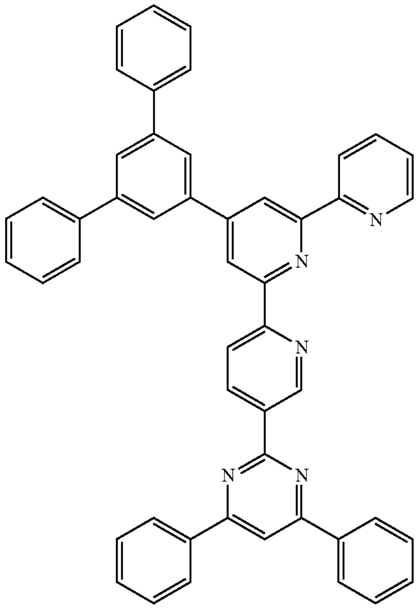
439
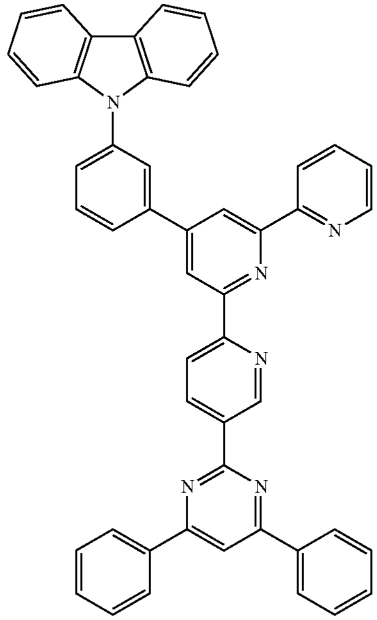
-continued
440
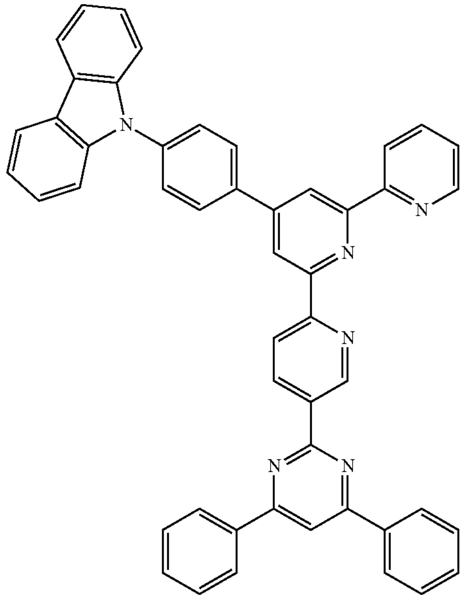
441
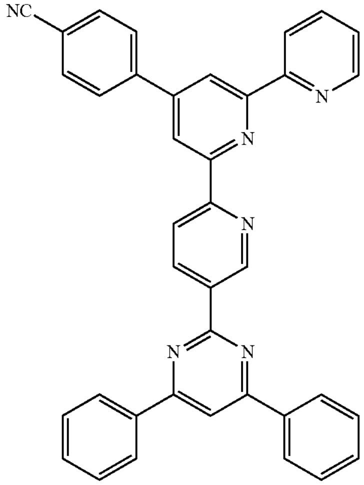
442
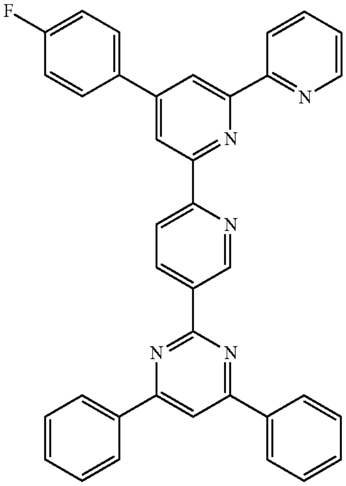

-continued
443
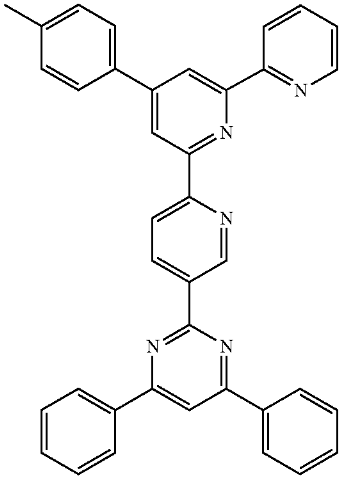
444
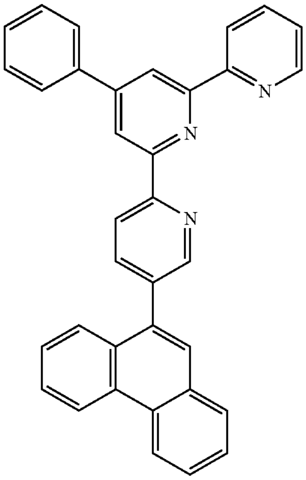
445
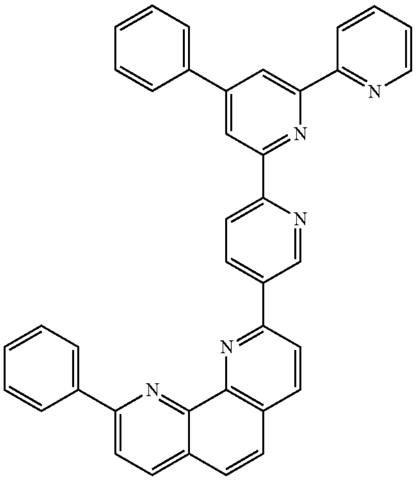
-continued
446
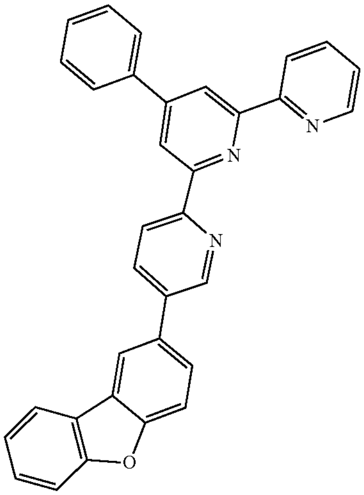
447
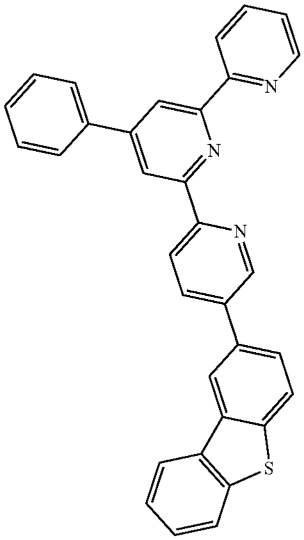
448
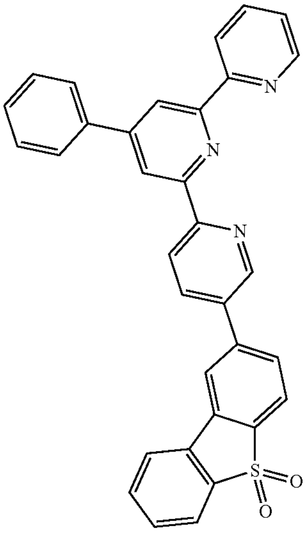

449
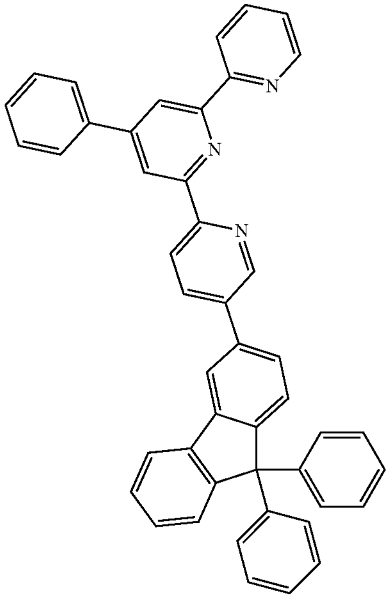
450
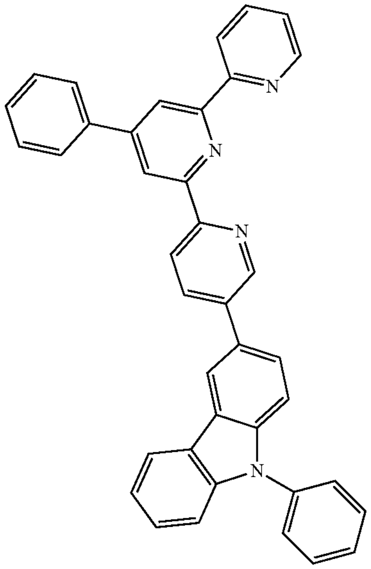
451
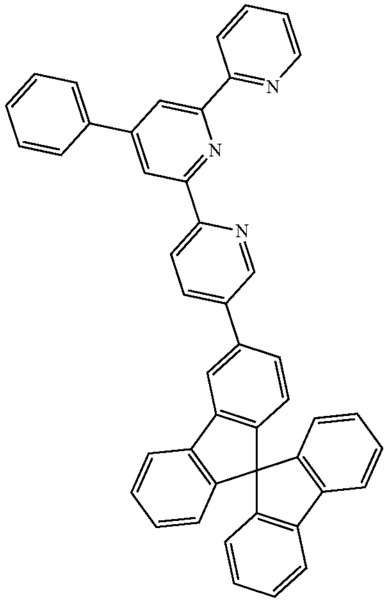
452
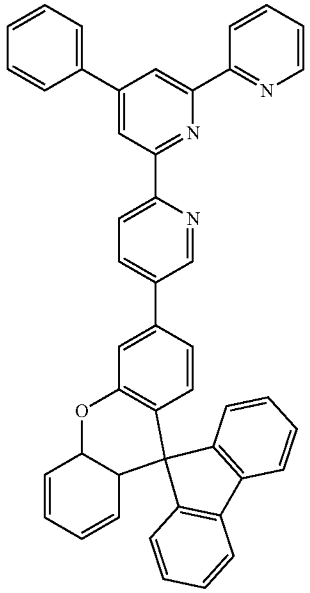
453
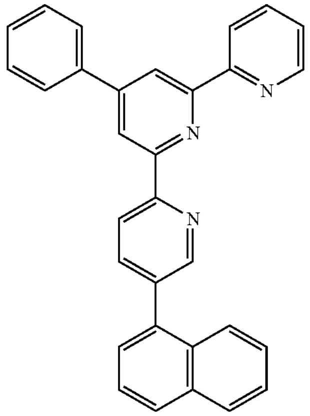

-continued
454
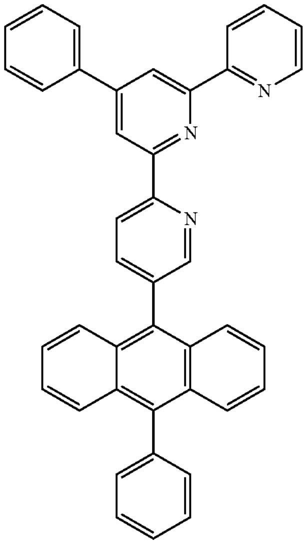
455
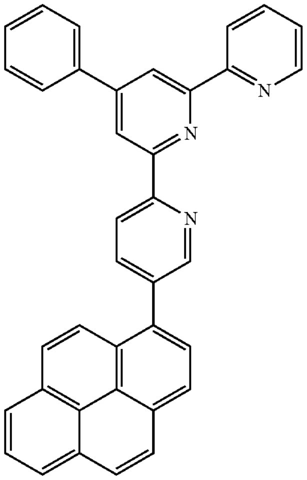
457
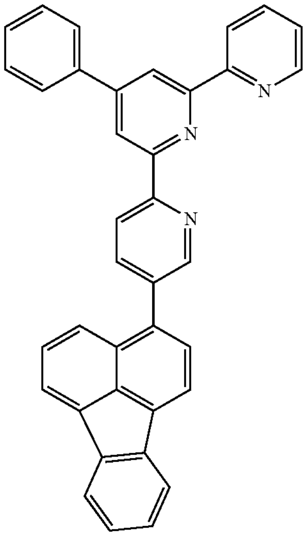
-continued
458
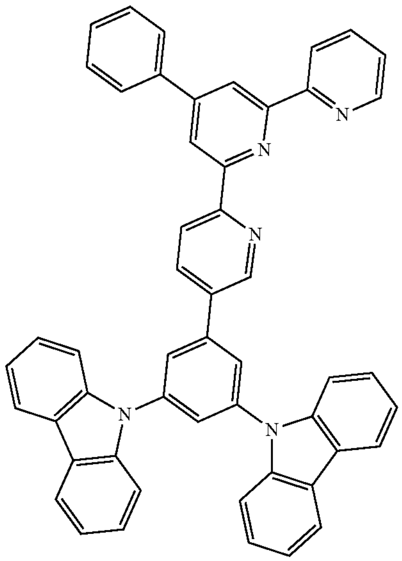
459
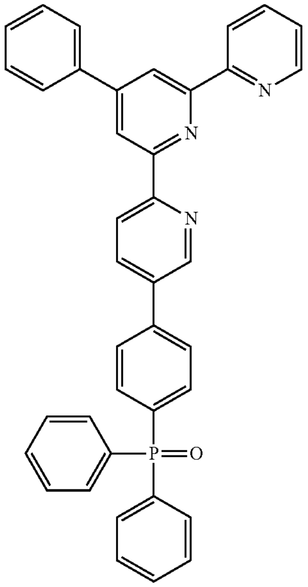
460
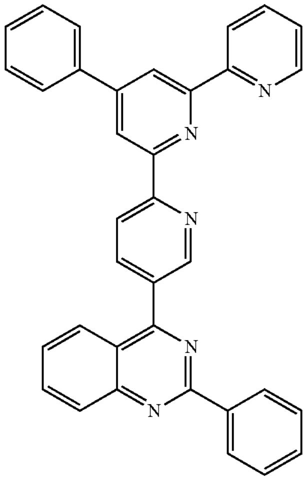

-continued
461
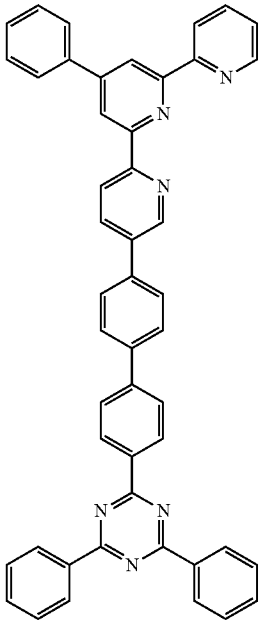
462
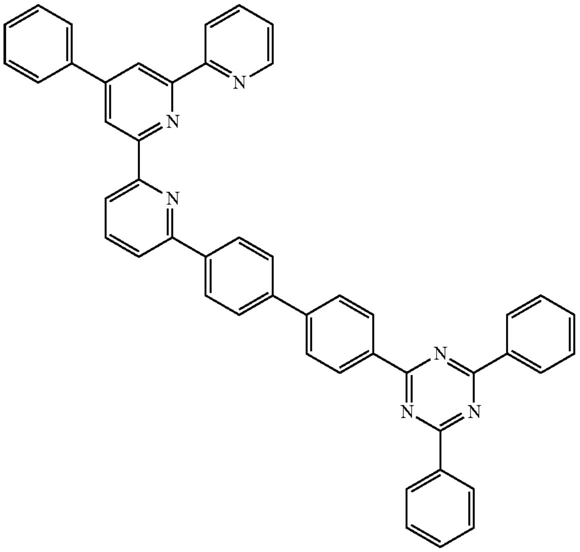
-continued
463
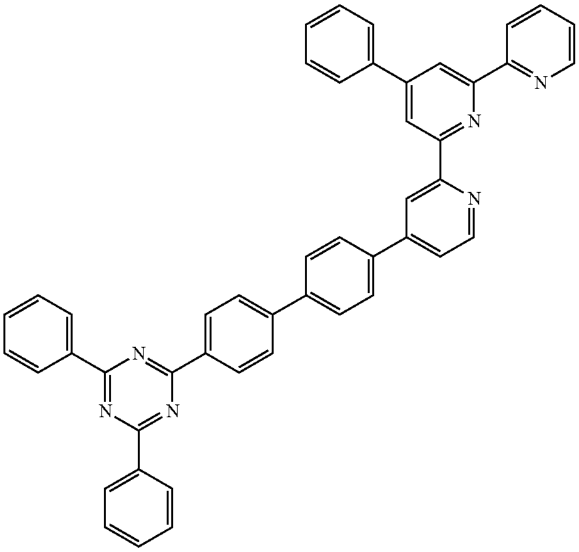
464
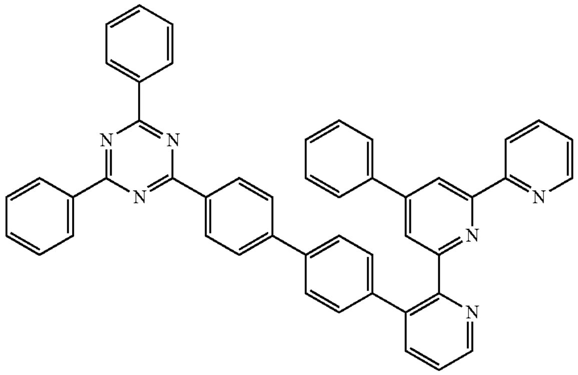
465
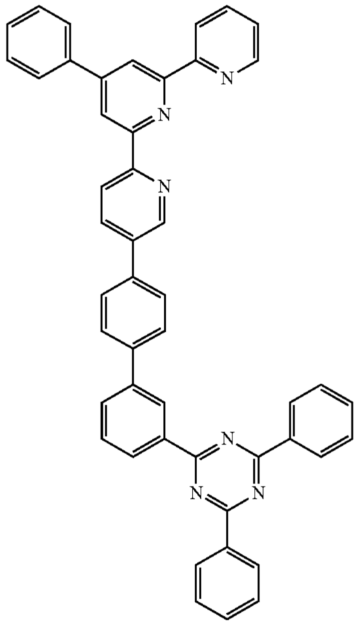

-continued
466
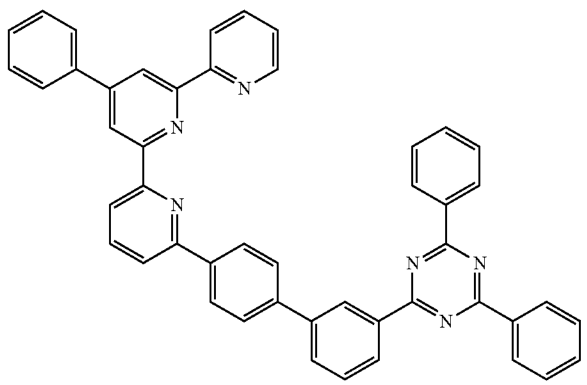
467
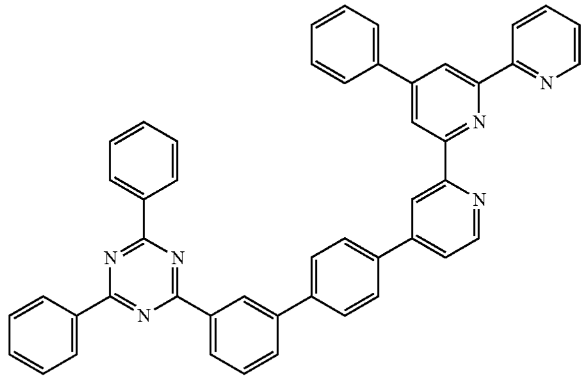
468
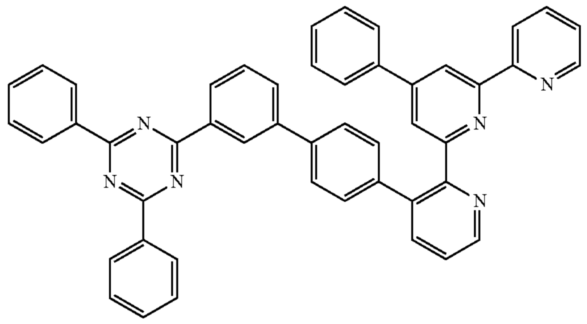
-continued
469
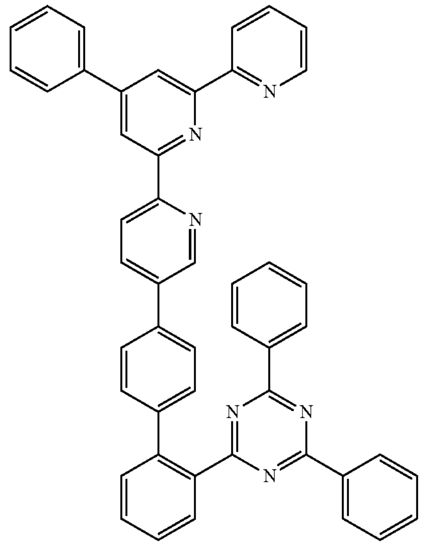
470
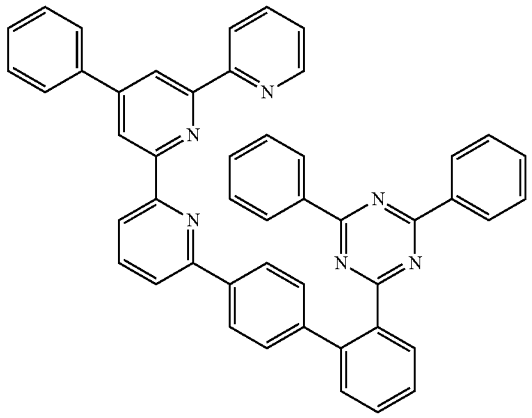
471
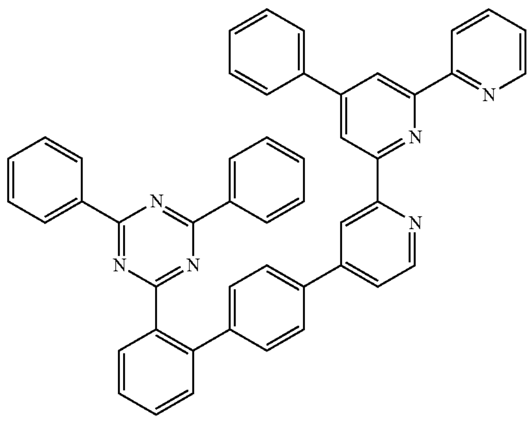

-continued
472
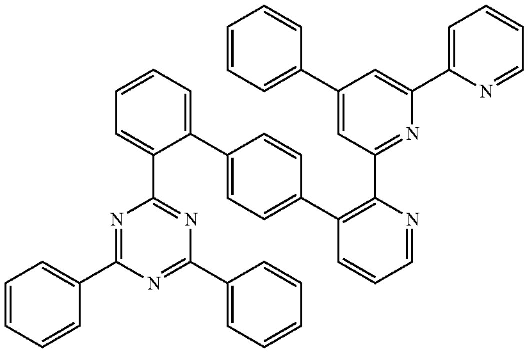
473
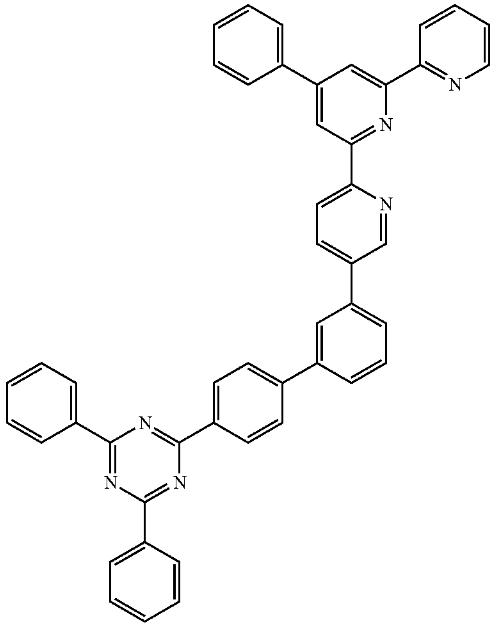
474
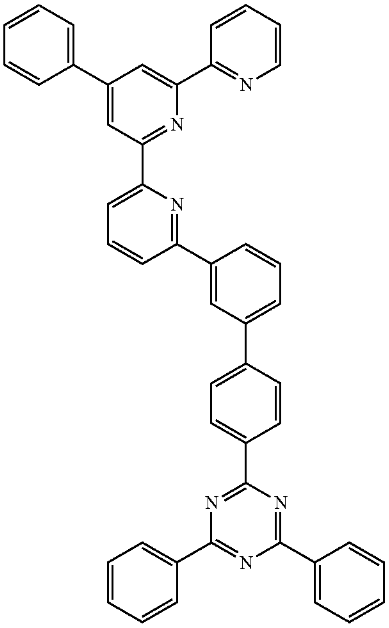
-continued
475
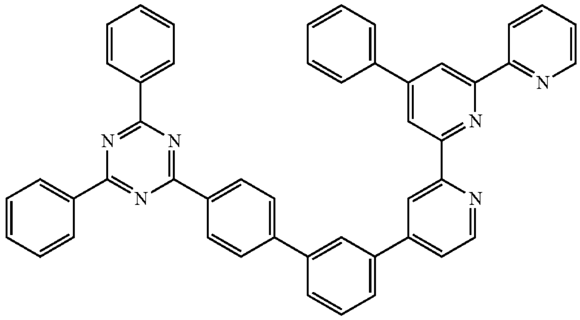
476
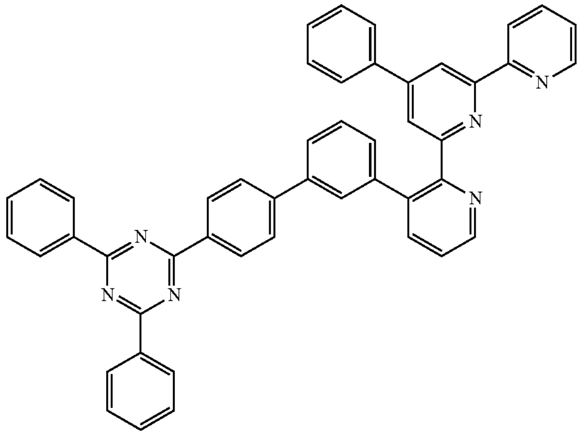
477
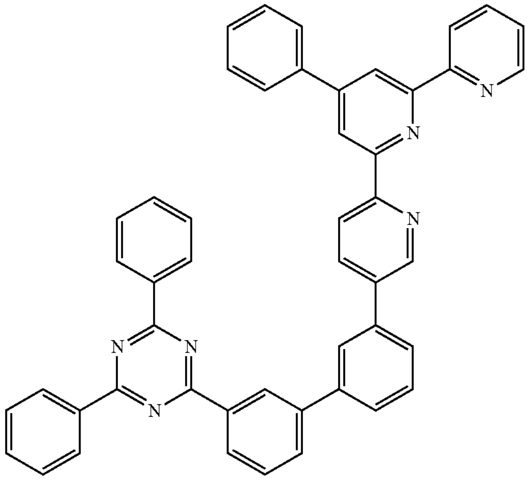

-continued
478
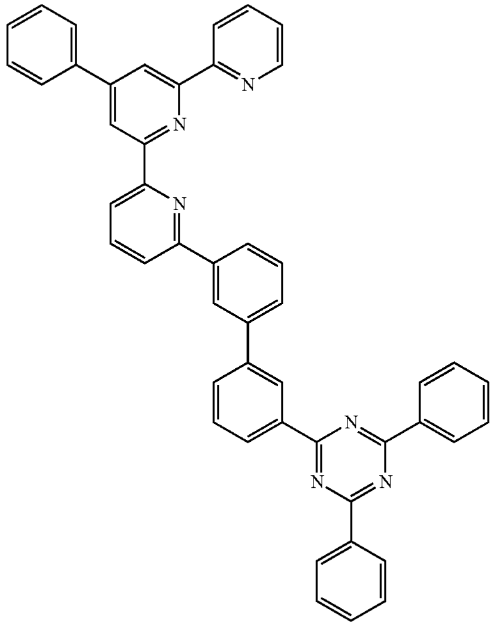
479
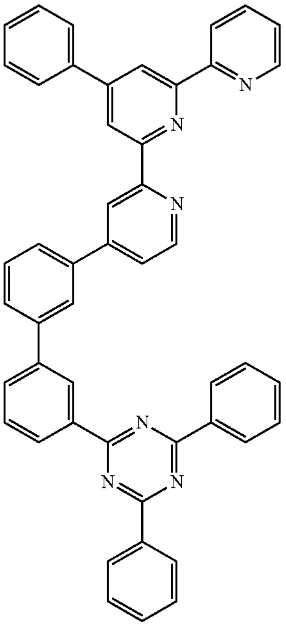
480
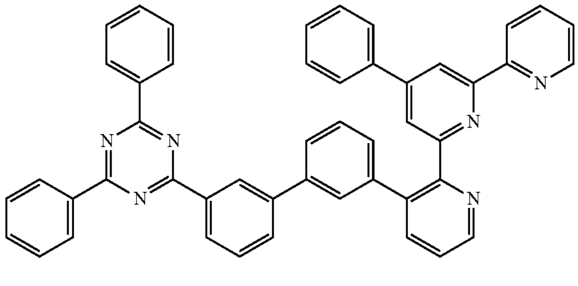
481
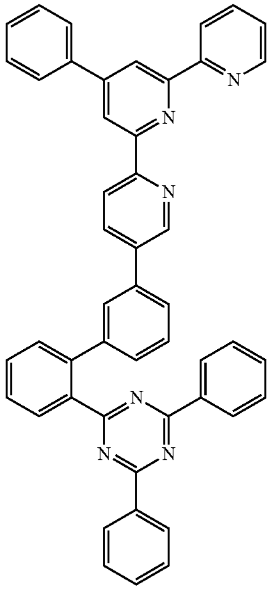
482
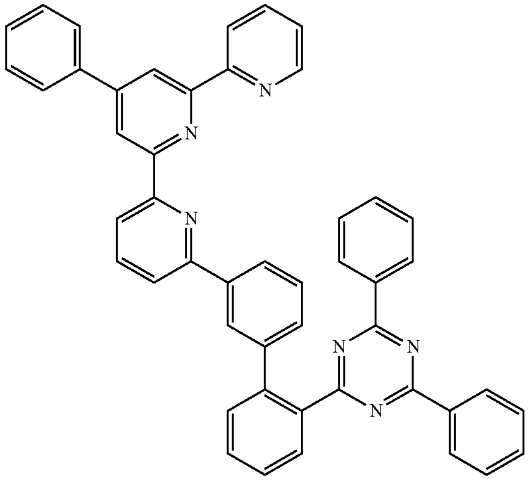
483
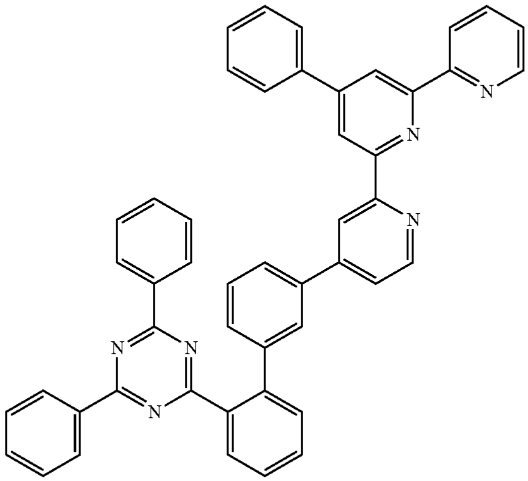

-continued
484
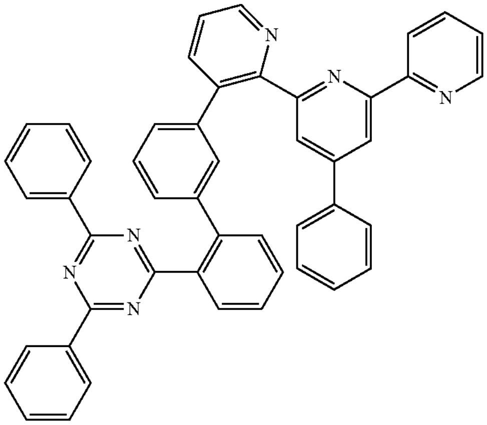
485
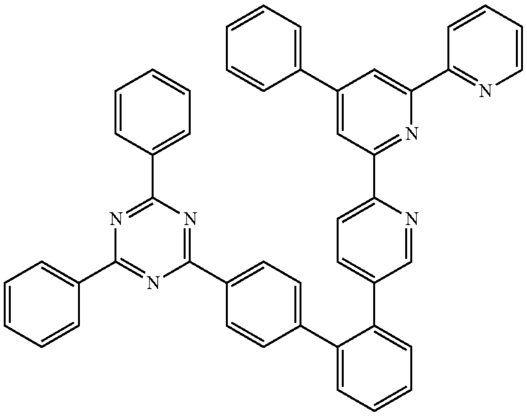
486
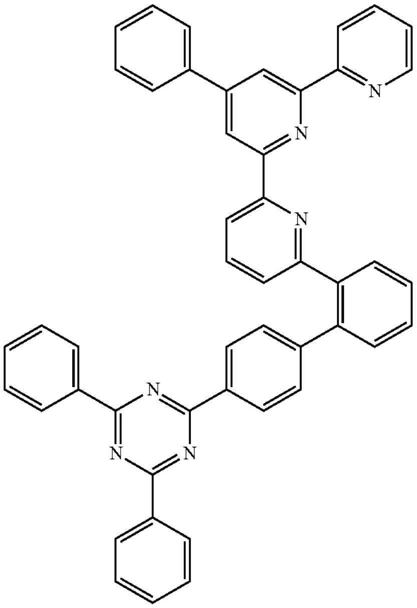
-continued
487
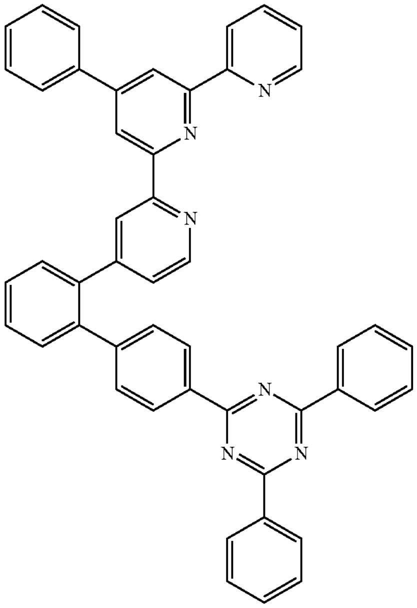
488
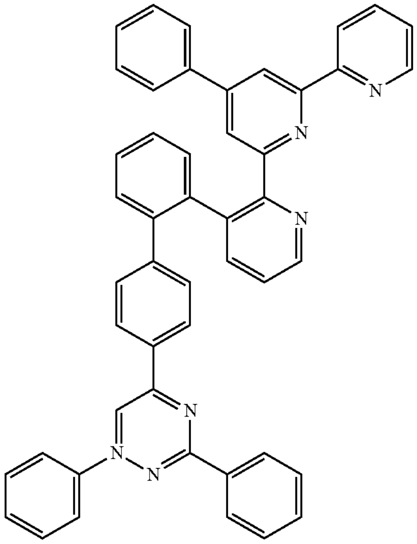

-continued
489
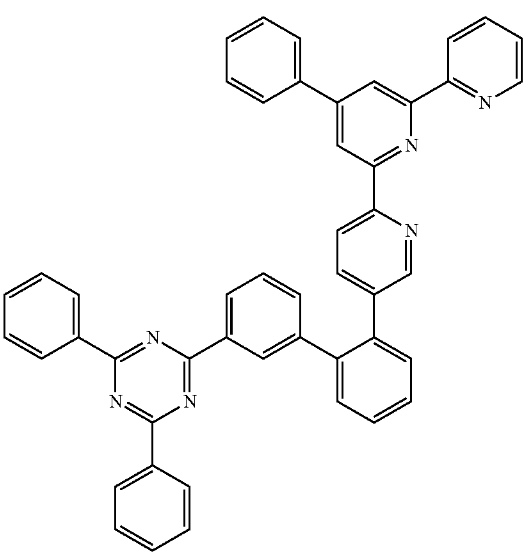
490
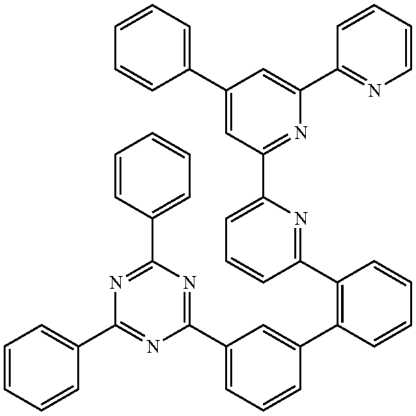
491
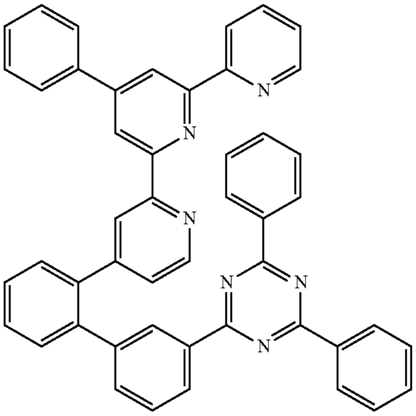
-continued
492
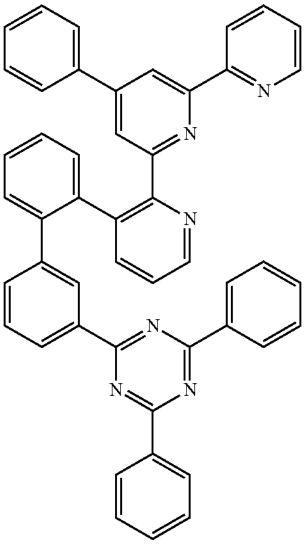
493
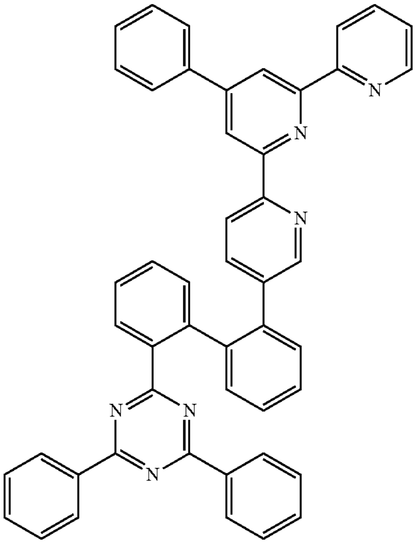

-continued
494
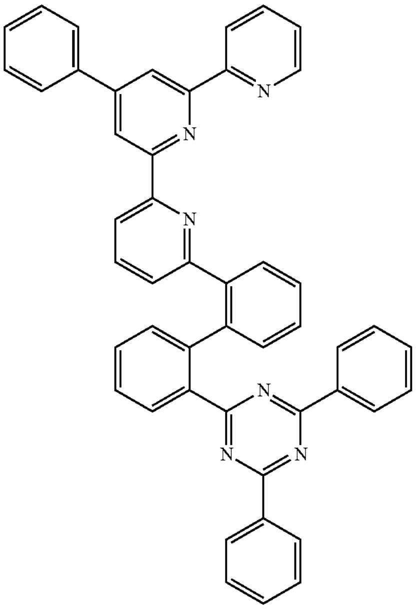
495
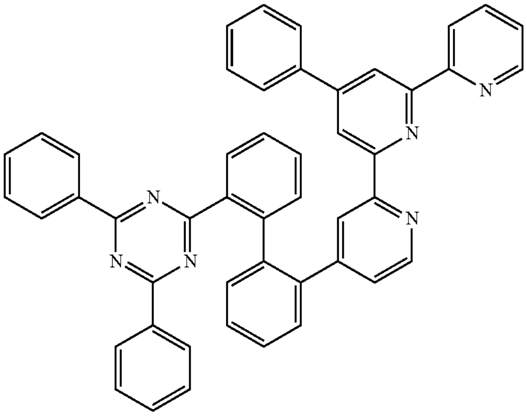
496
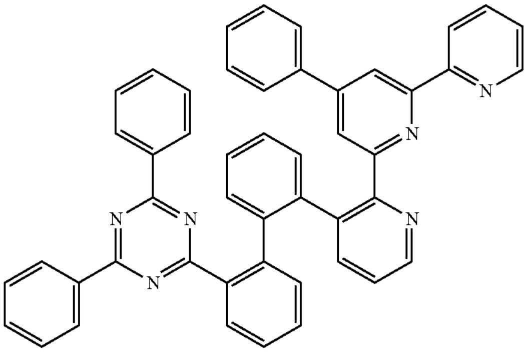
-continued
497
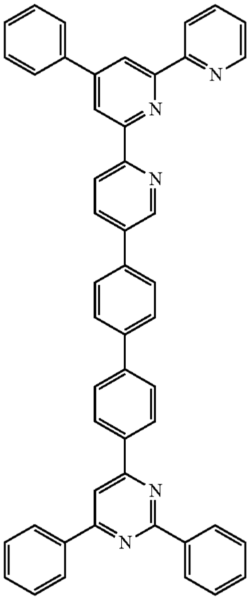
498
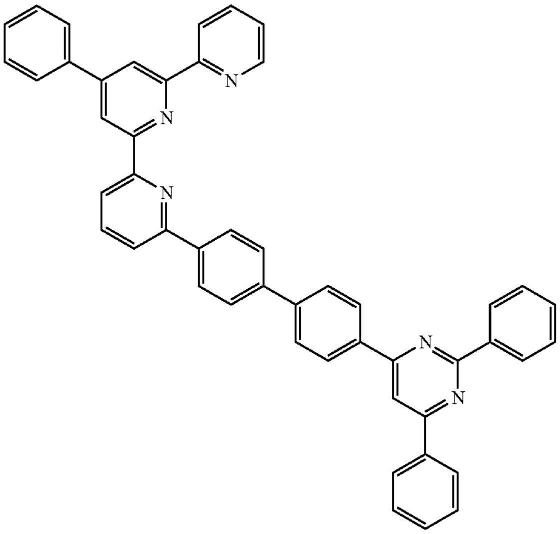

-continued
499
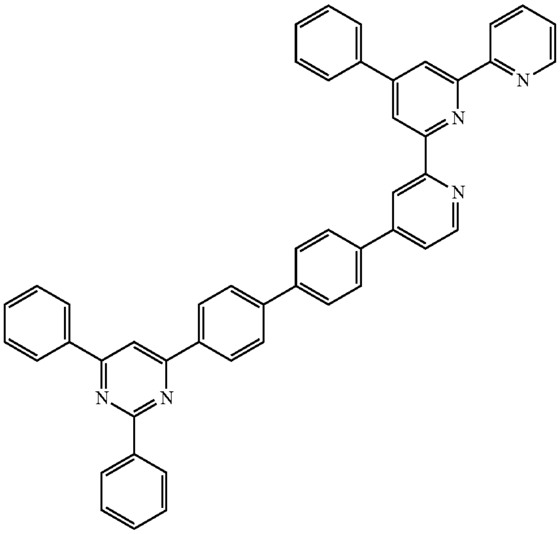
500
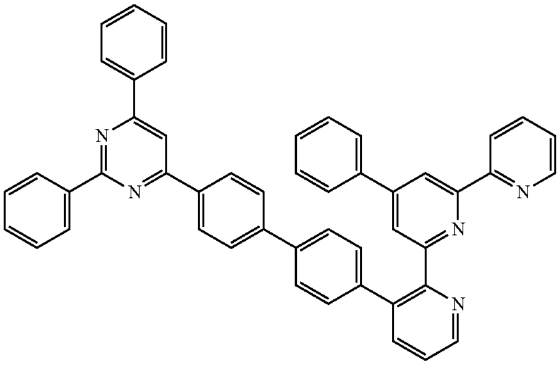
501
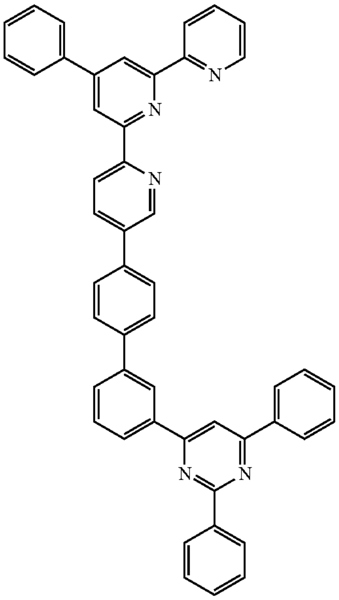
-continued
502
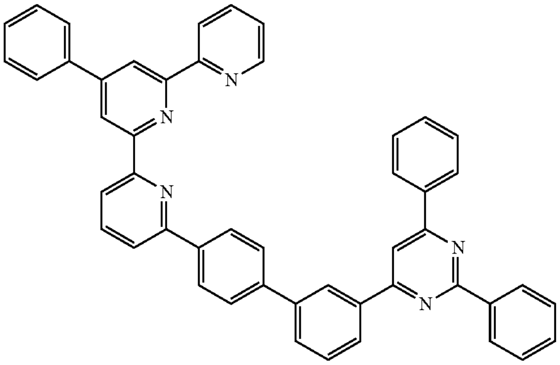
503
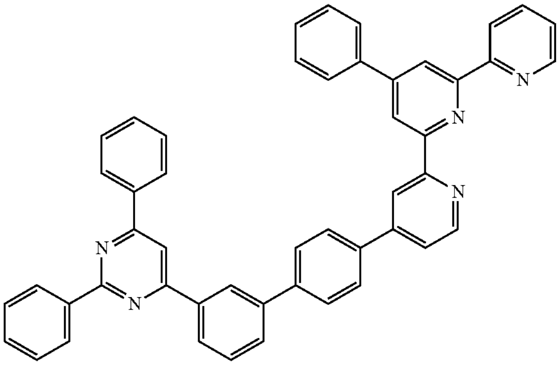
504
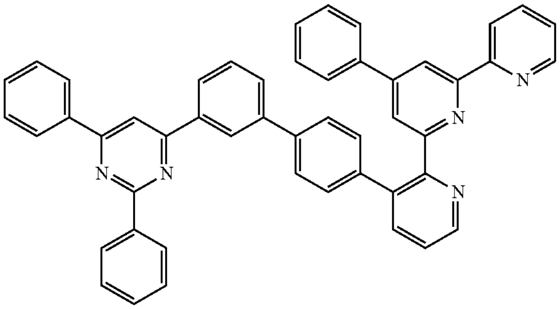
505
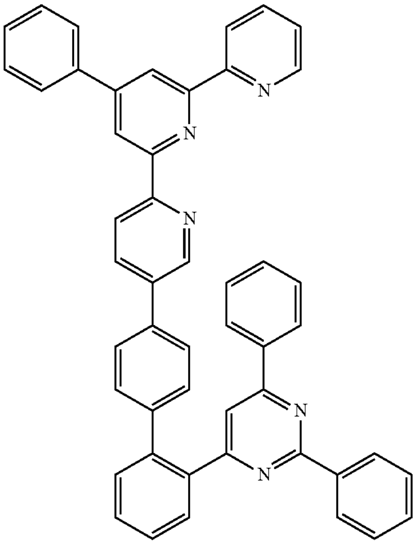

-continued
506
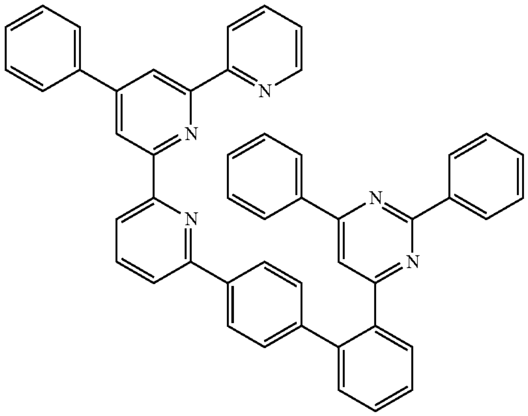
507
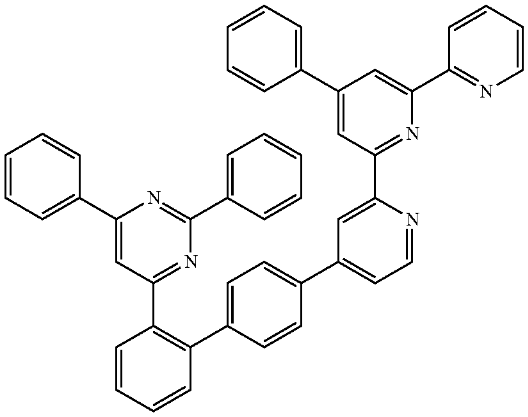
508
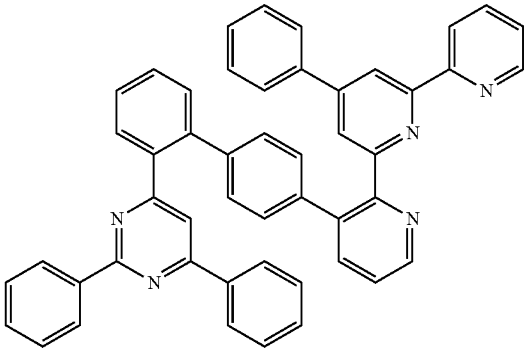
-continued
509
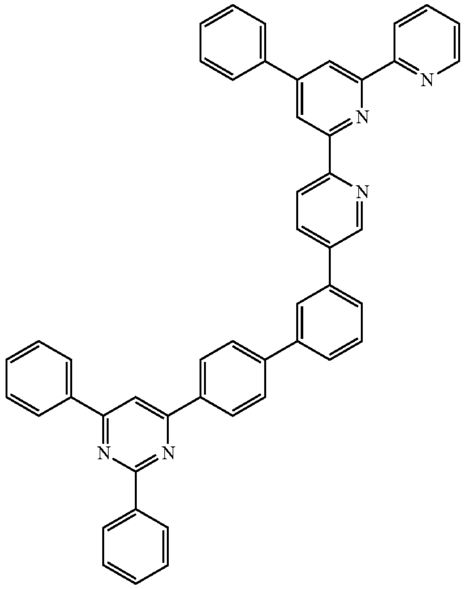
510
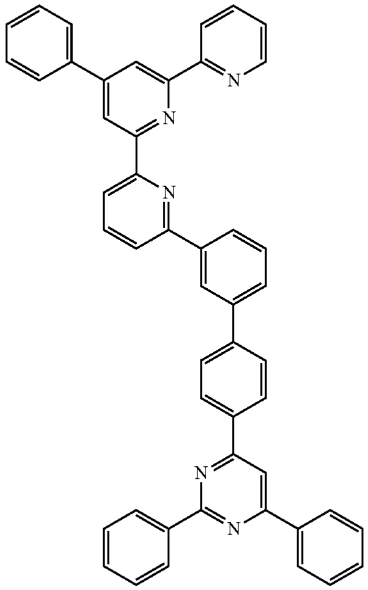
511
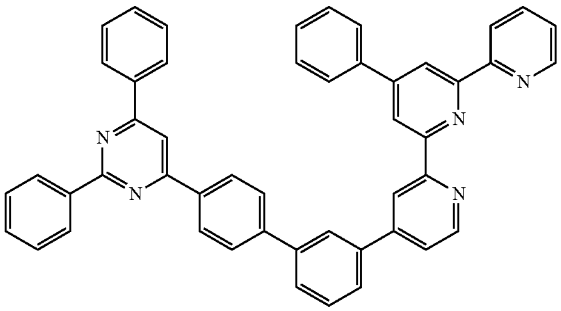

512
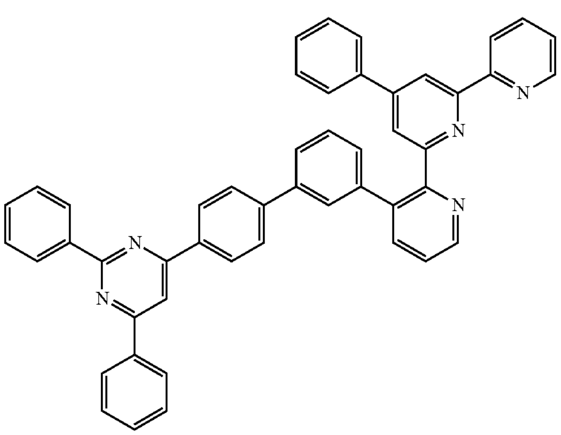
513
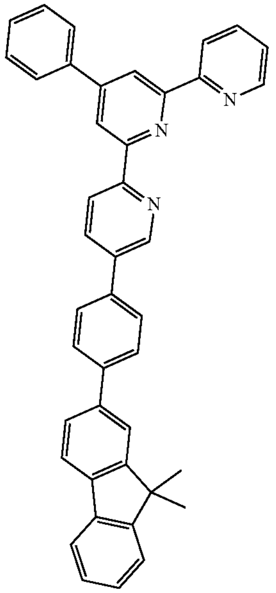
514
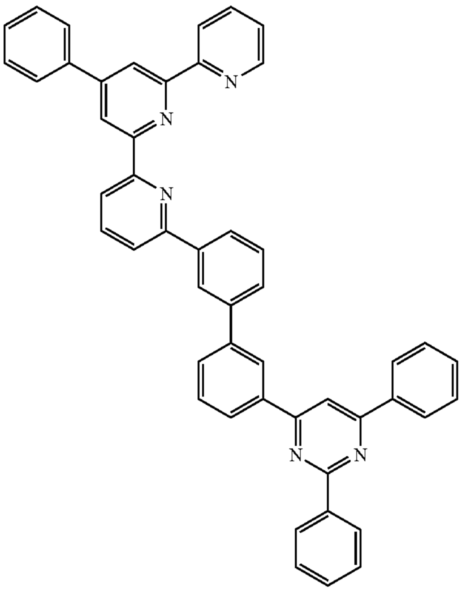
515
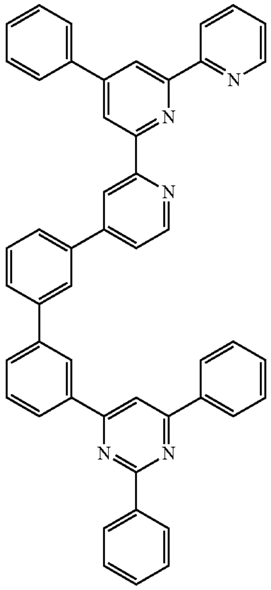
516
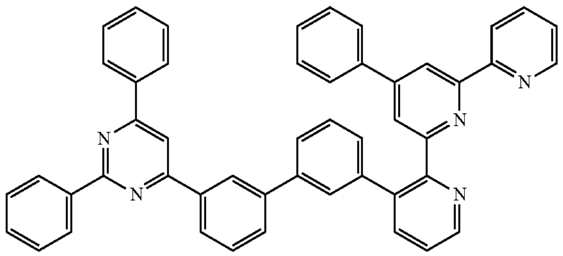
517
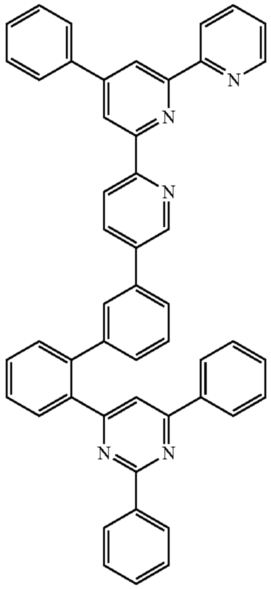

-continued
518
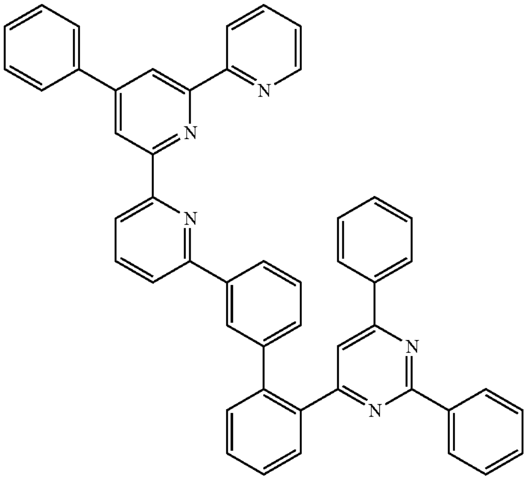
519
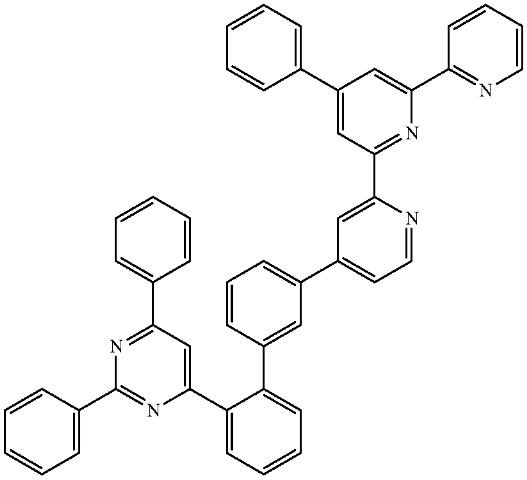
520
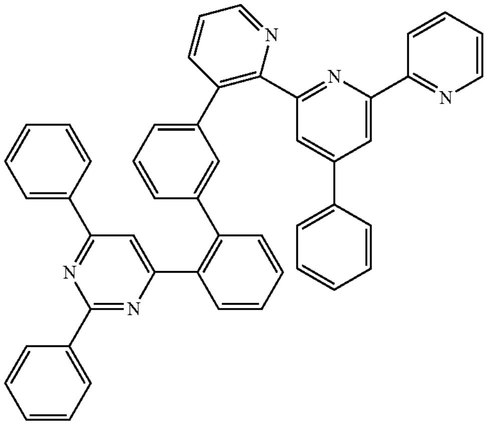
-continued
521
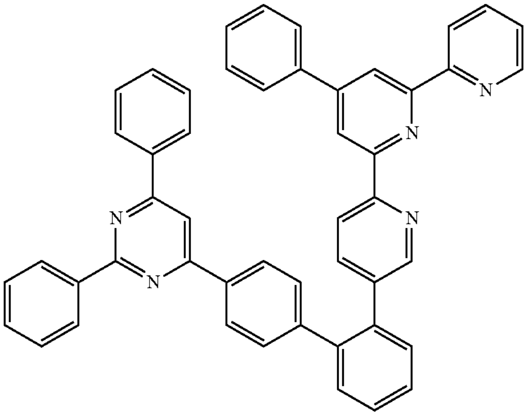
522
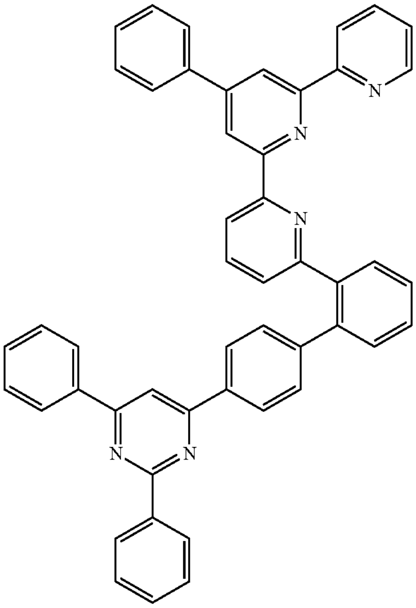
523
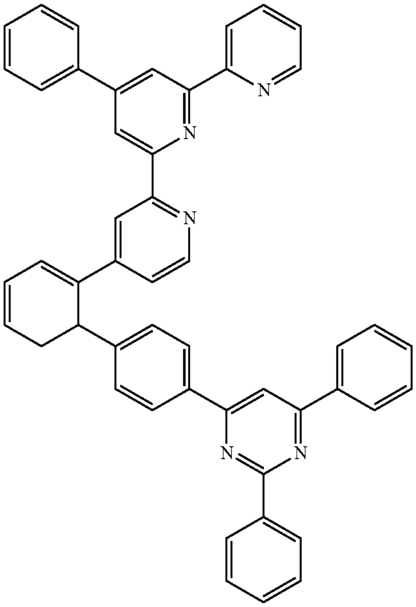

-continued
524
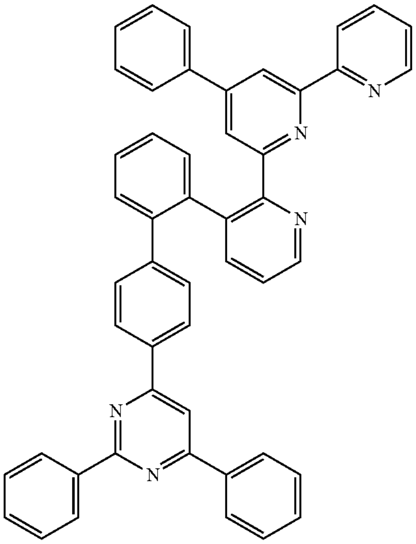
525
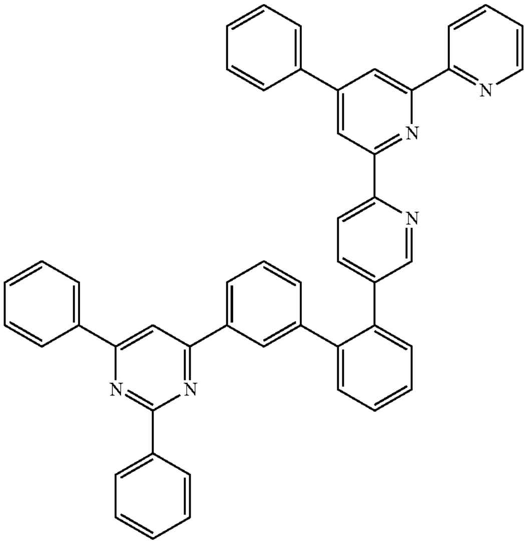
526
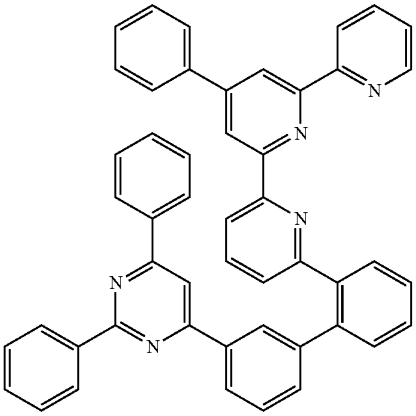
-continued
527
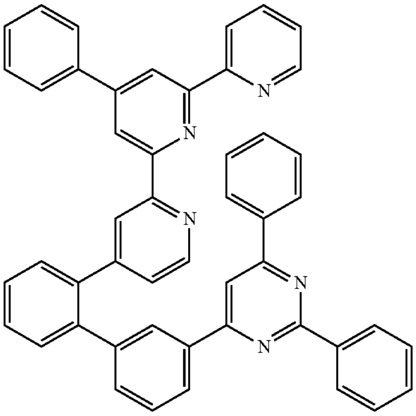
528
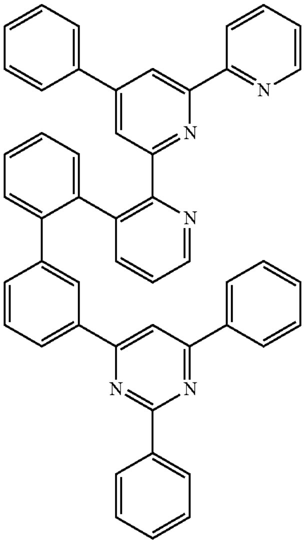
529
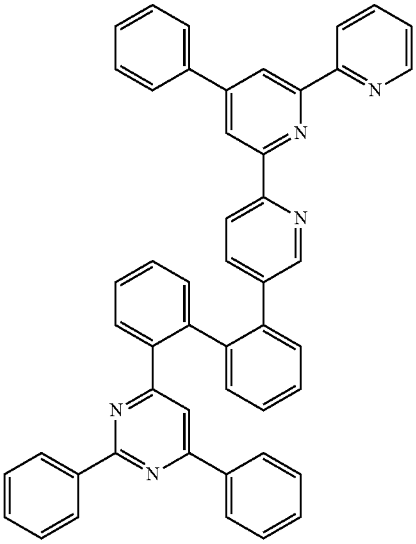

-continued
530
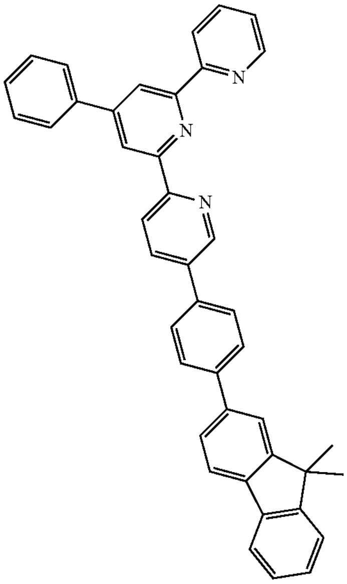
531
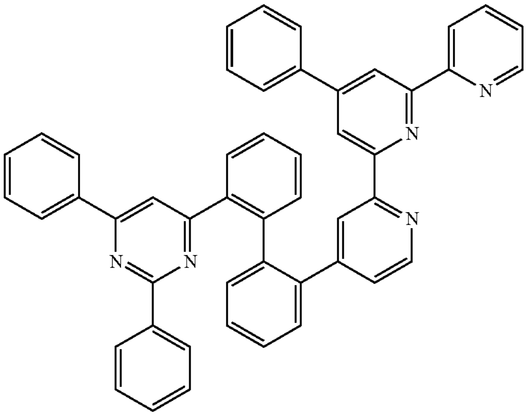
532
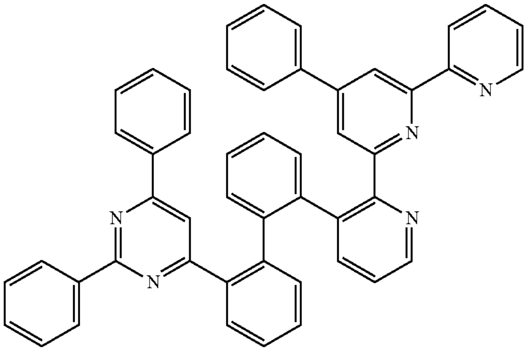
-continued
533
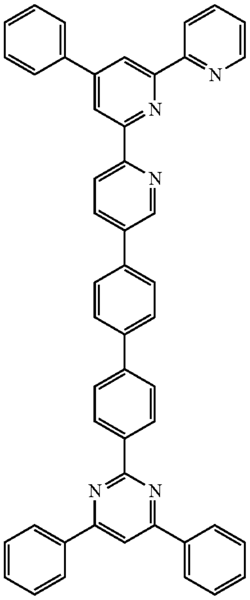
534
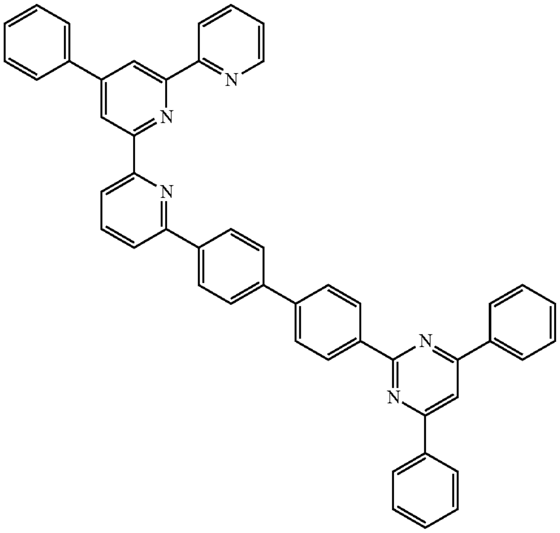

-continued
535
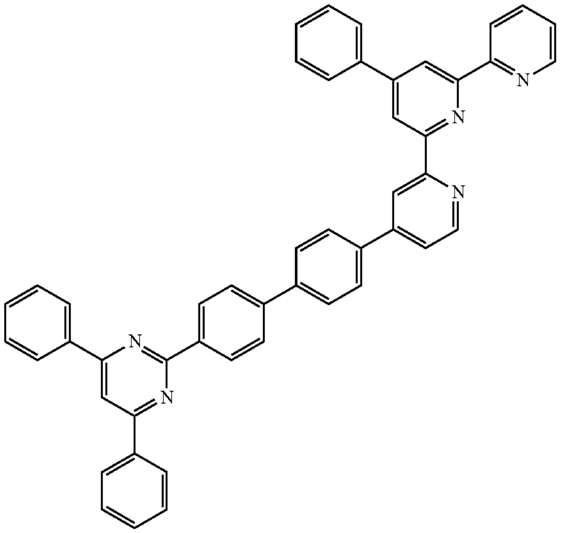
536
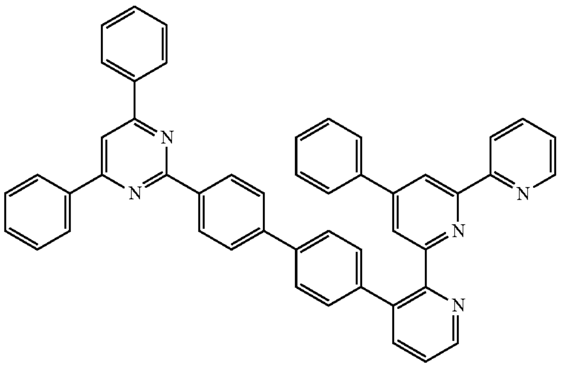
537
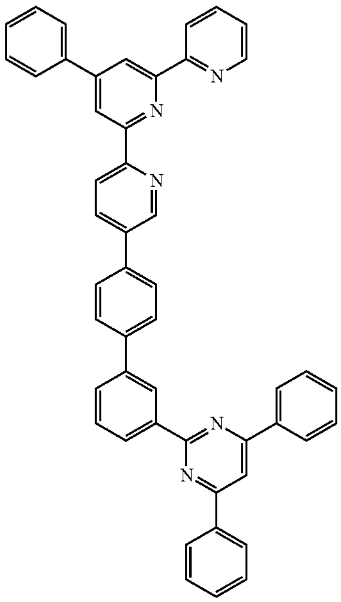
-continued
538
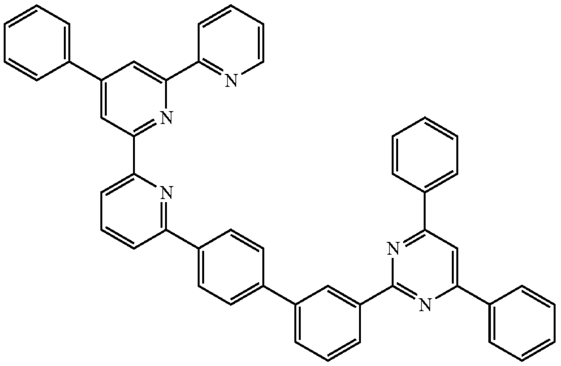
539
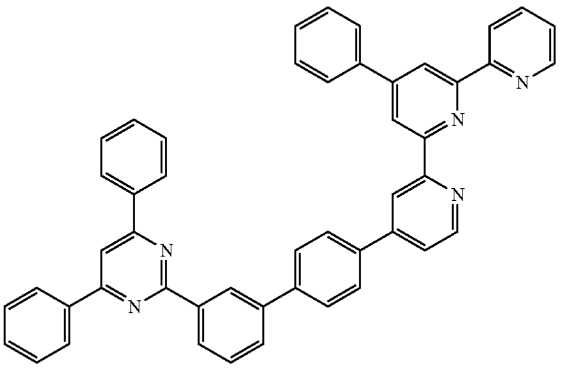
540
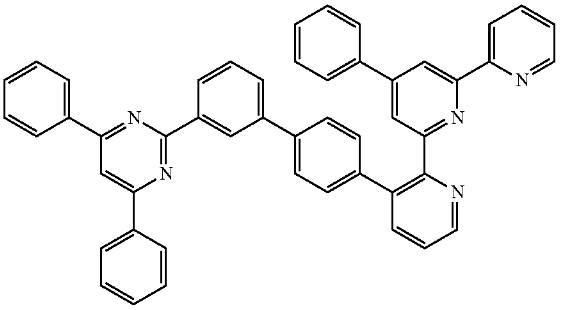
541
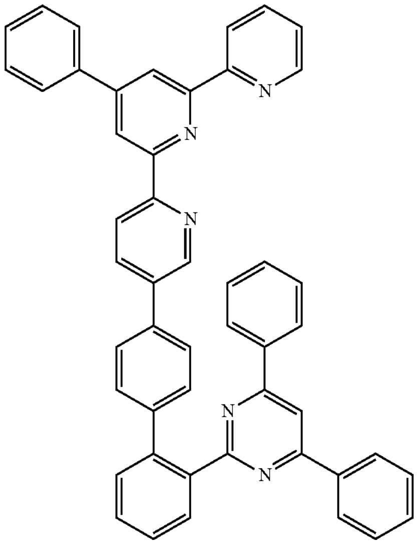

542
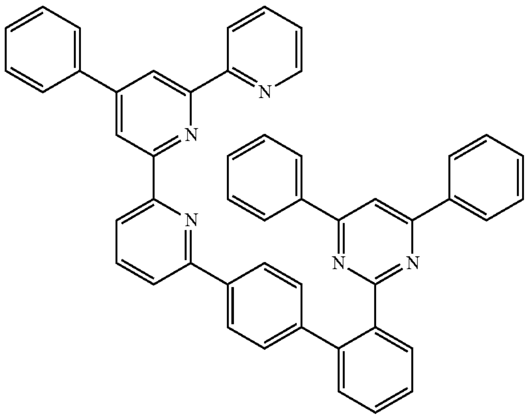
543
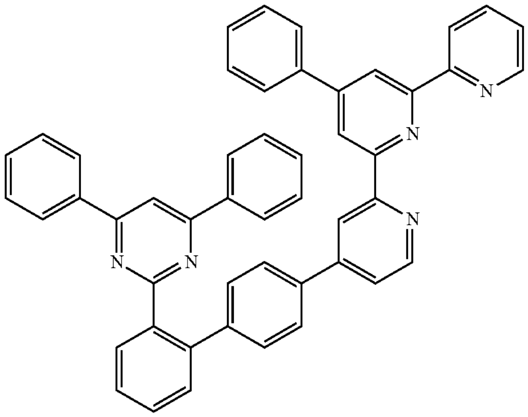
544
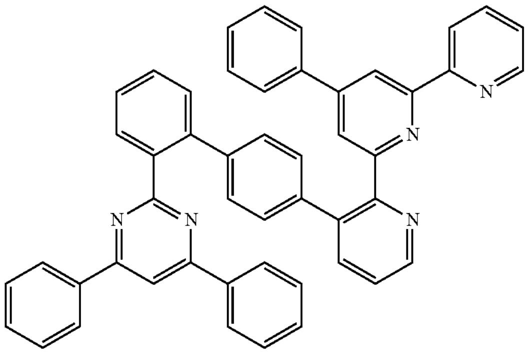
545
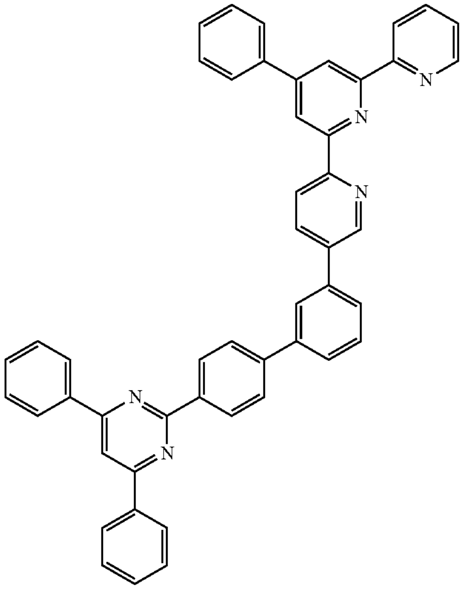
546
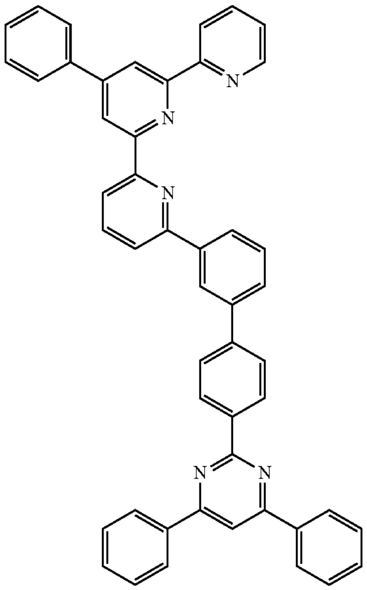
547
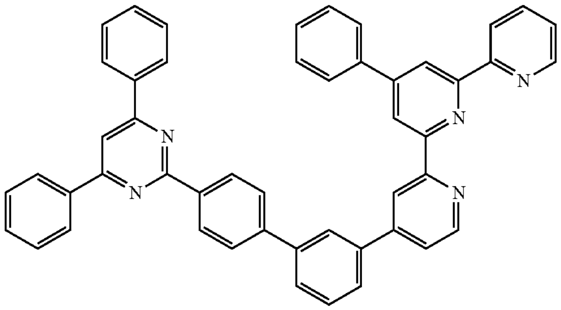

-continued
548
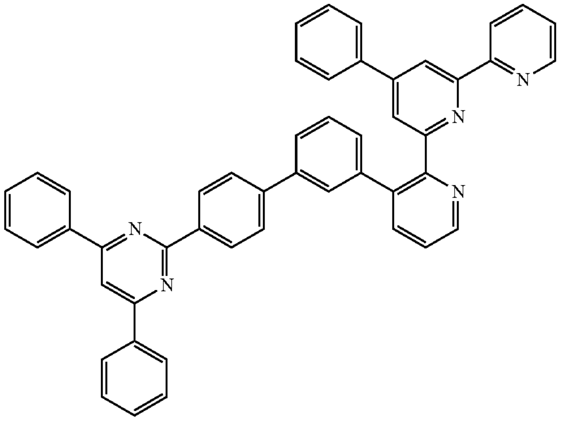
549
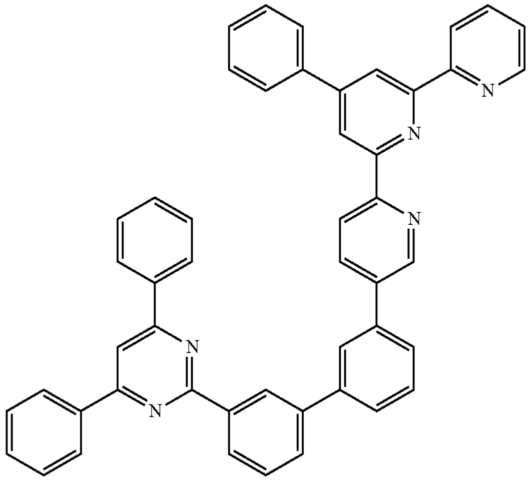
550
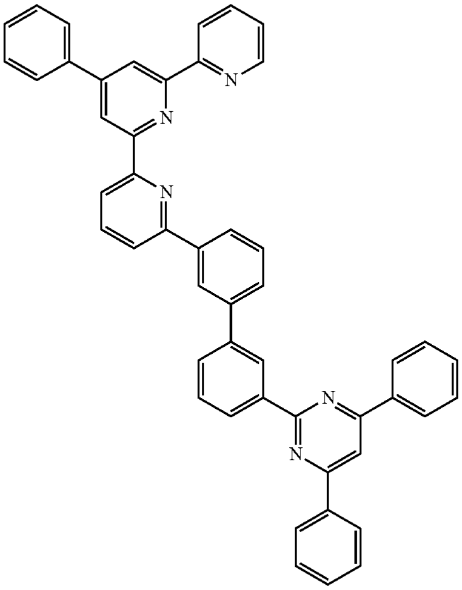
-continued
551
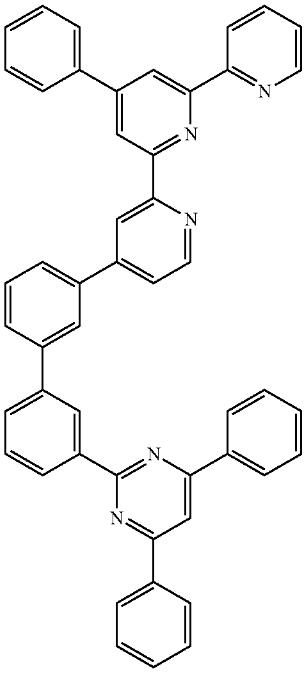
552
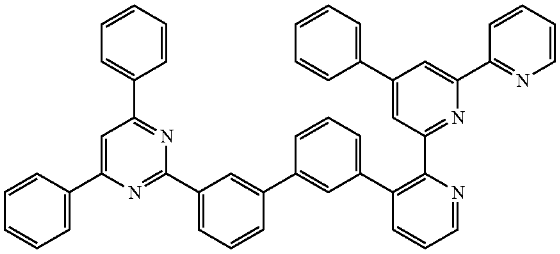
553
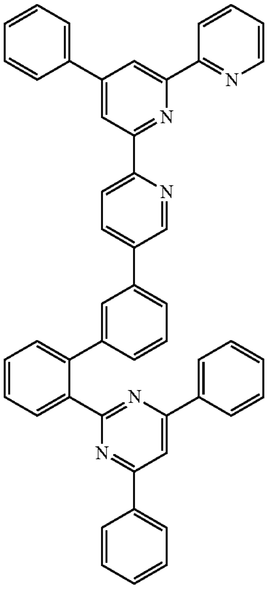

-continued
554
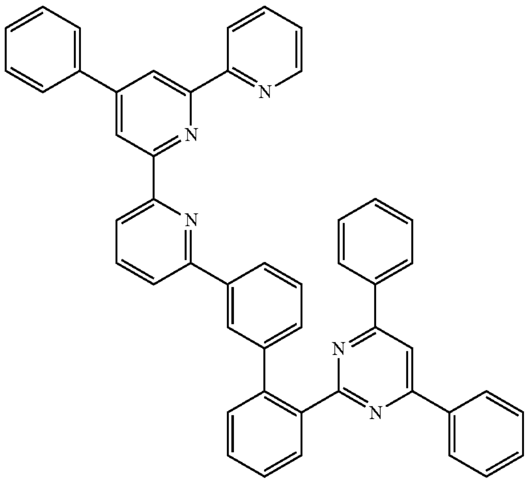
555
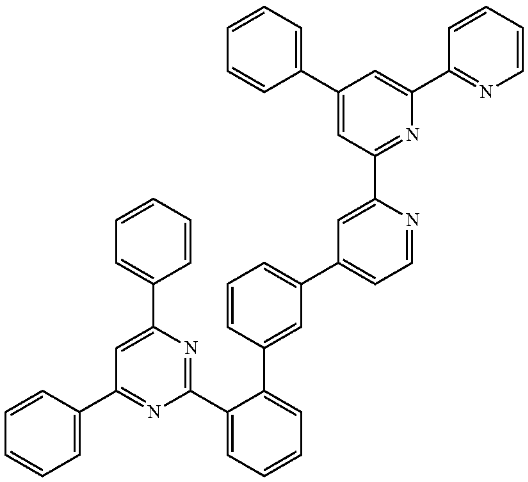
556
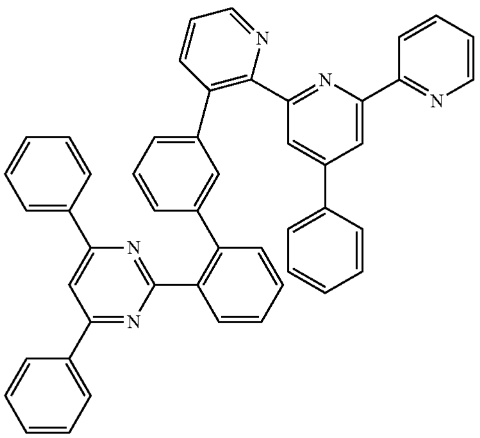
-continued
557
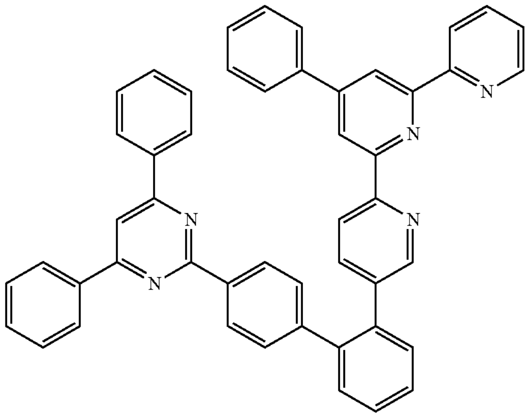
558
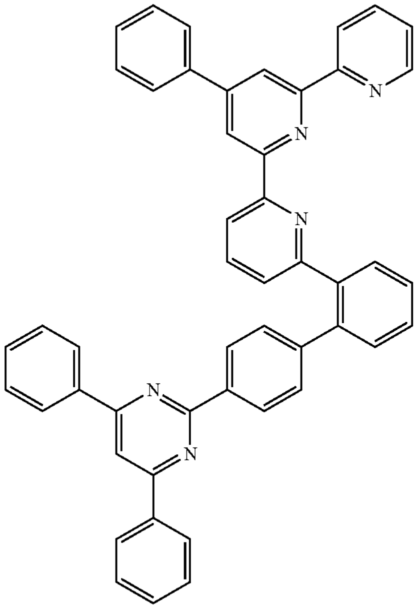
559
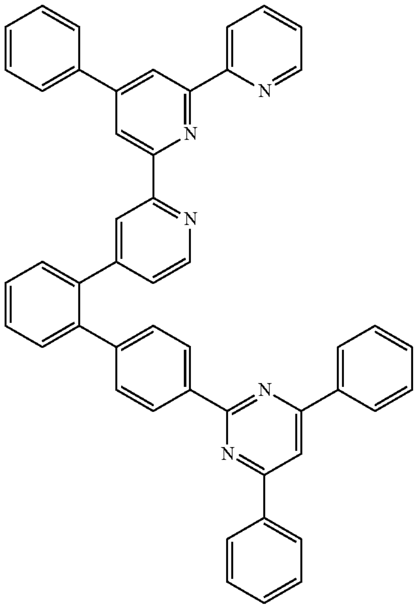

-continued
560
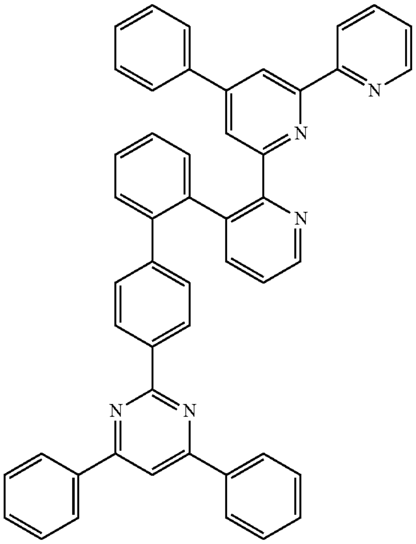
561
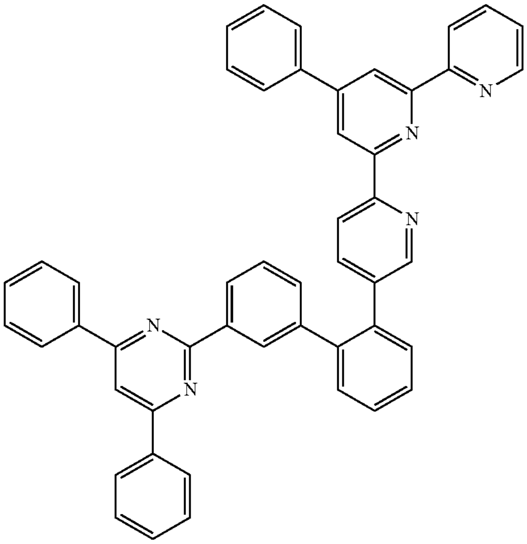
562
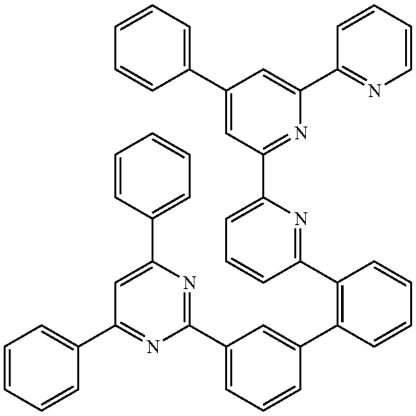
-continued
563
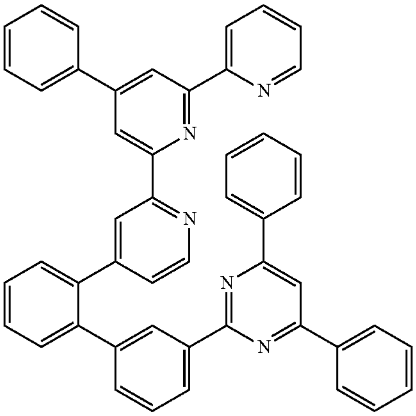
564
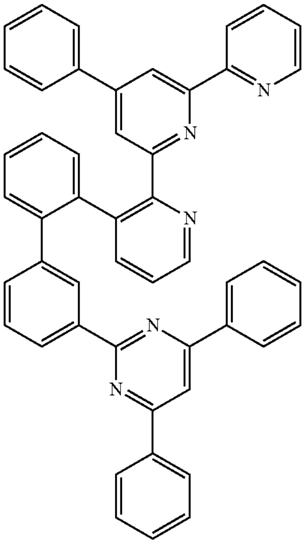
565
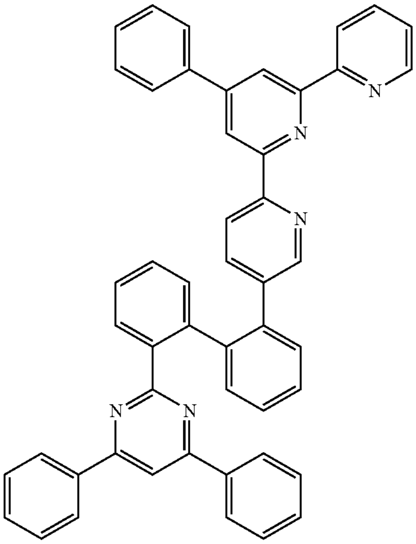

-continued
566
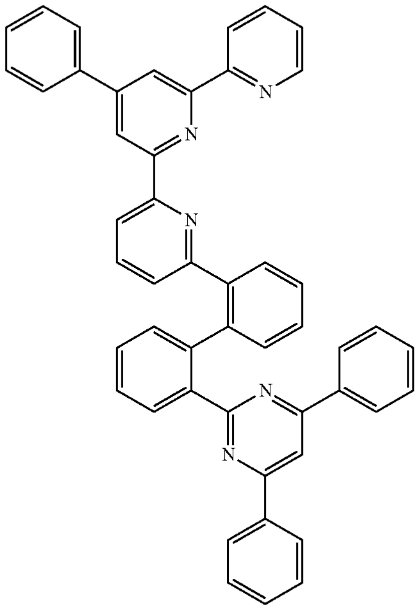
567
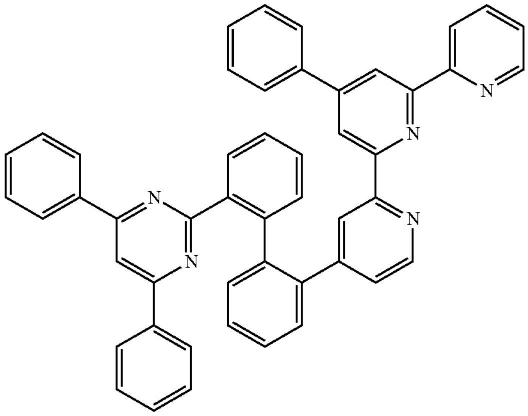
568
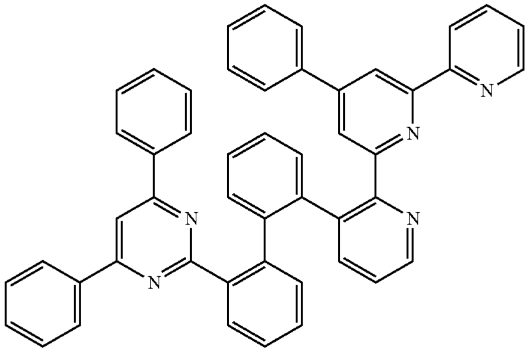
-continued
569
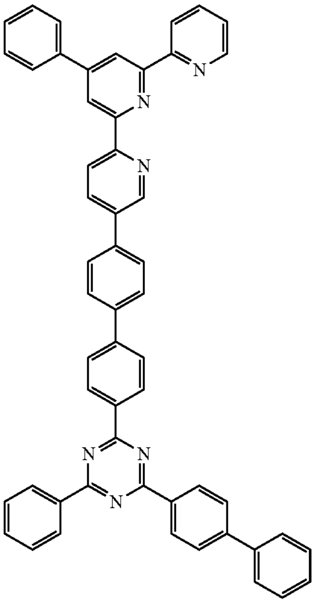
570
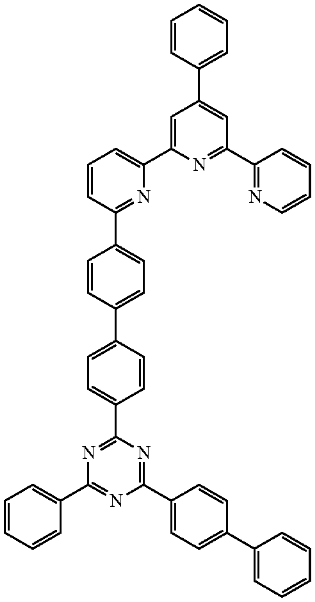

-continued
571
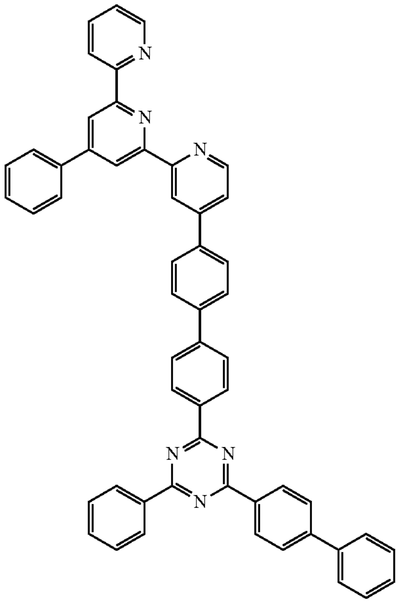
572
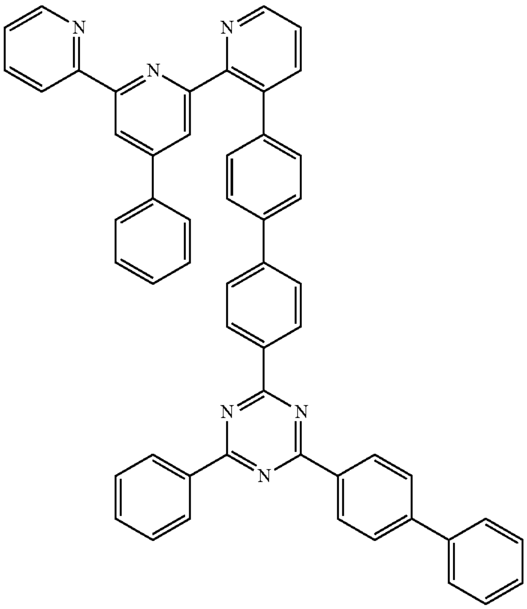
-continued
573
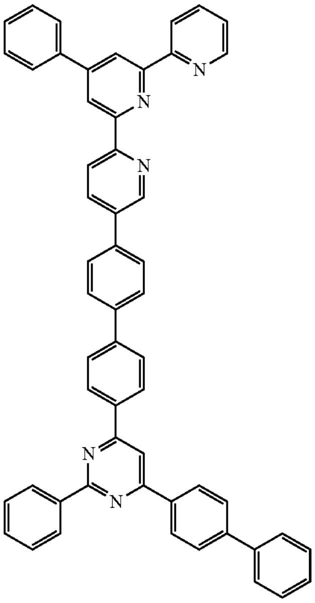
574
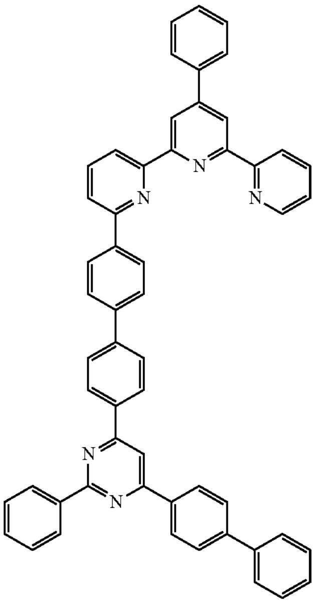

-continued
575
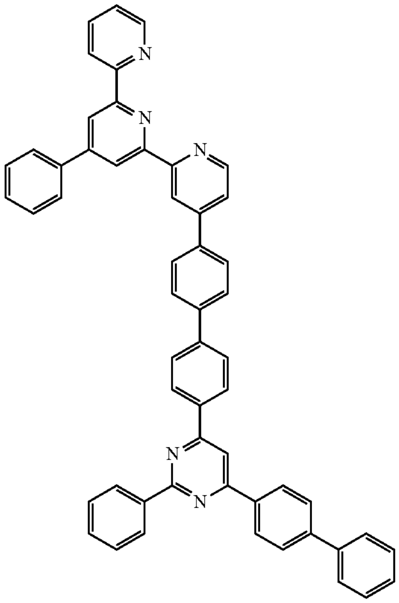
576
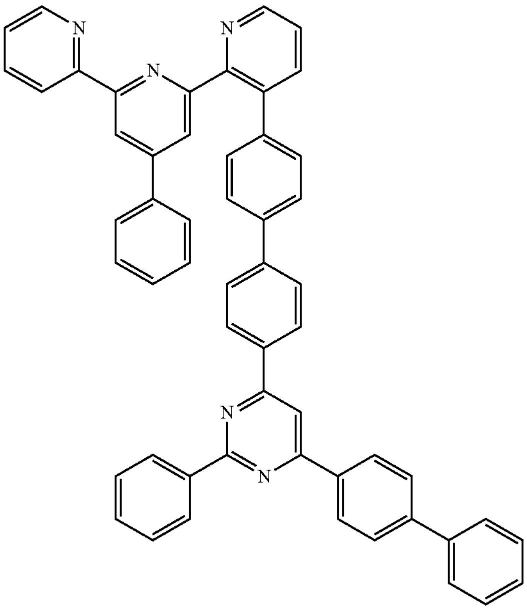
-continued
577
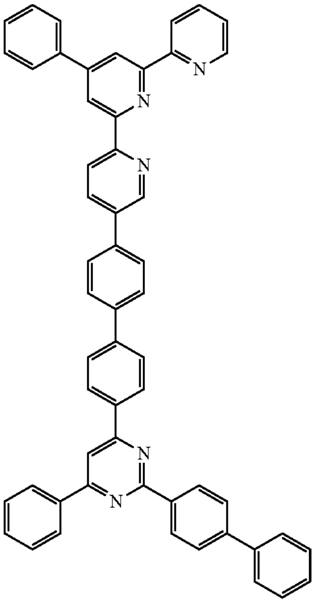
578
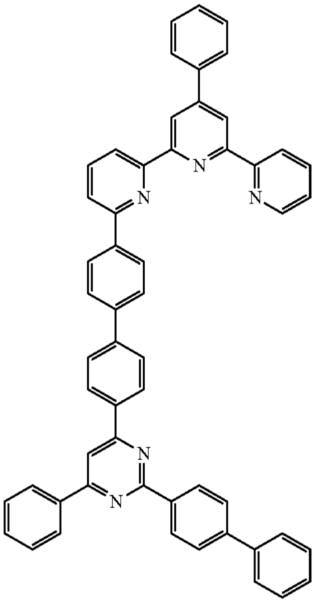

-continued
579
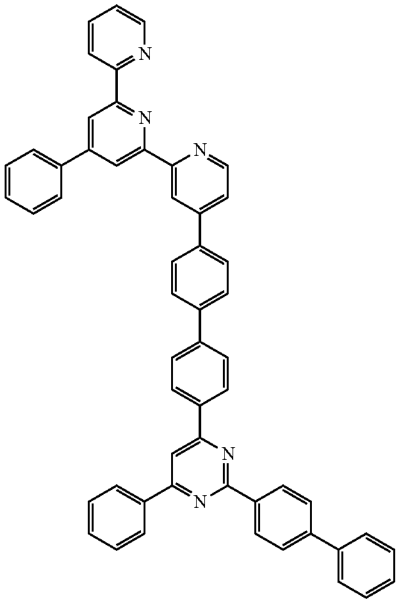
580
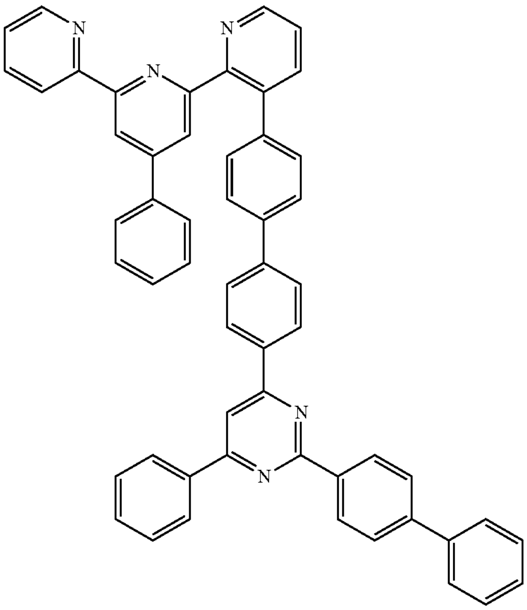
-continued
581
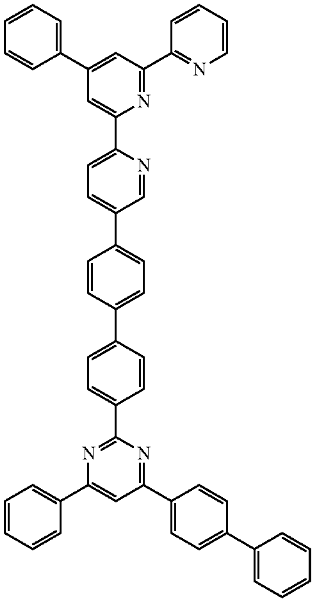
582
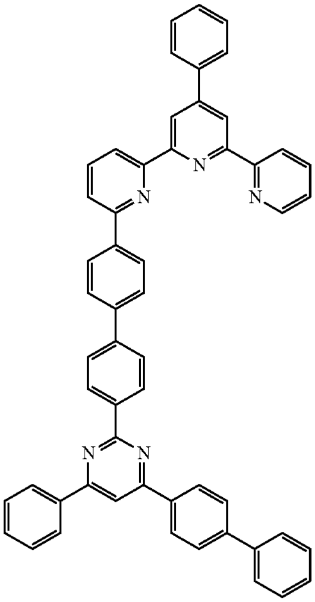

-continued
583
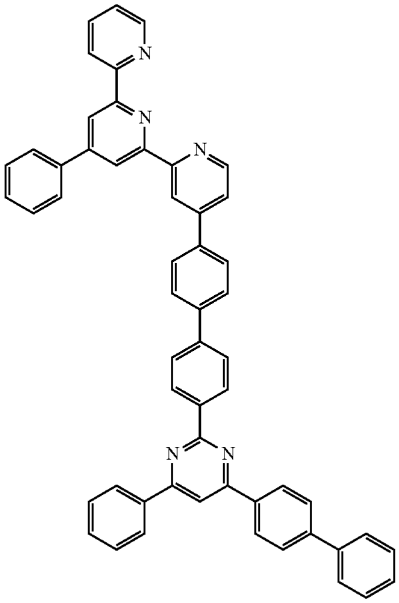
584
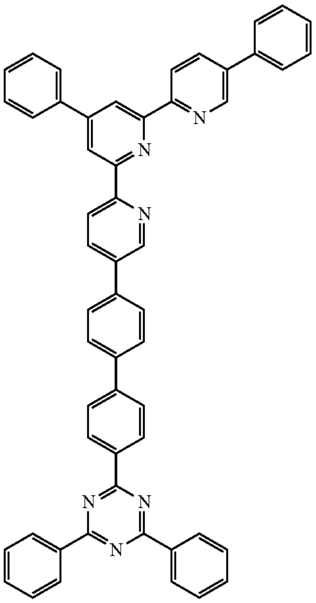
-continued
585
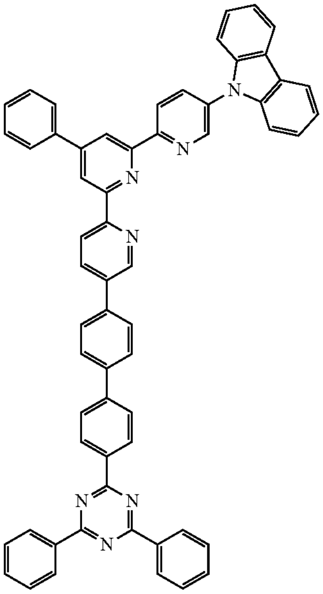
586
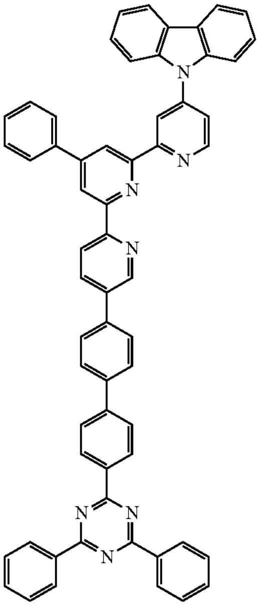

-continued
587
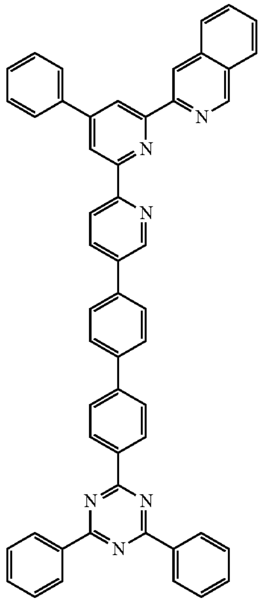
588
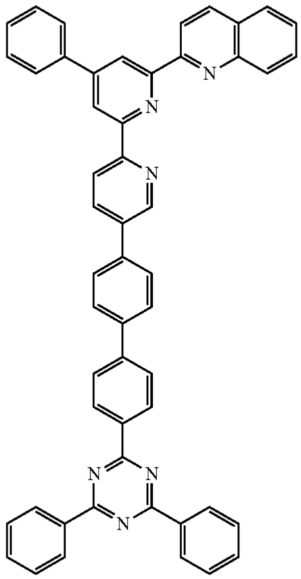
-continued
589
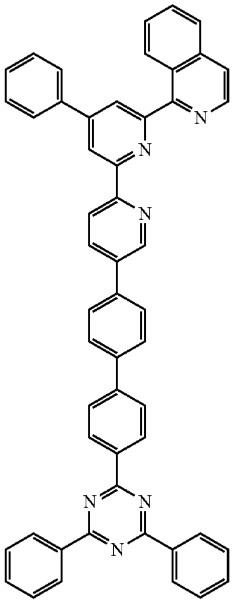
590
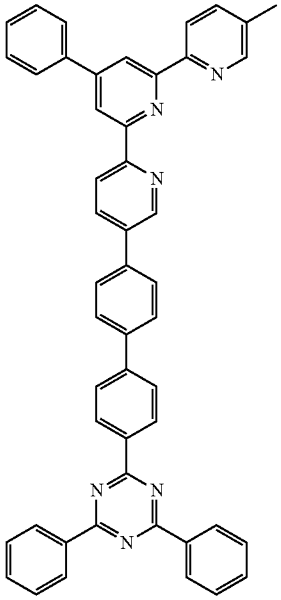

-continued
591
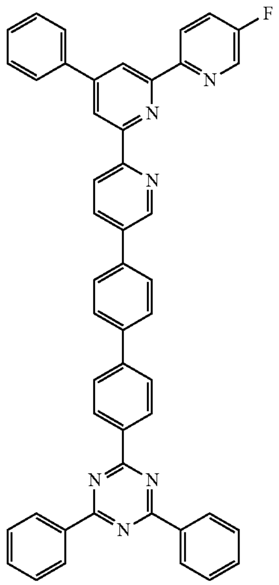
592
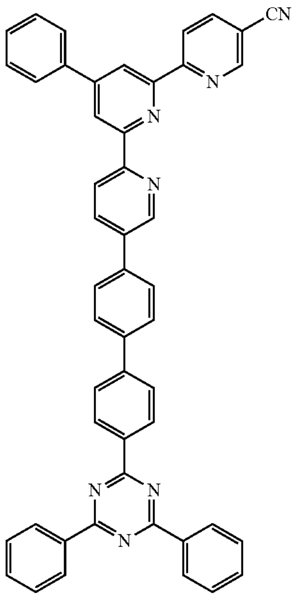
-continued
593
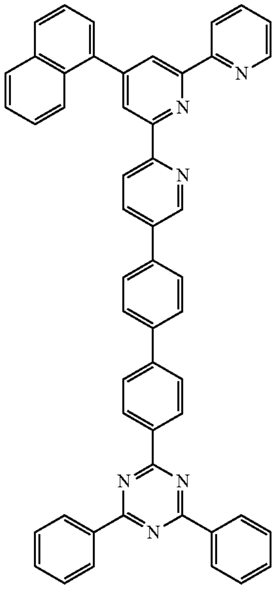
594
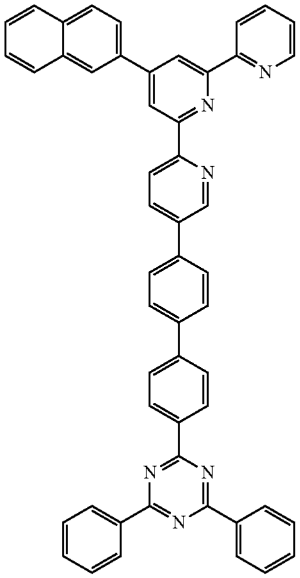

-continued
595
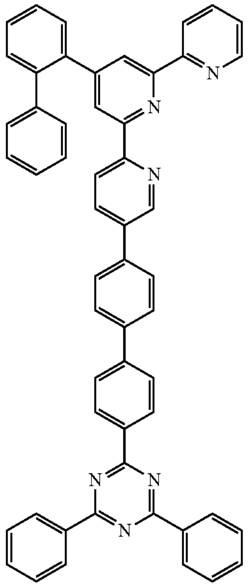
596
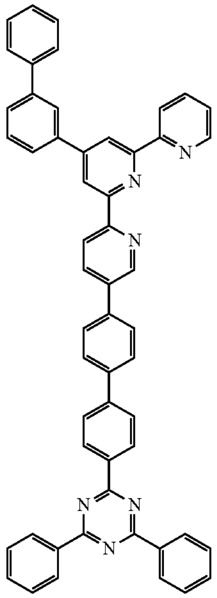
-continued
597
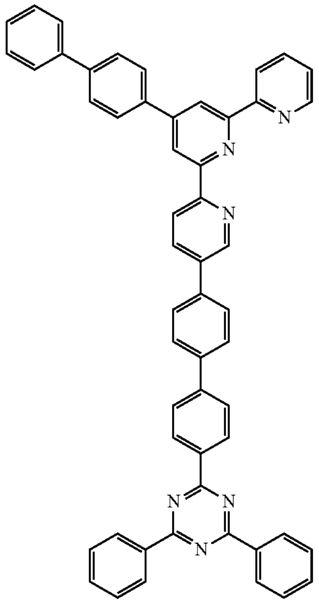
598
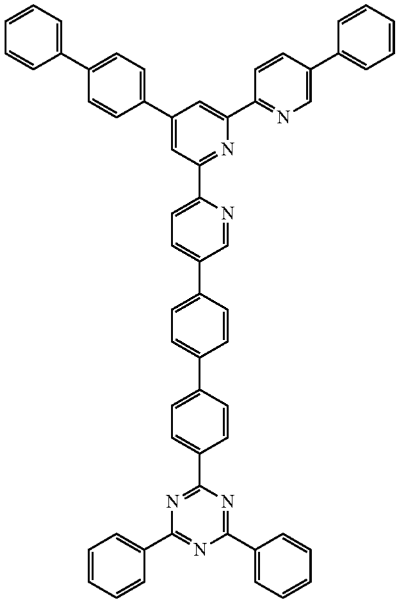

-continued
599
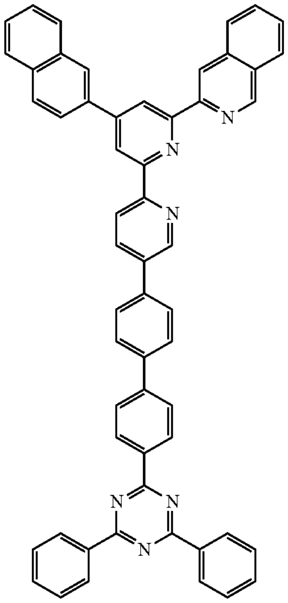
600
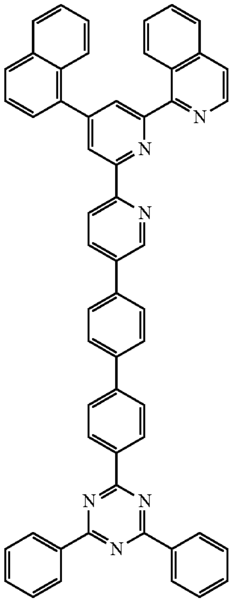
-continued
601
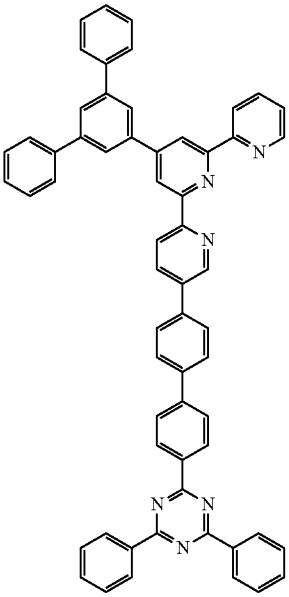
602
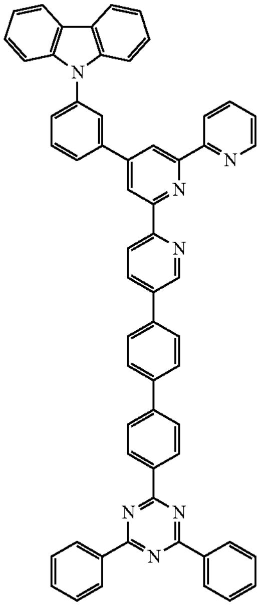

-continued
603
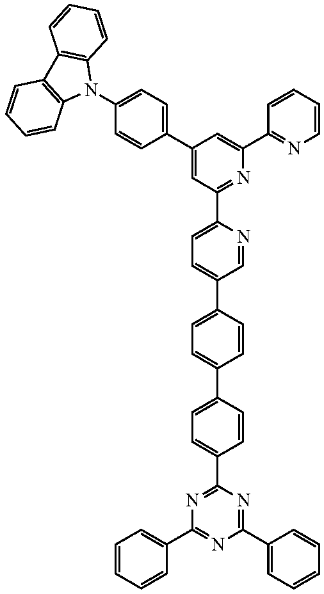
605
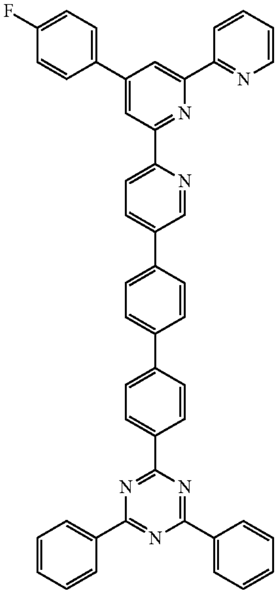
604
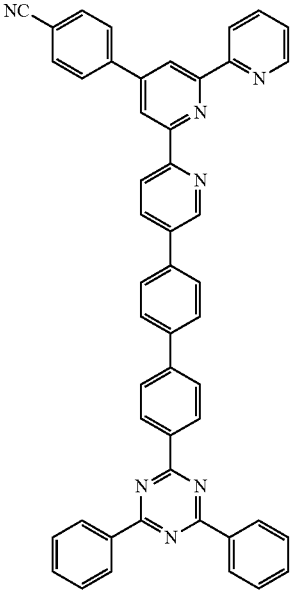
606
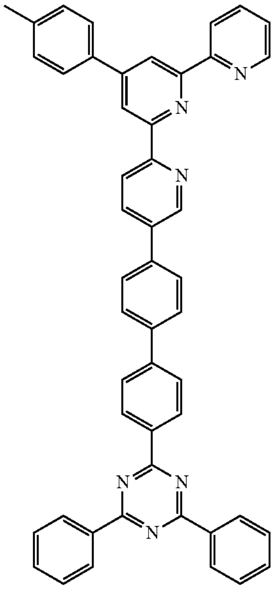

607
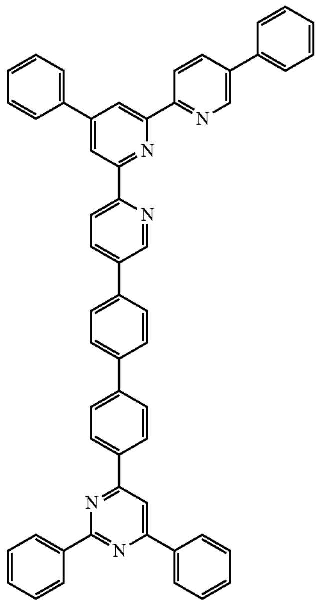
608
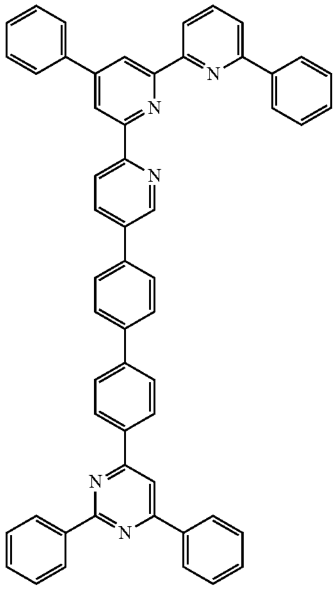
609
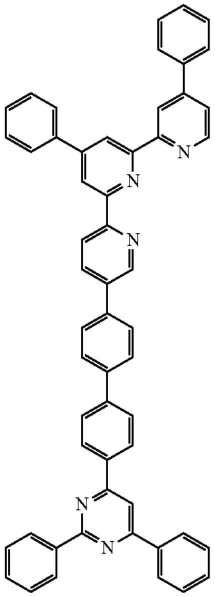
610
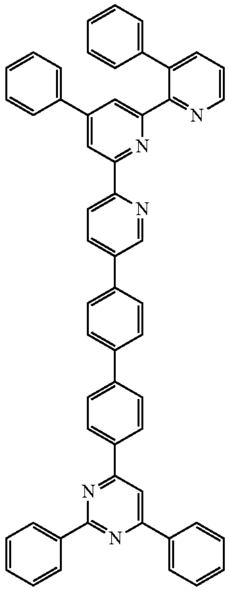

-continued
611
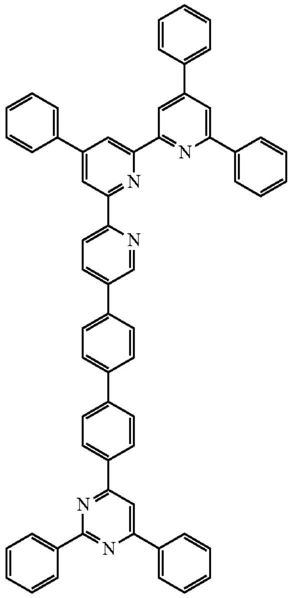
612
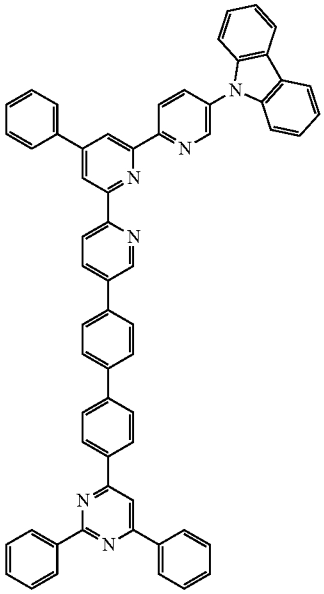
-continued
613
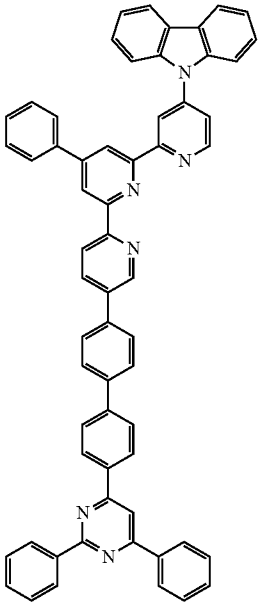
614
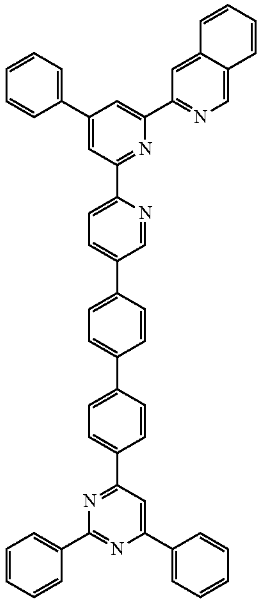

-continued
615
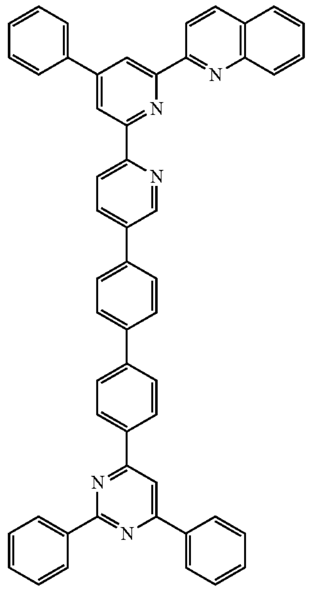
617
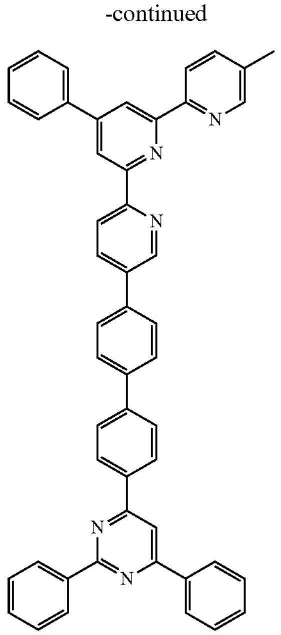
616
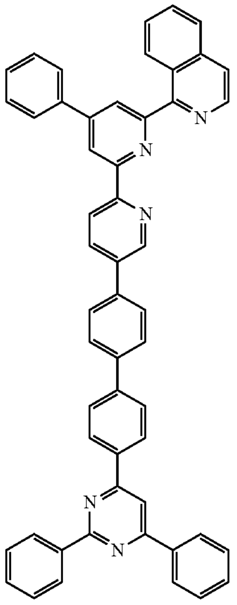
618
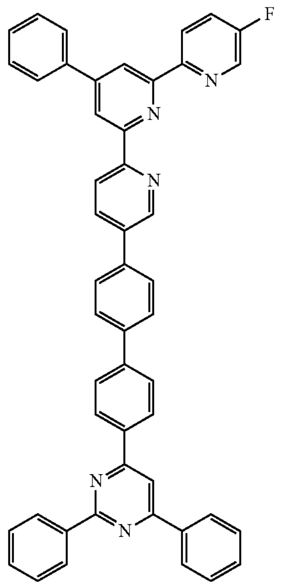

-continued
619
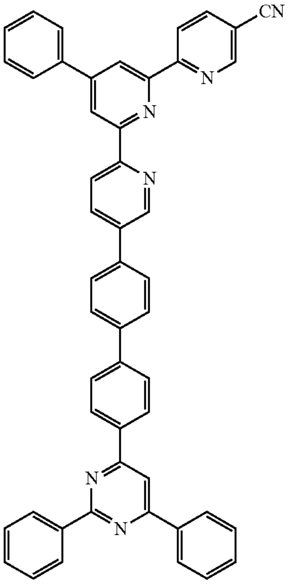
620
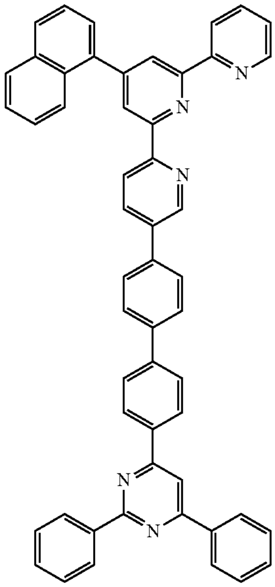
-continued
621
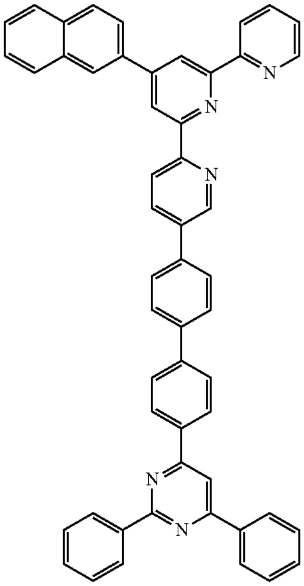
622
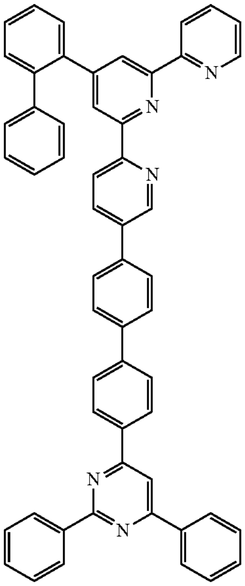

-continued
623
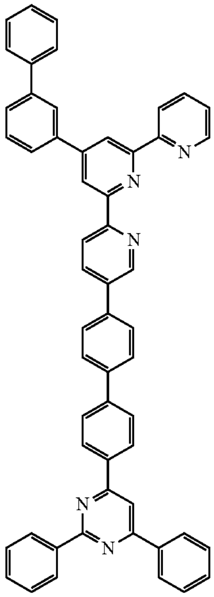
624
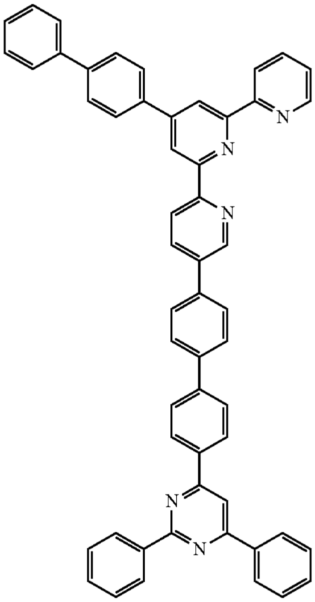
-continued
625
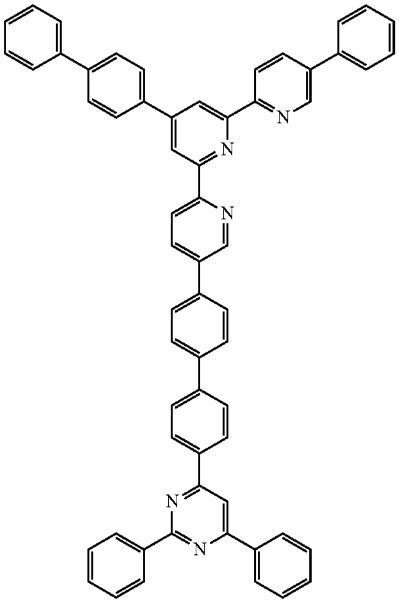
626
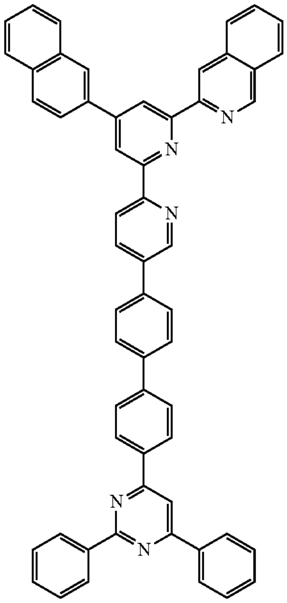

-continued
627
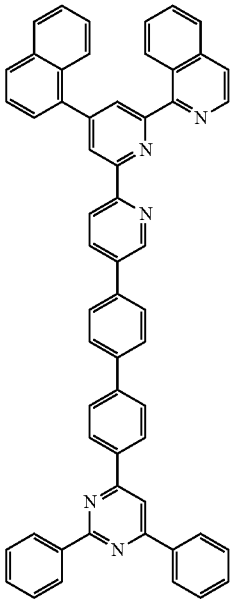
628
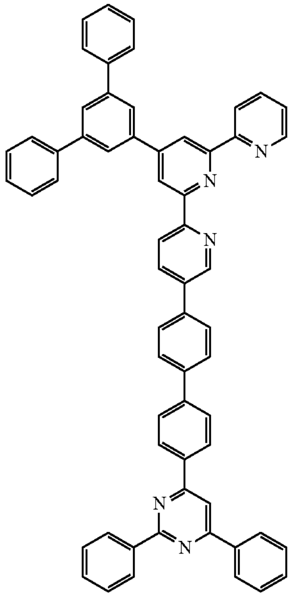
-continued
629
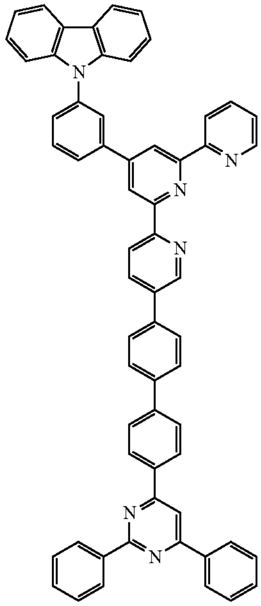
630
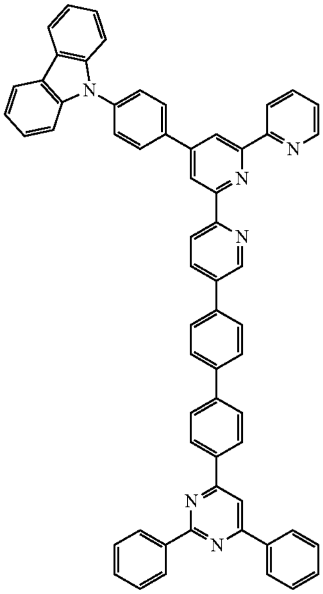

-continued
631
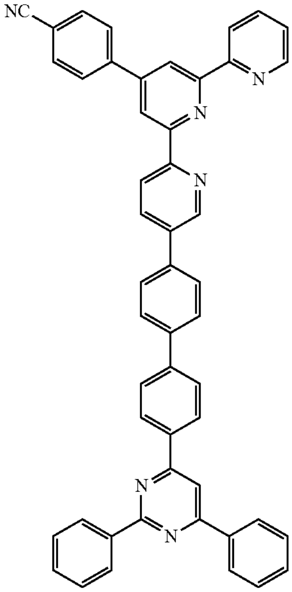
632
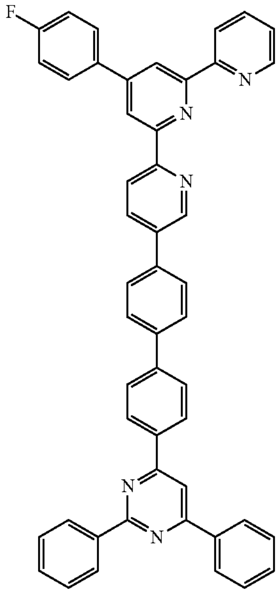
-continued
633
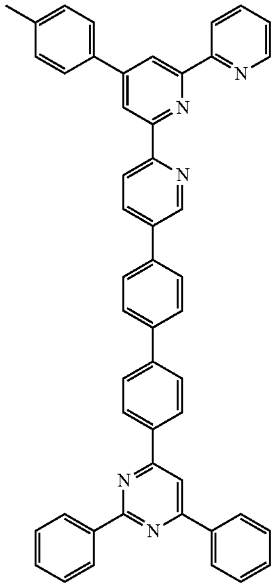
634
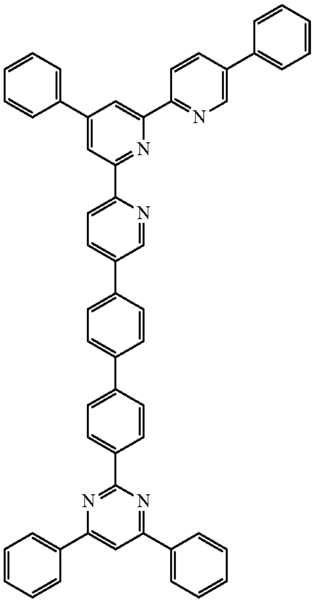

-continued
635
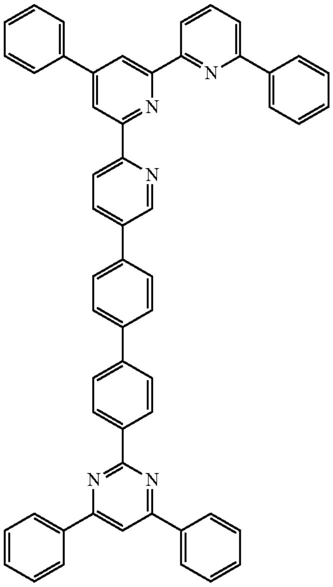
636
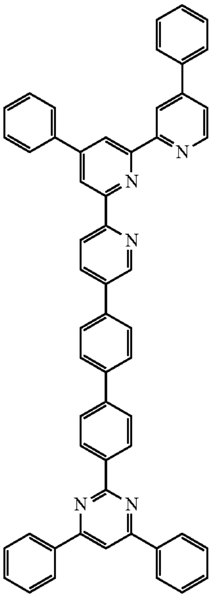
-continued
637
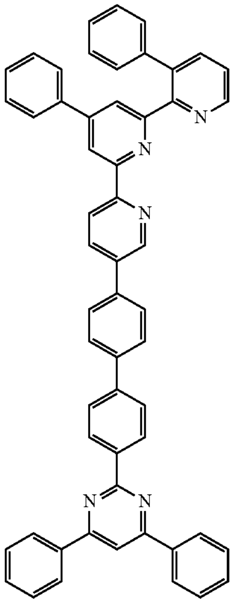
638
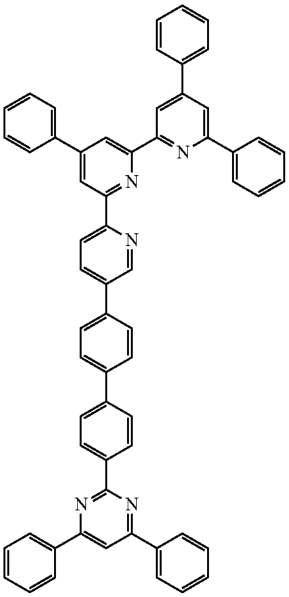

-continued
639
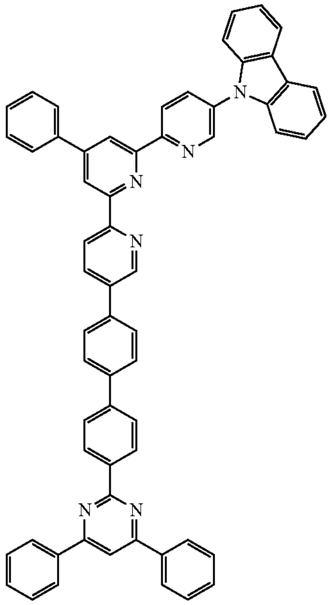
640
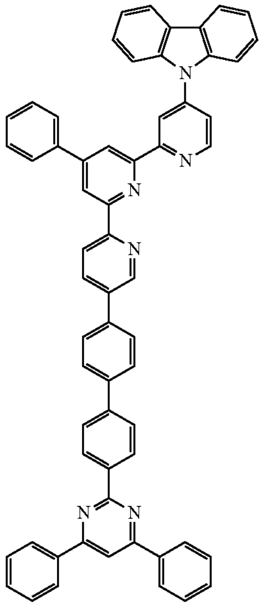
-continued
641
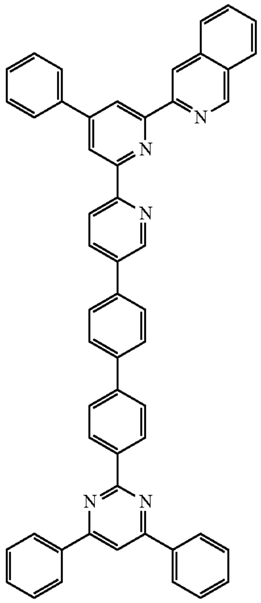
642
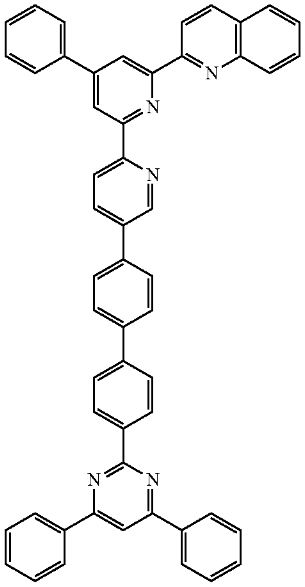

-continued
643
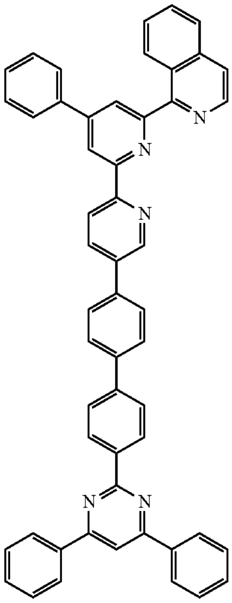
644
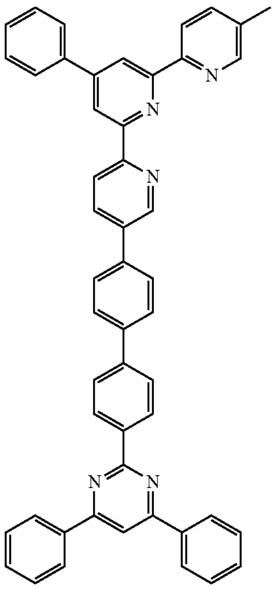
-continued
645
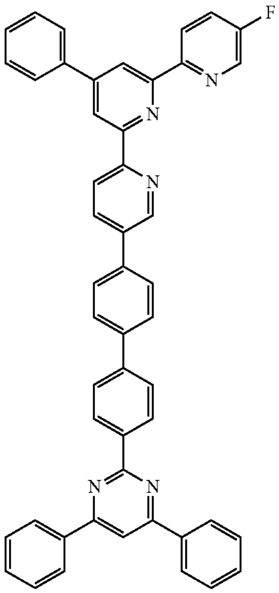
646
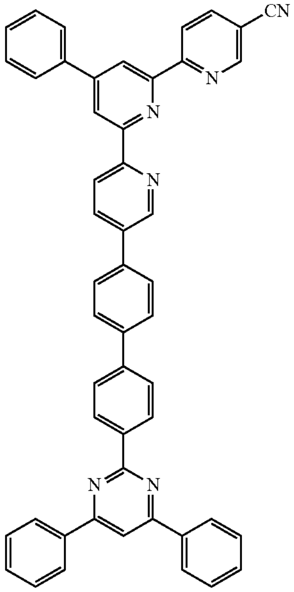

-continued
647
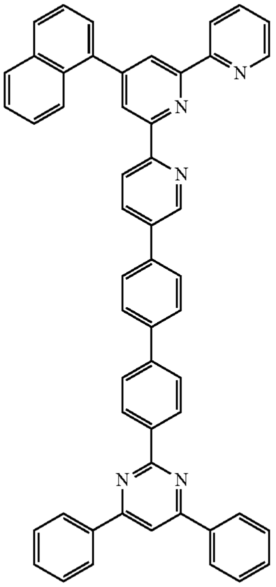
649
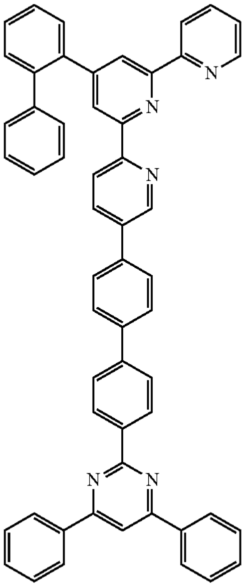
648
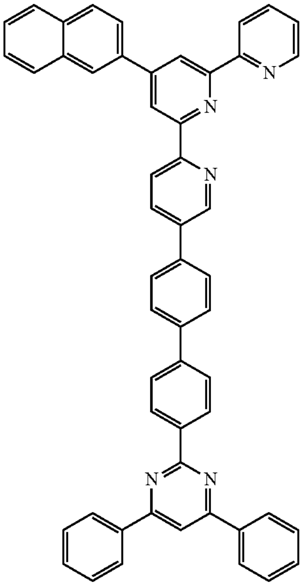
650
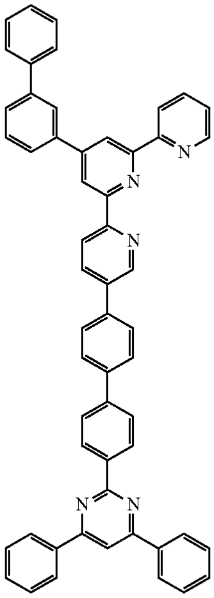

-continued
651
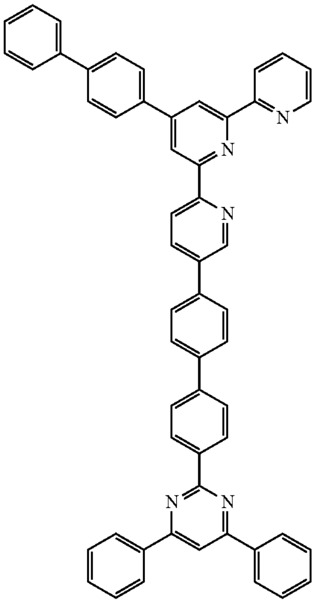
-continued
653
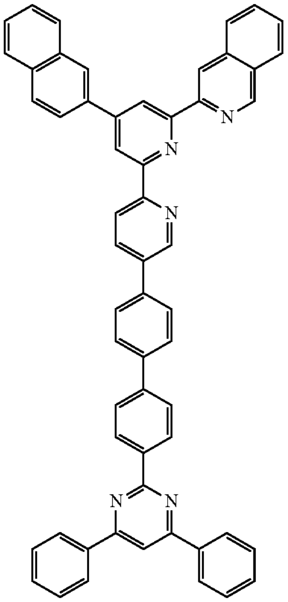
652
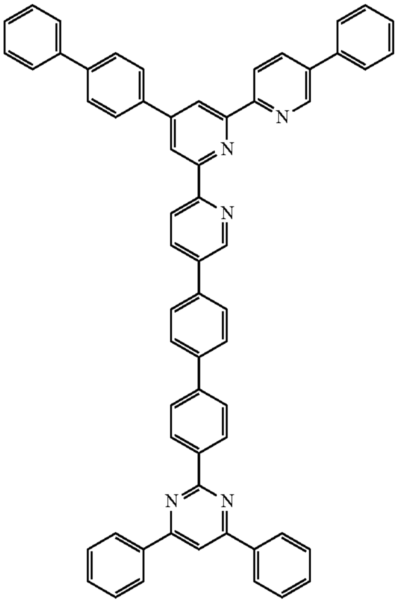
654
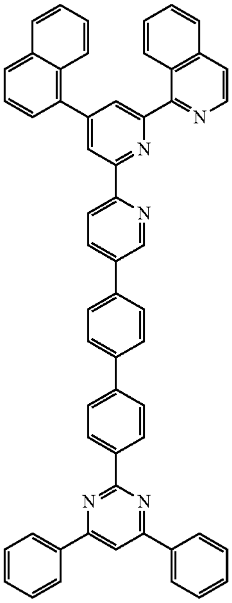

-continued
655
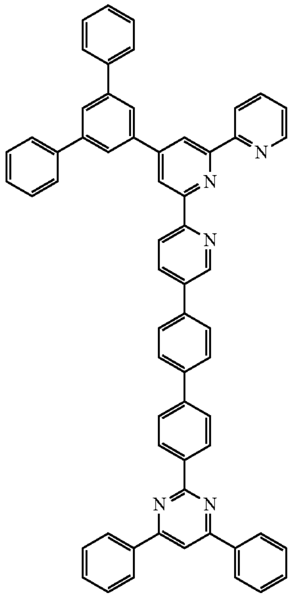
656
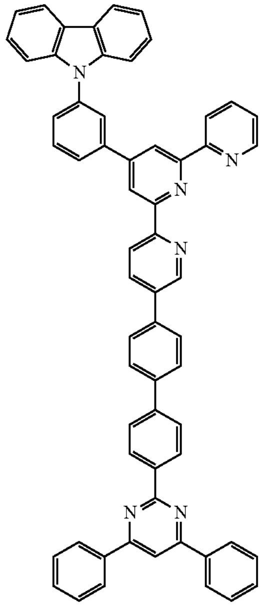
-continued
657
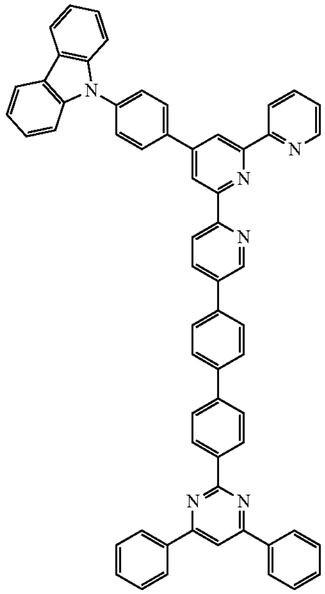
658
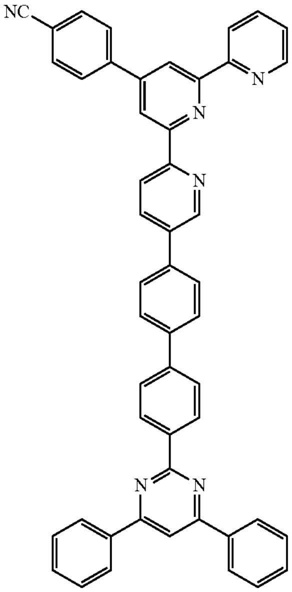

-continued
659
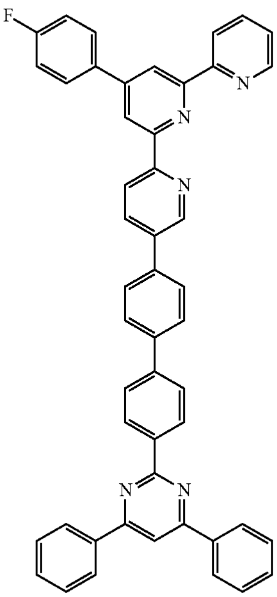
660
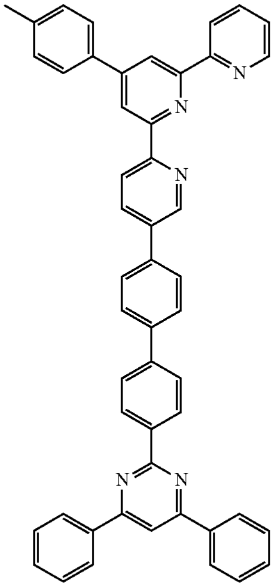
-continued
661
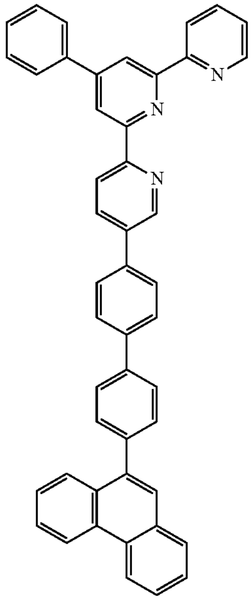
662
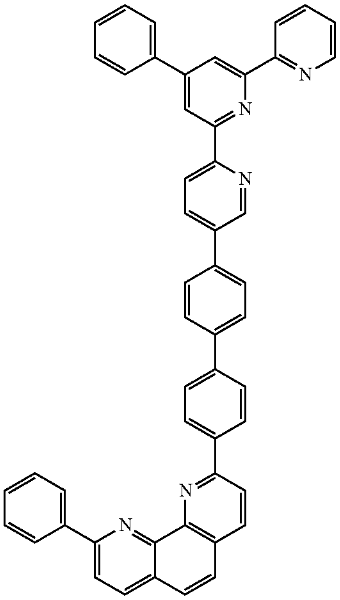

-continued
663
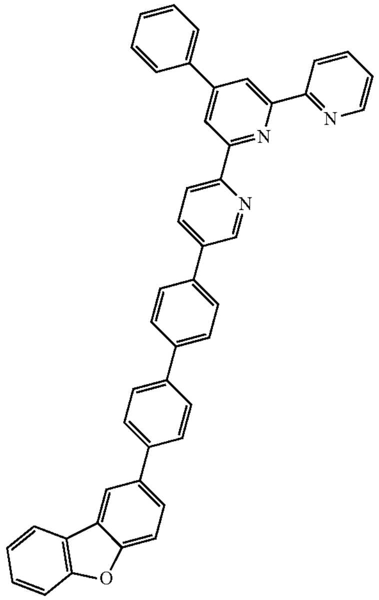
664
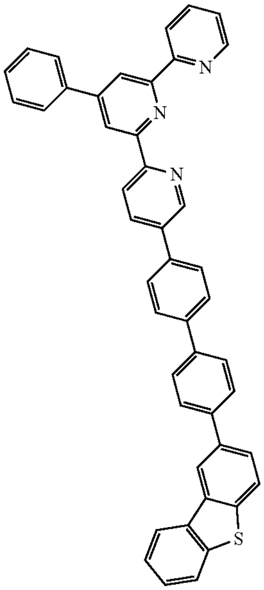
-continued
665
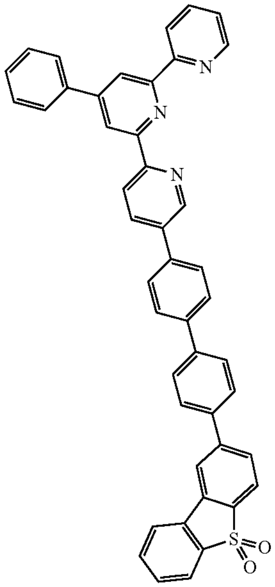
666
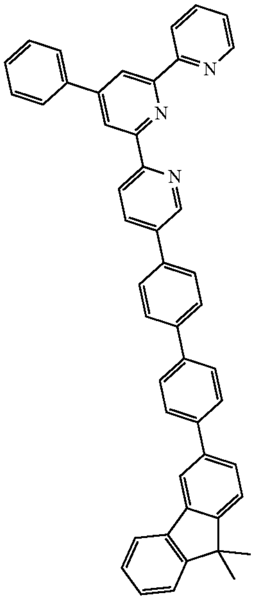

-continued
667
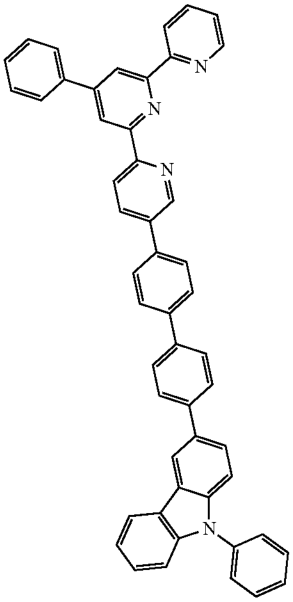
668
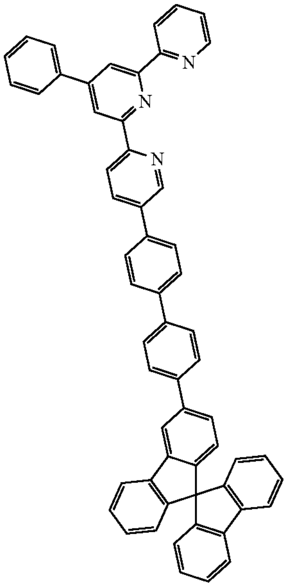
-continued
669
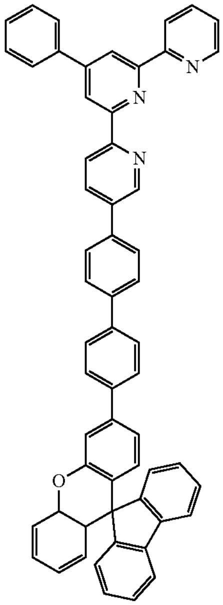
670
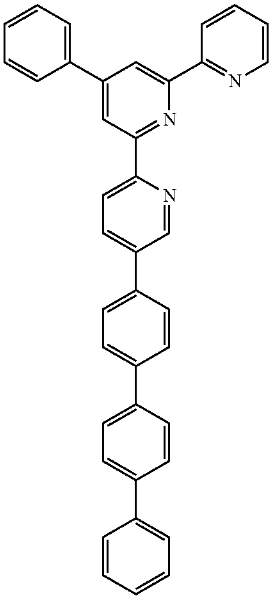

-continued

671

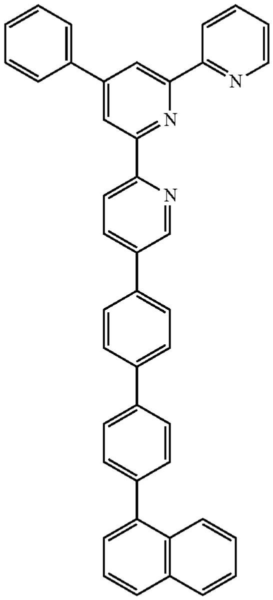

672

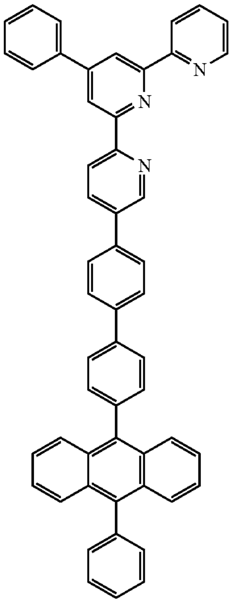

-continued

673

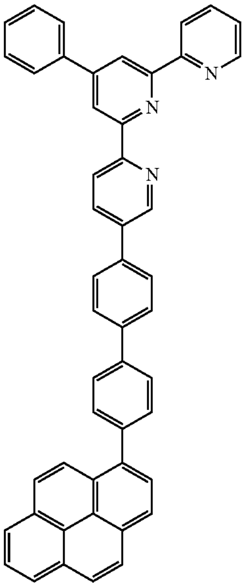

675

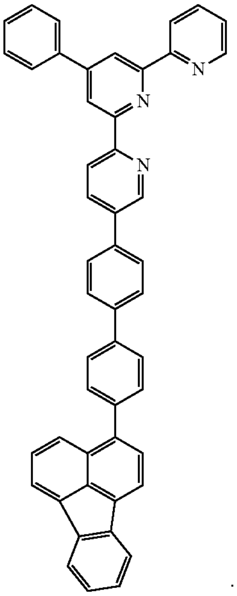

4. The organic light emitting device of claim 1, wherein the organic material layer includes the electron transfer layer, and the electron transfer layer includes one or more types of the heterocyclic compound.

5. The organic light emitting device of claim 1, wherein the organic material layer includes the hole blocking layer, and the hole blocking layer includes one or more types of the heterocyclic compound.

6. The organic light emitting device of claim 1, further comprising one layer selected from the group consisting of a light emitting layer, a hole injection layer, a hole transfer layer, an electron injection layer, and an electron blocking layer.

7. The organic light emitting device of claim 1 comprising:

the first electrode;

a first stack provided on the first electrode and including a first light emitting layer;

the charge generation layer provided on the first stack;

a second stack provided on the charge generation layer and including a second light emitting layer; and the second electrode provided on the second stack, and wherein the charge generation layer includes the heterocyclic compound.

8. The organic light emitting device of claim 7, wherein the charge generation layer includes an N-type charge generation layer, and the N-type charge generation layer includes the heterocyclic compound.

* * * * *